(12) United States Patent
Zhang et al.

(10) Patent No.: US 10,160,771 B2
(45) Date of Patent: Dec. 25, 2018

(54) HEPATITIS C VIRUS INHIBITORS AND USES THEREOF IN PREPARATION OF DRUGS

(71) Applicants: CHANGZHOU YINSHENG PHARMACEUTICAL CO., LTD., Changzhou, Jiangsu (CN); SICHUAN UNIVERSITY, Chengdu, Sichuan (CN)

(72) Inventors: Yang Zhang, Shanghai (CN); Chunli Shen, Shanghai (CN); Jian Li, Shanghai (CN); Shuhui Chen, Shanghai (CN); Guoping Hu, Shanghai (CN); Yuquan Wei, Chengdu (CN); Luoting Yu, Chengdu (CN); Xin Tao, Jiangsu (CN)

(73) Assignees: CHANGZHOU YINSHENG PHARMACEUTICAL CO., LTD., Changzhou (CN); SICHUAN UNIVERSITY, Chengdu (CN)

( * ) Notice: Subject to any disclaimer, the term of this patent is extended or adjusted under 35 U.S.C. 154(b) by 160 days.

(21) Appl. No.: 15/516,293

(22) PCT Filed: Feb. 6, 2015

(86) PCT No.: PCT/CN2015/072373
§ 371 (c)(1),
(2) Date: Mar. 31, 2017

(87) PCT Pub. No.: WO2015/124063
PCT Pub. Date: Aug. 27, 2015

(65) Prior Publication Data
US 2017/0253614 A1    Sep. 7, 2017

(30) Foreign Application Priority Data
Feb. 21, 2014    (CN) .......................... 2014 1 0058113

(51) Int. Cl.
| | | |
|---|---|---|
| *C07D 403/14* | (2006.01) |
| *C07D 498/04* | (2006.01) |
| *C07D 401/14* | (2006.01) |
| *C07D 405/14* | (2006.01) |
| *C07D 413/14* | (2006.01) |
| *C07D 233/64* | (2006.01) |
| *C07D 403/04* | (2006.01) |
| *C07D 409/14* | (2006.01) |
| *C07D 417/14* | (2006.01) |
| *C07D 491/048* | (2006.01) |
| *C07D 491/052* | (2006.01) |
| *C07D 491/113* | (2006.01) |
| *C07D 493/08* | (2006.01) |

(52) U.S. Cl.
CPC ......... *C07D 498/04* (2013.01); *C07D 233/64* (2013.01); *C07D 401/14* (2013.01); *C07D 403/04* (2013.01); *C07D 403/14* (2013.01); *C07D 405/14* (2013.01); *C07D 409/14* (2013.01); *C07D 413/14* (2013.01); *C07D 417/14* (2013.01); *C07D 491/048* (2013.01); *C07D 491/052* (2013.01); *C07D 491/113* (2013.01); *C07D 493/08* (2013.01)

(58) Field of Classification Search
CPC .............. C07D 403/14; C07D 491/048; C07D 491/052; A61K 31/407; A61K 31/4178; A61K 31/4184
USPC ........ 548/305.1, 311.7, 312.1, 453; 514/394, 514/397, 414, 415, 416
See application file for complete search history.

(56) References Cited

FOREIGN PATENT DOCUMENTS

| | | |
|---|---|---|
| CN | 102843909 A | 12/2012 |
| CN | 102863428 A | 1/2013 |
| CN | 102883718 A | 1/2013 |
| CN | 103304551 A | 9/2013 |
| CN | 103347878 A | 10/2013 |
| CN | 103459399 A | 12/2013 |
| CN | 104860931 A | 8/2015 |
| WO | WO-2010132601 A1 | 11/2010 |
| WO | WO-2012122716 A1 | 9/2012 |
| WO | WO-2012154777 A1 | 11/2012 |
| WO | WO-2013007106 A1 | 1/2013 |
| WO | WO-2013087743 A1 | 6/2013 |
| WO | WO-2013095275 A1 | 6/2013 |
| WO | WO-2013098313 A1 | 7/2013 |

OTHER PUBLICATIONS

1st Office Action in related CN201580009758.4.
Aug. 27, 2015 International Search Report issued in International Patent Application No. PCT/CN2015/072373.
Aug. 27, 2015 Written Opinion issued in International Patent Application No. PCT/CN2015/072373.
Jan. 1977 Berge et al., Pharmaceutical Salts, Journal of Pharmaceutical Science, 66: 1-19.
Feb. 1985 Maehr, A proposed new convention for graphic presentation of molecular geometry and topography, J. Chem. Ed., 62: 114-120.
Jun. 6, 2017, Notification to Make Divisional Application of CN106459009A.
2005 Alfonso R. Gennaro, Remington: The Science and Practice of Pharmacy, 21st Ed. Lippincott, Williams & Wilkins.
Aug. 22, 2018 Russian Office Action issued in Russian Patent Application No. 2016137637.

*Primary Examiner* — Deepak R Rao
(74) *Attorney, Agent, or Firm* — Harness, Dickey & Pierce, P.L.C.

(57) ABSTRACT

A series of hepatitis C virus (HCV) inhibitors and compositions and applications thereof in the preparation of drugs for treating chronic HCV infection. Especially, a series of compounds that are used as NS5A inhibitors, and compositions and uses thereof in the preparations of drugs.

7 Claims, No Drawings

HEPATITIS C VIRUS INHIBITORS AND USES THEREOF IN PREPARATION OF DRUGS

CROSS-REFERENCE TO RELATED APPLICATIONS

This application is a National Stage of International Application No. PCT/CN2015/072373, filed on Feb. 6, 2015 and published in Chinese as WO2015/124063 A1 on Aug. 27, 2015. This application claims the priority to Chinese Application No. 201410058113.7, filed on Feb. 21, 2014. The entire disclosures of the above applications are incorporated herein by reference.

FIELD OF INVENTION

The present invention relates to a hepatitis C virus (HCV) inhibitor and a composition thereof, and also relates to a use thereof in preparation of a drug for treating chronic HCV infection. Especially, the present invention relates to a series of compounds that are used as NS5A inhibitors, and compositions and uses thereof in the preparation of drugs.

PRIOR ARTS

HCV is one of the major human pathogens, it is estimated that there are about 0.17 billion chronic HCV infectors worldwide, which is 5 times the number of human immunodeficiency virus type-1 infectors. Chronic HCV infectors can develop into severe progressive liver diseases, including the liver cirrhosis and the hepatocellular carcinoma. Thus, the chronic HCV infection is the leading cause of death due to liver diseases in the world.

At present, the standard therapy of chronic HCV infection is through coadministration of α-interferon, ribavirin and a direct acting antiviral (DAA) drug, which is one of the drugs lisensed in recent two years. Although the curative effect is significantly improved compared to the coadministration of α-interferon and ribavirin, the therapy is ineffective for some chronic HCV infectors and the virus can become drug resistance. In addition, α-interferon and ribavirin have obvious adverse reactions. Therefore, a novel and effective drug for chronic HCV infection treatment is urgently desirable.

HCV is a single-stranded RNA virus, which belongs to a separate genus of the flaviviridae family. All members in the flaviviridae family are enveloped virus particles containing the strand RNA genome, which encodes all known viral specific proteins through the translation of a single uninterrupted open-reading frame (ORF).

There are considerable heterogeneities among the nucleotides of the HCV genome and the encoded amino acid sequences. It has been identified that there are at least 6 major genotypes and more than 50 subtypes. The distribution of main HCV genotypes varies in the world. Despite of a large number of studies on the role of genotypes for the pathogenesis and treatment, the clinical importance of HCV genetic heterogeneity is still unclear.

The HCV RNA genome has about 9500 nucleotides, with a single open-reading frame, encoding a single polyprotein of about 3000 amino acids. In the infected cells, the polyprotein is cleaved by cellular proteases and viral proteases at multiple sites to provide the structural and non-structural (NS) protein. As far as HCV, the formation of mature non-structural protein (NS2, NS3, NS4A, NS4B, NS5A and NS5B) was achieved by two kind of viral proteases. It is generally believed that the first kind (NS2) is a metal protease, cleaving at the NS2-NS3 junction site; the second protease is a serine protease contained in the N-terminal region of NS3 (also called the NS3 protease herein), which mediates all subsequent NS3 downstream cleavages, a cis-cleavage at the NS3-NS4A junction site, and trans-cleavages at the NS4A-NS4B, NS4B-NS5A and NS5A-NA5B junction sites. NS4A protein appears to have a variety of functions, for example, being a cofactor of NS3 protease and possibly assisting NS3 and other viral to replicate enzyme components to carry out the membrane localization. The NS3 protein also shows nucleoside triphosphatase and RNA helicase activities. The functions of the two proteins NS4B and NS5A are not completely clear, but they play an important role in the replication of HCV. NS4B is a transmembrane protein participating in the formation of virus replication complex. NS5A is a phosphorylated protein participating in viral RNA replication and viral particle formation. NS5B (also known as HCV polymerase) is a RNA-dependent RNA polymerase participating in RNA replication of HCV genome.

WO2013095275, WO2012122716, CN102863428A and etc. respectively reported a series of compounds as HCV inhibitors, whose effects in the aspects of activity, solubility and so on need to be further improved.

Content of the Present Invention

The aim of the present invention is to provide a compound represented by formula (I), (II), (III), (IV) or (V), or a pharmaceutical acceptable salt thereof,

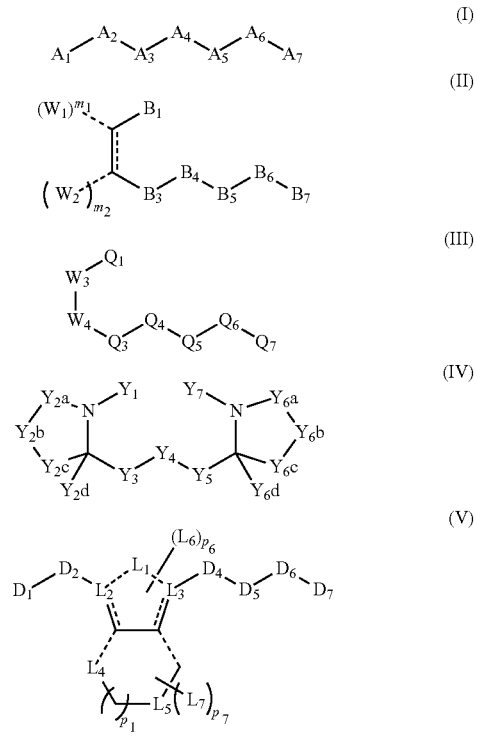

wherein, each of $A_1$, $A_7$, $B_1$, $B_7$, $Q_1$, $Q_7$, $Y_1$, $Y_7$, $D_1$ and $D_7$ independently represents a structural unit represented by formula (a),

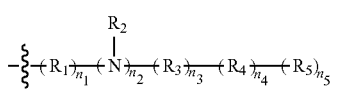

(a)

wherein, $R_1$ is selected from C=O, C=S, S(=O), S(=O)$_2$, C($R_{1a}$)($R_{1b}$);

$R_3$ is selected from C($R_{3a}$)($R_{3b}$), C=O, C=S, S(=O), S(=O)$_2$;

$R_4$ is selected from [a chain hydrocarbon group, a heterochain hydrocarbon group, a chain-hydrocarbon heteroatomic group, a cyclic hydrocarbon group, a heterocyclic group, a cyclic heteroatomic group] wherein two or more than two hydrogens are substituted;

each of $R_2$, $R_5$, $R_{1a}$, $R_{1b}$, $R_{3a}$ and $R_{3b}$ is independently selected from H, F, Cl, Br, I, CN or an optionally substituted [OH, SH, NH$_2$, PH$_2$, hydrocarbon group, hetero-hydrocarbon group, hydrocarbon heteroatomic group or hetero-hydrocarbon heteroatomic group];

optionally, $R_{1a}$ and $R_{1b}$, $R_{3a}$ and $R_{3b}$ form an optionally substituted 3- to 6-membered cycloalkyl; $n_1$ or $n_4$ is independently selected from 0 or 1;

$n_2$ is selected from $n_{2a}$, $n_{2b}$, $n_{2c}$, $n_2$ in $A_1$ is $n_{2a}$, $n_{2a}$ is selected from 3, 4, 5 or 6; $n_2$ in $B_1$ is $n_{2b}$, $n_{2b}$ is 0; $n_2$ in $A_7$, $B_7$, $Q_1$, $Q_7$, $Y_1$, $Y_7$, $D_1$, $D_7$ is $n_{2c}$, $n_{2c}$ is selected from 0, 1, 2, 3, 4, 5 or 6;

$n_3$ is selected from 0, 1, 2, 3, 4, 5 or 6;

$n_5$ is selected from 1, 2, 3 or 4;

when $n_1$, $n_2$, $n_3$ or $n_4$ is 0, the corresponding structural unit represents a single bond just for the linkage;

each of $A_2$, $A_6$, $B_6$, $Q_6$, $D_2$ and $D_6$ is independently selected from —C(=O)N($R_{6a}$)C($R_{6b}$)($R_{6c}$), CH$_2$, a single bond, O, S, C=O, C=S, S(=O), S(=O)$_2$ or a structural unit represented by formula (b),

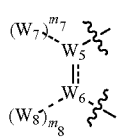

(b)

each of $W_1$ and $W_2$ is independently selected from H, F, Cl, Br, I, CN, =O, =S or an optionally substituted [OH, SH, NH$_2$, PH$_2$, hydrocarbon group, hetero-hydrocarbon group, hydrocarbon heteroatomic group or hetero-hydrocarbon heteroatomic group], optionally $W_1$ and $W_2$, $W_1$ and $W_1$, or $W_2$ and $W_2$ connect to form a ring; $m_1$, $m_2$ is selected from 0, 1, 2;

$W_3$ is selected from an optionally substituted NH or a single bond;

$W_4$ is selected from an optionally substituted [CH$_2$, CH$_2$—CH$_2$, CH=CH, NH, 3-6 membered hydrocarbon group or 3-6 membered hetero-hydrocarbon group], C≡C, a single bond, O, S, C=O, C=S, S(=O), S(=O)$_2$;

each of $R_{6a}$, $R_{6b}$ and $R_{6c}$ is independently selected from H, a $C_{1-6}$ alkyl or an alkoxyl;

each of $W_5$ and $W_6$ independently represents C, N, an optionally substituted [CH$_2$, CH, NH, CH$_2$—CH$_2$, CH=CH, 3-6 membered hydrocarbon group or 3-6 membered hetero-hydrocarbon group], C≡C, a single bond, O, S, C=O, C=S, S(=O), S(=O)$_2$;

each of $W_7$ and $W_8$ independently represents H, F, Cl, Br, I, CN, =O, =S or an optionally substituted [OH, SH, NH$_2$, PH$_2$, hydrocarbon group, hetero-hydrocarbon group, hydrocarbon heteroatomic group or hetero-hydrocarbon heteroatomic group], optionally $W_7$ and $W_8$, $W_7$ and $W_7$, or $W_8$ and $W_8$ connect to form a ring; $m_7$, $m_8$ is selected from 0, 1, 2;

$Y_{2b}$ is selected from O, S, C=O, C=S, S(=O), S(=O)$_2$, C≡C, an optionally substituted [NH, CH$_2$—CH$_2$, CH=CH, 3-6 membered hydrocarbon group or 3-6 membered heterohydrocarbon group];

each of $Y_{2a}$, $Y_{2c}$, $Y_{6a}$, $Y_{6b}$ and $Y_{6c}$ is independently selected from an optionally substituted [CH$_2$, NH, CH$_2$—CH$_2$, CH=CH, 3-6 membered hydrocarbon group or 3-6 membered hetero-hydrocarbon group], C≡C, a single bond, O, S, C=O, C=S, S(=O), S(=O)$_2$;

each of $Y_{2d}$ and $Y_{6d}$ is independently selected from H, F, Cl, Br, I, CN, =O, =S or an optionally substituted [OH, SH, NH$_2$, PH$_2$, hydrocarbon group, hetero-hydrocarbon group, hydrocarbon heteroatomic group or hetero-hydrocarbon heteroatomic group];

each of $A_3$, $A_5$, $B_3$, $B_5$, $Q_3$, $Q_5$, $Y_3$, $Y_5$ and $D_5$ is independently selected from CH$_2$, a single bond, O, S, C=O, C=S, S(=O), S(=O)$_2$ or a structural unit represented by formula (c);

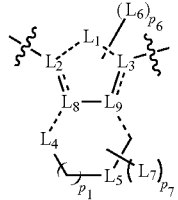

(c)

$L_1$ is independently selected from C, N, an optionally substituted [NH, CH, CH$_2$, CH$_2$—CH$_2$, CH=CH, 3-6 membered hydrocarbon group or 3-6 membered hetero-hydrocarbon group], C≡C, O, S, C=O, C=S, S(=O), S(=O)$_2$ or a single bond;

each of $L_2$, $L_3$, $L_4$, $L_5$, $L_8$ and $L_9$ is independently selected from C, N, an optionally substituted [NH, CH, CH$_2$, CH$_2$—CH$_2$, CH=CH, 3-6 membered hydrocarbon group or 3-6 membered hetero-hydrocarbon group], C≡C, O, S, C=O, C=S, S(=O), S(=O)$_2$;

each of $L_6$ and $L_7$ is independently selected from H, F, Cl, Br, I, CN, =O, =S or an optionally substituted [OH, SH, NH$_2$, PH$_2$, hydrocarbon group, hetero-hydrocarbon group, hydrocarbon heteroatomic group or hetero-hydrocarbon heteroatomic group];

each of $p_1$, $p_6$ and $p_7$ is independently selected from 0, 1, 2, 3, 4, 5 or 6;

$A_4$, $B_4$, $Q_4$, $Y_4$, $D_4$ are selected from CH$_2$, a single bond, O, S, C=O, C=S, S(=O), S(=O)$_2$, an aryl or a heteroaryl;

===== represents a single bond or a double bond;

------ represents a single bond, a double bond or no bond, when the ------ in

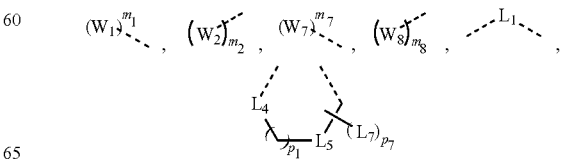

represents no bond, the structural unit does not exist;
optionally, the compound or the pharmaceutically acceptable salt thereof contains one or multiple chiral centers.

In certain embodiments of the present invention, the sub-structural unit in the above-mentioned structural unit

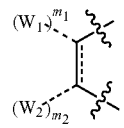

is represented by formula (f),

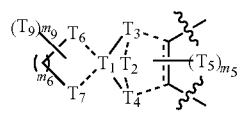

(f)

wherein, $T_1$ is independently selected from C, N, an optionally substituted [$CH_2$—$CH_2$, CH=CH, $CH_2$, CH, NH, 3-6 membered hydrocarbon group or 3-6 membered hetero-hydrocarbon group], C≡C, a single bond, O, S, C=O, C=S, S(=O), S(=O)$_2$;

each of $T_2$, $T_3$ and $T_4$ is independently selected from C, N, an optionally substituted [$CH_2$, $CH_2$—$CH_2$, CH=CH, CH, NH, 3-6 membered hydrocarbon group or 3-6 membered hetero-hydrocarbon group], C≡C, O, S, C=O, C=S, S(=O), S(=O)$_2$;

$T_5$ is selected from H, F, Cl, Br, I, CN, =O, =S or an optionally substituted [OH, SH, $NH_2$, $PH_2$, hydrocarbon group, hetero-hydrocarbon group, hydrocarbon heteroatomic group or hetero-hydrocarbon heteroatomic group];

$m_5$ is selected from 0, 1, 2, 3, 4, 5 or 6;

each of $T_6$ and $T_7$ is independently selected from O, S, an optionally substituted [NH, CH, $CH_2$, $CH_2$—$CH_2$, CH=CH, 3-6 membered hydrocarbon group or 3-6 membered hetero-hydrocarbon group], C≡C, a single bond, C=O, C=S, S(=O), S(=O)$_2$;

$T_9$ is selected from H, F, Cl, Br, I, CN, =O, =S or an optionally substituted [OH, SH, $NH_2$, $PH_2$, hydrocarbon group, hetero-hydrocarbon group, hydrocarbon heteroatomic group or hetero-hydrocarbon heteroatomic group];

$m_6$ is selected from 0, 1, 2, or 3, when $m_6$ is 0, the corresponding structural unit represents a single bond just for the linkage;

$m_9$ is selected from 0, 1, 2 3, 4, 5 or 6;

===== represents a single bond or a double bond;

------ represents a single bond, a double bond or no bond, when all the ------ in

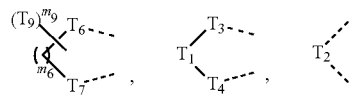

represent no bond, the structural unit does not exist, the two ------ attached to $T_2$ are not double bonds at the same time.

In certain embodiments of the present invention, the above-mentioned sub-structural unit represented by formula (f) is selected from the group consisting of:

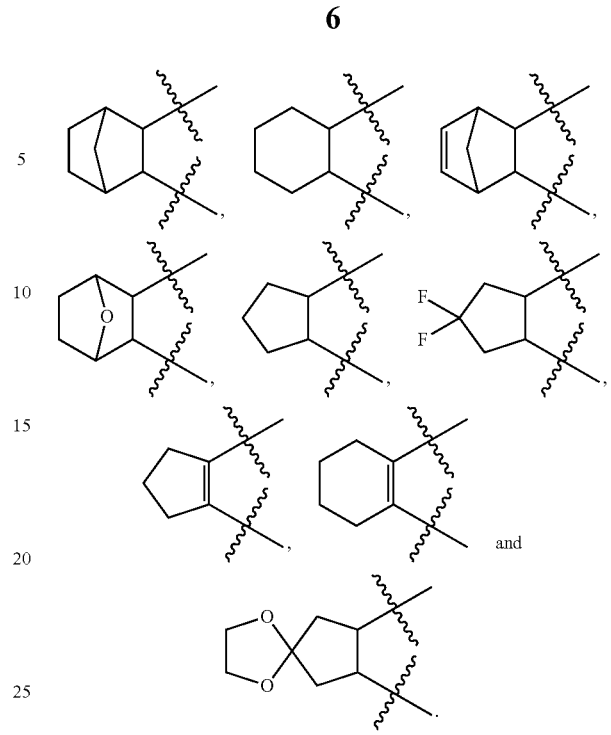

In certain embodiments of the present invention, the above-mentioned sub-structural unit represented by formula (f) is selected from the group consisting of:

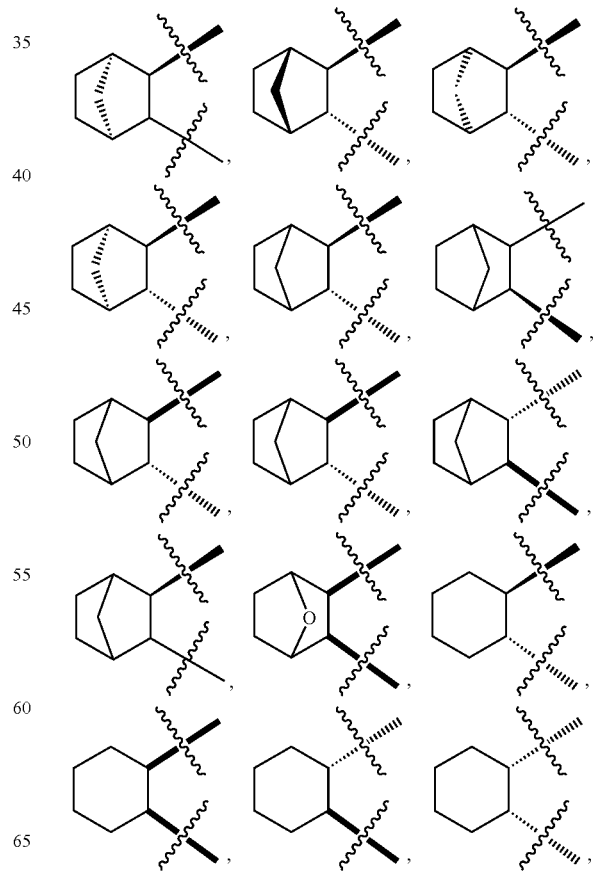

-continued

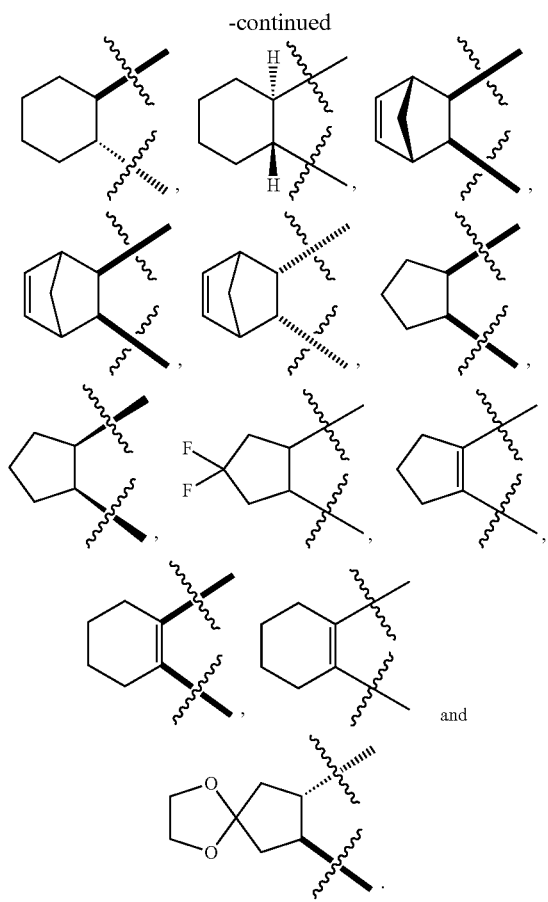

In certain embodiments of the present invention, the sub-structural unit of the above-mentioned structural unit (b) is represented by formula (g), (g)

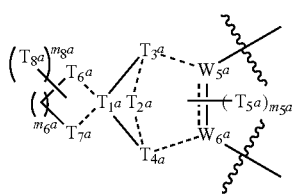

wherein, $T_{1a}$ is independently selected from C, N, an optionally substituted [$CH_2$—$CH_2$, CH=CH, $CH_2$, CH, NH, 3-6 membered hydrocarbon group or 3-6 membered hetero-hydrocarbon group], C≡C, a single bond, O, S, C=O, C=S, S(=O), S(=O)$_2$;

each of $T_{2a}$, $T_{3a}$ and $T_{4a}$ is independently selected from C, N, an optionally substituted [$CH_2$, $CH_2$—$CH_2$, CH=CH, CH, NH, 3-6 membered hydrocarbon group or 3-6 membered hetero-hydrocarbon group], C≡C, O, S, C=O, C=S, S(=O), S(=O)$_2$;

$T_{5a}$ is selected from H, F, Cl, Br, I, CN, =O, =S or an optionally substituted [OH, SH, $NH_2$, $PH_2$, hydrocarbon group, hetero-hydrocarbon group, hydrocarbon heteroatomic group or hetero-hydrocarbon heteroatomic group];

$m_{5a}$ is selected from 0, 1, 2, 3, 4, 5 or 6;

each of $W_{5a}$ and $W_{6a}$ is independently selected from C, N, an optionally substituted [$CH_2$, NH, CH, $CH_2$—$CH_2$, CH=CH, 3-6 membered hydrocarbon group or 3-6 membered hetero-hydrocarbon group], C≡C, a single bond, O, S, C=O, C=S, S(=O), S(=O)$_2$;

rach of $T_{6a}$ and $T_{7a}$ is independently selected from 0, S, an optionally substituted [NH, CH, $CH_2$, $CH_2$—$CH_2$, CH=CH, 3-6 membered hydrocarbon group or 3-6 membered hetero-hydrocarbon group], C≡C, a single bond, C=O, C=S, S(=O), S(=O)$_2$;

$T_{8a}$ is selected from H, F, Cl, Br, I, CN, =O, =S or an optionally substituted [OH, SH, $NH_2$, $PH_2$, hydrocarbon group, hetero-hydrocarbon group, hydrocarbon heteroatomic group or hetero-hydrocarbon heteroatomic group];

$m_{6a}$ is selected from 0, 1, 2, or 3, when $m_{6a}$ is 0, the corresponding structural unit represents a single bond just for the linkage;

$m_{8a}$ is selected from 0, 1, 2 3, 4, 5 or 6;

===== represents a single bond or a double bond;

----- represents a single bond, a double bond or no bond, when all the ----- in

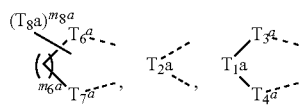

represent no bond, the structural unit and the sub-structural unit attached do not exist, the two ----- attached to $T_{1a}$ or $T_{2a}$ are not double bonds at the same time.

In certain embodiments of the present invention, the above-mentioned sub-structural unit represented by formula (g) is selected from the group consisting of:

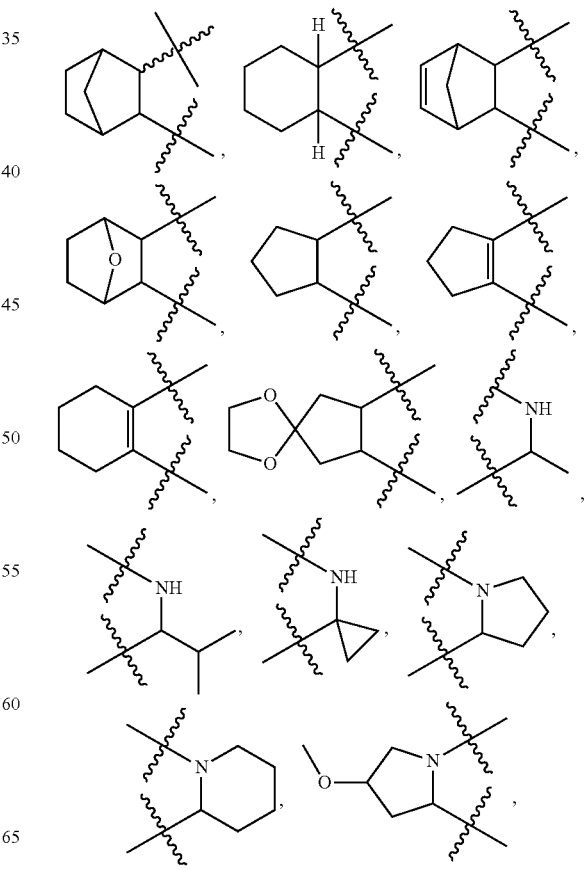

In certain embodiments of the present invention, the above-mentioned sub-structural unit represented by formula (g) is selected from the group consisting of:
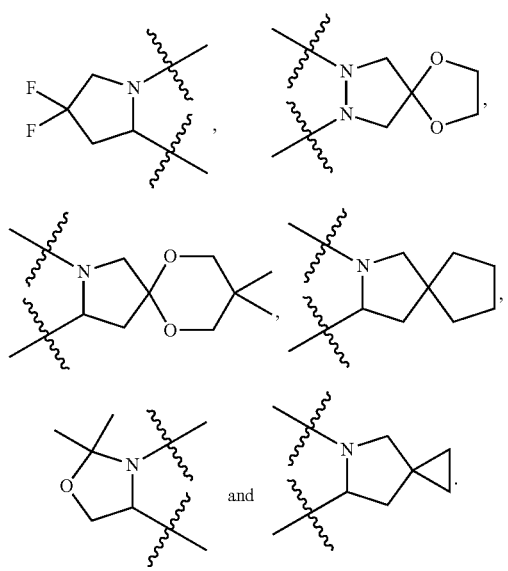
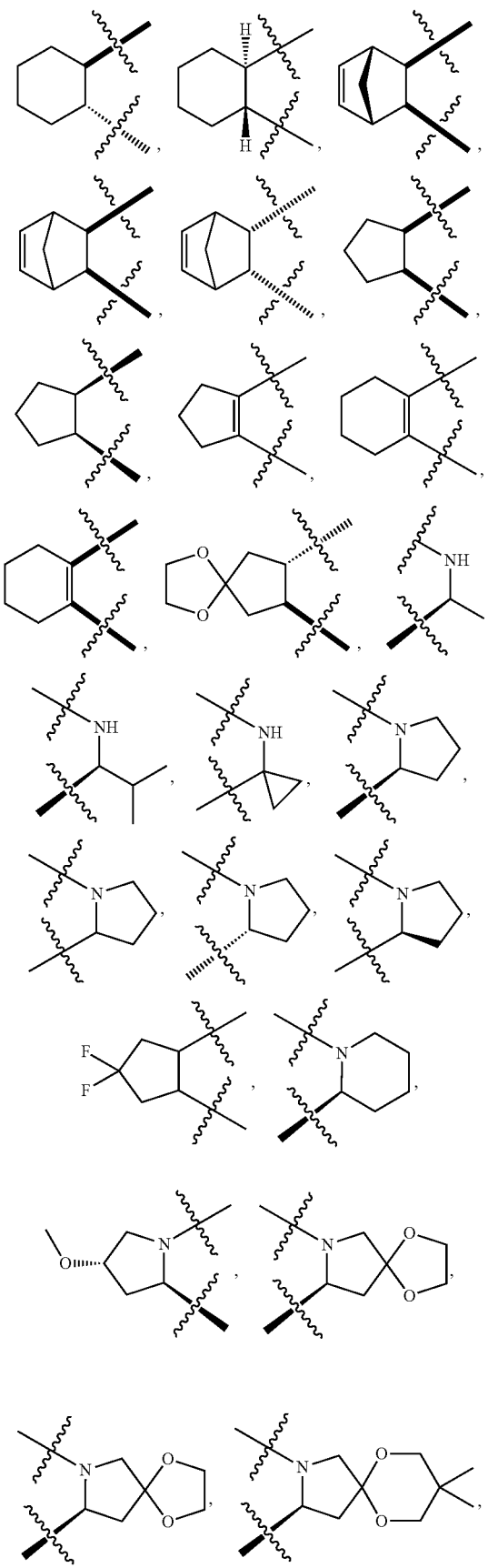

-continued

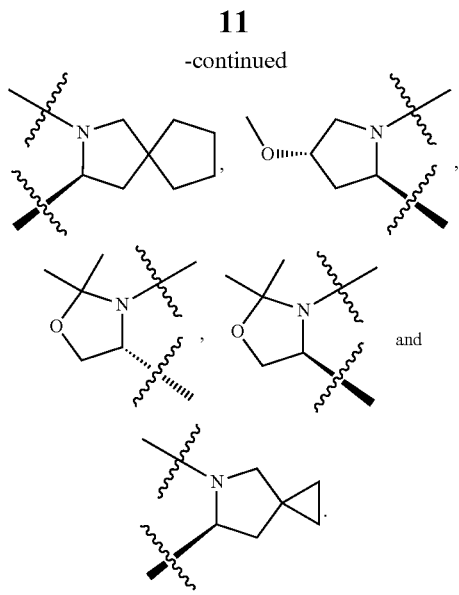

In certain embodiments of the present invention, the above-mentioned $Y_{2a}$ is an isopropyl.

In certain embodiments of the present invention, the above-mentioned $Y_{6b}$ is

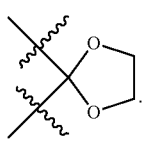

In certain embodiments of the present invention, the sub-structural unit of the above-mentioned structural unit

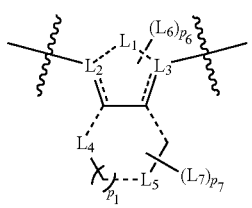

is an optionally substituted substituent selected from the group consisting of

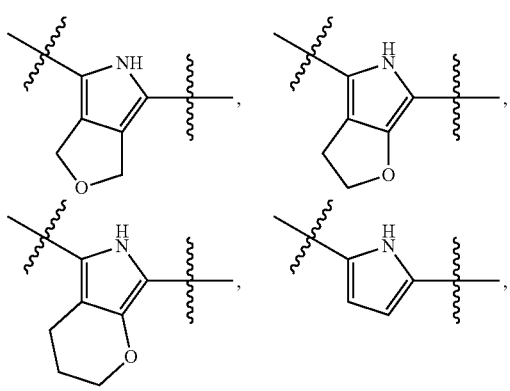

-continued

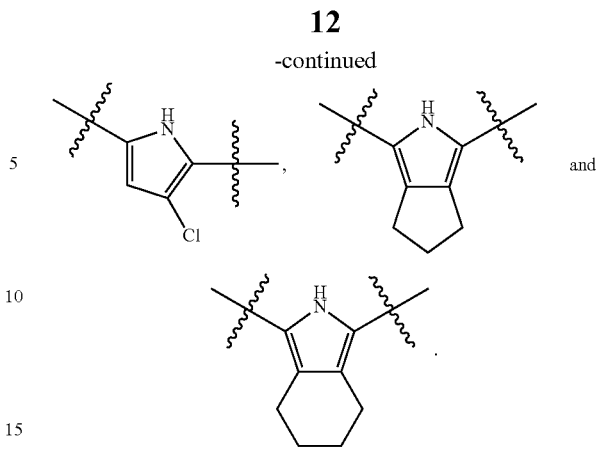

In certain embodiments of the present invention, the above-mentioned structural unit represented by formula (c) is an optionally substituted substituent selected from the group consisting of

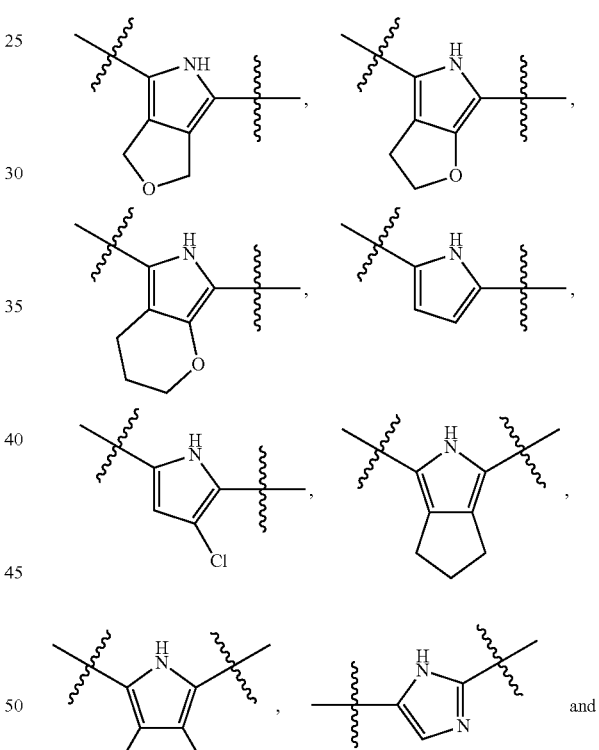

In certain embodiments of the present invention, each of the above-mentioned $A_4$, $B_4$, $Q_4$ and $Y_4$ is independently selected from a structural unit represented by formula (e), an optionally substituted benzene or an optionally substituted biphenyl;

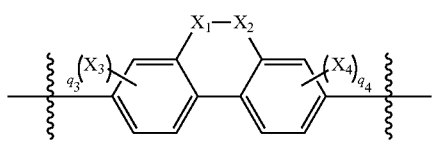

(e)

wherein, each of $X_1$ and $X_2$ is independently selected from a single bond, O, S, C=O, C=S, S=O, S(=O)$_2$ or an optionally substituted [CH$_2$, NH, PH, hydrocarbon group, hetero-hydrocarbon group, hydrocarbon heteroatomic group or hetero-hydrocarbon heteroatomic group]; each of $X_3$ and $X_4$ is independently selected from H, F, Cl, Br, I, CN, =O, =S or an optionally substituted [OH, SH, NH$_2$, PH$_2$, hydrocarbon group, hetero-hydrocarbon group, hydrocarbon heteroatomic group or hetero-hydrocarbon heteroatomic group]; each of $q_3$ and $q_4$ is independently selected from 0, 1, 2 or 3.

In certain embodiments of the present invention, each of the above-mentioned $A_4$, $B_4$, $Q_4$, $D_4$ and $Y_4$ is independently selected from the group consisting of:

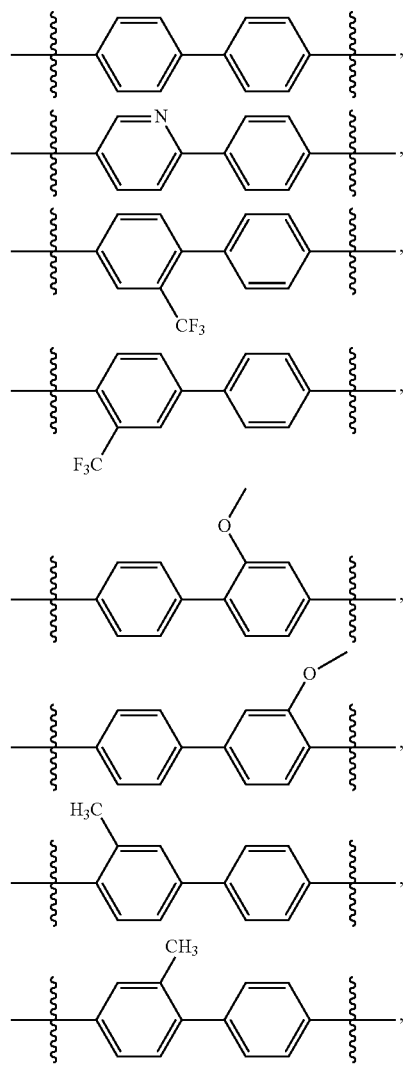

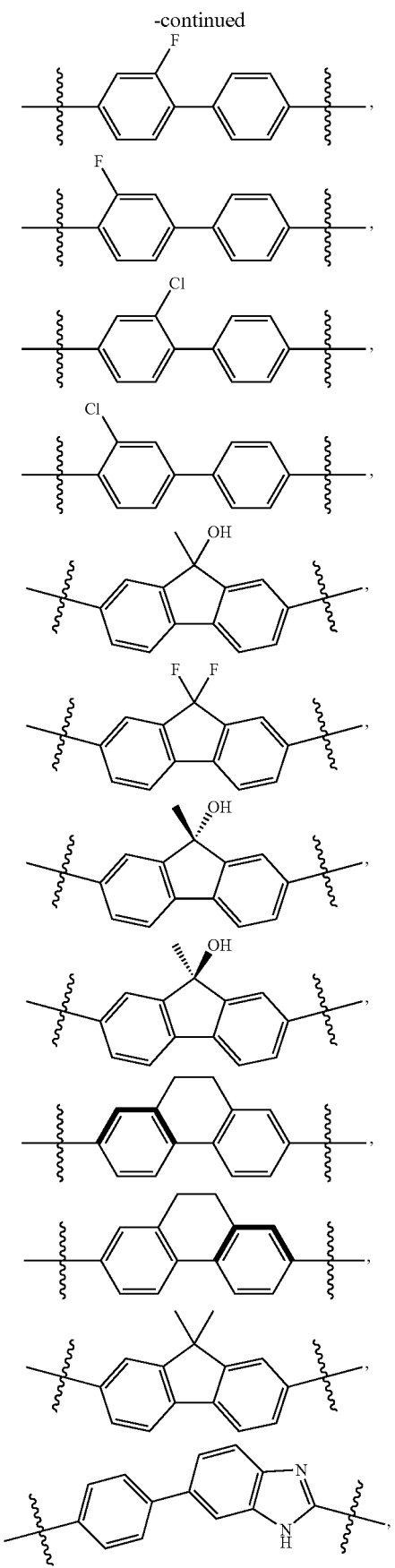

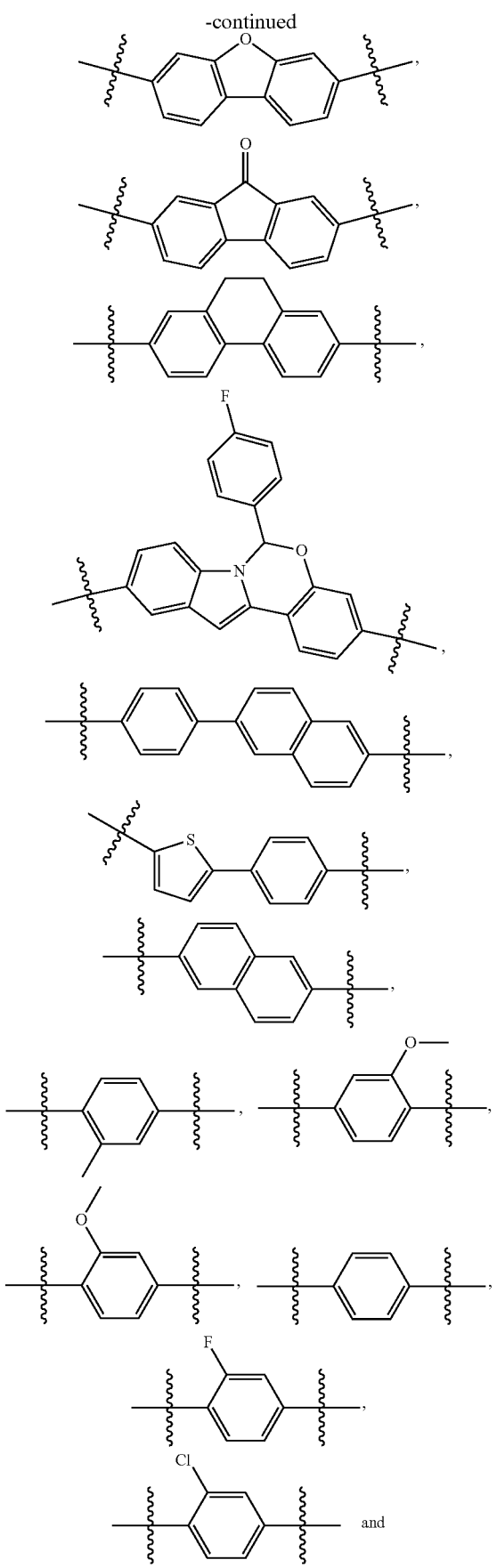

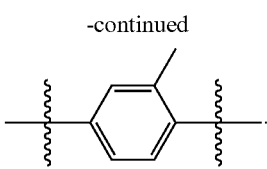

In certain embodiments of the present invention, the above-mentioned $R_4$ is selected from a 3-10 membered cyclic group or a hetero-cyclic group or a cyclo-heteroatomic group wherein two or more than two hydrogens are substituted, the heteroatom or the heteroatomic group is selected from N, O, S, S(=O) or S(=O)$_2$;

In certain embodiments of the present invention, the above-mentioned $R_4$ is a substituent selected from the group consisting of

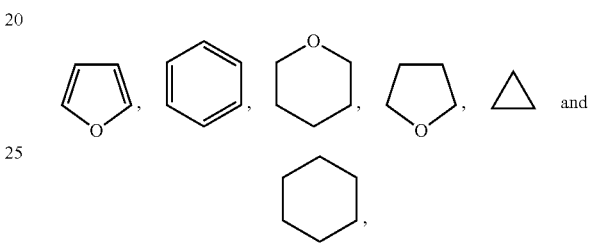

wherein two or more than two hydrogens are substituted.

In certain embodiments of the present invention, the above-mentioned $R_4$ is a substituent selected from the group consisting of

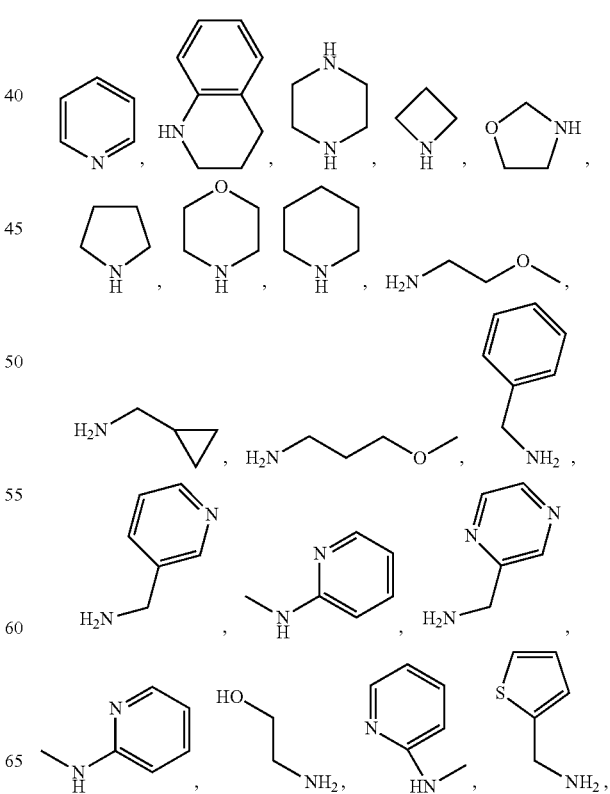

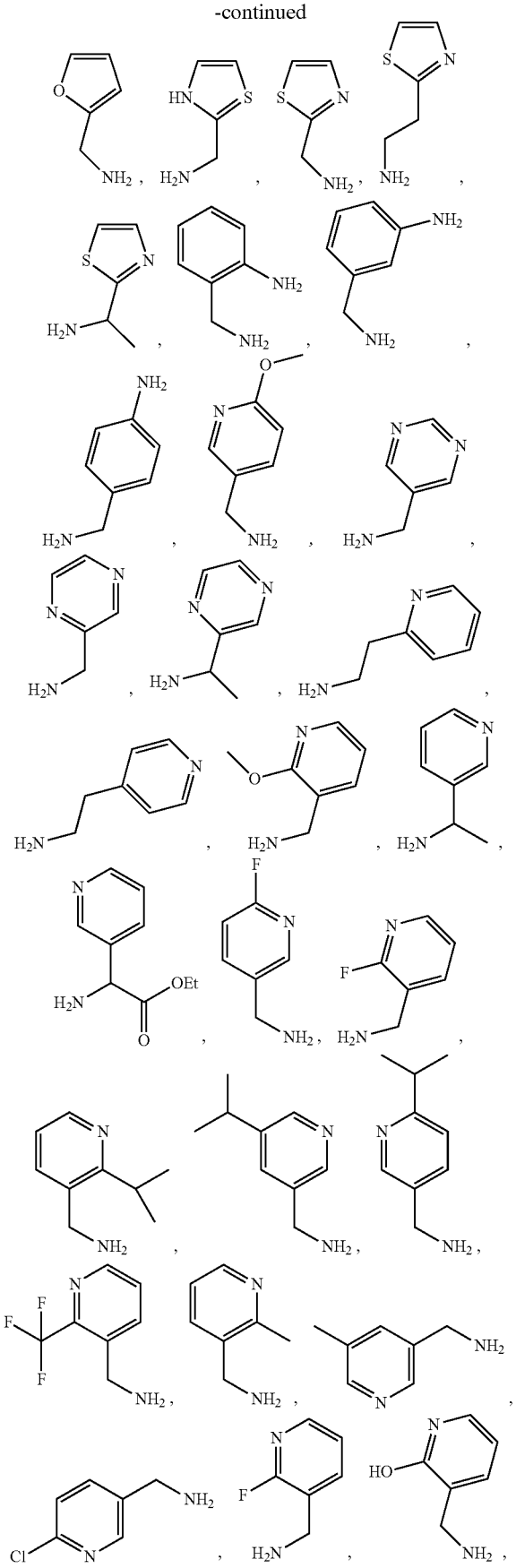
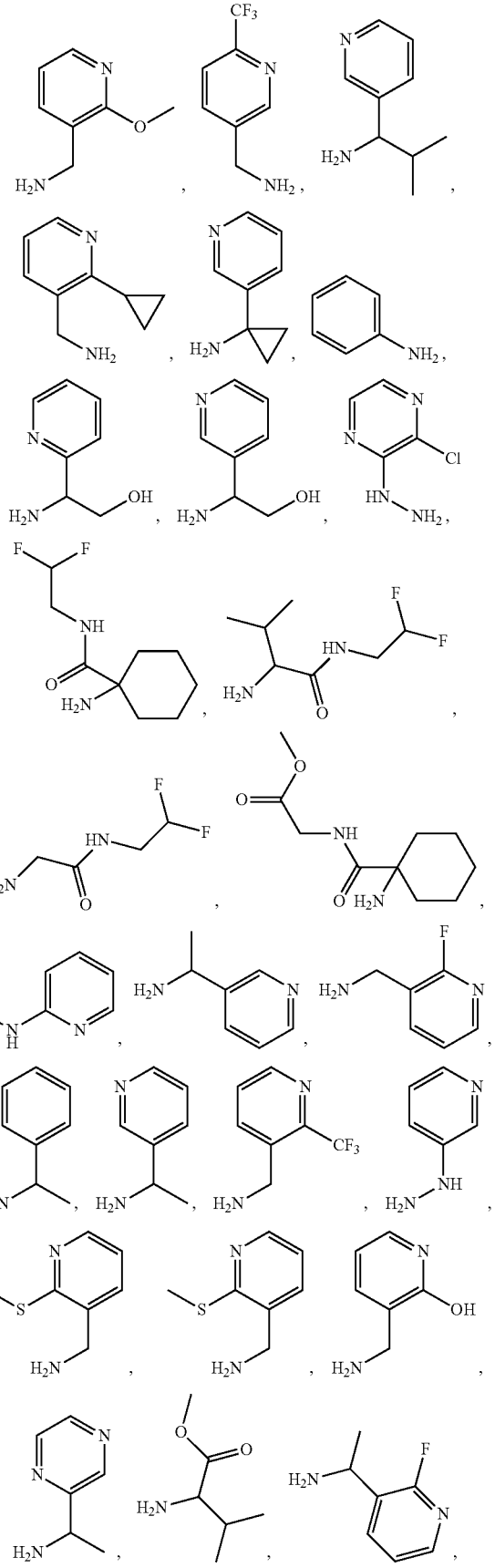

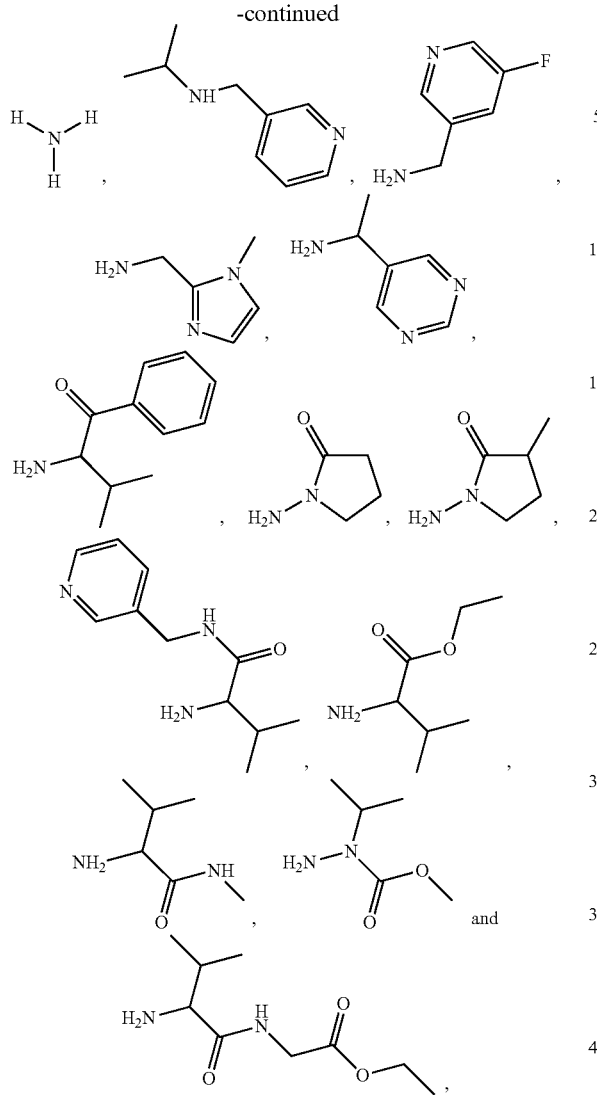
wherein two or more than two hydrogens are substituted.
In certain embodiments of the present invention, the above-mentioned R₄ is a substituent selected from the group consisting of
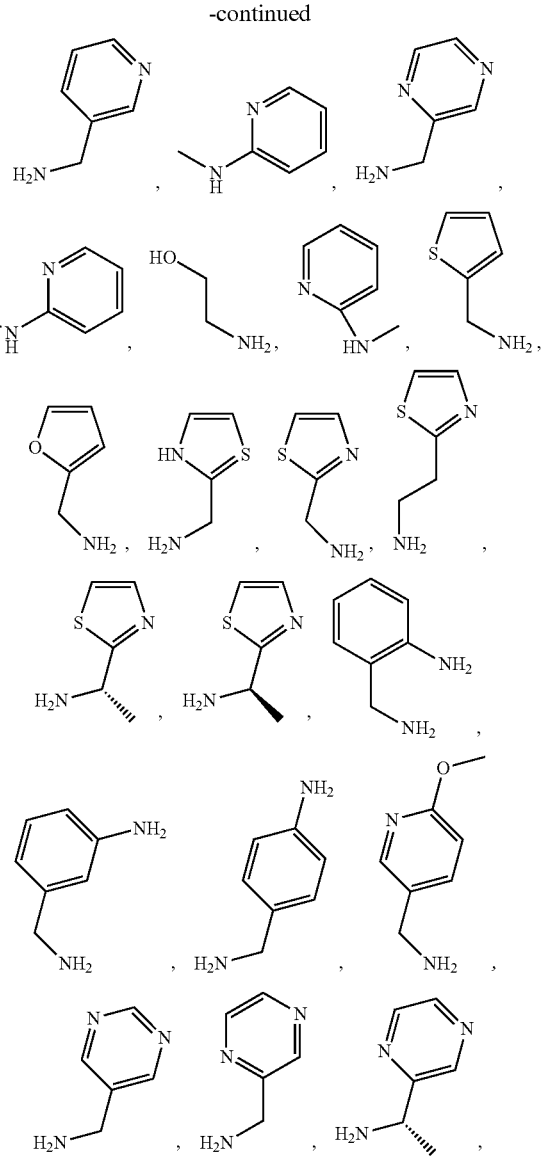
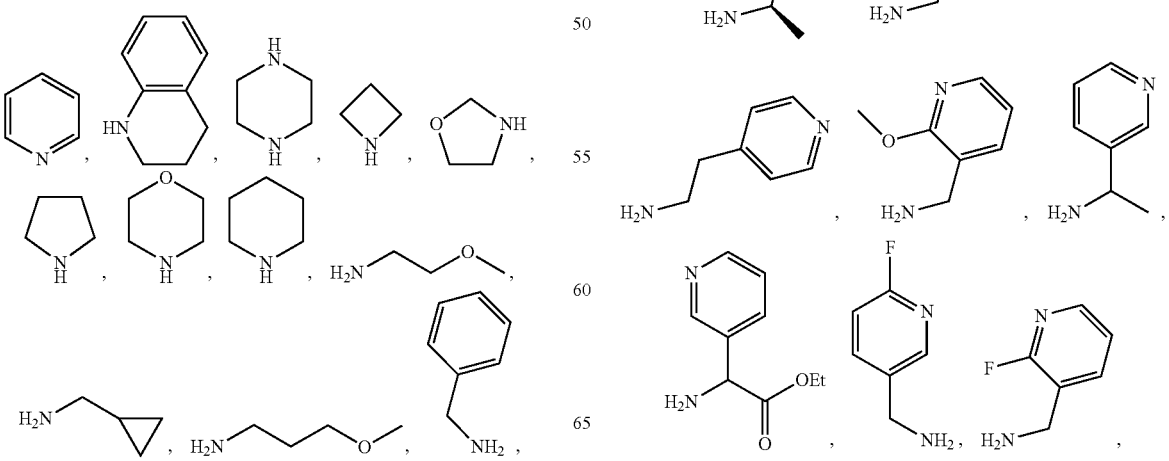

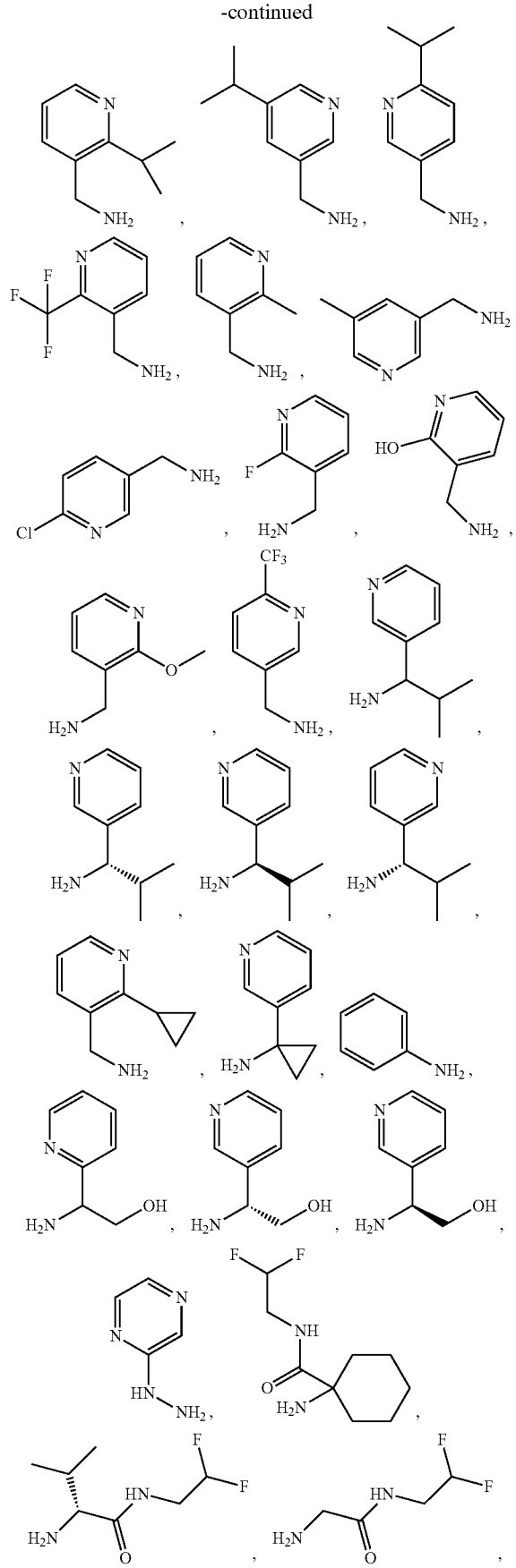
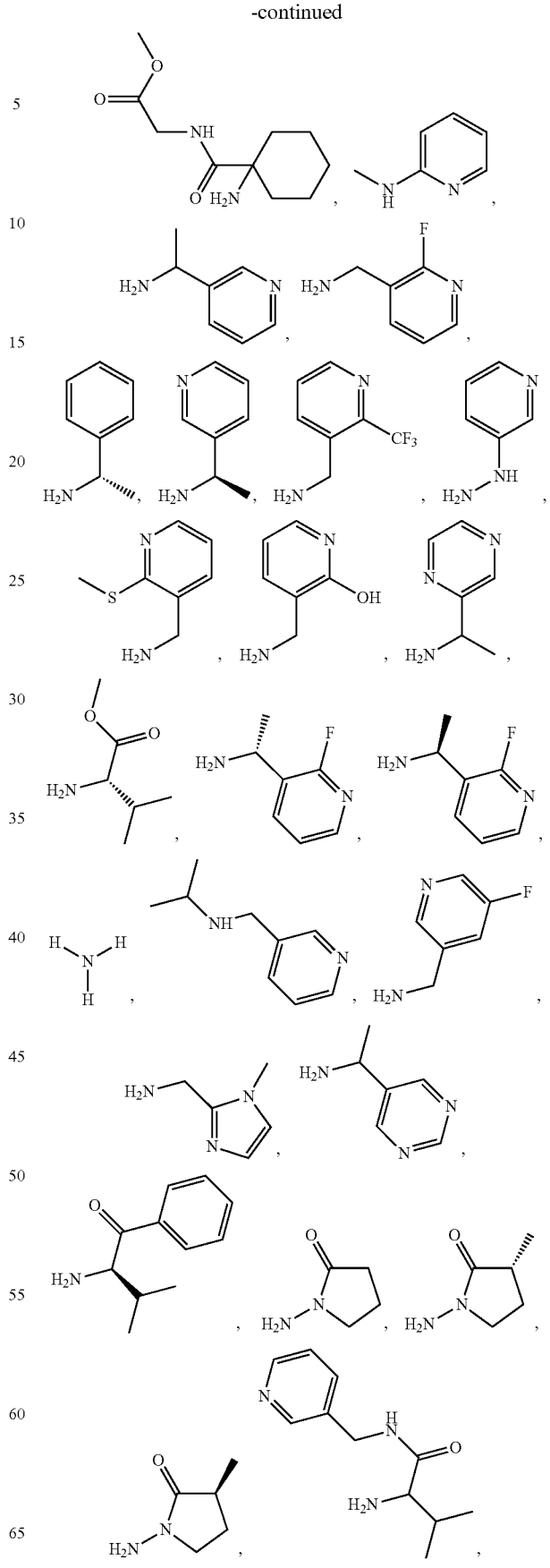

-continued

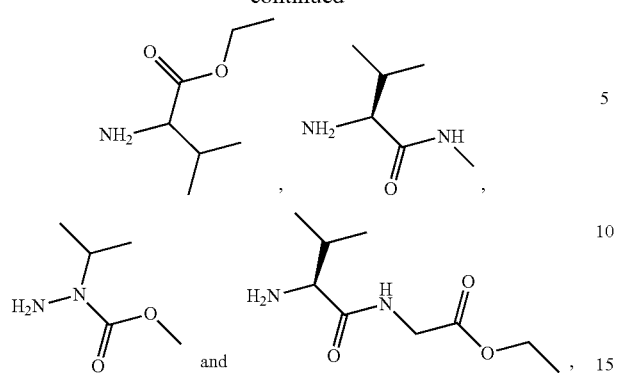

wherein two or more than two hydrogens are substituted.

In certain embodiments of the present invention, the above-mentioned $R_1$ is C=O, $R_5$ is H, $n_1$, $n_4$ and $n_5$ are 1, $n_2$ and $n_3$ are 0, $R_1$ and $R_4$ form an amide bond.

In certain embodiments of the present invention, the above-mentioned sub-structural unit represented by formula (a) is selected from the group consisting of:

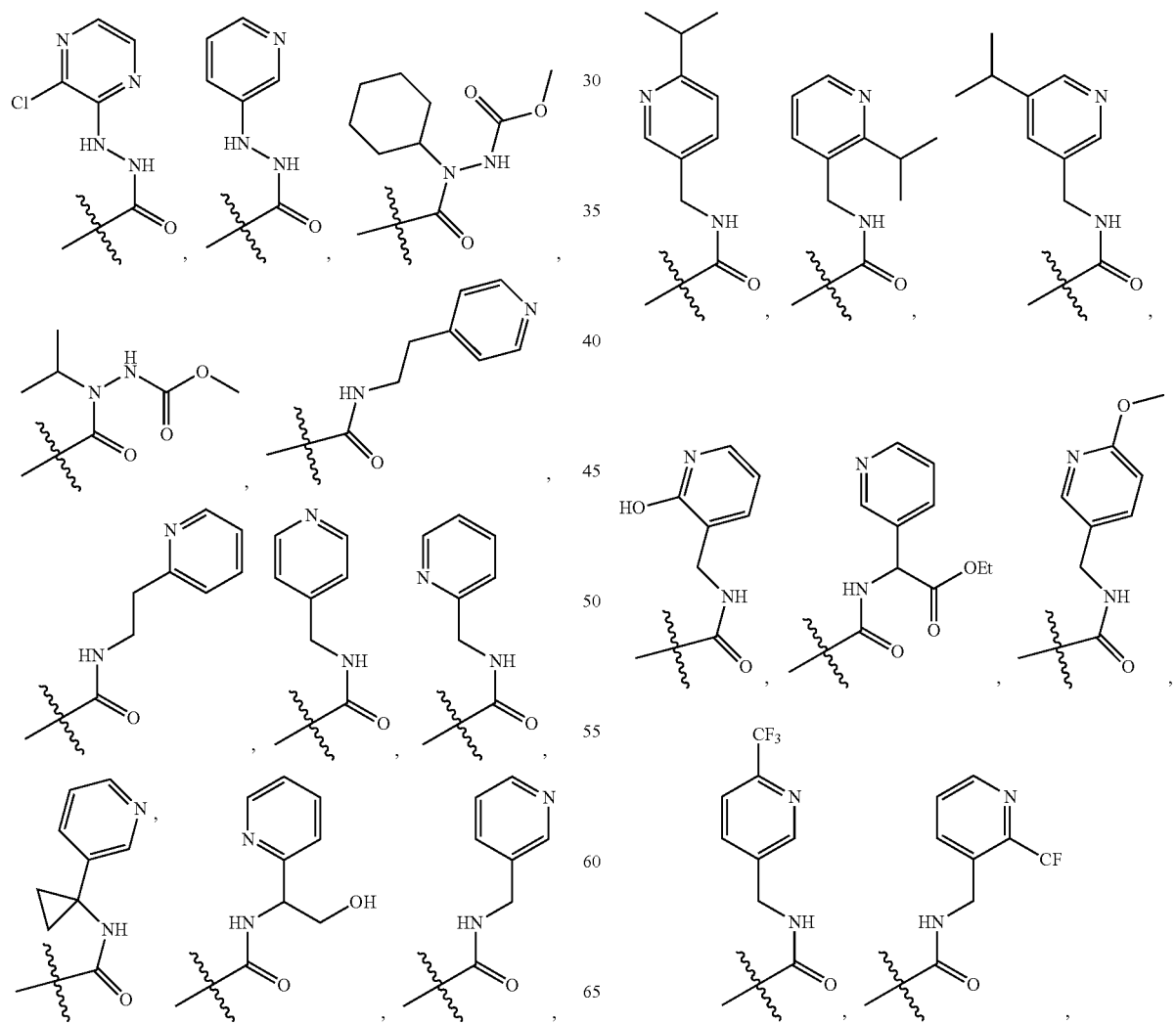

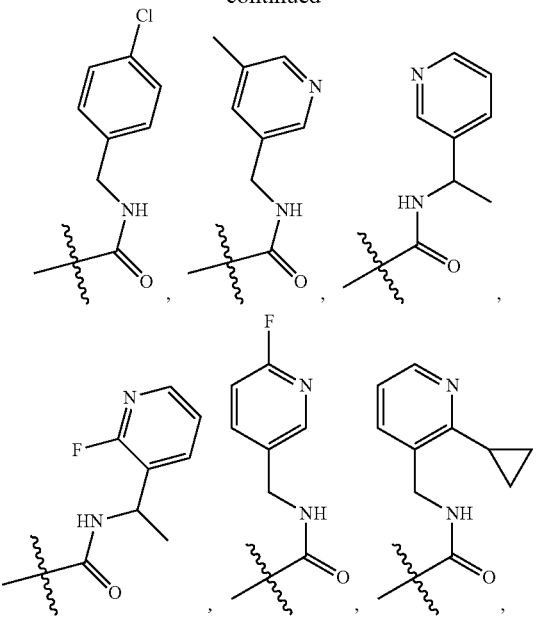

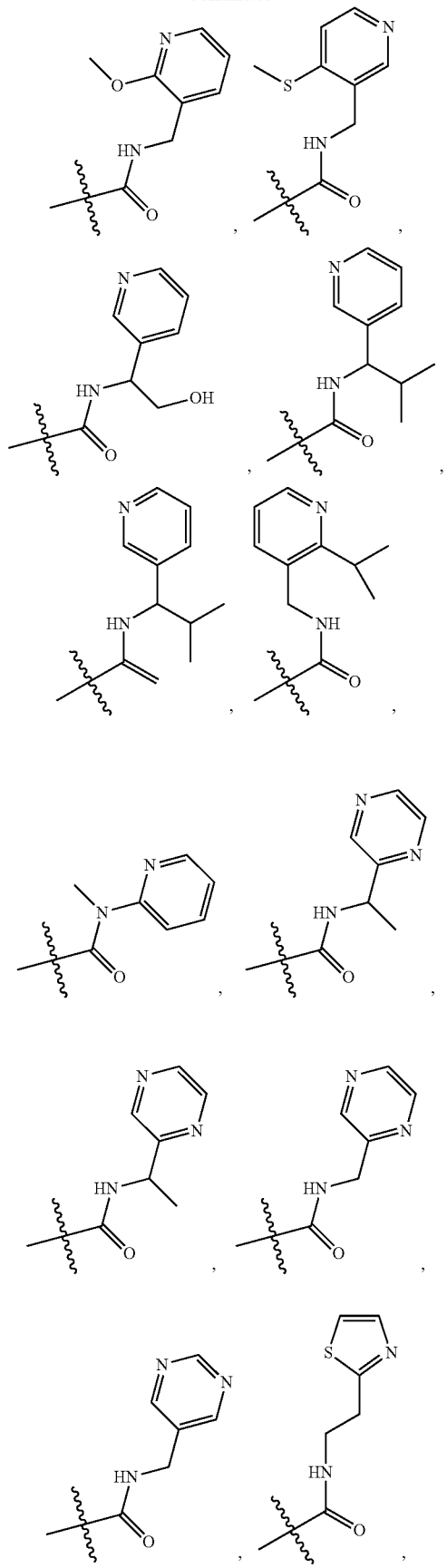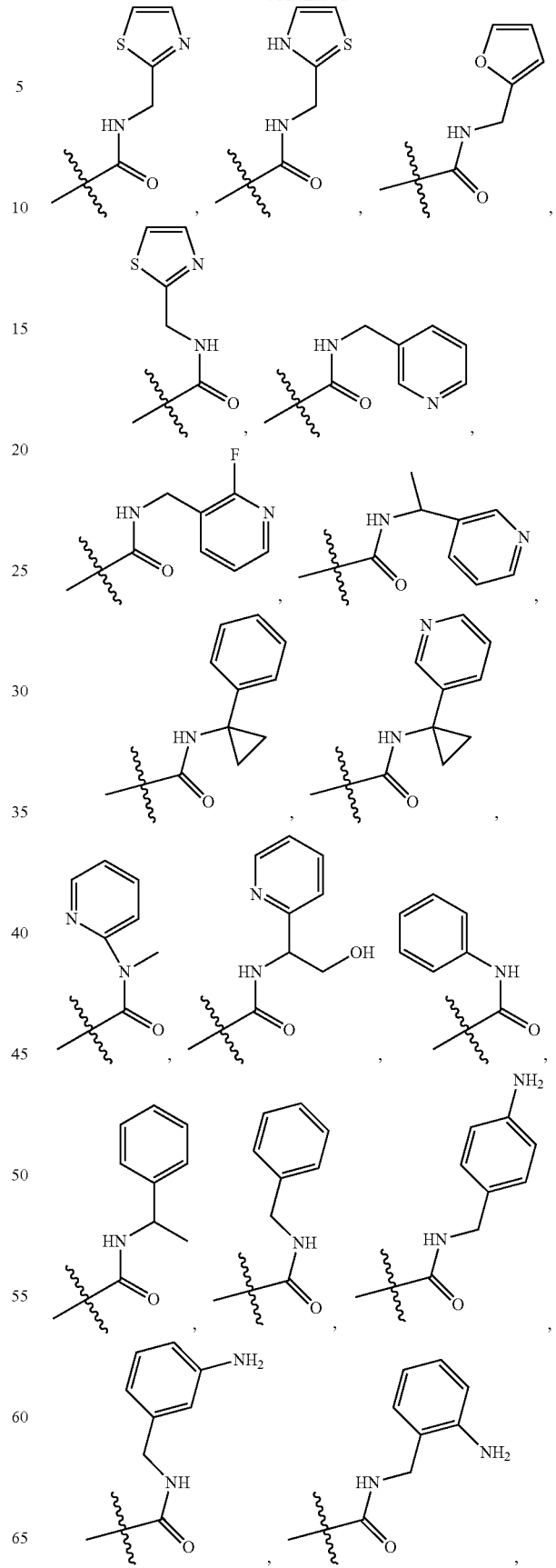

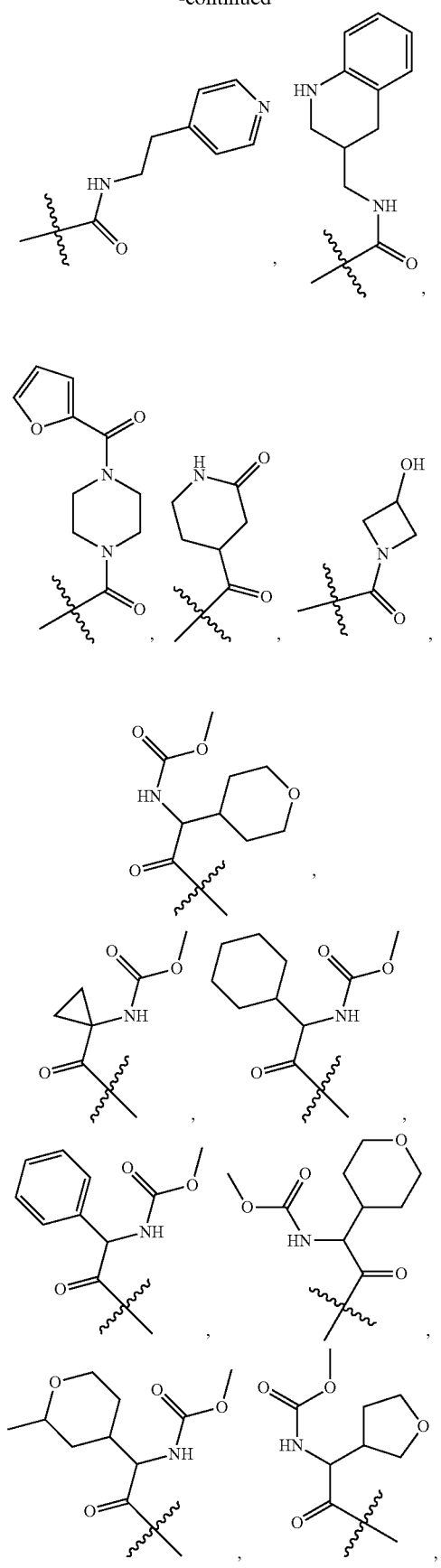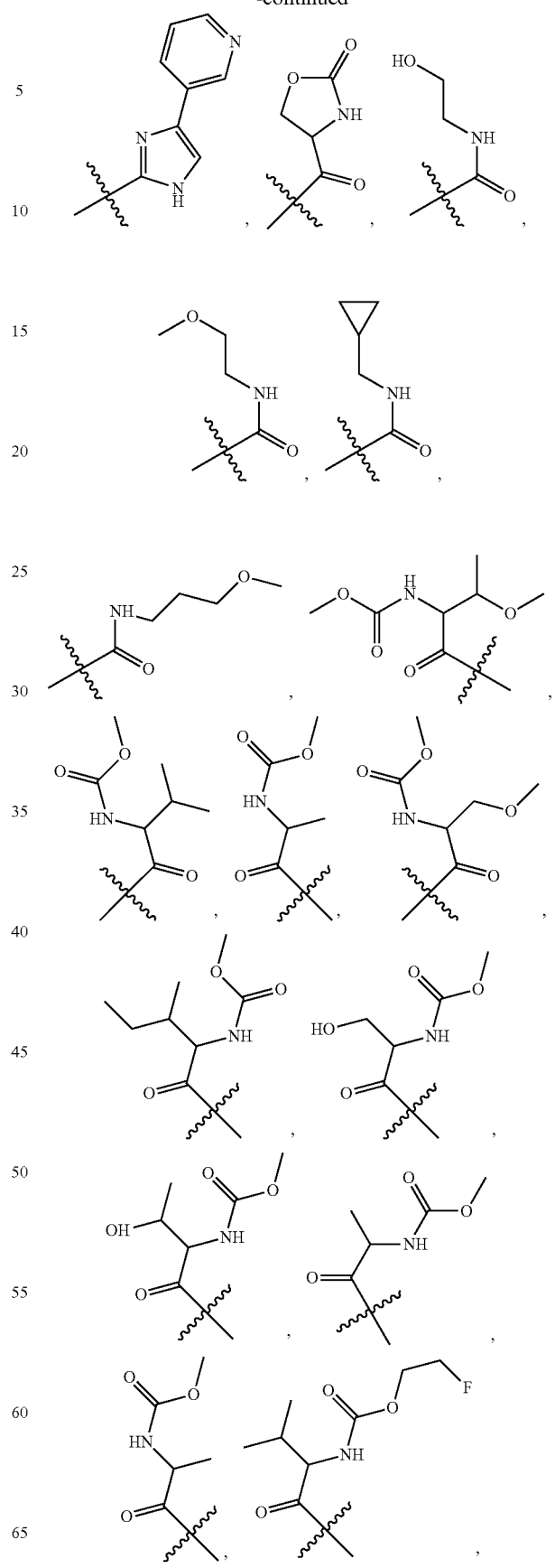

29
-continued
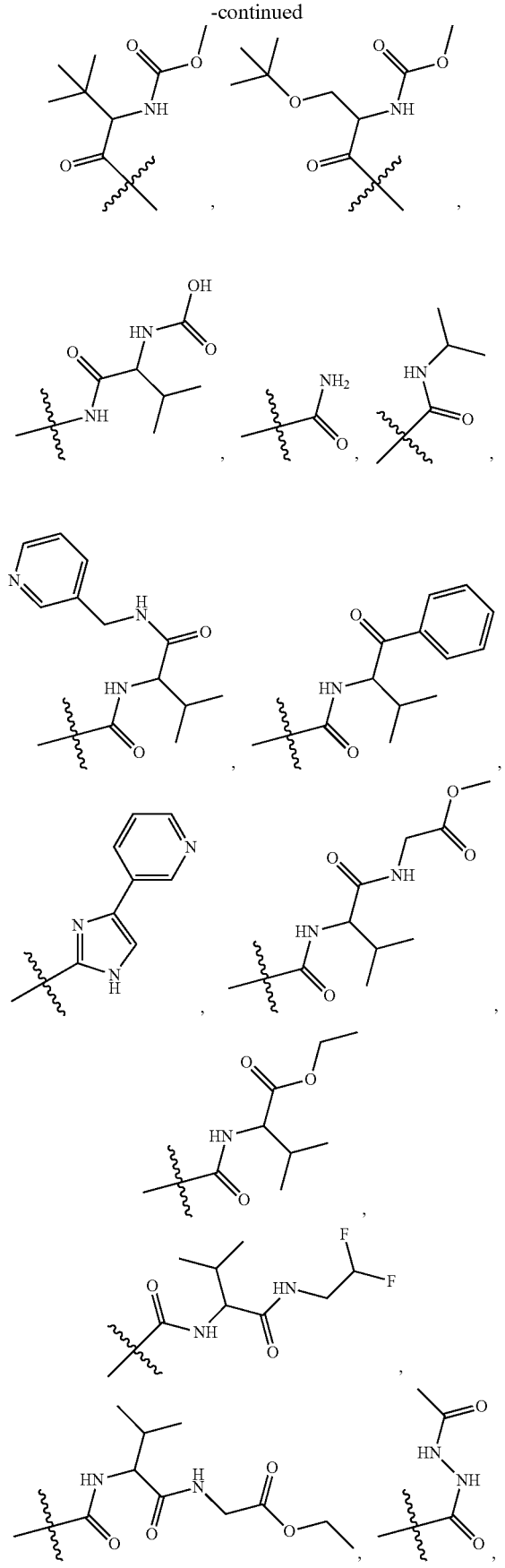
30
-continued
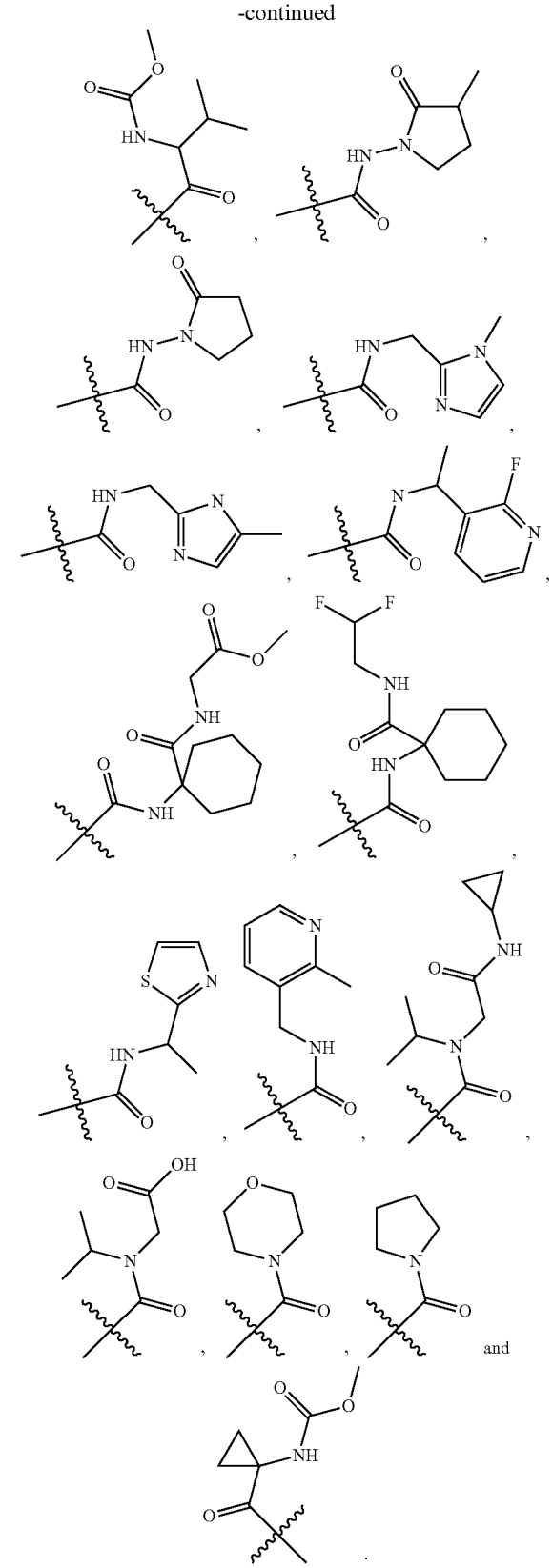
In certain embodiments of the present invention, the above-mentioned sub-structural unit represented by formula (a) is selected from the group consisting of

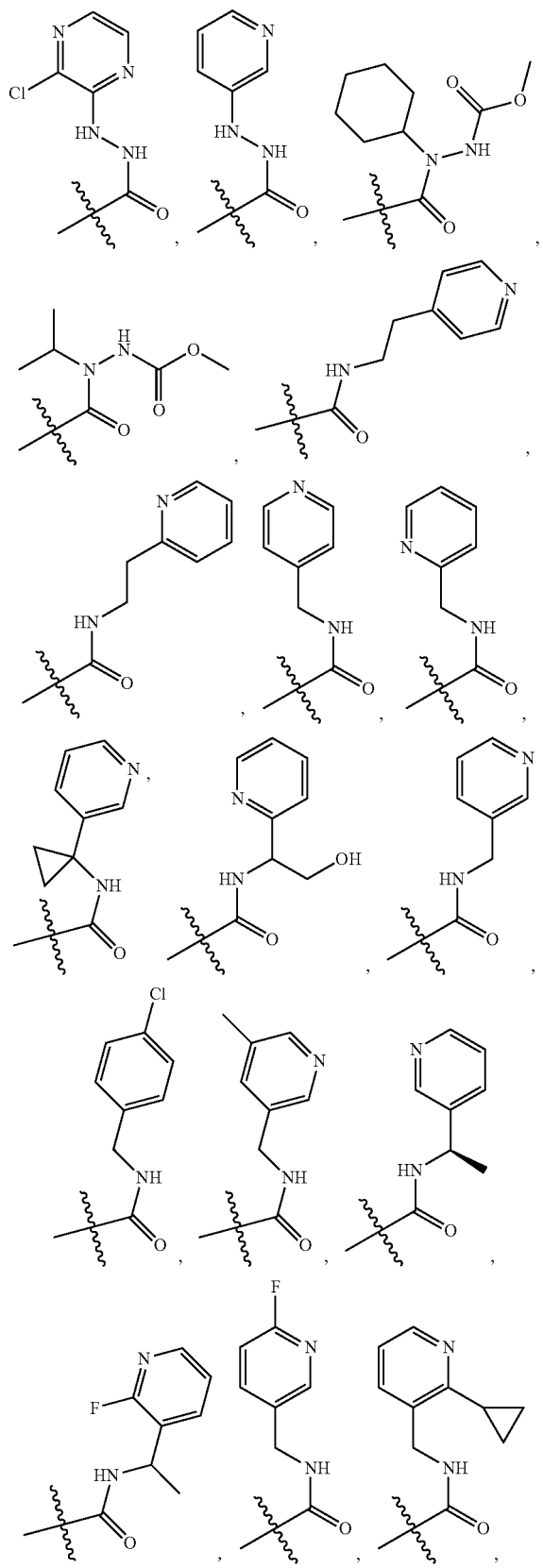
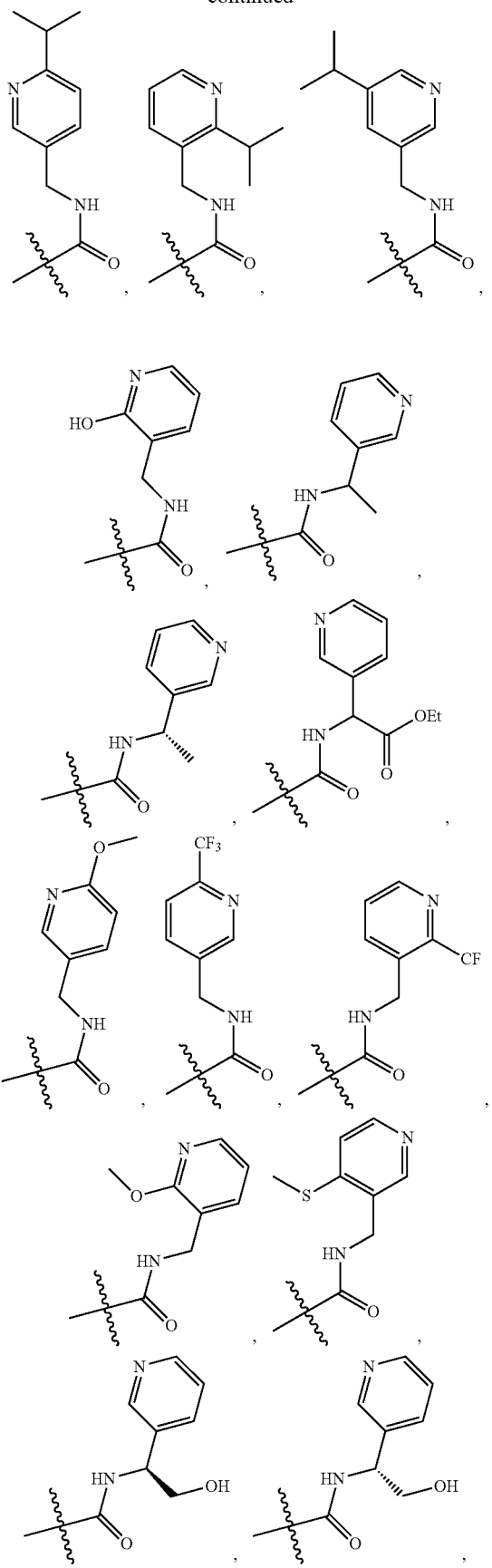

33
-continued

34
-continued

35
-continued
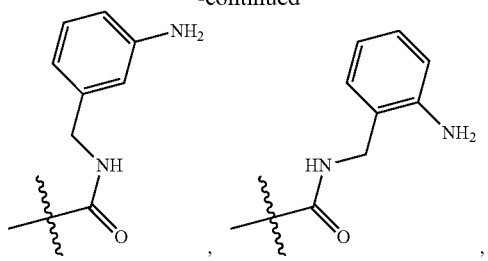
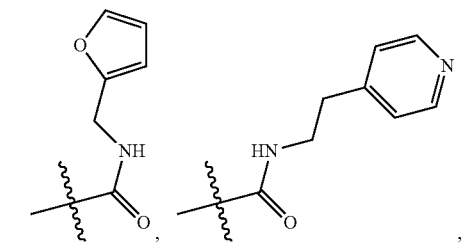
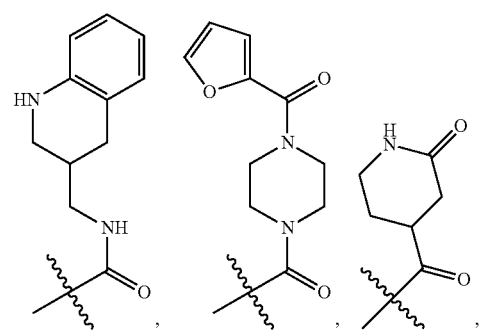
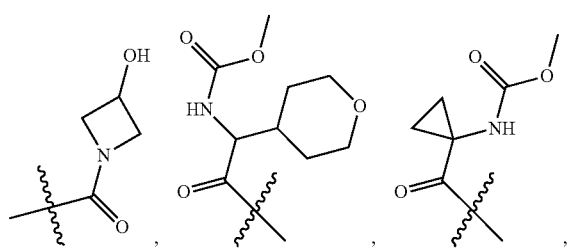
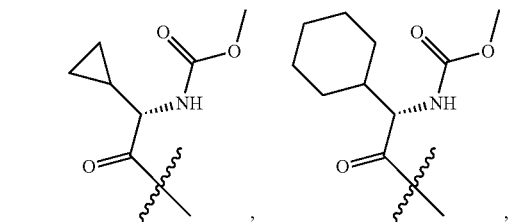
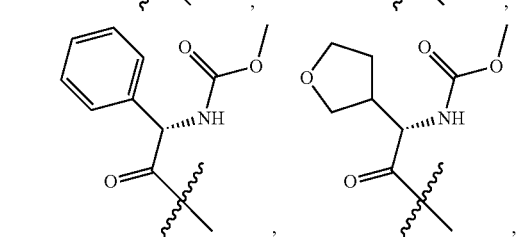
36
-continued
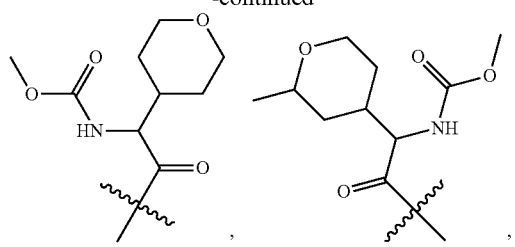
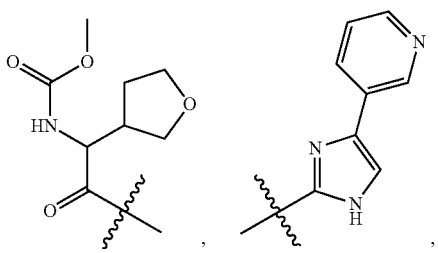
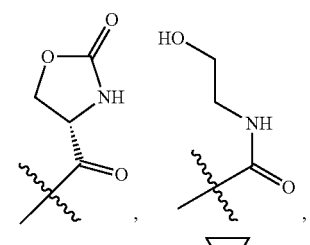
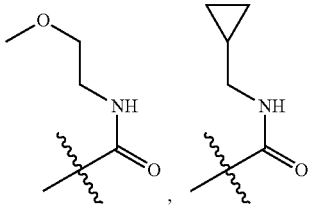
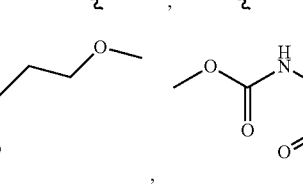
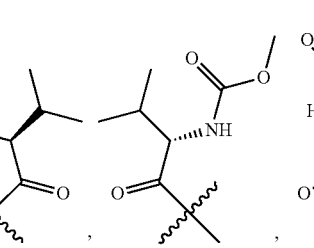
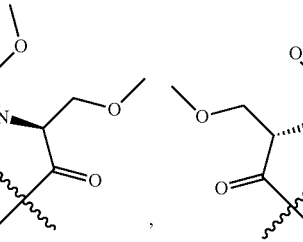

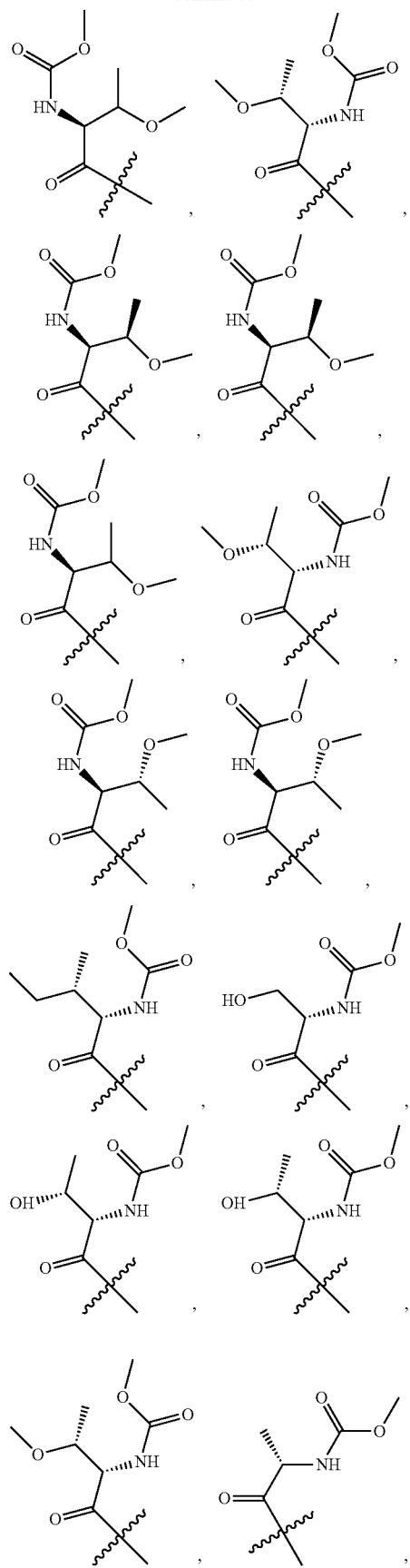
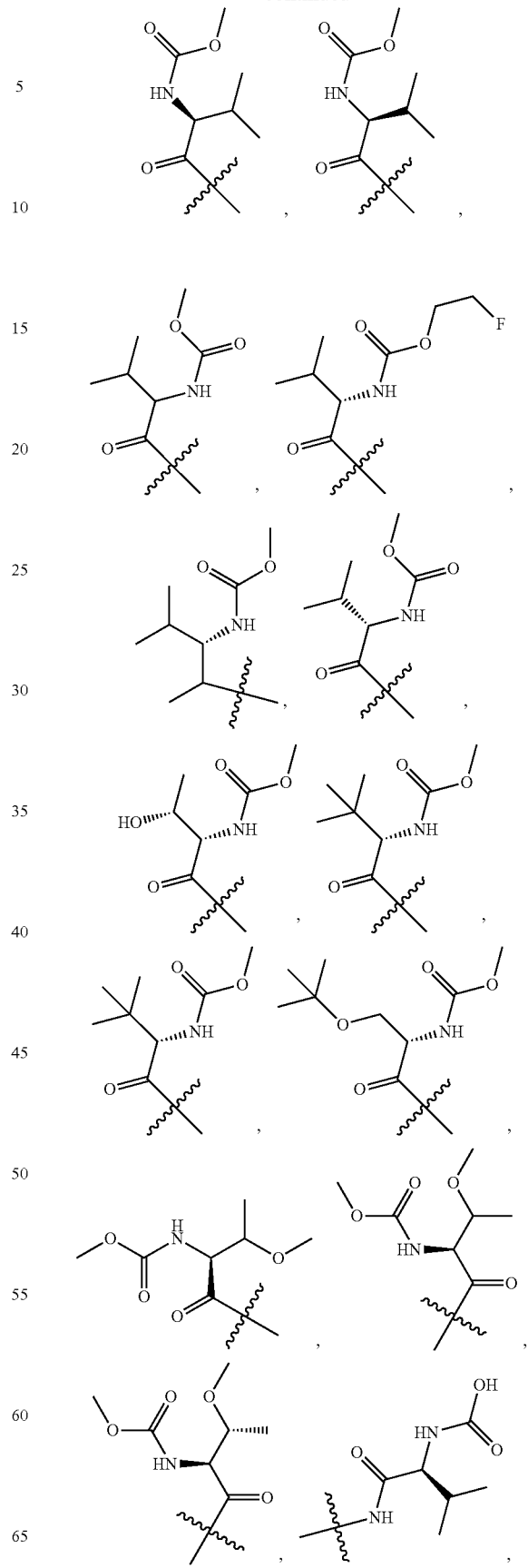

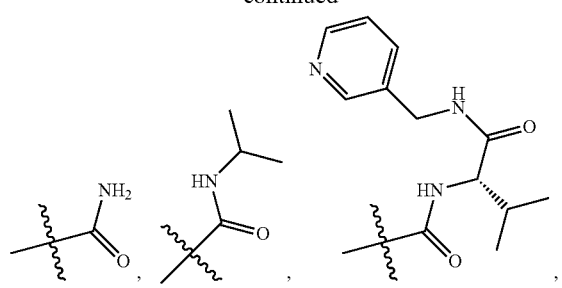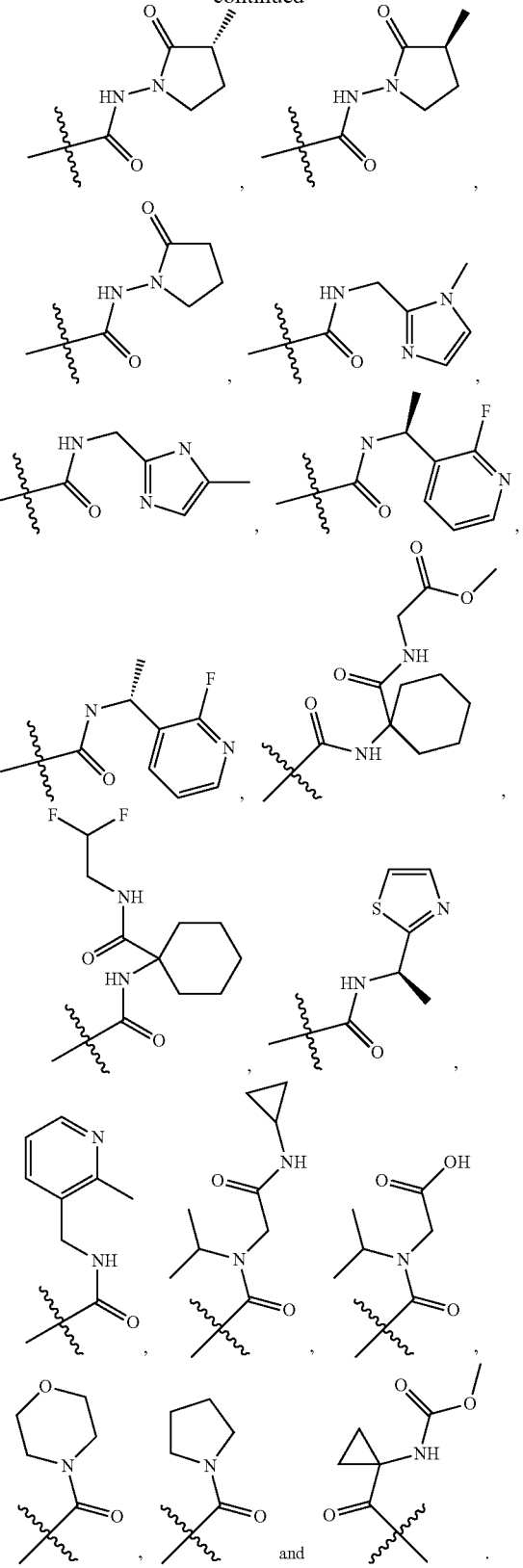
In certain embodiments of the present invention, each of the above-mentioned $R_2$, $R_5$, $R_{1a}$, $R_{1b}$, $R_{3a}$ and $R_{3b}$ is independently selected from H, F, Cl, Br, I, CN, an optionally substituted [OH, NH$_2$, alkyl, cycloalkyl, haloalkyl, hydroxy alkyl, alkoxy, alkoxy alkyl, alkylthiol, alkylthiol alkyl, alkoxycarbonyl, heterocycle-substituted carbonyl, alkoxy carbonyl amino], the heterocycle group is selected from a furyl, a thienyl, a pyrryl, a pyridyl, a pyrimidyl, a pyrazolyl or an imidazolyl.

In certain embodiments of the present invention, the number of carbon atoms contained in the alkyl fragment of the above-mentioned alkyl, haloalkyl, hydroxy alkyl, alkoxy, alkoxy alkyl, alkylthiol, alkylthiol alkyl, alkoxycarbonyl and alkoxy carbonyl amino is 1, 2, 3, 4, 5 or 6, the number of carbon atoms contained in the cycloalkyl are 3, 4, 5 or 6.

In certain embodiments of the present invention, each of the above-mentioned $R_2$, $R_5$, $R_{1a}$, $R_{1b}$, $R_{3a}$ and $R_{3b}$ is independently selected from H, F, Cl, Br, I, CN, =O, =S, an optionally substituted [OH, NH$_2$, methyl, isopropyl, cyclopropyl, butyl, tert-butyl, trifluoromethyl, hydroxymethyl, —CH(OH)CH$_3$, —CH$_2$CH$_2$OH, —CH$_2$CH$_2$(OH), —CH(OH)CH$_3$, methoxyl, methoxymethyl, —CH(CH$_3$)OCH$_3$, —CH$_2$CH$_2$OCH$_3$,

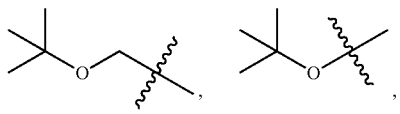

methylthiol, ethoxycarbonyl,

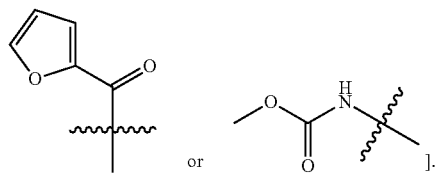

In certain embodiments of the present invention, the substituent for "optionally substituted" is selected from F, Cl, Br, I, CN, =O, =S, or an optionally substituted [OH, SH, NH$_2$, PH$_2$, hydrocarbon group, hetero-hydrocarbon group, hydrocarbon heteroatomic group and/or hetero-hydrocarbon heteroatomic group].

In certain embodiments of the present invention, the above-mentioned hydrocarbon group, hetero-hydrocarbon group, hydrocarbon heteroatomic group or hetero-hydrocarbon heteroatomic group is selected from an optionally substituted [C$_{1-12}$ hydrocarbon group, C$_{1-12}$ hetero-hydrocarbon group, C$_{1-12}$ hydrocarbon heteroatomic group, C$_{1-12}$ hydrocarbon heteroatomic group C$_{1-12}$ hydrocarbon group, —C$_{1-12}$OH, —C$_{0-12}$COOH, —OC$_{1-12}$COOH, —C$_{1-12}$CN, —C$_{0-12}$CONH$_2$, —C$_{0-12}$OC$_{1-12}$, —C$_{0-12}$CO C$_{1-12}$, —C$_{0-12}$COO C$_{1-12}$, —C$_{0-12}$O(O=)C C$_{1-12}$, —C$_{0-12}$S(=O) C$_{1-12}$ or —C$_{0-12}$S(=O)$_2$ C$_{1-12}$], wherein the above-mentioned group itself is optionally in the form of an aromatic ring, a hetero-aromatic ring, a aliphatic ring, a heteroaliphatic ring, an aliphatic chain and/or a hetero-aliphatic chain, and a number of the aromatic ring, hetero-aromatic ring, aliphatic ring, hetero-aliphatic ring, aliphatic chain and/or hetero-aliphatic chain, the ring-forming atom and the number thereof, the linking form between the rings, or the ring and the chain, or the chains can all be arbitrary under the premise of stability available in chemistry, each of the heteroatom and heteroatomic group is independently selected from O, S, N, S(=O) and/or S(=O)$_2$, a number of the heteroatom or heteroatomic group can be arbitrary under the premise of stability available in chemistry.

In certain embodiments of the present invention, the substituent for "optionally substituted" is selected from F, Cl, Br, I, CN, =O, =S, OH, SH, NH$_2$, a C$_{1-6}$ alkyl or a heteroalkyl or an alkyl heteroatomic group which is unsubstituted or substituted by a halogen, a hydroxyl or an amino, each of the heteroatom or heteroatomic group is independently selected from —CONH— which is substituted by a C$_{1-6}$ alkyl or unsubstituted, —CO$_2$—, —NH— which is substituted by a C$_{1-6}$ alkyl or unsubstituted, —O—, —S—, —C=NH which is substituted by a C$_{1-6}$ alkyl or unsubstituted, —C=O, —C=S, S(=O) and/or S(=O)$_2$, a number of the substituent, the heteroatom or the heteroatomic group can be arbitrary under the premise of stability available in chemistry.

In certain embodiments of the present invention, the substituent for "optionally substituted" is selected from a halogen, OH, SH, NH$_2$, CN, =O, =S, CF$_3$, —OCF$_3$ or —OCH$_3$.

In certain embodiments of the present invention, the above-mentioned compound is selected from the group consisting of:

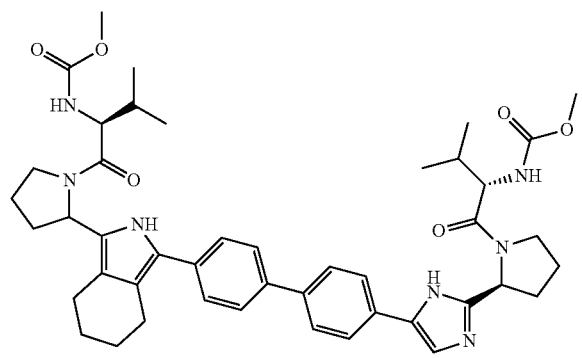

AG_015

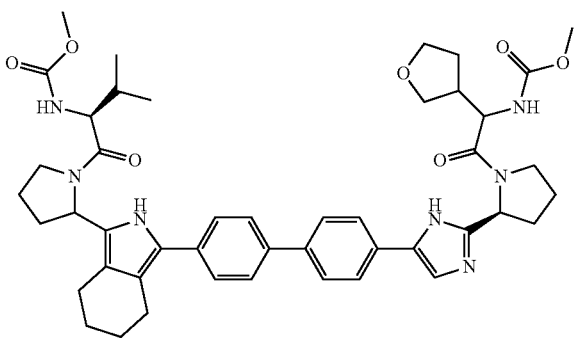

AG_046

-continued
AG_047
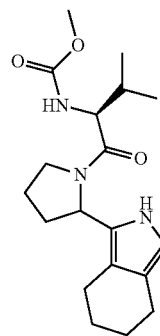
AG_040
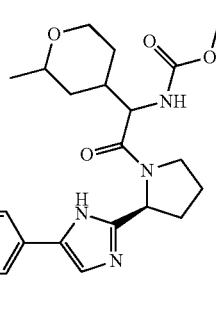
AG_027
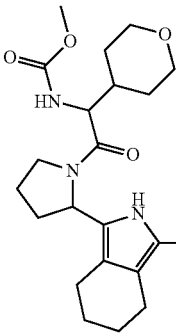
AG_045
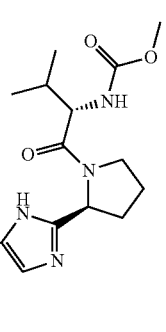
AG_015_A
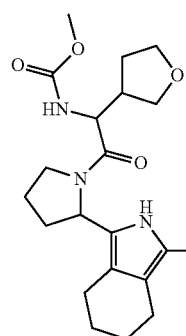
AG_067
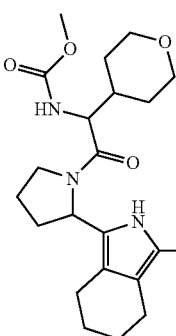
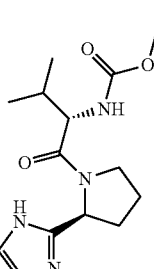
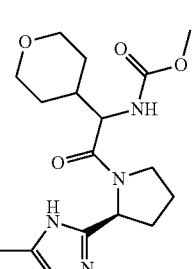
AG_078_A
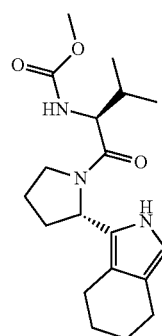
AG_078_B
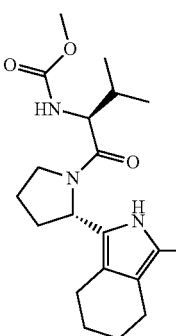
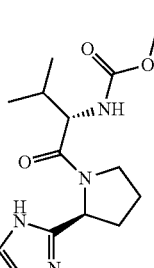
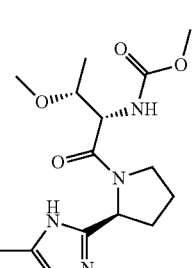
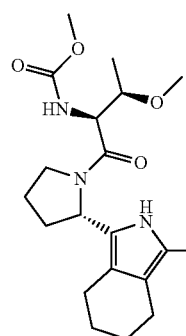
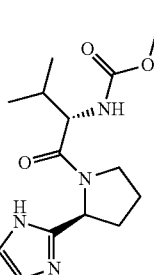
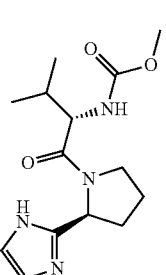

-continued
AG_014
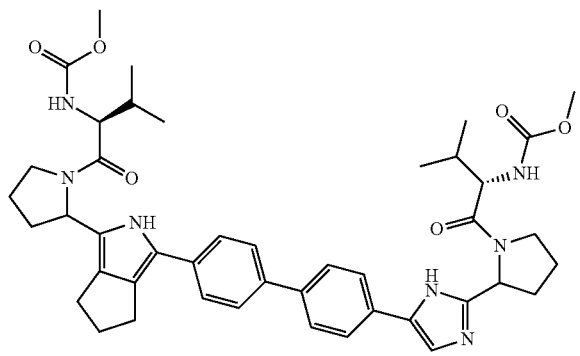
AG_025_A
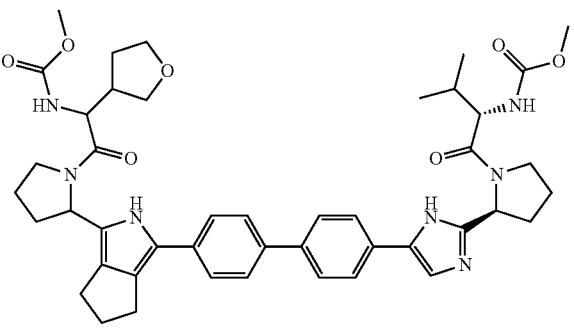
AG_025_B
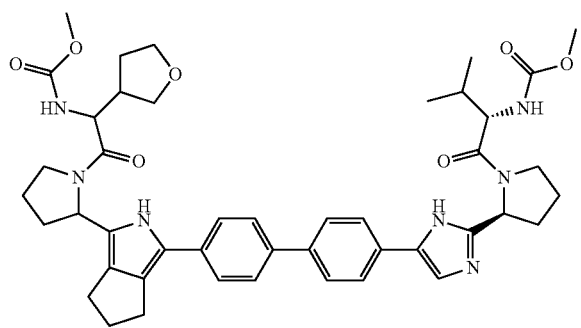
AG_025_C
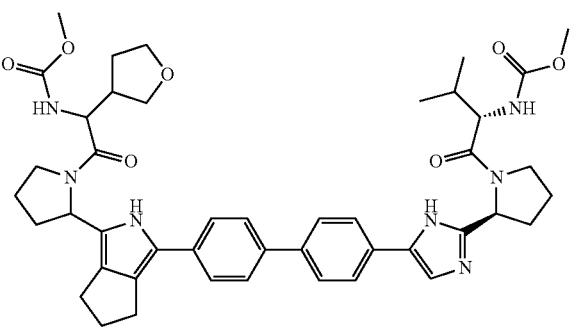
AG_014_A
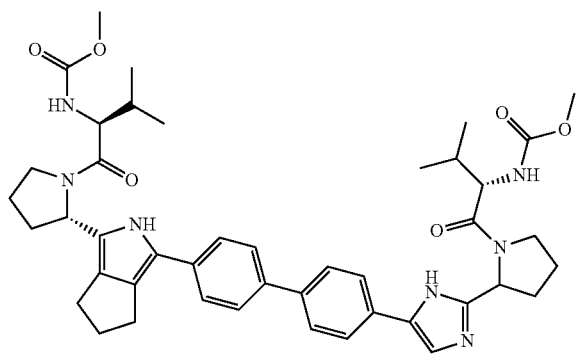
AG_026_A
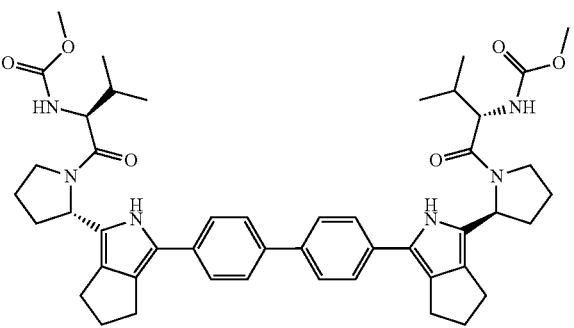
AG_026_A
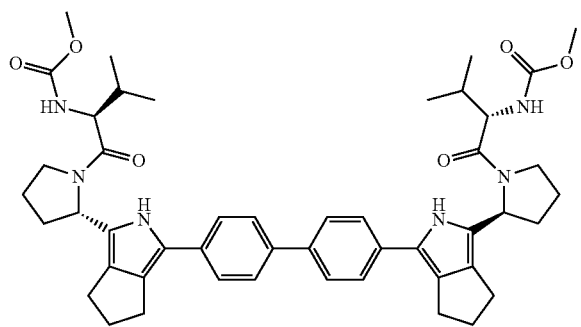
AG_048
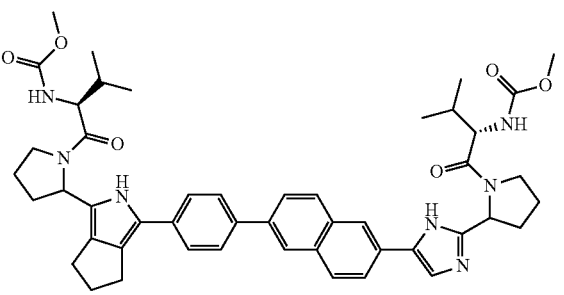

-continued
AG_049
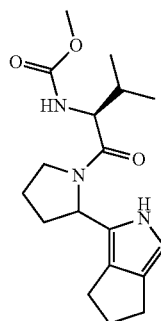
AG_050
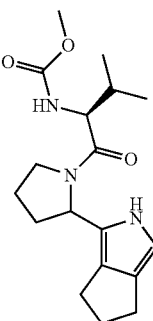
AG_063
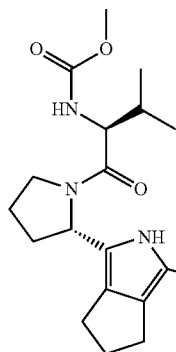
AG_066
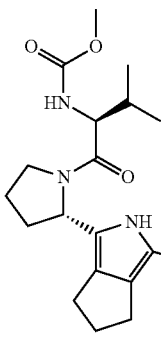
AG_068_A
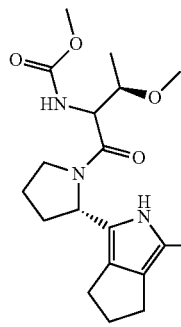
AG_068_B
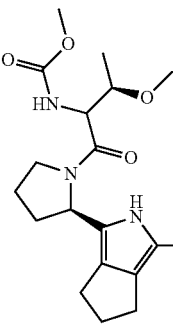
AG_069
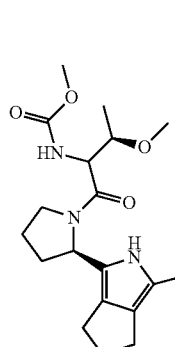
AG_089
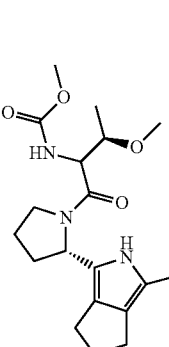

-continued
AG_092
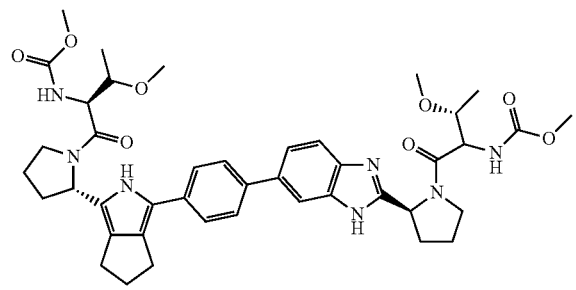
AG_093
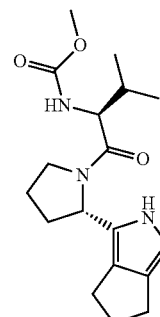
AG_084_A
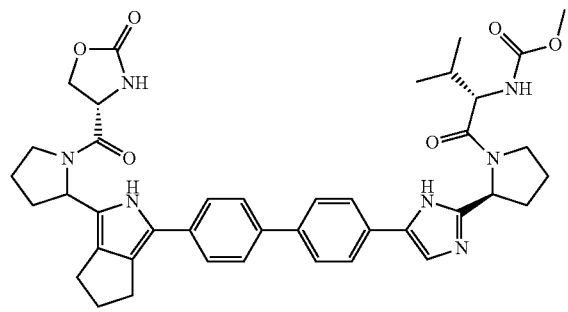
AG_091
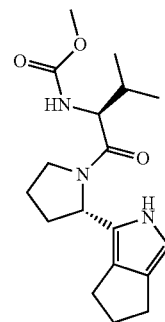
AG_090
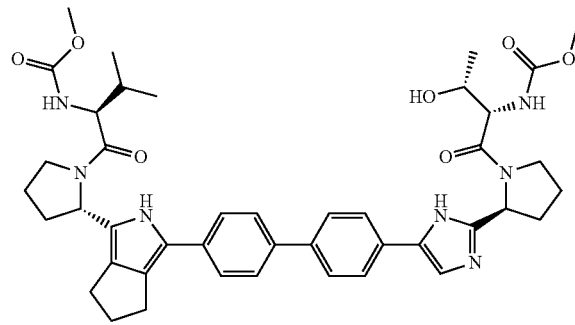
AG_086
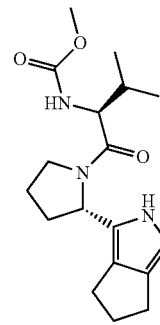
AG_036
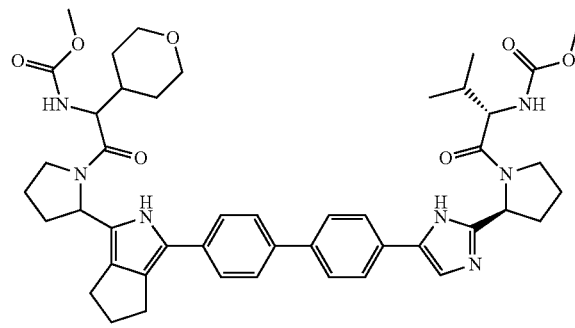
AG_042
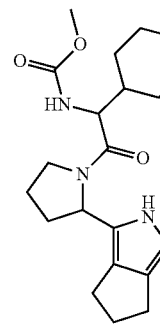

-continued
AG_035
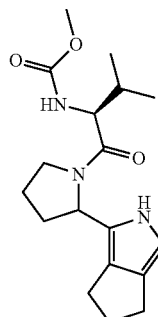
AG_051
AG_076
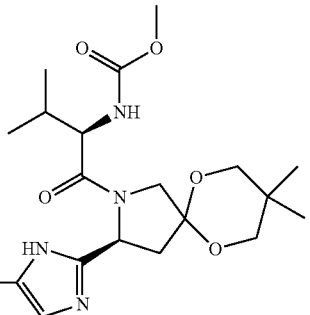
AG_106
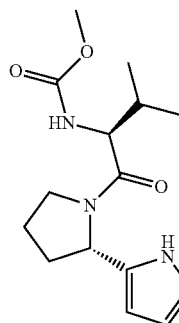
AG_115
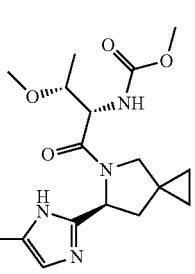
AG_110
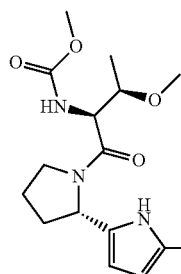
AG_101
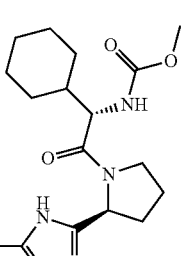
AG_107
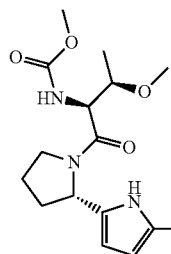
AG_100
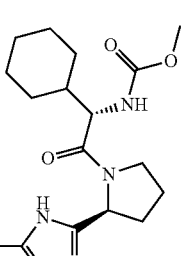
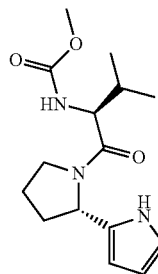
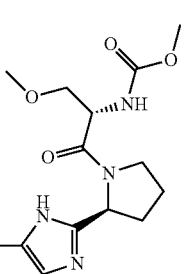

-continued
AG_099
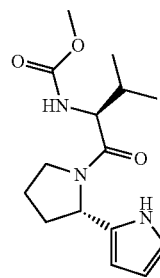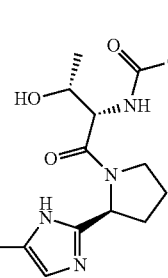
AG_098
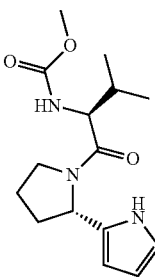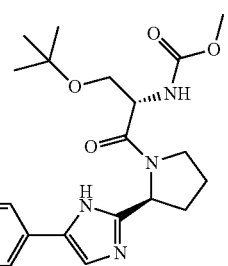
AG_061_A
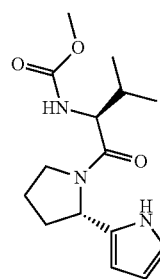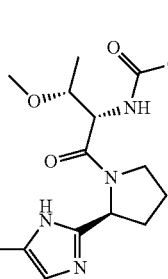
AG_102
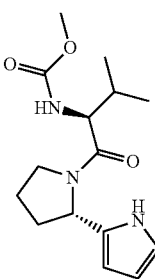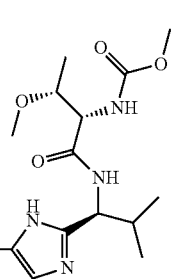
AG_072_A
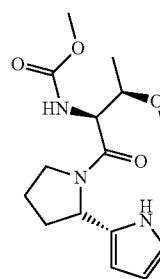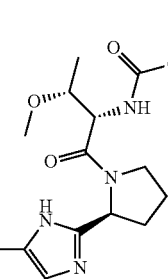
AG_120
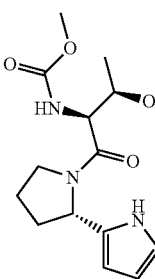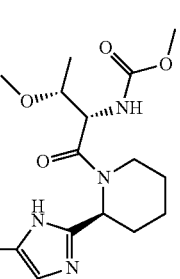
AG_054
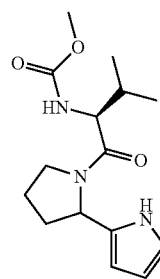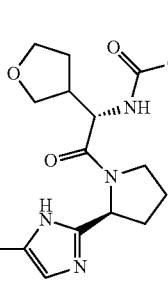
AG_001
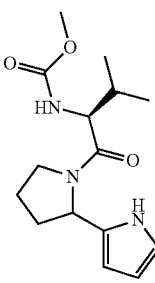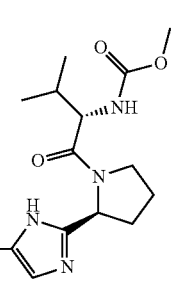
AG_011
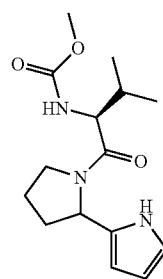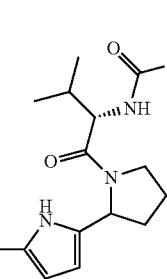
AG_022
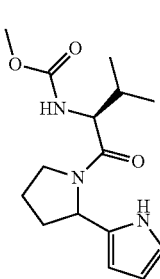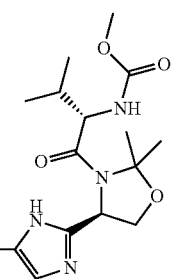

-continued
AG_052
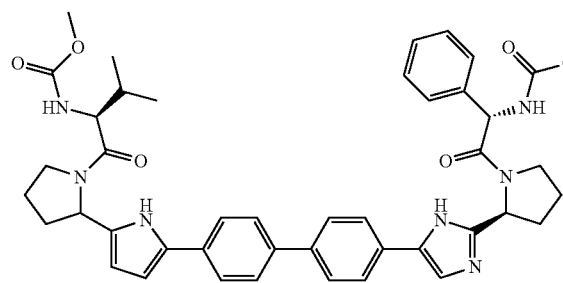 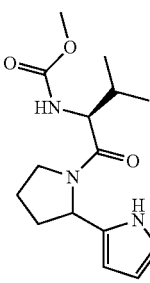 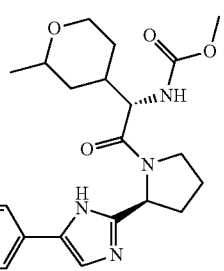
AG_053
AG_037
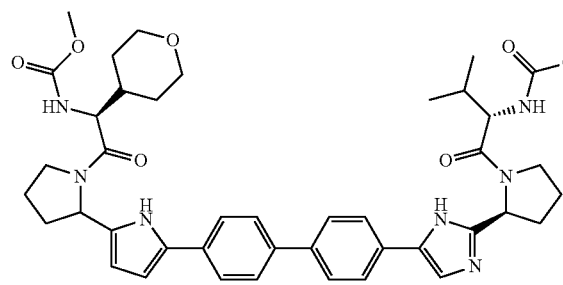 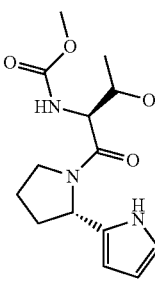 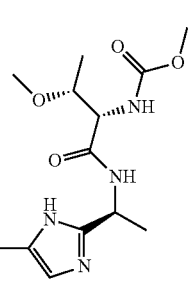
AG_112
AG_061_B
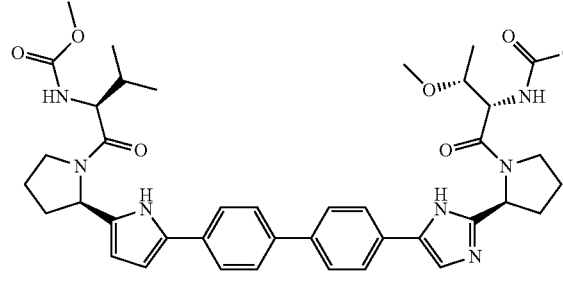 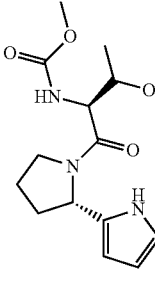
AG_119
AG_109
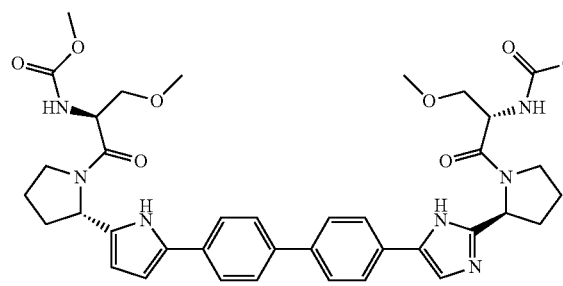 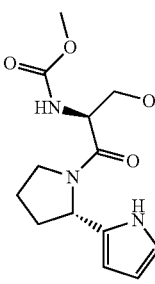
AG_108
AG_072_B
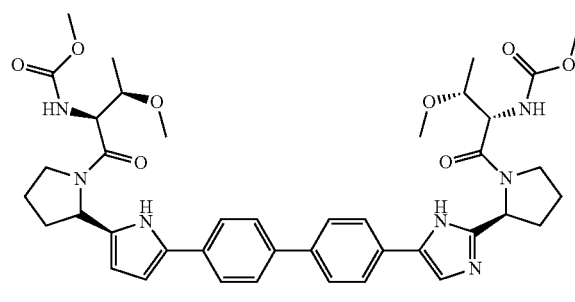 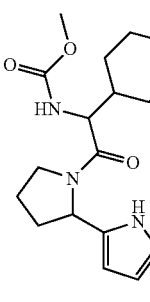 
AG_038

-continued
AG_062
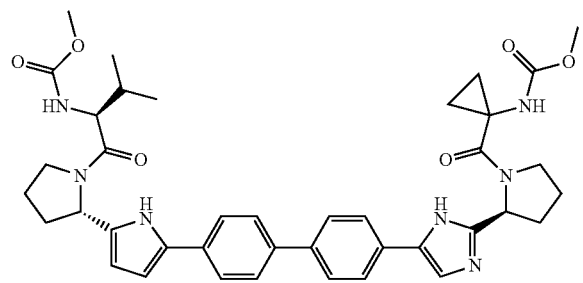
AG_097
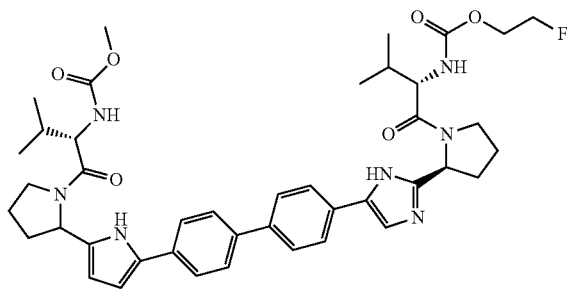
AG_060
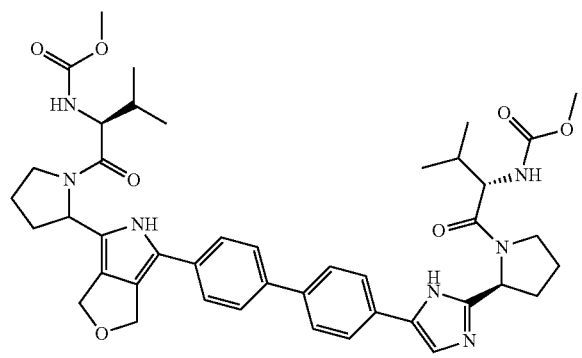
AG_060_B
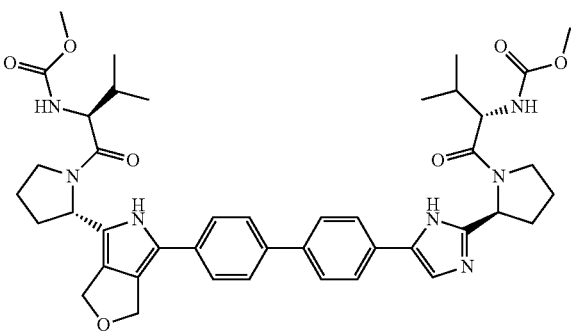
AG_077
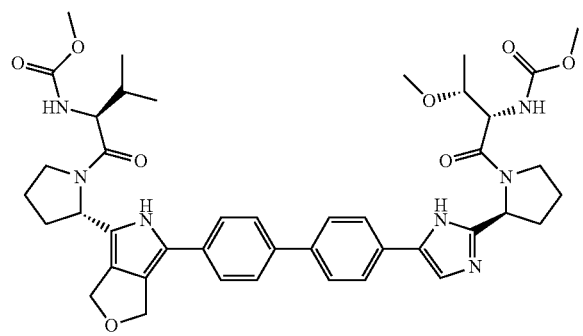
AG_104
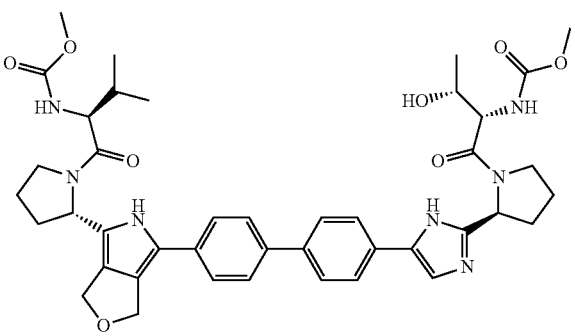
AG_079_A
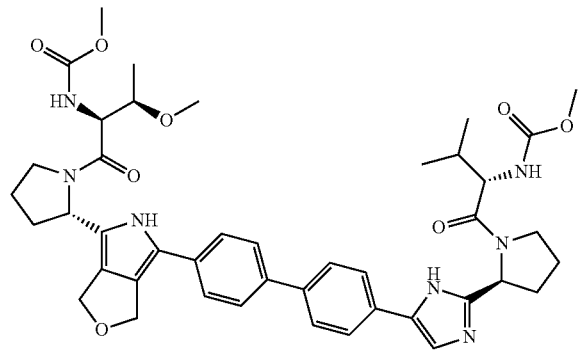
AG_079_B
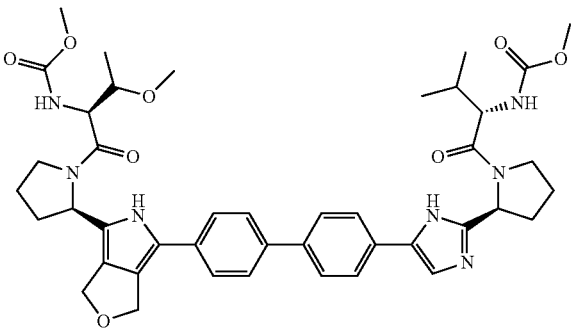

-continued
AG_123
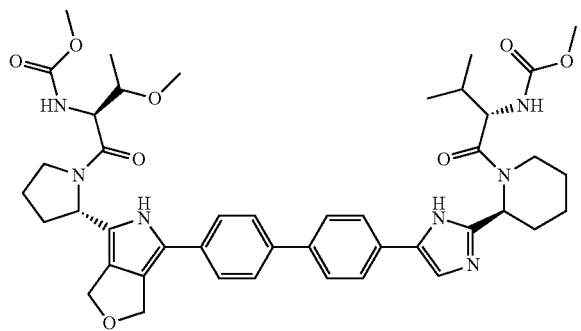
AG_124
AG_113
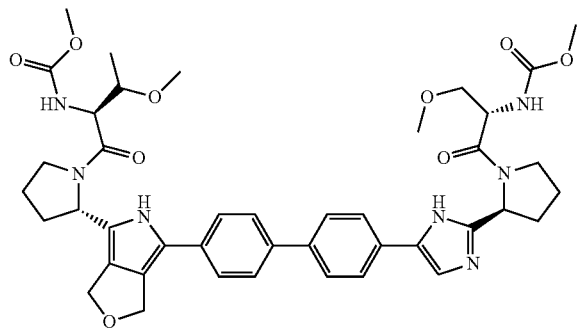
AG_080_A
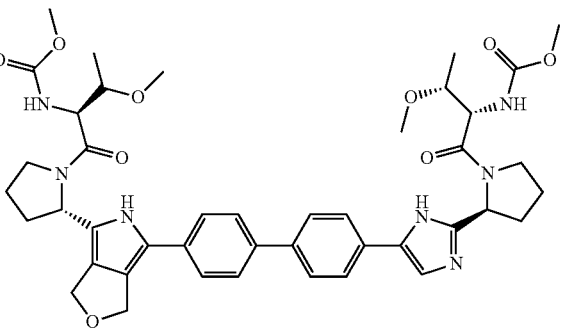
AG_080_B
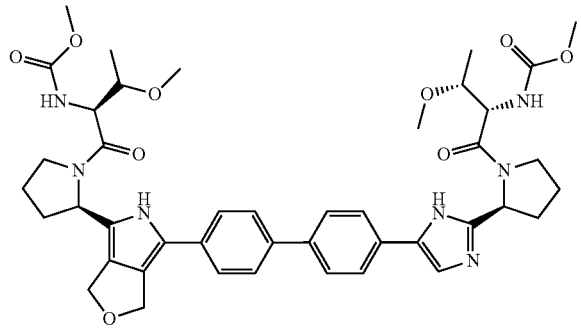
AG_088_A
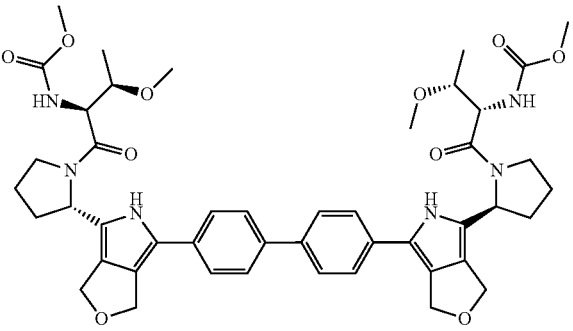
AG_105
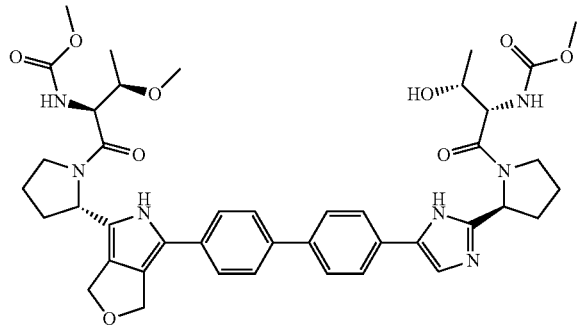
AG_116
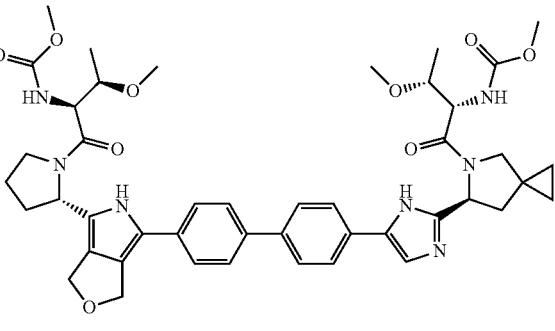

-continued
AG_117
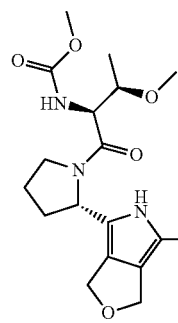
AG_111
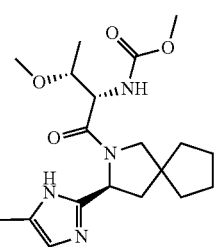
AG_122_A
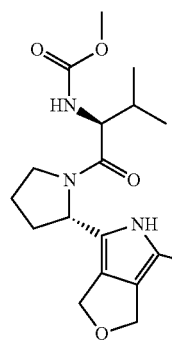
AG_122_B
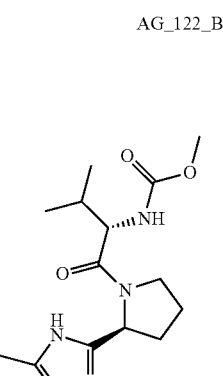
AG_114_A
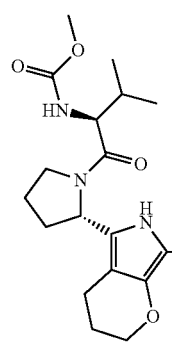
AG-114_B
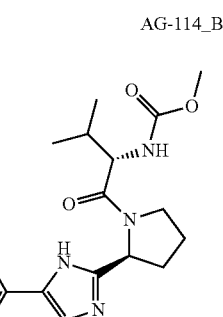
AG_121
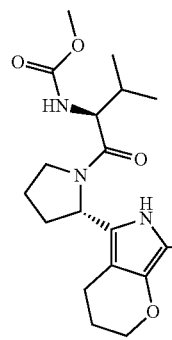
AG_095
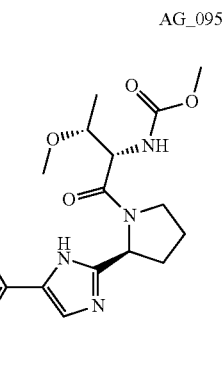

-continued
AG_094
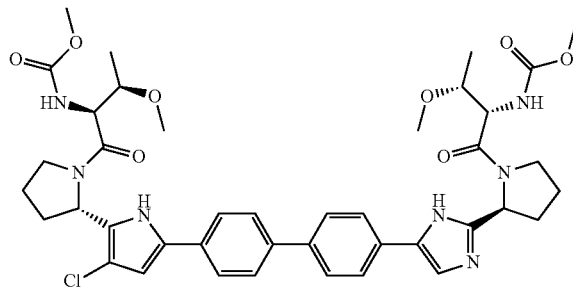
AG_087
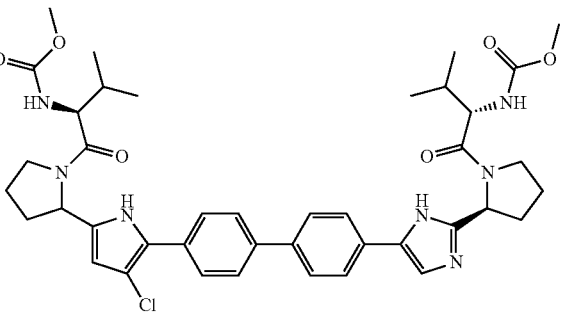
AG_118_B
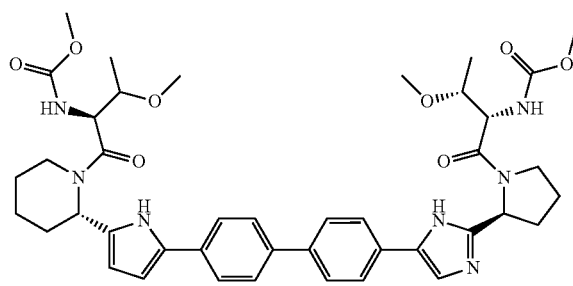
AG_096
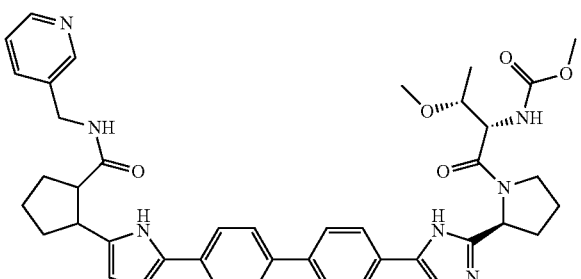
AG_103
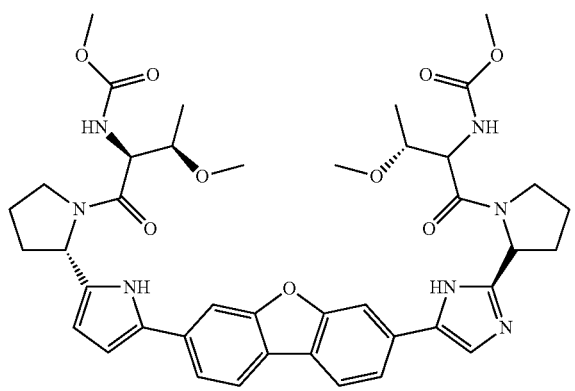
AG_085
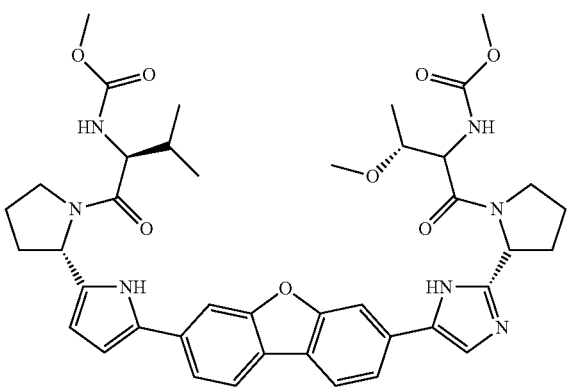
AG_081_A
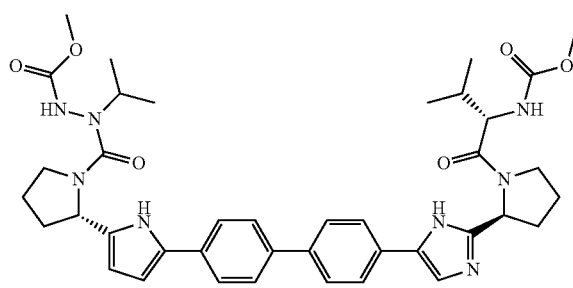
AG_081_B
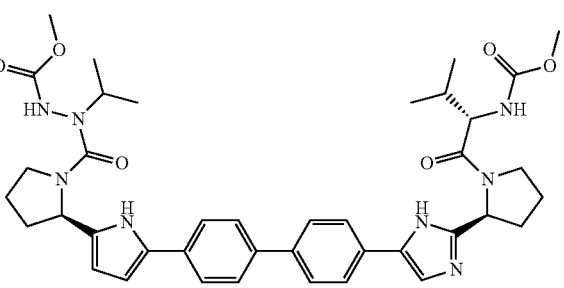

-continued
AA_007
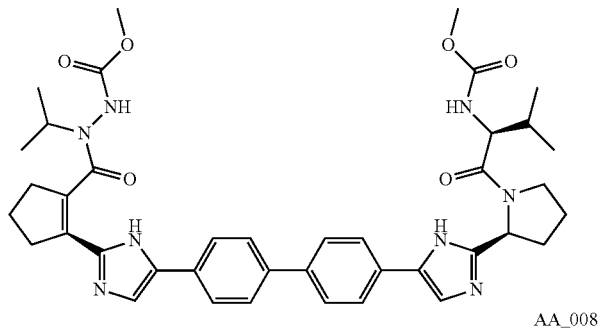
AA_033
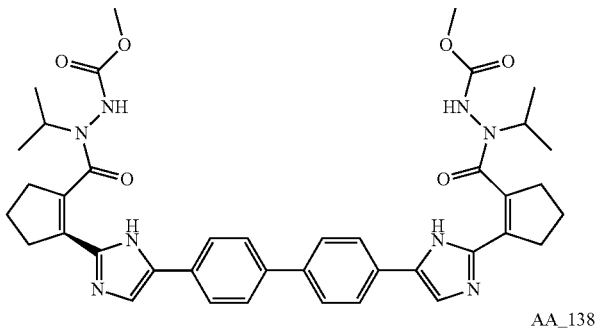
AA_008
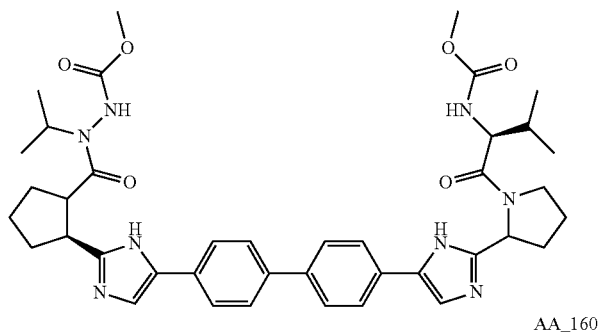
AA_138
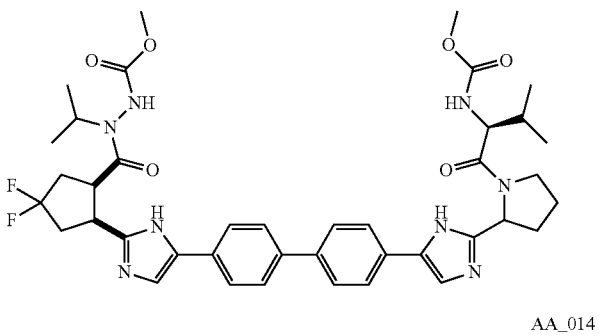
AA_160
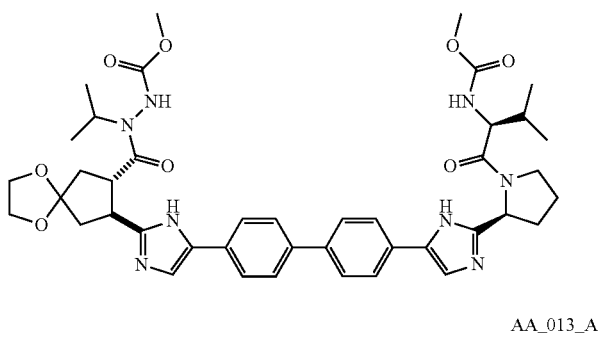
AA_014
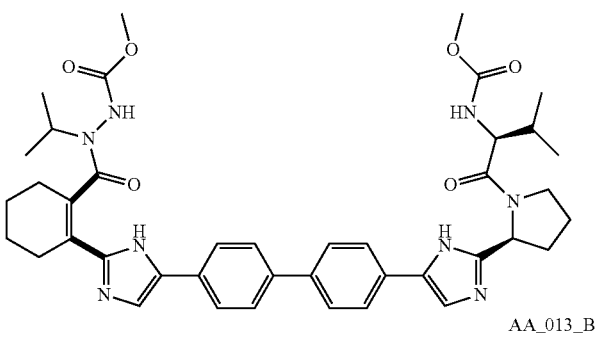
AA_013_A
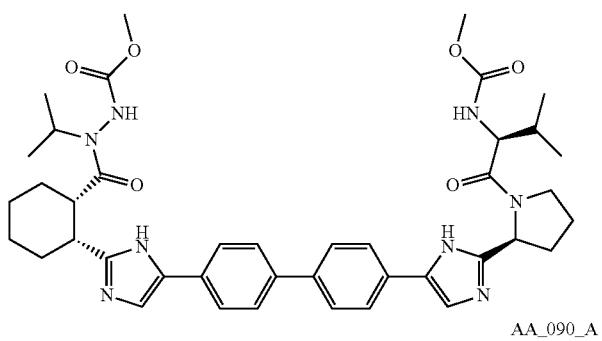
AA_013_B
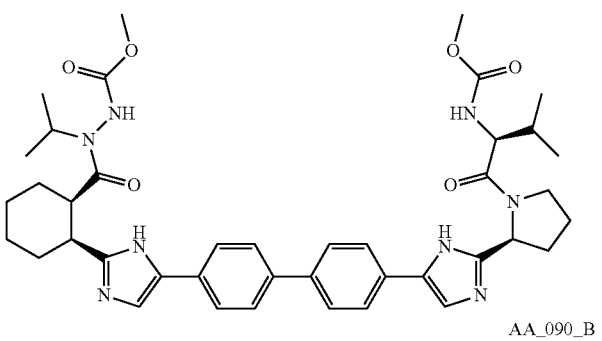
AA_090_A
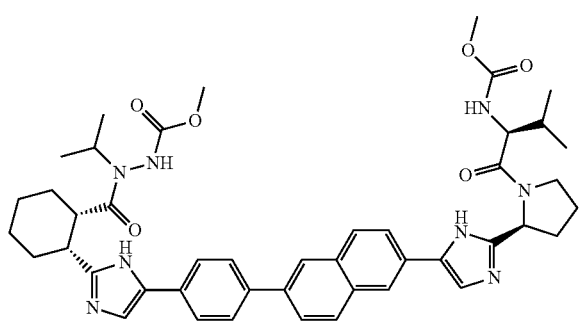
AA_090_B
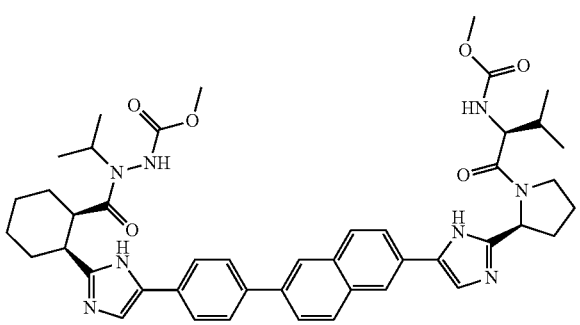

-continued
AA_029
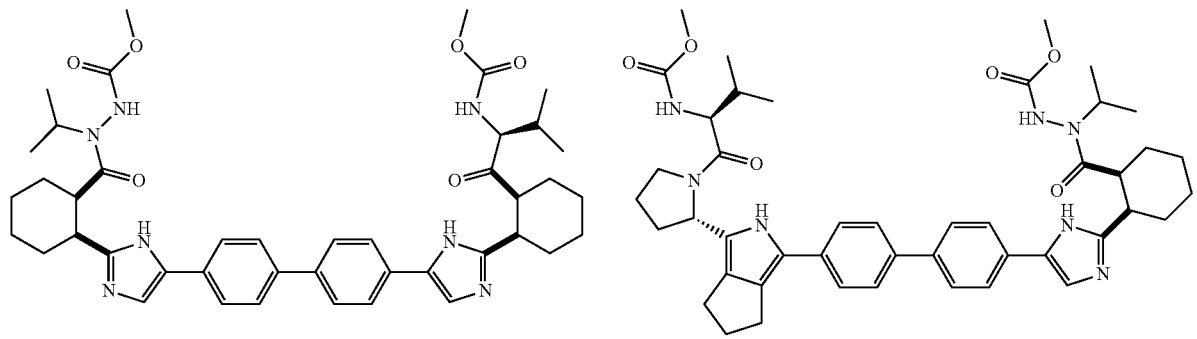
AA_100
AA_108
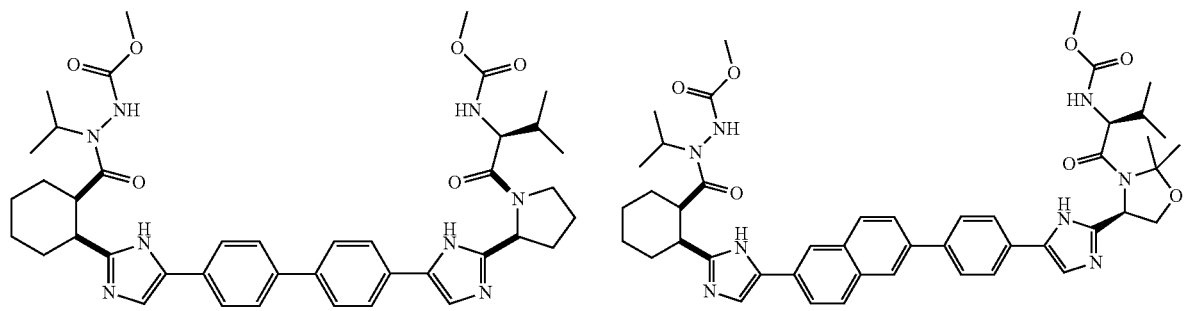
AA_072
AA_071
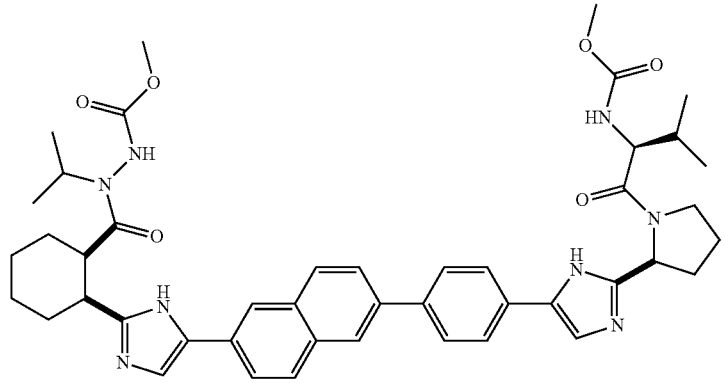
AA_073
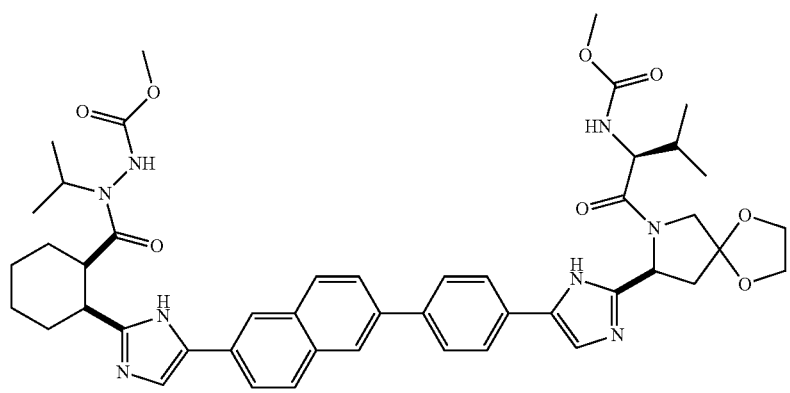

-continued
AA_074
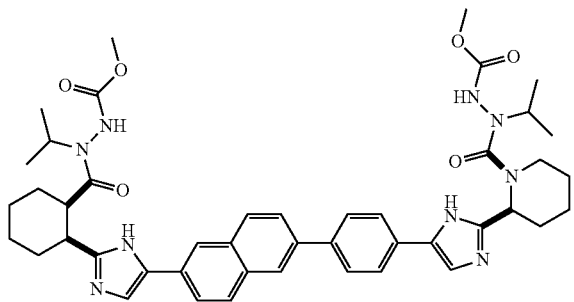
AA_075
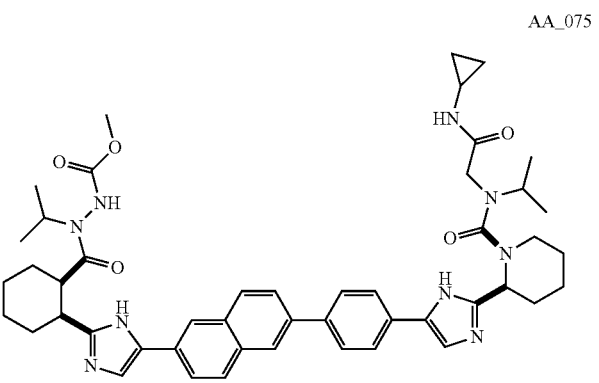
AA_076
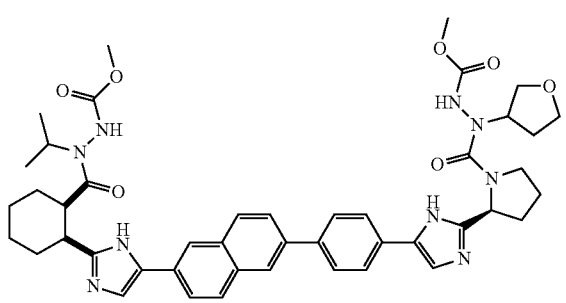
AA_078
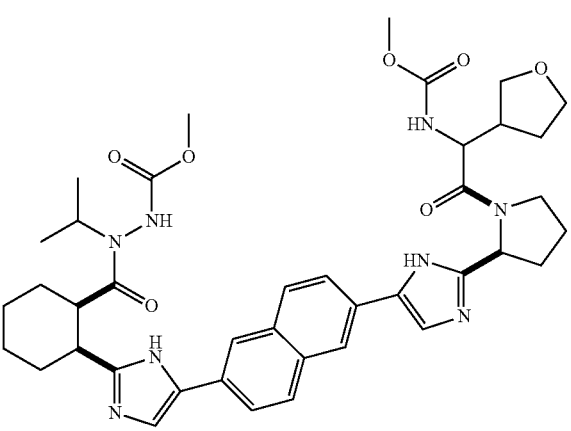
AA_079
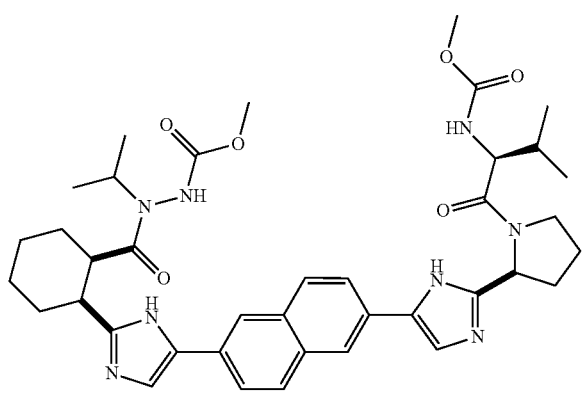
AA_092
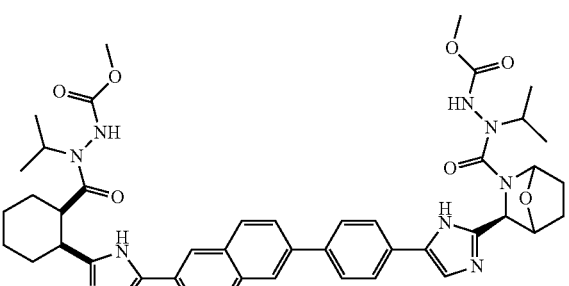
AA_094
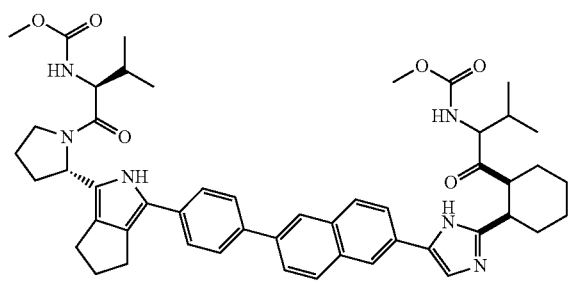
AA_096
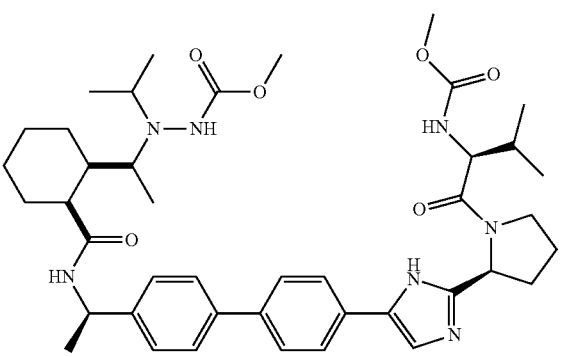

-continued
AA_097
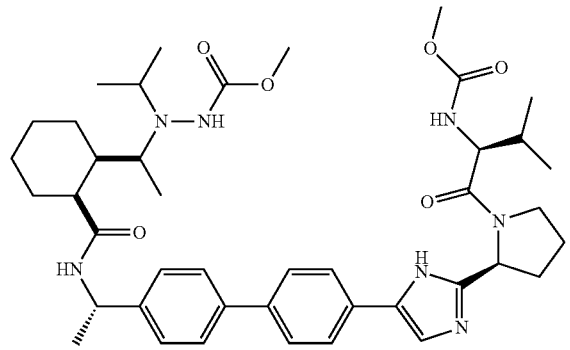
AA_106
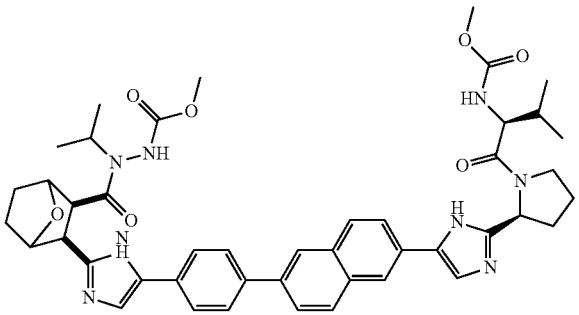
AA_089
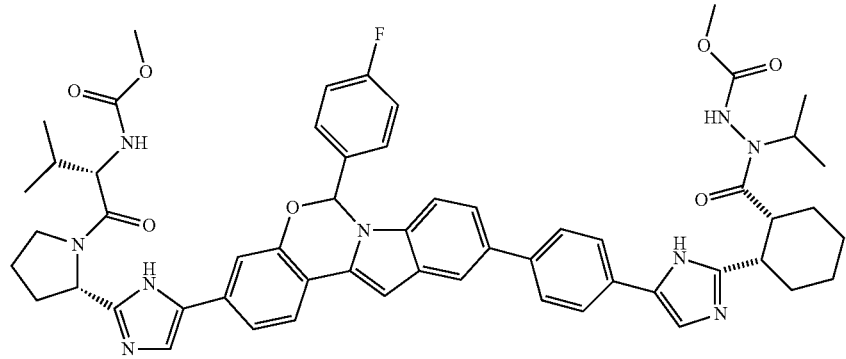
AA_091_A
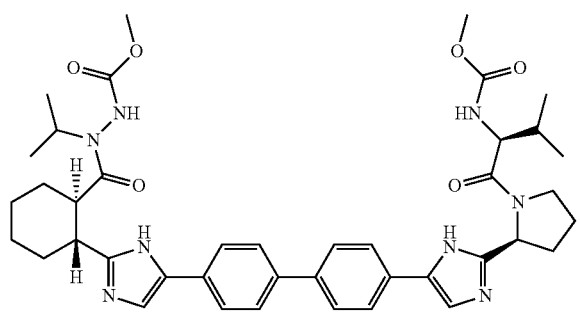
AA_091_B
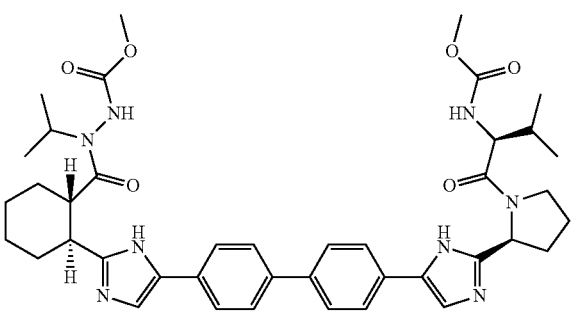
AA_109
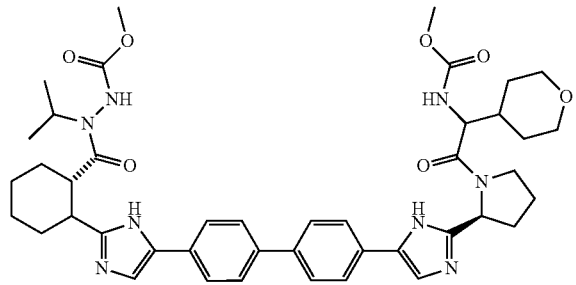
AA_122
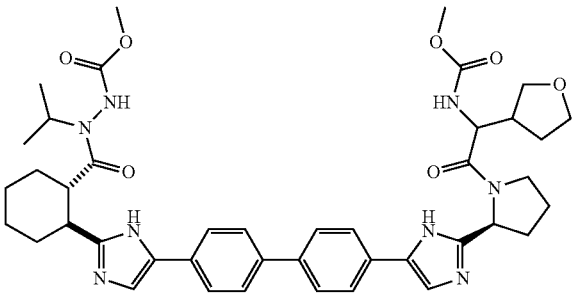

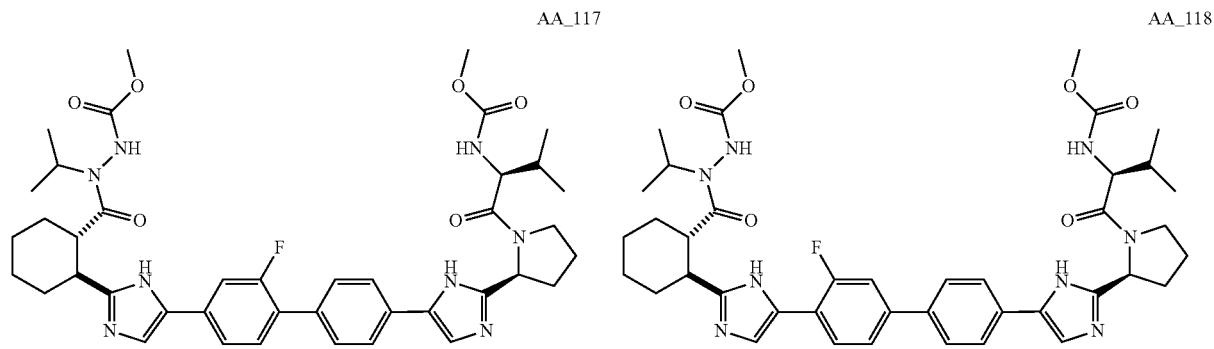
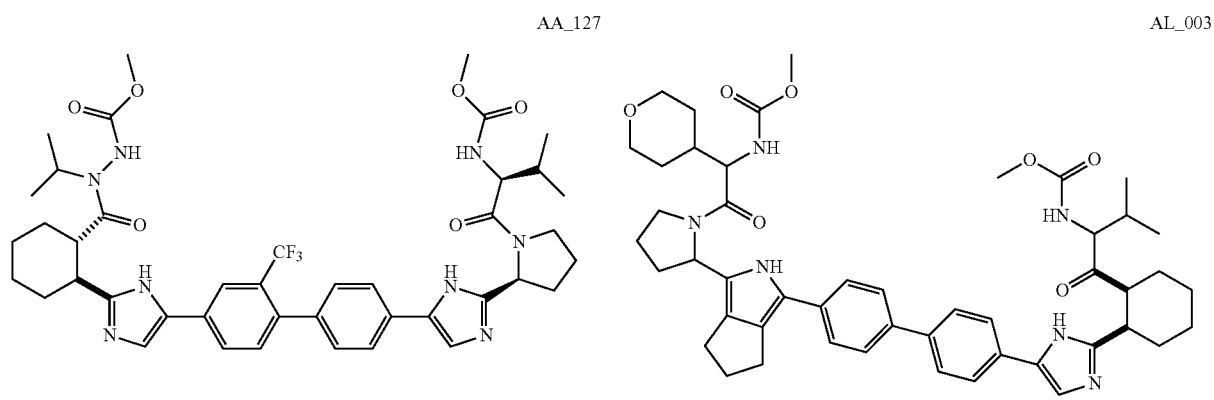
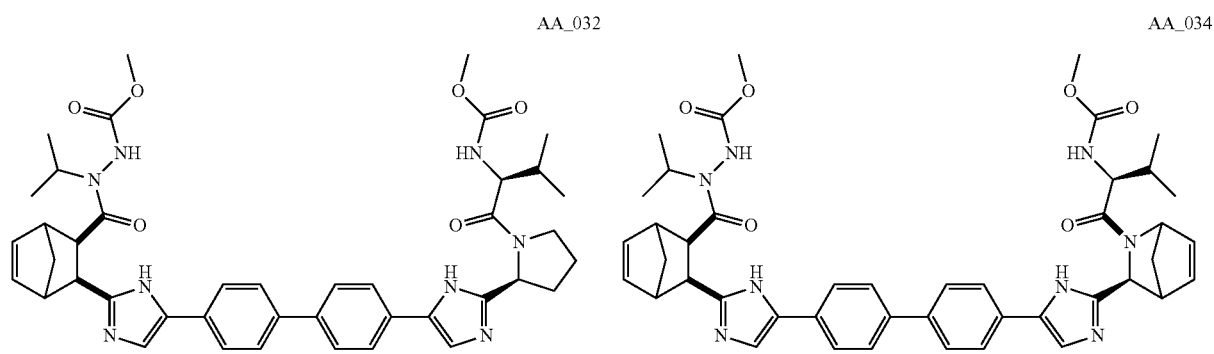
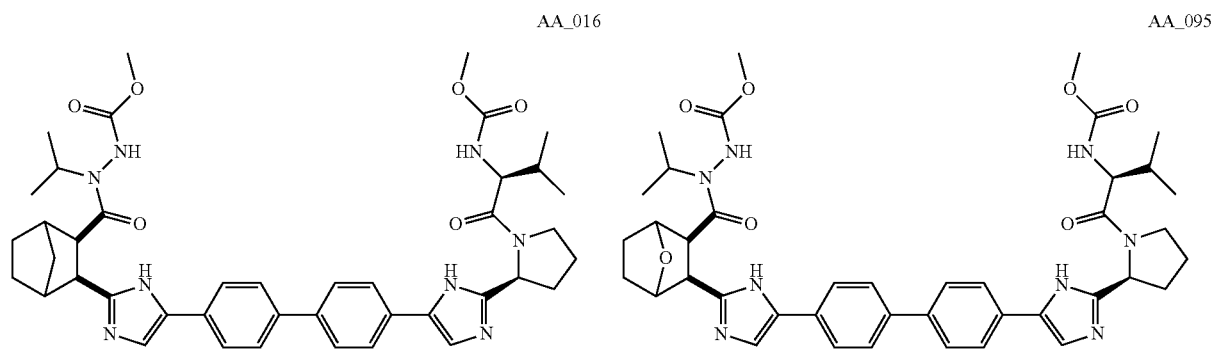

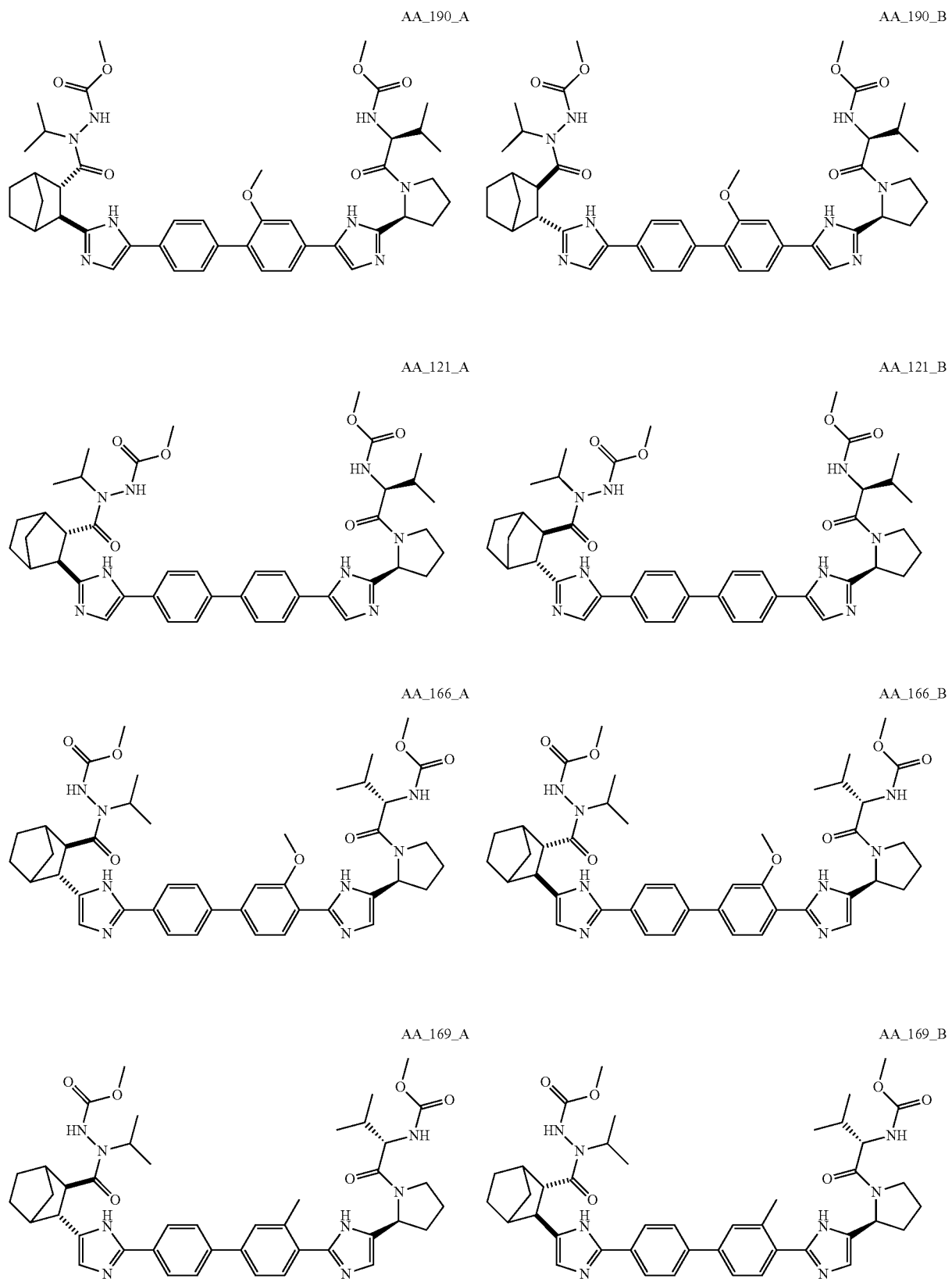

-continued
AA_156
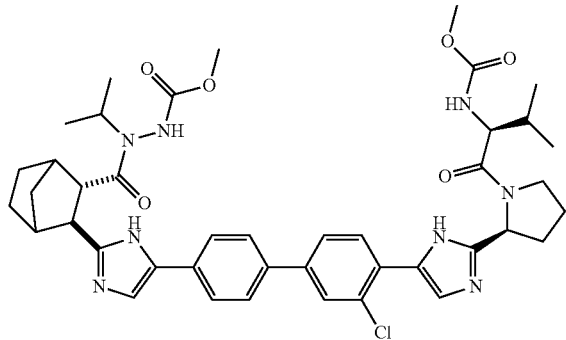
AA_167
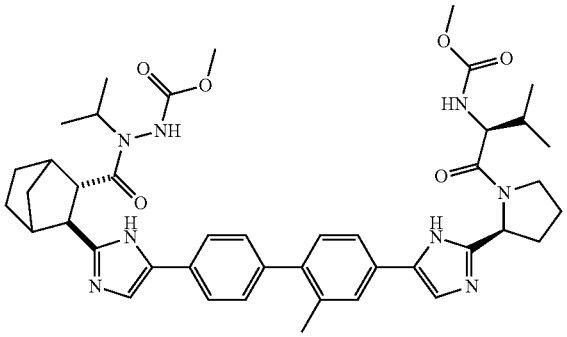
AA_155
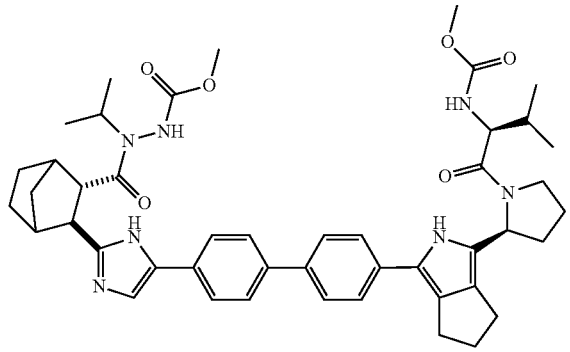
AA_158
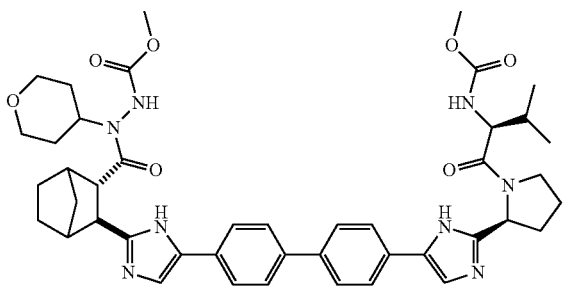
AA_027
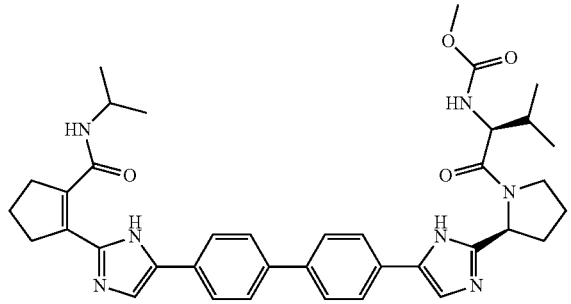
AA_047
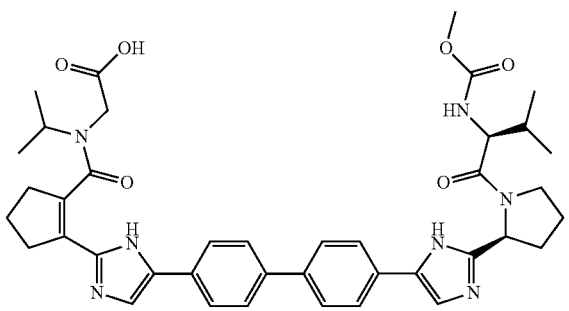
AA_064
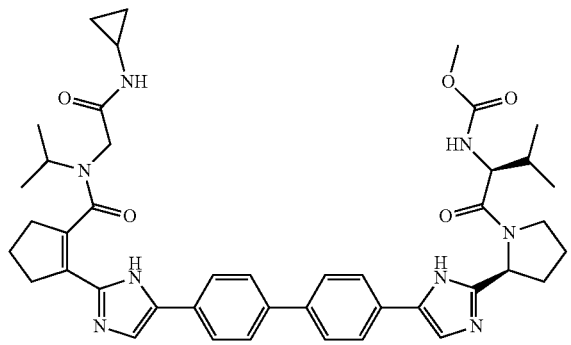
AA_065
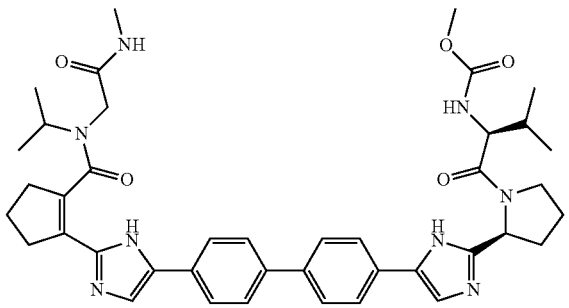

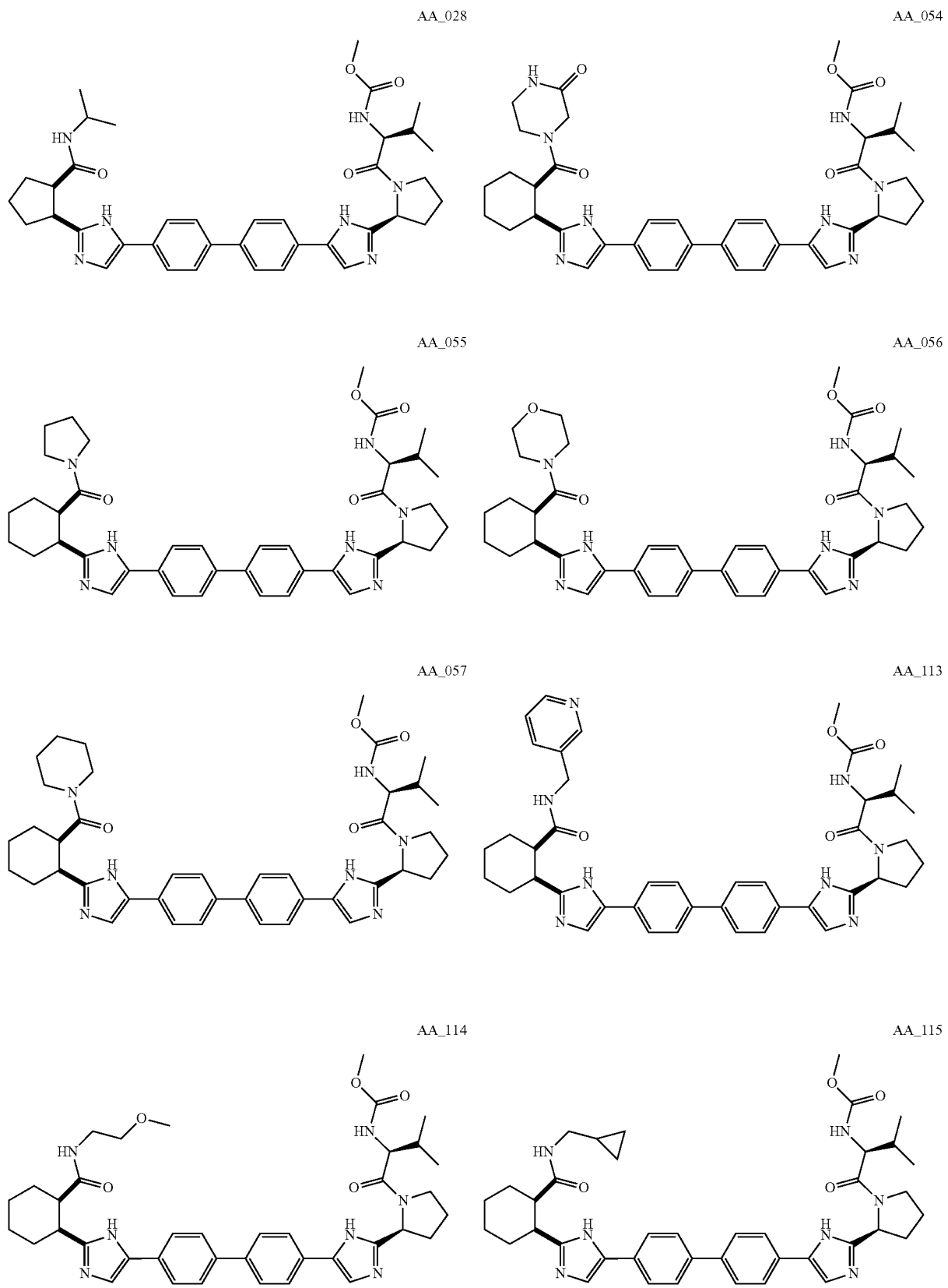

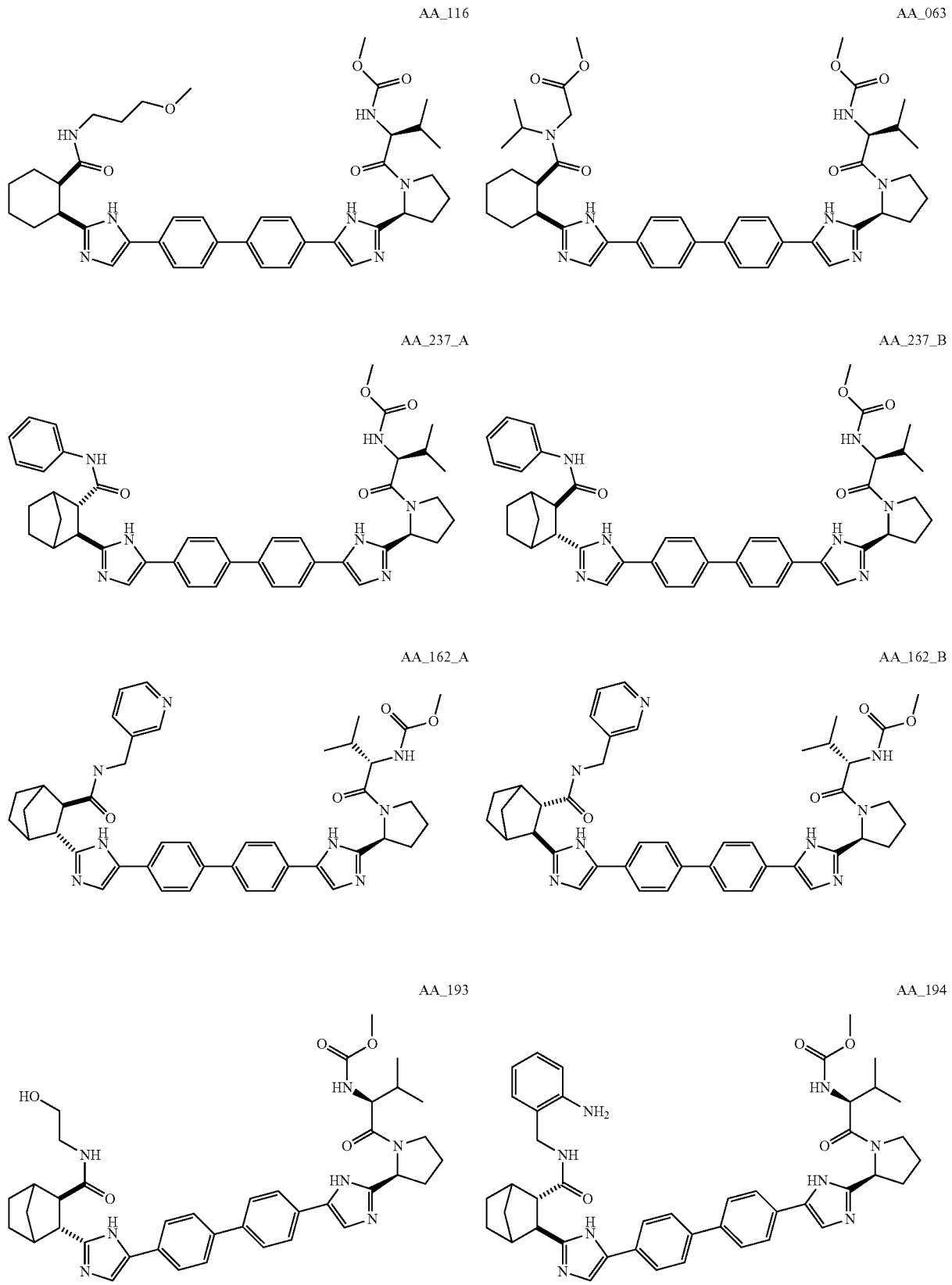

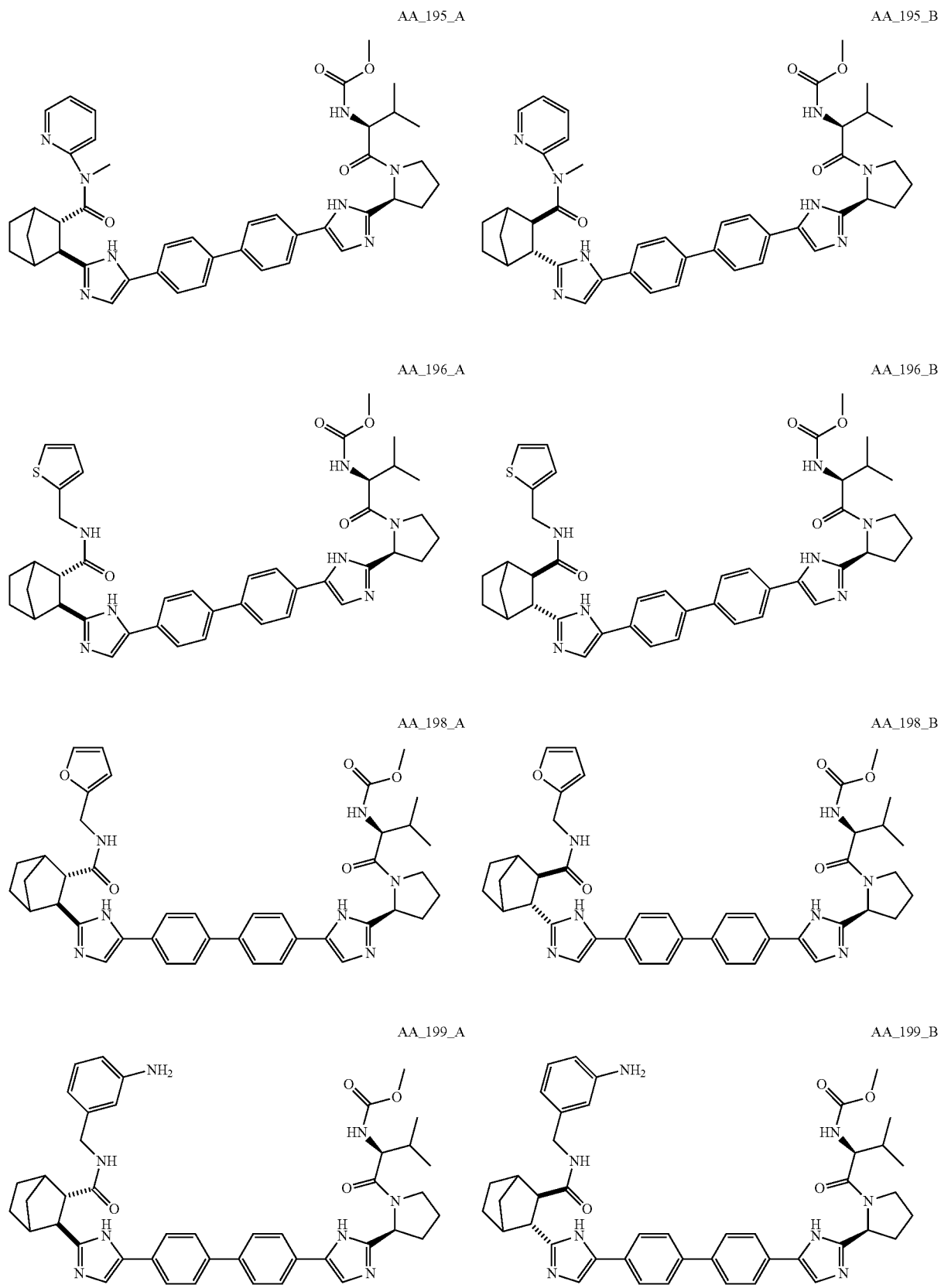

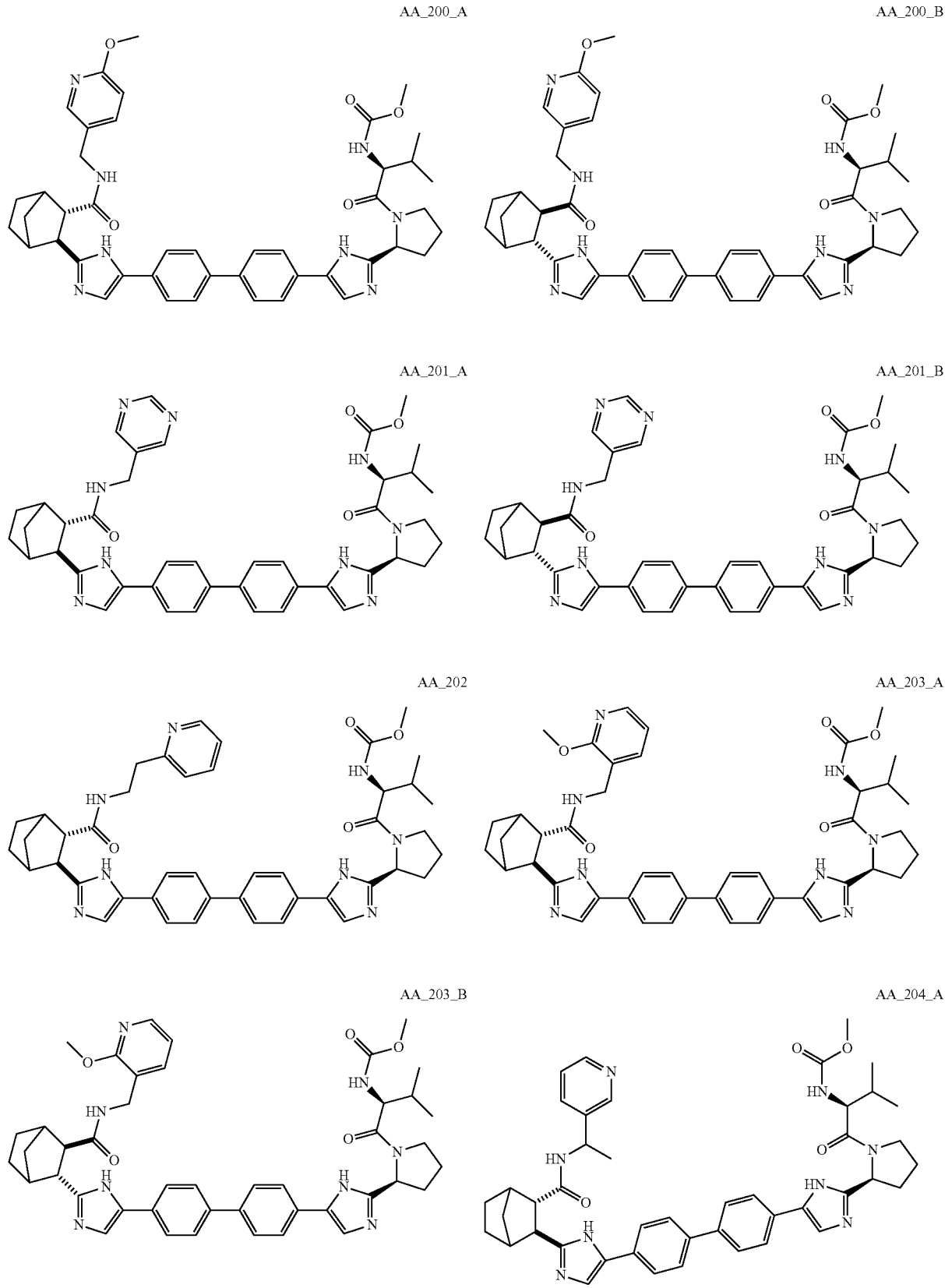

-continued
AA_204_B
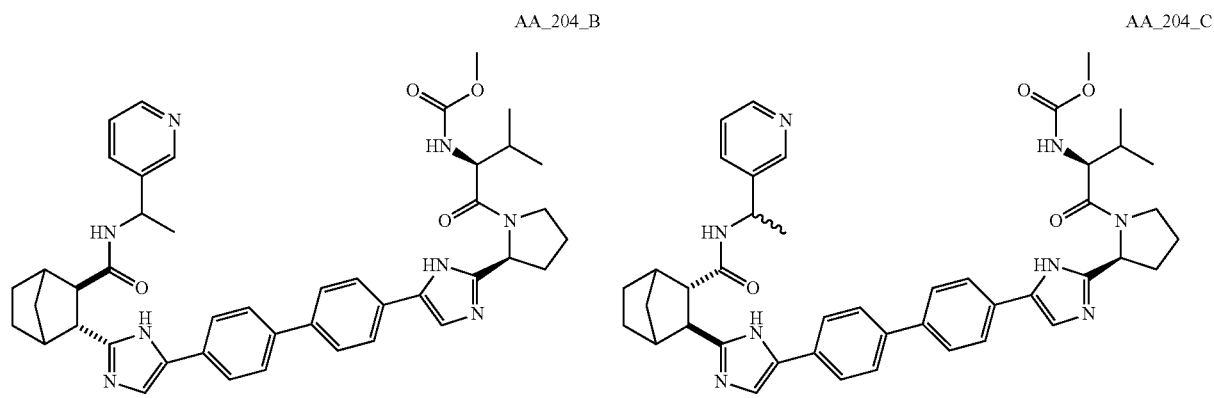
AA_204_C
AA_206_A
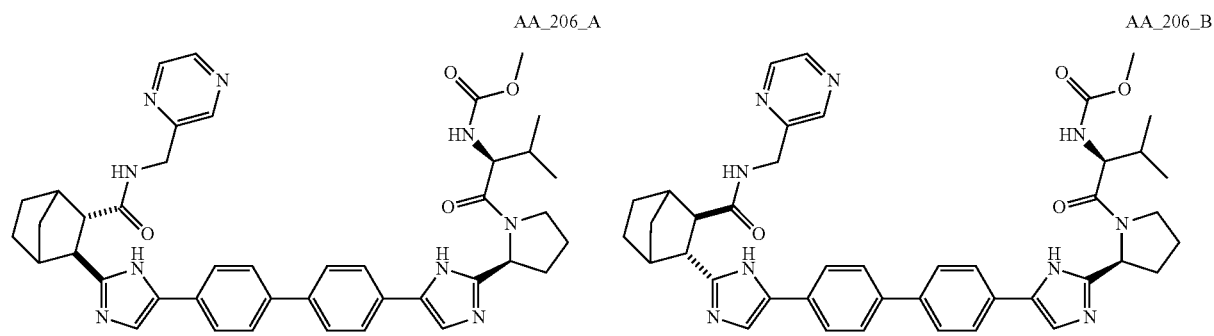
AA_206_B
AA_207_A
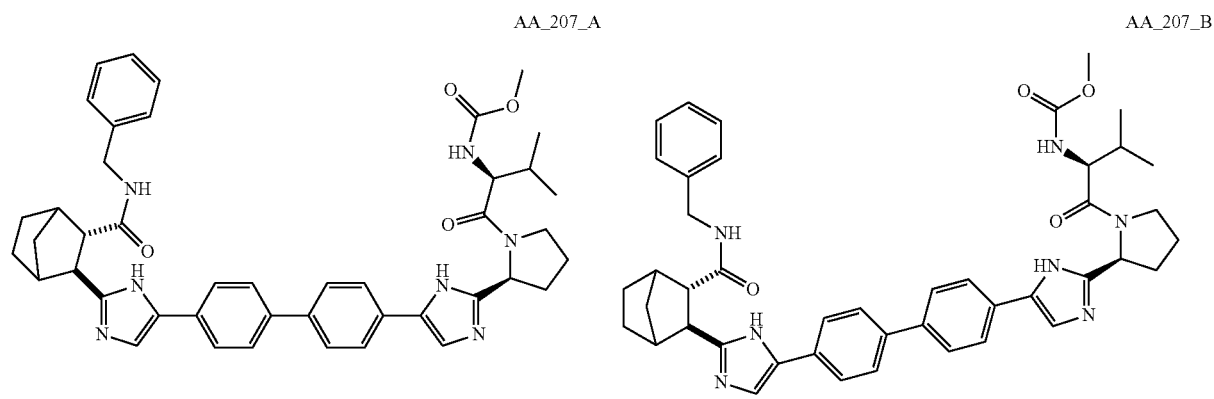
AA_207_B
AA_208_A
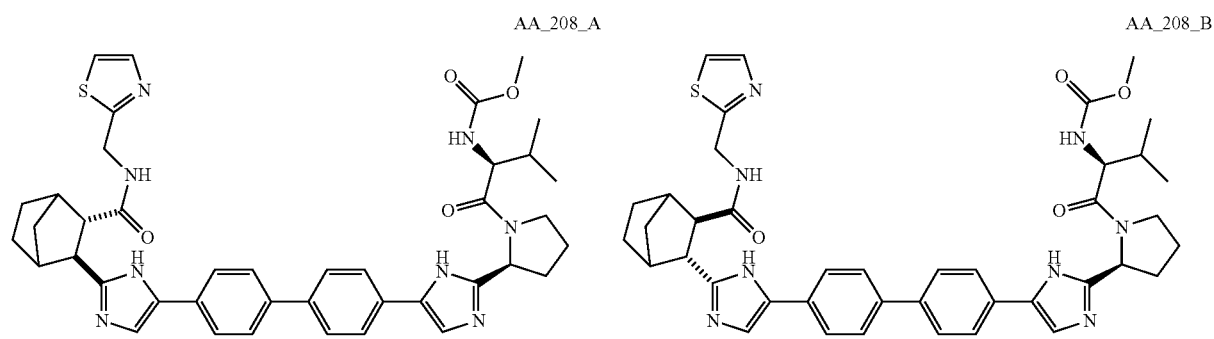
AA_208_B

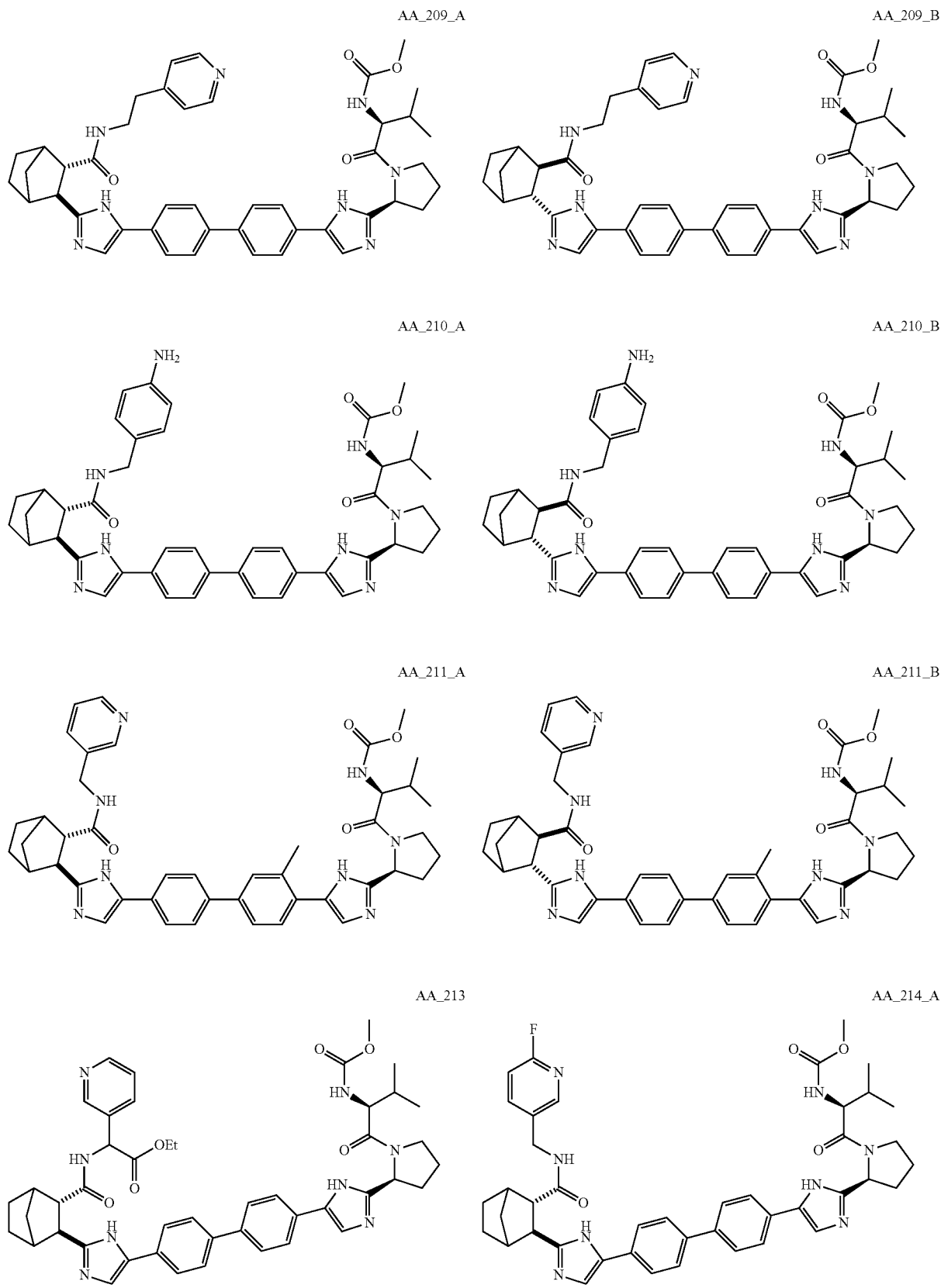

-continued
AA_214_B
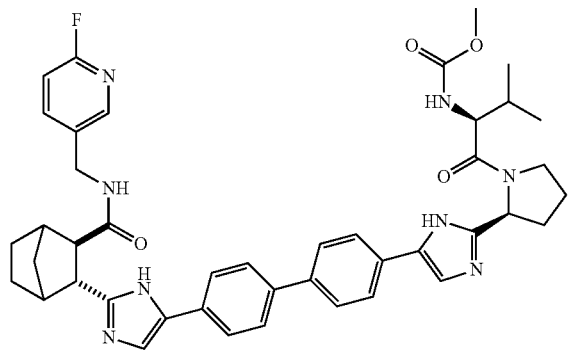
AA_215_A
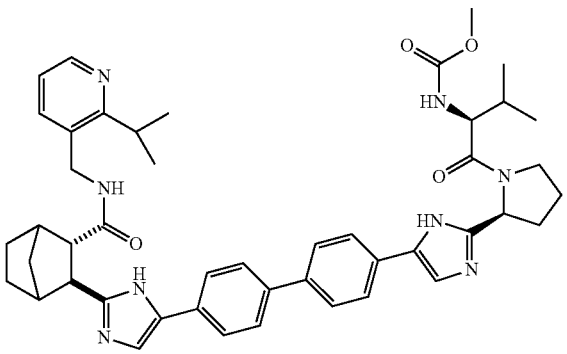
AA_215_B
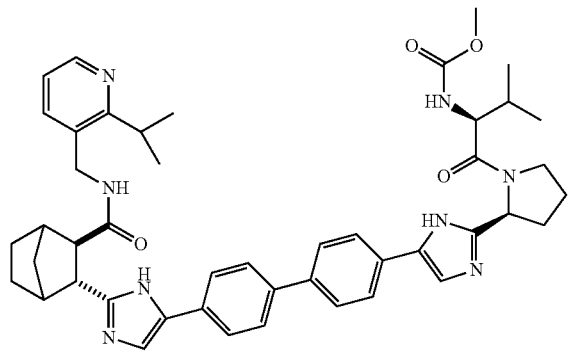
AA_216_A
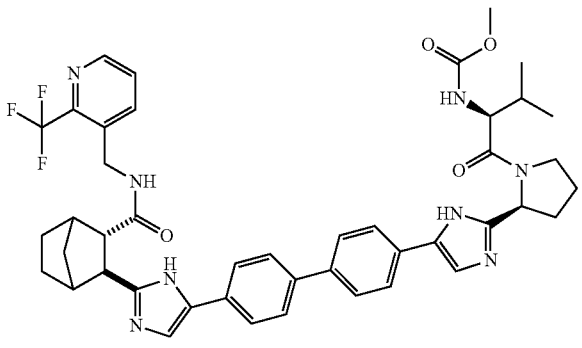
AA_216_B
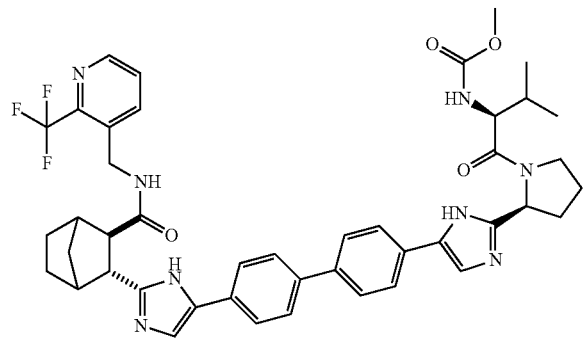
AA_217
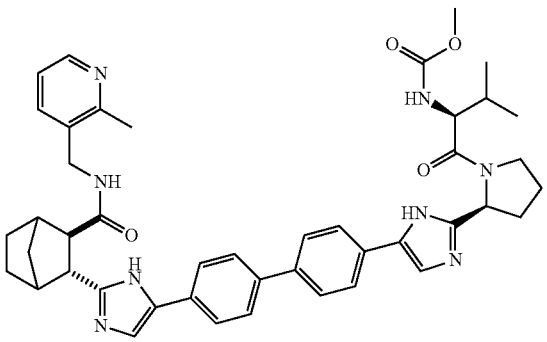
AA_218
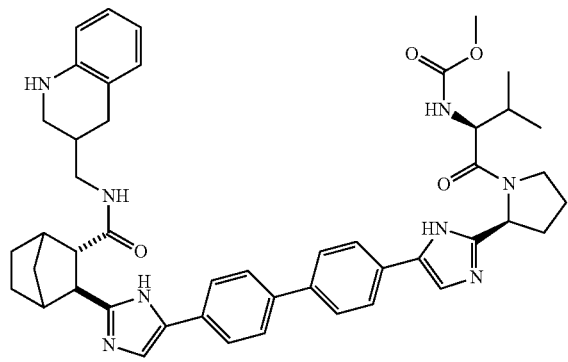
AA_224_A
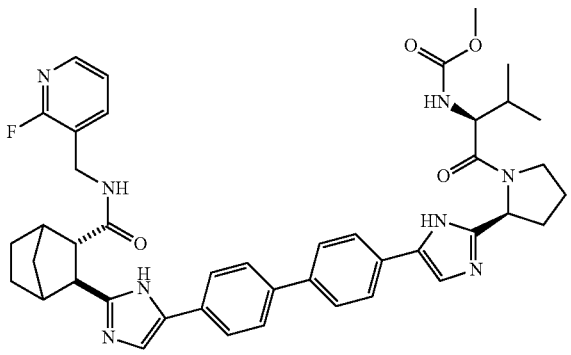

-continued
AA_224_B
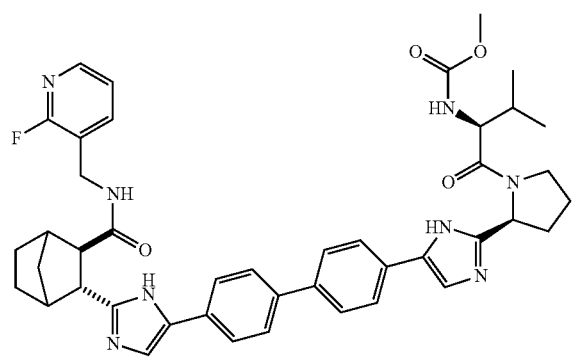
AA_228
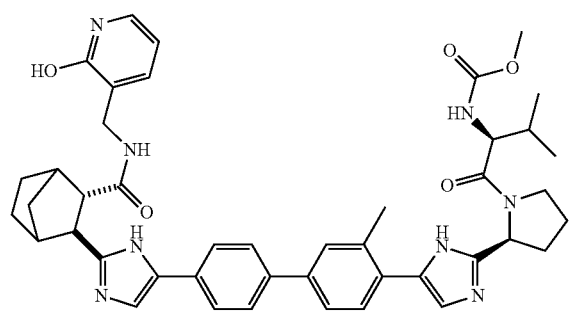
AA_232_A
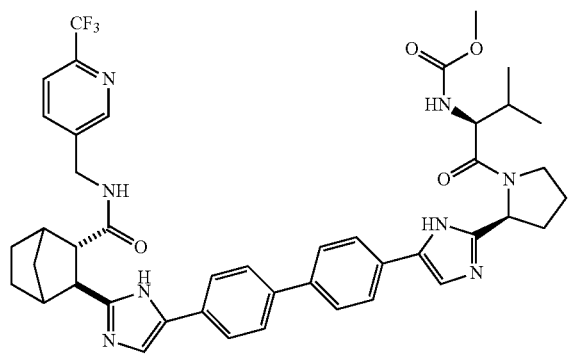
AA_232_B
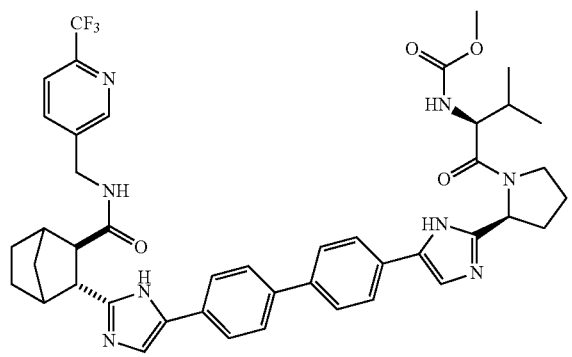
AA_233_A
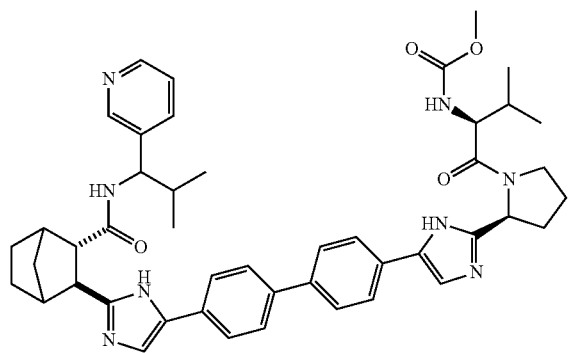
AA_233_B
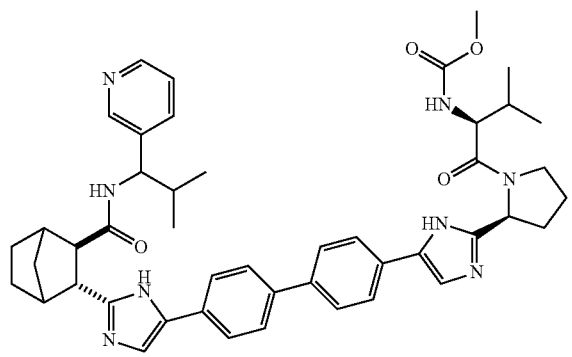
AA_233_C
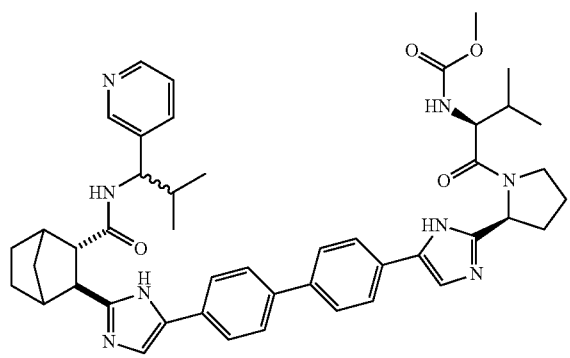
AA_234_A
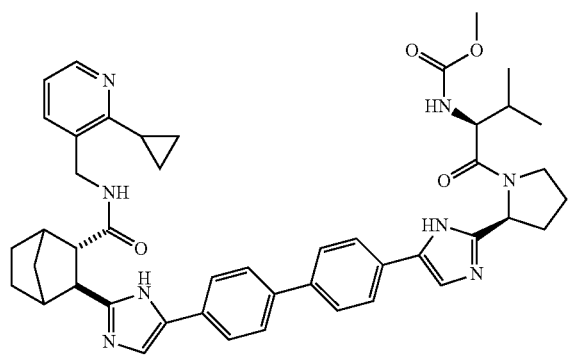

-continued
AA_234_B
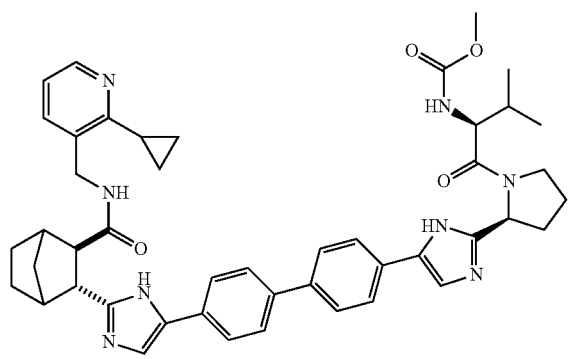
AA_235_A
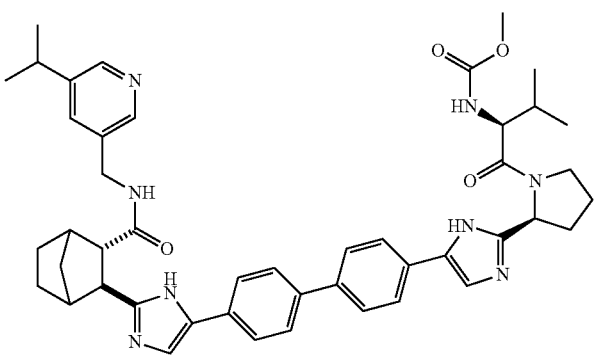
AA_236_A
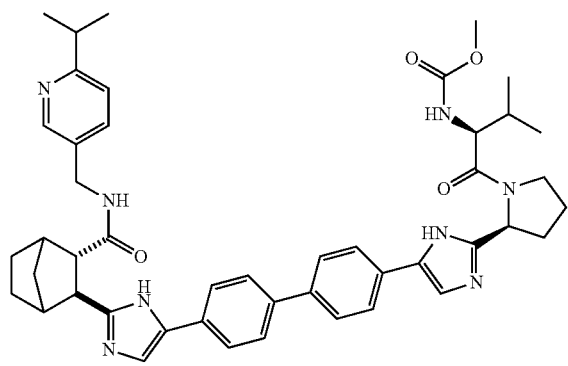
AA_243_B
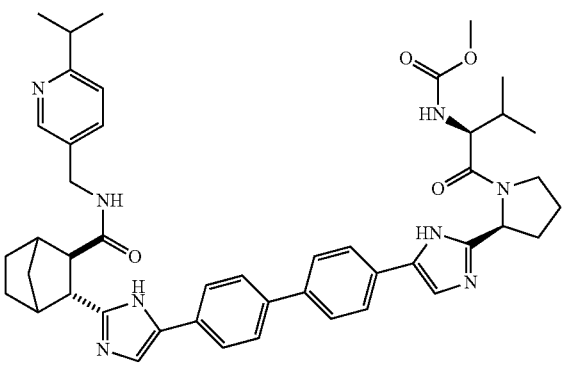
AA_243_A
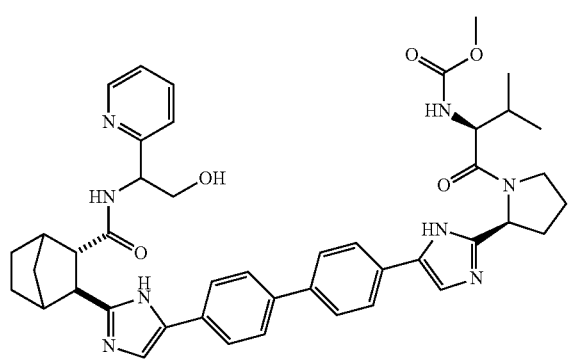
AA_243_B
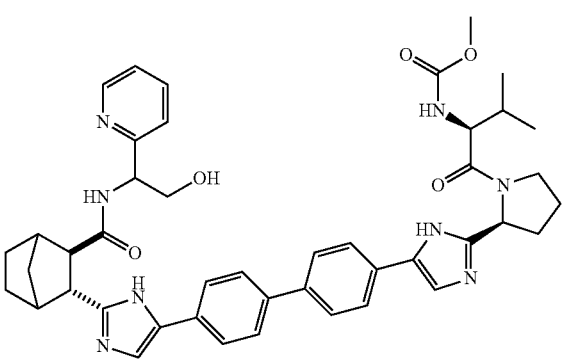
AA_244_
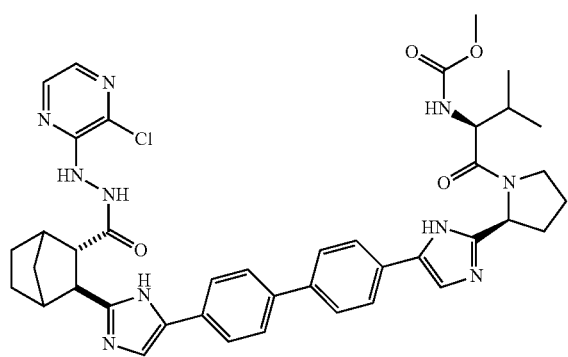
AA_275
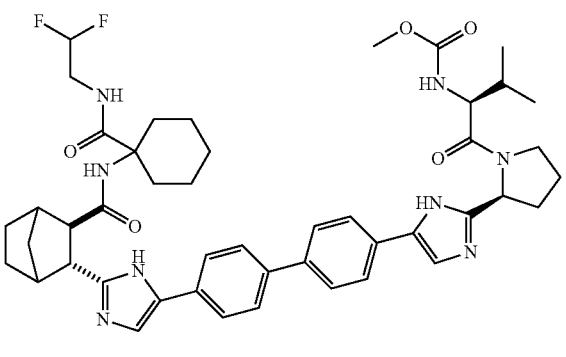

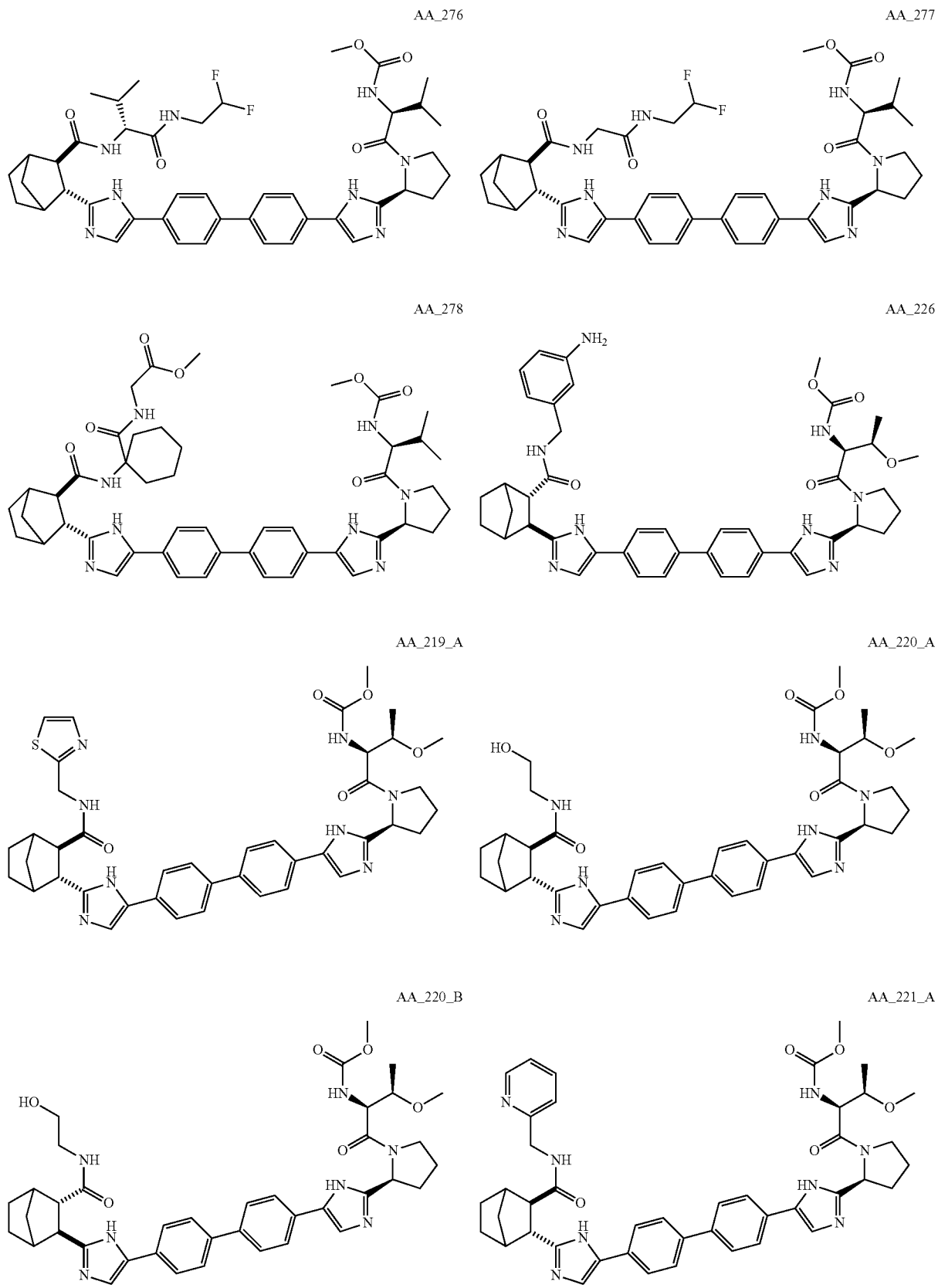

-continued
AA_222_A
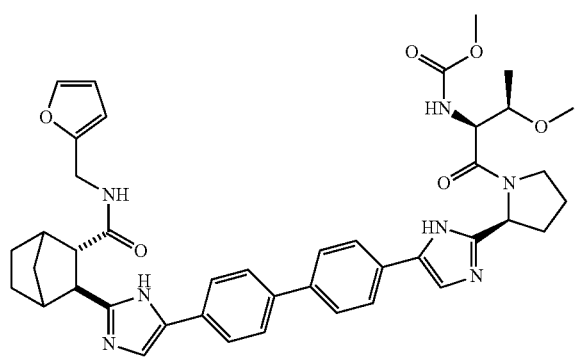
AA_223_A
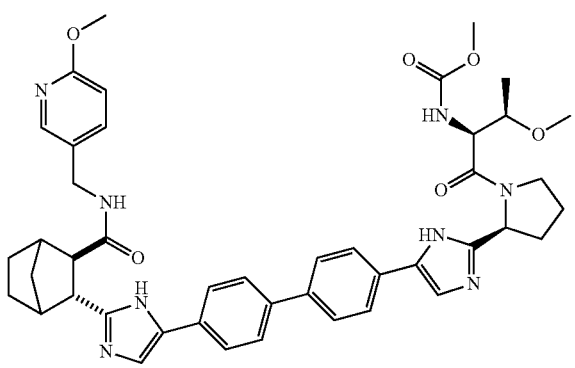
AA_223_B
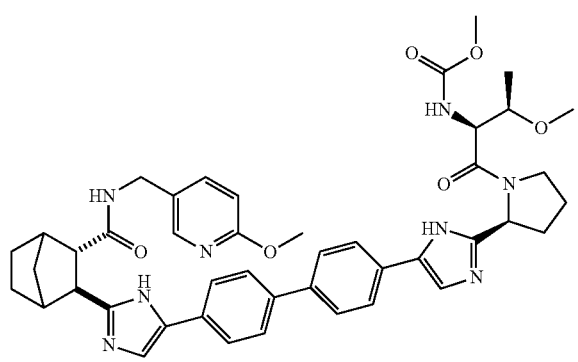
AA_227
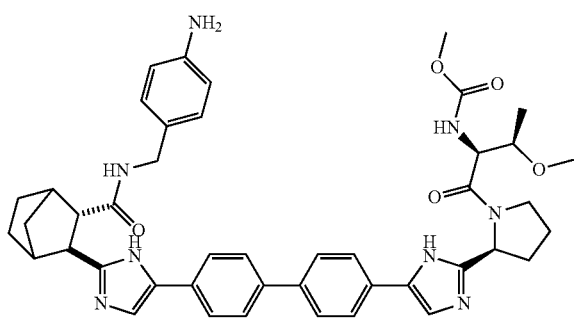
AA_245_A
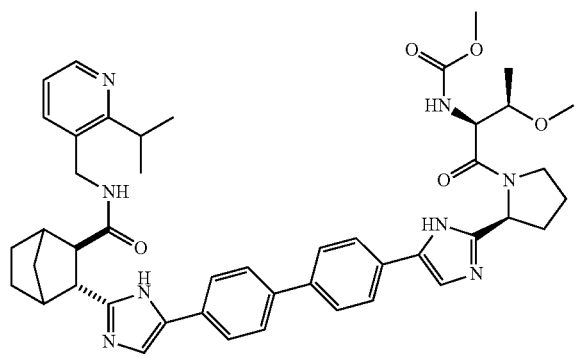
AA_245_B
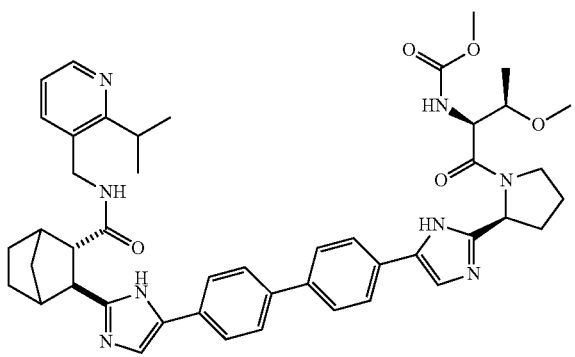
AA_246_A
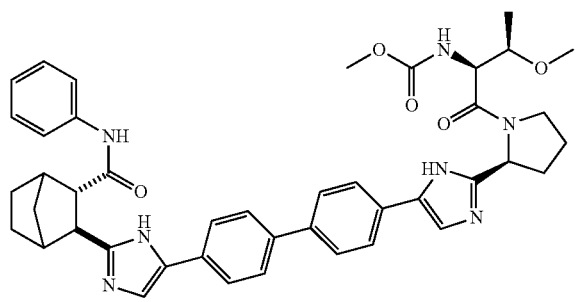
AA_246_B
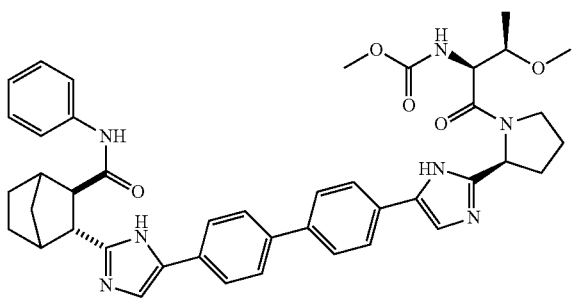

-continued
AA_247_A
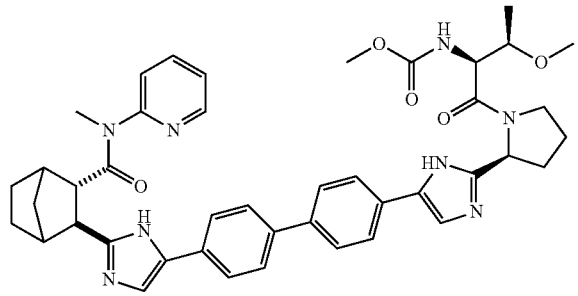
AA_247_B
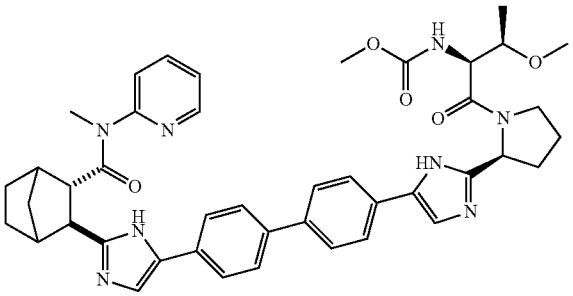
AA_248_A
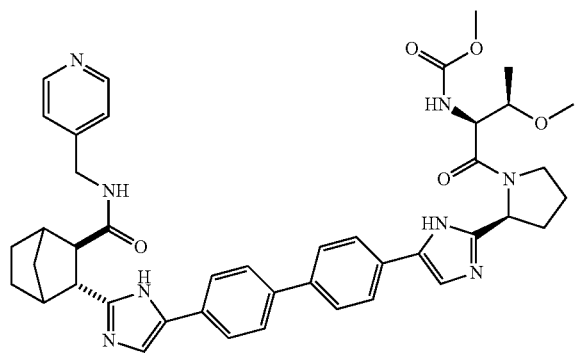
AA_248_B
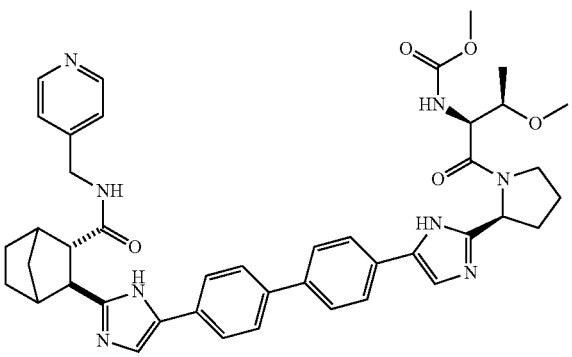
AA_249_A
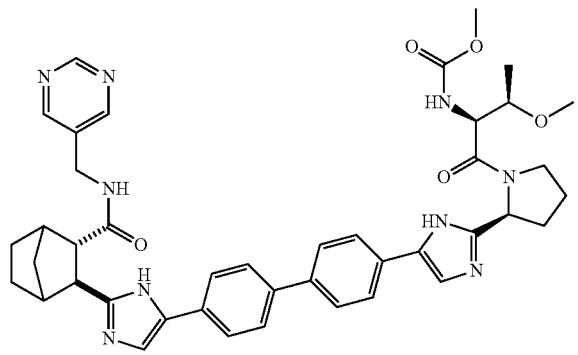
AA_250_A
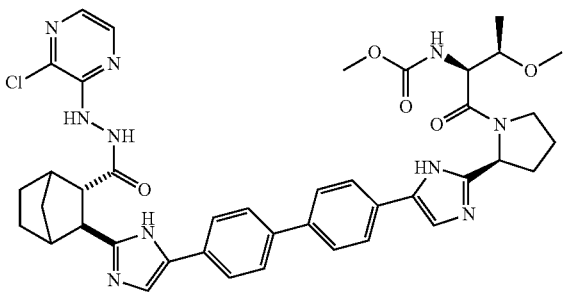
AA_250_B
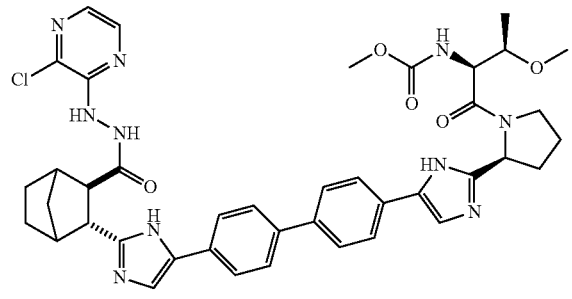
AA_251_A
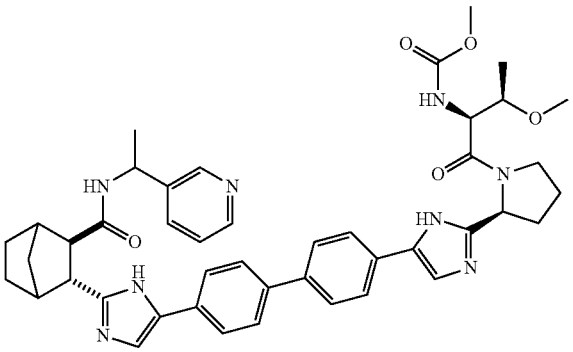

-continued
AA_251_B
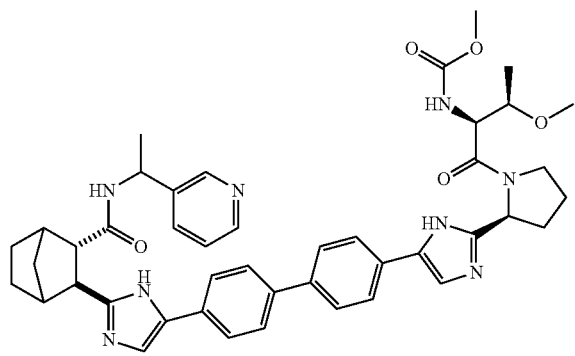
AA_251_C
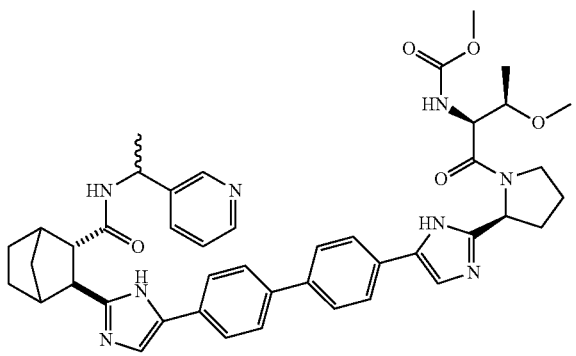
AA_252_A
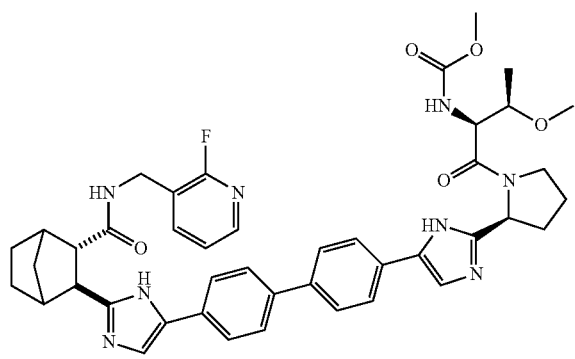
AA_252_B
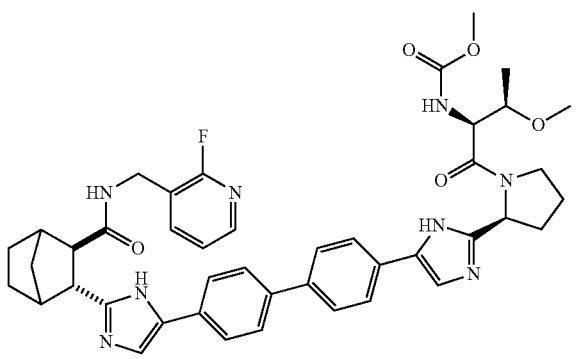
AA_253_A
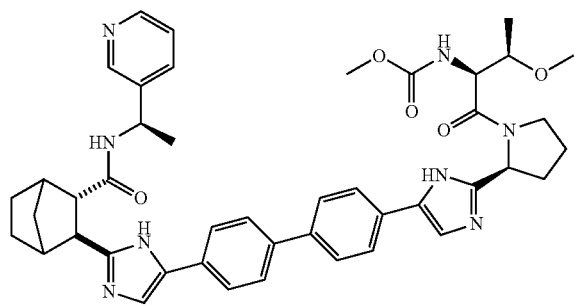
AA_253_B
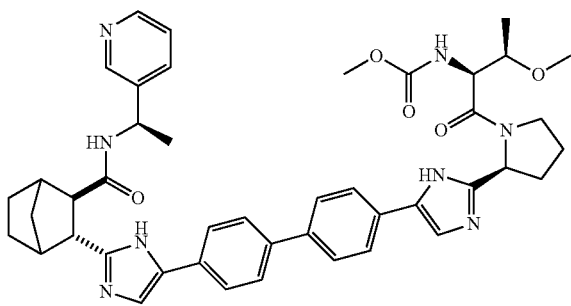
AA_253_C
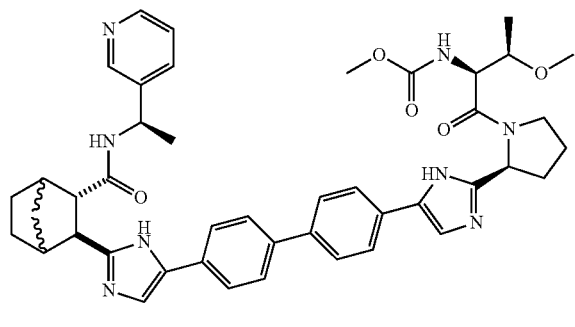
AA_254_A
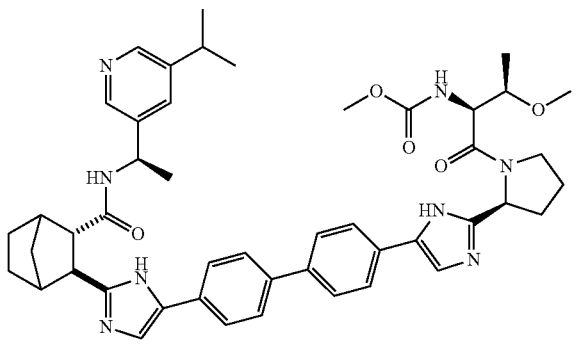

AA_255_A 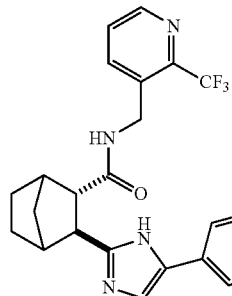 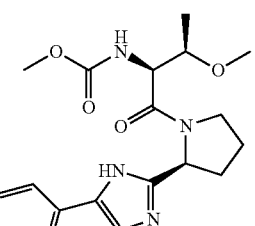
AA_255_B 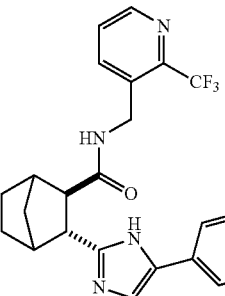 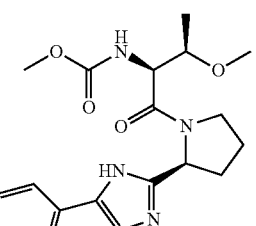
AA_256_A 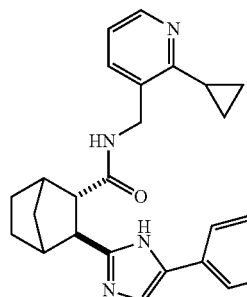 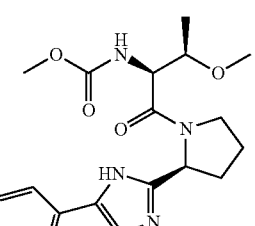
AA_257_A  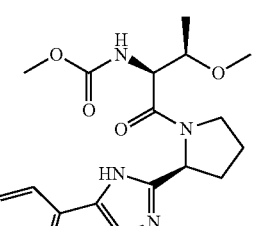
AA_258_B 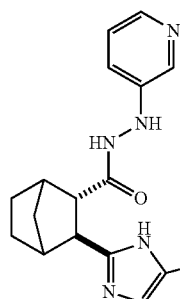 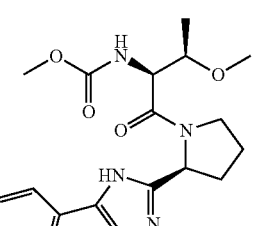
AA_259_A 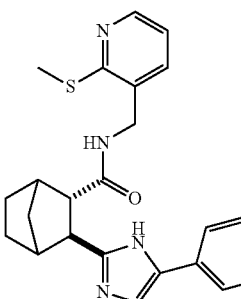 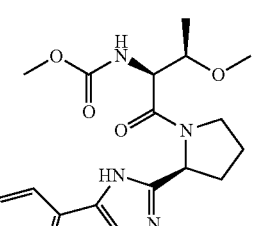
AA_260_B 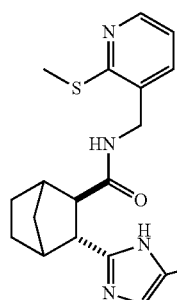 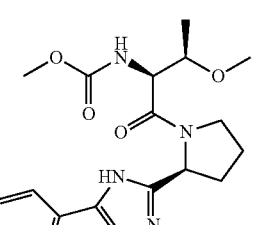
AA_261_A 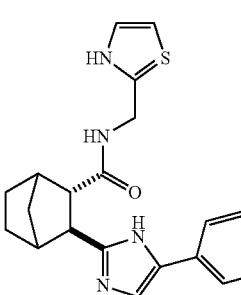 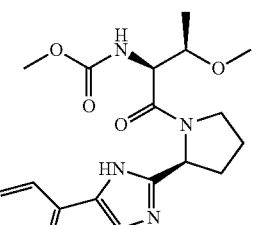
AA_262_B 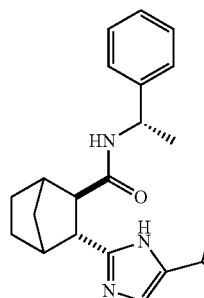 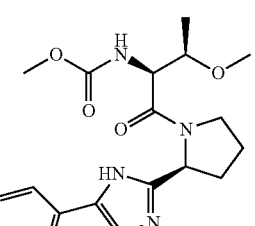
AA_263_B 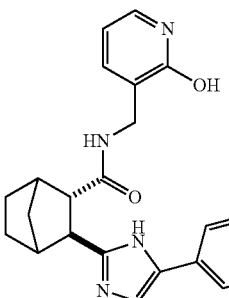 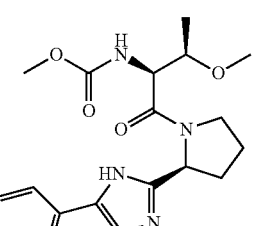

AA_264_A
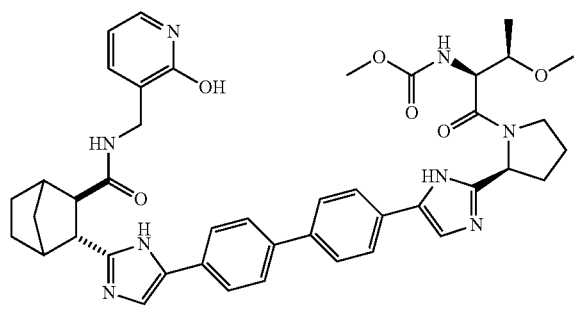
AA_263_C
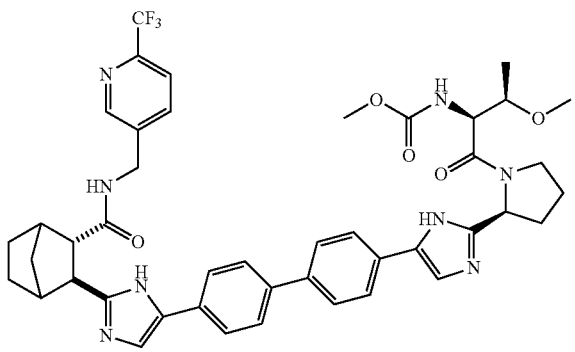
AA_264_B
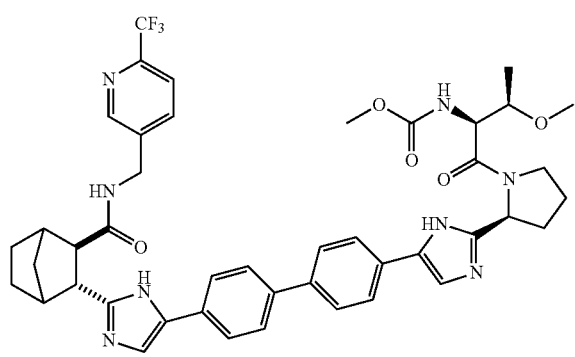
AA_265_A
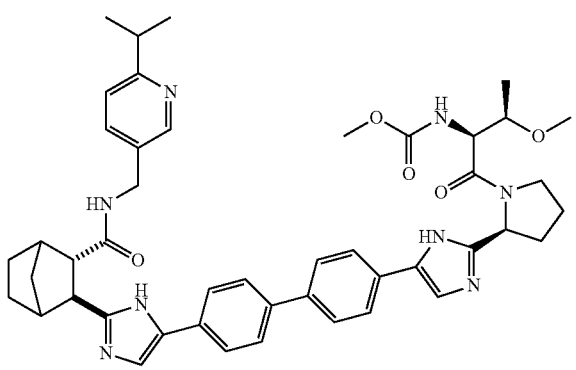
AA_265_B
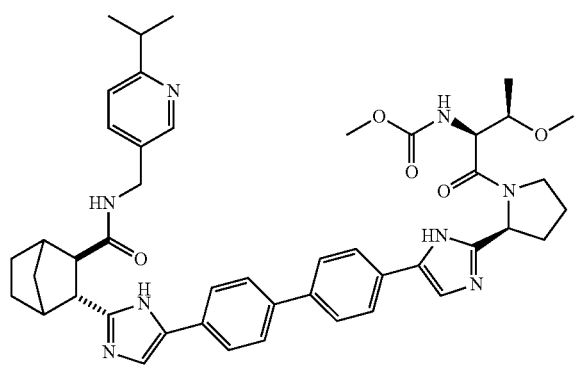
AA_266_A
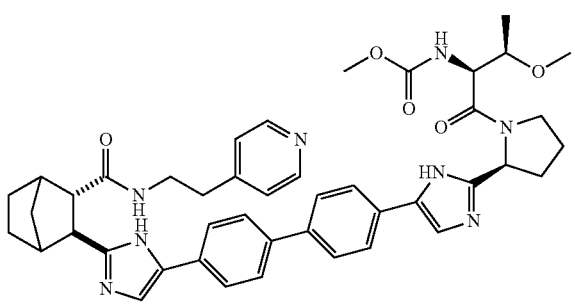
AA_266_B
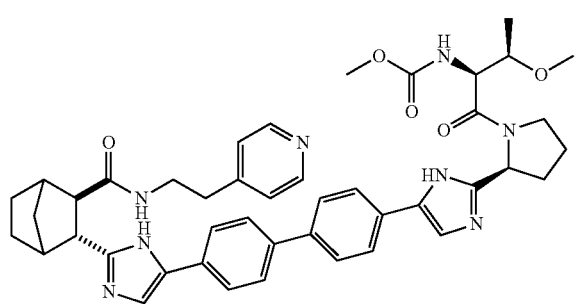
AA_267_A
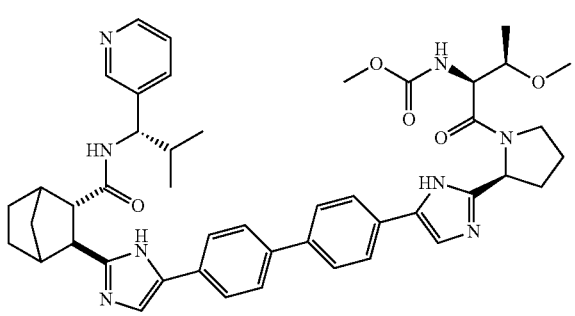

-continued
AA_267_B
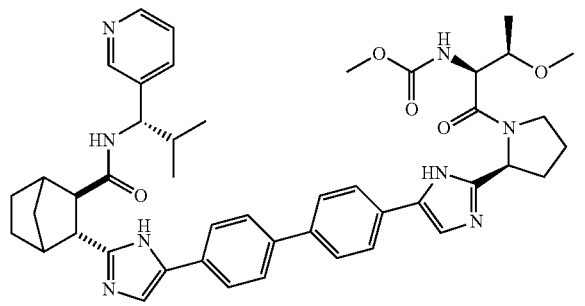
AA_268_A
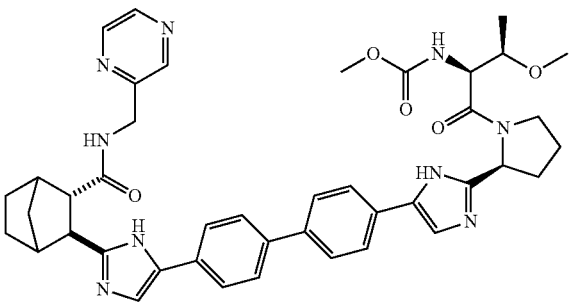
AA_268_B
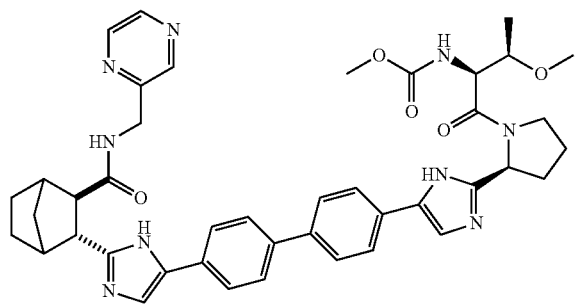
AA_271_A
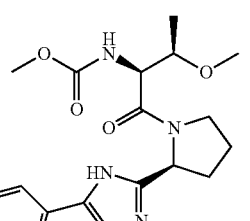
AA_271_B
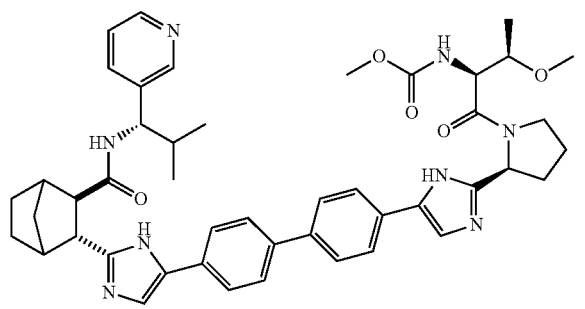
AA_272_B
AA_281_A
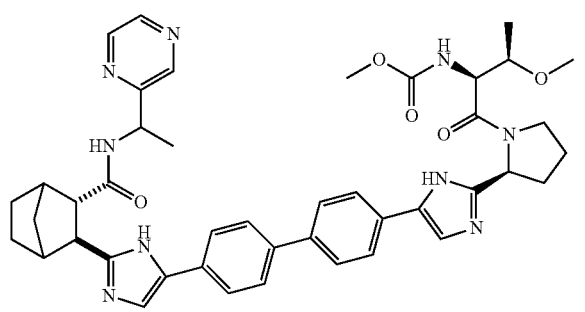
AA_281_B
AA_281_C
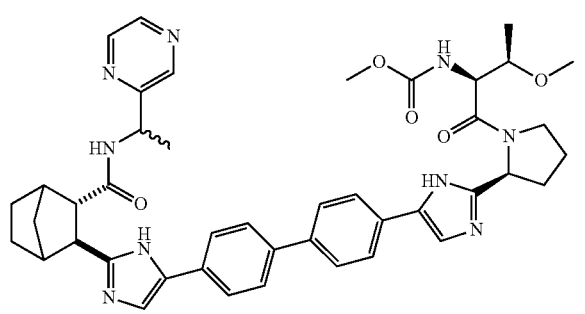
AA_192_A
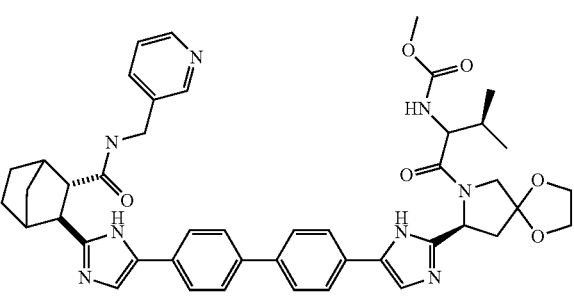

-continued
AA_192_B
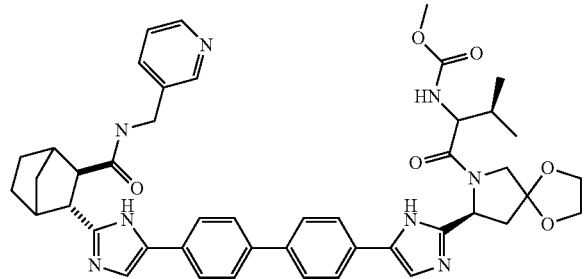
AA_179_A
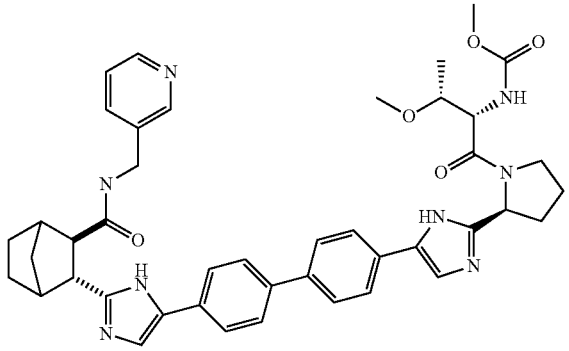
AA_179_B
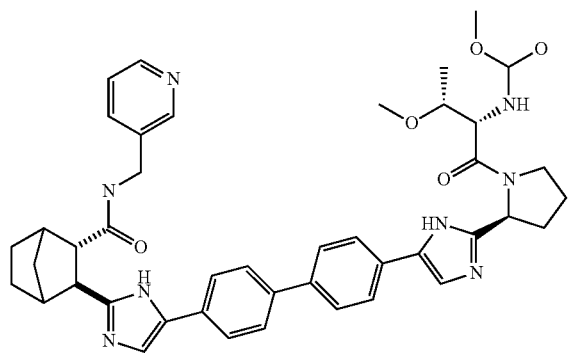
AA_191
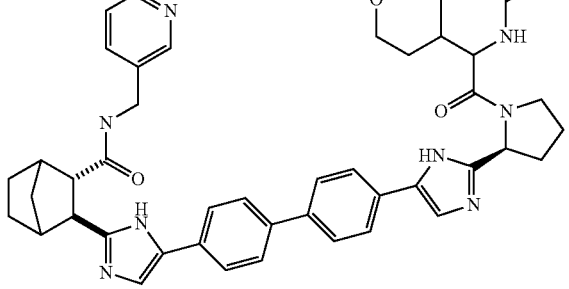
AA_197_A
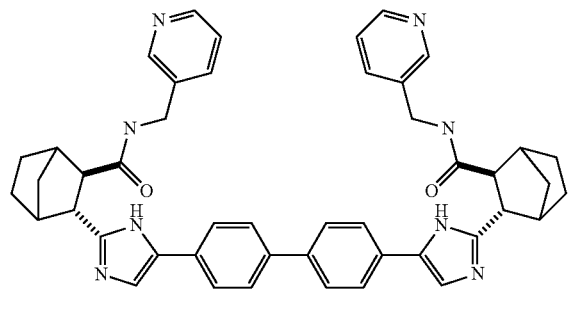
AA_180
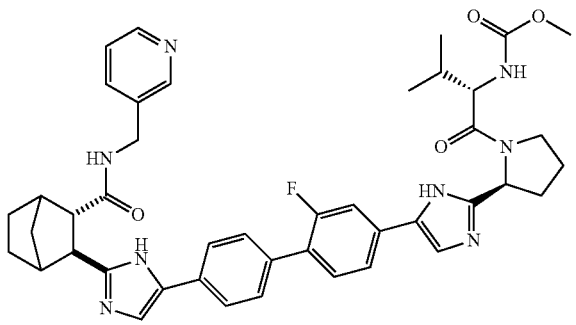 [SMILES: COC(=O)N[C@H](C(=O)N1CCC[C@H]1c1ncc(-c2ccc(-c3ccc(-c4cnc([C@H]5C6CCC(C6)[C@@H]5C(=O)NCc5cccnc5)[nH]4)cc3)c(F)c2)[nH]1)C(C)C]
AA_197_B
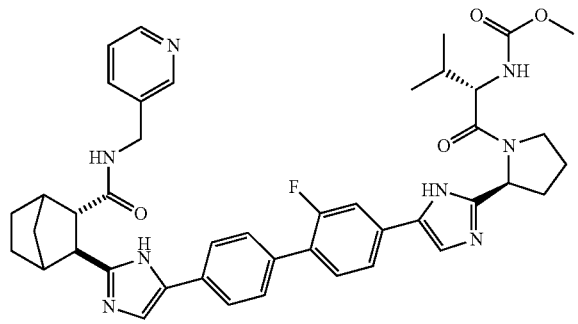 [SMILES: COC(=O)N[C@H](C(=O)N1CCC[C@H]1c1ncc(-c2ccc(-c3ccc(-c4cnc([C@H]5C6CCC(C6)[C@@H]5C(=O)NCc5cccnc5)[nH]4)cc3)c(F)c2)[nH]1)C(C)C]
AA_230_A
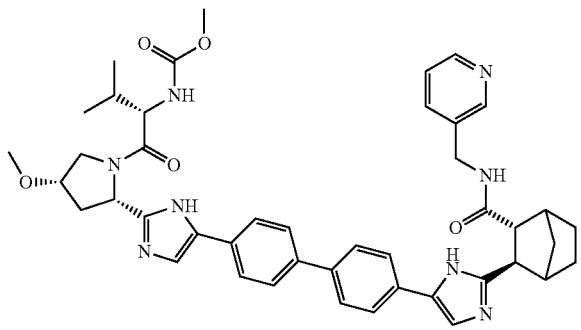 [SMILES: COC(=O)N[C@H](C(=O)N1C[C@@H](OC)C[C@H]1c1ncc(-c2ccc(-c3ccc(-c4cnc([C@@H]5C6CCC(C6)[C@H]5C(=O)NCc5cccnc5)[nH]4)cc3)cc2)[nH]1)C(C)C]

-continued
AA_230_B
AA_231_A
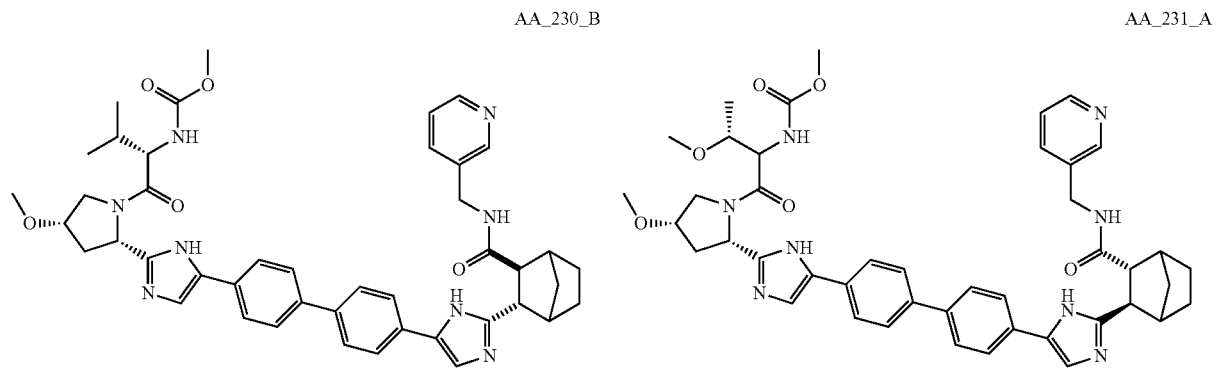
AA_231_B
AA_242_A
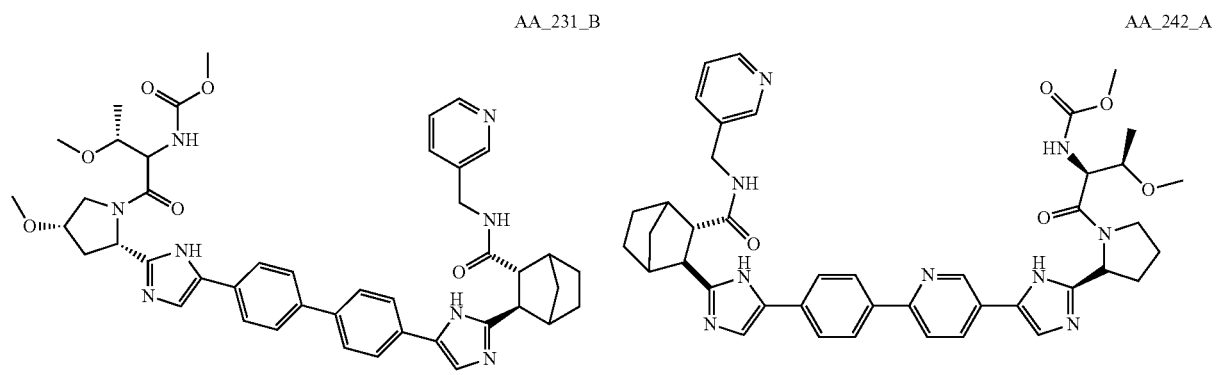
AA_242_B
AA_280_A
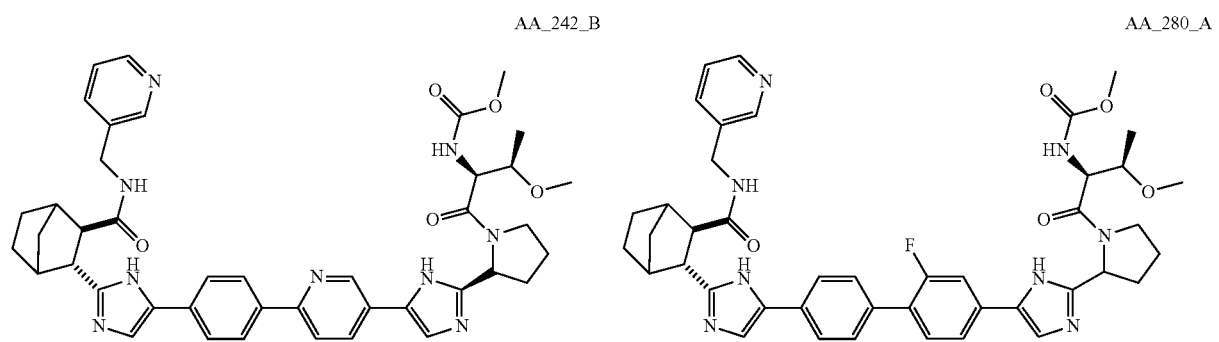
AA_280_B
AA_162_ENDOA2
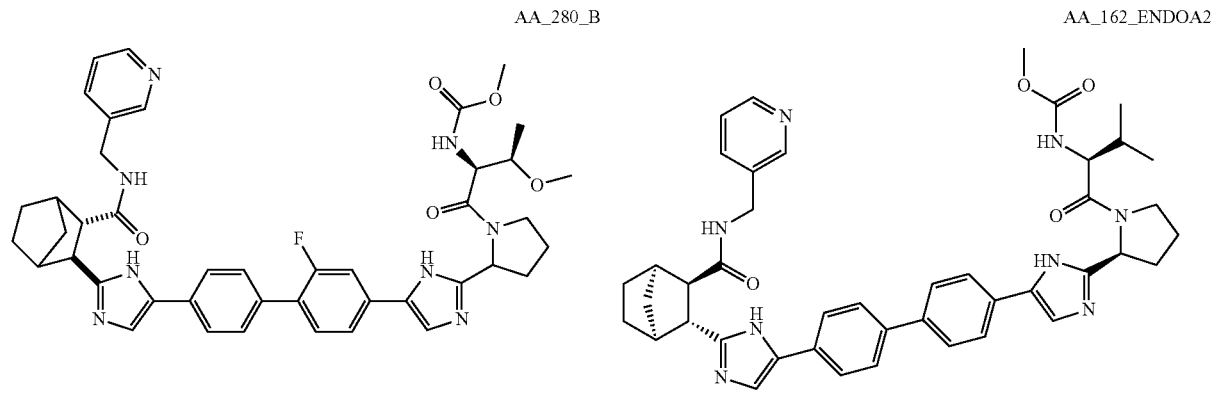

AA_273_ENDOA2
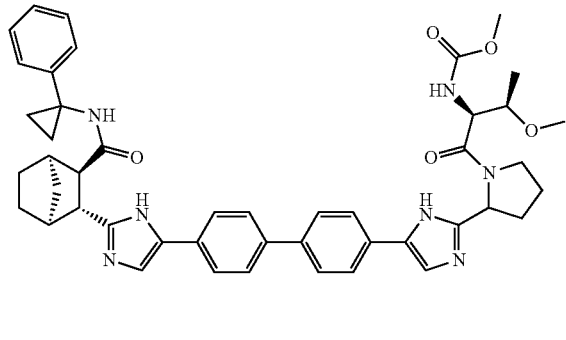
AA_195_ENDOA2
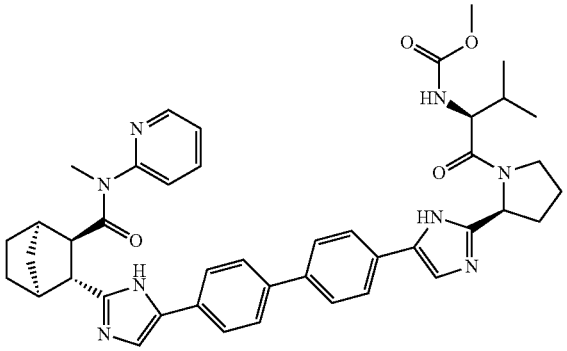 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)N(C)c5ccccn5)[nH]4)cc3)cc2)[nH]1)C(C)C]
AA_201_ENDOA2
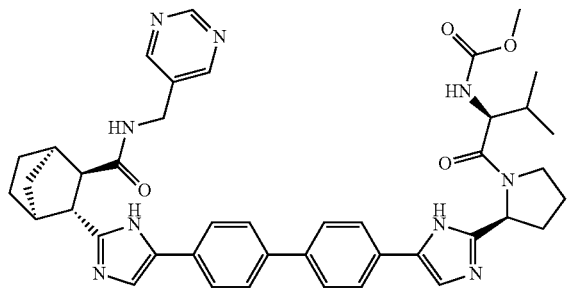 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)NCc5cncnc5)[nH]4)cc3)cc2)[nH]1)C(C)C]
AA_204_ENDOA2_A
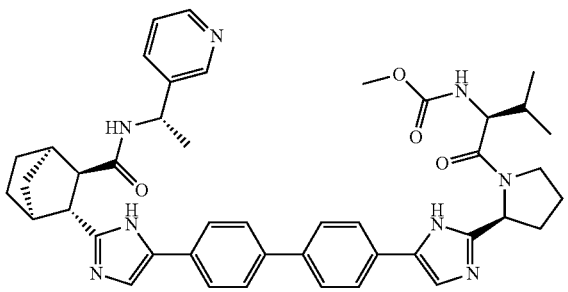
AA_204_ENDOA2_B
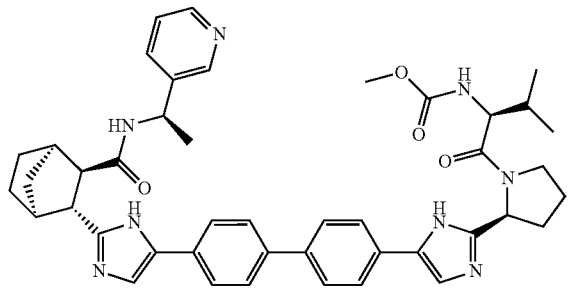
AA_206_ENDOA2
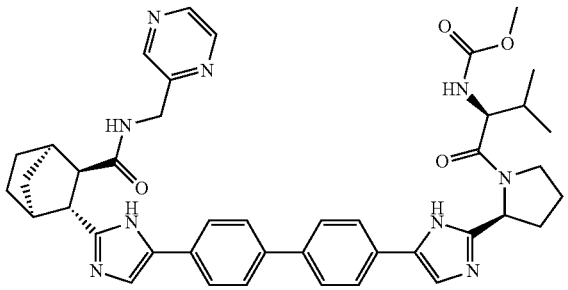
AA_208_ENDOA2
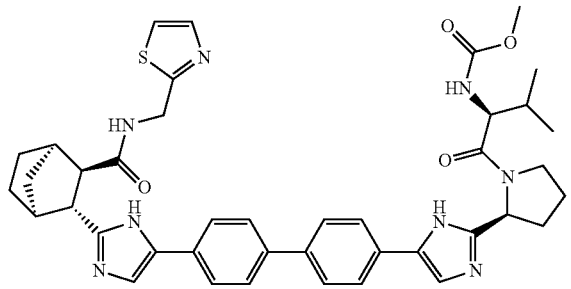 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)NCc5nccs5)[nH]4)cc3)cc2)[nH]1)C(C)C]
AA_214_ENDOA2
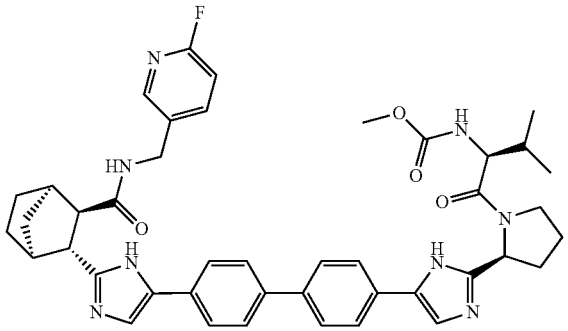 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)NCc5ccc(F)nc5)[nH]4)cc3)cc2)[nH]1)C(C)C]

-continued
AA_224_ENDOA2
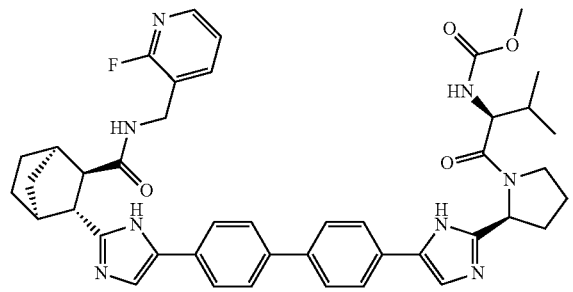
AA_233_ENDOA2_A
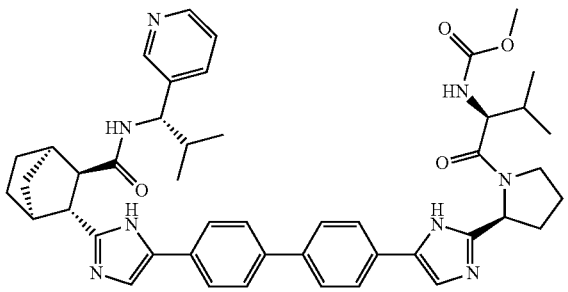 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)N[C@H](c5cccnc5)C(C)C)[nH]4)cc3)cc2)[nH]1)C(C)C]
AA_233_ENDOA2_B
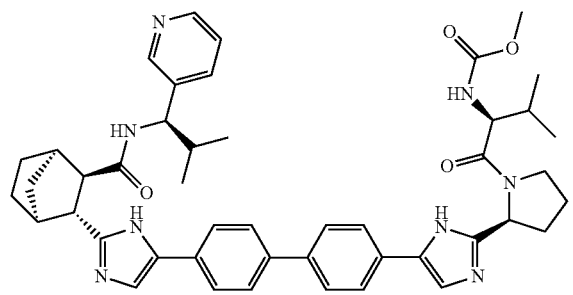
AA_243_ENDOA2_A
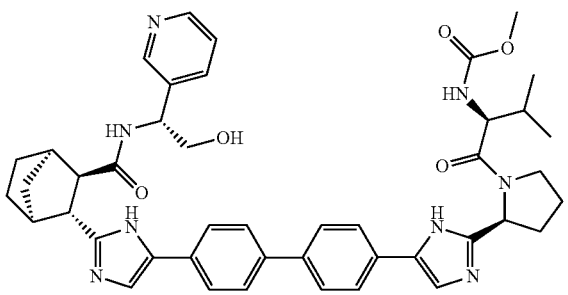
AA_243_ENDOA2_B
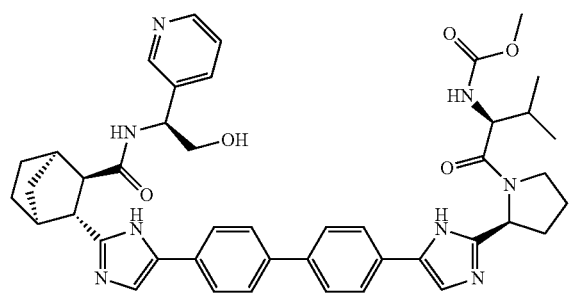
AA_270_ENDOA2_A
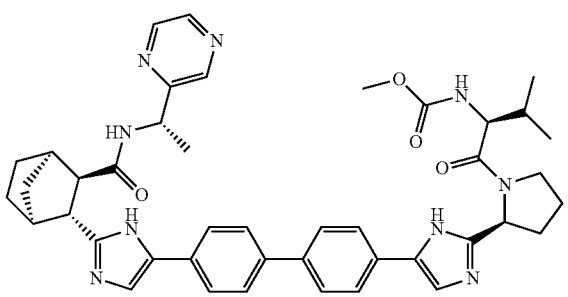 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)N[C@@H](C)c5cnccn5)[nH]4)cc3)cc2)[nH]1)C(C)C]
AA_270_ENDOA2_B
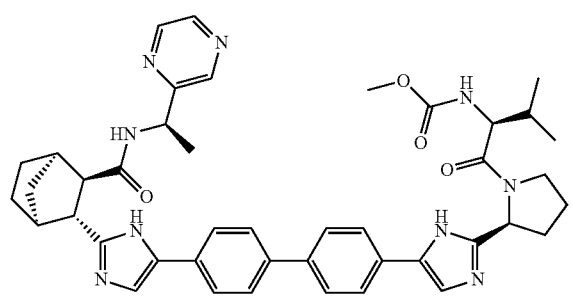 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)N[C@H](C)c5cnccn5)[nH]4)cc3)cc2)[nH]1)C(C)C]
AA_279_ENDOA2_A
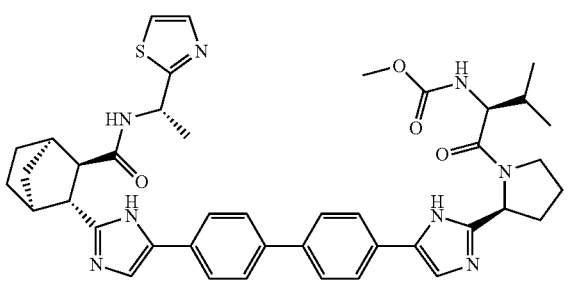
AA_279_ENDOA2_B
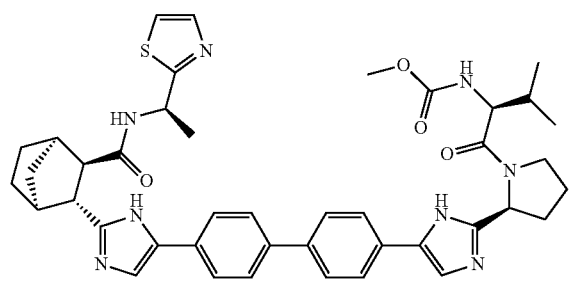 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)N[C@@H](C)c5nccs5)[nH]4)cc3)cc2)[nH]1)C(C)C]
AA_282_ENDOA2
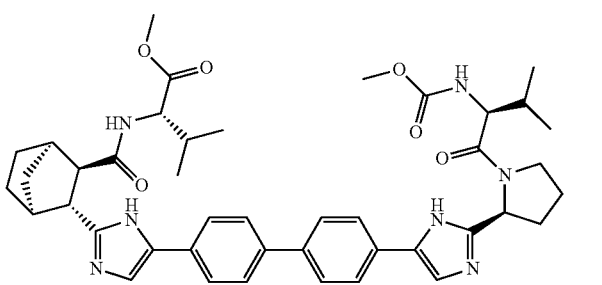 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)N[C@H](C(=O)OC)C(C)C)[nH]4)cc3)cc2)[nH]1)C(C)C]

-continued
AA_283_ENDOA2_A
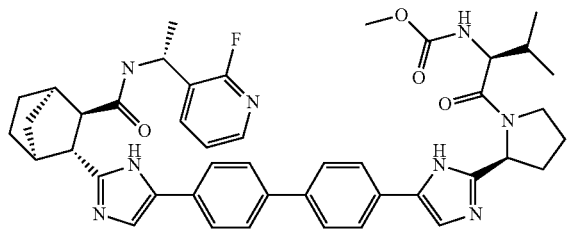 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)N[C@H](C)c5cccnc5F)[nH]4)cc3)cc2)[nH]1)C(C)C]
AA_283_ENDOA2_B
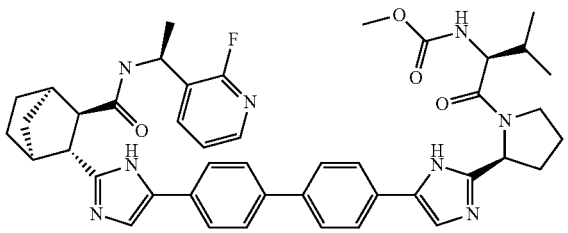 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)N[C@@H](C)c5cccnc5F)[nH]4)cc3)cc2)[nH]1)C(C)C]
AA_284_ENDOA2
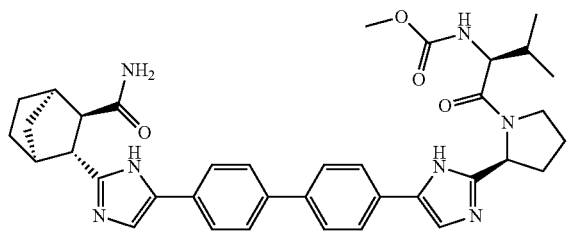 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(N)=O)[nH]4)cc3)cc2)[nH]1)C(C)C]
AA_285_ENDOA2
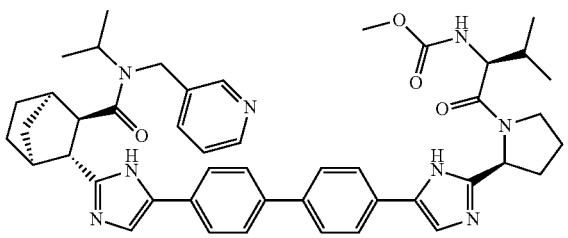 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)N(Cc5cccnc5)C(C)C)[nH]4)cc3)cc2)[nH]1)C(C)C]
AA_287_ENDOA2
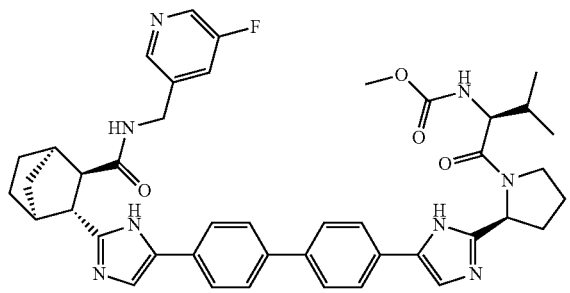 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)NCc5cncc(F)c5)[nH]4)cc3)cc2)[nH]1)C(C)C]
AA_288_ENDOA2
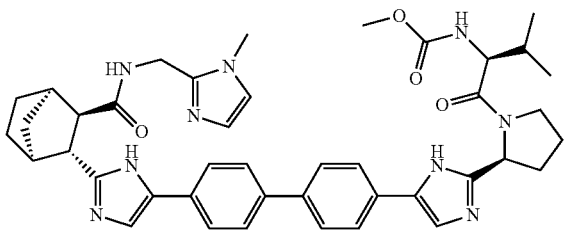 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)NCc5nccn5C)[nH]4)cc3)cc2)[nH]1)C(C)C]
AA_289_ENDOA2
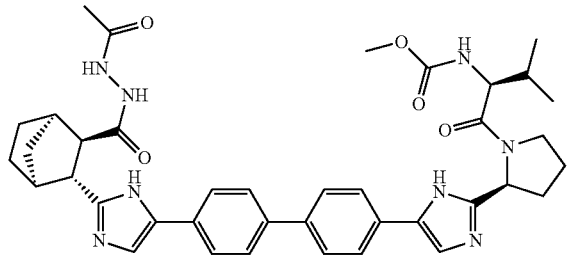 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)NNC(C)=O)[nH]4)cc3)cc2)[nH]1)C(C)C]
AA_290_ENDOA2
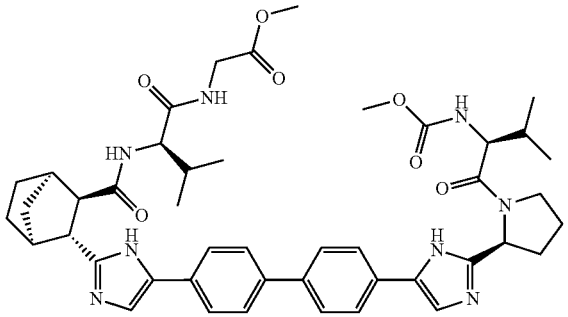 [SMILES: COC(=O)CNC(=O)[C@H](NC(=O)[C@@H]1[C@@H]2CC[C@@H](C2)[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C]
AA_291_ENDOA2
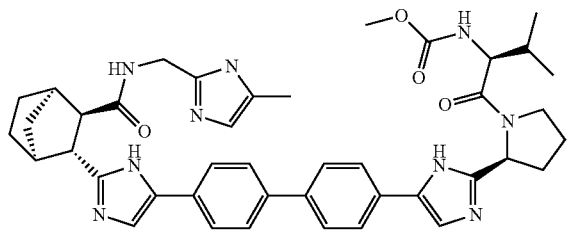
AA_292_ENDOA2_M
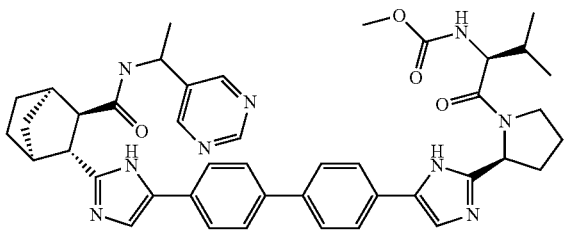 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)NC(C)c5cncnc5)[nH]4)cc3)cc2)[nH]1)C(C)C]

-continued
AA_293_ENDOA2
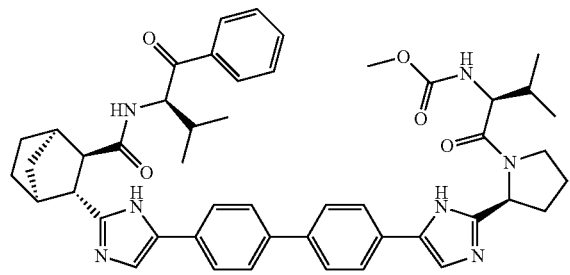 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)N[C@@H](C(=O)c5ccccc5)C(C)C)[nH]4)cc3)cc2)[nH]1)C(C)C]
AA_294_ENDOA2
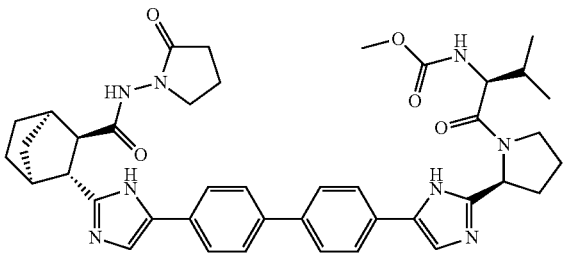 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)NN5CCCC5=O)[nH]4)cc3)cc2)[nH]1)C(C)C]
AA_295_ENDOA2_A
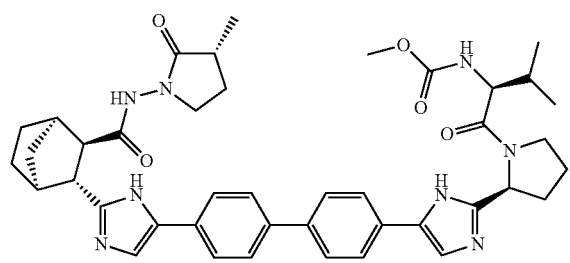
AA_295_ENDOA2_B
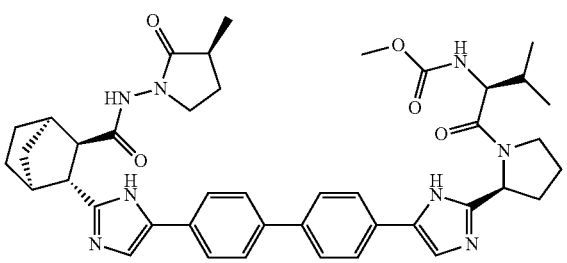 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)NN5CC[C@H](C)C5=O)[nH]4)cc3)cc2)[nH]1)C(C)C]
AA_296_ENDOA2
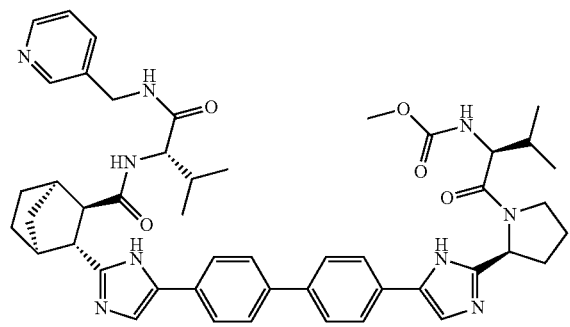 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)N[C@H](C(=O)NCc5cccnc5)C(C)C)[nH]4)cc3)cc2)[nH]1)C(C)C]
AA_297_ENDOA2
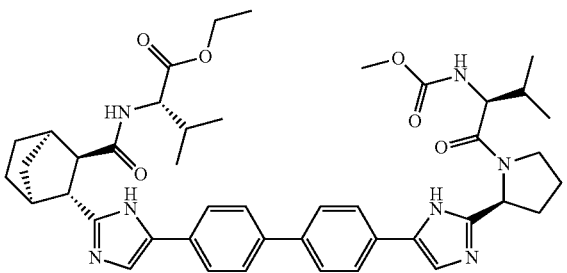 [SMILES: CCOC(=O)[C@@H](NC(=O)[C@@H]1[C@@H]2CC[C@@H](C2)[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C]
AA_298_ENDOA2
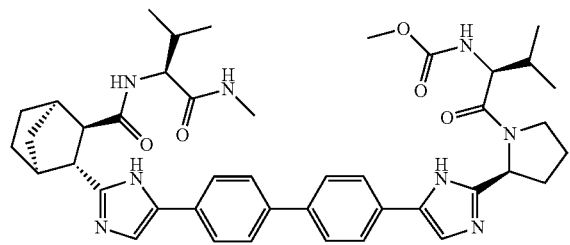 [SMILES: CNC(=O)[C@@H](NC(=O)[C@@H]1[C@@H]2CC[C@@H](C2)[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C]
AA_299_ENDOA2
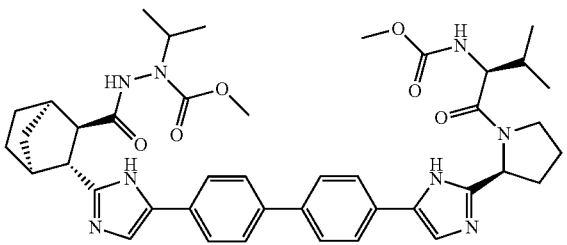 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)NN(C(=O)OC)C(C)C)[nH]4)cc3)cc2)[nH]1)C(C)C]
AA_300_ENDOA2
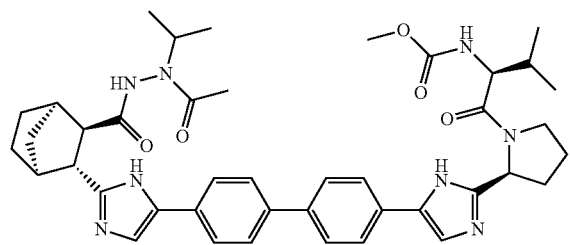 [SMILES: COC(=O)N[C@H](C(=O)N1CCC[C@H]1c1ncc(-c2ccc(-c3ccc(-c4cnc([C@@H]5[C@H]6CC[C@H](C6)[C@H]5C(=O)NN(C(C)=O)C(C)C)[nH]4)cc3)cc2)[nH]1)C(C)C]
AA_301_ENDOA2
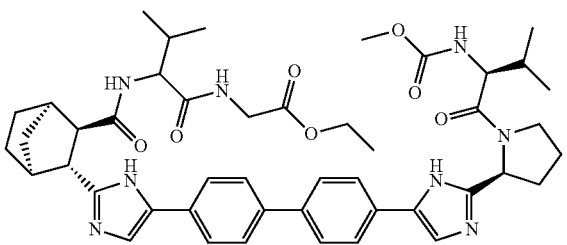 [SMILES: CCOC(=O)CNC(=O)[C@@H](NC(=O)[C@@H]1[C@@H]2CC[C@@H](C2)[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C]

-continued
AA_239
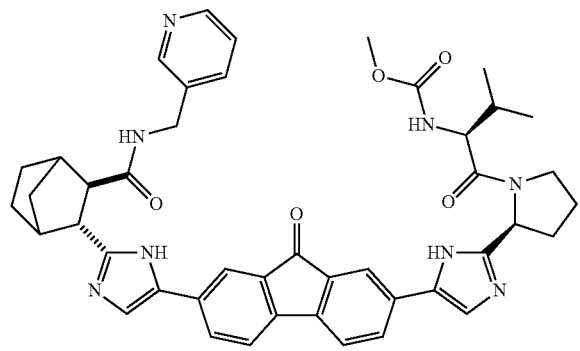
AA_238
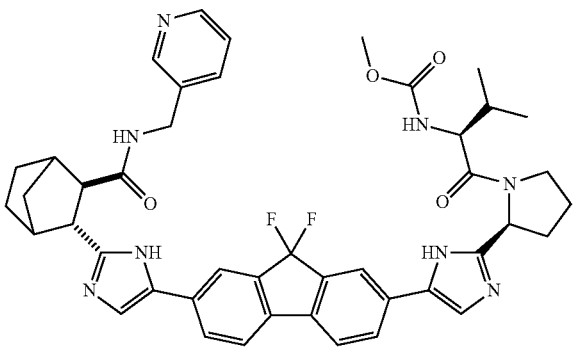
AA_241_A
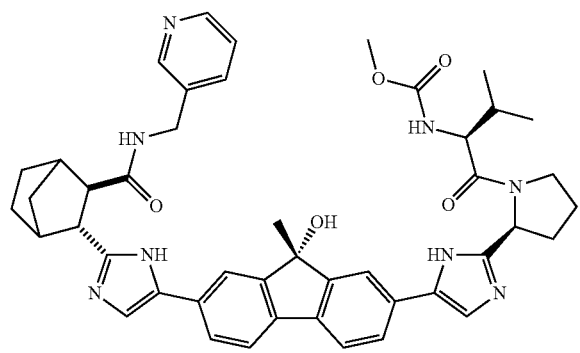
AA_241_B
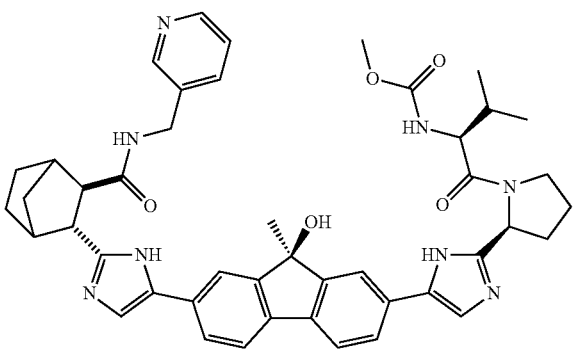
AA_242
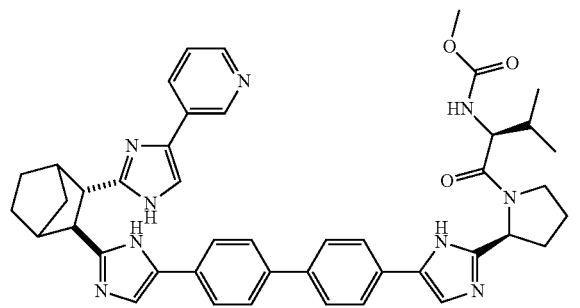
AA_150_A
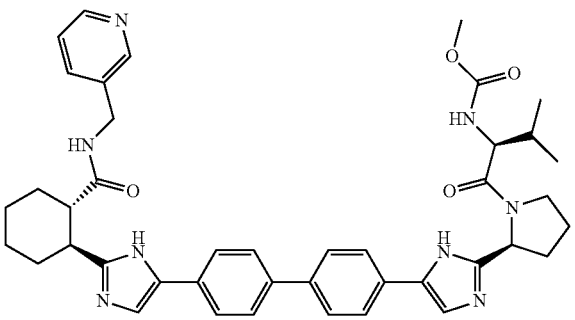
AA_150_B
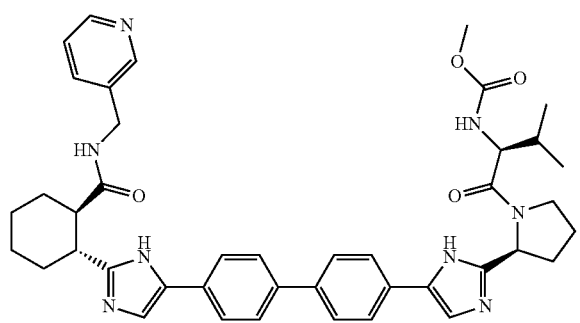
AA_184
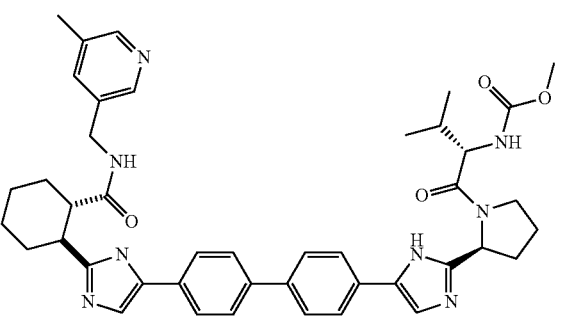 [SMILES: COC(=O)N[C@H](C(=O)N1CCC[C@H]1c1ncc(-c2ccc(-c3ccc(-c4cnc([C@H]5CCCC[C@@H]5C(=O)NCc5cncc(C)c5)[nH]4)cc3)cc2)[nH]1)C(C)C]

-continued

AA_185

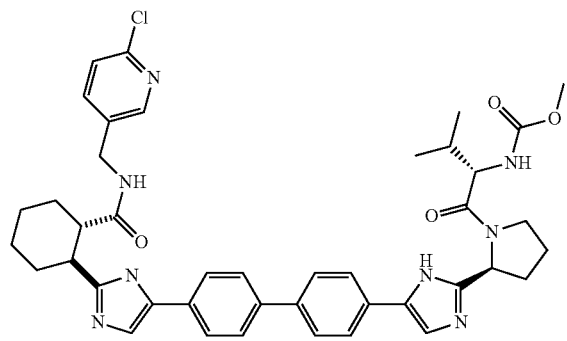 [SMILES: COC(=O)N[C@H](C(=O)N1CCC[C@H]1c1ncc(-c2ccc(-c3ccc(-c4cnc([C@H]5CCCC[C@@H]5C(=O)NCc5ccc(Cl)nc5)[nH]4)cc3)cc2)[nH]1)C(C)C]

AA_186

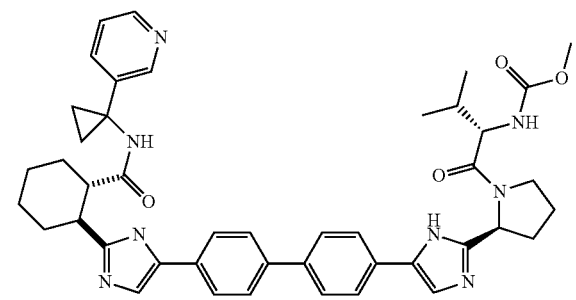 [SMILES: COC(=O)N[C@H](C(=O)N1CCC[C@H]1c1ncc(-c2ccc(-c3ccc(-c4cnc([C@H]5CCCC[C@@H]5C(=O)NC5(c6cccnc6)CC5)[nH]4)cc3)cc2)[nH]1)C(C)C]

AA_286

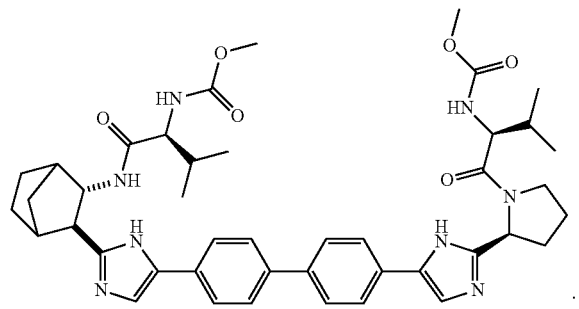

Another aim of the present invention is to provide a process for preparing the compound represented by formula (II), which comprises a step represented by scheme (S1):

(S1)

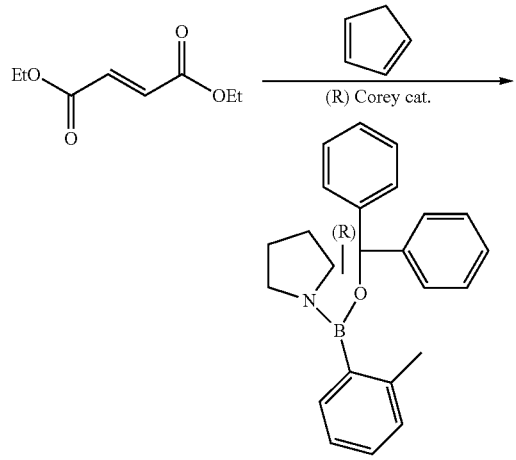

wherein the sub-structural unit of the structural unit

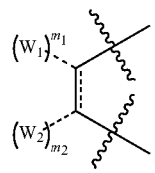

in the compound represented by formula (II) is

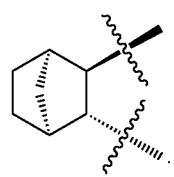

In certain embodiments of the present invention, the process for preparing the compound represented by formula (II) comprises a step represented by scheme (S2):

(S2)

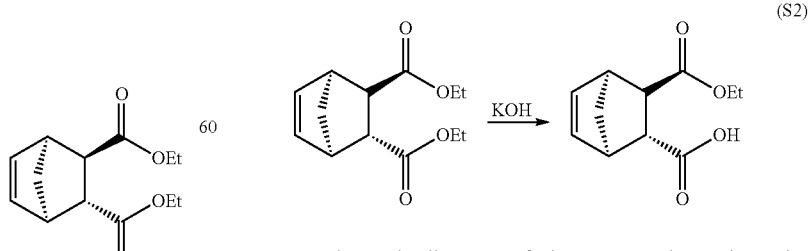

In certain embodiments of the present invention, the process for preparing the compound represented by formula (II) comprises a step represented by scheme (S3):

127 128
(S3)
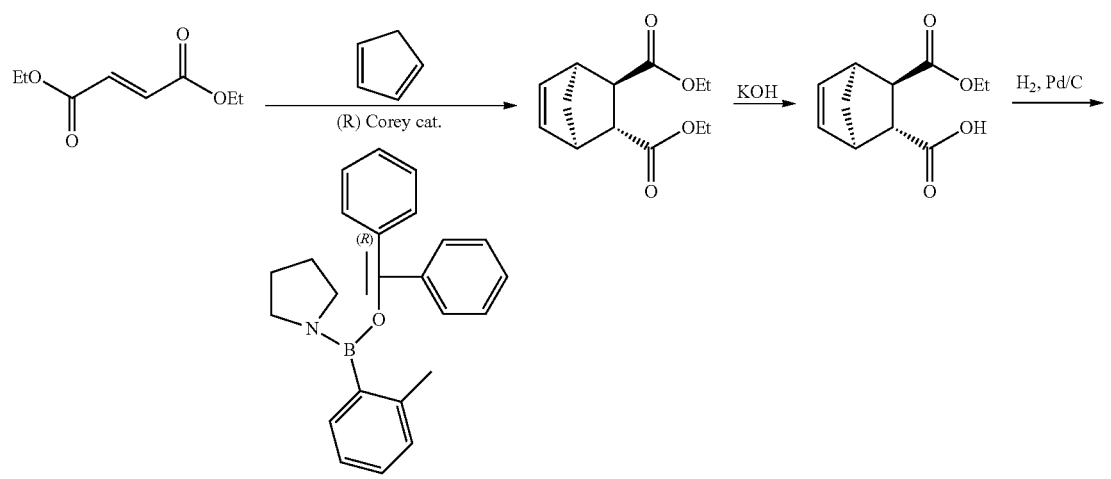
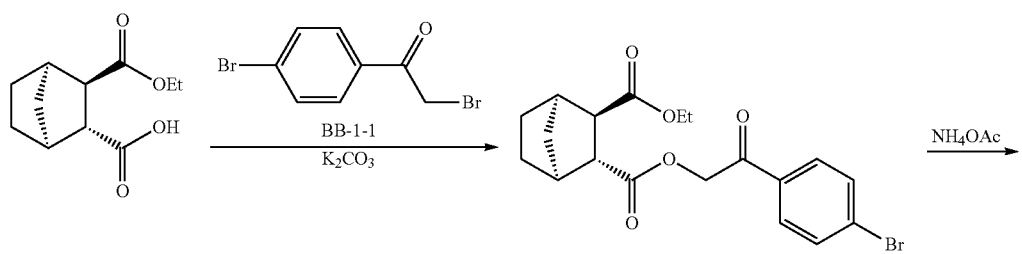
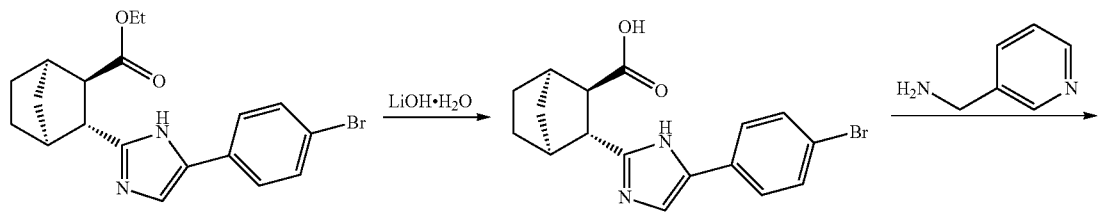
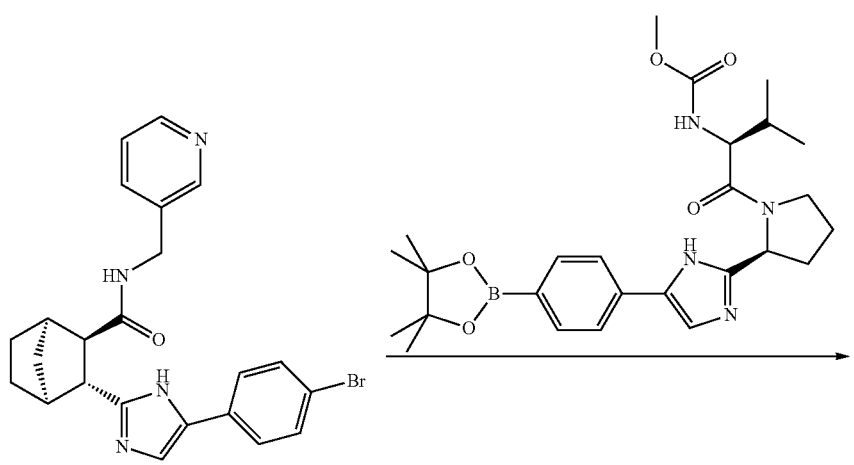

-continued

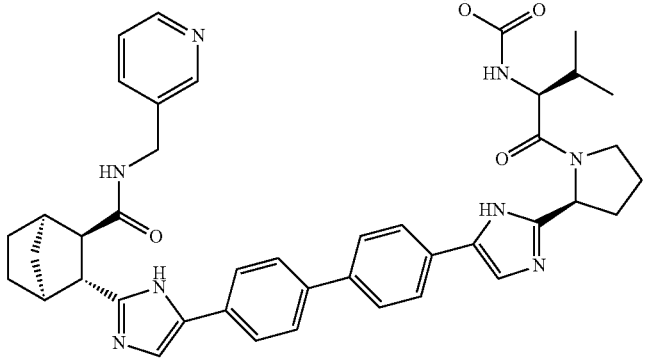

wherein the compound represented by formula (II) is

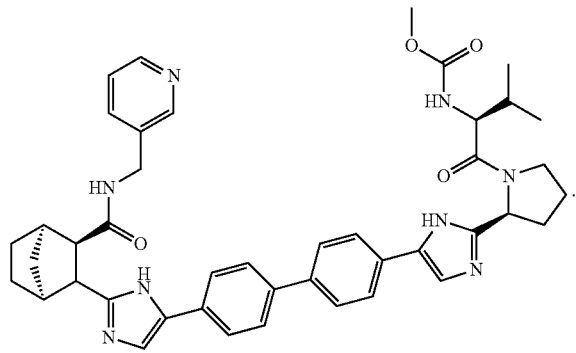

Another aim of the present invention is to provide a pharmaceutical composition, which comprises a therapeutically effective amount of the compound or the pharmaceutically acceptable salt thereof, and a pharmaceutically acceptable carrier.

Another aim of the present invention is to provide a use of the compound or the pharmaceutically acceptable salt thereof or the pharmaceutical composition in manufacturing a medicament for treating HCV.

Definition and Specification

Unless otherwise specified, the following terms and phrases used herein are intended to have the following meanings. A particular term or phrase should not be considered uncertain or unclear in the absence of a specific definition while should be understood according to the ordinary meaning. When a trade name appears herein, it refers to the corresponding commodity or its active ingredient.

$C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$.

The $C_{1-12}$ alkyl or heteroalkyl, $C_{3-12}$ cyclic group or heterocyclic hydrocarbon group, and the $C_{1-12}$ alkyl or heteroalkyl substituted by a $C_{3-12}$ cyclic hydrocarbon group or a heterocyclic hydrocarbon group include but not limited to:

a $C_{1-12}$ alkyl, a $C_{1-12}$ alkyl amino, a N,N-bis($C_{1-12}$ alkyl) amino, a $C_{1-12}$ alkoxyl, a $C_{1-12}$ alkyl acyl, a $C_{1-12}$ alkoxy-carbonyl, a $C_{1-12}$ alkyl sulfonyl, a $C_{1-12}$ alkyl sulfinyl, a $C_{3-12}$ cycloalkyl, a $C_{3-12}$ cycloalkyl amino, a $C_{3-12}$ heterocycloalkyl amino, a $C_{3-12}$ cycloalkoxy, a $C_{3-12}$ cycloalkyl acyl, a $C_{3-12}$ cycloalkoxy carbonyl, a $C_{3-12}$ cycloalkyl sulfonyl, a $C_{3-12}$ cycloalkyl sulfinyl; a 5-12 membered aryl or heteroaryl, a 5-12 membered aryl alkyl or heteroaryl alkyl;

a methyl, an ethyl, a n-propyl, an isopropyl, —CH$_2$C(CH$_3$)(CH$_3$)(OH), a cyclopropyl, a cyclobutyl, a propyl methylene, a cyclopropyl carbonyl, a benzyloxy, a trifluoromethyl, an aminomethyl, a hydroxymethyl, a methoxy, a formyl, a methoxy carbonyl, a methyl sulfonyl, a methyl sulfinyl, an ethoxy, an acetyl, an ethyl sulfonyl, an ethoxy carbonyl, a dimethylamino, a diethylamino, a dimethyl amino carbonyl, a diethyl amino carbonyl;

N(CH$_3$)$_2$, NH(CH$_3$), —CH$_2$CF$_3$, —CH$_2$CH$_2$CF$_3$, —CH$_2$CH$_2$F, —CH$_2$CH$_2$S(=O)$_2$CH$_3$, —CH$_2$CH$_2$CN,

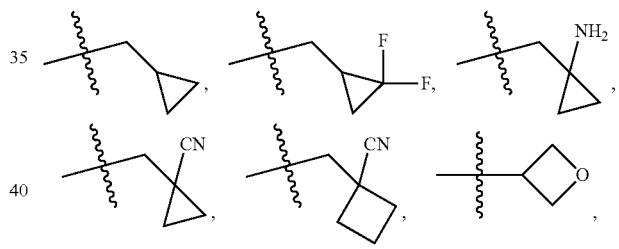

—CH$_2$CH(OH)(CH3)$_2$, —CH$_2$CH(F)(CH$_3$)$_2$, —CH$_2$CH$_2$F, —CH$_2$CF$_3$, —CH$_2$CH$_2$CF$_3$, —CH$_2$CH$_2$NH$_2$, —CH$_2$CH$_2$OH, —CH$_2$CH$_2$OCH$_3$, —CH$_2$CH$_2$CH$_2$OCH$_3$, —CH$_2$CH$_2$N(CH$_3$)$_2$, —S(=O)$_2$CH$_3$, —CH$_2$CH$_2$S(=O)$_2$CH$_3$,

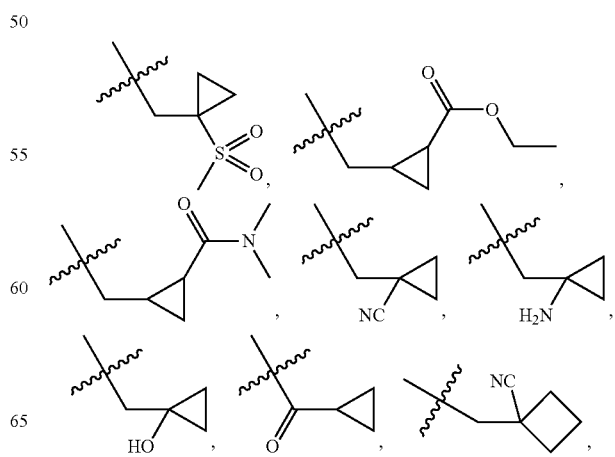

131
-continued
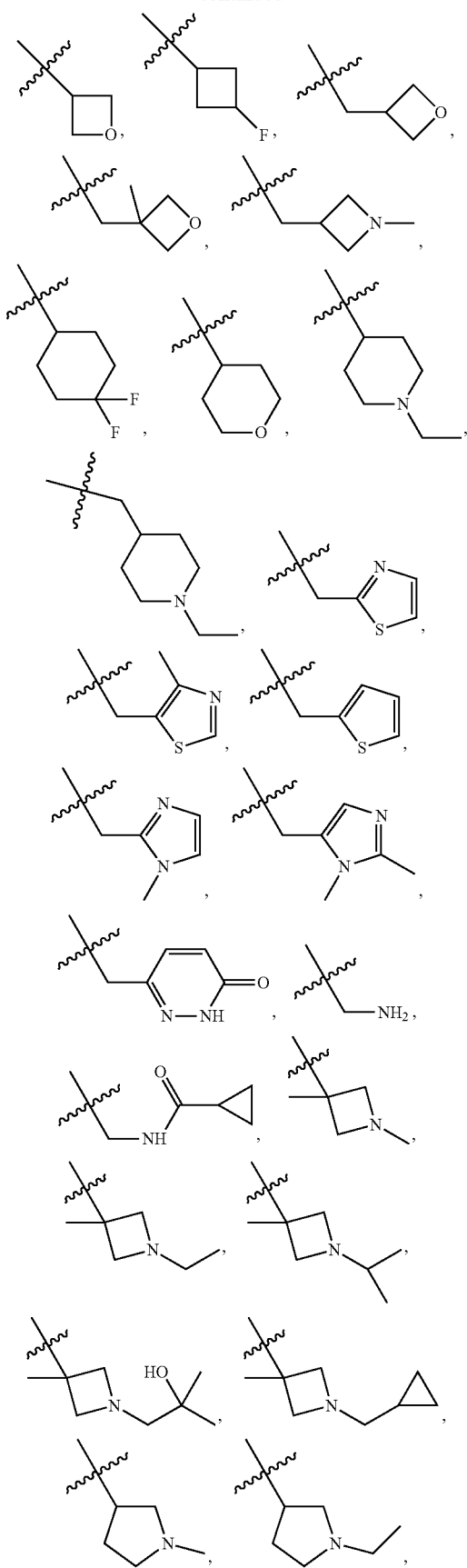
132
-continued
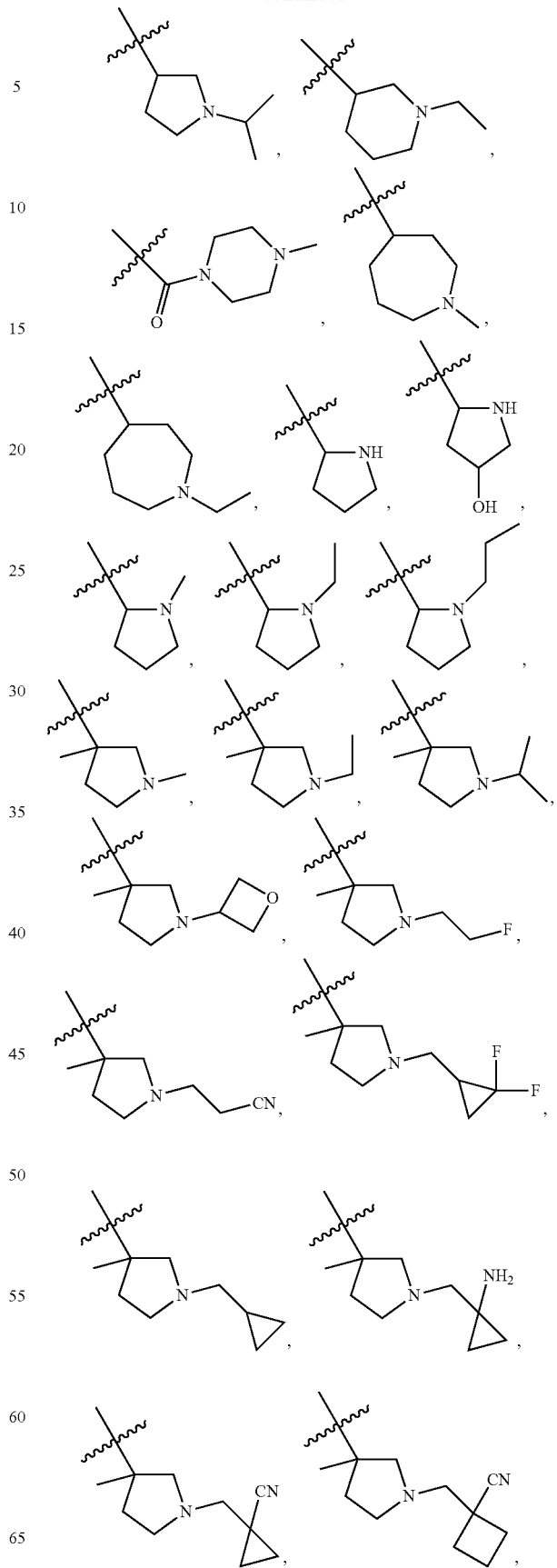

-continued
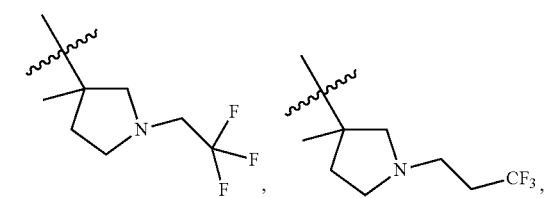
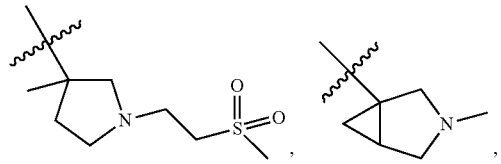
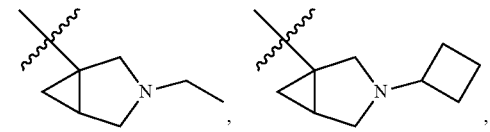
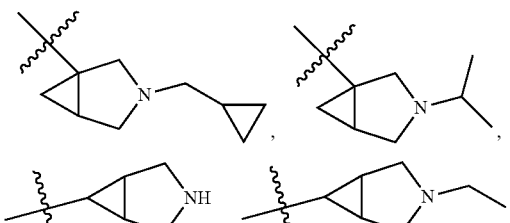
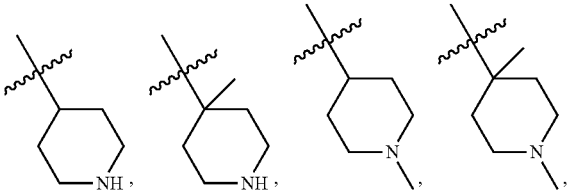
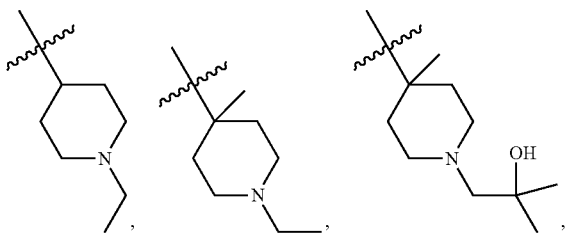
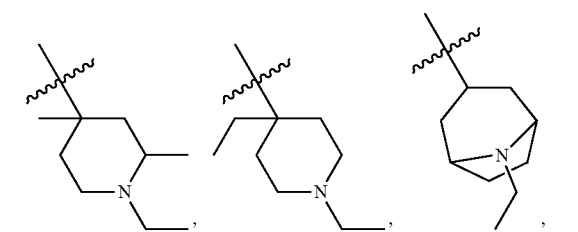
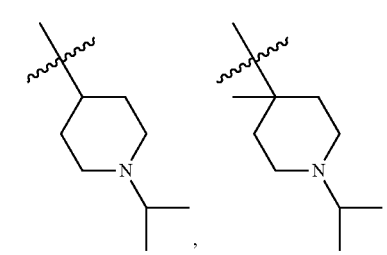
-continued
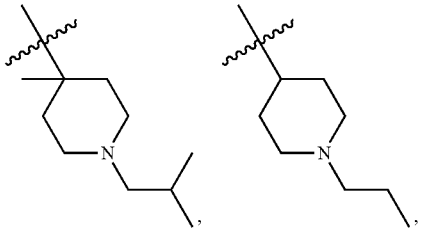
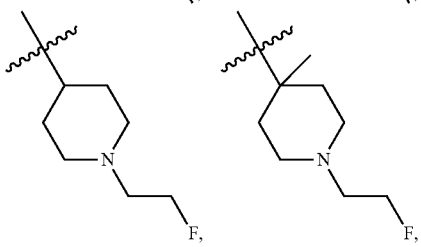
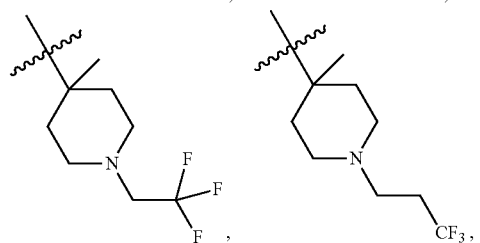
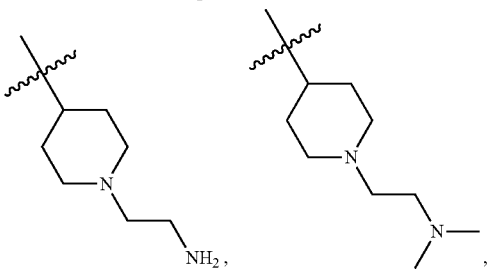
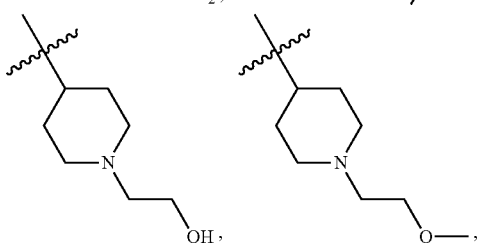
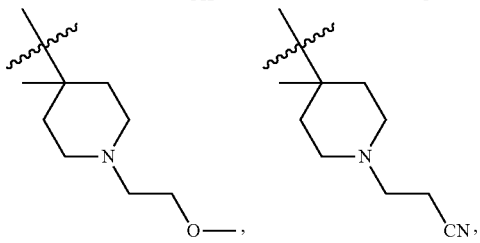
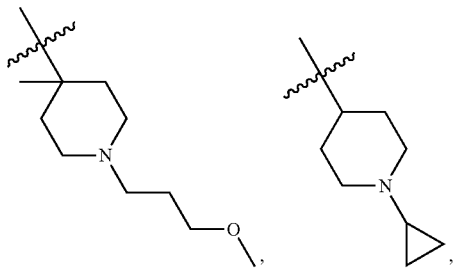

135
-continued
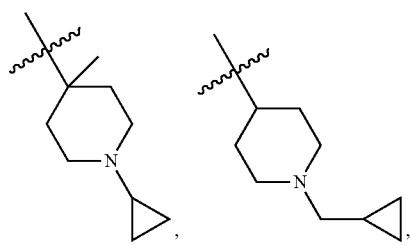
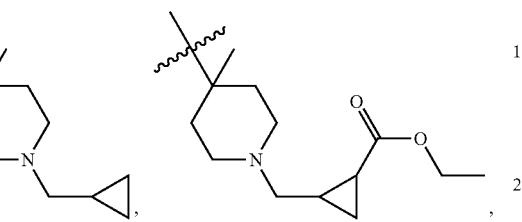
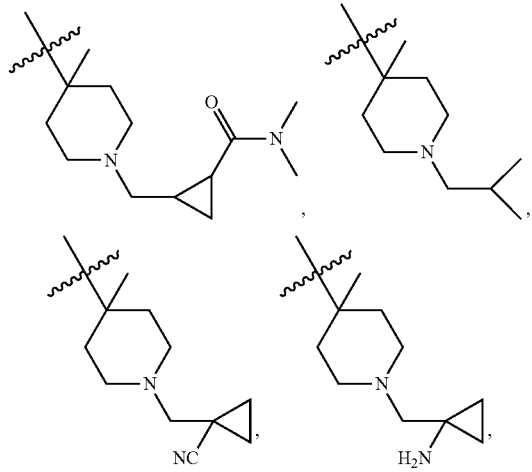
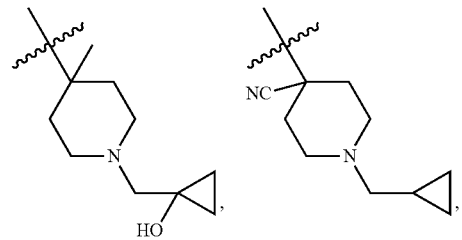
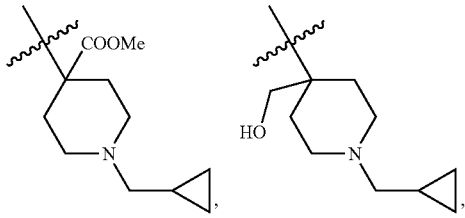
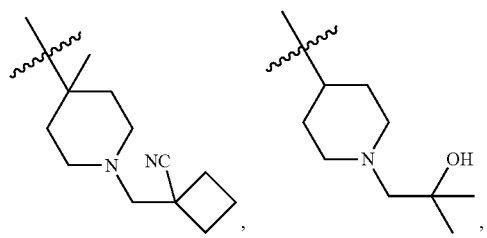
136
-continued
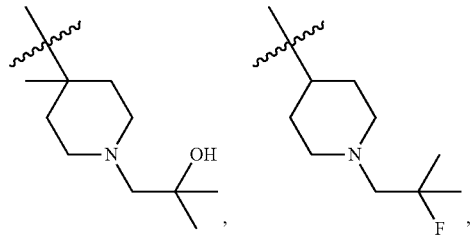
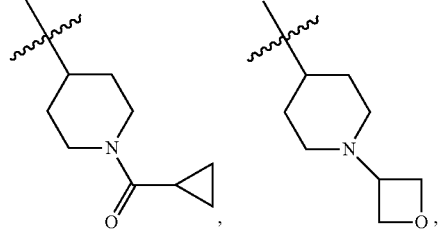
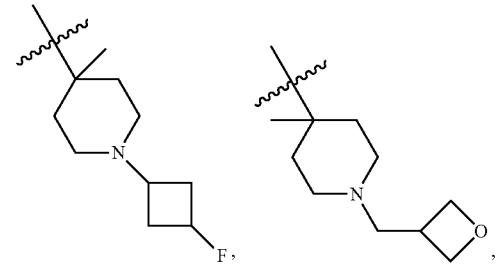
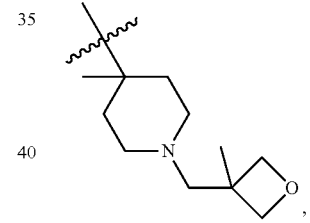
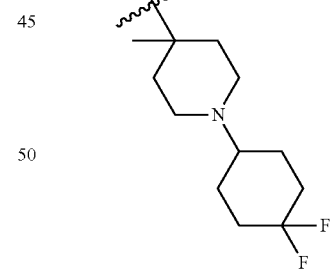
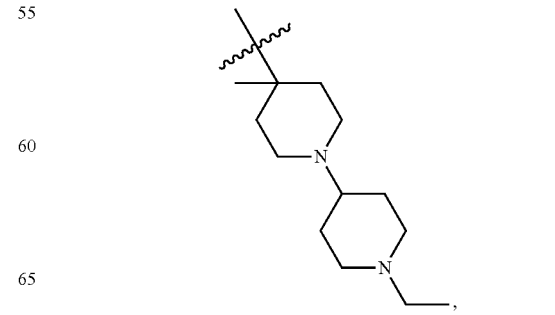

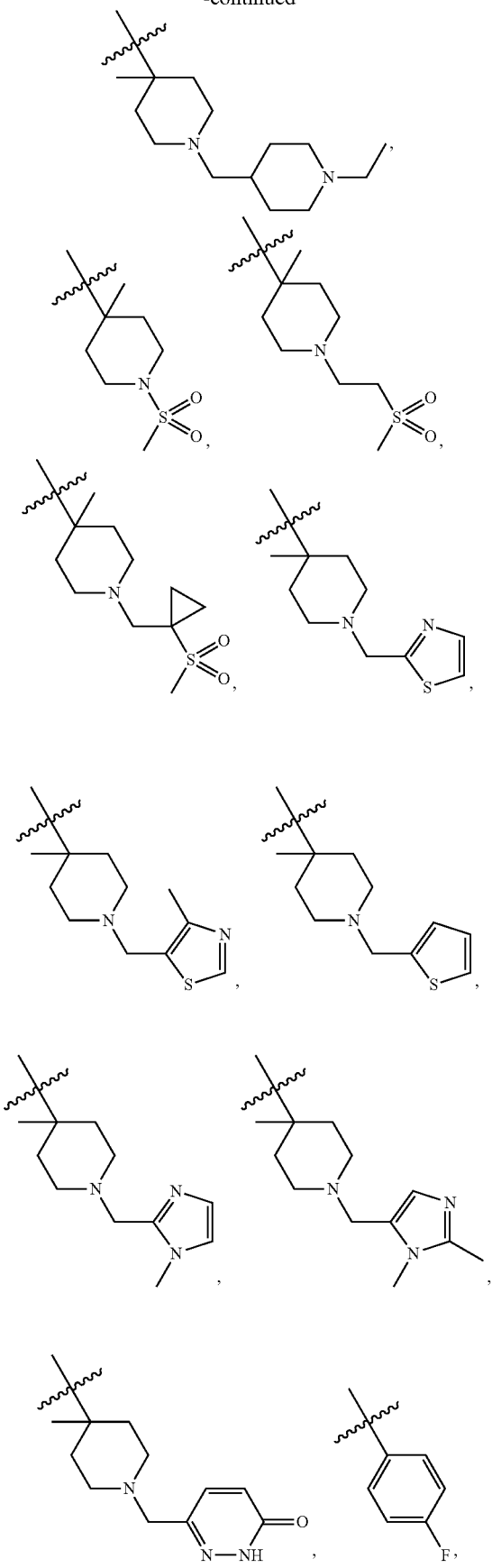

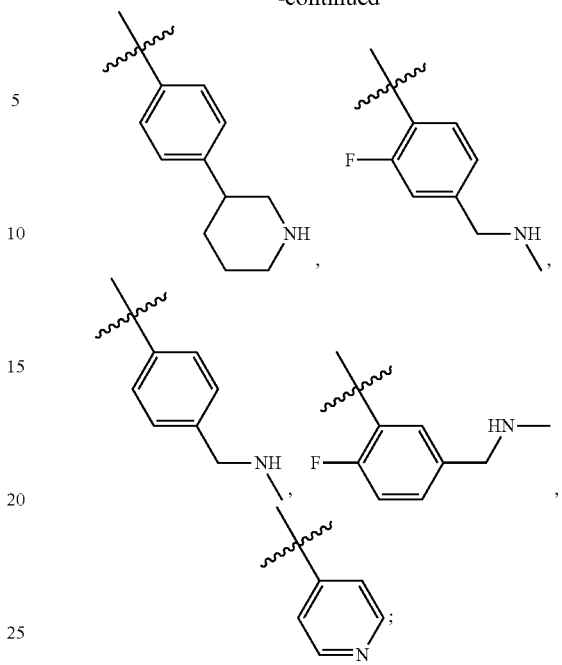

and a phenyl, a thiazolyl, a biphenyl, a naphthyl, a cyclopentyl, a furyl, a 3-pyrrolinyl, a pyrrolidinyl, a 1,3-dioxolanyl, a pyrazolyl, a 2-pyrazolinyl, a pyrazolidinyl, an imidazolyl, an oxazolyl, a thiazolyl, a 1,2,3-azolyl, a 1,2,3-triazolyl, a 1,2,4-triazolyl, a 1,3,4-thiadiazolyl, a 4H-pyranyl, a pyridyl, a piperidyl, a 1,4-dioxanyl, a morpholinyl, a pyridazinyl, a pyrimidinyl, a pyrazinyl, a piperazinyl, a 1,3,5-trithianyl, a 1,3,5-triazinyl, a benzofuranyl, a benzothiophenyl, an indolyl, a benzimidazolyl, a benzothiazolyl, a purinyl, a quinolinyl, an isoquinolinyl, a cinnolinyl or a quinoxalinyl;

Herein, the term "pharmaceutically acceptable" refers to that those compounds, materials, compositions and/or forms of administration are within the scope of reliable medical judgment and applicable for use in contact with human and animal tissue but without excess toxicity, irritation, allergic reactions or other problems or complications, which meet the reasonable benefit/risk ratio.

The term "pharmaceutically acceptable salt" refers to the salt of the compound of the present invention, which is prepared by the compound with specific substituent disclosed by the present invention and relatively non-toxic acid or alkali. When the compound of the present invention contains a relatively acidic functional group, an alkali-addition salt can be obtained by contacting the compound in a neutral form with a sufficient amount of alkali in a pure solution or a suitable inert solvent. The pharmaceutically acceptable alkali-addition salt includes the salt of sodium, potassium, calcium, ammonium, organic ammonia or magnesium or the like. When the compound of the present invention contains a relatively alkaline functional group, an acid-addition salt can be obtained by contacting the compound in a neutral form with a sufficient amount of acid in a pure solution or a suitable inert solvent. Examples of the pharmaceutically acceptable acid-addition salt include a salt of an inorganic acid, the inorganic acid includes such as hydrochloric acid, hydrobromic acid, nitric acid, carbonic acid, bicarbonate, phosphoric acid, hydrogen phosphate, dihydrogen phosphate, sulfuric acid, hydrogen sulfate, hydriodic acid, phosphorous acid etc; and a salt of an organic acid, the organic acid includes such as acetic acid, propionic acid, isobutyric acid, maleic acid, malonic acid, benzoic acid, succinic acid, suberic acid, fumaric acid, lactic acid, mandelic acid, phthalic acid, phenylsulfonic acid, p-toluene sulfonic acid, citric acid, tartaric acid, methylsulfonic acid and the like; and also includes a salt of an amino acid (e.g. arginine etc.), and a salt of an organic acid such as glucuronic acid and the like (see Berge et al., "Pharmaceutical Salts", Journal of Pharmaceutical Science 66: 1-19 (1977)). Some specific compounds of the present invention contains both alkaline and acidic functional groups which can be transformed to be any one of the alkali-addition or acid-addition salt.

Preferably, a neutral form of a compound is regenerated by contacting a salt with a base or an acid in a conventional manner and then separating the parent compound. The difference between a parent form of a compound and the various salt forms thereof lies in some physical properties, such as that the solubility in a polar solvent is different.

The "pharmaceutically acceptable salt" in the present invention is a derivative of the compound of the present invention, wherein the parent compound is modified by being salifyied with an acid or an alkali. Examples of the pharmaceutically acceptable salt include, but not limited to, an inorganic acid-addition or an organic acid-addition salt of an alkali such as amine, an acid radical such as an alkali metal or an organic salt of a carboxylic acid and so on. The pharmaceutically acceptable salt includes conventionally non-toxic salts or quaternary ammonium salts of the parent compound, such as a salt formed by a non-toxic inorganic acid or organic acid. The conventionally non-toxic salt includes, but not limited to, those salts derived from inorganic acids and organic acids, the inorganic acids or organic acids are selected from 2-acetoxybenzoic acid, 2-isethionic acid, acetic acid, ascorbic acid, phenylsulfonic acid, benzoic acid, bicarbonate, carbonic acid, citric acid, edetic acid, ethanedisulfonic acid, ethanesulfonic acid, fumaric acid, glucoheptonic acid, gluconic acid, glutamic acid, glycolic acid, hydrobromic acid, hydrochloric acid, hydriodate, hydroxyl, hydroxynaphthoic, hydroxyethanesulphonic acid, lactic acid, lactose, dodecanesulfonic acid, maleic acid, malic acid, mandelic acid, methanesulfonic acid, nitric acid, oxalic acid, pamoic acid, pantothenic acid, phenylacetic acid, phosphoric acid, polygalacturonan, propionic acid, salicylic acid, stearic acid, folinic acid, succinic acid, aminosulfonic acid, sulfanilic acid, sulphuric acid, tannic acid, tartaric acid and p-toluene sulfonic acid.

The pharmaceutically acceptable salt of the present invention can be prepared with a parent compound containing an acidic or an alkaline group in a conventional manner. Generally, a process for preparing the salt comprises that in water or an organic solvent or the mixture thereof, reacting these compounds in forms of free acids or alkalis with stoichiometric amount of proper alkalis or acids. In general, a non-aqueous medium is preferred such as ether, ethyl acetate, ethanol, isopropanol or acetonitrile and so on.

Except for the form of salt, the compound disclosed in the present invention also has a form of pro-drug. The pro-drug of the compound herein is easily transformed to the compound of the present invention via chemical changes under physiological conditions. Besides, the pro-drug can be transformed to the compound of the present invention via a chemical or biochemical method in vivo.

Some compounds of the present invention can exist in a form of non-solvate or solvate, including a hydrate form. In general, the solvate form is similar to the non-solvate form, both of which are included within the scope of the present invention. Some compounds of the present invention can exist in a polycrystalline or an amorphous form.

Some compounds of the present invention can contain asymmetric carbon atoms (optical centers) or double bonds. The racemic isomers, diastereomers, geometric isomers and single isomers are included within the scope of the present invention.

The diagrammatic representation of the racemic isomer, the ambiscalemic and scalemic or the enantiopure compound of the present invention is from Maehr, J. Chem. Ed. 1985, 62: 114-120. Unless otherwise indicated, the absolute configuration of a stereocenter is represented by the wedge and dashed lines. When the compound of the present invention contains an olefin double bond or other geometric asymmetric center, unless otherwise specified, E, Z geometric isomers are included. Similarly, all tautomeric forms are included within the scope of the present invention.

The compounds of the present invention may exist specific geometric or stereoisomeric isomers. The present invention envisages all of this class of compounds, including cis- and trans-isomers, (−)- and (+)-antimers, (R)- and (S)-antimers, diastereomers, (D)-isomers, (L)-isomers, as well as racemic mixtures and other mixtures thereof, such as enantiomers- or diastereoisomers-enriched mixtures, all of these mixtures are included within the scope of the present invention. Other asymmetric carbon atoms may exist in substituents such as an alkyl. All of these isomers and their mixtures are included within the scope of the present invention.

Optically active (R)- and (S)- isomers, (D)- and (L)-isomers can be prepared by asymmetric synthesis or chiral reagents or other conventional techniques. If an enantiomer of a certain compound of the present invention are required, asymmetric synthesis or derivatization of chiral auxiliaries can be employed in the preparation, in which the resulting diastereomer mixtures are isolated and the auxiliary groups are cleaved to provide the pure desired enantiomer. Or, when a molecule contains an alkaline functional group (such as amino) or an acidic functional group, (such as carboxyl group), diastereomer salts can be formed by it with an appropriate optical active acid or alkali, then fractional crystallization or chromatography known in the art is carried out to separate the diastereomers, thereby pure enantiomer is recycled. In addition, the separation of enantiomers and diastereomers is usually realized by chromatography, the chromatography employs a chiral stationary phase, and optionally combined with chemical derivatization (e.g. derivatization from an amine to carbamate).

One or more atoms constituting the compound of the present invention may comprise an unnatural proportion of atomic isotopes. For example, the compound can be labeled by a radioactive isotope, such as tritium ($^3H$), iodine-125 ($^{125}I$) or C-14 ($^{14}C$). All the variations in the isotopic composition of the compound disclosed in the present invention, whether radioactive or not, are included within the scope of the present invention.

The term "pharmaceutically acceptable carrier" refers to any formulation or carrier medium which is capable of delivering effective amount of the active substance disclosed in the present invention, does not interfere with the biological activity of the active substance, and is with no toxic side-effects on host or patient. Representative carrier includes water, oil, vegetables and minerals, cream base, lotion matrix, ointment matrix etc. The matrix comprises a suspension, a viscosity increaser, a transdermal enhancer etc. Their formulation are well known to the person in cosmetic or topical drug art. Other information regarding the carrier can refer to Remington: The Science and Practice of Pharmacy, 21st Ed., Lippincott, Williams & Wilkins (2005), the contents of which are incorporated herein by reference in its entireties.

The term "excipient" usually refers to a carrier, a diluent and/or a medium required for the preparation of an effective pharmaceutical composition.

In terms of drug or pharmacological active agents, the term "effective amount" or "therapeutically effective amount" refers to enough quantity of the drug or formulation that can achieve desired effects but is of no toxicity. For the oral formulation of the present invention, "an effective amount" of one active substance in the composition is the amount required to achieve desired effects while it is co-administration with another active substance. The determination of the effective amount varies from person to person, it depends on the age and the general situation of the recipient, also on the specific active substance. In a specific case, an appropriate effective amount can be determined by the person skilled in the art according to conventional tests.

The term "active ingredient", "therapeutic agent", "active substance" or "active agent" refers to a chemical entity, which can effectively treat disorders, diseases or conditions of a subject.

The term "substituted" refers to one or more hydrogen atom in a specific atom optionally substituted by a substituent, including a deuterium and a variant of hydrogen, as long as the valence state of the specific atom is normal and the compound obtained after substitution is stable. When the substituent is a ketone group (i.e. =O), it means that two hydrogen atoms are substituted. A substitution of ketone group will not occur in an aryl. The term "optionally substituted" means substituted or not substituted, unless otherwise specified, the type and number of substituents can be arbitrary under the premise of realizibility available in chemistry.

When any parameter (e.g. R) shows an occurrence for one or more than one time in the composition or structure of the compound, the definition of each occurrence is independent. Therefore, for example, if a group is substituted by 0 to 2 R substituent, the group may optionally be substituted by at most two R substituents, and each occurrence of R has independent options. In addition, the combination of substituents and/or their variants is allowed only if such combination will lead to a stable compound.

When bonds of a substituent can be crossly connected to two atoms of a ring, the substituent can be bonded to arbitrary atoms in the ring. When it does not specify through which atom contained in the listed substituent is it connected to the general structure formula including the compound that is not specifically mentioned, the substituent can be bonded through any of its atoms. The combination of substituents and/or their variants is allowed only if such combination will lead to a stable compound. For example, the structural unit

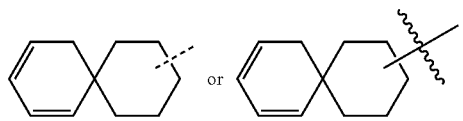

represents that the connection can occur on any atom in the cyclohexyl or cyclohexadienyl.

The substituent in alkyl and heteroalkyl group is generally called "alkyl substituent", which can be selected from but not limited to the group consisting of —R', —OR', =O, =NR', =N—OR', —NR'R", —SR', halogen, —SiR'R"R''', OC(O)R', —C(O)R', —CO$_2$R', —C(=O)NR'R", —OC(O)NR'R", —NR"C(O)R', NR' C(O)NR"R''', —NR"C(O)$_2$R', —NR''''—C(NR'R"R''')=NR'''', NR'''' C(NR'R")=NR''', —S(O)R', —S(O)$_2$R', —S(O)$_2$NR'R", NR"SO$_2$R', —CN, —NO$_2$, —N$_3$, —CH(Ph)$_2$ and fluoro(C$_1$-C$_4$)alkyl, the number of the substituent is between 0 and (2m'+1), wherein m' is the total number of the carbon atoms in the group. R', R", R''', R'''' and R'''''' are independently selected from H, substituted or unsubstituted heteroalkyl, substituted or unsubstituted aryl (e.g. aryl substituted by 1~3 of halogen), substituted or unsubstituted alkyl, alkoxy, thioalkoxy or aralkyl. When the compound of the present invention includes more than one R group, for example, each of the R group is independently selected, as each of R', R", R''', R'''' and R'''''' group is when more than one of them are included. When R' and R" are attached to the same nitrogen atom, they can form 5-, 6-, or 7-membered ring together with the nitrogen atom. For example, —NR'R" includes but not limited to 1-pyrrolidinyl and 4-morpholinyl. According to the above discussion on substituent, the person skilled in the art can understand, the term "alkyl" is intended to include a group formed by bonding a carbon atom to a non-hydrogen group, such as a halogenated alkyl (e.g. —CF$_3$, —CH$_2$CF$_3$) and an acyl (e.g. —C(O)CH$_3$, —C(O)CF$_3$, C(O)CH$_2$OCH$_3$, etc.).

Similar to the substituent in the alkyl group, the substituent in aryl and heteroaryl group is generally called "aryl substituent", which can be selected from such as —R', —OR', —NR'R", —SR', -halogen, —SiR'R"R''', OC(O)R', —C(O)R', —CO$_2$R', —C(=O)NR'R", —OC(O)NR'R", —NR"C(O)R', NR'C(O)NR"R''', —NR"C(O)$_2$R', —NR''''—C(NR'R"R''')=NR''', NR'''' C(NR'R")=NR''', —S(O)R', —S(O)$_2$R', —S(O)$_2$NR'R", NR"SO$_2$R', —CN, —NO$_2$, —N$_3$, —CH(Ph)$_2$, fluoro(C$_1$-C$_4$) alkoxy and fluoro (C$_1$-C$_4$)alkyl, etc., a number of the substituent ranges from 0 to the total opening valence of the aromatic ring; wherein R', R", R''', R'''' and R'''''' are independently and preferably selected from H, substituted or unsubstituted alkyl, substituted or unsubstituted heteroalkyl, substituted or unsubstituted aryl and substituted or unsubstituted heteroaryl. When the compound of the present invention includes more than one R group, for example, each of the R group is independently selected, as each of R', R", R''', R'''' and R'''''' group is when more than one of them are included.

Two substituents attached to adjacent atoms in an aryl or a heteroaryl ring can optionally be substituted by a substituent with a general formula as -T-C(O)—(CRR')q-U—, wherein the T and U are independently selected from —NR—, —O—, CRR'— or a single bond, q is an integer from 0 to 3. As an alternative, two substituents attached to adjacent atoms in an aryl or a heteroaryl ring can optionally be substituted by a substituent with a general formula as -A(CH$_2$)r B—, wherein the A and B are independently selected from —CRR'—, —O—, —NR—, —S—, —S(O)—, S(O)$_2$—, —S(O)$_2$NR'— or a single bond, r is an integer from 1 to 4. Optionally, a single bond in the new ring thereby formed can be replaced by a double bond. As an alternative, two substituents attached to adjacent atoms in an aryl or a heteroaryl ring can optionally be substituted by a substituent with a general formula as -A (CH$_2$)r B—, wherein the s and d are independently selected from an integer from 0 to 3, X is —O—, —NR', —S—, —S(O)—, —S(O)$_2$— or —S(O)$_2$NR'—. The substituent R, R', R" and R''' are respectively and preferably selected from hydrogen and substituted or unsubstituted (C$_1$-C$_6$) alkyl.

Unless otherwise specified, the term "halogenated" or "halogen" itself or as a part of another substituent refers to fluorine, chlorine, bromine or iodine atom. In addition, the term "halogenated alkyl" is intended to include monohalogenated alkyl and polyhalogenated alkyl. For example, the term "halogenated ($C_1$-$C_4$) alkyl" is intended to include but not limited to trifluoromethyl, 2, 2, 2-trifluoroethyl, 4-chlorobutyl and 3-bromopropyl, etc.

Examples of halogenated alkyl include but not limited to: trifluoromethyl, trichloromethyl, pentafluoroethyl, and pentachloroethyl. The alkoxy represents that the alkyl group with a specific number of carbon atoms is connected by an oxygen bridge. The $C_{1-6}$ alkoxy includes $C_1$, $C_2$, $C_3$, $C_4$, $C_5$ and $C_6$ alkoxy. Examples of alkoxy include but not limited to: methoxy, ethoxy, n-propoxy, iso-propoxy, n-butoxy, sec-butoxy, tert-butoxy, n-pentyloxy and S-pentyloxy. The "cycloalkyl" includes saturated cyclic group, such as cyclopropyl, cyclobutyl or cyclopentyl. The 3- to 7-membered cycloalkyl includes $C_3$, $C_4$, $C_5$, $C_6$ and $C_7$ cycloalkyl. The "alkenyl" includes linear or branched hydrocarbon chain, wherein any stable sites on the chain exist one or more C═C double bonds, such as vinyl and propenyl.

The term "halo" or "halogen" refers to fluorine, chlorine, bromine and iodine.

Unless otherwise specified, the term "hetero" refers to a heteroatom or a heteroatom group (i.e. a group containing a heteroatom), including atoms except carbon (C) and hydrogen (H) and groups containing these heteroatoms, such as including oxygen (O), nitrogen (N), sulfur (S), silicon (Si), germanium (Ge), aluminum (Al), boron (B), —O—, —S—, ═O, ═S, —C(═O)O—, —C(═O)—, —C(═S)—, —S(═O), —S(═O)$_2$—, and optionally substituted —C(═O)N(H)—, —N(H)—, —C(═NH)—, —S(═O)$_2$N(H)— or —S(═O) N(H)—.

Unless otherwise specified, the "ring" refers to substituted or unsubstituted cycloalkyl, heterocycloalkyl, cycloalkenyl, heterocycloalkenyl, cycloalkynyl, heterocycloalkynyl, aryl or heteroaryl. The ring includes a single ring, a joint ring, a spiro ring, a fused ring or a bridged ring. A number of the atoms in the ring is usually defined as the member of the ring, for example, "5- to 7-membered ring" is a ring looped with 5 to 7 atoms. Unless otherwise specified, the ring optionally contains 1~3 of heteroatoms. Therefore, "5- to 7-membered ring" includes, for example, phenyl pyridine and piperidinyl; on the other hand, the term "5- to 7-membered heterocycloalkyl" includes pyridyl and piperidinyl, but does not include phenyl. The term "ring" also includes a ring system containing at least one ring, wherein each ring is of the above definition independently.

Unless otherwise specified, the term "heterocycle" or "heterocyclic group" refers to a stable monocyclic, bicyclic or tricyclic ring containing a heteroatom or a heteroatom group, they can be saturated, partially unsaturated or unsaturated (aromatic), they contain carbon atoms and 1, 2, 3 or 4 of heteroatom in the ring which is independently selected from the group consisting of N, O and S, wherein any of the heterocycle can be fused to a benzene ring to form a bicyclic ring. Nitrogen and sulfur atoms can be optionally oxidized (i.e., NO and S(O)$_p$). The nitrogen atom can be substituted or unsubstituted (i.e. N or NR, wherein R is H or other substituent that has been defined herein). The heterocycle can be attached to the side group of any heteroatom or carbon atom to form a stable structure. If the formed compound is stable, the heterocycle described herein can be substituted on its carbon or nitrogen atom. The nitrogen atom in the heterocycle is optionally quaternized. As a preferred embodiment of the present invention, when the total number of S and O atoms contained in the heterocycle exceeds 1, these heteroatoms are not adjacent to each other. As another preferred embodiment of the present invention, the total number of S and O atoms in the heterocycle is no more than 1. As used herein, the term "aromatic heterocyclic group" or "heteroaryl" refers to a stable 5-, 6-, 7-membered monocycle or bicycle or 7-, 8-, 9- or 10-membered bicyclic heteroaromatic ring, which contains carbon atoms and 1, 2, 3 or 4 of heteroatom in the ring which independently selected from the group consisting of N, O and S. The nitrogen atom can be substituted or unsubstituted (i.e. N or NR, wherein R is H or other substituent that has been defined herein). Nitrogen and sulfur atoms can be optionally oxidized (i.e., NO and S(O)$_p$). It is worth noting that, the total number of S and O atoms in the heteroaromatic ring is no more than 1. Bridged rings are also included in the definition of the heterocycle. When one or more atoms (i.e. C, O, N, or S) are connected to two nonadjacent carbon atoms or nitrogen atoms, a bridged ring is formed. The preferred bridged ring includes but not limited to: one carbon atom, two carbon atoms, one nitrogen atom, two nitrogen atoms and one carbon-nitrogen group. It is worth noting that, a bridge always converts a monocyclic ring into a tricyclic ring. In the bridged ring, the substituent in the ring can also locate on the bridge.

Examples of heterocyclic compound include but not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indoalkenyl, indolinyl, indolizinyl, indolyl, 3H-indolyl, isatino group, isobenzofuranyl, pyran, isoindolyl, isoindolinyl, isoindolyl, indolyl, isoquinolyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, isooxazolyl, hydroxyl indyl, pyrimidyl, phenanthridinyl, phenanthrolinyl, phenazine, phenothiazine, benzopurinyl, phenoxazinyl, phthalazinyl, piperazinyl, piperidyl, oxopiperidinyl, 4-oxopiperidinyl, piperonyl, pteridyl, purinyl, pyranyl, pyrazinyl, pyrazolidinyl, pyrazolinyl, pyrazolyl, pyridazinyl, oxazolopyridine, pyridinoimidazole, pyridinothiazole, pyridyl, pyrimidyl, pyrrolidinyl, pyrrolinyl, 2H-pyrrolyl, pyrrolyl, pyrazolyl, quinazolinyl, quinolyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazyl, isothiazolylthienyl, thienyl, thiophenoxazolyl, thiophenothiazolyl, thiophenoimidazolyl, thienyl, triazinyl, 1,2,3-triazolyl, 1,2,4-triazolyl, 1,2,5-triazolyl, 1,3,4-triazolyl and xanthenyl. Fused ring and spiro ring compound are also included.

Unless otherwise specified, the term "hydrocarbon group" or its specific concept (such as alkyl, alkenyl, alkynyl, phenyl, etc.) itself or as a part of another substituent represents a linear, branched or cyclic hydrocarbon group or a combination thereof, which can be fully saturated, monocyclic or polycyclic unsaturated, can be monosubstituted, disubstituted or polysubstituted, can be univalent (such as methyl), bivalent (such as methylene) or multivalent (such as methenyl), can include bivalent or multivalent atomic groups, with a specified number of carbon atoms (such as that $C_1$-$C_{10}$ refers to having 1~10 carbon atoms). The term "alkyl" includes but not limited to an aliphatic hydrocarbon group and aromatic hydrocarbon group, the aliphatic hydrocarbon group includes linear and cyclic structures, specifically includes but not limited to alkyl, alkenyl and alkynyl, the aromatic hydrocarbon group includes but not limited to 6- to 12-membered aromatic hydrocarbon group such as benzene, naphthalene and the like. In some embodiments, the term "alkyl" refers to linear or branched groups or their combination, which can be completely saturated, monocyclic or polycyclic unsaturated, can include divalent and polyvalent groups. Examples of saturated hydrocarbon groups include but not limited to homologues or isomers of methyl, ethyl, n-propyl, iso-propyl, n-butyl, tert-butyl, iso-butyl, sec-butyl, iso-butyl, cyclohexyl, (cyclohexyl) methyl, cyclopropyl methyl, and n-amyl, n-hexyl, n-heptyl, n-octyl and the like. Unsaturated alkyl has one or more double or triple bond, examples of which includes but not limited to vinyl, 2-propenyl, butenyl, crotyl, 2-isopentenyl, 2-butadienyl, 2,4-(pentadienyl), 3-(1,4-pentadienyl), acetenyl, 1- and 3-propinyl, 3-butynyl, and more advanced homologues and isomers.

Unless otherwise specified, the term "heterohydrocarbon group" or its specific concepts (such as heteroalkyl, heteroalkenyl, heteroalkynyl, heteroaryl, etc.) itself or the term combining with another term refers to a stable linear, branched or cyclic hydrocarbon group or their combinations, which consists of a certain number of carbon atoms and at least one heteroatom. In some embodiments, the term "heteroalkyl" itself or the term combining with another term refers to a stable linear, branched hydrocarbon group or their combinations, which consists of a certain number of carbon atoms and at least one heteroatom. In a typical embodiment, the heteroatom is selected from the group consisting of B, O, N and S, in which the nitrogen and sulfur atoms are optionally oxidized, and the nitrogen atom is optionally quaternized. Heteroatoms B, O, N and S can be located in any internal position of the heterohydrocarbon group (including the position where hydrocarbon group is attached to the rest part of the molecule). Examples include but not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. At most two heteroatoms are adjacent, such as —$CH_2$—NH—$OCH_3$.

The terms "alkoxy", "alkylamino" and alkylthio" (or thioalkoxy) are the idiomatic expressions, which refers to the alkyl group is attached to the rest of molecule through an oxygen, an amino, or a sulfur atom, respectively.

Unless otherwise specified, the term "cyclohydrocarbon group", "heterocyclo hydrocarbon group" or its specific concepts (such as aryl, heteroaryl, cycloalkyl, heterocycloalkyl, cycloalkenyl, heterocyclovinyl, cycloalkynyl, heterocycloalkynyl, etc.) itself or the term combining with other terms respectively refers to a cyclic "hydrocarbon group", "heterohydrocarbon group". In addition, in terms of heterohydrocarbon group or heterocyclohydrocarbon group (such as heteroalkyl, heterocycloalkyl), heteroatoms can occupy the position where the heterocyclic ring is attached to the rest part of the molecule. Examples of the cycloalkyl include but not limited to cyclopentyl, cyclohexyl, 1-cyclohexenyl, 3-cyclohexenyl, cycloheptyl etc. Unrestricted examples of the heterocyclic group include 1-(1,2,5,6-tetrahydropyridinyl), 1-piperidyl, 2-piperidyl, 3-piperidyl, 4-morpholinyl, 3-morpholinyl, tetrahydrofuran-2-yl, tetrahydrofuranylindol-3-yl, tetrahydrothiophene-2-yl, tetrahydrothiophene-3-yl, 1-piperazinyl and 2-piperazinyl.

Unless otherwise specified, the term "aryl" refers to a polyunsaturated aromatic hydrocarbon substituent, which can be monosubstituted, disubstituted or multisubstituted, can be univalent, bivalent or multivalent. It can be monocyclic or polycyclic (preferably 1~3 rings). They fuse together or connect by a covalent linkage. The term "heteroaryl" refers to an aryl (or ring) containing 1~4 heteroatoms. In an exemplary embodiment, the heteroatom is selected from the group consisting of B, N, O, and S, in which the nitrogen and sulfur atoms are optionally oxidized, and the nitrogen atom is optionally quaternized. The heteroaryl group can be connected to the rest part of the molecule via a heteroatom. Unrestricted examples of an aryl or a heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzoimidazolyl, 5-indolyl, 1-isoquinolyl, 5-isoquinolyl, 2-quinoxalyl, 5-quinoxalyl, 3-quinolyl and 6-quinolyl. Any one of the substituents in the aryl and heteroaryl ring system is selected from the acceptable substituents described below.

For the sake of briefness, when used in combination with other terms (e.g. aryloxy, arylthio, aralkyl), the aryl includes the definition of aryl and heteroaryl ring defined above. Therefore, the term "aralkyl" is intended to include the groups that aryl attached to alkyl (e.g. benzyl, phenyl ethyl, pyridyl methyl), including those alkyls wherein carbon atoms (such as methylene) has been replaced by such as oxygen atoms, such as phenoxy methyl, 2-pyridyloxymethyl-3-(1-naphthoxy) propyl, etc.

The term "leaving group" refers to a functional group or atom which can be replaced by another functional group or atom through a substitution reaction (e.g., nucleophilic substitution reaction). For example, representative leaving groups include triflate; chlorine, bromine, iodine; sulfonate, such as mesylate, tosylate, p-bromobenzene sulfonate, p-tosylate etc.; acyloxy, such as acetoxy, trifluoroacetoxy and so on.

The term "protecting group" includes but not limited to "the protecting group of an amino", "the protecting group of a hydroxyl", or "the protecting group of a mercapto". The term "the protecting group of an amino" refers to a protecting group that is suitable for preventing side reactions occur at the nitrogen atom of an amino group. A representative protecting group of an amino includes but not limited to: formyl; acyl, such as alkanoyl (such as acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), triphenyl methyl (Tr), 1,1-bis-(4'-methoxyphenyl) methyl; silyl, such as trimethylsilyl (TMS) and tert-butyldimethylsilyl (TBS) and etc. The term "the protecting group of a hydroxyl" refers to a protecting group that is suitable for preventing side reactions of a hydroxyl group. A representative protecting group of a hydroxyl includes but not limited to: alkyl, such as methyl, ethyl, and tert-butyl; acyl, such as alkanoyl (such as acetyl); aryl methyl, such as benzyl (Bn), p-methoxybenzyl (PMB), 9-fluorenylmethyl (Fm) and diphenylmethyl (diphenylmethyl, DPM); silyl, such as trimethylsilyl (TMS) and tert-butyldimethylsilyl (TBS) and etc.

The compound of the present invention can be prepared through many synthetic methods which are well-known to the person skilled in the art, including the specific embodiments listed below and its combination with other chemical synthetic methods and the equivalent alternative methods which are known to the person skilled in the art, the preferred embodiments include but not limited to the embodiments of the present invention.

The solvents used in the present invention are commercially available. The present invention adopts the following abbreviations: aq represents water; HATU represents 2-(7-azabenzotriazol-1-yl)-N,N,N',N'-tetramethyluronium hexafluorophosphate; EDC represents N-(3-dimethylaminopropyl)-N'-ethyl carbodiimide hydrochloride; m-CPBA represents m-chloroperbenzoic acid; eq represents equivalent, equal-quantitative; CDI represents carbonyl diimidazole; DCM represents dichloromethane; PE represents petroleum ether; DIAD represents diisopropyl azodicarboxylate; DMF represents N,N-dimethylformamide; DMSO represents dimethylsulfoxide; EtOAc represents ethyl acetate; EtOH represents ethanol; MeOH represents methanol; Cbz represents benzyloxycarbonyl, a protecting group of an amino; Boc represents tert-butoxycarbonyl, a protecting group of an amine; HOAc represents acetic acid; NaCNBH$_3$ represents sodium cyanoborohydride; r.t. represents room temperature; O/N represents overnight; THF represents tetrahydrofuran; Boc$_2$O represents di-tert-butyl dicarbonate; TFA represents trifluoroacetic acid; DIPEA represents diisopropylethylamine; SOCl$_2$ represents thionyl chloride; CS$_2$ represents carbon disulfide; TsOH represents p-toluene sulfonic acid; NFSI represents N-fluorobenzenesulfonimide; NCS represents N-chlorosuccinimide; n-Bu$_4$NF represents tetrabutylammonium fluoride; iPrOH represents 2-propanol; mp represents melting point; LDA represents lithium diisopropylamide.

Compounds are named by manual work or software ChemDraw®, commercially available compounds are named in accordance with suppliers' catalogue.

Compared to the prior art, the compounds of the present invention are effective, lower-toxic, greatly improved on the aspects of activity, half-life, solubility and pharmacokinetics and etc. and even achieves unforeseeable progresses, more suitable for manufacturing a drug.

DETAILED DESCRIPTION OF THE PREFERRED EMBODIMENT

The following examples further illustrate the present invention, but it does not mean any unfavorable limitation to the present invention. Herein, the present invention has been described in details, the embodiments of which have been disclosed as well. It is obvious for the person skilled in the art to vary and improve the embodiments of the present invention in the case of not departing from the spirit and scope of the present invention.

Reference 1: Fragment BB-1

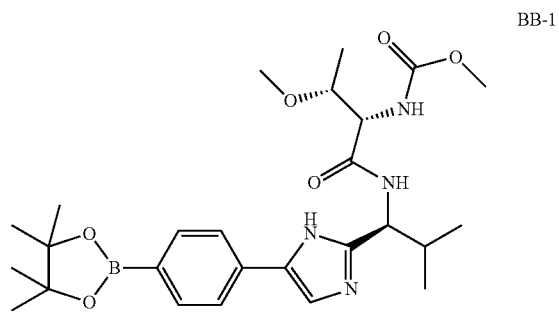

Synthetic Route:

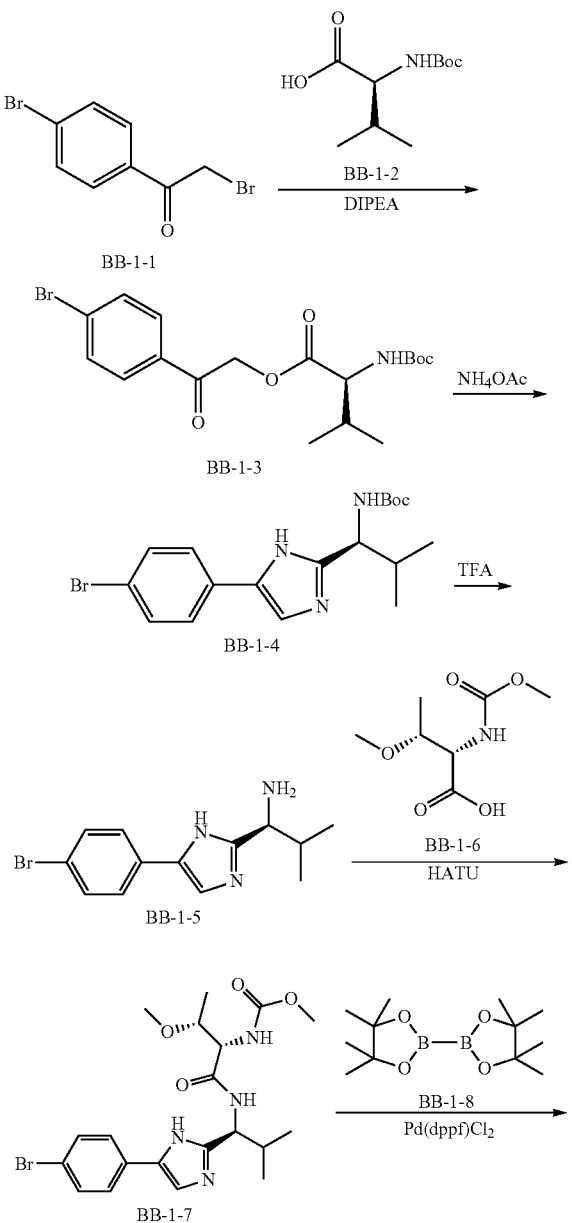

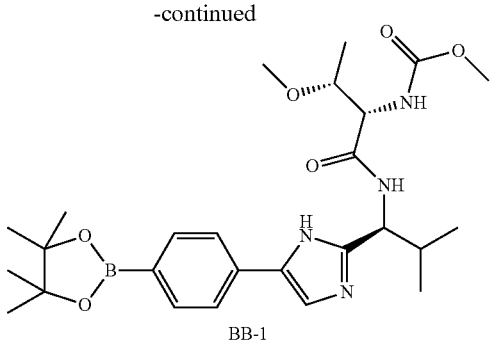

BB-1

Step 1: Synthesis of Compound BB-1-3

Compound BB-1-1 (1.38 g, 5.0 mmol) was dissolved in acetonitrile (15 mL), compound BB-1-2 (1.08 g, 5.0 mmol) was added, and then DIPEA (0.65 g, 5.0 mmol) was added gradually. After addition, the reaction was stirred to react overnight. The reaction solution was concentrated under reduced pressure to remove the solvent by a rotary evaporator, the obtained oil was diluted with H₂O (30 mL) and extracted with ethyl acetate (20 mL×2), the organic phases obtained twice were combined and dried over anhydrous sodium sulfate, the filtrate obtained after filtration was concentrated under reduced pressure to remove the solvent thereby delivering the title compound BB-1-3 (2.0 g, 9%). LCMS m/z: 314.0 [M-100]$^+$ Step 2: Synthesis of Compound BB-1-4

Compound BB-1-3 (2.0 g, 4.82 mmol) was dissolved in toluene (40 mL), ammonium acetate (5.6 g, 72.44 mmol) was added, and the reaction was heated to refluxing and stirred overnight. After cooling, the reaction solution was concentrated under reduced pressure to remove the solvent, the obtained oil was diluted with H₂O (60 mL) and extracted with ethyl acetate (30 mL×2), the organic phases obtained twice were combined and dried over anhydrous sodium sulfate, the filtrate obtained after filtration was concentrated under reduced pressure to remove the solvent thereby delivering the title compound BB-1-4 (1.8 g, 95%). LCMS m/z: 394.1 [M+1]$^+$ Step 3: Synthesis of Compound BB-1-5

Compound BB-1-4 (1.8 g, 4.56 mmol) was dissolved in dichloromethane (20 mL), after the solution was cooled to 0° C., trifluoroacetic acid (6 mL) was dripped gradually, and the reaction was stirred at room temperature for 5 h. The reaction solution was concentrated under reduced pressure to remove the solvent by a rotary evaporator, the obtained oil was neutralized with saturated sodium bicarbonate solution (pH=8) and extracted with ethyl acetate (20 mL×2), the organic phases obtained twice were combined and dried over anhydrous sodium sulfate, the filtrate obtained after filtration was concentrated under reduced pressure to remove the solvent thereby delivering the title compound BB-1-5 (1.1 g, 82%). LCMS m/z: 294.0 [M+1]$^+$ Step 4: Synthesis of Compound BB-1-7

Compound BB-1-5 (588 mg, 2.0 mmol) was dissolved in dichloromethane (20 mL), compound BB-1-6 (382 mg, 2.0 mmol), HATU (912 mg, 2.4 mmol) and DIPEA (309.6 mg, 2.4 mmol) were added sequentially, and the reaction mixture was stirred at room temperature for 2 h. H₂O (30 mL) was added and the organic phase obtained after layering was washed with NaCl solution once, the organic phase was dried over anhydrous sodium sulfate, and the oil was obtained after the solvent was removed under reduced pressure, then purified and separated by preparative silica gel plate chromatography (eluting reagent, EtOAc/PE, 3/1) to deliver the title compound BB-1-7 (510 mg, 55%). LCMS m/z: 467.1 [M+1]$^+$ Step 5: Synthesis of Compound BB-1

Compound BB-1-7 (200 mg, 0.428 mmol) was dissolved in DMF (6 mL), boron ester BB-1-8 (163 mg, 0.642 mmol), KOAc (84 mg, 0.856 mmol) and Pd(dppf)Cl₂ (15 mg, 0.02 mmol) were added sequentially. The air was replaced by nitrogen gas for 3 times and the reaction mixture was stirred at 110° C. for 3 h under nitrogen gas atmosphere. After cooling, the reaction solution was diluted with H₂O (30 mL) and extracted with ethyl acetate (20 mL×2), the organic phases obtained twice were combined and dried over anhydrous sodium sulfate, the filtrate obtained after filtration was concentrated under reduced pressure to remove the solvent thereby delivering the crude product, which was purified and separated by preparative silica gel plate chromatography (eluting reagent, EtOAc/PE, 3/1) to deliver the title compound BB-1 (70 mg, 32%). LCMS m/z: 515.3 [M+1]$^+$ Reference 2: Fragment BB-2

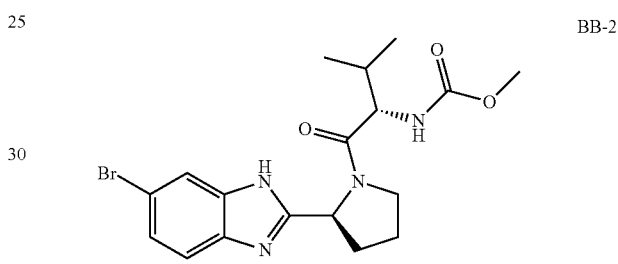

BB-2

Synthetic Route:

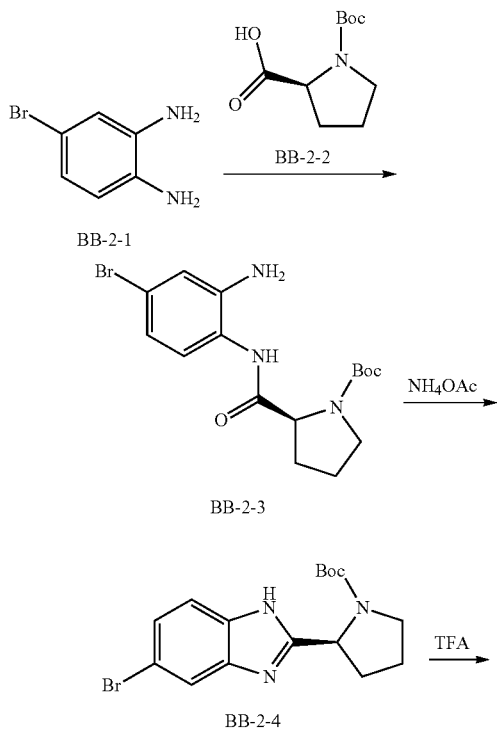

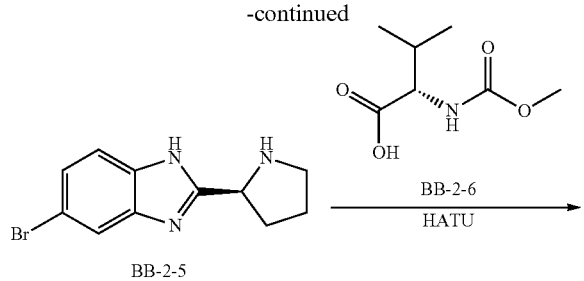

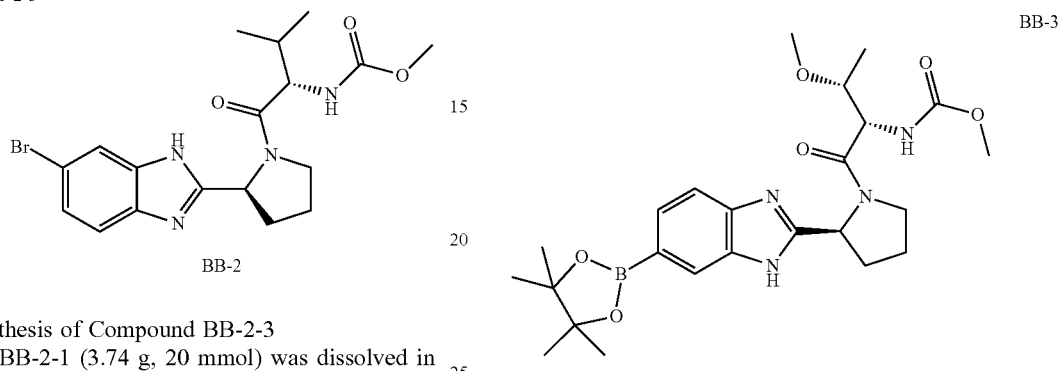

Step 1: Synthesis of Compound BB-2-3

Compound BB-2-1 (3.74 g, 20 mmol) was dissolved in DMF (100 mL), compound BB-2-2 (4.3 g, 20 mmol), HATU (8.36 g, 22 mmol) and DIPEA (3.87 g, 30 mmol) were added sequentially, the reaction mixture was stirred at room temperature for 5 h. The reaction solution was diluted with H$_2$O (200 mL) and extracted with ethyl acetate (200 mL×2), the organic phase obtained after layering was washed with saturated NaCl solution once, the organic phase was dried over anhydrous sodium sulfate, the solvent was removed under reduced pressure thereby delivering the title compound BB-2-3 (6.1 g, 79%). LCMS m/z: 384.1 [M+1]$^+$ Step 2: Synthesis of Compound BB-2-4

Compound BB-2-3 (6.0 g, 15.63 mmol) was dissolved in acetic acid (40 mL), ammonium acetate (12 g, 155.6 mmol) was added in portions. The reaction solution was heated to 90° C. and stirred for 3 h. After cooling, the reaction solution was diluted with H$_2$O (150 mL) and neutralized with 4N NaOH (pH=8), extracted with ethyl acetate (50 mL×2), the organic phases obtained twice were combined and dried over anhydrous sodium sulfate, the filtrate obtained after filtration was concentrated under reduced pressure to remove the solvent thereby delivering the title compound BB-2-4 (4.5 g, 79%). LCMS m/z: 366.1 [M+1]$^+$ Step 3: Synthesis of Compound BB-2-5

Compound BB-2-4 (4.5 g, 12.28 mmol) was dissolved in dichloromethane (45 mL), and cooled to 0° C., trifluoroacetic acid (9 mL) was dripped gradually, and the reaction was stirred at room temperature overnight. The reaction solution was concentrated under reduced pressure to remove the solvent by a rotary evaporator, the obtained oil was neutralized with saturated sodium bicarbonate solution (pH=8) and extracted with ethyl acetate (50 mL×2), the organic phases obtained twice were combined and dried over anhydrous sodium sulfate, the filtrate obtained after filtration was concentrated under reduced pressure to remove the solvent thereby delivering the title compound BB-2-5 (2.5 g, 76.5%). LCMS m/z: 266.0 [M+1]$^+$ Step 4: Synthesis of Compound BB-2

Compound BB-2-5 (532 mg, 2.0 mmol) was dissolved in dichloromethane (15 mL), compound BB-2-6 (385 mg, 2.2 mmol), HATU (836 mg, 2.2 mmol) and DIPEA (368 mg, 2.9 mmol) were added sequentially, the reaction mixture was stirred at room temperature overnight. H$_2$O (20 mL) was added and the organic phase obtained after layering was washed with saturated NaCl solution once, the organic phase separated was dried over anhydrous sodium sulfate, and the filtrate obtained after filtration was concentrated under reduced pressure to remove the solvent thereby delivering the oil, which was purified and separated by preparative silica gel plate chromatography (eluting reagent, EtOAc/PE, 3/1) to deliver the title compound BB-2 (200 mg, 24%). LCMS m/z: 423.1 [M+1]$^+$ Reference 3: Fragment BB-3

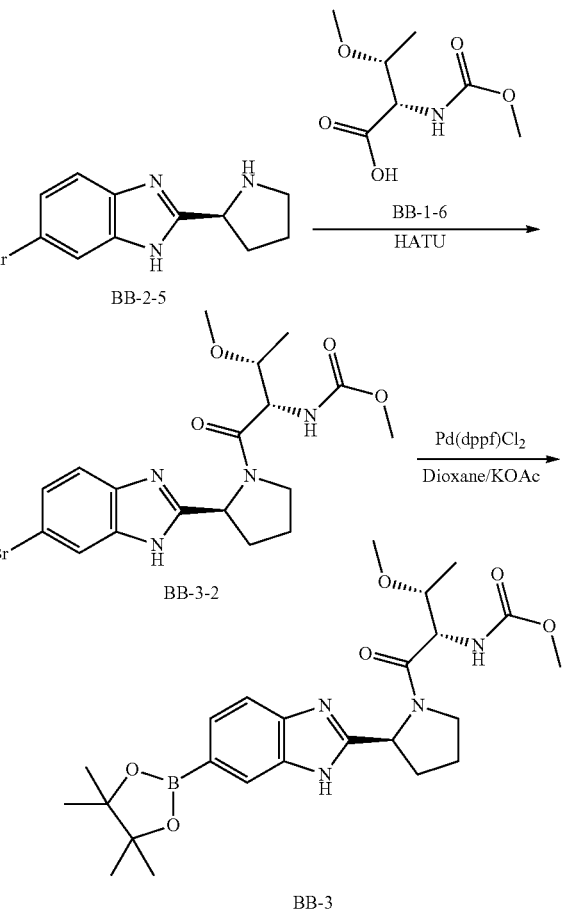

Synthetic Route:

Step 1: Synthesis of Compound BB-3-2

Compound BB-2-5 (532 mg, 2.0 mmol) was dissolved in dichloromethane (20 mL), compound BB-1-6 (420 mg, 2.2 mmol), HATU (912 mg, 2.4 mmol) and DIPEA (388 mg, 3.0 mmol) were added sequentially, the reaction mixture was stirred at room temperature overnight. H₂O (30 mL) was added and the organic phase obtained after layering was washed with saturated NaCl solution once, the organic phase separated was dried over anhydrous sodium sulfate, and the filtrate obtained after filtration was concentrated under reduced pressure to remove the solvent thereby delivering the oil, which was purified and separated by preparative silica gel plate chromatography (eluting reagent, EtOAc/PE, 3/1) to deliver the title compound BB-3-2 (750 mg, 85%). LCMS m/z: 439.1 [M+1]⁺

Step 2: Synthesis of Compound BB-3

Compound BB-3-2 (300 mg, 0.68 mmol) was dissolved in 1,4-dioxane (6 mL), bis(pinacolato)diboron (258 mg, 1.02 mmol), KOAc (135 mg, 1.38 mmol) and Pd(dppf)Cl₂ (30 mg, 0.04 mmol) were added sequentially. The air was replaced by nitrogen gas for 3 times and the reaction solution was stirred at 110° C. for 3 h under nitrogen gas atmosphere. After cooling, the reaction solution was diluted with H₂O (20 mL) and extracted with ethyl acetate (20 mL×2), the organic phases obtained twice were combined and dried over anhydrous sodium sulfate, the filtrate obtained after filtration was concentrated under reduced pressure to remove the solvent thereby obtaining the crude product, which was purified and separated by preparative silica gel plate chromatography (eluting reagent, EtOAc/PE, 3/1) to deliver the title compound BB-3 (235 mg, 71%). LCMS m/z: 487.3 [M+1]⁺

Reference 4: Fragment BB-4

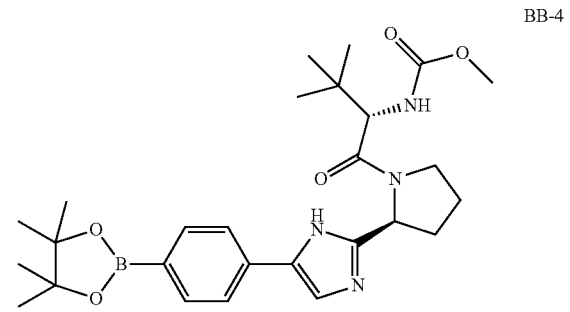

Synthetic Route:

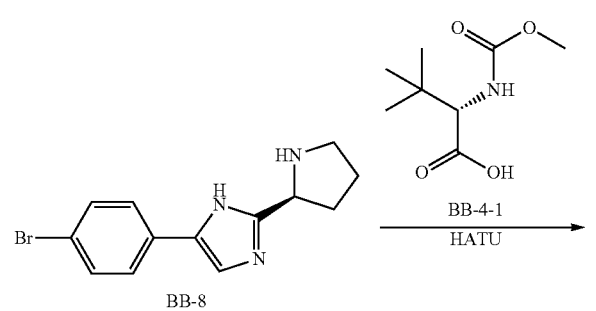

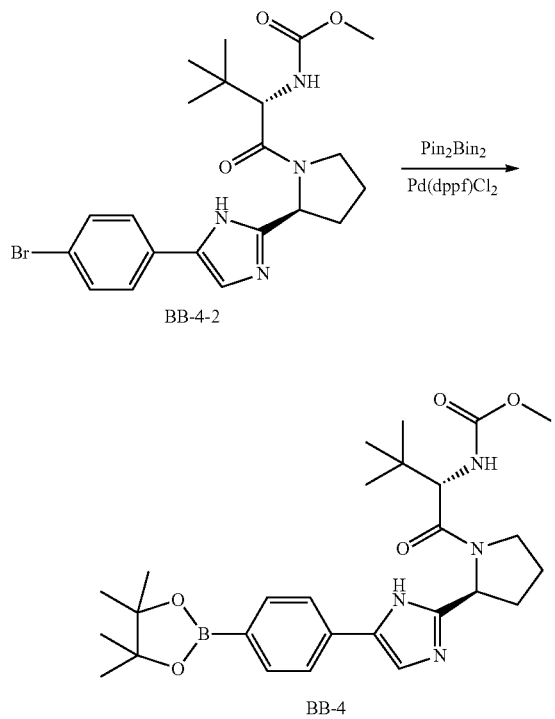

Step 1: Synthesis of Compound BB-4-2

Compound BB-8 (292 mg, 1.0 mmol) was dissolved in dichloromethane (6 mL), compound BB-4-1 (208 mg, 1.1 mmol), HATU (456 mg, 1.2 mmol) and DIPEA (260 mg, 2.0 mmol) were added sequentially, the reaction mixture was stirred at room temperature overnight. H₂O (30 mL) was added and the organic phase obtained after layering was washed with saturated NaCl solution once, the obtained organic phase was dried over anhydrous sodium sulfate, and the filtrate obtained after filtration was concentrated under reduced pressure to remove the solvent thereby delivering the title compound BB-4-2 (320 mg, 69%). LCMS m/z: 463.1 [M+1]⁺

Step 2: Synthesis of Compound BB-4

Compound BB-4-2 (320 mg, 0.69 mmol) was dissolved in DMF (10 mL), bis(pinacolato)diboron (262 mg, 1.03 mmol), KOAc (135 mg, 1.38 mmol) and Pd(dppf)Cl₂ (30 mg, 0.04 mmol) were added sequentially. The air was replaced by nitrogen gas for 3 times and the reaction solution was stirred at 110° C. for 3 h under nitrogen gas atmosphere. After cooling, the reaction solution was diluted with H₂O (20 mL) and extracted with ethyl acetate (20 mL×2), the organic phases obtained twice were combined and dried over anhydrous sodium sulfate, the filtrate obtained after filtration was concentrated under reduced pressure to remove the solvent thereby obtaining the crude product, which was purified and separated by preparative silica gel plate chromatography (eluting reagent, EtOAc/PE, 1/1) to deliver the title compound BB-4 (260 mg, 74%). LCMS m/z: 511.3 [M+1]⁺

Reference 5: Fragment BB-5

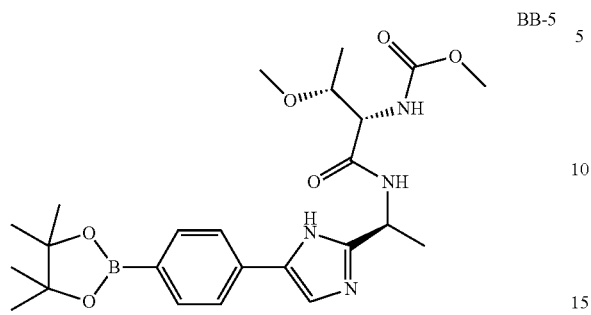

Synthetic Route:

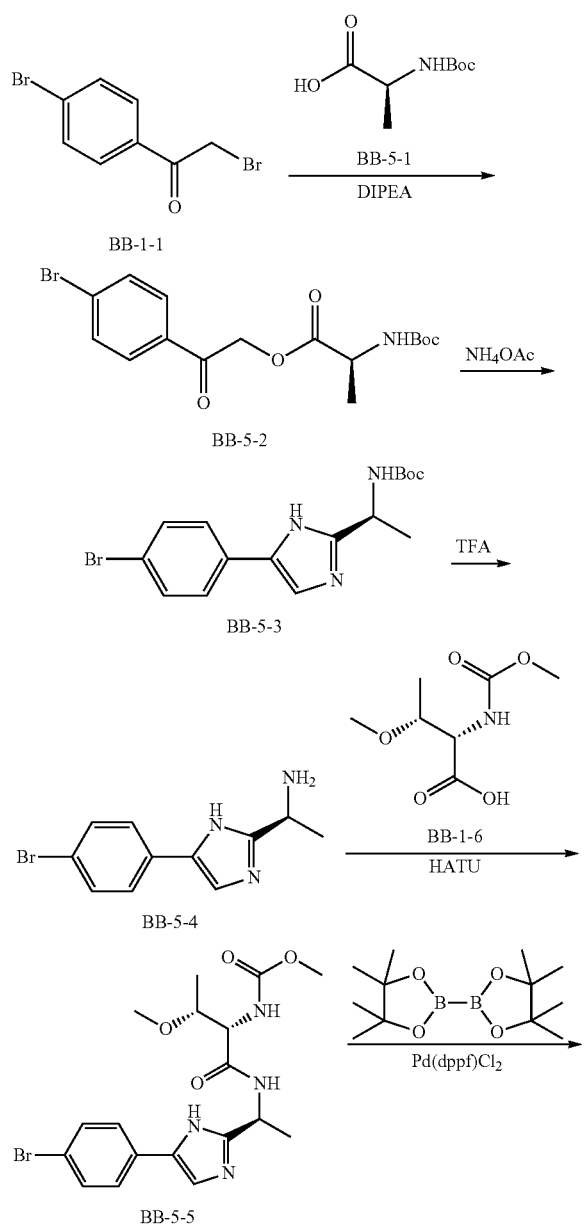

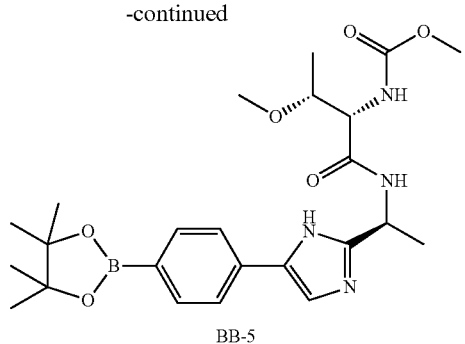

Step 1: Synthesis of Compound BB-5-2

Compound BB-1-1 (1.38 g, 5.0 mmol) was dissolved in acetonitrile (15 mL), compound BB-5-1 (0.95 g, 5.0 mmol) was added, and then DIPEA (0.65 g, 5.0 mmol) was added gradually. After addition, the reaction was stirred at room temperature overnight. The reaction solution was concentrated under reduced pressure to remove the solvent by a rotary evaporator, the resulting oil was diluted with $H_2O$ (30 mL) and extracted with ethyl acetate (20 mL×2), the organic phases obtained twice were combined and dried over anhydrous sodium sulfate, the filtrate obtained after filtration was concentrated under reduced pressure to remove the solvent thereby delivering the title compound BB-5-2 (1.8 g, 94%). LCMS m/z: 285.0 $[M-100]^+$ Step 2: Synthesis of Compound BB-5-3

Compound BB-5-2 (1.8 g, 4.66 mmol) was dissolved in toluene (50 mL), ammonium acetate (5.39 g, 69.91 mmol) was added, and the reaction was heated to refluxing and stirred overnight. After cooling, the reaction solution was concentrated under reduced pressure to remove the solvent, the resulting oil was diluted with $H_2O$ (80 mL) and extracted with ethyl acetate (60 mL×2), the organic phases obtained twice were combined and dried over anhydrous sodium sulfate, the filtrate obtained after filtration was concentrated under reduced pressure to remove the solvent thereby delivering the title compound BB-5-3 (1.6 g, 95%). LCMS m/z: 366.1 $[M+1]^+$ Step 3: Synthesis of Compound BB-5-4

Compound BB-5-3 (1.6 g, 4.36 mmol) was dissolved in dichloromethane (20 mL) and cooled to 0° C., trifluoroacetic acid (6 mL) was dripped gradually, and the reaction was stirred at room temperature for 5 h. The reaction solution was concentrated under reduced pressure to remove the solvent by a rotary evaporator, the resulting oil was neutralized with saturated sodium bicarbonate solution (pH=8) and extracted with ethyl acetate (20 mL×2), the organic phases obtained twice were combined and dried over anhydrous sodium sulfate, the filtrate obtained after filtration was concentrated under reduced pressure to remove the solvent thereby delivering the title compound BB-5-4 (1.0 g, 86%). LCMS m/z: 266.0 $[M+1]^+$ Step 4: Synthesis of Compound BB-5-5

Compound BB-5-4 (532 mg, 2.0 mmol) was dissolved in dichloromethane (20 mL), compound BB-1-6 (382 mg, 2.0 mmol), HATU (912 mg, 2.4 mmol) and DIPEA (516 mg, 2.4 mmol) were added sequentially, the reaction mixture was stirred at room temperature for 3 h. $H_2O$ (30 mL) was added and the organic phase obtained after layering was washed with NaCl solution once, the organic phase was dried over anhydrous sodium sulfate, and the oil was obtained after the solvent was removed under reduced pressure, purified and separated by preparative silica gel plate chromatography (eluting reagent, EtOAc/PE, 3/1) to deliver the title compound BB-5-5 (400 mg, 46%). LCMS m/z: 439.1 [M+1]⁺

Step 5: Synthesis of Compound BB-5

Compound BB-5-5 (400 mg, 0.91 mmol) was dissolved in 1, 4-dioxane (20 mL), bis(pinacolato)diboron(345 mg, 1.36 mmol), KOAc (178 mg, 1.82 mmol) and Pd(dppf)Cl₂ (35 mg, 0.047 mmol) were added sequentially. The air was replaced by nitrogen gas for 3 times and the reaction solution was stirred at 110° C. for 3 h under nitrogen gas atmosphere. After cooling, the reaction solution was diluted with H₂O (30 mL) and extracted with ethyl acetate (20 mL×2), the organic phases obtained twice were combined and dried over anhydrous sodium sulfate, the filtrate obtained after filtration was concentrated under reduced pressure to remove the solvent thereby obtaining the crude product, which was purified and separated by preparative silica gel plate chromatography (eluting reagent, EtOAc/PE, 2/1) to deliver the title compound BB-5 (300 mg, 68%). LCMS m/z: 487.3 [M+1]⁺

Reference 6: Fragment BB-6

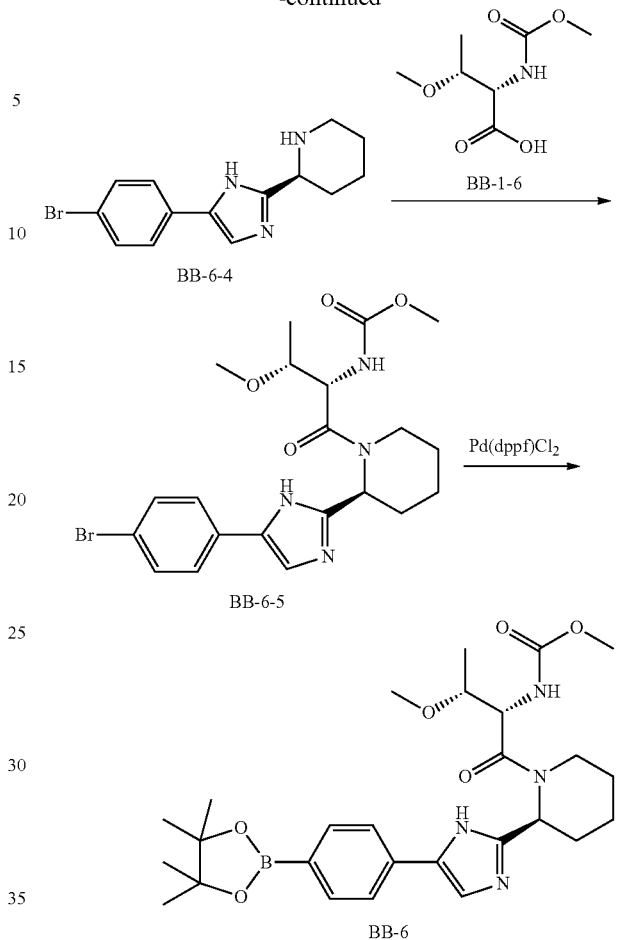

Synthetic route:

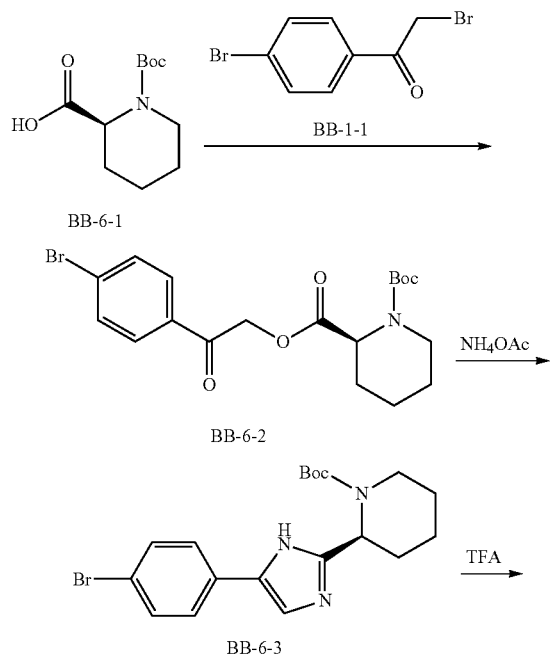

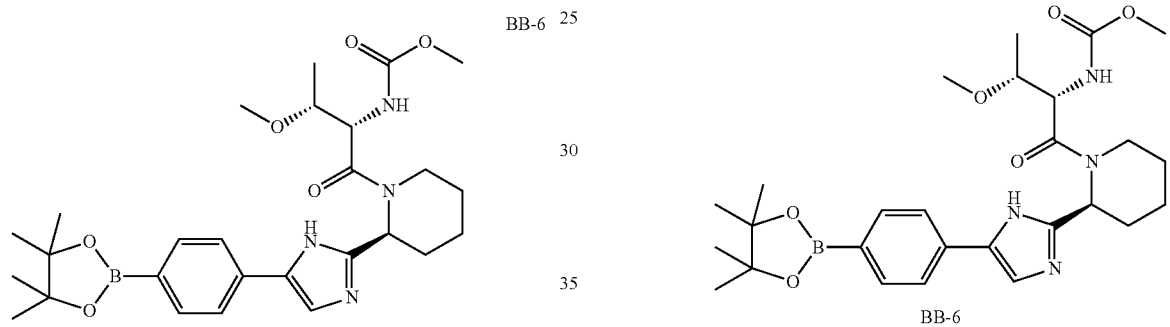

Step 1: Synthesis of Compound BB-6-2

Compound BB-6-1 (4.6 g, 20 mmol) was dissolved in acetonitrile (70 mL), compound BB-1-1 (5.56 g, 20 mmol) was added, and then DIPEA (2.58 g, 20 mmol) was added gradually. After addition, the reaction was stirred at room temperature overnight. The reaction solution was concentrated under reduced pressure to remove the solvent by a rotary evaporator, the resulting oil was diluted with H₂O (100 mL) and extracted with ethyl acetate (60 mL×2), the organic phases obtained twice were combined and dried over anhydrous sodium sulfate, the filtrate obtained after filtration was concentrated under reduced pressure to remove the solvent thereby delivering the title compound BB-6-2 (8.4 g, 99%). LCMS m/z: 326.0 [M-100]⁺

Step 2: Synthesis of Compound BB-6-3

Compound BB-6-2 (8.4 g, 19.7 mmol) was dissolved in toluene (120 mL), ammonium acetate (22.9 g, 297.4 mmol) was added, and the reaction was heated to refluxing and stirred overnight. After cooling, the reaction solution was concentrated under reduced pressure to remove the solvent, the resulting oil was diluted with H₂O (200 mL) and extracted with ethyl acetate (150 mL×2), the organic phases obtained twice were combined and dried over anhydrous sodium sulfate, the filtrate obtained after filtration was concentrated under reduced pressure to remove the solvent thereby delivering the title compound BB-6-3 (7.8 g, 98%). LCMS m/z: 406.0 [M+1]⁺

Step 3: Synthesis of Compound BB-6-4

Compound BB-6-3 (7.1 g, 17.5 mmol) was dissolved in dichloromethane (75 mL) and cooled to 0° C., trifluoroacetic acid (30 mL) was dripped gradually, and the reaction was stirred at room temperature for 4 h. The reaction solution was concentrated under reduced pressure to remove the solvent by a rotary evaporator, the resulting oil was neutralized with saturated sodium bicarbonate solution (pH=8) and extracted with ethyl acetate (100 mL×2), the organic phases obtained twice were combined and dried over anhydrous sodium sulfate, the filtrate obtained after filtration was concentrated under reduced pressure to remove the solvent thereby delivering the title compound BB-6-4 (5.0 g, 93%). LCMS m/z: 306.0 [M+1]$^+$ Step 4: Synthesis of Compound BB-6-5

Compound BB-6-4 (305 mg, 1.0 mmol) was dissolved in dichloromethane (10 mL), compound BB-1-6 (191 mg, 1.0 mmol), HATU (456 mg, 1.2 mmol) and DIPEA (258 mg, 2.0 mmol) were added sequentially, the reaction was stirred at room temperature for 3 h. H$_2$O (15 mL) was added and the organic phase obtained after layering was washed with NaCl solution once, the organic phase was dried over anhydrous sodium sulfate, and the oil was obtained after the solvent was removed under reduced pressure, purified and separated by preparative silica gel plate chromatography (eluting reagent, EtOAc/PE, 3/1) to deliver the title compound BB-6-5 (250 mg, 52%). LCMS m/z: 479.0 [M+H]$^+$ Step 5: Synthesis of Compound BB-6

Compound BB-6-5 (160 mg, 0.33 mmol) was dissolved in DMF (4 mL), bis(pinacolato)diboron(129 mg, 0.51 mmol), KOAc (65 mg, 0.66 mmol) and Pd(dppf)Cl$_2$ (12 mg, 0.016 mmol) were added sequentially. The air was replaced by nitrogen gas for 3 times and the reaction solution was stirred at 110° C. for 2 h under nitrogen gas atmosphere. After cooling, the reaction solution was diluted with H$_2$O (10 mL) and extracted with ethyl acetate (10 mL), the organic phases obtained were combined and dried over anhydrous sodium sulfate, the filtrate obtained after filtration was concentrated under reduced pressure to remove the solvent thereby obtaining the crude product, which was purified and separated by preparative silica gel plate chromatography (eluting reagent, EtOAc/PE, 1/1) to deliver the title compound BB-6 (90 mg, 52%). LCMS m/z: 527.2 [M+1]$^+$ Reference 7: Fragment BB-7

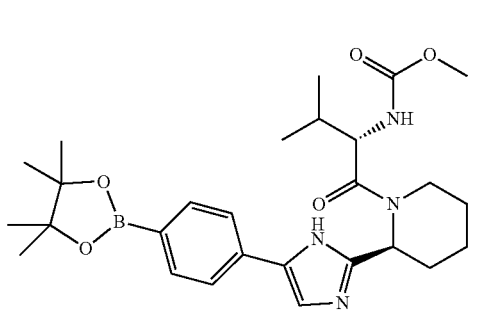

BB-7

Synthetic Route:

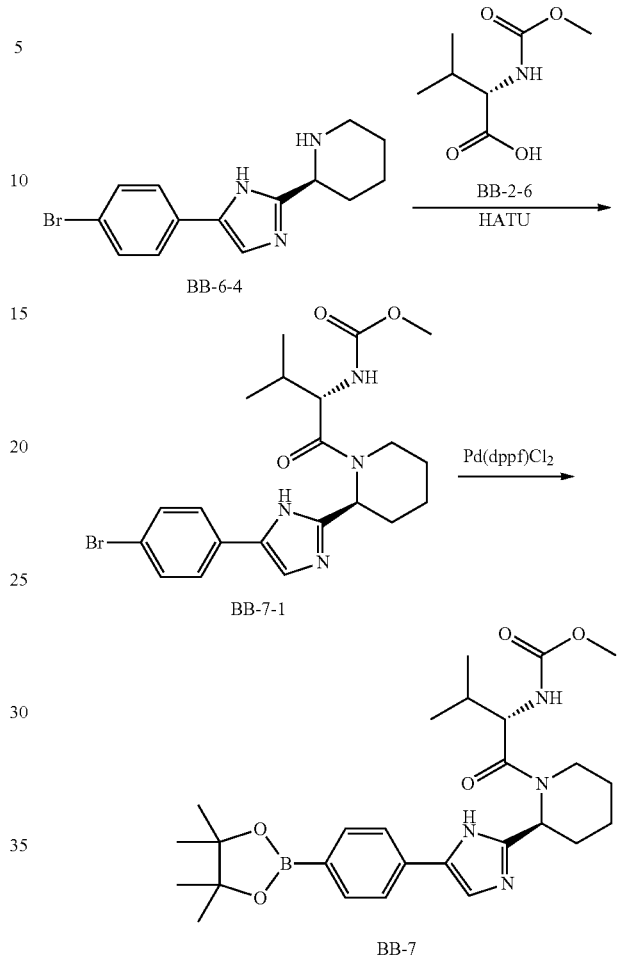

Step 1: Synthesis of Compound BB-7-1

Compound BB-6-4 (305 mg, 1.0 mmol) was dissolved in dichloromethane (10 mL), compound BB-2-6 (175 mg, 1.0 mmol), HATU (456 mg, 1.2 mmol) and DIPEA (258 mg, 2.0 mmol) were added sequentially, the reaction was stirred at room temperature for 3 h. H$_2$O (15 mL) was added and the organic phase obtained after layering was washed with saturated NaCl solution once, the organic phase was dried over anhydrous sodium sulfate, and the oil was obtained after the solvent was removed under reduced pressure, purified and separated by preparative silica gel plate chromatography (eluting reagent, EtOAc/PE, 3/1) to deliver the title compound 7-1 (260 mg, 56%). LCMS m/z: 463.0 [M+1]$^+$ Step 2: Synthesis of Compound BB-7

Compound BB-7-1 (160 mg, 0.33 mmol) was dissolved in DMF (4 mL), bis(pinacolato)diboron(129 mg, 0.49 mmol), KOAc (65 mg, 0.66 mmol) and Pd(dppf)Cl$_2$ (12 mg, 0.016 mmol) were added sequentially. The air was replaced by nitrogen gas for 3 times and the reaction solution was stirred at 110° C. for 2 h under nitrogen gas atmosphere. After cooling, the reaction solution was diluted with H$_2$O (10 mL) and extracted with ethyl acetate (10 mL), the organic phases obtained were combined and dried over anhydrous sodium sulfate, the filtrate obtained after filtration was concentrated under reduced pressure to remove the solvent thereby obtaining the crude product, which was purified and separated by preparative silica gel plate chromatography (eluting reagent, EtOAc/PE, 1/1) to deliver the title compound BB-7 (110 mg, 62%). LCMS m/z: 511.2 [M+1]+

Reference 8: Fragment BB-8

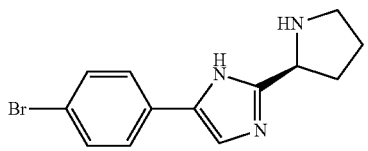

Synthetic Route:

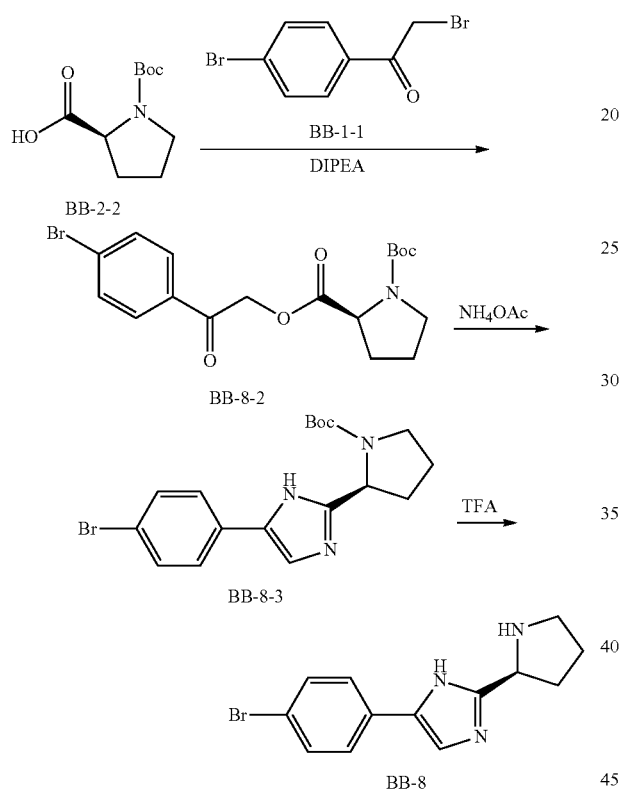

Step 1: Synthesis of Compound BB-8-2

Compound BB-2-2 (2.15 g, 10 mmol) was dissolved in acetonitrile (40 mL), compound BB-1-1 (2.78 g, 10 mmol) was added, and then DIPEA (1.29 g, 10 mmol) was added gradually. After addition, the reaction was stirred at room temperature overnight. The reaction solution was concentrated under reduced pressure to remove the solvent by a rotary evaporator, the resulting oil was diluted with H$_2$O (50 mL) and extracted with ethyl acetate (30 mL×2), the organic phases obtained twice were combined and dried over anhydrous sodium sulfate, the filtrate obtained after filtration was concentrated under reduced pressure to remove the solvent thereby delivering the title compound BB-8-2 (3.9 g, 95%). LCMS m/z: 312.0 [M-100]+

Step 2: Synthesis of Compound BB-8-3

Compound BB-8-2 (3.9 g, 9.47 mmol) was dissolved in toluene (70 mL), ammonium acetate (7.3 g, 94.8 mmol) was added, and the reaction was heated to refluxing overnight. After cooling, the reaction solution was concentrated under reduced pressure to remove the solvent, the resulting oil was diluted with H$_2$O (50 mL) and extracted with ethyl acetate (40 mL×2), the organic phases obtained twice were combined and dried over anhydrous sodium sulfate, the filtrate obtained after filtration was concentrated under reduced pressure to remove the solvent thereby delivering the title compound BB-8-3 (3.2 g, 86%). LCMS m/z: 392.1 [M+1]+

Step 3: Synthesis of Compound BB-8

Compound BB-8-3 (3.0 g, 7.65 mmol) was dissolved in dichloromethane (60 mL) and cooled to 0° C., trifluoroacetic acid (20 mL) was dripped gradually, and the reaction was stirred at room temperature for 5 h. The reaction solution was concentrated under reduced pressure to remove the solvent by a rotary evaporator, the resulting oil was neutralized with saturated sodium bicarbonate solution (pH=8) and extracted with ethyl acetate (40 mL×2), the organic phases obtained twice were combined and dried over anhydrous sodium sulfate, the filtrate obtained after filtration was concentrated under reduced pressure to remove the solvent thereby delivering the title compound BB-8 (2.2 g, 99%). LCMS m/z: 292.0 [M+1]+

Reference 9: Fragment BB-9

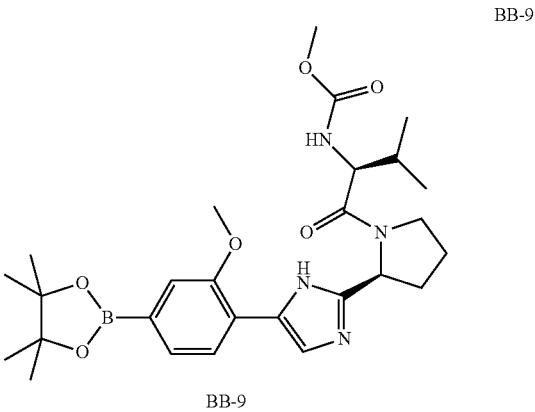

Synthetic Route:

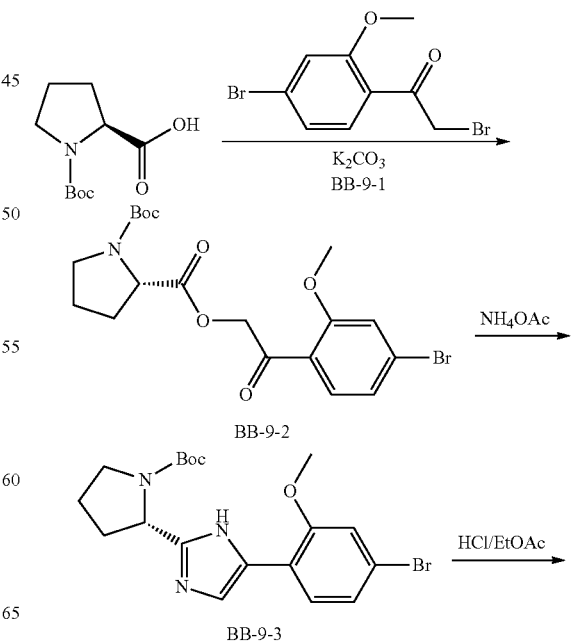

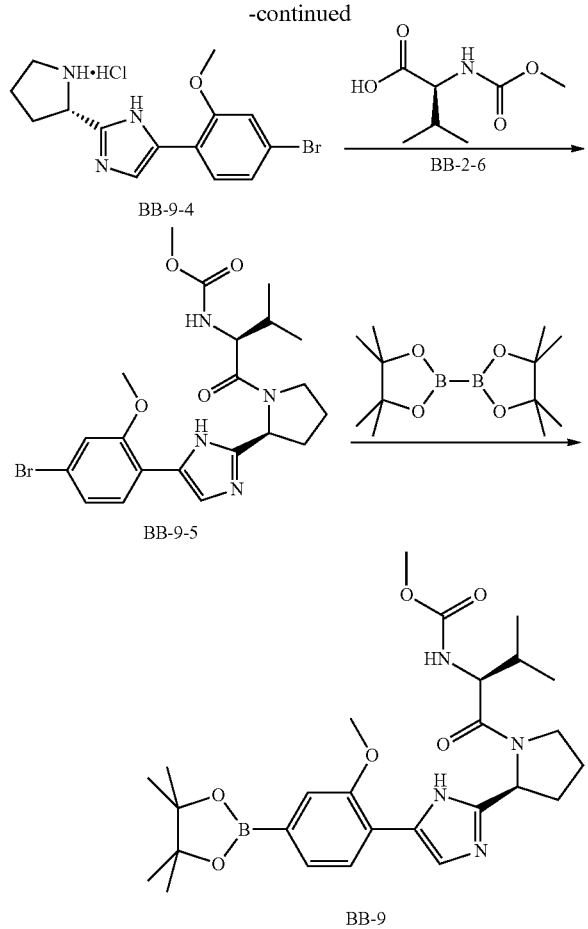

intermediate BB-9-4. The product is directly used for the next step without purification.

Step 4: Synthesis of Compound BB-9-5

At room temperature, the white solid intermediate BB-9-4 (0.242 g, 0.67 mmol), N-Moc-L-valine (BB-2-6, 0.18 g, 0.94 mmol) and DIPEA (0.31 g, 2.39 mmol) were dissolved in DMF (3 mL), HATU (0.39 g, 1.02 mmol) was added. The reaction mixture was stirred at room temperature for 3 h, after the reaction was complete as detected by TLC, the reaction mixture was quenched with $H_2O$ (10 mL), and extracted with ethyl acetate (50 mL×3). The organic phases were combined and dried over anhydrous sodium sulfate, filtrated, the filtrate was concentrated under reduced pressure to remove the solvent, the residue was subject to silica gel column chromatography (PE/EtOAc=3:2→pure EtOAc) to deliver the target compound BB-9-5 (yellow solid, 0.22 g, yield 68%). MS m/z: 481.0 [M+1]$^+$ Step 5: Synthesis of Compound BB-9

At room temperature, compound BB-9-5 (0.22 g, 0.46 mmol), bis(pinacolato)diboron (0.14 g, 0.55 mmol) were dissolved in dioxane (4 mL), KOAc (0.09 g, 0.93 mmol) and Pd(dppf)Cl$_2$ (0.03 g, 0.04 mmol) were added under nitrogen gas atmosphere. The reaction mixture react under 110° C. microwave for 45 min, after the reaction was complete as detected by TLC, the reaction mixture was cooled to room temperature, filtrated, the filtrate was concentrated under reduced pressure to remove the solvent, the residue was subject to silica gel column chromatography (PE/EtOAc=3:2→pure EtOAc) to deliver the target compound BB-9 (0.17 g, yield 70%). MS m/z: 572.1 [M+H]$^+$ Reference 10: Fragment BB-10

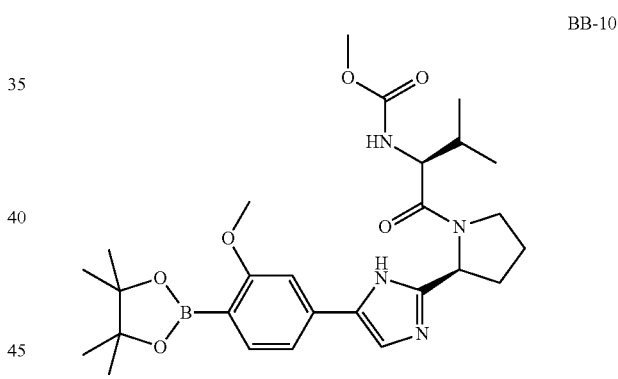

BB-10

Step 1: Synthesis of Compound BB-9-2

Compound N-Boc-L-proline (4.30 g, 20 mmol) and potassium carbonate (3.86 g, 27.97 mmol) were suspended in acetonitrile (100 mL), compound BB-9-1 (3.31 g, 10.75 mmol) was added at room temperature. The reaction was stirred at room temperature for 4 h. After the reaction was complete as detected by TLC, the solvent was removed to deliver the title compound BB-9-2 (white solid, 1.26 g, yield 14%). The product is directly used for the next step without purification. MS m/z: 343.7 [M-Boc+H]$^+$ Step 2: Synthesis of Compound BB-9-3

At room temperature, compound BB-9-2 (0.80 g, 1.81 mmol) was dissolved in toluene (50 mL), ammonium acetate (7.67 g, 99.61 mmol) was added. The reaction mixture was heated to refluxing under nitrogen gas atmosphere, stirred overnight, after the reaction was complete as detected by TLC, the reaction mixture was cooled to room temperature, quenched with $H_2O$ (30 mL), and extracted with ethyl acetate (50 mL×3). The organic phases were combined and dried over anhydrous sodium sulfate, filtrated, the filtrate was concentrated under reduced pressure to remove the solvent, the residue was subject to silica gel column chromatography (PE/EtOAc=3:2→pure EtOAc) to deliver the target compound BB-9-3 (white powder, 0.29 g, yield 38%). MS m/z: 422.0 [M+1]$^+$ Step 3: Synthesis of Compound BB-9-4

At room temperature, compound BB-9-3 (5.00 g, 11.84 mmol) was added into a hydrogen chloride/ethyl acetate solution (HCl/EA, 4 mol/L, 20 mL), stirred at room temperature for 2 h. After the reaction was complete as detected by TLC, the solvent was removed to deliver the white solid Synthetic Route:

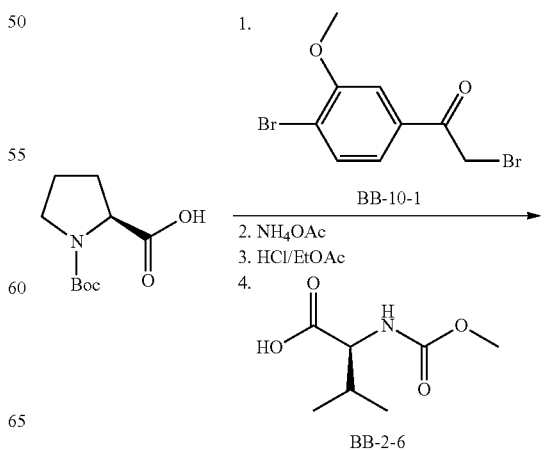

165
-continued

166
Synthetic Route:

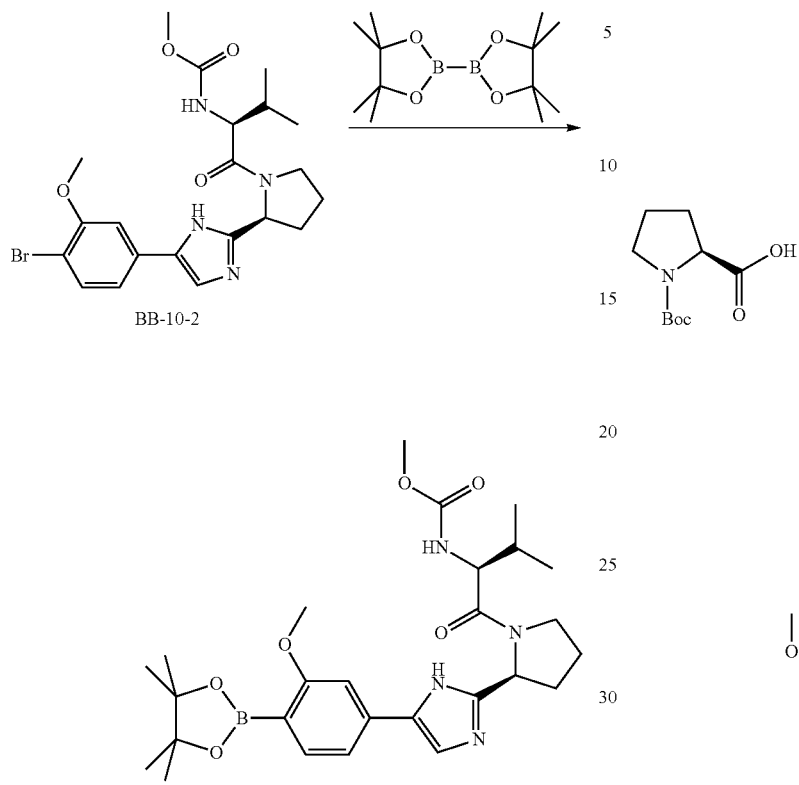

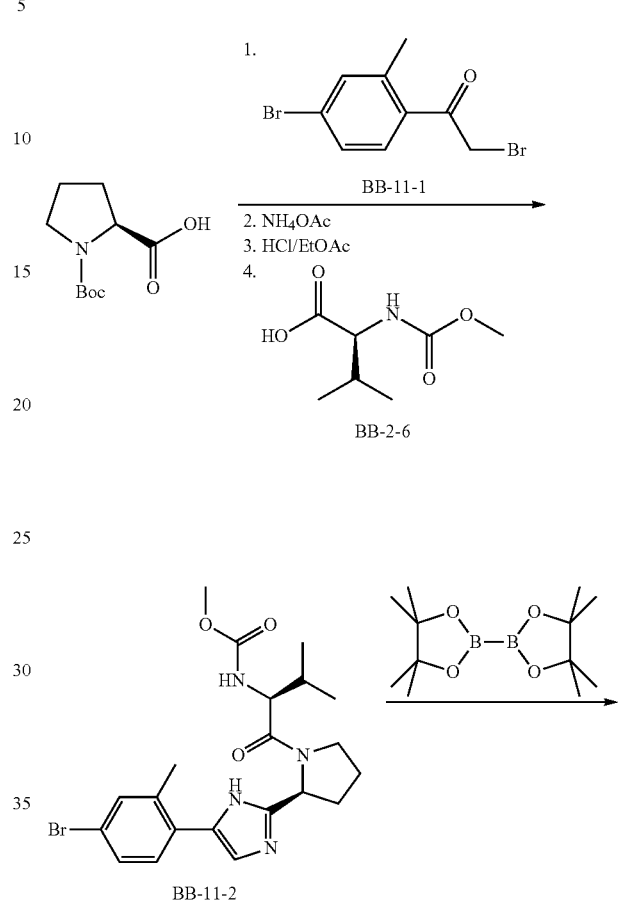

Step 1: Synthesis of Compound BB-10-2

Compound BB-10-2 could be synthesized according to the synthetic steps 1-4 in reference 9 (BB-9). LCMS m/z: 479.1 [M+H]+

Step 2: Synthesis of Compound BB-10

Compound BB-10 could be synthesized according to the synthetic step 5 in reference 9 (BB-9). LCMS m/z: 527.1 [M+H]+

Reference 11: Fragment BB-11

1p;2p

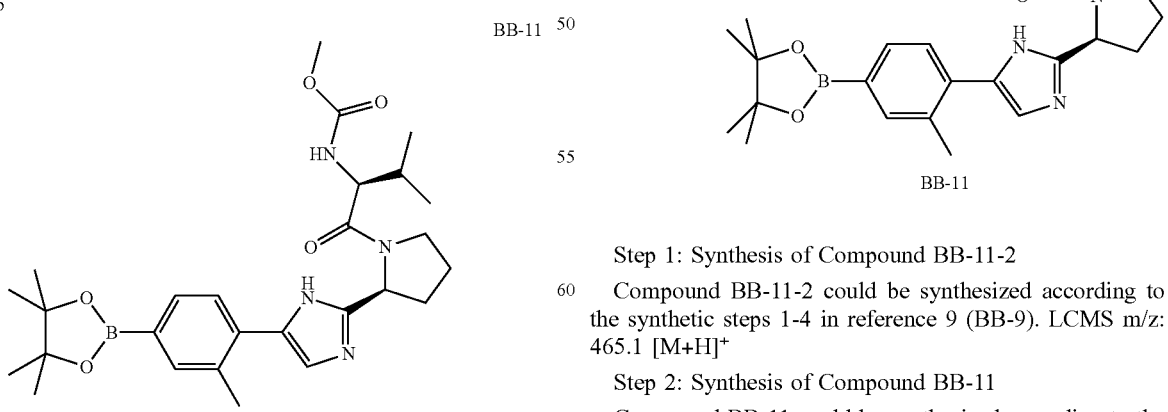

Step 1: Synthesis of Compound BB-11-2

Compound BB-11-2 could be synthesized according to the synthetic steps 1-4 in reference 9 (BB-9). LCMS m/z: 465.1 [M+H]+

Step 2: Synthesis of Compound BB-11

Compound BB-11 could be synthesized according to the synthetic step 5 in reference 9 (BB-9). LCMS m/z: 511.3 [M+H]+

Reference 12: Fragment BB-12
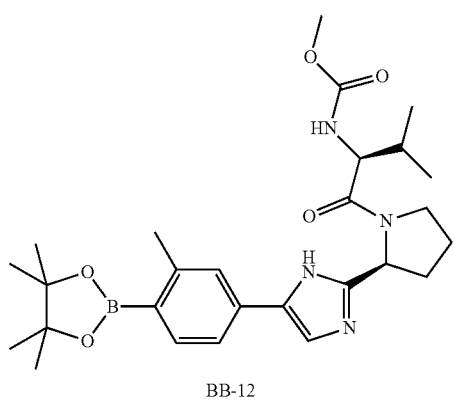
BB-12
Synthetic Route:
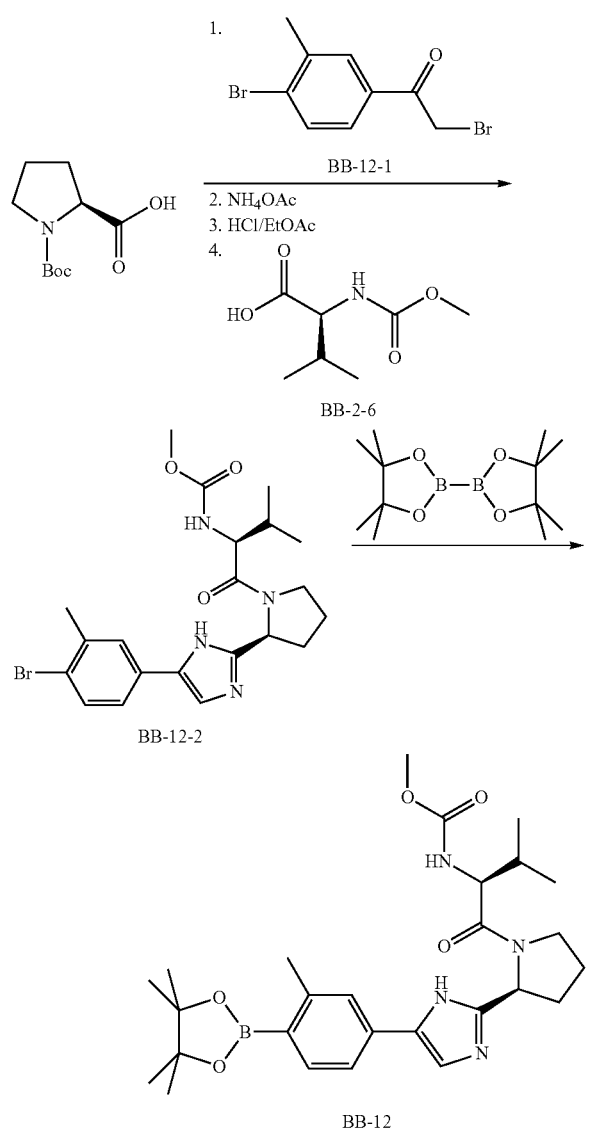
Step 1: Synthesis of Compound BB-12-2
Compound BB-12-2 could be synthesized according to the synthetic steps 1-4 in reference 9 (BB-9). LCMS m/z: 464.9 [M+H]$^+$
Step 2: Synthesis of Compound BB-12
Compound BB-12 could be synthesized according to the synthetic step 5 in reference 9 (BB-9). LCMS m/z: 488.0 [M+Na]$^+$
Reference 13: Fragment BB-13
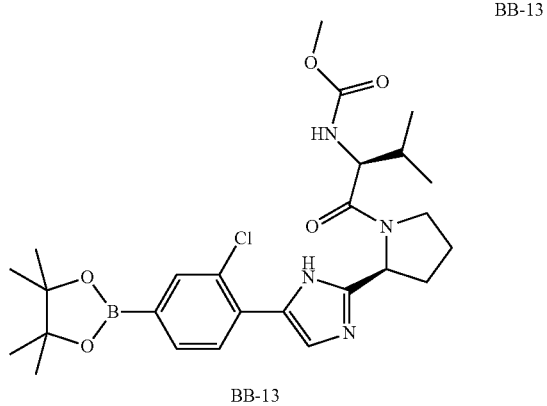
BB-13
Synthetic Route:
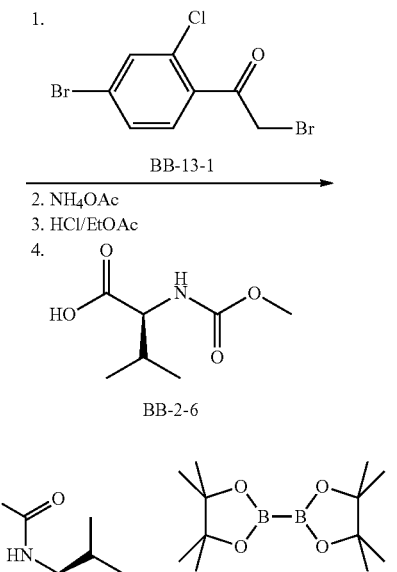

-continued

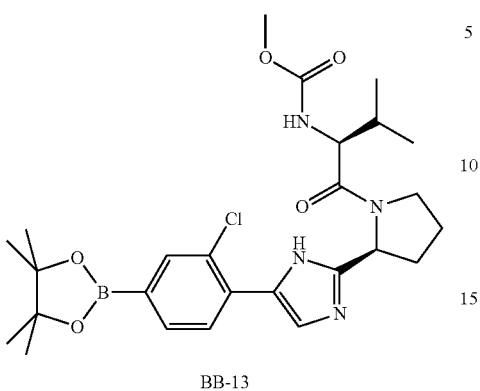

BB-13

Step 1: Synthesis of Compound BB-13-2

Compound BB-13-2 could be synthesized according to the synthetic steps 1-4 in reference 9 (BB-9). LCMS m/z: 485.1 [M+H]+

Step 2: Synthesis of Compound BB-13

Compound BB-13 could be synthesized according to the synthetic step 5 in reference 9 (BB-9). LCMS m/z: 531.2 [M+H]+

Reference 14: Fragment BB-14

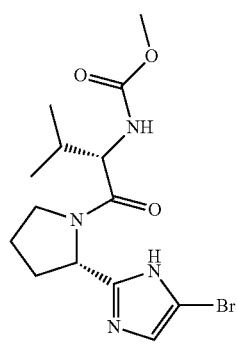

Synthetic Route:

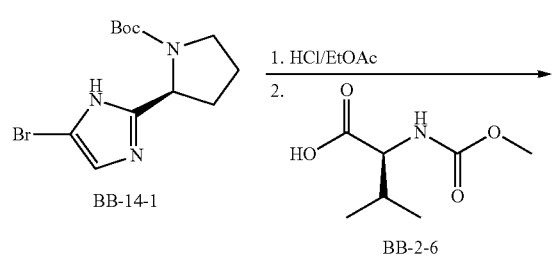

-continued

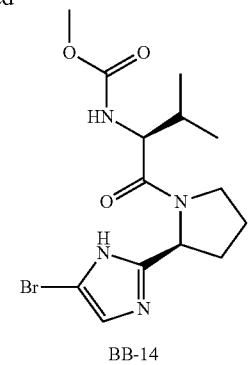

BB-14

Step 1: Synthesis of Compound BB-14

Compound BB-14-1 (600 mg, 1.90 mmol) was dissolved in ethyl acetate (5 mL) and added in hydrogen chloride/ethyl acetate (HCl/EA, 4 mol/L, 20 mL), stirred at room temperature for 3 h. After the reaction was complete as detected by TLC, the solvent was removed by a rotary evaporator thereby obtaining the white solid intermediate (410 mg). The white solid intermediate (410 mg, 1.63 mmol), N-Moc-L-valine (BB-2-6, 399 mg, 2.09 mmol), and DIPEA (735 mg, 5.70 mmol) were dissolved in DMF (10 mL), HATU (1.08 g, 2.84 mmol) was added. The reaction mixture was stirred at room temperature overnight. After the reaction was complete as detected by TLC, the reaction was quenched with H2O (10 mL), and extracted with ethyl acetate (50 mL×3). The organic phases were combined and dried over anhydrous sodium sulfate, filtrated, the filtrate was concentrated under reduced pressure to remove the solvent, the residue was purified by silica gel column chromatography (PE/EtOAc=1/1→pure EtOAc) to deliver the target compound BB-14 (white solid, 306 mg, yield 43.2%). MS m/z: 374.9 [M+H]+

Reference 15: Fragment BB-15

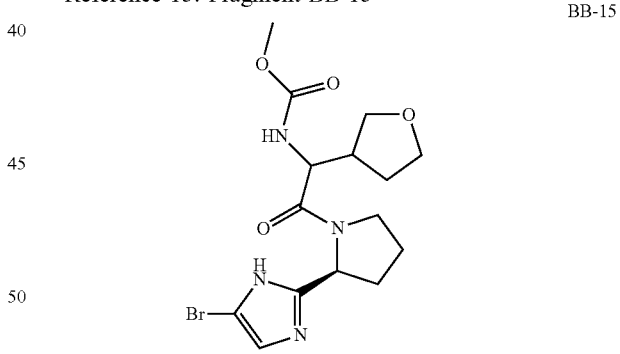

BB-15

Synthetic Route:

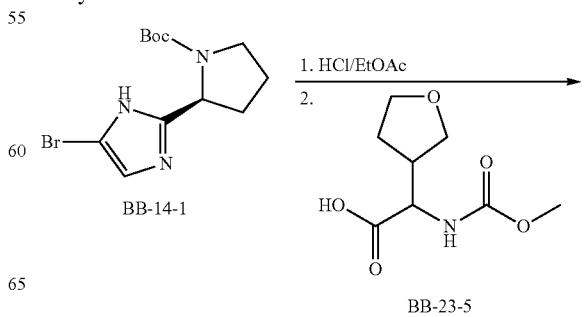

-continued

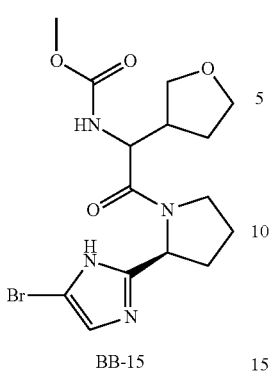

BB-15

Step 1: Synthesis of Compound BB-15

Compound BB-15 could be synthesized according to the synthetic step 1 in reference 14 (BB-14). ¹H NMR (CDCl₃, 400 MHz): δ 6.90 (s, 1 H), 5.23-5.22 (m, 1 H), 4.58-4.40 (m, 1 H), 4.13-3.88 (m, 4 H), 3.70 (s, 3 H), 3.21-3.20 (m, 2 H), 2.88-2.51 (m, 2 H), 2.16-2.07 (m, 3 H), 1.97-1.79 (m, 2 H).

Reference 16: Fragment BB-16

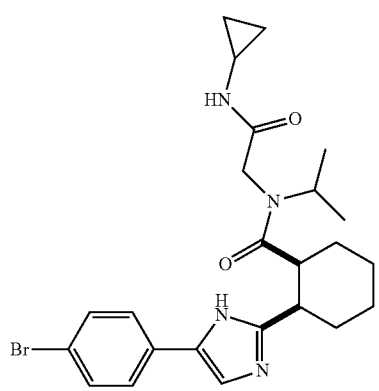

BB-16

Synthetic Route:

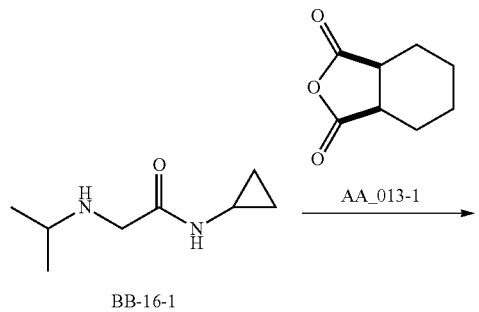

-continued

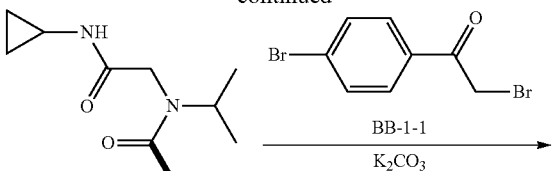

BB-16-2

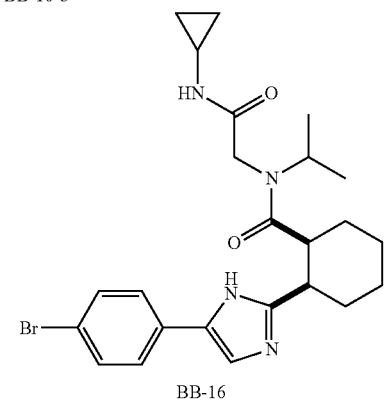

BB-16-3

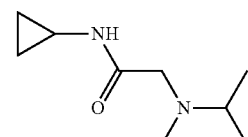

BB-16

Step 1: Synthesis of Compound BB-16-2

At room temperature, compound BB-16-1 (4.1 g, 26.2 mmol) was dissolved in THF (20 mL), cis-1,2-cyclohexane-dicarboxylic anhydride (AA_013-1, 2.0 g, 13.0 mmol) was added under nitrogen gas atmosphere. The reaction mixture was stirred at room temperature for 6 h. After the reaction was complete as detected by TLC, the solvent was removed by a rotary evaporator thereby delivering the target compound BB-16-2 (colorless jelly, 3.5 g, yield 83.2%). The product was directly used for the next step without purification. ¹H NMR (CDCl₃, 400 MHz): δ 7.78 (s, 1 H), 5.23-5.22 (m, 1 H), 3.47 (s, 2 H), 3.06-3.03 (m, 1 H), 2.78-2.60 (m, 2 H), 2.08 (brs, 1 H), 1.86 (m, 1 H), 1.65-1.51 (m, 2 H), 1.27-1.23 (m, 4 H), 1.20 (d, J=6.4 Hz, 6 H), 0.80-0.63 (m, 2 H), 0.58-0.57 (m, 2 H).

Step 2: Synthesis of Compound BB-16-3

Compound BB-16-2 (3.5 g, 10.79 mmol) and potassium carbonate (3.1 g, 22.5 mmol) were suspended in DMF (25 mL), 2,4'-dibromoacetophenone (BB-1-1, 3.1 g, 11.2 mmol) was added at room temperature. The reaction mixture was stirred at room temperature for 2 h. After the reaction was complete as detected by TLC, the reaction was quenched with H₂O (20 mL), and extracted with ethyl acetate (50 mL×3). The organic phases were combined and dried over anhydrous sodium sulfate, filtrated, the filtrate was concentrated under reduced pressure to remove the solvent, the residue was purified by silica gel column chromatography (PE/EtOAc=4:1÷1:4) to deliver the target compound BB-16-3 (4.8 g, yield 87.8%). MS m/z: 530.7 [M+Na]⁺

Step 3: Synthesis of Compound BB-16

At room temperature, compound BB-16-3 (1.50 g, 2.96 mmol) was dissolved in toluene (200 mL), ammonium acetate (11.88 g, 154.09 mmol) was added. the reaction mixture was heated to refluxing under nitrogen gas atmosphere, and stirred overnight. After the reaction was complete as detected by TLC, the reaction mixture was cooled to room temperature, quenched with H₂O (30 mL), and extracted with ethyl acetate (50 mL×3). The organic phases were combined and dried over anhydrous sodium sulfate, filtrated, the filtrate was concentrated under reduced pressure to remove the solvent, the residue was subject to silica gel column chromatography (PE/EtOAc=2:3÷pure EtOAc) to deliver the target compound BB-16 (light yellow powder, 0.95 g, yield 66.0%). MS m/z: 489.3 [M+H]⁺

Reference 21: Fragment BB-21

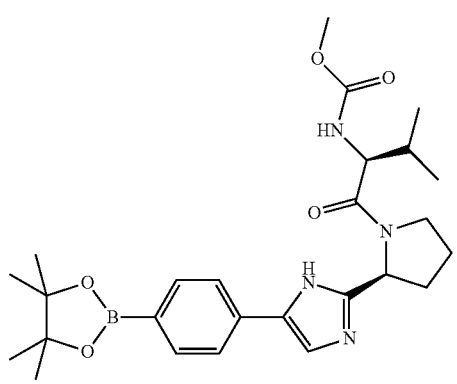

BB-21

Synthetic Route:

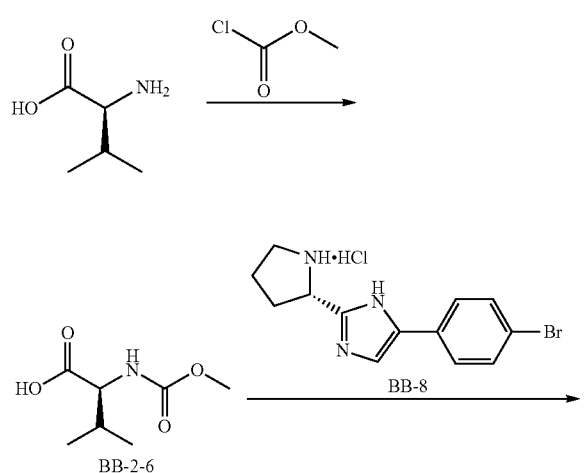

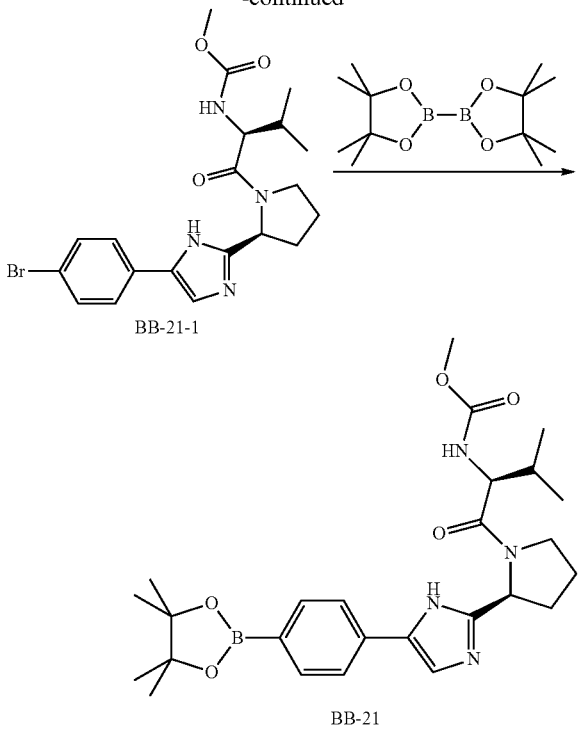

Step 1: Synthesis of Compound BB-2-6

L-valine (100 g, 751 mmol) was added in NaOH solution (2 mol/L, 535 mL). The mixture was cooled to 5° C. or below with an ice bath, methylchloroformate (118.13 g, 1.25 mmol) was added dropwise, and stirred at room temperature overnight. After the reaction was complete as detected by TLC, the reaction mixture was cooled to 5° C. or below with an ice bath and conc. hydrochloric acid was added to adjust pH to about 5. The solid precipitation was collected and washed with H₂O (100 mL), dried to deliver the target compound BB-2-6 (white solid, 141 g, yield 98.2%). The product was directly used for the next step without purification. ¹H NMR (CDCl₃ 400 MHz): δ 5.19 (d, J=8.8 Hz, 1 H), 4.32 (dd, J=8.8 Hz, J=4.4 Hz, 1 H), 3.71 (s, 3 H), 2.26-2.18 (m, 1 H), 1.01 (d, J=7.2 Hz, 3 H), 0.94 (d, J=6.4 Hz, 3 H).

Step 2: Synthesis of Compound BB-21-1

The EDC HCl (26.3 g, 136.9 mmol), N-Moc-L-valine (BB-2-6, 17.6 g, 92.05 mmol), and DIPEA (35.4 g, 274.4 mmol) were dissolved in anhydrous dichloromethane (500 mL). After the mixture was stirred for 10 min at room temperature, compound BB-8 (reference 8, 30 g, 102.7 mmol) was added. The reaction mixture was stirred at room temperature overnight under nitrogen gas atmosphere. After the reaction was complete as detected by TLC, the reaction was quenched with H₂O (20 mL) and the organic phase was washed with 10% hydrochloric acid until pH was 5-6, then washed with saturated brines (100 mL) and dried over anhydrous sodium sulfate. After filtration, the filtrate was concentrated under reduced pressure to remove the solvent thereby delivering the compound BB-21-1 (gray foam solid, 35 g, yield 76%). The product was directly used for the next step without purification. MS m/z: 449.0 [M+H]⁺

Step 3: Synthesis of Compound BB-21

At room temperature, compound BB-21-1 (80 g, 178 mmol), bis(pinacolato)diboron (90 g, 354 mmol) were dissolved in dioxane (600 mL). KOAc (35 g, 357 mmol) and Pd(dppf)Cl$_2$ (13 g, 1.78 mmol) were added under nitrogen gas atmosphere. The reaction solution was heated to 90° C. and stirred overnight under nitrogen gas atmosphere. After the reaction was complete as detected by TLC, the reaction mixture was cooled to room temperature. After filtration, the filtrate was concentrated under reduced pressure to remove the solvent, the residue was subject to silica gel column chromatography (PE/EtOAc=20:1→8:1) to deliver the target compound BB-21 (gray solid, 70 g, yield 80%). MS m/z: 519.1 [M+Na]$^+$ Reference 22: Fragment BB-22

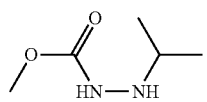

Synthetic Route:

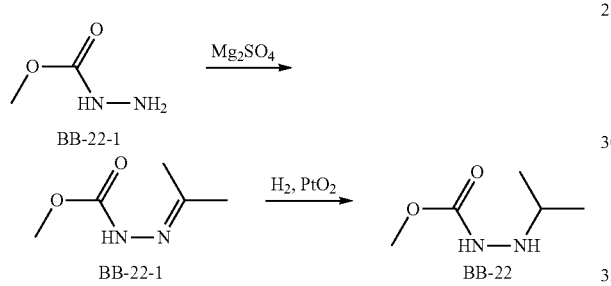

Step 1: Synthesis of Compound BB-22-2

At room temperature, methyl carbazate (BB-22-1, 3 g, 33 mmol) was dissolved in acetone (30 mL), anhydrous magnesium sulfate (8 g, 67 mmol) was added under nitrogen gas atmosphere. The reaction system was heated to reflux and stirred for 2 h. After the reaction was complete as detected by TLC, the reaction mixture was cooled to room temperature. After filtration, the solvent of the filtrate was removed by a rotary evaporator thereby delivering the target compound BB-2-2 (white solid, 3.8 g, yield 87.8%). The product was directly used for the next step without purification. $^1$H NMR (CDCl$_3$, 400 MHz): δ 3.82 (brs, 3 H), 2.06 (d, J=1.6 Hz, 3 H), 1.85 (s, 3 H).

Step 2: Synthesis of Compound BB-22

At room temperature, compound BB-22-2 (3 g, 23.1 mmol) was dissolved in a mixed solvent of ethyl acetate/acetic acid (30 mL/3 mL), platinum dioxide (0.3 g) was added under nitrogen gas atmosphere. The reaction mixture was reacted for 12 h at 50° C. and under a pressure of 50 psi, then cooled to room temperature. After filtration, the solvent of the filtrate was removed by a rotary evaporator thereby delivering the target compound BB-22 (colorless oil, 2.9 g, yield 95.1%). The product was directly used for the next step without purification. $^1$H NMR (CDCl$_3$, 400 MHz): δ 3.62 (s, 3 H), 3.25 (brs, 1 H), 1.04 (d, J=6.4 Hz, 6 H).

Reference 23: Fragment BB-23

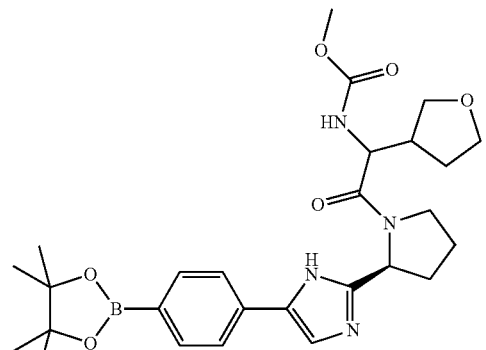

Synthetic Route:

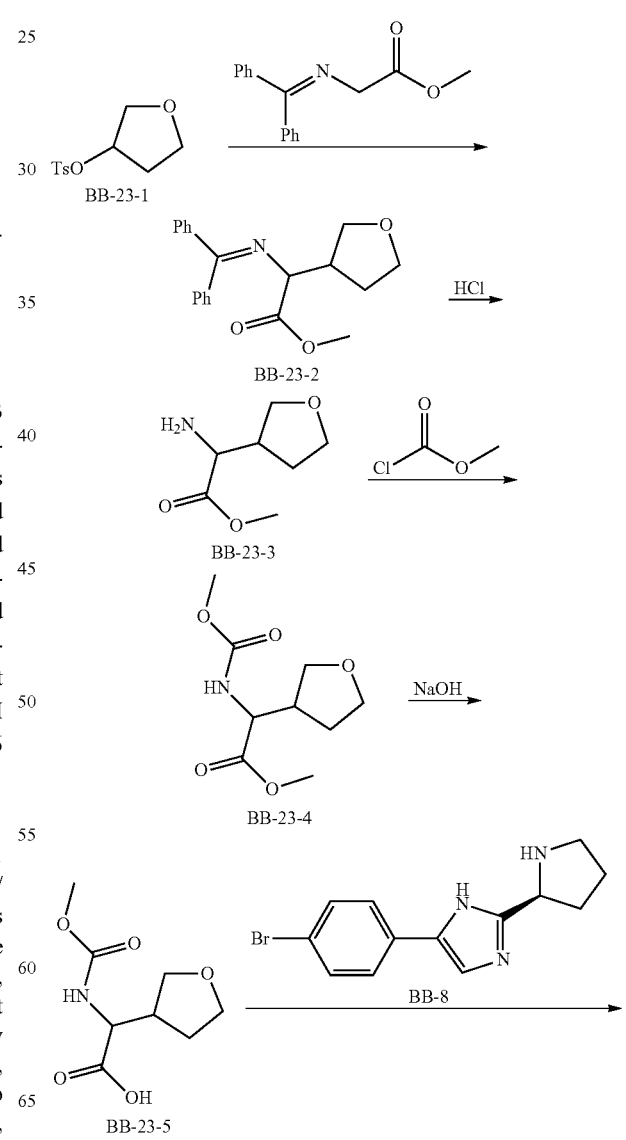

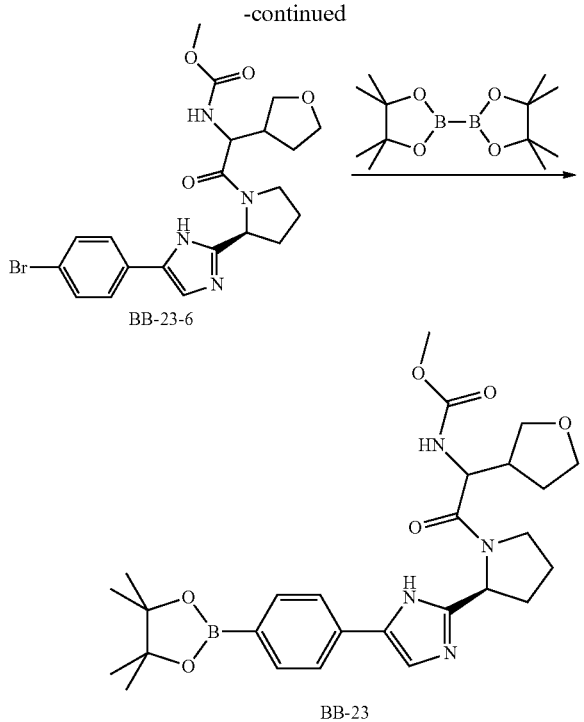

BB-23-6

BB-23

Step 1: Synthesis of Compound BB-23-2

3-Tosyltetrahydrofuran (BB-23-1, 3 g, 12.4 mmol), N-(diphenylmethylene) glycine methyl ester (1.49 g, 5.88 mmol) were dissolved in toluene (30 mL) at room temperature, LiHMDS (1 mol/L in THF, 7.1 mL, 7.1 mmol) was added dropwise under nitrogen gas atmosphere. The reaction mixture was heated to 100° C. under nitrogen gas atmosphere and stirred overnight. After the reaction was complete as detected by TLC, the reaction mixture was cooled to room temperature and quenched with $H_2O$ (20 mL), extracted with ethyl acetate (50 mL×3). The organic phases were combined and dried over anhydrous sodium sulfate. After filtration, the filtrate was concentrated under reduced pressure to remove the solvent, the residue was subject to silica gel column chromatography (PE/EtOAc=35:1→5:1) to deliver the target compound BB-3-2 (orange oil, 1.52 g, yield 80%). $^1$H NMR (CDCl$_3$, 400 MHz): δ 7.67-7.65 (m, 2 H), 7.48-7.36 (m, 6 H), 7.22-7.20 (m, 2 H), 4.10 (t, J=7.6 Hz, 1 H), 3.94-3.92 (m, 1 H), 3.79-3.46 (m, 5 H), 3.64-3.46 (m, 1 H), 3.05-3.01 (m, 1 H), 2.07-2.02 (m, 1 H), 1.81-1.61 (m, 1 H).

Step 2: Synthesis of Compound BB-23-3

At room temperature, compound BB-23-2 (12.2 g, 37.8 mmol) was dissolved in THF (100 mL), hydrochloric acid (2 mol/L, 75.5 mL, 151 mmol) was added dropwise, the reaction mixture was stirred at room temperature for 4 h. After the reaction was complete as detected by TLC, the solvent was removed by a rotary evaporator and the mixture was washed with petroleum ether (50 mL×3). NaOH was added into the reaction system to adjust pH to 8-9, and then the system was extracted with ethyl acetate (50 mL×3). The organic phases were combined and dried over anhydrous sodium sulfate. After filtration, the filtrate was subject to a rotary evaporator to remove the solvent thereby delivering the target compound BB-23-3 (orange oil, 3.2 g, yield 53.4%). $^1$H NMR (CDCl$_3$, 400 MHz): δ 3.90-3.85 (m, 2 H), 3.73-3.68 (m, 5 H), 3.37 (dd, J=20.8, J=7.2 Hz, 1 H), 2.52-2.46 (m, 1 H), 1.99-1.96 (m, 1 H), 1.78-1.77 (m, 1 H).

Step 3: Synthesis of Compound BB-23-4

At room temperature, compound BB-23-3 (2.88 g, 18.1 mmol) was dissolved in dichoromethane (50 mL), DIPEA (7.0 g, 54.3 mmol) was added, then methylchloroformate (1.88 g, 19.9 mmol) was dripped, and the mixture was stirred at room temperature for 4 h. After the reaction was complete as detected by TLC, the solvent was removed under reduced pressure, the residue was subject to silica gel column chromatography (PE/EtOAc=20:1→2:1) to deliver the target compound BB-23-4 (yellow oil, 2.8 g, yield 71.2%). $^1$H NMR (CDCl$_3$, 400 MHz): δ 5.38 (brs, 1 H), 4.42-4.38 (m, 1 H), 3.92-3.90 (m, 2 H), 3.78 (s, 3 H), 3.75-3.68 (m, 6 H), 2.71-2.67 (m, 1 H), 2.08-1.81 (m, 2 H).

Step 4: Synthesis of Compound BB-23-5

At room temperature, compound BB-23-4 (3.25 g, 15.0 mmol) was dissolved in a mixed solvent of methanol/$H_2O$ (100 mL/100 mL), NaOH (1.2 g, 30.0 mmol) was added. The reaction mixture was heated to 75° C. and stirred for 3 h. After the reaction was complete as detected by TLC, the reaction mixture was adjusted to pH 1-2 with 2N hydrochloric acid, and extracted with ethyl acetate (200 mL×2). The organic phases were combined and dried over anhydrous sodium sulfate. After filtration, the filtrate was subject to a rotary evaporator to remove the solvent thereby delivering the target compound BB-23-5 (orange oil, 2.9 g, yield 95.4%). $^1$H NMR (CDCl$_3$, 400 MHz): δ 5.60 (dd, J=26.4, J=8.4 Hz, 1 H), 4.40 (brs, 1 H), 3.99-3.89 (m, 2 H), 3.79-3.72 (m, 5 H), 2.80-2.77 (m, 1 H), 2.13-2.07 (m, 1 H), 1.92-1.80 (m, 1 H).

Step 5: Synthesis of Compound BB-23-6

At room temperature, compound BB-23-5 (550 mg, 2.71 mmol), compound BB-8 (400 mg, 1.37 mmol), and DIPEA (763 mg, 5.91 mmol) were dissolved in DMF (10 mL), HATU (958 mg, 2.52 mmol) was added. The reaction mixture was stirred at room temperature for 3 h. After the reaction was complete as detected by TLC, the solvent was removed under reduced pressure. The residue was subject to silica gel column chromatography (PE/EtOAc=10:1→pure EtOAc) to deliver the target compound BB-2-6 (yellow solid, 540 mg, yield 82.5%). MS m/z: 476.8 [M+H]$^+$

Step 6: Synthesis of Compound BB-23

Compound BB-23 could be synthesized according to the synthetic step 3 in reference 21 (BB-21). MS m/z: 525.0 [M+H]$^+$ Reference 24: Fragment BB-24

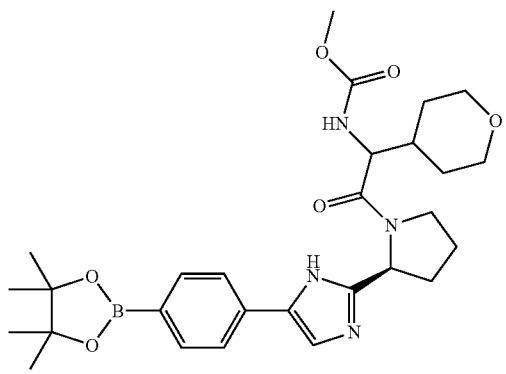

BB-24

Synthetic Route:

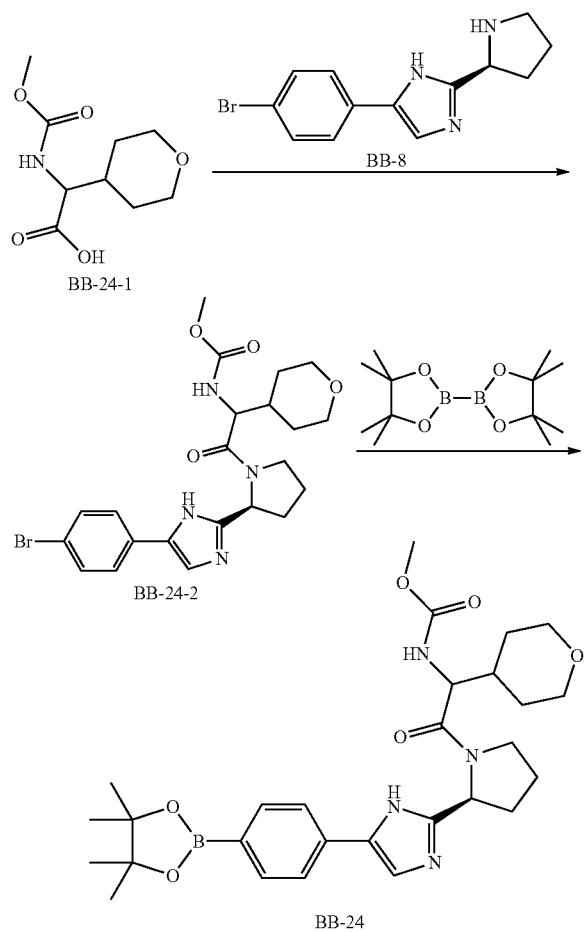

Step 1: Synthesis of Compound BB-24-2

Compound BB-24-2 could be synthesized according to the synthetic step 5 in reference 23 (BB-23). MS m/z: 492.9 [M+H]$^+$ Step 2: Synthesis of Compound BB-24

Compound BB-24 could be synthesized according to the synthetic step 3 in reference 21 (BB-21). MS m/z: 539.2 [M+H]$^+$ Reference 25: Fragment BB-25

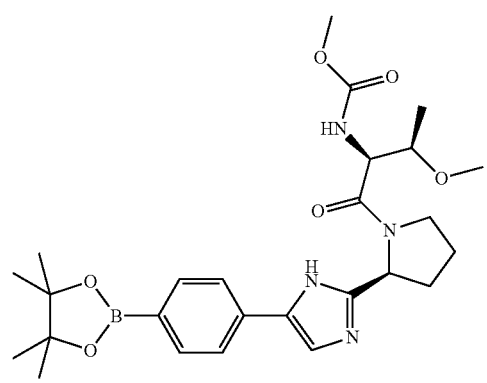

Synthetic Route:

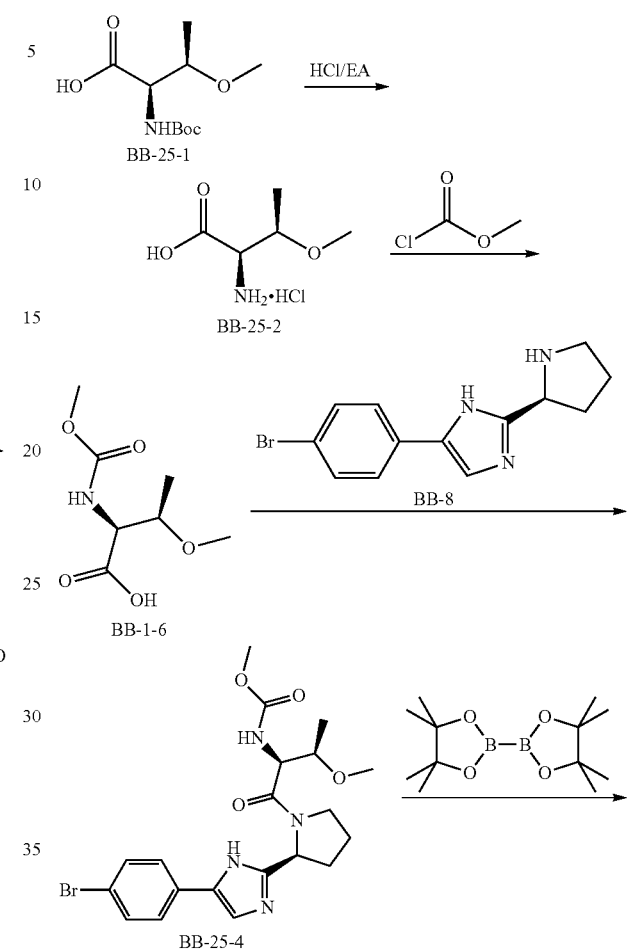

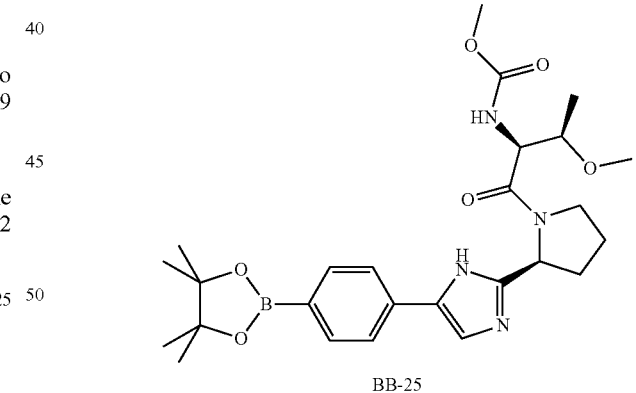

Step 1: Synthesis of Compound BB-25-2

Compound BB-25-1 (18.0 g, 77.2 mmol) was dissolved in ethyl acetate (50 mL), a solution of HCl in ethyl acetate (4 mol/L, 50 mL) was added, the reaction mixture was stirred at room temperature for 2 h. After the reaction was complete as detected by TLC, the solvent was removed under reduced pressure thereby delivering the target compound BB-25-2 (light yellow, 13.0 g, yield 100%). The product is directly used for the next step without purification. $^1$H NMR (400 MHz, DMSO-d6): δ 8.37 (brs, 3H), 3.81-3.88 (m, 2H), 3.23 (s, 3H), 1.20 (d, J=6.4 Hz, 3H).

Step 2: Synthesis of Compound BB-25-3

NaOH (12.2 g, 305 mmol) was dissolved in H₂O (200 mL), cooled to 0° C., compound BB-25-2 (13.0 g, 76.6 mmol) was added, when fully dissolved, methylchloroformate (7.2 g, 76.2 mmol) was dripped. After the addition, the reaction mixture was stirred at room temperature overnight. After the reaction was complete as detected by TLC, the reaction mixture was adjusted to pH=3 with 1N hydrochloric acid and extracted with ethyl acetate (30 mL×3). The organic phases were combined and washed with saturated brines and dried over anhydrous sodium sulfate. After filtration, the filtrate was concentrated under reduced pressure to remove the solvent thereby delivering the compound BB-25-3 (white solid, 8.0 g, yield 54.8%). The product was directly used for the next step without purification. ¹H NMR: (400 MHz, DMSO-d6) δ 12.65 (brs, 1H), 7.02 (d, J=9.0 Hz, 1H), 4.04-4.01 (m, 2H), 3.76-3.74 (m, 1H), 3.51 (s, 3H), 3.81 (s, 3H), 1.96 (s, 3H).

Step 3: Synthesis of Compound BB-25-4

Compound BB-25-4 could be synthesized according to the synthetic step 5 in reference 23 (BB-23). MS m/z: 465.0 [M+H]⁺

Step 4: Synthesis of Compound BB-25

Compound BB-25 could be synthesized according to the synthetic step 3 in reference 21 (BB-21). MS m/z: 513.1 [M+H]⁺

Reference 26: Fragment BB-26

BB-26

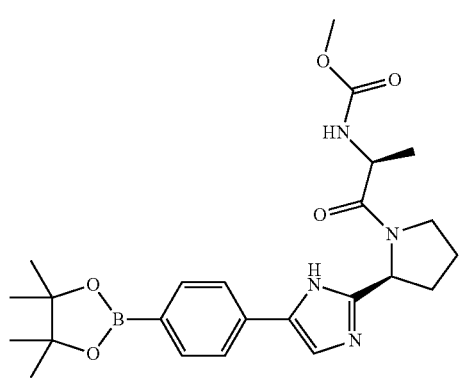

Synthetic Route:

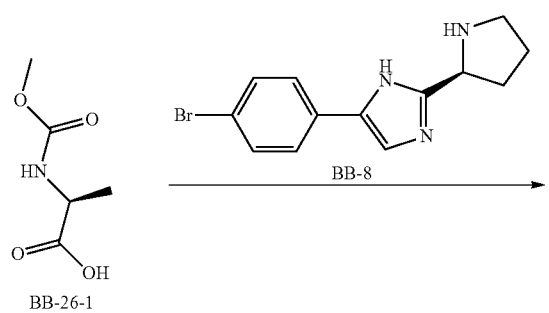

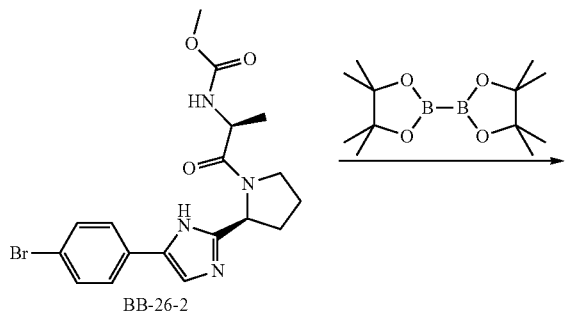

BB-26-2

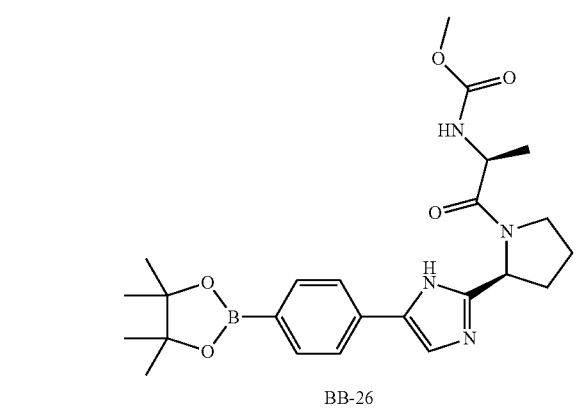

BB-26

Step 1: Synthesis of Compound BB-26-2

Compound BB-26-2 could be synthesized according to the synthetic step 5 in reference 23 (BB-23). MS m/z: 422.9 [M+H]⁺

Step 2: Synthesis of Compound BB-26

Compound BB-26 could be synthesized according to the synthetic step 3 in reference 21 (BB-21). MS m/z: 469.2 [M+H]⁺

Reference 27: Fragment BB-27

BB-27

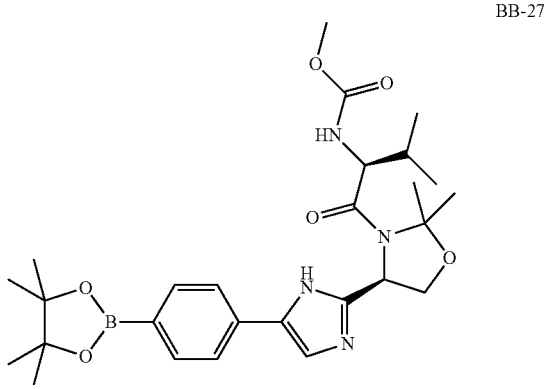

Synthetic Route:

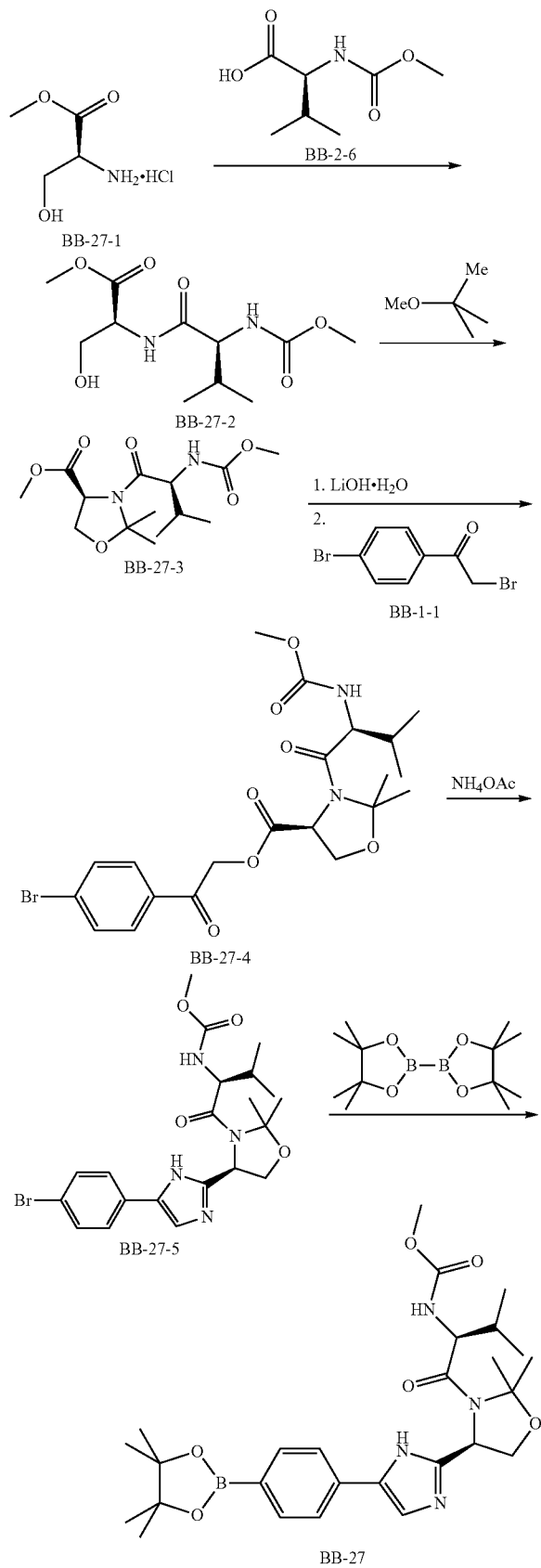

Step 1: Synthesis of Compound BB-27-2

At room temperature, N-Moc-L-valine (BB-2-6, 10 g, 52.3 mmol) was dissolved in THF (200 mL), cooled to −30° C., TEA (11.6 g, 114.9 mmol), isobutyl chloroformate (9.36 g, 68.1 mmol) were added. After the mixture react at −30° C. for 1 h, L-serine hydrochloride (BB-27-1, 10.6 g, 68.4 mmol) was added. The mixture further react at −30° C. for 3 h and then warmed to room temperature and stirred overnight. After the reaction was complete as detected by TLC, the solvent was removed by a rotary evaporator. The residue was dissolved in ethyl acetate (200 mL), washed with saturated brines (50 mL×3). The organic phase was dried over anhydrous sodium sulfate. After filtration, the solvent of the filtrate was removed by a rotary evaporator thereby delivering the target compound BB-27-2 (white solid, 12.34 g, yield 765.3%). The product was directly used for the next step without purification. MS m/z: 276.8 [M+H]$^+$ Step 2: Synthesis of Compound BB-27-3

At room temperature, compound BB-27-2 (20 g, 72.39 mmol), p-toluenesulfonic acid monohydrate (3.64 g, 19.14 mmol) were dissolved in THF (200 mL), 2,2-dimethoxypropane (37.7 g, 36.22 mmol) was added. The reaction system was heated to reflux and stirred overnight. After the reaction was complete as detected by TLC, ethyl acetate (400 mL) was added, the mixture was washed with saturated sodium bicarbonate solution (50 mL×2), saturated brines (50 mL×2) sequentially. The organic phase was dried over anhydrous sodium sulfate, filtrated, the solvent of the filtrate was removed by a rotary evaporator thereby delivering the target compound BB-27-3 (yellow oil, 5.0 g, yield 21.8%). The product was directly used for the next step without purification. MS m/z: 339.1 [M+Na]$^+$ Step 3: Synthesis of Compound BB-27-4

Compound BB-27-3 (1.8 g, 5.69 mmol) was added in a mixed solvent of THF/t-butanol/H$_2$O(36 mL/9 mL/9 mL), lithium hydroxide monohydrate (478.38 mg, 11.39 mmol) was added, the mixture was stirred at 30° C. for 2 h. After the reaction was complete as detected by TLC, the reaction mixture was adjusted to pH=3 with 1N hydrochloric acid and extracted with ethyl acetate (30 mL×3). The organic phases were combined and washed with saturated brines (20 mL), dried over anhydrous sodium sulfate. After filtration, the solvent of the filtrate was removed by a rotary evaporator thereby delivering the intermediate as yellow solid (1.7 g, yield 98.8%). The intermediate (1.7 g, 5.62 mmol), 2,4'-dibromoacetophenone (BB-1-1, 1.99 g, 17.15 mmol) were dissolved in acetonitrile (60 mL), TEA (1.49 g, 14.7 mmol) was added at room temperature. The reaction mixture was stirred at 50° C. overnight. After the reaction was complete as detected by TLC, the solvent was removed by a rotary evaporator. The residue was dissolved in ethyl acetate (200 mL), washed with saturated brines (40 mL×3). The organic phase was dried over anhydrous sodium sulfate, filtrated, the filtrate was concentrated under reduced pressure to remove the solvent thereby delivering the target compound BB-27-4 (yellow solid, 2.8 g, yield 99.6%). The product was directly used for the next step without purification. MS m/z: 500.9 [M+H]$^+$ Step 4: Synthesis of Compound BB-27-5

Compound BB-27-4 (2.8 g, 5.61 mmol) was dissolved in dioxane (100 mL), ammonium acetate (8.64 g, 112.2 mmol) was added. The reaction mixture was heated to 110° C. under nitrogen gas atmosphere, stirred overnight. After the reaction was complete as detected by TLC, the reaction mixture was cooled to room temperature, filtrated, the solvent of the filtrate was removed by a rotary evaporator. The residue was subject to silica gel column chromatography (PE/EtOAc=2:1) to deliver the target compound BB-27-5 (yellow solid, 1.2 g, yield 44.4%). MS m/z: 481.3 [M+H]+

Step 5: Synthesis of Compound BB-27

Compound BB-27 could be synthesized according to the synthetic step 3 in reference 21 (BB-21). MS m/z: 527.3 [M+H]+

Reference 28: Fragment BB-28

Synthetic Route:

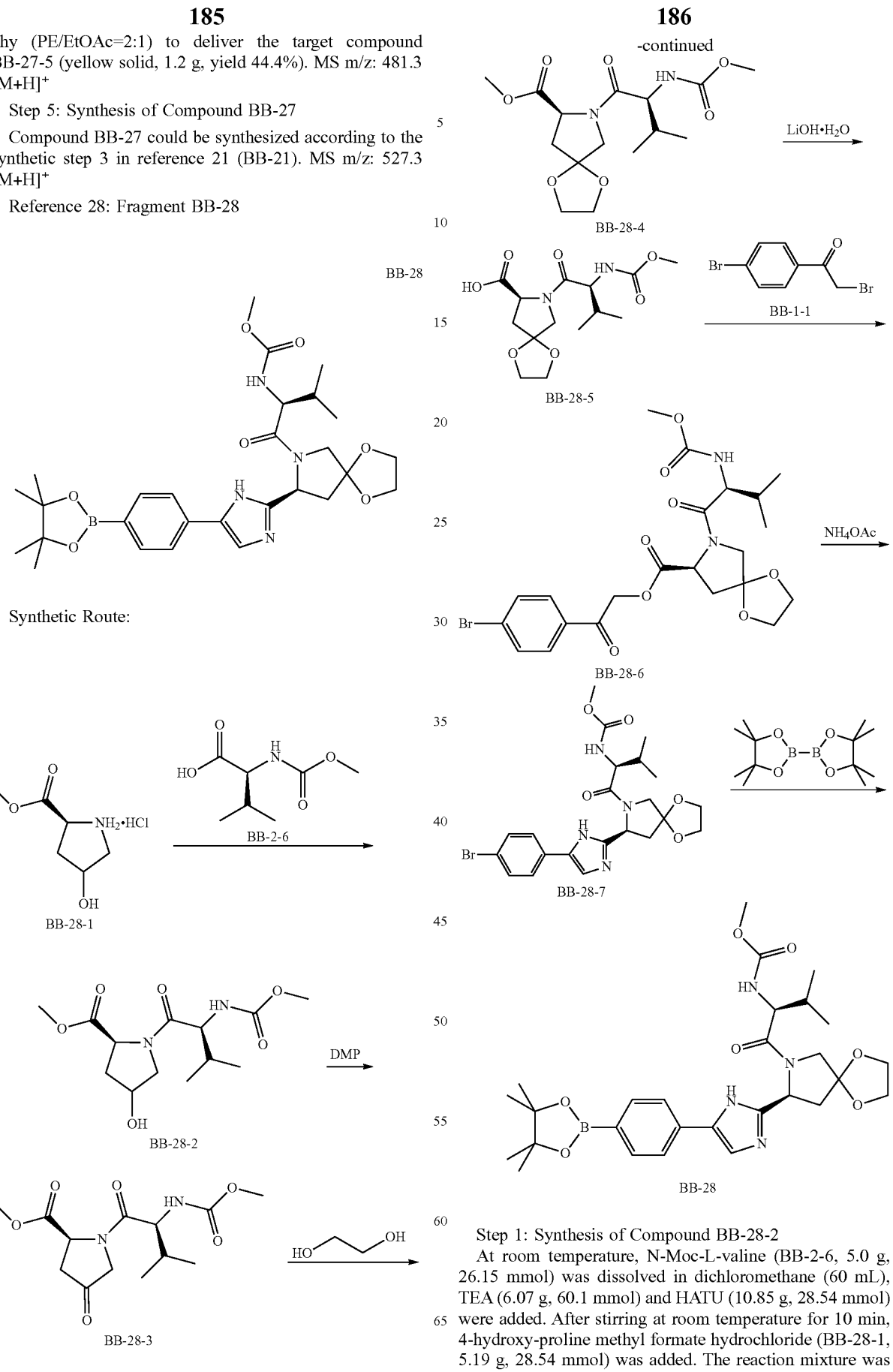

Step 1: Synthesis of Compound BB-28-2

At room temperature, N-Moc-L-valine (BB-2-6, 5.0 g, 26.15 mmol) was dissolved in dichloromethane (60 mL), TEA (6.07 g, 60.1 mmol) and HATU (10.85 g, 28.54 mmol) were added. After stirring at room temperature for 10 min, 4-hydroxy-proline methyl formate hydrochloride (BB-28-1, 5.19 g, 28.54 mmol) was added. The reaction mixture was stirred at room temperature for 4 h. After the reaction was complete as detected by TLC, the reaction was quenched with saturated sodium bicarbonate solution (30 mL). The layers were separated, the aqueous phase was extracted with dichloromethane (20 mL×3). The organic phases were combined and dried over anhydrous sodium sulfate. After filtration, the solvent of the filtrate was removed by a rotary evaporator. The residue was subject to silica gel column chromatography (PE/EtOAc=1:1) to deliver the target compound BB-28-2 (white solid, 2.0 g, yield 23.2%). MS m/z: 303.0 [M+H]$^+$ Step 2: Synthesis of Compound BB-28-3

Compound BB-28-2 (2.0 g, 6.62 mmol) was dissolved in DCM (50 mL), Dess-Martin oxidizing agent (DMP, 5.71 g, 13.46 mmol) was added at room temperature, the mixture was stirred at room temperature overnight. After the reaction was complete as detected by TLC, the reaction was quenched with 5% sodium thiosulfate solution (50 mL), saturated sodium bicarbonate solution (100 mL) was added. After stirred for 10 min, the mixture was extracted with DCM (100 mL×3). The organic phases were combined and dried over anhydrous sodium sulfate, after filtration, the solvent of the filtrate was removed by a rotary evaporator. The residue was subject to silica gel column chromatography (PE/EtOAc=1:1) to deliver the target compound BB-28-3 (white solid, 1.0 g, yield 50.3%). MS m/z: 301.0 [M+H]$^+$ Step 3: Synthesis of Compound BB-28-4

Compound BB-28-3 (1.0 g, 3.33 mmol) and glycol (2.68 g, 43.28 mmol) were dissolved in toluene (75 mL), p-toluenesulfonic acid monohydrate (126.15 mg, 660 mmol) was added. The reaction system was heated to reflux under nitrogen gas atmosphere, stirred overnight. After the reaction was complete as detected by TLC, the reaction mixture was cooled to room temperature and ethyl acetate (30 mL) was added. The system was washed with saturated sodium bicarbonate solution (50 mL×3), saturated brines (50 mL) sequentially. The organic phase was dried over anhydrous sodium sulfate, filtrated, the solvent of the filtrate was removed by a rotary evaporator. The residue was subject to silica gel column chromatography (PE/EtOAc=1:1) to deliver the target compound BB-28-4 (white solid, 900 mg, yield 78.3%). MS m/z: 344.9 [M+H]$^+$ Step 4: Synthesis of Compound BB-28-5

Compound BB-28-4 (900 mg, 2.62 mmol) was added in a mixed solvent of THF/t-butanol/H$_2$O(20 mL/5 mL/5 mL), lithium hydroxide monohydrate (239.82 g, 5.71 mmol) was added, the mixture was stirred at room temperature overnight. After the reaction was complete as detected by TLC, the reaction mixture was adjusted to pH=3 with 1N hydrochloric acid and extracted with ethyl acetate (20 mL×3). The organic phases were combined and washed with saturated brines (20 mL), dried over anhydrous sodium sulfate. After filtration, the filtrate was concentrated by a rotary evaporator to remove the solvent thereby delivering the target compound BB-28-5 (white solid, 680 mg, yield 78.8%). The product was directly used for the next step without purification. MS m/z: 352.9 [M+Na]$^+$ Step 5: Synthesis of Compound BB-28-6

Compound BB-28-5 (680 mg, 2.06 mmol), 2,4'-dibromoacetophenone (BB-1-1, 685 mg, 2.47 mmol) were dissolved in acetonitrile (30 mL), TEA (385.8 mg, 3.82 mmol) was added at room temperature. The reaction mixture was stirred at 50° C. overnight. After the reaction was complete as detected by TLC, the solvent was removed by a rotary evaporator. The residue was dissolved in ethyl acetate (100 mL), washed with saturated brines (20 mL×3). The organic phase was dried over anhydrous sodium sulfate, filtrated, the filtrate was concentrated under reduced pressure to remove the solvent thereby delivering the target compound BB-28-6 (yellow solid, 1.02 g, yield 93.9%). The product was directly used for the next step without purification. MS m/z: 528.8 [M+H]$^+$ Step 6: Synthesis of Compound BB-28-7

Compound BB-28-6 (1.02 g, 1.93 mmol) was dissolved in dioxane (20 mL), ammonium acetate (1.6 g, 21 mmol) was added. The reaction system was heated to 110° C. under nitrogen gas atmosphere, stirred overnight. After the reaction was complete as detected by TLC, the reaction mixture was cooled to room temperature. After filtration, the filtrate was concentrated by a rotary evaporator to remove the solvent. The residue was subject to silica gel column chromatography (PE/EtOAc=1:1) to deliver the target compound BB-28-7 (yellow solid, 650 mg, yield 66.3%). MS m/z: 508.8 [M+H]$^+$ Step 7: Synthesis of Compound BB-28

At room temperature, compound BB-28-7 (100 mg, 0.20 mmol), bis(pinacolato)diboron (55.05 mg, 0.22 mmol) were dissolved in dioxane (2 mL), KOAc (63.74 mg, 0.65 mmol) and Pd(dppf)Cl$_2$ (11 mg, 0.02 mmol) were added under nitrogen gas atmosphere. The reaction mixture was heated to reflux under nitrogen gas atmosphere and stirred for 4 h. After the reaction was complete as detected by TLC, the reaction mixture was cooled to room temperature. After filtration, the filtrate was concentrated by a rotary evaporator to remove the solvent. The residue was subject to silica gel column chromatography (PE/EtOAc=1:1) to deliver the target compound BB-28 (yellow solid, 45 mg, yield 40.6%). MS m/z: 555.0 [M+H]$^+$ Reference 29: Fragment BB-29

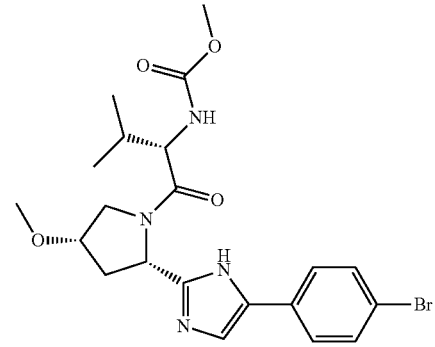

BB-29

Synthetic Route:

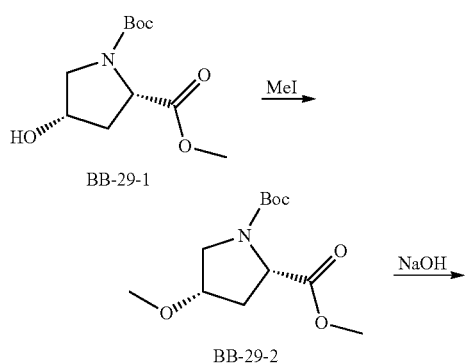

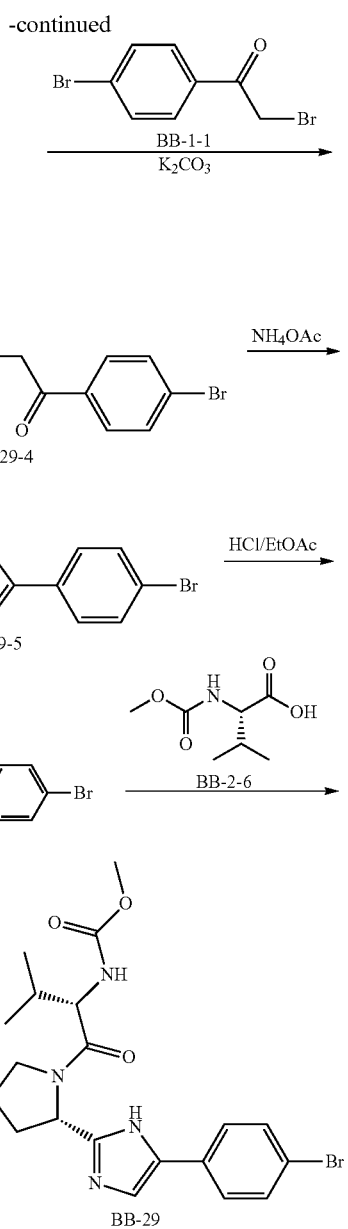

Step 1: Synthesis of Compound BB-29-2

NaH (1.96 g, 48.9 mmol) was suspended in THF (60 mL), cooled to 0° C., compound BB-29-1 (8.0 g, 32.6 mmol) was dripped under nitrogen gas atmosphere. After dripping, the mixture was stirred for 2 h at 0° C. MeI (8.0 g, 48.9 mmol) was added at 0° C., the mixture was stirred at this temperature for further 2.5 h. After the reaction was complete as detected by TLC, the reaction was quenched with $H_2O$ (10 mL) and extracted with ethyl acetate (80 mL×3). The organic phases were combined and dried over anhydrous sodium sulfate. After filtration, the filtrate was concentrated under reduced pressure to remove the solvent. The residue was subject to silica gel column chromatography (PE/EtOAc=9:1→1:1) to deliver the target compound BB-29-2 (colorless oil, 5.5 g, yield 65.2%). $^1$H NMR (CDCl$_3$, 400 MHz): δ 4.33-4.25 (m, 1 H), 3.93-3.89 (m, 1 H), 3.70 (s, 3 H), 3.59-3.47 (m, 2 H), 3.44 (s, 3 H), 2.03-1.98 (m, 2 H), 1.43 (s, 9 H).

Step 2: Synthesis of Compound BB-29-3

At room temperature, compound BB-29-2 (5.5 g, 21.3 mmol) was dissolved in a mixed solvent of methanol/$H_2O$ (30 mL/30 mL), NaOH (1.7 g, 42.6 mmol) was added. The reaction system was heated to 60° C. and stirred for 8 h. After the reaction was complete as detected by TLC, most solvent was removed under reduced pressure and then the mixture was cooled to 0° C. 2N Hydrochloric acid was dripped to adjust pH to 3-4, the mixture was extracted with ethyl acetate (80 mL×3). The organic phases were combined and dried over anhydrous sodium sulfate. After filtration, the filtrate was concentrated by a rotary evaporator to remove the solvent thereby delivering the target compound BB-29-3 (yellow oil, 5.0 g, yield 95.8%). The product was directly used for the next step without purification. $^1$H NMR (CDCl$_3$, 400 MHz): δ 4.42-4.14 (m, 1 H), 3.99-3.98 (m, 1 H), 3.65-3.53 (m, 2 H), 3.33 (s, 3 H). 2.31-2.05 (m, 2 H), 1.47 (s, 9 H).

Step 3: Synthesis of Compound BB-29-4

Compound BB-29-3 (5.0 g, 20.3 mmol) and 2,4'-dibromoacetophenone (BB-1-1, 6.2 g, 22.3 mmol) were dissolved in DMF (50 mL), $K_2CO_3$ (5.6 g, 40.6 mmol) was added slowly. The reaction system was stirred overnight at room temperature. After the reaction was complete as detected by TLC, the reaction was quenched with $H_2O$ (30 mL) and extracted with ethyl acetate (100 mL×3). The organic phases were combined and dried over anhydrous sodium sulfate. After filtration, the filtrate was concentrated under reduced pressure to remove the solvent. The residue was subject to silica gel column chromatography (PE/EtOAc=20:1→1:1) to deliver the target compound BB-29-4 (red solid, 3.5 g, yield 41.7%). $^1$HNMR (CDCl$_3$, 400 MHz): δ 7.79-7.76 (m, 2 H), 7.67-7.65 (m, 2 H), 5.58-5.18 (m, 2 H), 4.55-4.50 (m, 1 H), 4.16-4.05 (m, 1 H). 3.67-3.37 (m, 2 H), 3.36 (s, 3 H), 2.50-2.40 (m, 2 H), 1.47 (s, 9H).

Step 4: Synthesis of Compound BB-29-5

At room temperature, compound BB-29-4 (3.5 g, 7.9 mmol) was dissolved in toluene (70 mL), ammonium acetate (6.1 g, 79.1 mmol) was added. The reaction system was heated to 120° C. under nitrogen gas atmosphere, stirred for 6 h. After the reaction was complete as detected by TLC, the reaction mixture was cooled to room temperature and ethyl acetate (50 mL×3) was added. The mixture was washed with $H_2O$ (30 mL×2). The organic phase was dried over anhydrous sodium sulfate. After filtration, the filtrate was concentrated under reduced pressure to remove the solvent. The residue was subject to silica gel column chromatography (PE/EtOAc=9:1→1:1) to deliver the target compound BB-29-5 (red oil, 3.0 g, yield 88.9%). LC/MS m/z: 424.0 [M+H]$^+$ Step 5: Synthesis of Compound BB-29-6

Compound BB-29-5 (2.0 g, 4.7 mmol) was dissolved in ethyl acetate (5 mL), cooled to 0° C., hydrogen chloride/ethyl acetate solution (HCl/EA, 4M, 30 mL) was added and the mixture was stirred for 2 h at 0° C. After the reaction was complete as detected by TLC, the solvent was removed under reduced pressure at room temperature thereby delivering the target compound BB-29-6 (green solid, 1.69 g, yield 99.4%). The product was directly used for the next step without purification. LC/MS m/z: 323.9 [M+3]$^+$ Step 6: Synthesis of Compound BB-29

At room temperature, compound BB-29-6 (885 mg, 2.96 mmol), N-Moc-L-valine (BB-2-6, 518.2 mg, 2.96 mmol) and DIPEA (954 mg, 7.4 mmol) were dissolved in DMF (10 mL), HATU (1.41 g, 3.7 mmol) was added. The reaction mixture was stirred at room temperature for 1 h. After the reaction was complete as detected by TLC, the reaction was quenched with $H_2O$ (10 mL) and extracted with ethyl acetate (30 mL×3). The organic phases were combined and dried over anhydrous sodium sulfate. After filtration, the filtrate was concentrated under reduced pressure to remove the solvent. The residue was subject to silica gel column chromatography (PE/EtOAc=1:1→pure EtOAc) to deliver the target compound BB-29 (red oil, 841 mg, yield 71.3%). LC/MS m/z: 480.4 [M+H]$^+$. 501.1 [M+Na]$^+$ Reference 30: Fragment BB-30

Reference 31: Fragment BB-31

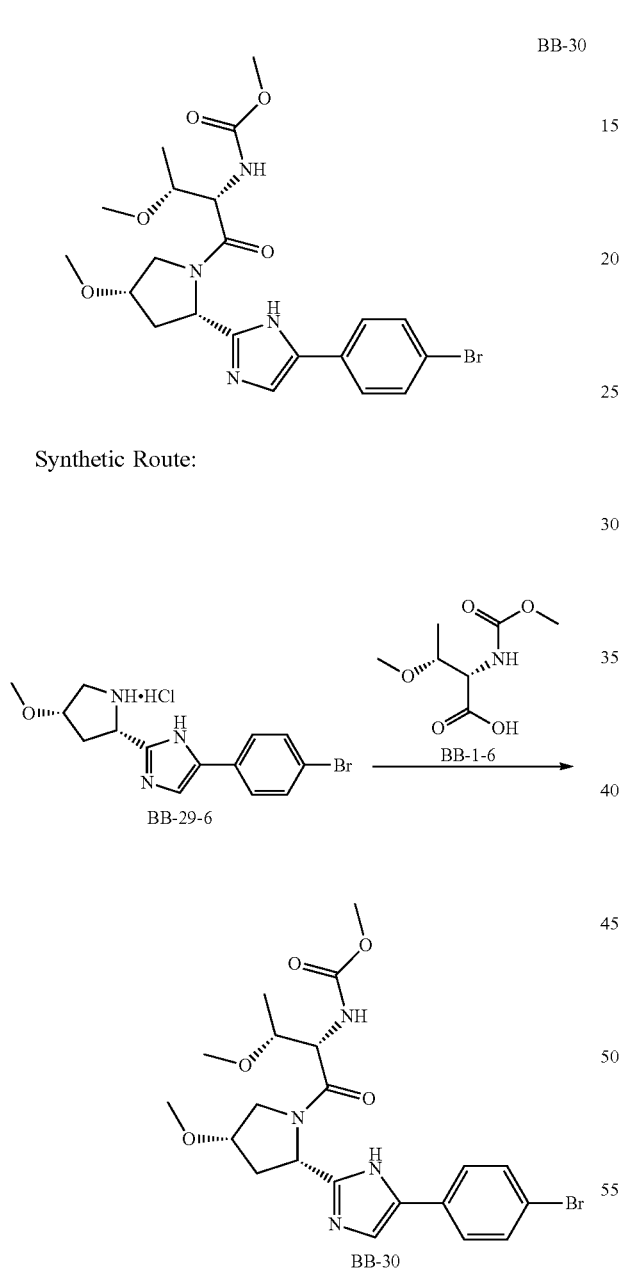

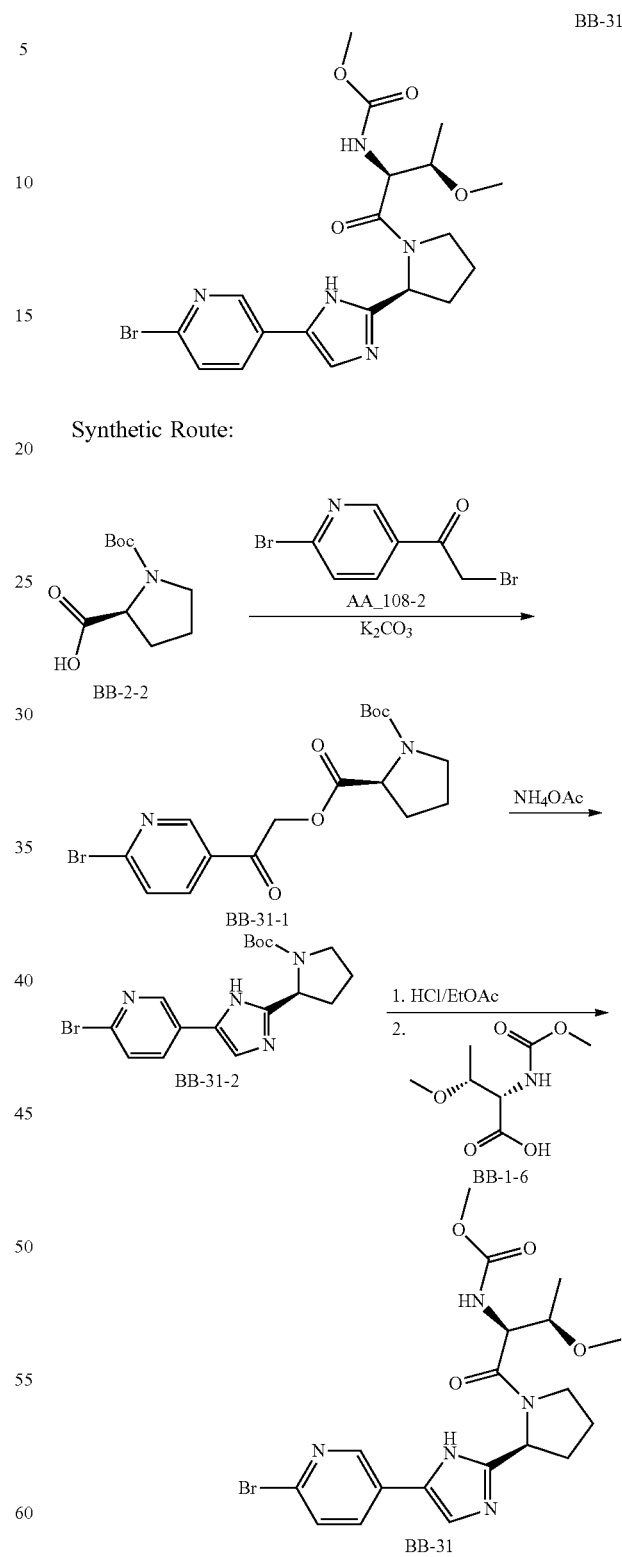

Synthetic Route:

Step 1: Synthesis of Compound BB-30

Compound BB-30 (1.1 g, yield 90.2%) was obtained according to the synthetic step 6 in reference 29 (BB-29), with compound BB-29-6 (885 mg, 2.46 mmol), compound BB-1-6 (566 mg, 2.96 mmol), DIPEA (954 mg, 7.4 mmol), HATU (1.41 g, 3.7 mmol) as starting materials. LCMS m/z: 496.4 [M+H]$^+$ Step 1: Synthesis of Compound BB-31-1

Compound BB-2-2 (1.40 g, 6.50 mmol) and DIPEA (1.01 g, 7.81 mmol) were dissolved in acetonitrile (15 mL), cooled to 0° C., compound AA_108-2 (2.00 g, 7.15 mmol) was added slowly. The reaction mixture was stirred for 0.5 h at 0° C. After the reaction was complete as detected by TLC, the solvent was removed under reduced pressure. The residue was subject to silica gel column chromatography (PE/EtOAc=2:1) to deliver the target compound BB-31-1 (white solid, 1.26 g, yield 33%). LC/MS m/z: 435.0 [M+Na]⁺.

Step 2: Synthesis of Compound BB-31-2

At room temperature, compound BB-31-1 (1.26 g, 3.04 mmol) was dissolved in toluene (50 mL), ammonium acetate (2.34 g, 30.39 mmol) was added. The reaction system was heated to reflux under nitrogen gas atmosphere and stirred overnight. After the reaction was complete as detected by TLC, the reaction mixture was cooled to room temperature and ethyl acetate (50 mL) was added. The mixture was washed with H$_2$O (30 mL×2). The organic phase was dried over anhydrous sodium sulfate. After filtration, the filtrate was concentrated under reduced pressure to remove the solvent. The residue was subject to silica gel column chromatography (PE/EtOAc=2:3→pure EtOAc) to deliver the target compound BB-31-2 (white solid, 0.72 g, yield 60%). LC/MS m/z: 394.8 [M+H]⁺

Step 3: Synthesis of Compound BB-31

Compound BB-31-2 (0.72 g, 1.82 mmol) was dissolved in ethyl acetate (10 mL), cooled to 0° C., hydrogen chloride/ethyl acetate solution (HCl/EA, 4M, 30 mL) was added and the mixture was stirred for 1 h at room temperature. After the reaction was complete as detected by TLC, the solvent was removed under reduced pressure at room temperature thereby delivering white solid, which was directly used for the next step without purification. At room temperature, the white solid, compound BB-1-6 (0.52 g, 2.73 mmol), DIPEA (1.06 g, 8.19 mmol) were dissolved in DMF (4 mL), HATU (1.04 g, 2.73 mmol) was added. The reaction mixture was stirred at room temperature for 3 h. After the reaction was complete as detected by TLC, the reaction was quenched with H$_2$O (10 mL) and extracted with ethyl acetate (30 mL×3). The organic phases were combined and dried over anhydrous sodium sulfate. After filtration, the filtrate was concentrated under reduced pressure to remove the solvent. The residue was subject to silica gel column chromatography (PE/EtOAc=2:3→pure EtOAc) to deliver the target compound BB-31 (yellow solid, 0.85 g, yield 92%). LC/MS m/z: 466.0 [M+H]⁺.

Reference 32: Fragment BB-32

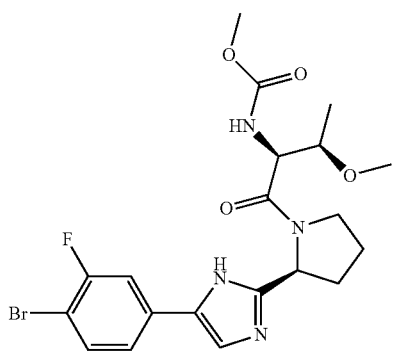

BB-32

Synthetic Route:

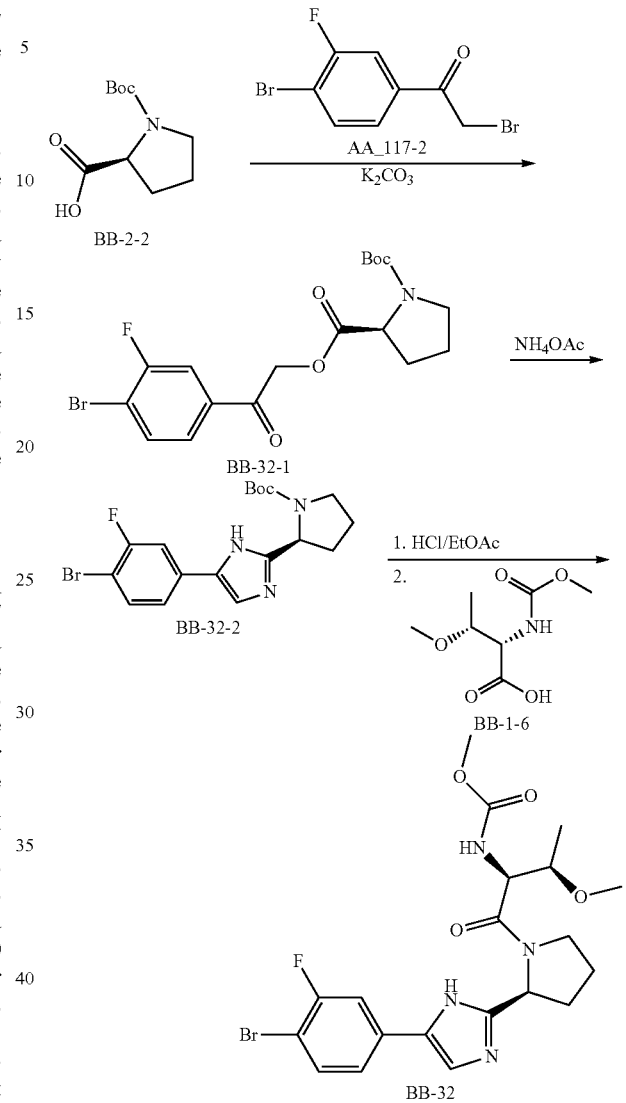

Step 1: Synthesis of Compound BB-32-1

Compound BB-2-2 (1.96 g, 9.22 mmol) and DIPEA (1.43 g, 11.06 mmol) were dissolved in acetonitrile (15 mL), cooled to 0° C., compound AA_117-2 (3.00 g, 10.14 mmol) was added slowly. The reaction mixture was stirred for 1 h at 0° C. After the reaction was complete as detected by TLC, the solvent was removed under reduced pressure. The residue was subject to silica gel column chromatography (PE/EtOAc=2:1) to deliver the target compound BB-32-1 (brown jelly, 3.7 g, yield 94.4%). LC/MS m/z: 329.8 [M-Boc+H]⁺.

Step 2: Synthesis of Compound BB-32-2

Compound BB-32-2 (3.0 g, yield 85.0%) was obtained according to the synthetic step 2 in reference 31 (BB-31), with compound BB-32-1 (3.93 g, 9.13 13mmol), ammonium acetate (7.04 g, 91.34 mmol) as starting materials. LCMS m/z: 310.0 [M-Boc+H]⁺

Step 3: Synthesis of Compound BB-32

Compound BB-32 (yellow solid, 0.6 g, yield 43%) was obtained according to the synthetic step 3 in reference 31 (BB-31), with compound BB-32-2 (3.0 g, 7.31 mmol), hydrogen chloride/ethyl acetate solution (HCl/EA, 4M, 100 mL), compound BB-1-6 (566 mg, 2.96 mmol), DIPEA (1.31 g, 10.10 mmol), HATU (1.65 g, 4.33 mmol) as starting materials. ¹H NMR (CDCl₃, 400 MHz): δ 7.49 (dd, J=8.0 Hz, J=2.8 Hz, 1 H), 7.34 (d, J=8.0 Hz, 1 H), 7.27 (s, 1 H), 7.19 (s, 1 H), 5.70 (d, J=8.0 Hz), 5.31 (m, 1 H), 4.58 (m, 1 H), 3.73 (m, 2 H), 3.70 (s, 3 H), 3.27 (s, 3 H), 2.85 (m, 1 H), 2.22 (m, 1 H), 1.44 (m, 1 H), 1.19 (d, J=8.0 Hz, 1 H), 0.88 (m, 1 H).}

Reference 33: Fragment BB-33

BB-33

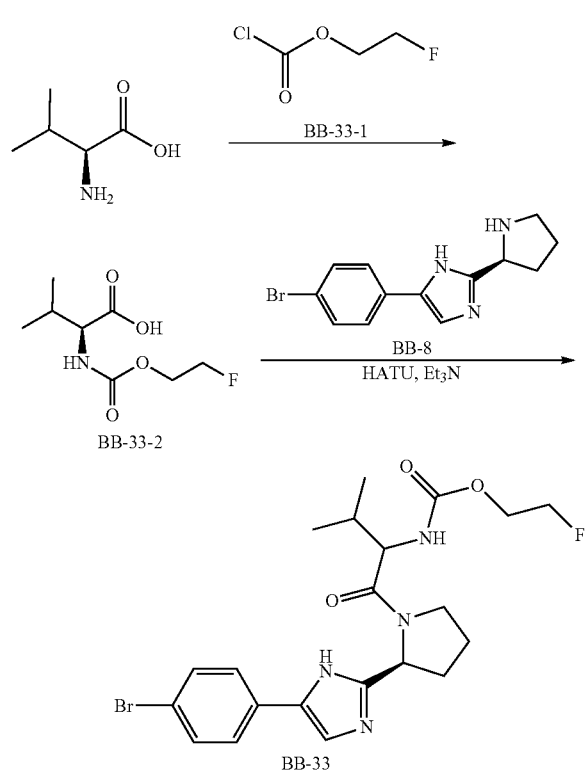

Synthetic Route:

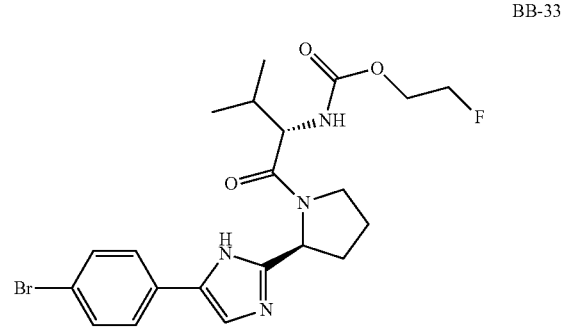

Step 1: Synthesis of Compound BB-33-2

With an ice bath, compound L-valine (300 mg, 2.56 mmol) was dissolved in NaOH aqueous solution (1N, 5 mL), compound BB-33-2 (356 mg, 2.82 mmol) was added after 10 min and the mixture was stirred for 8 h at room temperature. After the reaction was complete, hydrochloric acid solution (6N, 10 mL) was added to adjust pH to 4, then the target compound BB-33-2 (170 mg, 32%) was obtained by freeze-drying. LCMS m/z: 208.1 [M+H]⁺.

Step 2: Synthesis of Compound BB-33

Compound BB-33-2 (170 mg, 0.82 mmol) was dissolved in dichloromethane (5 mL), compound BB-8 (240 mg, 0.82 mmol), HATU (374 mg, 0.98 mmol) and TEA (249 mg, 2.46 mmol) were added sequentially. The reaction mixture was stirred for 2 h at room temperature. H₂O (100 mL) was added, the reaction mixture was extracted with dichloromethane (3×30 mL), the organic phase was dried over anhydrous sodium sulfate, the solvent was removed under reduced pressure. The concentrated liquid was subject to silica gel column chromatography (eluting reagent: 10% DCM/MeOH) to deliver the target compound BB-33 (350 mg, 89%). LCMS m/z: 481.1 [M+H]⁺.

Reference 34: Fragment BB-34

BB-34

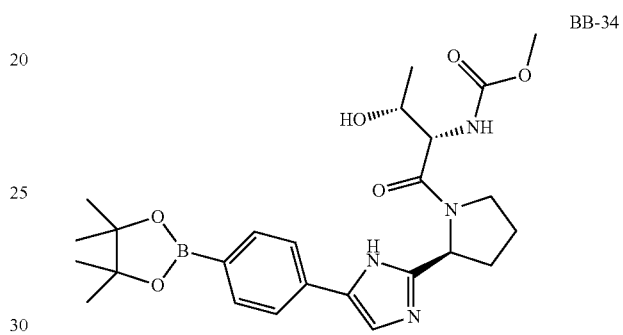

Synthetic Route:

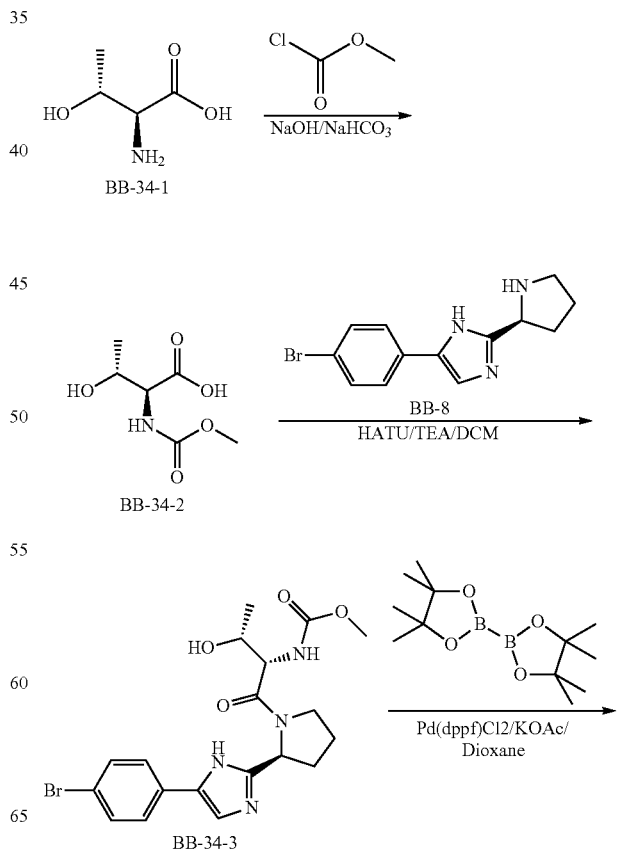

-continued

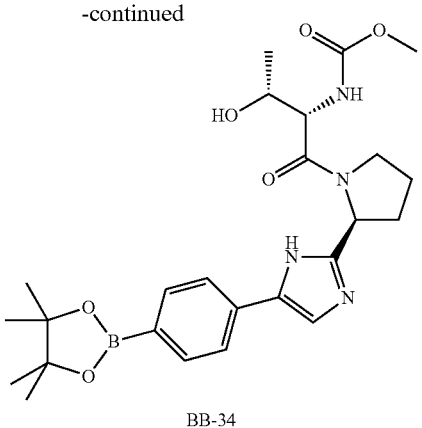

BB-34

Step 1: Synthesis of Compound BB-34-2

NaOH (0.7 g, 17.5 mmol) was dissolved in H$_2$O (20 mL), cooled to 0° C., compound BB-34-1 (2.0 g, 16.8 mmol) and NaHCO$_3$ (0.8 g, 8.4 mmol) were added. After fully dissolution, methylchloroformate (1.6 g, 16.8 mmol) was dripped and the reaction mixture was stirred at room temperature overnight. 1N Hydrochloric acid was added to adjust pH to 3 and the mixture was extracted with ethyl acetate (30 mL×3). The organic phases were combined, washed with saturated brines and dried over anhydrous sodium sulfate. The solvent was removed under reduced pressure thereby delivering the compound BB-34-2 (white solid, 1.5 g, 40.5%), which was directly used for the next step without purification. $^1$H NMR (400 MHz, DMSO-d$_6$): δ: 8.38 (br, 3H), 4.12 (s, 1H), 3.76-3.65 (m, 2H), 3.27 (s, 3H).

Step 2: Synthesis of Compound BB-34-3

Compound BB-8 (1.5 g, 5.1 mmol), compound BB-34-2 (0.9 g, 5.1 mmol) and HATU (2.1 g, 5.6 mmol) were dissolved in dichloromethane (10.0 mL). After TEA (1.5 g, 15.3 mmol) was added slowly at room temperature, the reaction mixture was further stirred overnight at room temperature. H$_2$O (20 mL) was added, the reaction mixture was extracted with dichloromethane (20 mL×3). The organic phases were combined and washed with saturated brines, dried over anhydrous sodium sulfate, the solvent was removed under reduced pressure. The residue was subject to silica gel thin layer chromatography (developing reagent: DCM/MeOH=10/1) to deliver the target compound BB-34-3 (brown oil, 570.0 mg, yield 20.5%). LCMS m/z: 453.0 [M+H]$^+$.

Step 3: Synthesis of Compound BB-34

Compound BB-34-3 (451.0 mg, 1.0 mmol), potassium acetate (196.0 mg, 2.0 mmol) and bis(pinacolato)diboron (280.0 mg, 1.1 mmol) were dissolved in dioxane (10 mL), Pd(dppf)Cl$_2$ (39.0 mg, 0.05 mmol) was added. The reaction mixture was heated to reflux and stirred for 2 h under nitrogen gas atmosphere. The reaction solution was cooled to room temperature and diluted with ethyl acetate (15 mL), washed with H$_2$O and saturated brines, dried over anhydrous sodium sulfate, the solvent was removed under reduced pressure. The residue was subject to silica gel thin layer chromatography (developing reagent: DCM/MeOH=20/1) to deliver the target compound BB-34 (light brown liquid, 150.0 mg, yield 30.0%). LCMS m/z: 499.2 [M+H]$^+$.

The embodiments listed in the following table were synthesized according to the synthetic steps 1-2 in reference BB-34.

| References | Structure | Fragment 1 |
| --- | --- | --- |
| Reference 35 | 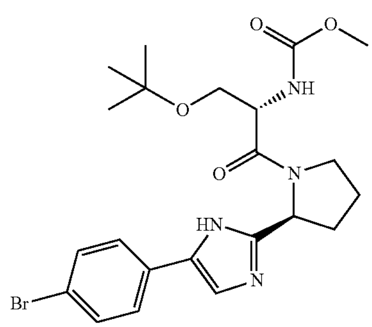 | BB-8 |
| Reference 36 | 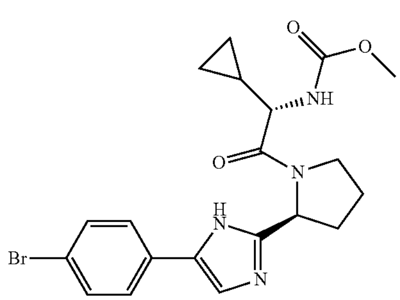 | BB-8 |

| | | |
|---|---|---|
| Reference 37 | 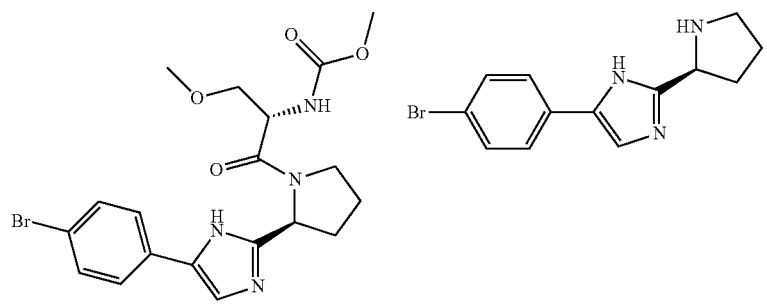 | BB-8 |
| Reference 38 | 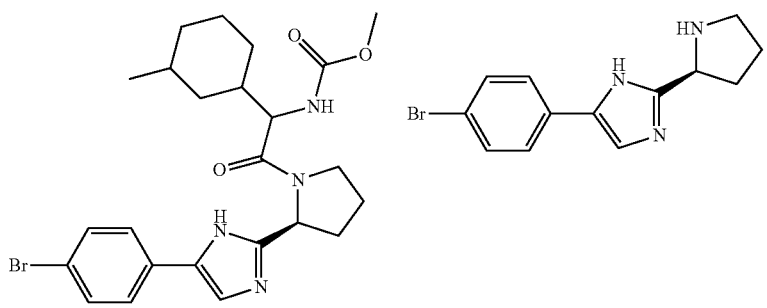 | BB-8 |
| Reference 39 | 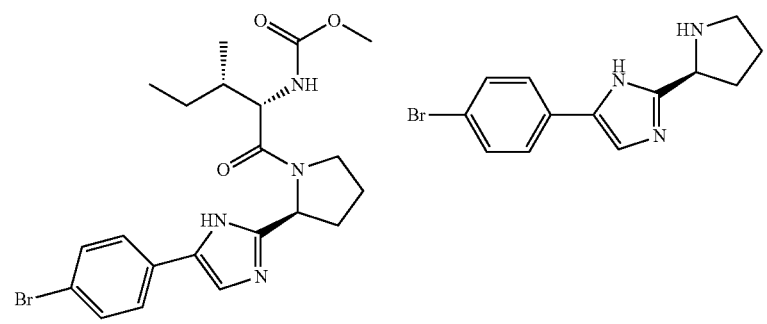 | BB-8 |
| Reference 69 | 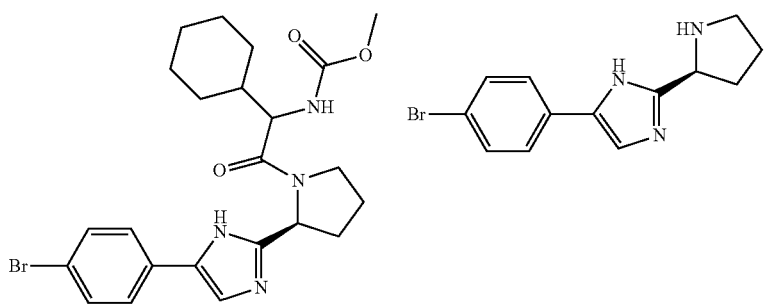 | BB-8 |
| Reference 70 | 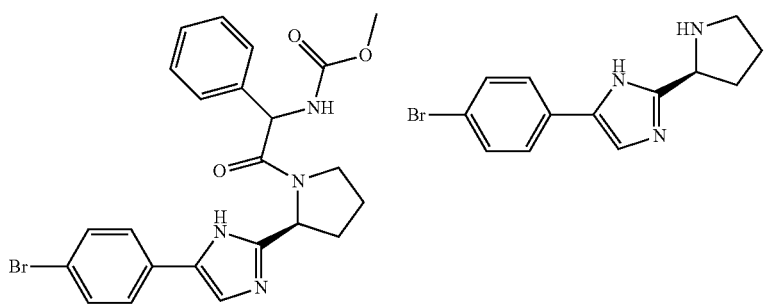 | BB-8 |

-continued
| | | | |
|---|---|---|---|
| Reference 71 | 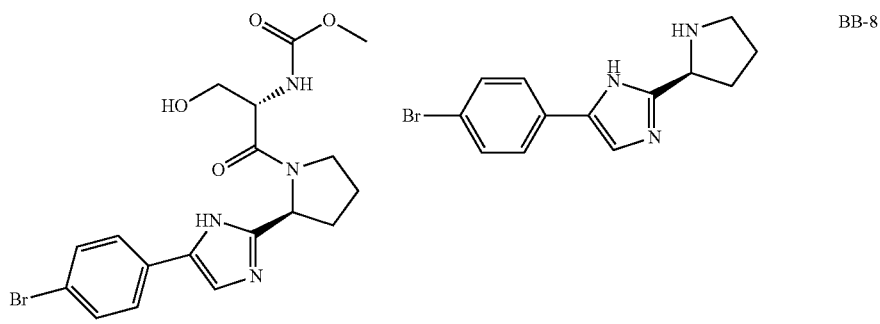 | 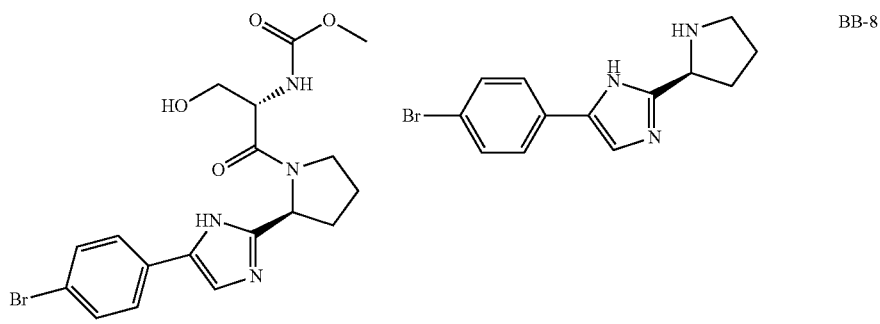 | BB-8 |
| Reference 72 | 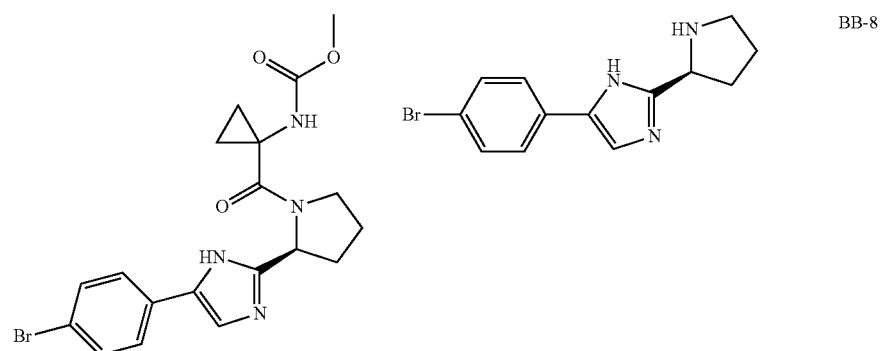 | 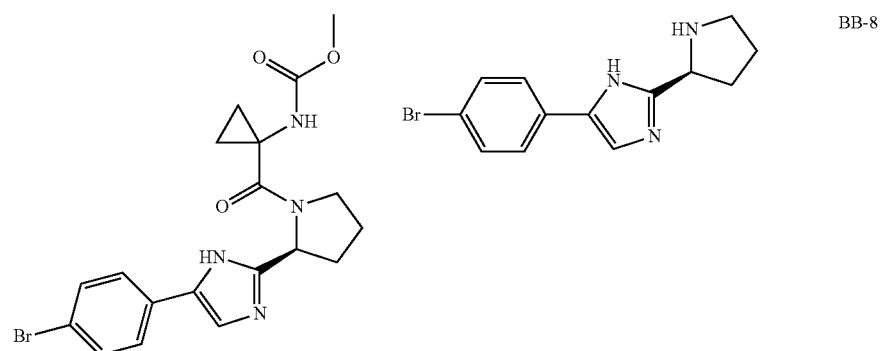 | BB-8 |
| References | Fragment 2 | MS m/z | Compounds |
|---|---|---|---|
| Reference 35 | 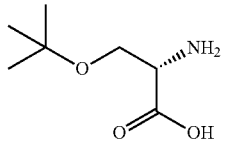 | 493.1 [M + H]+ | BB-35 |
| Reference 36 | 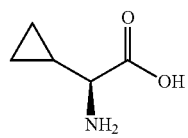 | 447 (M + H)+ | BB-36 |
| Reference 37 | 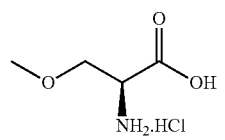 | 453.0 [M + H]+ | BB-37 |
| Reference 38 | 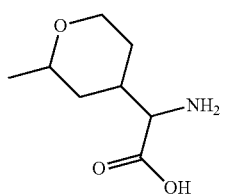 | 506.1 | BB-38 |
| Reference 39 | 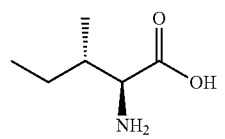 | 464.2 [M + H]+ | BB-39 |

-continued
| Reference 69 |  | 492.9 | BB-69 |
| --- | --- | --- | --- |
| Reference 70 |  | 484.0 [M + H]+ | BB-70 |
| Reference 71 | 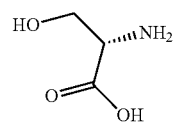 | 438.2 [M + H]+ | BB-71 |
| Reference 72 | 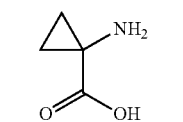 | 434.1 [M + H]+ | BB-72 |
Reference 40: Fragment BB-40
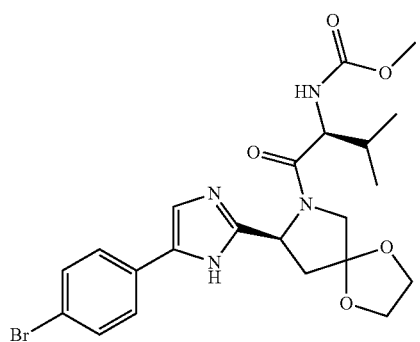
Synthetic Route:
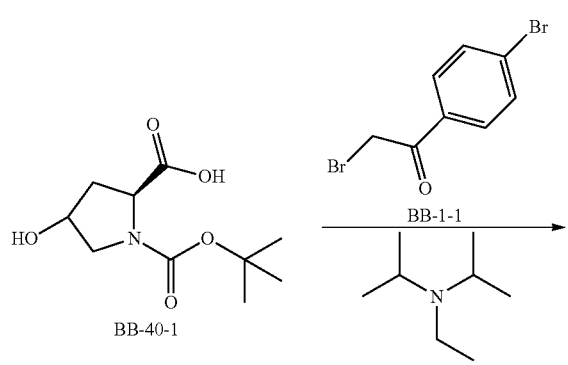
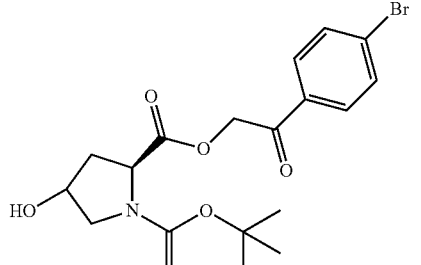
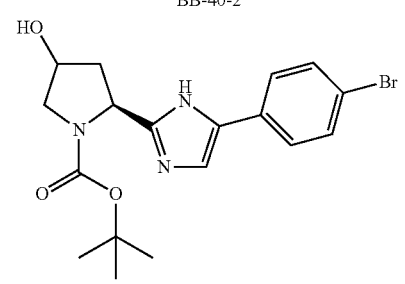
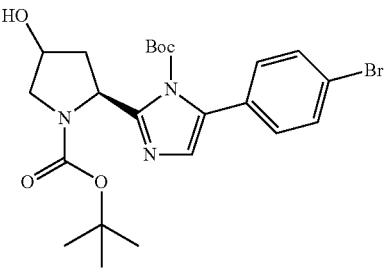

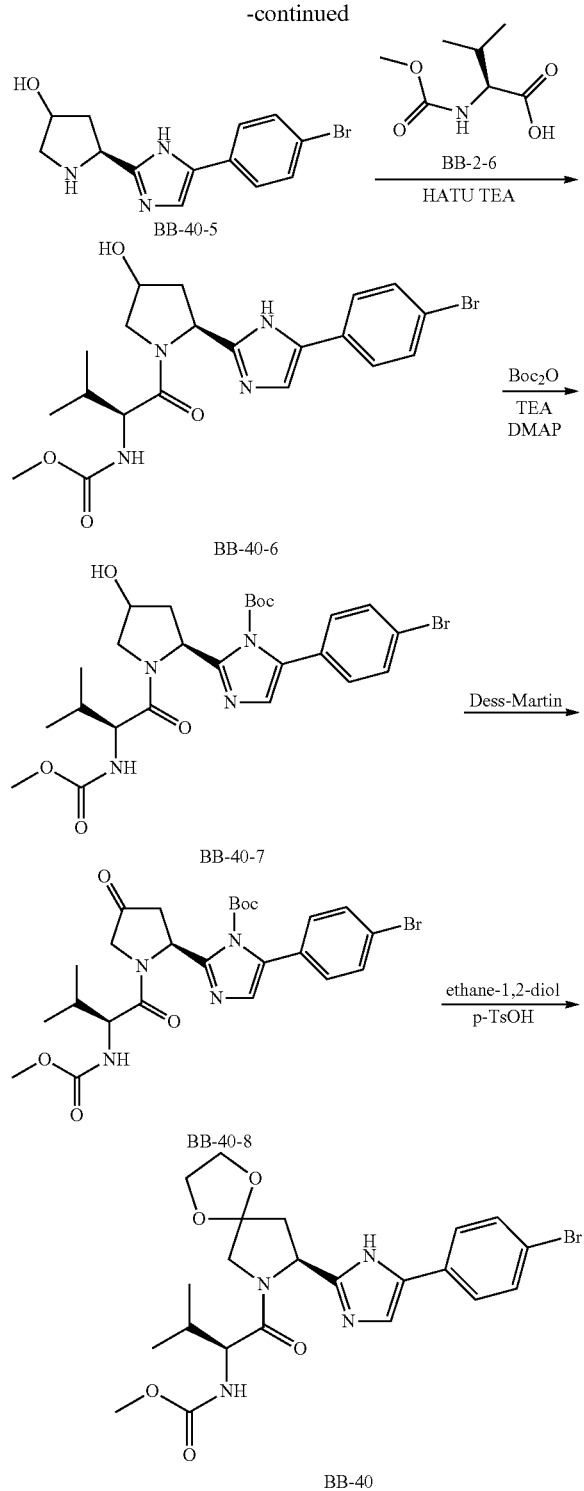

Step 1: Synthesis of Compound BB-40-2

Compound BB-40-1 (10 g, 43.24 mmol) was dissolved in acetonitrile (165 mL), compound BB-1-1 (12 g, 43.24 mmol) and DIPEA (5.59 g, 43.24 mmol) were added sequentially. The reaction mixture was stirred at room temperature overnight. The solvent was removed under reduced pressure, H$_2$O (100 mL) was added, the mixture was extracted with ethyl acetate (200 mL×2). The organic phases were combined and concentrated under reduced pressure to remove the solvent thereby delivering the target compound BB-40-2 (18 g, 97%). LCMS m/z: 330.0 [M-100+H]$^+$ Step 2: Synthesis of Compound BB-40-3

Compound BB-40-2 (18 g, 42.03 mmol) was dissolved in toluene (350 mL), ammonium acetate (32.4 g, 420.30 mmol) was added. The reaction solution was heated to reflux and stirred overnight. The solvent was removed under reduced pressure, H$_2$O (100 mL) was added and the mixture was extracted with ethyl acetate (300 mL×2). The organic phases were combined and the solvent was removed under reduced pressure to deliver the target compound BB-40-3 (14 g, 82%). $^1$H NMR (400 MHz, Methanol-d$_4$) δ: 7.61-7.59 (m, 2H), 7.51-7.49 (m, 2H), 7.40-7.38 (m, 1H), 5.01-4.99 (m, 1H), 4.45 (s, 1H), 3.77-3.73 (m, 1H), 3.58-3.55 (m, 1H), 2.37-2.32 (m, 1H), 2.19-2.14 (m, 1H), 1.43 (s, 3H), 1.22 (s, 6H).

Step 3: Synthesis of Compound BB-40-4

Compound BB-40-3 (14 g, 34.29 mmol) was dissolved in dichloromethane (250 mL), Boc$_2$O (8.23 g, 37.72 mmol), TEA (10.41 g, 102.87 mmol) and DMAP (0.208 g, 1.71 mmol) were added. The reaction solution was stirred at room temperature for 3 h. H$_2$O (100 mL) was added, the mixture was extracted with dichloromethane (300 mL×2). The organic phases were combined and the solvent was removed under reduced pressure. The residue was subject to silica gel column chromatography (eluting system: 60% EtOAc/PE) to deliver the target compound BB-40-4 (11 g, 63%).

Step 4: Synthesis of Compound BB-40-5

Compound BB-40-4 (2 g, 3.93 mmol) was dissolved in dichloromethane (10 mL), 4N HCl/1,4-dioxane (40 mL) was dripped slowly at 0° C., and then the reaction mixture was stirred at room temperature for 3 h. The solvent was removed under reduced pressure thereby delivering the target compound BB-40-5 (1.2 g, 100%). LCMS m/z: 310.0 [M+H]$^+$ Step 5: Synthesis of Compound BB-40-6

Compound BB-40-5 (1.2 g, 3.89 mmol) was dissolved in DMF (30 mL), BB-2-6 (750 mg, 4.28 mmol), HATU (1.77 g, 4.67 mmol) and TEA (1.97 g, 19.47 mmol) were added and the reaction mixture was stirred at room temperature for 5 h. The reaction was quenched with H$_2$O and extracted with ethyl acetate (30 mL×2). The organic phases were combined and the solvent was removed under reduced pressure. The residue was subject to silica gel column chromatography (eluting system: 100% EtOAc) to deliver the target compound BB-40-6 (1.3 g, 72%). LCMS m/z: 467.1 [M+H]$^+$ Step 6: Synthesis of Compound BB-40-7

Compound BB-40-6 (800 mg, 1.72 mmol) was dissolved in dichloromethane (20 mL), Boc$_2$O (394 mg, 1.806 mmol), TEA (522 mg, 5.16 mmol) and DMAP (10 mg, 0.086 mmol) were added. The reaction solution was stirred at room temperature for 3 h. H$_2$O (10 mL) was added and the mixture was extracted with dichloromethane (20 mL×2). The organic phases were combined and the solvent was removed under reduced pressure. The residue was subject to silica gel column chromatography (eluting system: 60% EtOAc/PE) to deliver the target compound BB-40-7 (400 mg, 41%). LCMS m/z: 567.0 [M+H]$^+$ Step 7: Synthesis of Compound BB-40-8

Dess-Martin reagent (1125 mg, 2.65 mmol) was dissolved in dichloromethane (20 mL), compound BB-40-7 (500 mg, 0.884 mmol) was added at 0° C., and then the reaction mixture was stirred at room temperature for 3 h. The reaction was quenched with saturated sodium bicarbonate solution and extracted with dichloromethane (20 mL×2). The organic phases were combined and the solvent was removed under reduced pressure. The residue was subject to silica gel column chromatography (eluting system: 50% EtOAc/PE) to deliver the target compound BB-40-8 (400 mg, 80%).

Step 8: Synthesis of Compound BB-40

Compound BB-40-78 (100 mg, 0.177 mmol) was dissolved in toluene (7 mL), 1,2-ethylene glycol (55 mg, 0.885 mmol) and p-TsOH (7 mg, 0.035 mmol) were added. The reaction mixture was stirred at reflux overnight. After cooling, the reaction mixture was diluted with ethyl acetate (10 mL). The organic phase was washed with sodium bicarbonate solution, then extracted with ethyl acetate (2×10 mL). The organic phases were combined and the solvent was removed under reduced pressure. The residue was subject to silica gel column chromatography (eluting system: 50% EtOAc/PE) to deliver the target compound BB-40 (25 mg, 28%). LCMS m/z: 509.0 [M+H]$^+$ The embodiment listed in the following table was synthesized according to the synthetic steps 5-8 in reference BB-40:

Synthetic Route:

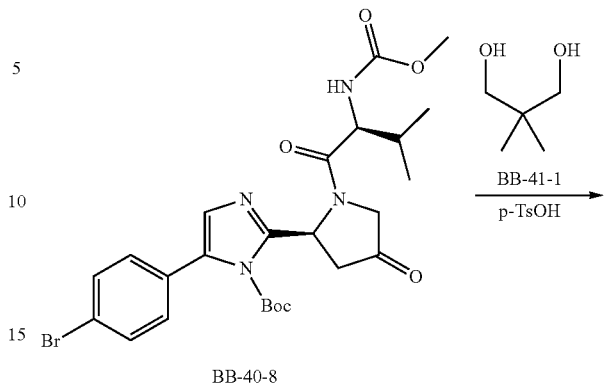

| References | Structure | Fragment 1 | |
|---|---|---|---|
| References 41 | (structure shown) | (structure shown) | BB-40-5 |

| References | Fragment 2 | | MS m/z | Compounds |
|---|---|---|---|---|
| References 41 | (structure shown) | BB-1-6 | 523.0 [M + H]$^+$ | BB-41 |

Reference 42: Fragment BB-42

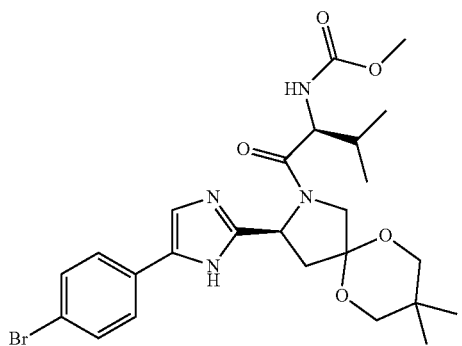

BB-42

-continued

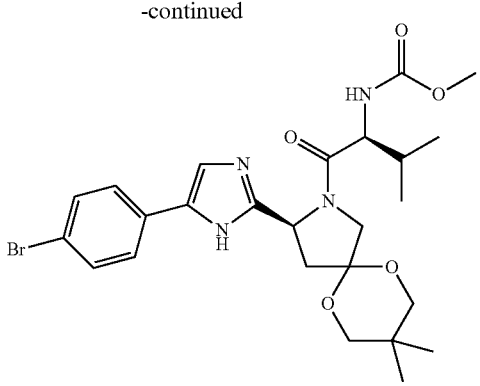

BB-42

Step 1: Synthesis of Compound BB-41

Compound BB-40-8 (300 mg, 0.532 mmol) was dissolved in toluene (20 mL), compound BB-41-1 (277 mg, 2.66 mmol) and p-TsOH (10 mg, 0.053 mmol) were added. The reaction solution was stirred at reflux overnight. After cooling, the reaction mixture was diluted with ethyl acetate (10 mL). The organic phase was washed with sodium bicarbonate solution, and then extracted with ethyl acetate (2×10 mL). The organic phases were combined and the solvent was removed under reduced pressure. The residue was subject to silica gel column chromatography (eluting system: 50% EtOAc/PE) to deliver the target compound BB-41 (120 mg, 41%). LCMS m/z: 551.0 [M+H]+

Reference 43: Fragment BB-43

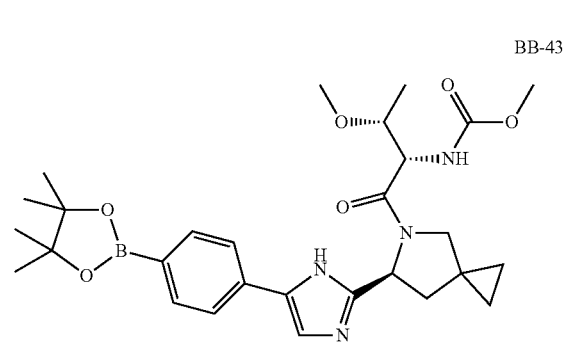

Synthetic Route:

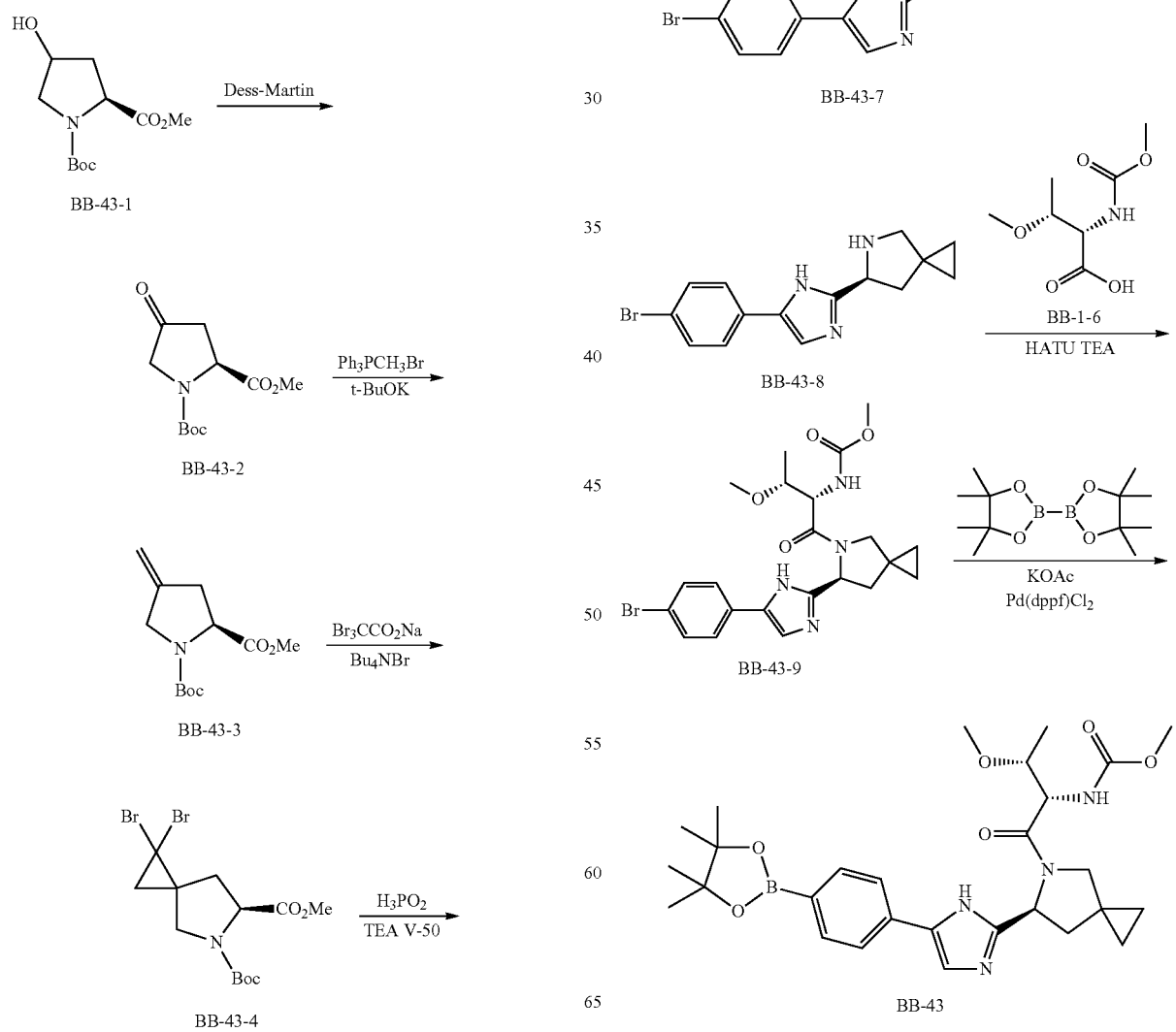

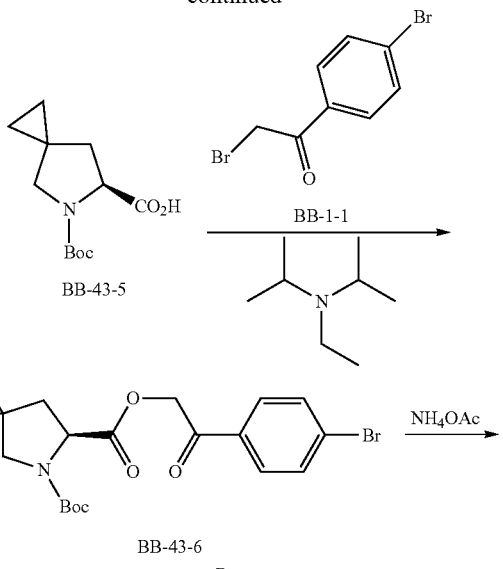

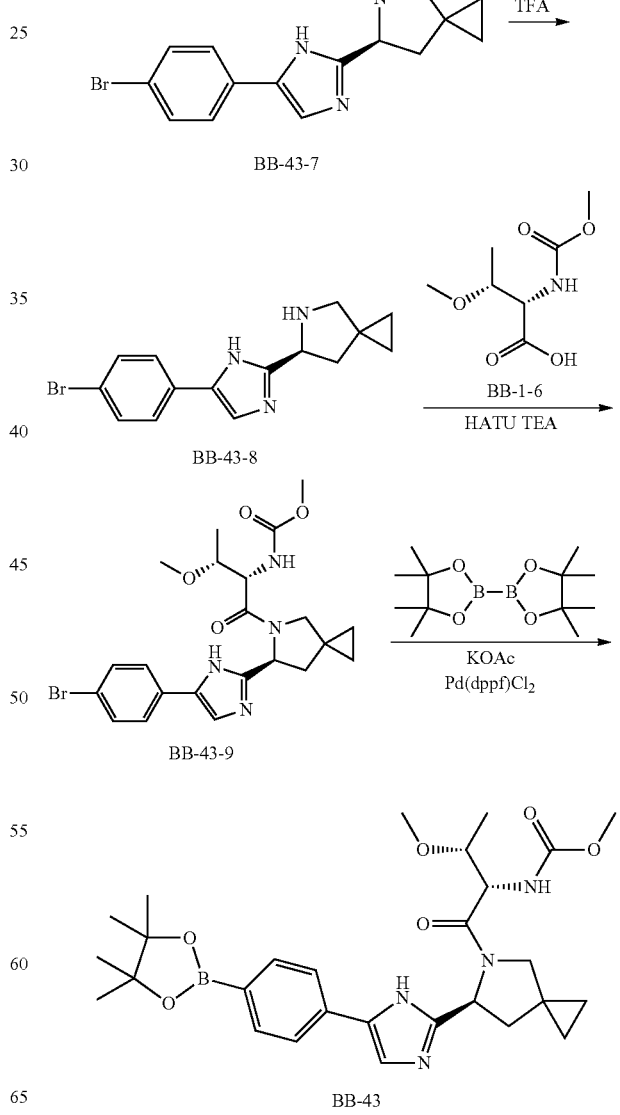

Step 1: Synthesis of Compound BB-43-2

Compound BB-43-1 (9 g, 36.69 mmol) was dissolved in DCM (200 mL), Dess-Martin agent (31 g, 73.38 mmol) and NaHCO$_3$ (6.2 g, 73.38 mmol) were added, then the mixture was stirred at room temperature for 3 h. The reaction was quenched with H$_2$O and extracted with DCM (100 mL×2). The organic phases were combined and the solvent was removed under reduced pressure. The residue was subject to silica gel column chromatography (eluting system: 15% EtOAc/PE) to deliver the target compound BB-43-2 (8 g, 90%). $^1$H NMR (400 MHz, CDCl$_3$) δ: 4.81-4.69 (m, 1 H), 3.90-3.87 (m, 1 H), 3.75 (s, 3 H), 2.94-2.90 (m, 1 H), 2.62-2.55 (m, 1 H), 1.51-1.44 (m, 9 H).

Step 2: Synthesis of Compound BB-43-3

Methyl triphenyl phosphonium bromide (14.69 g, 41.11 mmol) was dissolved in THF (70 mL), t-BuOK (41 Ml, 1.0M THF solution, 41.11 mmol) was added at 0° C. The mixture was stirred at this temperature for 2 h, then compound BB-43-2 (5 g, 20.55 mmol) was added. The reaction solution was warmed to room temperature and stirred for 2 h. The reaction was quenched with H$_2$O and extracted with ethyl acetate (100 mL×2). The organic phases were combined and the solvent was removed under reduced pressure. The residue was subject to silica gel column chromatography (eluting system: 7% EtOAc/PE) to deliver the target compound BB-43-3 (2.5 g, 50%). $^1$H NMR (400 MHz, CDCl$_3$) δ: 5.01-4.98 (m, 2 H), 4.48-4.37 (m, 1 H), 4.08-4.04 (m, 2 H), 3.71 (s, 3 H), 2.96-2.94-3.75 (m, 1 H), 2.63-2.60 (m, 1 H), 1.46-1.41 (m, 9 H)

Step 3: Synthesis of Compound BB-43-4

Compound BB-43-3 (1 g, 4.41 mmol) and tetrabutyl ammonium bromide (0.027 mg, 0.083 mmol) were dissolved in DCE (10 mL), sodium tribromoacetate (3.30 g, 10.36 mmol) was added. The reaction mixture was heated to 70° C. and stirred for 3 h under nitrogen gas atmosphere. The reaction mixture was cooled to room temperature and the solvent was removed under reduced pressure. The residue was washed with 20% EtOAc/PE (3×50 mL) to deliver the target compound BB-43-4 (1.5 g, 88%). $^1$H NMR (400 MHz, CDCl$_3$) δ: 4.65-4.34 (m, 1 H), 3.91-3.84 (m, 1 H), 3.78-3.71 (m, 3 H), 3.53-3.43 (m, 1 H), 2.65-2.35 (m, 2 H), 2.04-1.75 (m, 2 H), 1.60-1.25 (m, 9 H).

Step 4: Synthesis of Compound BB-43-5

Compound BB-43-4 (2.1 g, 5.26 mmol) was dissolved in H$_2$O (25 mL), H$_3$PO$_2$ (3.13 g, 47.36 mmol), TEA (5.32 g, 52.62 mmol) and V-50 (142 mg, 0.53 mmol) were added. The reaction mixture was heated to 100° C., 0.1eq. V-50 was added every 30 min and 1 eq. V-50 was added in total. The reaction solution was heated at 100° C. overnight. The solvent was removed under reduced pressure. 2N NaOH (20 mL) was added, the mixture was extracted with ethyl acetate (30 mL×2). The aqueous phase was adjusted to pH=4-5 with 2N HCl and extracted with ethyl acetate (50 mL×2). The organic phases were combined and the solvent was removed under reduced pressure thereby delivering the target compound BB-43-5 (1 g, 79%). $^1$H NMR (400 MHz, CDCl$_3$) δ: 4.45-4.25 (m, 1H), 3.37-3.17 (m, 2H), 2.42-2.20 (m, 1H), 2.02-2.00 (m, 1H), 1.41-1.31 (m, 9H), 0.57-0.51 (m, 4H).

Step 5: Synthesis of Compound BB-43-6

Compound BB-43-5 (150 mg, 0.622 mmol) was dissolved in acetonitrile (5 mL), compound BB-1-1 (173 mg, 0.622 mmol) and DIPEA (80 mg, 0.622 mmol) were added sequentially, and then the reaction mixture was stirred at room temperature for 2 h. The solvent was evaporated under reduced pressure, H$_2$O (50 mL) was added, the mixture was extracted with ethyl acetate (20 mL×2). The organic phases were combined and the solvent was removed under reduced pressure thereby delivering the target compound BB-43-6 (135 mg, 50%). LCMS m/z: 340.0 [M-100+H]$^+$ Step 6: Synthesis of Compound BB-43-7

Compound BB-43-6 (130 mg, 0.297 mmol) was dissolved in toluene (5 mL), ammonium acetate (229 mg, 2.97 mmol) was added, and the reaction mixture was stirred at reflux overnight. The solvent was evaporated under reduced pressure, H$_2$O (10 mL) was added, the mixture was extracted with ethyl acetate (20 mL×2). The organic phases were combined and the solvent was removed under reduced pressure. The concentrated liquid was subject to silica gel column chromatography (eluting system: 30% EtOAc/PE) to deliver the target compound BB-43-7 (110 mg, 81%). LCMS m/z: 420.1 [M+H]$^+$ Step 7: Synthesis of Compound BB-43-8

Compound BB-43-7 (110 mg, 0.263 mmol) was dissolved in dichloromethane (3 mL), TFA (1 mL) was added, and then the reaction mixture was stirred at room temperature for 2 h. The solvent was removed under reduced pressure, H$_2$O (3 mL) was added. 2N NaOH aqueous solution was added to adjust pH to 10, and the mixture was extracted with dichloromethane (20 mL×3). The organic phases were combined and the solvent was removed under reduced pressure thereby delivering the target compound BB-43-8 (70 mg, 84%). LCMS m/z: 320.1 [M+H]$^+$ Step 8: Synthesis of Compound BB-43-9

Compound BB-43-8 (70 mg, 0.220 mmol) was dissolved in dichloromethane (5 mL), BB-1-6 (46 mg, 0.242 mmol), HATU (100 mg, 0.264 mmol) and TEA (67 mg, 0.660 mmol) were added and the reaction mixture was stirred at room temperature for 1 h. The reaction was quenched with H$_2$O and extracted with dichloromethane (30 mL×2). The organic phases were combined and the solvent was removed under reduced pressure. The resulting residue was subject to silica gel column chromatography (eluting system: 100% EtOAc) to deliver the target compound BB-43-9 (90 mg, 83%). LC/MS m/z: 491.0 [M+H]$^+$ Step 9: Synthesis of Compound BB-43

Compound BB-43-9 (90 mg, 0.183 mmol) and bis(pinacolato)diboron (93 mg, 0.366 mmol) were dissolved in DMF (5 mL), Pd(dppf)Cl$_2$ (10 mg, 0.014 mmol) and KOAc (54 mg, 0.550 mmol) were added sequentially. The reaction mixture was stirred at 80-90° C. for 4 h under nitrogen gas atmosphere. The reaction mixture was diluted with ethyl acetate (20 mL) and H$_2$O (10 mL) was added. The organic phase obtained from extraction was dried over anhydrous sodium sulfate. After filtration, the filtrate was concentrated under reduced pressure to remove the solvent. The concentrated liquid was subject to silica gel column chromatography (eluting reagent, 100% EtOAc) to deliver the target compound BB-43 (80 mg, 88%). LCMS m/z: 539.2 [M+1]$^+$ The embodiment listed in the following table was synthesized according to the synthetic steps 8-9 in reference BB-43:

| References | Structure | Fragment 1 | |
|---|---|---|---|
| References 45 | 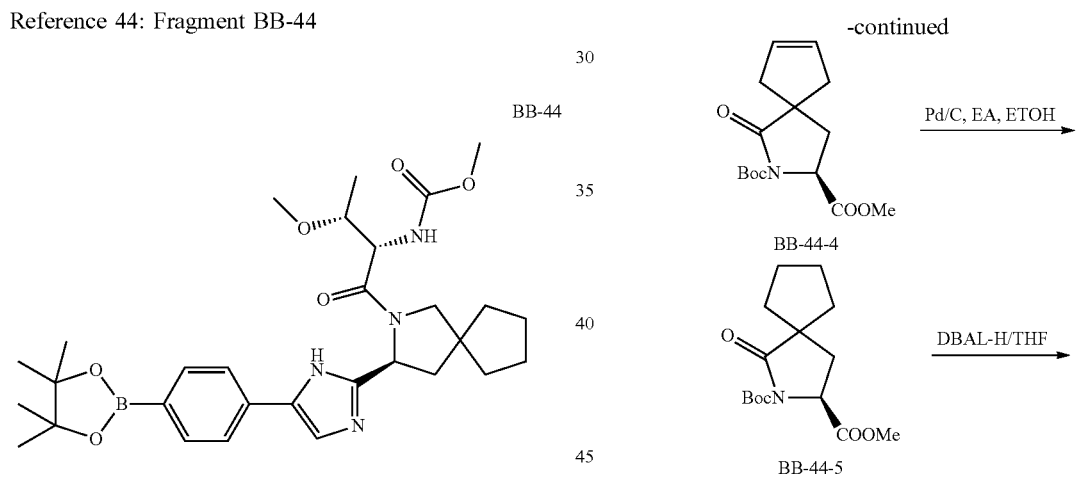 | | BB-43-8 |
| References | Fragment 2 | | MS m/z | Compounds |
|---|---|---|---|---|
| References 45 | | BB-2-6 | 475.2<br>477.2<br>[M + H]+ | BB-45 |
Reference 44: Fragment BB-44
Synthetic Route:
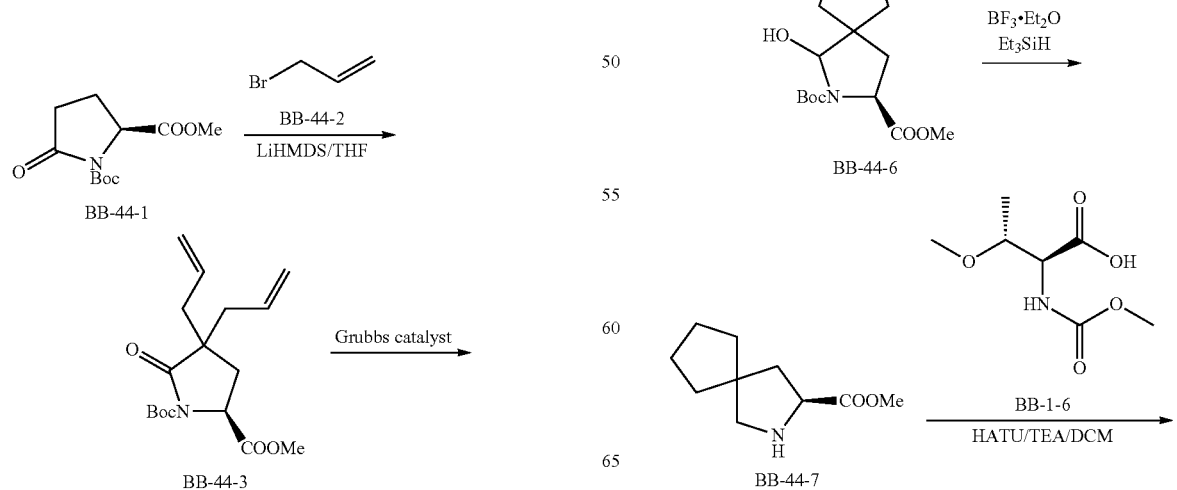

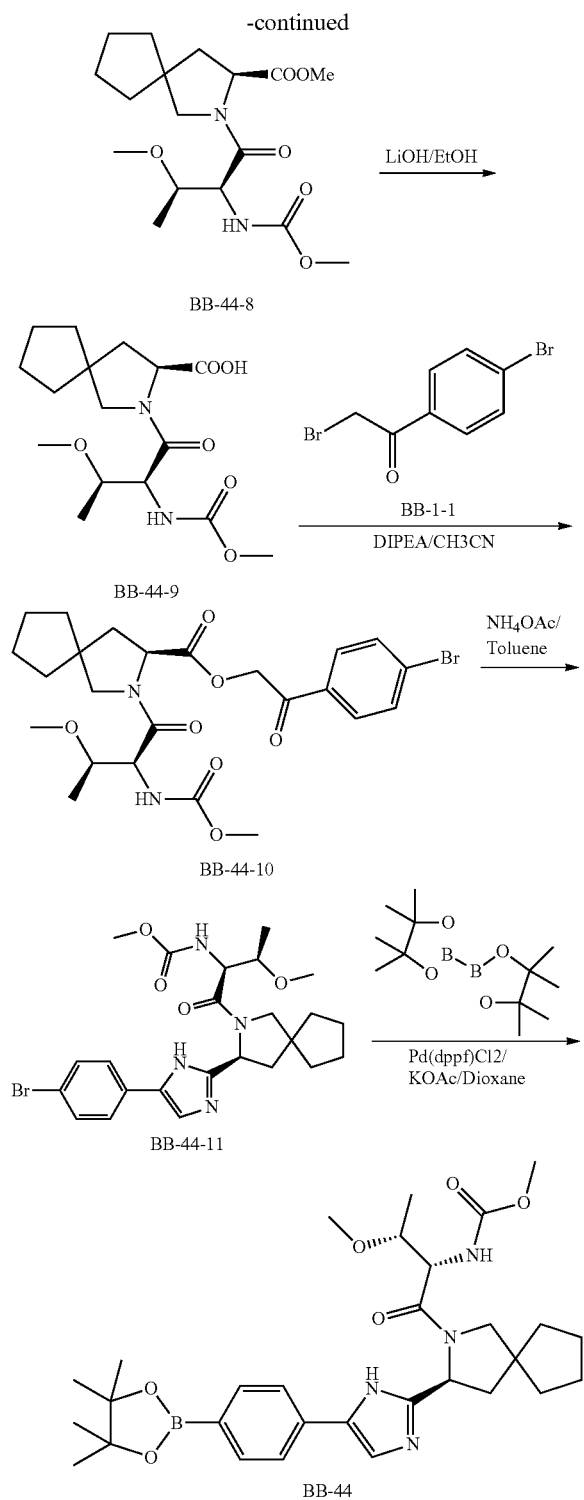

Step 1: Synthesis of Compound BB-44-3

Compound BB-44-1 (15.0 g, 61.5 mmol) was dissolved in THF (600 mL), cooled to −78° C., LHMDS solution (135 mL, 1M in THF, 135.0 mmol) was dripped slowly. After dripping, the reaction mixture was stirred for further 2 h and then warmed to room temperature slowly and stirred overnight. The reaction solution was cooled to −78° C. again and BB-44-2 (130 mmol) was added, then warmed to room temperature slowly and stirred for 3 h. The reaction was quenched with saturated ammonium chloride aqueous solution (10.0 mL) and extracted with ethyl acetate (200 mL×3). The organic phases were combined and washed with saturated brines, dried over anhydrous sodium sulfate. The solvent was removed under reduced pressure, the residue was subject to silica gel column chromatography (eluting system: PE/EtOAc=10/1) to deliver the target compound BB-44-3 (colorless oil, 6.0 g, yield 30.3%). LCMS m/z: 669.2 [2M+Na]$^+$ Step 2: Synthesis of Compound BB-44-4

Compound BB-44-3 (2.0 g, 6.2 mmol) was dissolved in dichloromethane (120 mL), Grubbs 1$^{st}$ catalyst (0.2 g, 0.3 mmol) was added at room temperature, and the mixture was stirred at room temperature for 2 days. The reaction was quenched with lead acetate and stirred for 2 h. The reaction mixture was concentrated under reduced pressure to remove the solvent, the resulting residue was subject to silica gel column chromatography (eluting system: PE/EtOAc=10/1) to deliver the target compound BB-44-4 (colorless oil, 2.5 g, yield 92.5%). LCMS m/z: 613.3 [2M+Na]$^+$ Step 3: Synthesis of Compound BB-44-5

Compound BB-44-4 (2.9 g, 10.0 mmol) was dissolved in a mixed solvent of ethyl acetate (15 mL) and ethanol (15 mL), 10% Pd/C (300.0 mg) was added under nitrogen gas atmosphere. Hydrogen gas was introduced for three times thereby replacing the atmosphere and then the reaction mixture was stirred overnight under hydrogen gas atmosphere. The reaction mixture was filtrated to remove the Pd/C, and the filtrate was evaporated under reduced pressure to remove the solvent thereby delivering the target compound BB-44-5 (colorless oil, 1.6 g, yield 54.0%). $^1$H NMR (400 MHz, CDCl$_3$): δ: 4.54-4.50 (m, 1H), 3.76 (s, 3H), 2.26-2.19 (m, 1H), 2.04-1.93 (m, 3H), 1.82-1.78 (m, 2H), 1.66-1.54 (m, 4H), 1.48 (s, 9H).

Step 4: Synthesis of Compound BB-44-6

Compound BB-44-5 (0.9 g, 3.0 mmol) was dissolved in THF (30 mL), cooled to −78° C., a solution of DBAL-H in toluene (1M, 9.0 mL, 9.0 mmol) was dripped slowly. After dripping, the reaction mixture was warmed to room temperature and stirred for 1 h. The reaction solution was cooled to −78° C. again and quenched with methanol (10 mL), stirred for 30 min and then warmed to room temperature. Ethyl acetate (30 mL×3) was used to extraction. The organic phases were combined and washed with saturated brines, dried over anhydrous sodium sulfate. The solvent was removed under reduced pressure, the residue was subject to silica gel column chromatography (eluting system: PE/EtOAc=1/1) to deliver the target compound BB-44-6 (colorless oil, 0.9 g, yield 90.0%).

Step 5: Synthesis of Compound BB-44-7

Compound BB-44-6 (0.8 g, 2.6 mmol) and triethyl silicane (0.75 g, 6.5 mmol) were dissolved in dichloromethane (15 mL), cooled to −78° C., boron trifluoride ether solution (6.5 mL, 6.5 mmol) was dripped slowly. Triethyl silicane (750 mg) and boron trifluoride ether solution (6.5 mL) were added again after 30 min. The reaction mixture was stirred at −78° C. for 2 h, quenched with saturated sodium bicarbonate solution, extracted with dichloromethane (30 mL×3). The organic phases were combined and washed with saturated brines, dried over anhydrous sodium sulfate. The solvent was removed under reduced pressure, the resulting residue was separated by silica gel column chromatography (eluting system: PE/EtOAc=1/1) to deliver the target compound BB-44-7 (colorless liquid, 0.3 g, yield 62.7%). $^1$H NMR (400 MHz, CDCl$_3$): δ: 3.84 (t, J=8.0 Hz, 1H), 3.72 (s, 3H), 2.90 (d, J=10.1 Hz, 1H), 2.73 (d, J=10.1 Hz, 1H), 2.08-2.05 (m, 4H), 1.78 (dd, J=12.6, 7.1 Hz, 1H), 1.62-1.53 (m, 6H).

Step 6: Synthesis of Compound BB-44-8

Compound BB-44-7 (360.0 mg, 2.0 mmol), compound BB-1-6 (410.3 mg, 2.2 mmol) and HATU (1.1 g, 3.0 mmol) were dissolved in dichloromethane (20 mL), TEA (600.7 mg, 6.0 mmol) was added at room temperature. The reaction mixture was stirred at room temperature overnight, H₂O (20 mL) was added, and extracted with dichloromethane (20 mL×3). The organic phases were combined and washed with saturated brines, dried over anhydrous sodium sulfate. The solvent was removed under reduced pressure, the resulting residue was subject to silica gel thin layer chromatography (developing system: DCM/MeOH=10/1) to deliver the target compound BB-44-8 (light brown liquid, 50 mg, yield 71.4%). LCMS m/z: 357.1 [M+H]⁺

Step 7: Synthesis of Compound BB-44-9

Compound BB-44-8 (100.0 mg, 0.28 mmol) was dissolved in EtOH (5.0 mL), LiOH H₂O (14.2 mg, 0.34 mmol) was added, and then the reaction mixture was stirred at room temperature overnight. 1N HCl was added to adjust pH to 3, the mixture was extracted with ethyl acetate (10 mL×3). The organic phases were combined and washed with saturated brines, dried over anhydrous sodium sulfate. The solvent was removed under reduced pressure thereby delivering the crude product BB-44-9 (white solid, 90.0 mg, 93.7%). The product was directly used for the next step without purification. LCMS m/z: 343.1 [M+H]⁺

Step 8: Synthesis of Compound BB-44-10

Compound BB-44-9 (90.0 mg, 0.26 mmol), compound BB-1-1 (73.0 mg, 0.26 mmol) and DIPEA (33.4 mg, 0.26 mmol) were dissolved in acetonitrile (5.0 mL), the reaction mixture was stirred at room temperature overnight. The solvent was removed under reduced pressure thereby delivering the crude product BB-44-10 (brown oil, 140.0 mg, 100%). The product was directly used for the next step without purification. LCMS m/z: 539.0 [M+H]⁺

Step 9: Synthesis of Compound BB-44-11

Compound BB-44-10 (90.0 mg, 0.26 mmol) was dissolved in toluene (10 mL), ammonium acetate (138.6 mg, 1.8 mmol) was added at room temperature, and the reaction mixture was heated to reflux and stirred overnight. The solvent was removed under reduced pressure, the obtained obtained residue was subject to silica gel plate thin layer chromatography (developing system: DCM/MeOH=20/1) to deliver the target compound BB-44-11 (light brown liquid, 80.0 mg, yield 86.0%). LCMS m/z: 519.1 [M+H]⁺

Step 10: Synthesis of Compound BB-44

Compound BB-44-11 (50.0 mg, 0.09 mmol), KOAc (17.6 mg, 0.18 mmol) and bis(pinacolato)diboron (36.6 mg, 0.14 mmol) were dissolved in dioxane (10 mL), Pd(dppf)Cl₂ (3.0 mg, 0.0024 mmol) was added. The reaction mixture was stirred at reflux for 2 h under nitrogen gas atmosphere, then cooled to room temperature and diluted with ethyl acetate (15 mL), washed with H₂O and saturated brines, dried over anhydrous sodium sulfate. The solvent was removed under reduced pressure, the obtained residue was subject to silica gel plate thin layer chromatography (developing system: DCM/MeOH=20/1) to deliver the target compound BB-44 (light brown liquid, 35 mg, yield 64.8%). LCMS m/z: 567.2 [M+H]⁺

Reference 46: Fragment BB-46

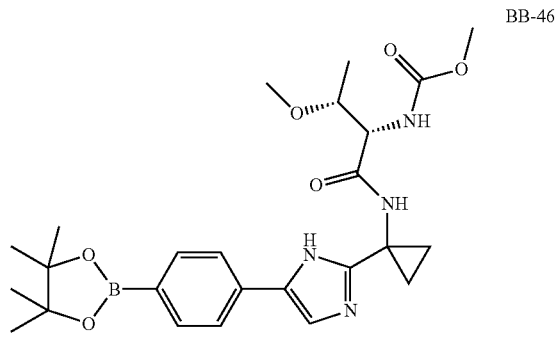

Synthetic Route:

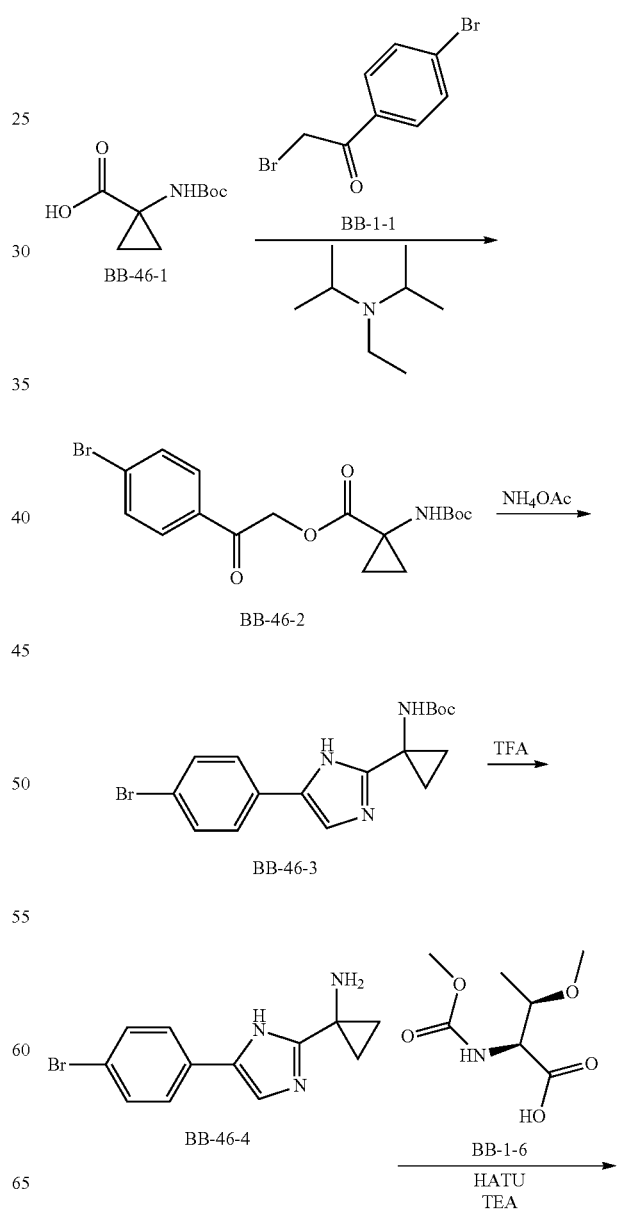

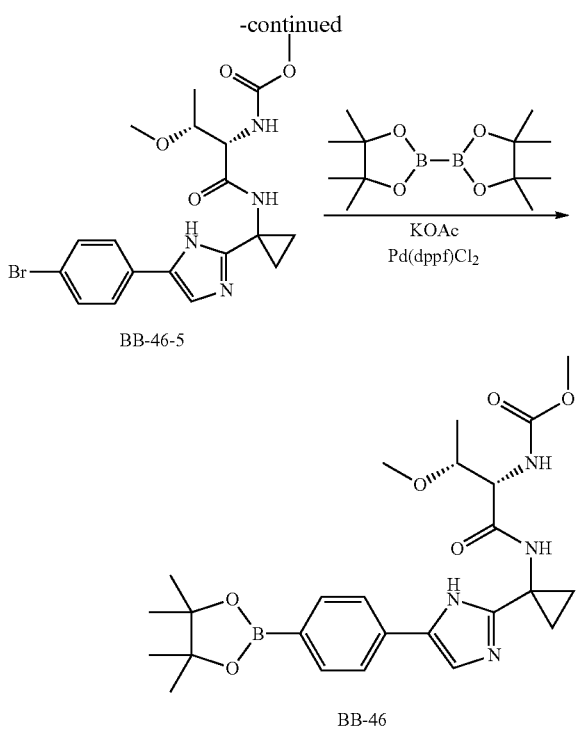

Step 1: Synthesis of Compound BB-46-2

Compound BB-46-1 (3.2 g, 15.90 mmol) was dissolved in acetonitrile (60 mL), compound BB-1-1 (4.42 g, 15.90 mmol) and DIPEA (2.06 g, 15.90 mmol) were added sequentially, the reaction mixture was stirred at room temperature for 2 h. The solvent was removed under reduced pressure, H₂O (50 mL) was added, the mixture was extracted with ethyl acetate (100 mL×2). The organic phases were combined and the solvent was removed under reduced pressure thereby delivering the target compound BB-46-2 (6.33 g, 100%). LCMS m/z: 297.9 [M-100+H]⁺

Step 2: Synthesis of Compound BB-46-3

Compound BB-46-2 (6.3 g, 15.82 mmol) was dissolved in toluene (350 mL), ammonium acetate (12.19 g, 158.2 mmol) was added, and the reaction mixture was heated to reflux and stirred overnight. The solvent was evaporated under reduced pressure, H₂O (100 mL) was added, the mixture was extracted with ethyl acetate (300 mL×2). The organic phases were combined and the solvent was removed under reduced pressure. The concentrated liquid was subject to silica gel column chromatography (eluting system: 90% EtOAc/PE) to deliver the target compound BB-46-3 (4.5 g, yield 75%). LCMS m/z: 380.0 [M+H]⁺

Step 3: Synthesis of Compound BB-46-4

Compound BB-46-3 (0.9 g, 2.38 mmol) was dissolved in dichloromethane (12 mL), TFA (4 mL) was added, and then the reaction mixture was stirred at room temperature for 4 h. H₂O (10 mL) was added and 2N NaOH aqueous solution was used to adjust pH to 10. The mixture was extracted with dichloromethane (20 mL×3), the organic phases were combined and the solvent was removed under reduced pressure thereby delivering the target compound BB-46-4 (600 mg, 91%). LCMS m/z: 280.0 [M+H]⁺

Step 4: Synthesis of Compound BB-46-5

Compound BB-46-4 (600 mg, 2.16 mmol) was dissolved in dichloromethane (30 mL), compound BB-1-6 (454 mg, 2.37 mmol), HATU (984 mg, 2.59 mmol) and TEA (655 mg, 6.47 mmol) were added, and the reaction mixture was stirred at room temperature for 1 h. The reaction was quenched with H₂O and extracted with dichloromethane (30 mL×2). The organic phased were combined and the solvent was removed under reduced pressure, the resulting residue was subject to silica gel column chromatography (eluting system: 100% EtOAc) to deliver the target compound BB-46-5 (900 mg, 92%). LCMS m/z: 453.0 [M+H]⁺

Step 5: Synthesis of Compound BB-46

Compound BB-46-5 (300 mg, 0.665 mmol) and bis(pinacolato)diboron (338 mg, 1.33 mmol) were dissolved in dioxane (10 mL), Pd(dppf)Cl₂ (30 mg, 0.040 mmol) and KOAc (196 mg, 1.99 mmol) were added. The reaction mixture was stirred at 80-90° C. for 4 h under nitrogen gas atmosphere, and then diluted with ethyl acetate (20 mL). H₂O (10 mL) was added, the organic phase obtained was dried over anhydrous sodium sulfate. After filtration, the solvent was removed under reduced pressure. The concentrated liquid was subject to silica gel column chromatography (eluting system: 100% EtOAc) to deliver the target compound BB-46 (200 mg, 60%). LCMS m/z: 499.3 [M+H]⁺

Reference 47: Fragment BB-47

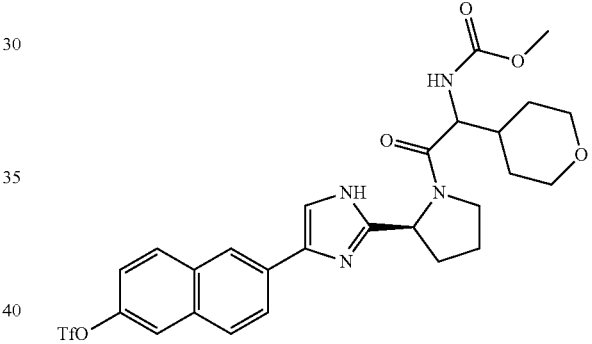

BB-47

Synthetic Route:

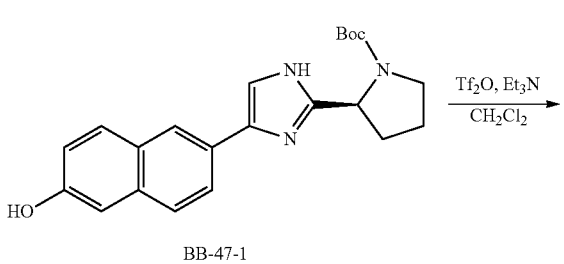

BB-47-1

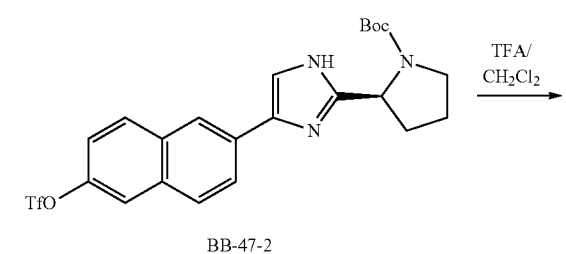

BB-47-2

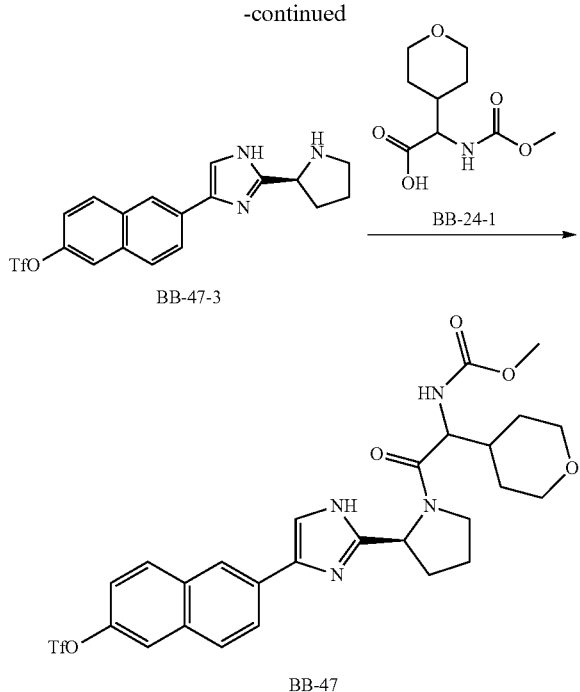

Step 2: Synthesis of Compound BB-47-3

Compound BB-47-2 (128 mg, 0.25 mmol) was dissolved in dichloromethane (2 mL). TFA (1.6 mL) was dripped with an ice bath. The reaction mixture was stirred at room temperature for 2 h, and then diluted with dichloromethane (20 mL). H₂O (10 mL) and saturated sodium bicarbonate solution (5 mL) were added, and the obtained organic phase was dried over anhydrous sodium sulfate. The solvent was removed under reduced pressure thereby delivering the target compound BB-47-3 (50 mg, 81.97%). LCMS m/z: 412.0 [M+H]⁺

Step 3: Synthesis of Compound BB-47

Compound BB-47-3 (47.35 mg, 0.12 mmol)) was dissolved in dichloromethane (3 mL), compound BB-24-1 (25 mg, 0.12 mmol), HATU (53.2 mg, 0.14 mmol) and DIPEA (31.0 mg, 0.24 mmol) were added sequentially. The reaction mixture was stirred at room temperature for 12 h. H₂O (15 mL) was added and the reaction mixture was extracted with dichloromethane (30 mL×3). The organic phase was dried over anhydrous sodium sulfate and the solvent was removed under reduced pressure. The concentrated liquid was subject to silica gel column chromatography (eluting system: 10% DCM/MeOH) to deliver the target compound BB-47 (30 mg, 42.7%). LCMS m/z: 611.2 [M+H]⁺

The embodiment listed in the following table was synthesized according to the synthetic step 1 in reference RR-47:

| References | Structure | Fragment 1 | |
|---|---|---|---|
| References 73 | (TfO-naphthyl-imidazole-pyrrolidine-valine-NHCO₂Me structure) | (TfO-naphthyl-imidazole-pyrrolidine-NH structure) | BB-47-3 |

| References | Fragment 2 | MS m/z | Compounds |
|---|---|---|---|
| References 73 | (MeO-CO-NH-valine-OH structure) BB-2-6 | 569.2 [M + H]⁺ | BB-73 |

Step 1: Synthesis of Compound BB-47-2

Compound BB-47-1 (50 mg, 0.132 mmol) and TEA (20 mg, 0.20 mmol) were dissolved in dichloromethane (3 mL). With an ice bath, trifluoromethanesulfonic anhydride (40.9 mg, 0.145 mmol) was dissolved in dichloromethane (1 mL) firstly, and then the formed solution was dripped into the reaction solution. The reaction mixture was stirred at room temperature for 12 h. Saturated ammonium chloride solution (10 mL) was added, the reaction mixture was extracted with dichloromethane (30 mL×3). The organic phase was dried over anhydrous sodium sulfate, the solvent was removed under reduced pressure, the concentrated liquid was subject to silica gel column chromatography (eluting system: 10% DCM/MeOH) to deliver the target compound BB-47-2 (24 mg, 36.4%).

Reference 48: Fragment BB-48

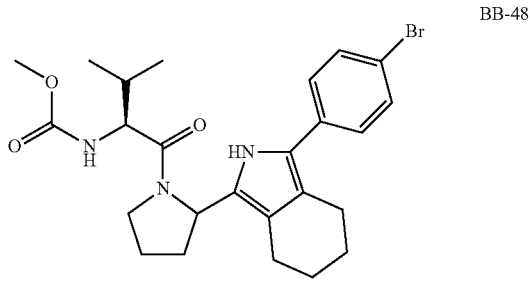

Synthetic Route:

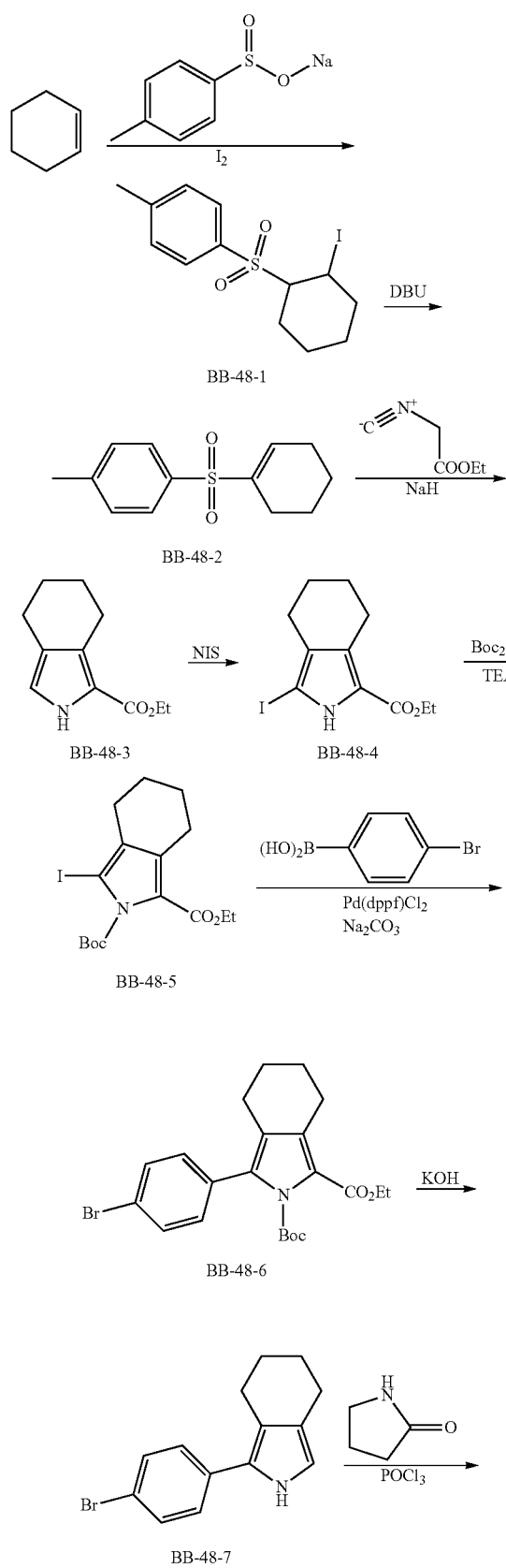

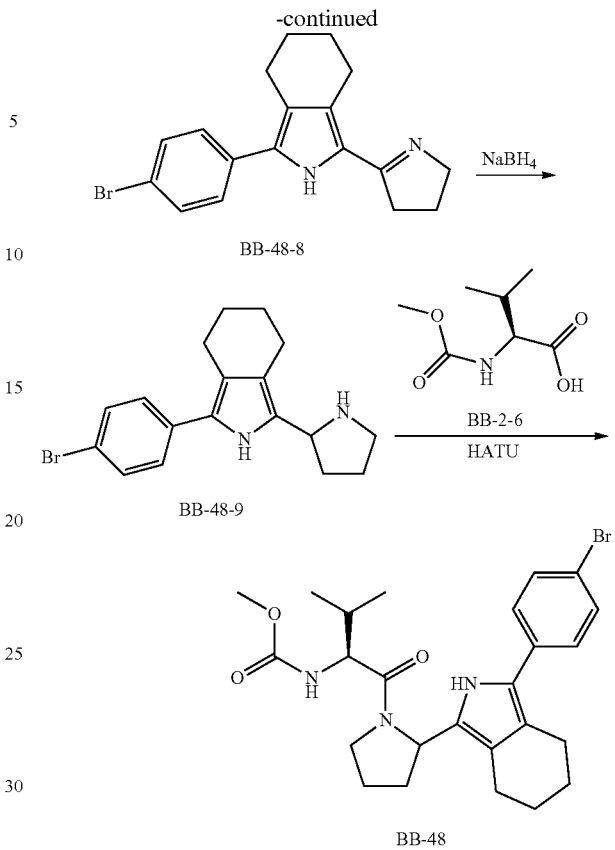

Step 1: Synthesis of Compound BB-48-1

Cyclopentene (30 g, 365 mmol) and sodium p-tolylsulfinate (108 g, 606 mol) were dissolved in a biphasic solvent formed by $H_2O$ (400 mL) and dichloromethane (400 mL) sequentially, iodine (92.7 g, 365 mol) was added in portions. The reaction mixture was stirred at room temperature overnight. Dichloromethane (400 mL) was added, and the reaction mixture was washed with saturated sodium bicarbonate aqueous solution (500 mL), saturated sodium bisulfite aqueous solution (50 mL), saturated brines (50 mL) respectively. The organic phase was dried over anhydrous sodium sulfate, the solvent was removed under reduced pressure thereby delivering the target compound BB-48-1 (brown oil, 133 g, yield 100%).

Step 2: Synthesis of Compound BB-48-2

Compound BB-48-1 (133 g, 365 mmol) was dissolved in toluene (1000 mL), DBU (55.6 g, 365 mol) was dripped slowly, and the mixture was stirred at room temperature for further 2 h. The solid in the reaction solution was filtrated, the filtrate was washed with 1M HCl solution (100 mL), saturated sodium bicarbonate aqueous solution (200 mL), brines (200 mL) sequentially. The organic phase was dried over anhydrous sodium sulfate and the solvent was removed under reduced pressure thereby delivering the target compound BB-48-2 (gray solid, 70 g, yield 81%). $^1$H NMR (400 MHz, $CDCl_3$) δ: 7.55-7.45 (m, 2H), 7.35-7.28 (m, 2H), 7.02 (s, 1H), 2.48 (s, 3H), 2.25-2.15 (m, 4H), 1.65-1.53 (m, 4H).

Step 3: Synthesis of Compound BB-48-3

With an ice bath, a solution of compound BB-48-2 (23 g, 97.3 mmol) and ethyl isocyanoacetate (27.5 g, 243.3 mmol) in THF (200 mL) was dripped slowly into a suspension of NaH (9.7 g, 243.3 mmol) in THF (200 mL). The reaction mixture was stirred for 1 h under an ice bath, and slowly warmed to room temperature, stirred for further 2 h. The reaction was quenched with methanol (50 mL), the solvent was removed under reduced pressure. The mixture was diluted with ethyl acetate (200 mL), washed with saturated brines (50 mL). The obtained organic phase was dried over anhydrous sodium sulfate, the solvent was removed under reduced pressure, the residue was subject to silica gel column chromatography (PE/EtOAc=5/1) to deliver the target compound BB-48-3 (white solid, 17 g, yield 97%). $^1$H NMR (400 MHz, CDCl$_3$) δ: 8.76 (br, 1H), 6.63 (s, 1H), 4.31-4.25 (m, 2H), 2.82-2.791 (m, 2H), 2.55-2.52 (m, 2H), 1.77-1.70 (m, 4H), 1.33 (m, 3H).

Step 4: Synthesis of Compound BB-48-4

Compound BB-48-3 (8 g, 41.4 mmol) was dissolved in THF (100 mL), NIS (11.2 g, 49.77 mmol) was added slowly, and the reaction mixture was stirred at room temperature overnight. The solvent was evaporated under reduced pressure, the mixture was diluted with ethyl acetate (100 mL) and washed with saturated brines (50 mL). The organic phases were combined and dried over anhydrous sodium sulfate, the solvent was removed under reduced pressure, the residue was subject to silica gel column chromatography (PE/EtOAc=6/1) to deliver the target compound BB-48-4 (white solid, 9.5 g, yield 71%). LCMS m/z: 320.40 [M+H]$^+$ Step 5: Synthesis of Compound BB-48-5

Compound BB-48-4 (9.5 g, 29.77 mmol) was dissolved in dichloromethane (100 mL), Boc$_2$O (7.8 g, 35.7 mmol) and TEA (9.04 g, 89.3 mmol) were added sequentially. The reaction mixture was stirred at room temperature for 3 h, and then washed with saturated brines (50 mL). The organic phase was dried over anhydrous sodium sulfate, the solvent was removed under reduced pressure, the residue was subject to silica gel column chromatography (PE/EtOAc=7/1) to deliver the target compound BB-48-5 (light yellow solid, 10 g, yield 80%). $^1$H NMR (400 MHz, CDCl$_3$) δ: 4.31-4.25 (q, 2H), 2.79-2.76 (m, 2H), 2.45-2.32 (m, 2H), 1.77-1.70 (m, 4H),1.1.63 (s, 9H), 1.33 (m, 3H).

Step 6: Synthesis of Compound BB-48-6

Compound BB-48-5 (7 g, 16.7 mmol) and 4-bromophenylboronic acid (3.35 g, 16.7 mmol) were dissolved in 1,4-dioxane/H$_2$O=5:1 (100 mL), Pd(dppf)Cl$_2$ (1.38 g, 1.67 mmol) and Na$_2$CO$_3$ (5.31 g, 50.1 mmol) were added sequentially. The reaction mixture was stirred at 100° C. for 4 h under nitrogen gas atmosphere. H$_2$O (30 mL) was added and the mixture was extracted with ethyl acetate (100 mL×3). The organic phases were combined and dried over anhydrous sodium sulfate, concentrated under reduced pressure, the residue was subject to silica gel column chromatography (eluting system: PE/EtOAc=3/1) to deliver the target compound BB-48-6 (light yellow solid, 3 g, yield 40%). LCMS: m/z 394.3 [M-56+H]$^+$ Step 7: Synthesis of Compound BB-48-7

KOH (0.63 g, 11.15 mmol) was added into ethylene glycol (50 mL), the reaction mixture was stirred at reflux for 1 h, and then compound BB-48-6 (1 g, 2.23 mmol) was added, the mixture was stirred at reflux for further 1 h. The reaction mixture was cooled to room temperature, poured into H$_2$O, extracted with dichloromethane (100 mL×3). The organic phases were combined and dried over anhydrous sodium sulfate, the solvent was removed under reduced pressure thereby delivering the target product BB-48-7 (brown solid, 0.5 g, yield 81%). LCMS m/z: 278.0 [M+H]$^+$ Step 8: Synthesis of Compound BB-48-8

Under an ice bath, POCl$_3$ (1.39 g, 9.05 mmol) was added dropwise into a solution of compound BB-48-7 (0.5 g, 1.81 mmol) and 2-pyrrolidone (0.77 g, 9.05 mmol) in 1,2-dichloroethane (50 mL). The reaction mixture was stirred for 1 h under an ice bath, then warmed to room temperature and stirred for further 2 h. The reaction solution was slowly added dropwise into the saturated sodium acetate solution (50 mL). At 0° C., 10M KOH solution was added to adjust pH to 11. The mixture was extracted with dichloromethane (50 mL×3). The organic phases were combined and dried over anhydrous sodium sulfate, the solvent was removed under reduced pressure thereby delivering the target product BB-48-8 (red brown solid, 0.2 g, yield 32%). LCMS m/z: 343.0 [M+H]$^+$ Step 9: Synthesis of Compound BB-48-9

Compound BB-48-8 (200 mg, 0.582 mmol) was dissolved in dichloromethane/MeOH (1:1, 20 mL), NaBH$_4$ (220 mg, 5.83 mmol) was added, and the reaction mixture was stirred at reflux overnight. The reaction was quenched with H$_2$O (10 mL), extracted with dichloromethane (50 mL×2). The organic phases were combined and dried over anhydrous sodium sulfate, the solvent was removed under reduced pressure thereby delivering the target product BB-48-9 (oil, 150 mg, yield 74%). LCMS m/z: 345.1 [M+H]$^+$ Step 10: Synthesis of Compound BB-48

Compound BB-48-9 (180 mg, 0.52 mmol) was dissolved in dichloromethane (5 mL), BB-2-6 (110 mg, 0.63 mmol), HATU (296 mg, 0.78 mmol)) and TEA (158 mg, 1.56 mmol) were added sequentially, and the reaction mixture was stirred at room temperature for 2 h. H$_2$O (10 mL) was added and the reaction mixture was extracted with dichloromethane (50 mL×3). The organic phases were combined and dried over anhydrous sodium sulfate, the solvent was removed under reduced pressure, the residue was separated by silica gel column chromatography (eluting system: PE/EtOAc=3/1) to deliver the target compound BB-48 (off-white semi-solid, 150 mg, yield 57%). LCMS m/z: 502.1 [M+H]$^+$ The compounds listed in the following table were synthesized according to the synthetic step 10 in reference BB-48 and separated by HPLC:

| References | Structure | Fragment 1 | |
|---|---|---|---|
| Reference 49 | 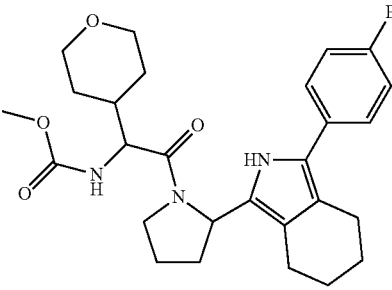 | 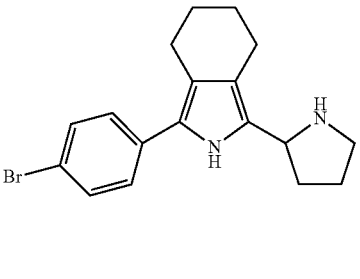 | BB-48-9 |

| | | | |
|---|---|---|---|
| Reference 50 | 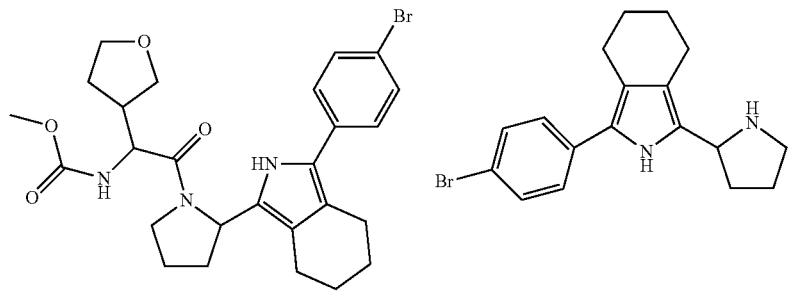 | | BB-48-9 |
| Reference 51 | 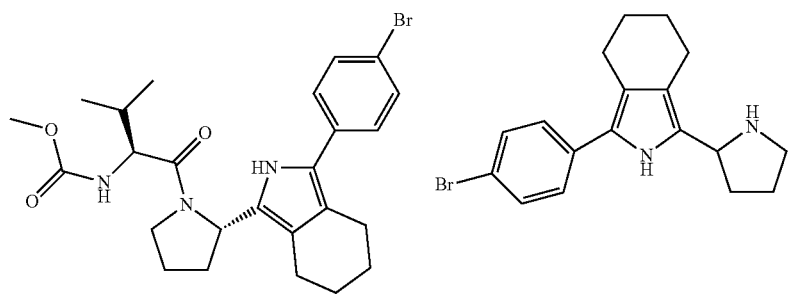 | | BB-48-9 |
| Reference 52 | 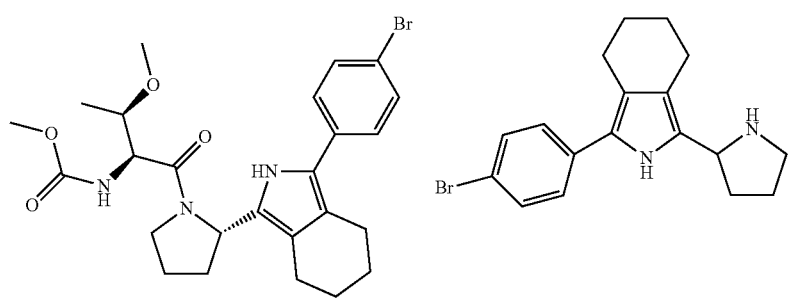 | | BB-48-9 |
| Reference 53 | 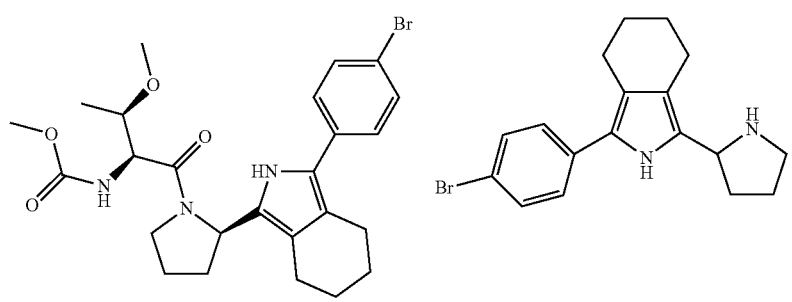 | | BB-48-9 |
| References | Fragment 2 | | MS m/z | Compounds |
|---|---|---|---|---|
| Reference 49 | 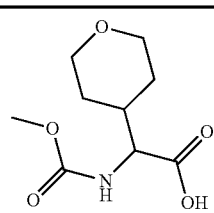 | BB-24-1 | 545.3 [M + H]⁺ | BB-49 |
| Reference 50 | 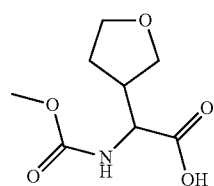 | BB-23-5 | 531.2 [M + H]⁺ | BB-50 |

-continued
| | | | | |
|---|---|---|---|---|
| Reference 51 | 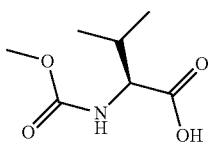 | BB-2-6 | 503.3 [M + H]+ | BB-51 |
| Reference 52 | 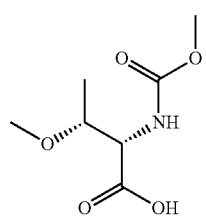 | BB-1-6 | 519.1 [M + H]+ | BB-52 |
| Reference 53 | 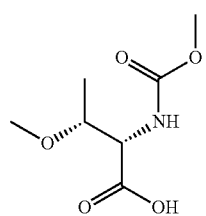 | BB-1-6 | 519.1 [M + H]+ | BB-53 |
Reference 54: Fragment BB-54
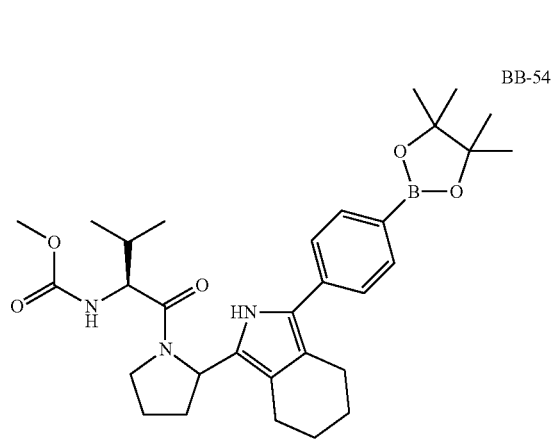
BB-54
Synthetic Route:
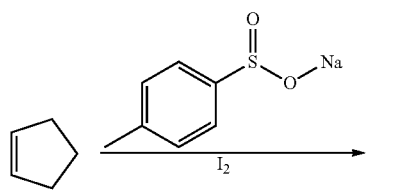
BB-54-1
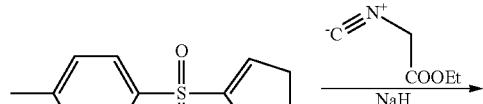
BB-54-2
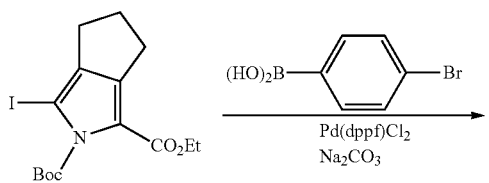
BB-54-3 → BB-54-4
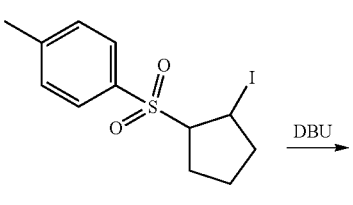
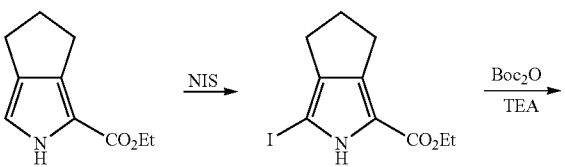
BB-54-5
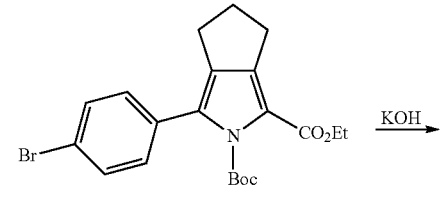
BB-54-6

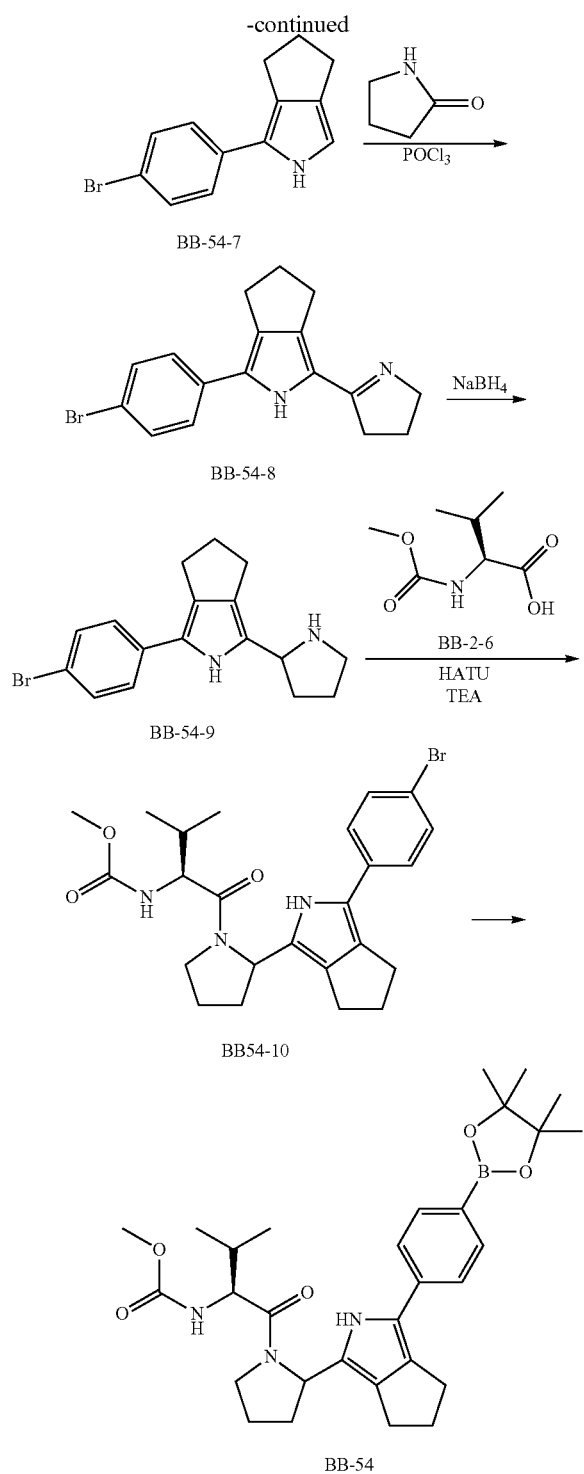

Step 1: Synthesis of Compound BB-54-1

Cyclopentene (3 g, 44.04 mmol) and sodium p-tolylsulfinate (13.34 g, 74.87 mmol) were dissolved in H$_2$O (40 mL) and dichloromethane (40 mL) respectively, iodine (11.18 g, 44.04 mmol) was added in portions. The reaction mixture was stirred at room temperature overnight. Dichloromethane (40 mL) was added, the organic phase was obtained after extraction, which was washed with saturated sodium bicarbonate aqueous solution (50 mL), saturated sodium bisulfite aqueous solution (5 mL) and saturated brines (50 mL). The organic phase was dried over anhydrous sodium sulfate. After filtration, the solvent was removed under reduced pressure thereby delivering the target compound BB-54-1 (15.42 g, 100%).

Step 2: Synthesis of Compound BB-54-2

Compound BB-54-1 (15.42 g, 44.04 mmol) was dissolved in toluene (100 mL), DBU (6.80 g, 44.04 mmol) was added, and the mixture was stirred at room temperature for 1 h. The solid in the reaction mixture was filtrated and the filtrate was washed with 1M HCl solution (50 mL), NaHCO$_3$ (50 mL), saturated brines (50 mL) sequentially. The organic phase was dried over anhydrous sodium sulfate. After filtration, the solvent was removed under reduced pressure thereby delivering the target compound BB-54-2 (5 g, 41%). $^1$H NMR (400 MHz, CDCl$_3$) δ: 7.78-7.76 (m, 2 H), 7.33-7.31 (m, 2 H), 6.40 (s, 1 H), 2.53-2.50 (m, 4 H), 2.43 (s, 3 H), 2.04-1.97 (m, 2 H).

Step 3: Synthesis of Compound BB-54-3

Under an ice bath, a solution of compound BB-54-2 (5 g, 22.49 mmol) and ethyl isocyanoacetate (6.42 g, 56.23 mmol) in THF (30 mL) was dripped slowly into a solution of NaH (2.25 g, 56.23 mmol) in THF (50 mL). The reaction mixture was stirred for 1 h at 0° C. and then stirred for further 30 min at room temperature. The reaction was quenched with methanol, the solvent was removed under reduced pressure, the concentrated liquid was subject to silica gel column chromatography (eluting reagent: 12% EtOAc/PE) to deliver the target compound BB-54-3 (3 g, 74%). $^1$H NMR (400 MHz, CDCl$_3$) δ: 8.70 (br, 1H), 6.57 (s, 1H), 4.30-4.25 (m, 2H), 2.83-2.80 (m, 2H), 2.65-2.61 (m, 2H), 2.38-2.33 (m, 2H), 1.34-1.31 (m, 3H).

Step 4: Synthesis of Compound BB-54-4

Compound BB-54-3 (1 g, 5.58 mmol) was dissolved in THF (20 mL), NIS (1.51 g, 6.70 mmol) was added, and the reaction mixture was stirred at room temperature overnight. The reaction mixture was washed with saturated brines (20 mL×2), the organic phase was dried over anhydrous sodium sulfate. After filtration, the solvent was removed under reduced pressure, the concentrated liquid was separated by silica gel column chromatography (eluting reagent: 8% EtOAc/PE) to deliver the target compound BB-54-4 (1.57 g, 92%). LCMS m/z: 306.0 [M+H]$^+$ Step 5: Synthesis of Compound BB-54-5

Compound BB-54-4 (1.57 g, 5.15 mmol) was dissolved in dichloromethane (20 mL), Boc$_2$O (1.24 g, 5.66 mmol) and TEA (1.56 g, 15.44 mmol) were added sequentially. The reaction mixture was stirred at room temperature for 3 h. The reaction solution was concentrated and subject to silica gel column chromatography (eluting reagent: 10% EtOAc/PE) to deliver the target compound BB-54-5 (2 g, 96%). $^1$H NMR (400 MHz, CDCl$_3$) δ: 4.28-4.22 (m, 2H), 2.85-2.82 (m, 2H), 2.54-2.51 (m, 2H), 2.31-2.27 (m, 2H), 1.59 (s, 9H), 1.32-1.29 (m, 3H).

Step 6: Synthesis of Compound BB-54-6

Compound BB-54-5 (2 g, 4.94 mmol) and 4-bromophenylboronic acid (0.99 g, 4.94 mmol) were dissolved in 1,4-dioxane/H$_2$O=5:1 (30 mL), Pd(dppf)Cl$_2$ (0.2 g, 0.27 mmol) and Na$_2$CO$_3$ (1.57 g, 14.81 mmol) were added sequentially. The reaction solution was stirred at 100° C. for 4 h under nitrogen gas atmosphere, and then diluted with ethyl acetate (100 mL). H$_2$O (30 mL) was added and the obtained organic phase was dried over anhydrous sodium sulfate. After filtration, the solvent was removed under reduced pressure, the concentrated liquid was separated by silica gel column chromatography (eluting system: 7% EtOAc/PE) to deliver the target compound BB-54-6 (1.3 g, 61%). LCMS m/z: 380.0 [M-56+H]$^+$ Step 7: Synthesis of Compound BB-54-7

KOH (650 mg, 11.51 mmol) was dissolved in ethylene glycol (50 mL), heated to reflux for 1 h, and then compound BB-54-6 (1 g, 2.30 mmol) was added, refluxed for further 0.5 h. After H$_2$O was added, the reaction mixture was extracted with dichloromethane (30 mL×2). The organic phase was dried over anhydrous sodium sulfate. After filtration, the solvent was removed under reduced pressure thereby delivering the target product BB-54-7 (500 mg, 83%). LCMS m/z: 262.0 [M+H]$^+$ Step 8: Synthesis of Compound BB-54-8

Under an ice bath, POCl$_3$ (1050 mg, 6.87 mmol) was added dropwise into a solution of compound BB-54-7 (450 mg, 1.72 mmol) and 2-pyrrolidone (584 mg, 6.87 mmol) in 1,2-dichloroethane (20 mL), and the reaction mixture was stirred at room temperature for 2 h. The reaction mixture was poured into saturated sodium acetate solution. 10M KOH aqueous solution was added to adjust pH of the aqueous phase to 11 at 0° C., the mixture was extracted with dichloromethane (30 mL×2). The organic phase was dried over anhydrous sodium sulfate. After filtration, the solvent was removed under reduced pressure thereby delivering the target product BB-54-8 (450 mg, 79%). $^1$H NMR (400 MHz, CDCl$_3$) δ: 7.48-7.38 (m, 4H), 5.85-5.65 (br, 1H), 3.95-3.82 (m, 2H), 3.41-3.37 (m, 2H), 2.46-2.44 (m, 2H), 2.29-2.27 (m, 2H), 2.18-2.14 (m, 2H), 2.00-1.95 (m, 2H).

Step 9: Synthesis of Compound BB-54-9

Compound BB-54-8 (200 mg, 0.607 mmol) was dissolved in dichloromethane/MeOH=1:1 (20 mL), NaBH$_4$ (460 mg, 12.15 mmol) was added, and the reaction mixture was stirred at reflux for 1 h. The reaction was quenched with H$_2$O (10 mL) and extracted with dichloromethane (30 mL×2). The organic phase was dried over anhydrous sodium sulfate. After filtration, the solvent was removed under reduced pressure thereby delivering the target product BB-54-9 (160 mg, 80%). LCMS m/z: 331.0 [M+H]$^+$ Step 10: Synthesis of Compound BB-54-10

Compound BB-54-9 (80 mg, 0.242 mmol) was dissolved in dichloromethane (5 mL), compound BB-2-6 (42 mg, 0.242 mmol), HATU (92 mg, 0.242 mmol) and TEA (73 mg, 0.725 mmol) were added sequentially, and the reaction mixture was stirred at room temperature for 1 h. H$_2$O was added and the reaction mixture was extracted with dichloromethane (30 mL×3). The organic phase was dried over anhydrous sodium sulfate. After filtration, the solvent was removed under reduced pressure, the concentrated liquid was subject to silica gel column chromatography (eluting system: 50% EtOAc/PE) to deliver the target compound BB-54-10 (55 mg, 47%).

Step 11: Synthesis of Compound BB-54

Compound BB-54 was synthesized according to the synthetic step 3 in reference BB-34, with compound BB-54-10 as starting material.

The compounds listed in the following table were synthesized according to the synthetic step 10 in reference BB-54 and separated by HPLC:

| References | Structure | Fragment 1 |
| --- | --- | --- |
| Reference 55 | 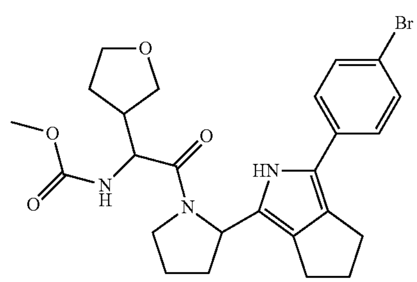 | BB-54-9 |
| Reference 56 | 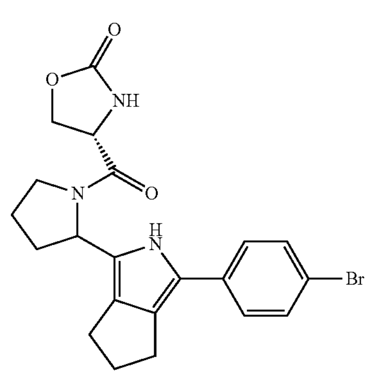 | BB-54-9 |

-continued
| Reference | Fragment 1 | Fragment 2 ref |
|---|---|---|
| Reference 57 | 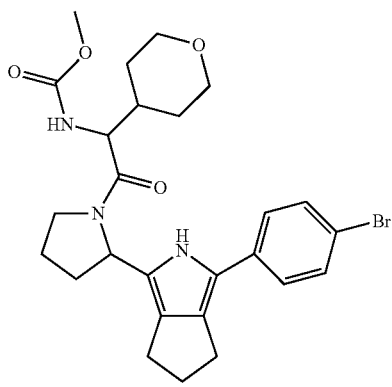 | BB-54-9 |
| Reference 67 | 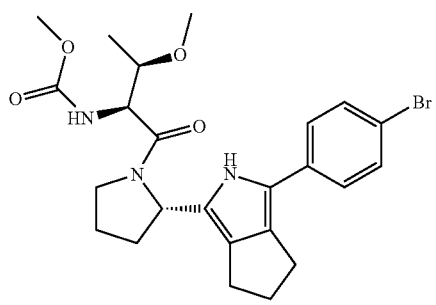 | BB-54-9 |
| Reference 68 | 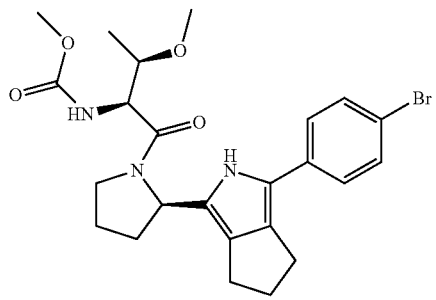 | BB-54-9 |
| References | Fragment 2 | | MS m/z | Compounds |
|---|---|---|---|---|
| Reference 55 | 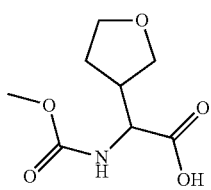 | BB-23-5 | 516.1 [M + H]$^+$ | BB-55 |
| Reference 56 | 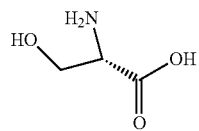 | | 444.1 [M + H]$^+$ | BB-56 |
| Reference 57 | 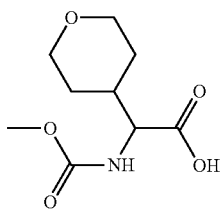 | BB-24-1 | 530.1 [M + H]$^+$ | BB-57 |

-continued
| | | | | |
|---|---|---|---|---|
| Reference 67 | 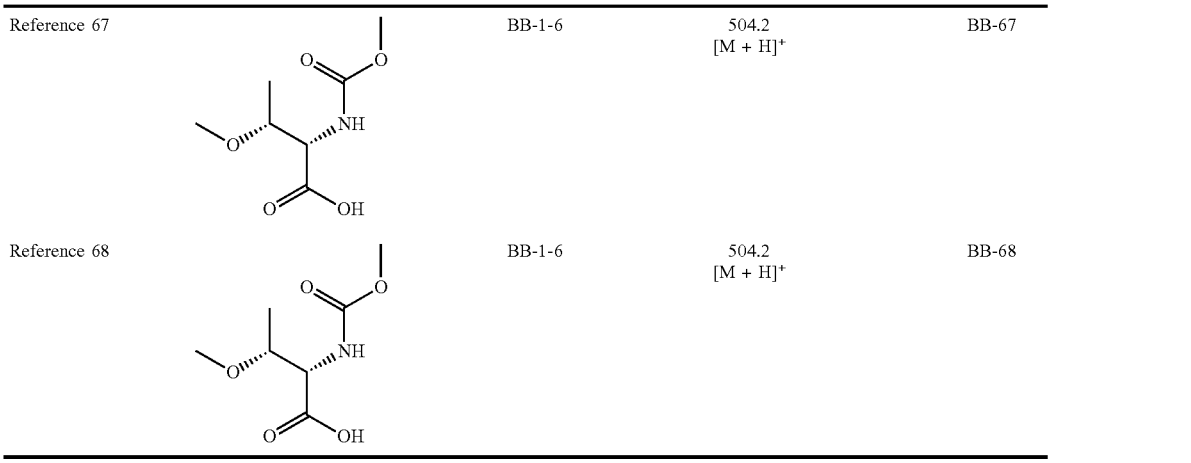 | BB-1-6 | 504.2 [M + H]⁺ | BB-67 |
| Reference 68 | | BB-1-6 | 504.2 [M + H]⁺ | BB-68 |
Reference 58: Fragment BB-58-A and BB-58-B
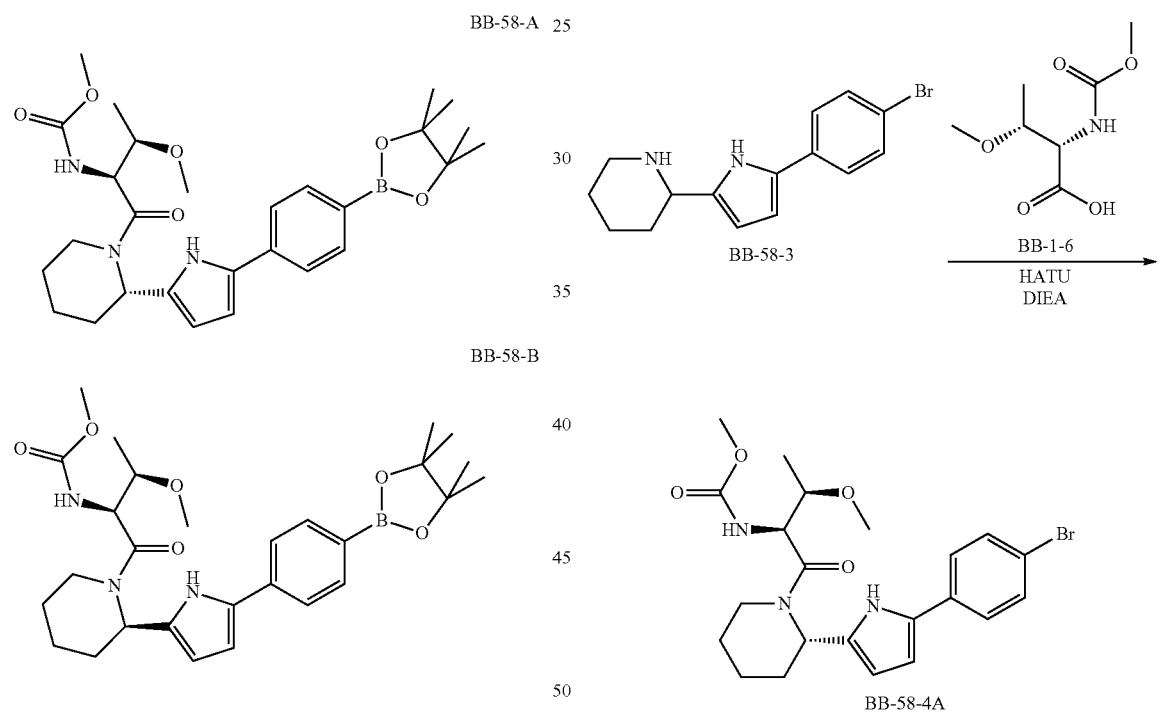
Synthetic Route:
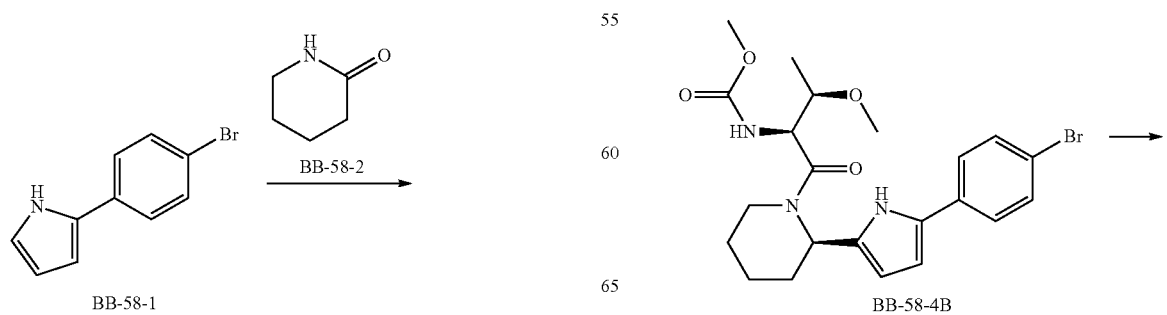

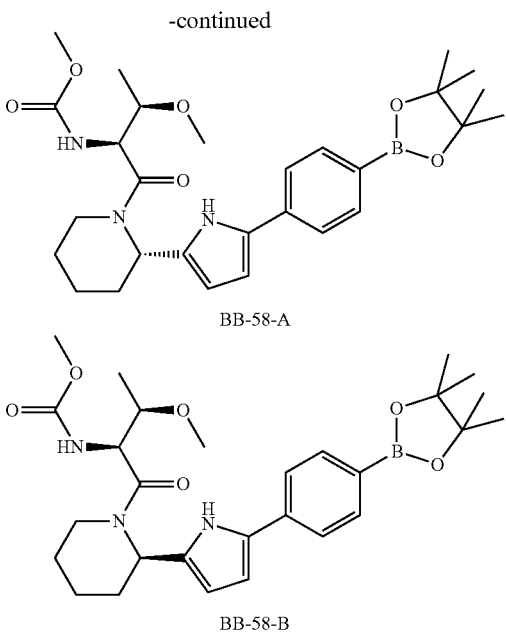

BB-58-A

BB-58-B

Step 1: Synthesis of Compound BB-58-3

Compound BB-58-1 (270 mg, 1.22 mmol) and compound BB-58-2 (723 mg, 7.29 mmol) were dissolved in dichloromethane (30 mL). Under an ice bath, POCl$_3$ (932 mg, 6.08 mmol) was added slowly, the reaction mixture was stirred overnight under nitrogen gas atmosphere. The reaction was quenched by slowly pouring the reaction solution into a solution of saturated sodium acetate in ice water. 10M NaOH solution was added to adjust pH to about 9-10, the mixture was extracted with dichloromethane (50 mL×3). The organic phases were combined and dried over anhydrous sodium sulfate. After filtration, the filtrate was concentrated under reduced pressure. The residue was dissolved in methanol (50 mL), and under an ice bath, NaBH$_4$ (399 mg, 10.55 mmol) was added slowly. The mixture was stirred at room temperature for 2 h. The reaction was quenched with saturated brines (10 mL) and extracted with dichloromethane (50 mL×3). The organic phases were combined and dried over anhydrous sodium sulfate. After filtration, the filtrate was concentrated under reduced pressure thereby delivering the crude target product BB-58-3 (purple oil, 310 mg, yield 84%). LCMS m/z: 305 [M+H]$^+$ Step 2: Synthesis of Compound BB-58-4A and BB-58-4B Compound BB-58-3 (310 mg, 1.02 mmol) and compound BB-1-6 (233 mg, 1.22 mmol) and HATU (463 mg, 1.22 mmol) were dissolved in dichloromethane (20 mL), TEA (205 mg, 2.03 mmol) was added slowly under an ice bath. The reaction mixture was stirred overnight under nitrogen gas atmosphere. The reaction was quenched with saturated NaHCO$_3$ solution (10 mL) and extracted with dichloromethane (30 mL×3). The organic phases were combined and dried over anhydrous sodium sulfate. After filtration, the filtrate was concentrated under reduced pressure. The obtained crude product was purified and separated by preparative silica gel plate (eluting system: PE:EA=1:1) to deliver the target compound BB-58-4A (light purple solid, 110 mg, yield 23%) and BB-58-4B (light purple solid, 120 mg, yield 25%). LCMS m/z: 478 [M+H]$^+$ Step 3: Synthesis of Compound BB-58-A Compound BB-58-4A (40 mg, 0.084 mmol), bis(pinacolato)diboron (43 mg, 0.084 mmol) were dissolved in a mixed solvent of DMF/THF/H$_2$O (2 mL/2 mL/2 mL), Pd(dppf)Cl$_2$ (6 mg, 0.0084 mmol) and Na$_2$CO$_3$ (27 mg, 0.25 mmol) were added. The atmosphere was replaced by nitrogen gas for 3 times and the reaction mixture was heated to 90° C. and stirred for 2 h under nitrogen gas atmosphere. Stop heating and the system was cooled naturally. H$_2$O (10 mL) was added and the reaction mixture was extracted with ethyl acetate (10 mL×3). The ethyl acetate phases were combined and washed with saturated brines (10 mL), dried over anhydrous sodium. The solvent was evaporated under reduced pressure and the crude product was purified and separated by preparative HPLC to deliver the target compound BB-58-A (white solid, 8 mg, yield 12%). $^1$H-NMR (400 MHz, CDCl$_3$): δ: 10.59 (br, 0.4H), 9.10 (br, 1H), 7.75-7.50 (m, 8H), 7.21 (s, 1H), 6.52-6.48 (m, 1H), 6.21-6.03 (m, 2H), 5.82-5.71 (m, 2H), 5.37-5.05 (m, 2H), 4.62-4.57 (m, 2H), 3.84-3.68 (m, 10H), 3.39-3.26 (m, 5H), 3.11-2.73 (m, 2H), 2.62-2.45 (m, 2H), 1.87-1.70 (m, 4H), 1.71-1.42 (m, 4H), 1.30-1.14 (m, 6H); LCMS m/z: 784 [M+H]$^+$ Reference 59: Fragment BB-59-A and BB-59-B

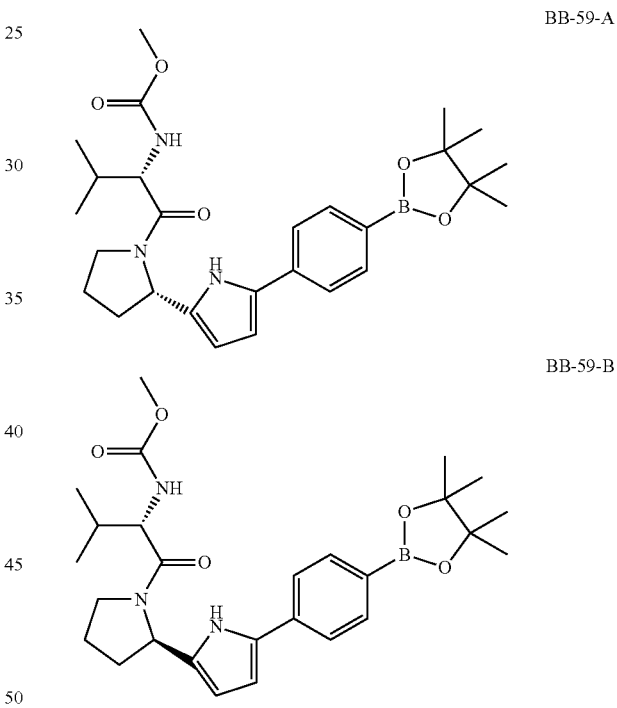

BB-59-A

BB-59-B

Synthetic Route:

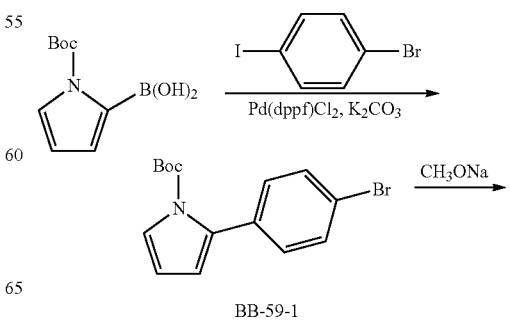

BB-59-1

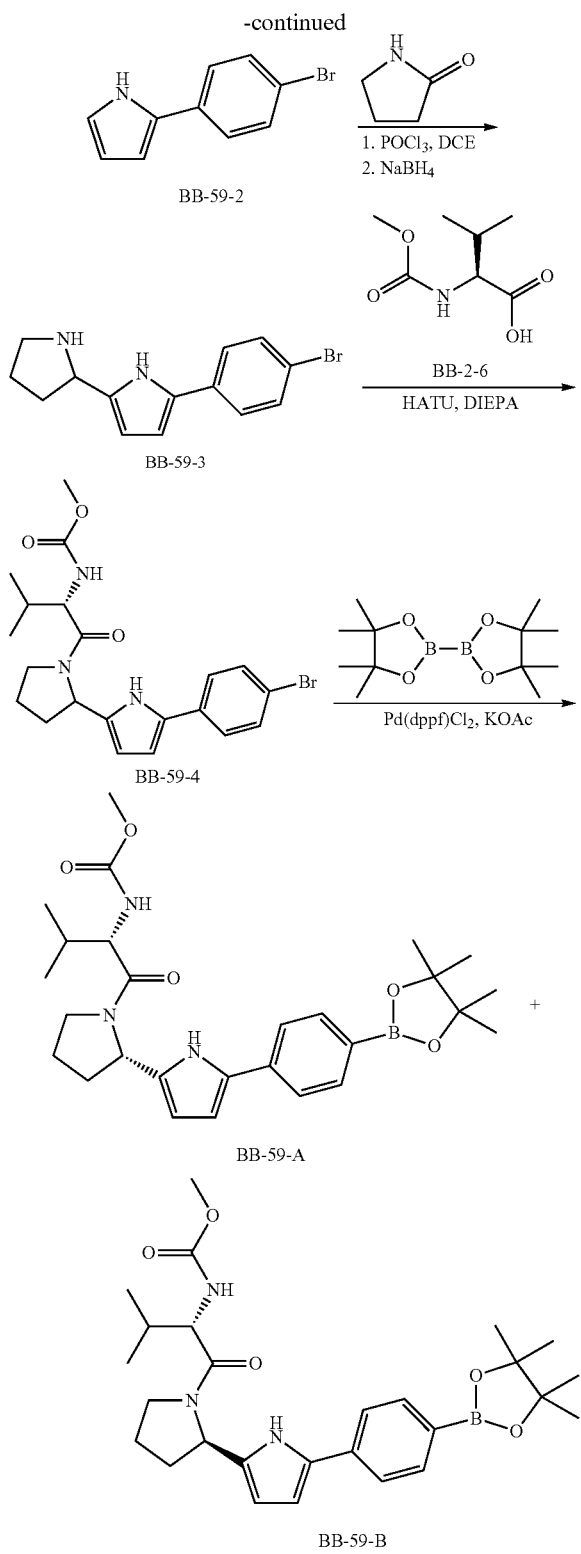

Step 1: Synthesis of Compound BB-59-1

In a 250 mL round-bottom flask, 1-Boc-2-pyrrolyl boronic acid (4.2 g, 19.90 mmol) and 1-bromo-4-iodobenzene (6.19 g, 21.89 mmol), catalyst Pd(dppf)Cl$_2$ (1.45, 1.99 mmol), K$_2$CO$_3$ (8.29 g, 59.71 mmol) were dissolved in dioxane (150 mL) and H$_2$O (50 mL), the reaction mixture was heated to 80° C. and stirred for 2 h under nitrogen gas atmosphere. After the reaction was complete, H$_2$O (200 mL) was added and the reaction mixture was extracted with ethyl acetate (150 mL×3). The organic phase was washed with saturated brines, dried over anhydrous sodium sulfate. After filtration, the filtrate was concentrated under reduced pressure and the obtained crude product was purified and separated by silica gel column chromatography (eluting reagent: PE:EA=10:1) to deliver the target compound BB-59-1 (white solid, 620 mg, yield 81%). $^1$H-NMR (400 MHz, CDCl$_3$): δ: 7.48-7.44 (m, 2H), 7.34-7.33 (m, 1H), 7.22-7.20 (m, 2H), 6.22-6.17 (m, 2H), 1.39 (s, 9H). LCMS m/z: 754 [M+H]$^+$ Step 2: Synthesis of Compound BB-59-2

Compound BB-59-1 (3.3 g, 10.24 mmol) was dissolved in a mixed solvent of methanol (50 mL) and THF (50 mL), MeONa (4.43 g, 81.94 mmol) was added slowly, and the mixture was stirred at room temperature for 3 h. The reaction was quenched with H$_2$O and extracted with ethyl acetate (50 mL×3). The organic phases were combined and dried over anhydrous sodium sulfate. After filtration, the filtrate was concentrated under reduced pressure to deliver the target compound BB-59-2 (gray solid, 2.1 g, 92%).

Step 3: Synthesis of Compound BB-59-3

Compound BB-59-2 (2.1 g, 9.46 mmol) and 2-pyrrolidone (5.63 g, 66.19 mmol) were dissolved in dichloromethane (50 mL), POCl$_3$ (7.25 g, 47.28 mmol) was added slowly under an ice bath, the reaction mixture was stirred overnight under nitrogen gas atmosphere. The reaction was quenched by pouring the reaction solution into a solution of saturated sodium acetate in ice water slowly. 10M NaOH solution was added to adjust pH to about 9-10 and the mixture was extracted with dichloromethane (100 mL×3). The organic phases were combined and dried over anhydrous sodium sulfate. After filtration, the filtrate was concentrated under reduced pressure. The residue was dissolved in methanol (100 mL), NaBH$_4$ (4.91 g, 129.68 mmol) was added slowly under an ice bath, and the mixture was stirred at room temperature for 2 h. The reaction was quenched with saturated brines and extracted with dichloromethane (100 mL×3). The organic phases were combined and dried over anhydrous sodium sulfate. After filtration, the filtrate was concentrated under reduced pressure to deliver the crude target product BB-59-3 (purple oil, 2.3 g, 80%). LCMS m/z: 291 [M+H]$^+$ Step 4: Synthesis of Compound BB-59-4

Compound BB-59-3 (500 mg, 1.72 mmol) and compound BB-2-6 (361 mg, 2.06 mmol) and HATU (783 mg, 2.06 mmol) were dissolved in dichloromethane (30 mL), DIPEA (444 mg, 3.44 mmol) was added slowly under an ice bath, and the reaction mixture was stirred overnight under nitrogen gas atmosphere. The reaction was quenched with saturated NaHCO$_3$ solution and extracted with ethyl acetate (30 mL×3). The organic phases were combined and dried over anhydrous sodium sulfate. After filtration, the filtrate was concentrated under reduced pressure. The obtained crude product was purified and separated by silica gel column chromatography (eluting reagent: PE:EA=1:1) to deliver the target compound BB-59-4 (light purple solid, 620 mg, yield 81%). LCMS m/z: 448 [M+H]$^+$ Step 5: Synthesis of Compound BB-59-A and BB-59-B Compound BB-59-4 (620 mg, 1.38 mmol), bis(pinacolato)diboron (527 mg, 2.07 mmol), KOAc (541 mg, 5.52 mmol) and Pd(dppf)Cl$_2$ (103 mg, 0.14 mmol) were placed in a 50 mL three-neck flask, under nitrogen gas atmosphere, 1,4-dioxane (20 mL) was injected. The reaction system was heated to 90° C. and stirred overnight. Stop heating and cool naturally. After filtration, the filter cake was washed with ethyl acetate twice and the resulting filtrate was concentrated under reduced pressure to remove the solvent. The crude product was purified and separated by silica gel column chromatography (eluting reagent: PE:EA=1:1) to deliver the target compound BB-59-A (gray solid, 190 mg, yield 28%) and BB-59-B (gray solid, 260 mg, yield 38%). LCMS m/z: 496 [M+H]$^+$ The compounds listed in the following table were synthesized according to the synthetic steps 4-5 in reference BB-59-A/B and separated by HPLC:

| References | Structure | Fragment 1 | |
|---|---|---|---|
| Reference 60 | 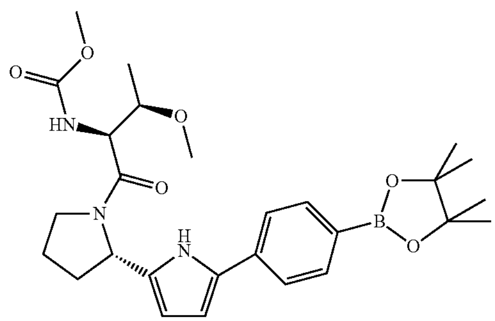 | | BB-59-3 |
| Reference 61 | 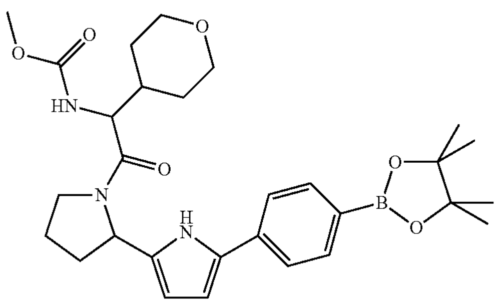 | | BB-59-3 |
| Reference 62 | 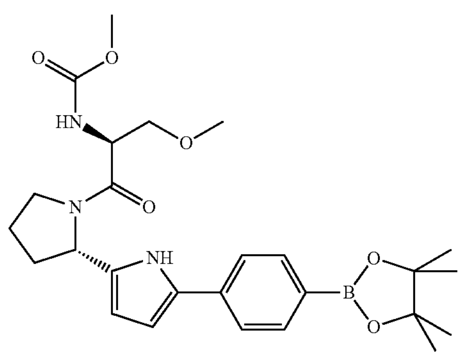 | | BB-59-3 |

| References | Fragment 2 | | MS m/z | Compounds |
|---|---|---|---|---|
| Reference 60 | | BB-1-6 | 512.2 [M + H]$^+$ | BB-60 |
| Reference 61 | | BB-24-1 | 538.3 [M + H]$^+$ | BB-61 |

| Reference 62 | 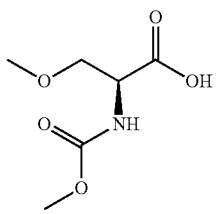 | 497.9 [M + H]+ | BB-62 |
Reference 63: Fragment BB-63-A and BB-63-B
BB-63-A
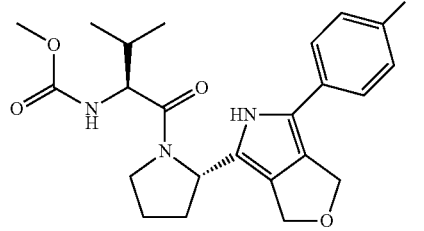
BB-63-B
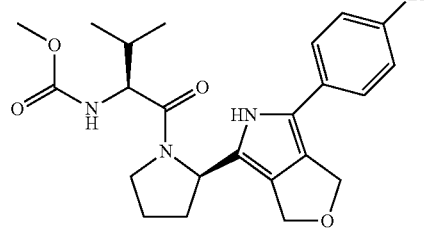
Synthetic Route:
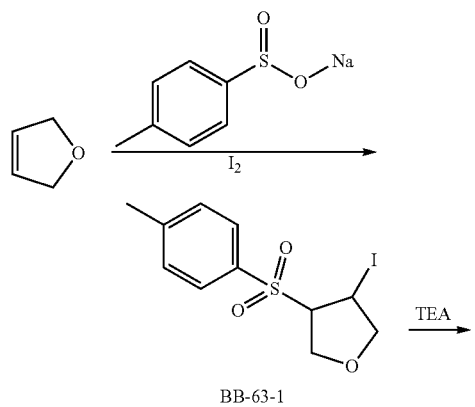
BB-63-1
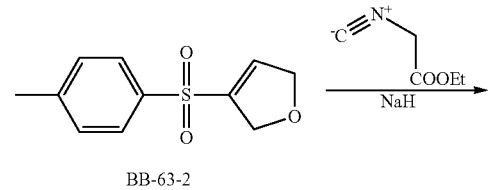
BB-63-2
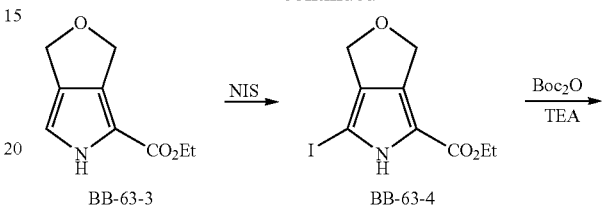
BB-63-3 → BB-63-4
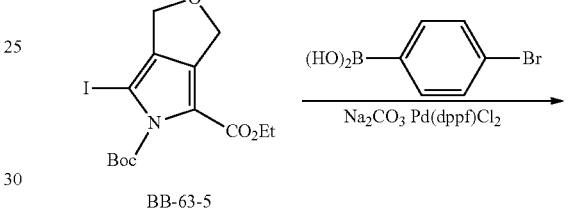
BB-63-5
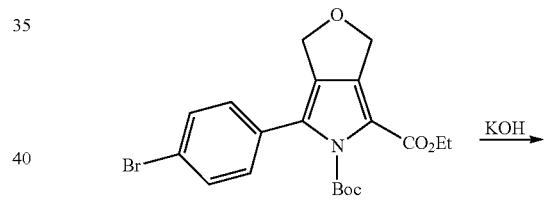
BB-63-6
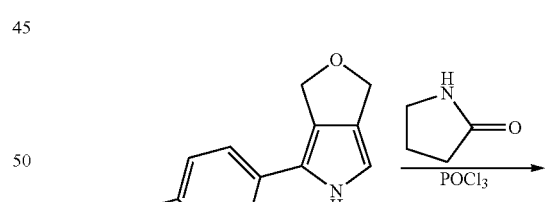
BB-63-7
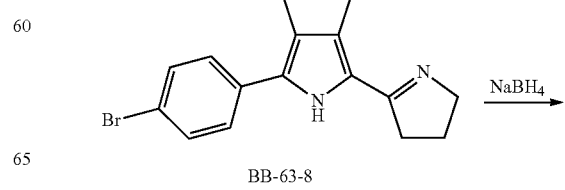
BB-63-8

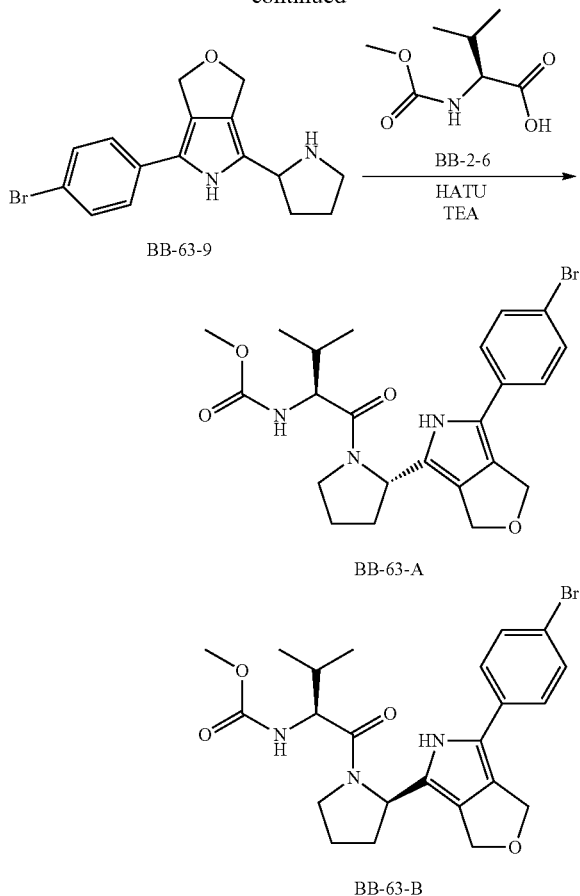

Step 1: Synthesis of Compound BB-63-1

2,5-Dihydrofuran (7 g, 99.9 mmol) and sodium p-tolyl-sulfinate (18.2 g, 1.1.9 mol) were dissolved in a mixed solvent of $H_2O$ (400 mL) and dichloromethane (400 mL), iodine (25.9 g, 101.9 mol) was added in portions, and the reaction mixture was stirred at room temperature overnight. Dichloromethane (400 mL) was added, the organic phase obtained from the extraction was washed with saturated sodium bicarbonate aqueous solution (200 mL), saturated sodium bisulfite aqueous solution (50 mL), saturated brines (100 mL) respectively. The organic phase was dried over anhydrous sodium sulfate, the solvent was removed under reduced pressure thereby delivering the target compound BB-63-1 (oil crude, 35 g, 100%).

Step 2: Synthesis of Compound BB-63-2

Compound BB-63-1 (35 g, 99.9 mmol) was dissolved in acetonitrile (500 mL), TEA (21 mL, 149.8 mol) was added, and the mixture was stirred at room temperature for 2 h. The solvent was evaporated under reduced pressure, the residue was diluted with ethyl acetate (500 mL) and washed with 1M HCl solution (50 mL), saturated sodium bicarbonate aqueous solution (50 mL), brines (50 mL) respectively. The organic phase was dried over anhydrous sodium sulfate, the solvent was removed under reduced pressure thereby delivering the target compound BB-63-2 (light yellow solid, 15 g, yield 67%). $^1$H-NMR (400 MHz, $CDCl_3$) δ: 7.89-7.82 (m, 2H), 7.35-7.33 (m, 2H), 6.77 (s, 1H), 4.77-4.69 (m, 4H), 2.44 (s, 3H).

Step 3: Synthesis of Compound BB-63-3

Under an ice bath, a solution of compound BB-63-2 (7 g, 31.2 mmol) and ethyl isocyanoacetate (5.32 g, 46.8 mmol) in THF (50 mL) was dripped slowly into a suspension of NaH (3.12 g, 78.1 mmol) in THF (100 mL). The reaction mixture was stirred at 0° C. for 1 h and slowly warmed to room temperature, stirred for further 2 h. The reaction was quenched with methanol (20 mL), concentrated under reduced pressure to remove the solvent, the residue was separated by silica gel column chromatography (eluting reagent: EtOAc/PE=½) to deliver the target compound BB-63-3 (gray solid, 2 g, yield 35%). LCMS m/z: 182.1 $[M+H]^+$.

Step 4: Synthesis of Compound BB-63-4

Compound BB-63-3 (2 g, 11 mmol) was dissolved in THF (50 mL), NIS (2.98 g, 13.3 mmol) was added, and the reaction mixture was stirred at room temperature overnight. The solvent was removed under reduced pressure, the mixture was diluted with ethyl acetate (100 mL) and washed with saturated brines (50 mL). The organic phase was dried over anhydrous sodium sulfate, concentrated under reduced pressure to remove the solvent, the residue was separated by silica gel column chromatography (eluting reagent: EtOAc/PE=⅕) to deliver the target compound BB-63-4 (light yellow solid, 1.5 g, yield 44%). $^1$H NMR (400 MHz, $CDCl_3$) δ: 4.87 (s, 2H), 4.52 (s, 2H), 4.1 (t, J=7.1 Hz, 2H), 1.23 (q, J=6.8 Hz, 3H). LCMS m/z: 308.1 $[M+H]^+$ Step 5: Synthesis of Compound BB-63-5

Compound BB-63-4 (1.5 g, 4.88 mmol) was dissolved in dichloromethane (20 mL), $Boc_2O$ (1.28 g, 5.86 mmol), TEA (1.48 g, 14.7 mmol) were added sequentially, and the mixture was stirred at room temperature for 3 h. The solvent was evaporated under reduced pressure, the residue was separated by silica gel column chromatography (eluting reagent: EtOAc/PE=⅙) to deliver the target compound BB-63-5 (colorless solid, 4 g, yield 70%). LCMS m/z: 353.2 $[M+H-55]^+$.

Step 6: Synthesis of Compound BB-63-6

Compound BB-63-5 (1.4 g, 3.44 mmol) and 4-bromophenylboronic acid (0.76 g, 3.78 mmol) were dissolved in 1,4-dioxane/$H_2O$=5:1 (100 mL), Pd(dppf)$Cl_2$ (0.3 g, 0.344 mmol) and $Na_2CO_3$ (1.1 g, 10.3 mmol) were added sequentially, and the reaction mixture was stirred at 100° C. for 4 h under nitrogen gas atmosphere. The reaction mixture was diluted with ethyl acetate (100 mL). $H_2O$ (30 mL) was added and the organic phase obtained from extraction was dried over anhydrous sodium sulfate, the solvent was removed under reduced pressure, the residue was separated by silica gel column chromatography (eluting system: EtOAc/PE=½) to deliver the target compound BB-63-6 (white solid, 0.7 g, yield 46%). LCMS m/z: 379.9 $[M-56+H]^+$ Step 7: Synthesis of Compound BB-63-7

KOH (1.3 g, 22.9 mmol) was dissolved in ethylene glycol (50 mL), the reaction mixture was stirred at reflux for 1 h, and then compound BB-63-6 (2 g, 4.58 mmol) was added, the mixture was stirred at reflux for further 1 h. The reaction mixture was cooled to room temperature and poured into ice-water (100 mL), extracted with dichloromethane (50 mL×2). The organic phases were combined and dried over anhydrous sodium sulfate, the solvent was removed under reduced pressure thereby delivering the target product BB-63-7 (brown solid, 0.5 g, yield 41%). 1H NMR (400 MHz, $CDCl_3$) δ: 8.41 (br, 1H), 7.41-7.39 (m, 2H), 7.05-7.03 (m, 2H), 9.48 (s, 1H), 4.98 (s, 2H), 4.84 (s, 2H). LCMS m/z: 263.9 $[M+H]^+$ Step 8: Synthesis of Compound BB-63-8

Under an ice bath, POCl$_3$ (1.74 g, 11.4 mmol) was added dropwise into a solution of compound BB-63-7 (0.5 g, 1.89 mmol) and 2-pyrrolidone (0.81 g, 9.47 mmol) in 1,2-dichloroethane (50 mL), the reaction mixture was stirred at room temperature for 2 h. After the reaction was complete, the mixture was poured into saturated sodium acetate solution (50 mL). At 0° C., 10M KOH aqueous solution was added to adjust pH of the aqueous phase to 11, the mixture was extracted with dichloromethane (50 mL×3). The organic phases were combined and dried over anhydrous sodium sulfate, the solvent was removed under reduced pressure thereby delivering the target product BB-63-8 (brown solid, 0.3 g, yield 48%). LCMS m/z: 333.0 [M+H]$^+$ Step 9: Synthesis of Compound BB-63-9

Compound BB-63-8 (0.3 g, 0.91 mmol) was dissolved in dichloromethane/MeOH (1:1, 20 mL), NaBH$_4$ (0.34 g, 9.06 mmol) was added, the reaction mixture was stirred at reflux overnight. The reaction was quenched with H$_2$O (10 mL) and extracted with dichloromethane (50 mL×2). The organic phases were combined and dried over anhydrous sodium sulfate, the solvent was removed under reduced pressure thereby delivering the target product BB-63-9 (brown solid, 0.1 g, yield 33%). LCMS m/z: 335.0 [M+H]$^+$ Step 10: Synthesis of Compound BB-63-A and BB-63-B Compound BB-63-9 (100 mg, 0.3 mmol) was dissolved in dichloromethane (5 mL), compound BB-2-6 (63 mg, 0.36 mmol), HATU (0.17 g, 0.45 mmol) and TEA (91 mg, 0.9 mmol) were added sequentially. The reaction mixture was stirred at room temperature for 2 h. H$_2$O (20 mL) was added and the reaction mixture was extracted with dichloromethane (50 mL×3). The organic phases were combined and dried over anhydrous sodium sulfate, the solvent was removed under reduced pressure, the residue was separated by silica gel column chromatography (eluting system: EtOAc/PE=⅓) to deliver the target compound BB-63-A (light yellow solid, 50 mg, yield 34%) and the target compound BB-63-B (light yellow solid, 50 mg, yield 34%). LCMS m/z: 490.1 [M+H]$^+$ The compounds listed in the following table were synthesized according to the synthetic step 10 in reference BB-63-A/B:

| References | Structure | Fragment 1 | |
|---|---|---|---|
| Reference 64A | (structure) | (structure) | BB-63-9 |
| Reference 64B | (structure) | (structure) | BB-63-9 |

| References | Fragment 2 | | MS m/z | Compounds |
|---|---|---|---|---|
| Reference 64A | (structure) | BB-1-6 | 508.2 [M + H]$^+$ | BB-64-A |

| Reference 64B | 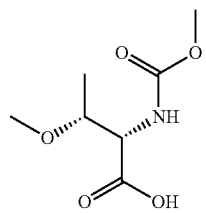 | BB-1-6 | 508.2 [M + H]+ | BB-64-B |
Reference 65: Fragment BB-65-A and BB-65-B
BB-65-A
BB-65-B
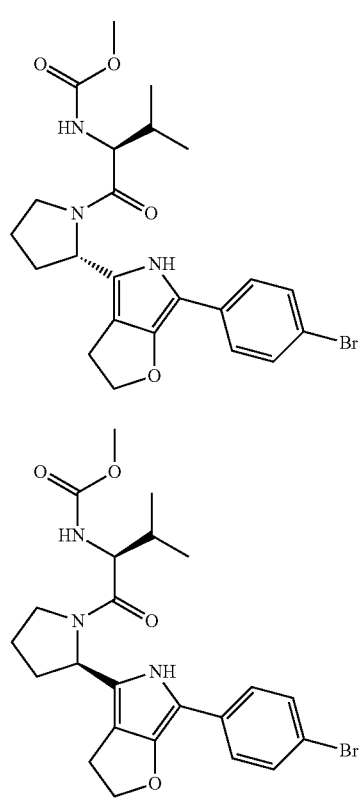
Synthetic Route:
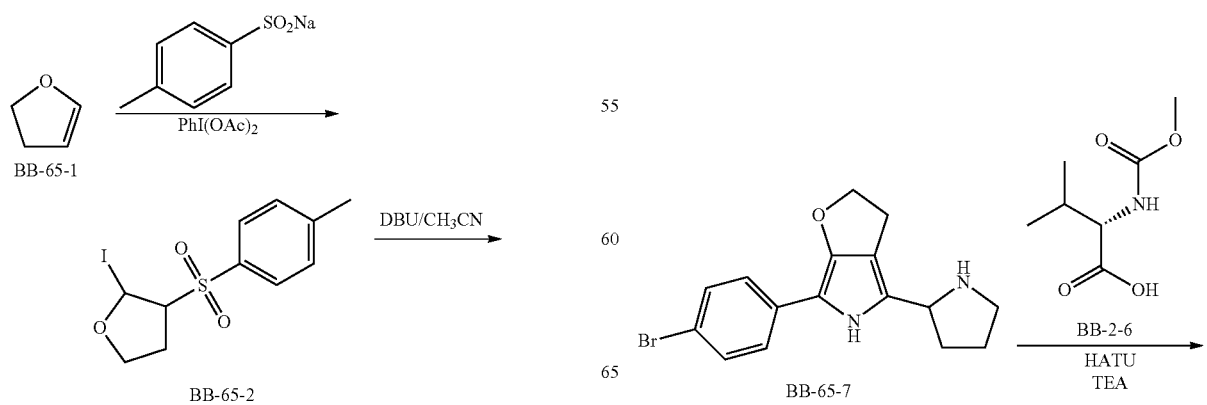
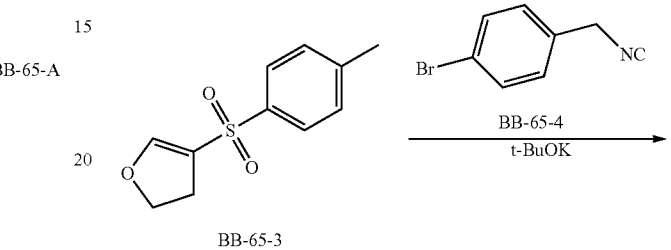
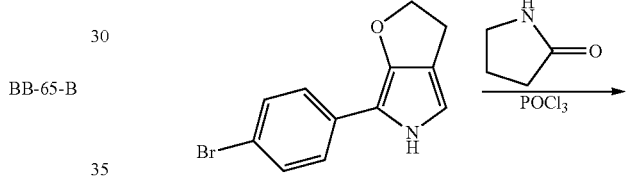
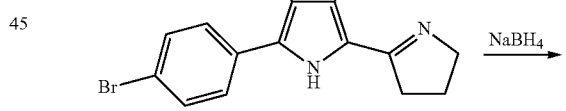

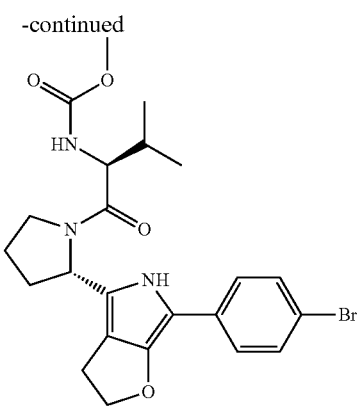

BB-65-A

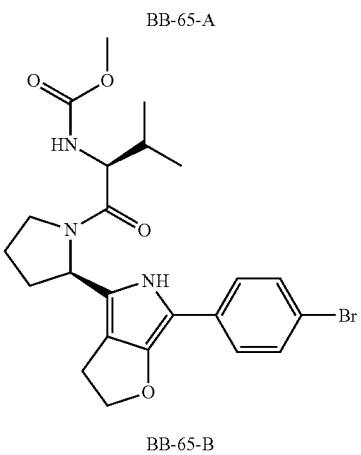

BB-65-B

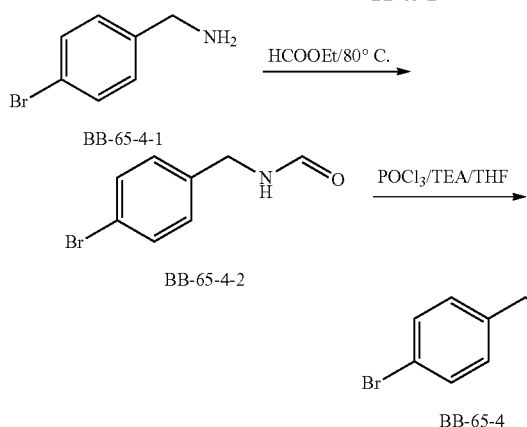

Step 1: Synthesis of Compound BB-65-2

Compound BB-65-1 (1 g, 14.27 mmol) and sodium p-tolylsulfinate (10.17 g, 57.07 mmol), KI (2.37 g, 14.27 mmol) were dissolved in acetonitrile (100 mL), iodosobenzene diacetate (6.89 g, 21.40 mmol) was added, and the reaction mixture was stirred at room temperature for 1 h. The reaction was quenched with saturated sodium thiosulfate (100 mL), and saturated sodium carbonate solution (100 mL) was added, the mixture was extracted with ethyl acetate (200 mL×3). The organic phases were combined and the solvent was removed under reduced pressure thereby delivering the target compound BB-65-2 (3 g, 60%).

Step 2: Synthesis of Compound BB-65-3

Compound BB-65-2 (3 g, 8.52 mmol) was dissolved in acetonitrile (40 mL), DBU (6.07 g, 34.08 mol) was added, and the mixture was stirred at room temperature for 1 h, then washed with 1M HCl solution (50 mL), NaHCO$_3$ (20 mL), saturated brines (20 mL) sequentially. The solvent was removed under reduced pressure, the concentrate liquid was separated by silica gel column chromatography (eluting reagent: 40% EtOAc/PE) to deliver the target compound BB-65-3 (700 mg, 37%). $^1$H NMR (400 MHz, CDCl$_3$) δ: 7.77-7.75 (d, 2H, J=8.4 Hz), 7.33-7.31 (d, 2H, J=8.0 Hz), 7.19-7.18 (m, 1H), 4.62-4.57 (m, 2H), 2.81-2.75 (m, 2H), 2.43 (s, 3H).

Step 3: Synthesis of Compound BB-65-5

Compound BB-65-4-1 (250.0 g, 255.0 mmol) was dissolved in ethyl formate (1.5 L), the reaction mixture was heated to reflux and stirred overnight. The solvent was removed under reduced pressure thereby obtaining the crude product BB-65-4-2 (white solid, 287.0 g), which was directly used for the next step without further purification. Under an ice bath, POCl$_3$ (226.1 g, 1.5 mol) was slowly added dropwise into a solution of compound BB-65-4-2 (287.0 g, 1.3 mmol) and TEA (526.2 g, 5.2 mol) in THF (1.5 L). The ice bath was removed after dripping, the reaction mixture was stirred at room temperature until the reaction was complete. The reaction mixture was slowly poured into vigorously stirred ice-water, extracted with dichloromethane (1.0 L×3). The organic phases were combined and washed with saturated brines, dried over anhydrous sodium sulfate, the solvent was removed under reduced pressure thereby delivering the crude product BB-65-4 (white solid, 254.8 g), which was directly used for the next step without further purification. Compound BB-65-3 (1 g, 5.35 mmol) and BB-65-4 (1.57 g, 8.03 mmol) were dissolved in THF (20 mL). At 0° C., t-BuOK solution (1M in THF, 16 mL, 16.00 mmol) was dripped, and then the mixture was stirred at room temperature for 2 h. The reaction was quenched with H$_2$O and extracted with ethyl acetate (50 mL×3). The organic phases were combined, the solvent was removed under reduced pressure, the concentrated liquid was separated by silica gel column chromatography (eluting reagent: 20% EtOAc/PE) to deliver the target compound BB-65-5 (360 mg, 25%). LCMS m/z: 265.9 [M+H]$^+$.

Step 4: Synthesis of Compound BB-65-6

Under an ice bath, POCl$_3$ (836 mg, 5.45 mmol) was added dropwise into a solution of compound BB-65-5 (360 mg, 1.36 mmol) and 2-pyrrolidone (580 mg, 6.82 mmol) in 1,2-dichloroethane (30 mL), and the reaction mixture was stirred at room temperature for 2 h. The reaction solution was poured into saturated sodium acetate solution, and then at 0° C., 10M KOH aqueous solution was added to adjust pH of the aqueous phase to 11. The mixture was extracted with dichloromethane (30 mL×2), the organic phase was dried over anhydrous sodium sulfate. After filtration, the solvent was removed under reduced pressure thereby delivering the target product BB-65-6 (250 mg, 55%). LCMS m/z: 331.0 [M+H]$^+$ Step 5: Synthesis of Compound BB-65-7

Compound BB-65-6 (250 mg, 0.755 mmol) was dissolved in dichloromethane/MeOH=1:1 (20 mL), NaBH$_4$ (286 mg, 7.55 mmol) was added, the reaction mixture was stirred at reflux for 1 h. The reaction was quenched with H$_2$O and extracted with dichloromethane (30 mL×2). The organic phase was dried over anhydrous sodium sulfate. After filtration, the solvent was removed under reduced pressure thereby delivering the target product BB-65-7 (250 mg, 100%).

Step 6: Synthesis of Compound BB-65-A and BB-65-B

Compound BB-65-7 (250 mg, 0.750 mmol) was dissolved in dichloromethane (10 mL), compound BB-2-6 (145 mg, 0.825 mmol), HATU (342 mg, 0.900 mmol) and TEA (228 mg, 2.25 mmol) were added sequentially. The reaction mixture was stirred at room temperature for 1 h. H₂O was added and the reaction mixture was extracted with dichloromethane (30 mL×3). The organic phase was dried over anhydrous sodium sulfate. After filtration, the solvent was removed under reduced pressure, the concentrated liquid was separated by silica gel column chromatography (eluting system: 60% EtOAc/PE) to deliver the target compound BB-65-A (90 mg, 24%) and BB-65-B (90 mg, 24%). LCMS m/z: 492.0 [M+H]⁺

Reference 66: Fragment BB-66-A and BB-66-B

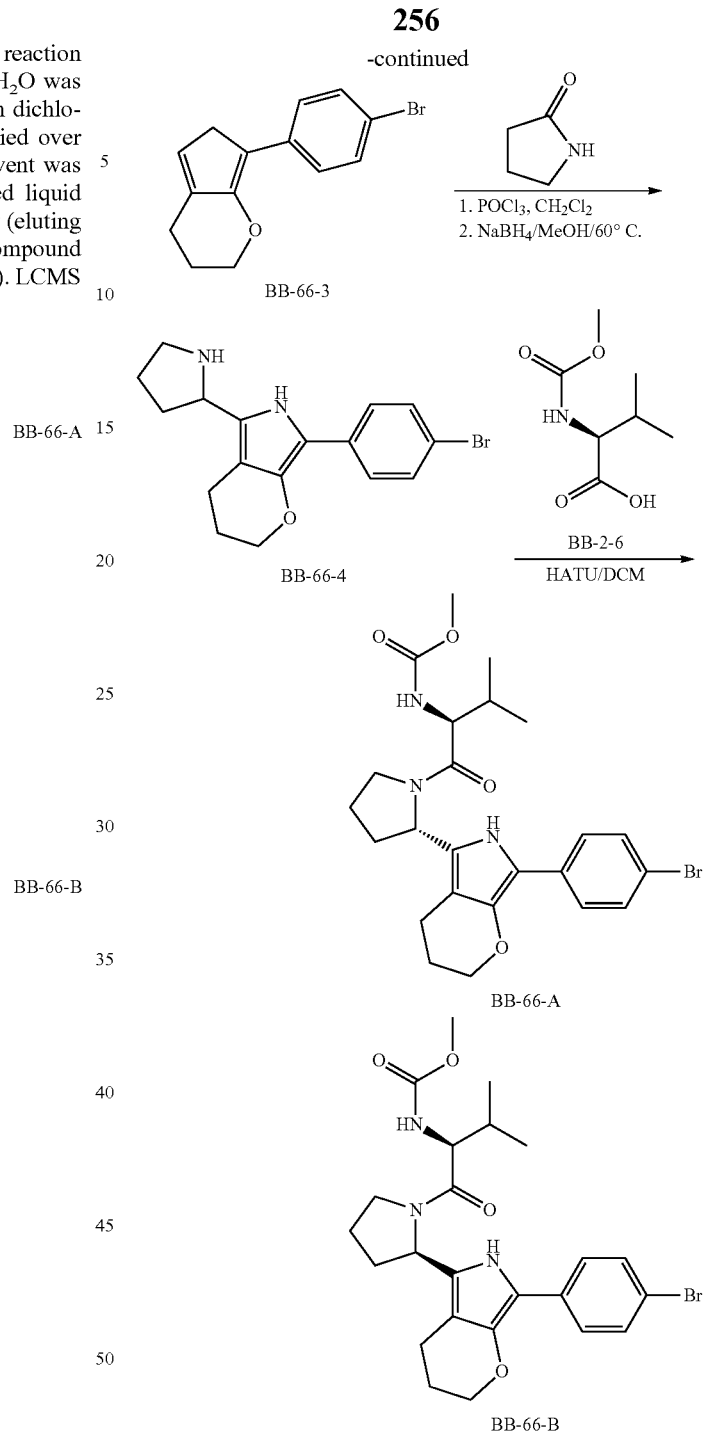

Synthetic Route:

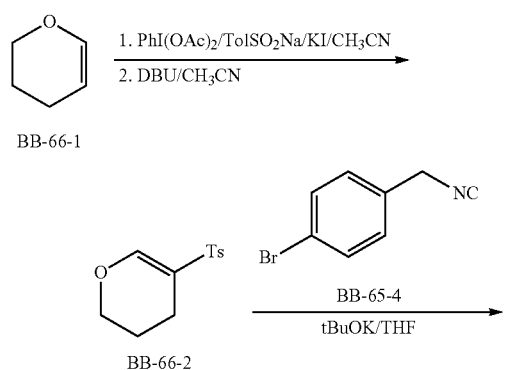

Step 1: Synthesis of Compound BB-66-2

At room temperature, iodosobenzene diacetate (4.8 g, 15.0 mmol) was slowly added into a suspension of sodium p-tolylsulfinate (7.1 g, 40.0 mmol) and KI (1.6 g, 10.0 mmol) in acetonitrile (40 mL). After addition, the mixture was stirred vigorously at room temperature for further 1 h. Then the reaction was quenched with saturated sodium sulfite solution (100 mL) and neutralized with saturated sodium bicarbonate solution to weak base (pH=8-9), stirred for further 0.5 h, extracted with ethyl acetate (500 mL×3). The organic phases were combined and washed with H₂O (100 mL) and saturated brines (100 mL), dried over anhydrous sodium sulfate, the solvent was removed under reduced pressure thereby delivering the crude product. The obtained crude product was dissolved in acetonitrile (40 mL), DBU (6.7 g, 38.0 mol) was added to form a dark-brown solution, stirred at the temperature for 2 h and filtrated. The filtrate was washed with 1M HCl solution (50 mL), saturated sodium bicarbonate solution (50 mL) and saturated brines (50 mL), and dried over anhydrous sodium sulfate. The solvent was removed under reduced pressure, the residue was separated by silica gel column chromatography (developing reagent: PE/EtOAc=10/1, eluting reagent: PE/EtOAc=10/1) to deliver the target compound BB-66-2 (white solid, 700.0 mg, yield 30.4%). $^1$H NMR (400 MHz, CDCl$_3$): δ: 7.72 (d, 2H, J=8.0 Hz), 7.57 (s, 1H), 7.29 (d, 2H, J=8.0 Hz), 4.05 (t, 2H, J=12.0), 2.41 (s, 3H), 2.15 (t, 2H, J=12.0), 1.67-1.60 (m, 2H).

Step 2: Synthesis of Compound BB-66-3

Under an ice bath, a solution of t-BuOK in THF (1M, 12.6 mL, 12.6 mmol) was dripped slowly into a solution of compound BB-65-4 (1.0 g, 4.2 mmol) and compound BB-66-2 (1.2 g, 6.3 mmol) in THF (10 mL). The ice bath was removed after the addition of t-BuOK, then the reaction mixture was stirred at room temperature until the reaction was complete. The reaction was quenched with H$_2$O (10 mL) and extracted with ethyl acetate (20 mL×3). The organic phases were combined and washed with saturated brines (10 mL), dried over anhydrous sodium sulfate, the solvent was removed under reduced pressure, the residue was separated by silica gel column chromatography (developing reagent: PE/EtOAc=1/1, eluting reagent: PE/EtOAc=1/1) to deliver the target compound BB-66-3 (gray white solid, 200.0 mg, yield: 28.6%). LCMS m/z: 278.0 [M+H]$^+$.

Step 3: Synthesis of Compound BB-66-4

Under an ice bath, POCl$_3$ (643.8 mg, 4.2 mmol) was slowly added dropwise into a solution of compound BB-66-3 (200.0 mg, 0.7 mmol) and compound 2-pyrrolidone (306.0 mg, 3.5 mmol) in THF (5 mL). The ice bath was removed after the addition of POCl$_3$, the reaction mixture was stirred at room temperature until the reaction was complete. The reaction solution was slowly poured into vigorously stirred sodium acetate aqueous solution (10 mL), and then neutralized to pH≈9 with 2N NaOH aqueous solution. After the mixture was extracted with dichloromethane (20 mL×3), the organic phases were combined and washed with saturated brines, dried over anhydrous sodium sulfate. The solvent was removed under reduced pressure thereby delivering the crude product. The crude product was dissolved in methanol (10 mL) and NaBH$_4$ was added slowly under an ice bath, and then the reaction solution was heated to reflux and stirred overnight. The reaction was quenched with H$_2$O and extracted with ethyl acetate (20 mL×3). The organic phases were combined and washed with saturated brines (20 mL), dried over anhydrous sodium sulfate, the solvent was removed under reduced pressure thereby delivering the crude product BB-66-4 (white solid, 200.0 mg, yield: 80.6%).

Step 4: Synthesis of Compound BB-66-A and BB-66-B

Compound BB-66-4 (200.0 mg, 0.5 mmol), compound BB-2-6 (111.0 mg, 0.6 mmol) and HATU (228.0 mg, 0.6 mmol) were dissolved in dichloromethane (10.0 mL), TEA (101.2 mg, 8.4 mmol) was slowly dripped at room temperature, and the reaction mixture was stirred at room temperature overnight. H$_2$O (20 mL) was added, the reaction mixture was extracted with dichloromethane (20 mL×3). The organic phases were combined and washed with saturated brines (20 mL), dried over anhydrous sodium sulfate, the solvent was removed under reduced pressure, the residue was separated by silica gel thin layer chromatography (developing reagent: DCM/MeOH=10/1) to deliver the target compound BB-66-A (purple solid, 20 mg, yield: 12.0%) and compound BB-66-B (purple solid, 15.0 mg). LCMS m/z: 506.0 [M+H]$^+$ Embodiment 1: AG_015

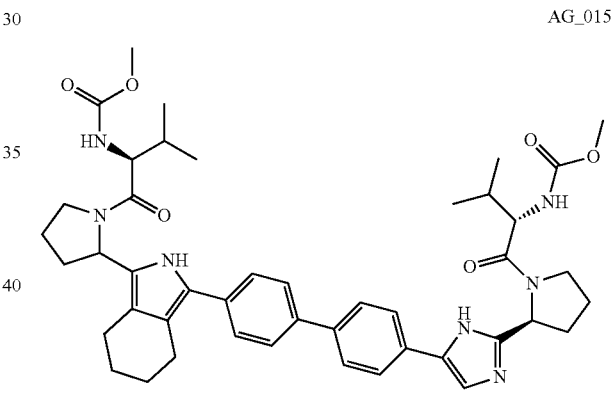

AG_015

Synthetic Route:

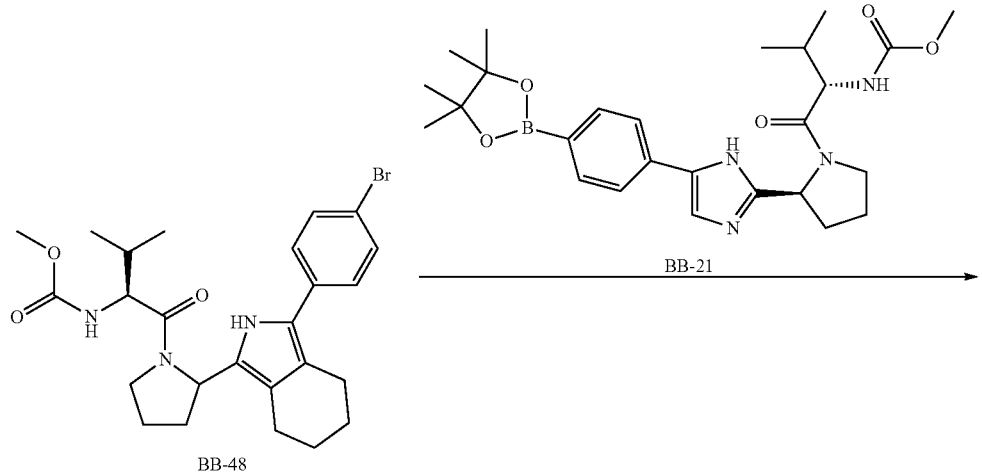

-continued

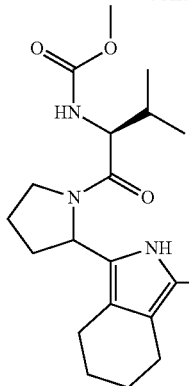 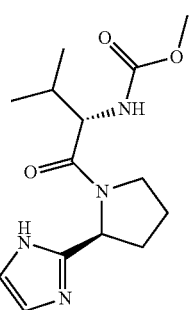

AG_015

Step 1: Synthesis of Compound AG_015

Compound BB-48 (20 mg, 39.8 mmol) and compound BB-21 (47 mg, 0.11 mmol) were dissolved in THF/DMF/H$_2$O=1:1:1 (6 mL), Pd(dppf)Cl$_2$ (3 mg, 3.98 mmol) and Na$_2$CO$_3$ (12 mg, 119 mmol) were added sequentially. The reaction mixture was stirred at 100° C. for 4 h under nitrogen gas atmosphere. H$_2$O (10 mL) was added and the reaction mixture was extracted with ethyl acetate (20 mL×3). The organic phases were combined and dried over anhydrous sodium sulfate. The solvent was removed under reduced pressure, the residue was separated by preparative chromatography to deliver the target compound AG_015 (white powder, 5 mg, yield: 15%). $^1$H NMR (400 MHz, CDCl$_3$) δ: 10.76 (br, 1H), 9.46 (br, 1H), 9.08 (br, 1H), 7.80-7.33 (m, 9H), 5.51-5.23 (m, 3H), 4.62-4.26 (m, 1H), 4.18-4.06 (m, 1H), 3.86-3.61 (m, 7H), 3.37-3.30 (m, 1H), 2.77-2.64 (m, 2H), 2.57-2.37 (m, 2H), 2.17-2.06 (m, 2H), 2.06-1.99 (m, 6H), 1.81-1.69 (m, 7H), 0.90-0.43 (m, 12H). LCMS m/z: 792.6[M+H]$^+$.

The compounds listed in the following table were synthesized according to the synthetic method and HPLC purification of step 1 in synthesizing AG_015:

| Em-bodi-ments | Structure | Fragment 1 | Fragment 2 | MS m/z |
|---|---|---|---|---|
| 2 | AG_046 | BB-48 | BB-23 | 820.3 [M + H]+ |
| 3 | AG_047 | BB-48 | BB-38 | 848.3 [M + H]+ |

| Em-bodi-ments | Structure | Fragment 1 | Fragment 2 | MS m/z |
|---|---|---|---|---|
| 4 | AG_040 | BB-49 | BB-21 | 834.5 [M + H]+ |
| 5 | AG_027 | BB-50 | BB-21 | 820.5 [M + H]+ |

-continued

| Embodiments | Structure | Fragment 1 | Fragment 2 | MS m/z |
|---|---|---|---|---|
| 6 | AG_045 | BB-48 | BB-24 | 877.3 [M + H]+ |
| 7 | AG_015_A | BB-48 | BB-21 | 792.2 [M + H]+ |

| Em-bodi-ments | Structure | Fragment 1 | Fragment 2 | MS m/z |
|---|---|---|---|---|
| 8 | AG_067 | BB-48 | BB-25 | 808.2 [M + H]+ |
| 9 | AG_078_A | BB-52 | BB-21 | 808.3 [M + H]+ |

| Em-bodi-ments | Structure | Fragment 1 | Fragment 2 | MS m/z |
|---|---|---|---|---|
| 10 | AG_078_B | BB-53 | BB-21 | 808.3 [M + H]+ |

Embodiment 11: AG_014

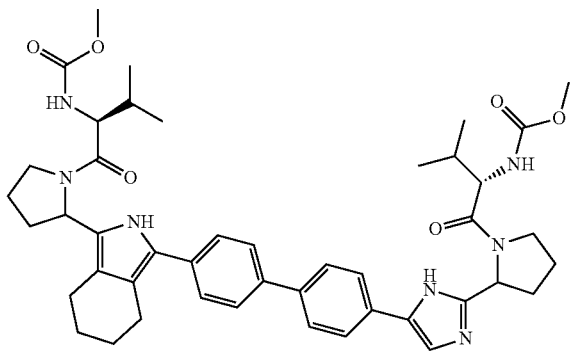

AG_014

Synthetic Route:

Step 1: Synthesis of Compound AG_014

Compound BB-54-10 (55 mg, 0.113 mmol) and compound BB-21 (47 mg, 0.113 mmol) were dissolved in THF/DMF/H$_2$O=1:1:1 (6 mL), Pd(dppf)Cl$_2$ (5 mg, 0.007 mmol) and Na$_2$CO$_3$ (36 mg, 0.338 mmol) were added sequentially. The reaction mixture was stirred at 100° C. for 4 h under nitrogen gas atmosphere, and then diluted with ethyl acetate (20 mL). H$_2$O (10 mL) was added and the organic phase obtained from extraction was dried over anhydrous sodium sulfate. After filtration, the solvent was removed under reduced pressure, the concentrated liquid was purified by preparative chromatography to deliver the target compound AG_014 (30 mg, 34%). $^1$H NMR (400 MHz, CDCl$_3$) δ: 7.88-7.63 (m, 7H), 7.63-7.53 (m, 1H), 7.49-7.38 (m, 1H), 5.25-5.23 (m, 1H), 4.52-4.42 (m, 2H), 4.22-4.12 (m, 1H), 3.67-3.63 (m, 2H), 3.63-3.61 (m, 7H), 3.50-3.45 (m, 1H), 2.80-2.60 (m, 2H), 2.57-2.52 (m, 4H), 2.45-2.25 (m, 4H), 2.24-2.01 (m, 6H), 0.99-0.88 (m, 12H). LCMS: m/z, 778.5 [M+H]$^+$ The compounds listed in the following table were synthesized according to the synthetic method and HPLC purification of step 1 in synthesizing AG_014:

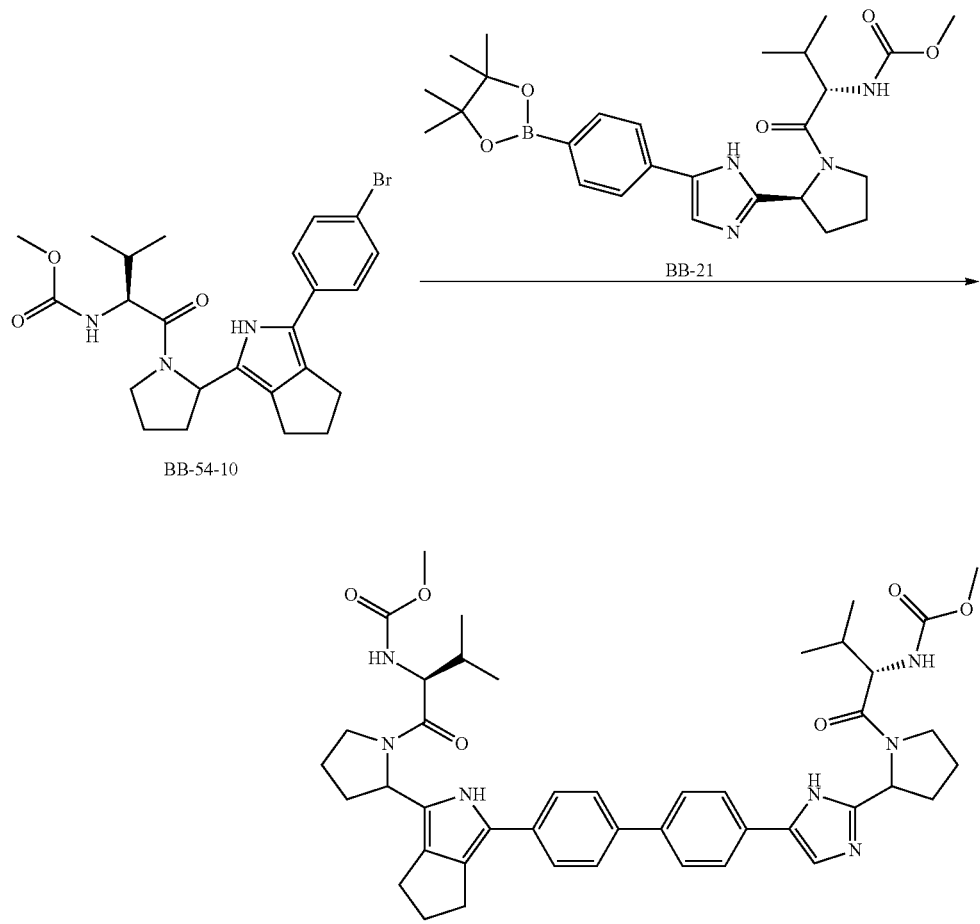

AG_014

| Embodiments | Structure | Fragment 1 | Fragment 2 | MS m/z |
|---|---|---|---|---|
| 12 | AG_025_A | BB-55 | BB-21 | 806.3 [M + H]+ |
| 13 | AG_025_B | BB-55 | BB-21 | 806.5 [M + H]+ |

| Embodiments | Structure | Fragment 1 | Fragment 2 | MS m/z |
|---|---|---|---|---|
| 14 | AG_025_C | BB-55 | BB-21 | 806.5 [M + H]+ |
| 15 | AG_014_A | BB-54-10 | BB-21 | 778.5 [M + H]+ |

| Embodiments | Structure | Fragment 1 | Fragment 2 | MS m/z |
|---|---|---|---|---|
| 16 | AG_026_A | BB-54-10 | BB-54 | 817.4 [M + H]+ |
| 17 | AG_048 | BB-54 | BB-73 | 828.3 [M + H]+ |

-continued

| Em-bodi-ments | Structure | Fragment 1 | Fragment 2 | MS m/z |
|---|---|---|---|---|
| 18 | AG_049 | BB-54-10 | BB-23 | 806.5 [M + H]⁺ |
| 19 | AG_050 | BB-54 | BB-38 | 834.4 [M + H]⁺ |

| Embodiments | Structure | Fragment 1 | Fragment 2 | MS m/z |
|---|---|---|---|---|
| 20 | AG_063 | BB-54 | BB-2 | 752.4 [M + H]+ |
| 21 | AG_066 | BB-54 | BB-25-4 | 794.4 [M + H]+ |

| Embodiments | Structure | Fragment 1 | Fragment 2 | MS m/z |
|---|---|---|---|---|
| 22 | AG_068_A | BB-67 | BB-25 | 810.3 [M + H]⁺ 405.7 [1/2 M + H]⁺ |
| 23 | AG_068_B | BB-68 | BB-25 | 810.4 [M + H]⁺ 405.7 [1/2 M + H]⁺ |

| Embodiments | Structure | Fragment 1 | Fragment 2 | MS m/z |
|---|---|---|---|---|
| 24 | AG_069 | BB-54 | BB-40 | 836.3 [M + H]+ 418.7 [1/2 M + H]+ |
| 25 | AG_089 | BB-67 | BB-41 | 868.4 [M + H]+ 434.7 [1/2 M + H]+ |

-continued

| Embodiments | Structure | Fragment 1 | Fragment 2 | MS m/z |
|---|---|---|---|---|
| 26 | AG_092 | BB-67 | BB-3 | 784.3 [M + H]⁺ 392.7 [1/2 M + H]⁺ |
| 27 | AG_093 | BB-54 | BB-42 | 792.3 [M + H]⁺ 398.7 [1/2 M + H]⁺ |

| Embodiments | Structure | Fragment 1 | Fragment 2 | MS m/z |
|---|---|---|---|---|
| 28 | AG_084_A | BB-56 | BB-21 | 734.3 [M + H]+ |
| 29 | AG_091 | BB-54 | BB-37 | 780.3 [M + H]+ |

| Embodiments | Structure | Fragment 1 | Fragment 2 | MS m/z |
|---|---|---|---|---|
| 30 | AG_090 | BB-54-10 | BB-34 | 780.4 [M + H]+ |
| 31 | AG_086 | BB-54 | BB-36 | 776 [M + H]+ |

| Embodiments | Structure | Fragment 1 | Fragment 2 | MS m/z |
|---|---|---|---|---|
| 32 | AG_036 | BB-57 | BB-21 | 820 [M + H]+ |
| 33 | AG_042 | BB-57 | BB-24 | 862 [M + H]+ |

| Embodiments | Structure | Fragment 1 | Fragment 2 | MS m/z |
|---|---|---|---|---|
| 34 | AG_035 | BB-54 | BB-24-2 | 719.4 [M + H]+ |
| 35 | AG_051 | BB-54 | BB-47 | 870.4 [M + H]+ |

| Embodiments | Structure | Fragment 1 | Fragment 2 | MS m/z |
|---|---|---|---|---|
| 36 | AG_076 | BB-59-A | BB-42 | 838.4 [M + H]+ 419.7 [1/2 M + H]+ |
| 37 | AG_106 | BB-60 | BB-46-5 | 756.3 [M + H]+ 378.8 [1/2 M + H]+ |

| Embodiments | Structure | Fragment 1 | Fragment 2 | MS m/z |
|---|---|---|---|---|
| 38 | AG_115 | BB-60 | BB-45 | 796.3 [M + H]+ |
| 39 | AG_110 | BB-60 | BB-44-11 | 824.4 [M + H]+ |

| Embodiments | Structure | Fragment 1 | Fragment 2 | MS m/z |
|---|---|---|---|---|
| 40 | AG_101 | BB-59-A | BB-69 | 778.3 [M + H]+ |
| 41 | AG_107 | BB-59-A | BB-39 | 752.4 [M + H]+ |

| Embodiments | Structure | Fragment 1 | Fragment 2 | MS m/z |
|---|---|---|---|---|
| 42 | AG_100 | BB-59-A | BB-37 | 740.2 [M + H]+ |
| 43 | AG_099 | BB-59-A | BB-34-3 | 740.3 [M + H]+ |

-continued

| Em-bodi-ments | Structure | Fragment 1 | Fragment 2 | MS m/z |
|---|---|---|---|---|
| 44 | AG_098 | BB-59-A | BB-35 | 782.2 [M + H]+ |
| 45 | AG_061_A | BB-59-A | BB-25-4 | 754.2 [M + H]+ |

| Embodiments | Structure | Fragment 1 | Fragment 2 | MS m/z |
|---|---|---|---|---|
| 46 | AG_102 | BB-59-A | BB-1-7 | 756 [M + H]⁺ |
| 47 | AG_072_A | BB-60 | BB-25-4 | 770 [M + H]⁺ |

| Embodiments | Structure | Fragment 1 | Fragment 2 | MS m/z |
|---|---|---|---|---|
| 48 | AG_120 | BB-60 | BB-6-5 | 784 [M + H]+ |
| 49 | AG_054 | BB-59-4 | BB-23 | 766 [M + H]+ |

| Embodiments | Structure | Fragment 1 | Fragment 2 | MS m/z |
|---|---|---|---|---|
| 50 | AG_001 | BB-59-4 | BB-21 | 738 [M + H]+ |
| 51 | AG_011 | BB-59-4 | BB-59 | 737 [M + H]+ |

| Embodiments | Structure | Fragment 1 | Fragment 2 | MS m/z |
|---|---|---|---|---|
| 52 | AG_022 | BB-59-4 | BB-27 | 768 [M + H]+ |
| 53 | AG_052 | BB-59 | BB-70 | 772 [M + H]+ |

| Embodiments | Structure | Fragment 1 | Fragment 2 | MS m/z |
|---|---|---|---|---|
| 54 | AG_053 | BB-59 | BB-38 | 794 [M + H]+ |
| 55 | AG_037 | BB-61 | BB-21-1 | 780 [M + H]+ |

| Embodiments | Structure | Fragment 1 | Fragment 2 | MS m/z |
|---|---|---|---|---|
| 56 | AG_112 | BB-60 | BB-5-5 | 744 [M + H]+ |
| 57 | AG_061_B | BB-59-B | BB-25-4 | 754 [M + H]+ |

| Embodiments | Structure | Fragment 1 | Fragment 2 | MS m/z |
|---|---|---|---|---|
| 58 | AG_119 | BB-60 | BB-71 | 742 [M + H]+ |
| 59 | AG_109 | BB-62 | BB-37 | 742 [M + H]+ |

| Embodiments | Structure | Fragment 1 | Fragment 2 | MS m/z |
|---|---|---|---|---|
| 60 | AG_108 | BB-62 | BB-34-3 | 742 [M + H]+ |
| 61 | AG_072_B | BB-60 | BB-25-4 | 770 [M + H]+ |

-continued

| Em-bodi-ments | Structure | Fragment 1 | Fragment 2 | MS m/z |
|---|---|---|---|---|
| 62 | AG_038 | BB-61 | BB-54-10 | 819 [M + H]+ |
| 63 | AG_097 | BB-59-A | BB-72 | 722 [M + H]+ |

-continued

| Embodiments | Structure | Fragment 1 | Fragment 2 | MS m/z |
|---|---|---|---|---|
| 64 | AG_062 | BB-59 | BB-33 | 770.2 [M + H]⁺ |

Embodiment 65: AG_060

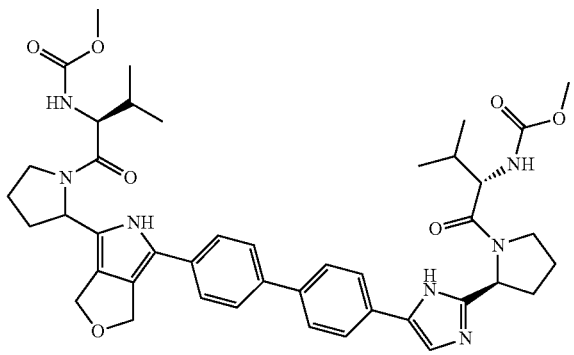

AG_060

Synthetic Route:

Step 1: Synthesis of Compound AG_060

Compound BB-63 (mixture of BB-63-A and BB-63-B, 30 mg, 61.2 mmol) and compound BB-21 (37 mg, 73.4 mmol) were dissolved in THF/DMF/H$_2$O=1:1:1 (6 mL), Pd(dppf)Cl$_2$ (5 mg, 6.12 mmol) and Na$_2$CO$_3$ (20 mg, 183.5 mmol) were added sequentially. The reaction mixture was stirred at 100° C. for 4 h under nitrogen gas atmosphere, and then diluted with ethyl acetate (20 mL). H$_2$O (10 mL) was added and the organic phase obtained from extraction was dried over anhydrous sodium sulfate. The solvent was removed under reduced pressure, the residue was purified by preparative chromatography to deliver the target compound AG_060 (white powder, 20 mg, yield: 42%). $^1$H NMR (400 MHz, CDCl$_3$) δ: 10.81 (br, 1H), 10.42 (br, 1H), 10.02 (br, 1H), 7.78-7.71 (m, 1H), 7.58-7.43 (m, 5H), 7.25-7.21 (m, 3H), 5.63-5.59 (m, 2H), 5.46-5.41 (m, 2H), 5.03 (s, 2H), 4.93-4.87 (m, 2H), 4.49-4.41 (m, 2H), 3.9 6-3.49 (m, 8H), 3.11-3.09 (m, 1H), 2.53-2.34 (m, 1H), 2.26-1.90 (m, 8H), 1.11-0.87 (m, 12H). LCMS m/z: 780.5 [M+H]$^+$

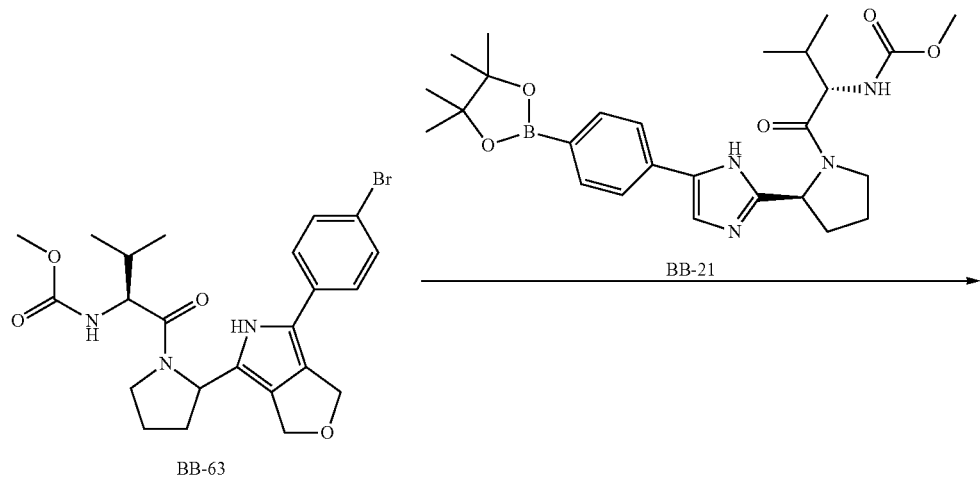

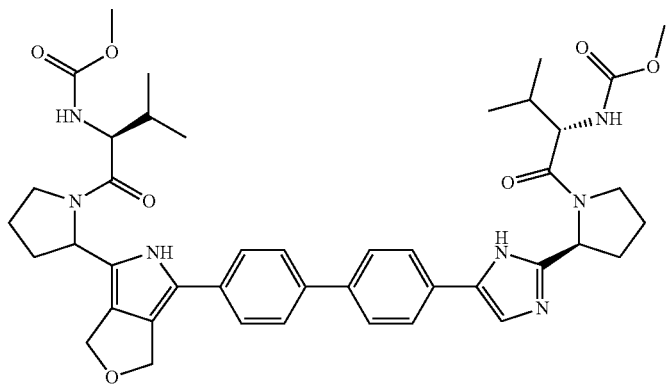

AG_060

Embodiment 66: AG_060_B

Synthetic Route:

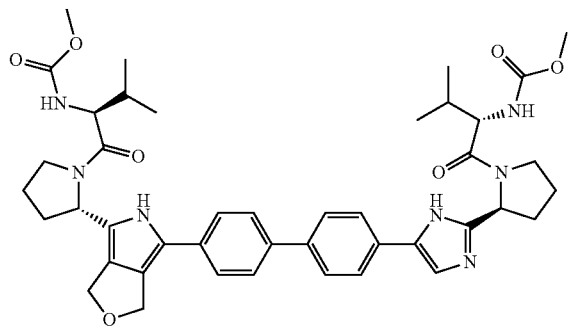

AG_060_B

Step 1: Synthesis of Compound AG_060_B

Compound BB-63-A (30 mg, 61.2 mmol) and compound BB-21 (36 mg, 73.4 mmol) were dissolved in THF/DMF/$H_2O$=1:1:1 (6 mL), Pd(dppf)$Cl_2$ (5 mg, 6.1 mmol) and $Na_2CO_3$ (19 mg, 183.5 mmol) were added sequentially. The reaction mixture was stirred at 100° C. for 4 h under nitrogen gas atmosphere, and then diluted with ethyl acetate (20 mL). $H_2O$ (10 mL) was added and the organic phase obtained from extraction was dried over anhydrous sodium sulfate. The solvent was removed under reduced pressure, the residue was purified by preparative chromatography to deliver the target compound AG_060_B (white powder, 10 mg, yield: 19%). $^1$H NMR (400 MHz, CDCl$_3$) δ: 10.79 (br, 1H), 10.41 (br, 1H), 10.01 (br, 1H), 7.78-7.72 (m, 1H), 7.57-7.44 (m, 5H), 7.24-7.20 (m, 3H), 5.64-5.59 (m, 2H), 5.46-5.39 (m, 2H), 5.01 (s, 2H), 4.93-4.86 (m, 2H), 4.47-4.41 (m, 2H), 3.9 4-3.49 (m, 8H), 3.11-3.08 (m, 1H), 2.51-2.34 (m, 1H), 2.27-1.90 (m, 8H), 1.12-0.86 (m, 12H). LCMS m/z: 780.3 [M+H]$^+$ The compounds listed in the following table were synthesized according to the synthetic method and HPLC purification of step 1 in synthesizing AG_060_B:

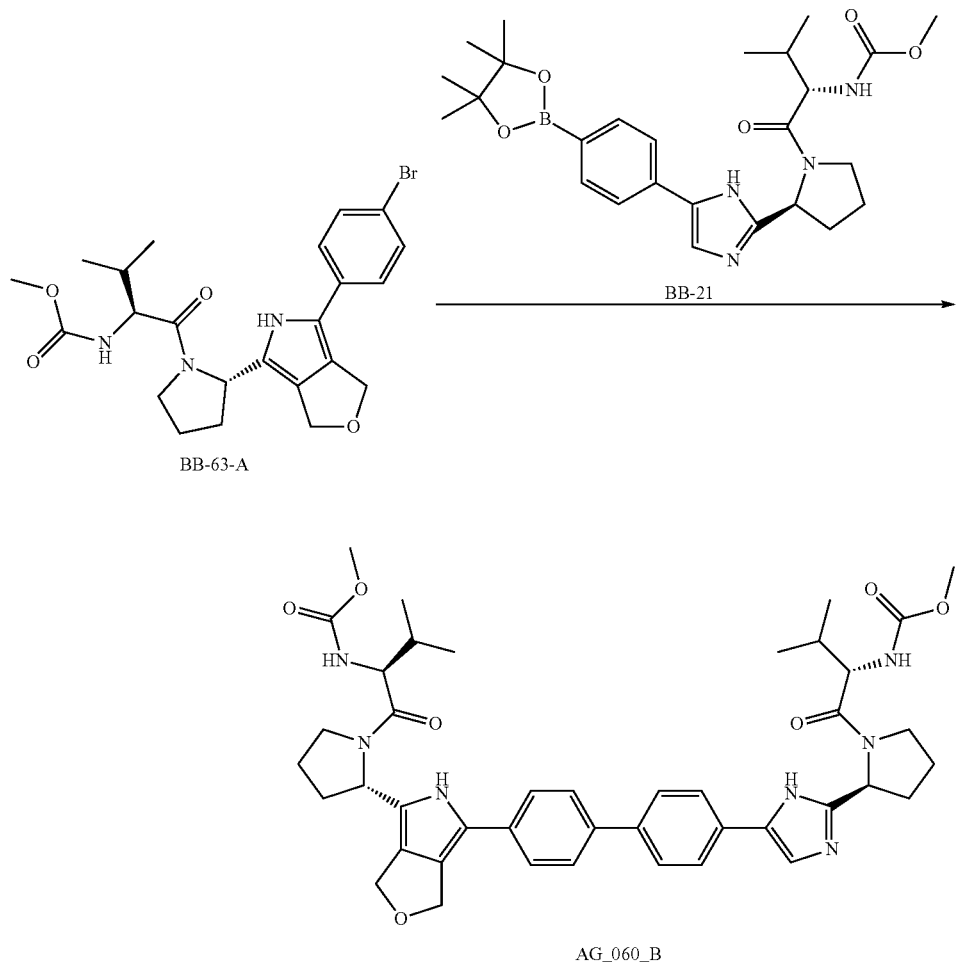

AG_060_B

| Em-bodi-ments | Structure | Fragment 1 | Fragment 2 | MS m/z |
|---|---|---|---|---|
| 67 | AG_077 | BB-63-A | BB-25 | 796.2 [M + H]+ |
| 68 | AG_104 | BB-63-A | BB-34 | 782.3 [M + H]+ |

| Embodiments | Structure | | | |
|---|---|---|---|---|
| | | Fragment 1 | Fragment 2 | MS m/z |
| 69 | AG_079_A | BB-64-A | BB-21 | 796.2 [M + H]+ |
| 70 | AG_079_B | BB-64-B | BB-21 | 796.2 [M + H]+ |

| Em-bodi-ments | Structure | Fragment 1 | Fragment 2 | MS m/z |
|---|---|---|---|---|
| 71 | AG_123 | BB-64-A | BB-7 | 405.63 [M/2 + H]+ |
| 72 | AG_124 | BB-64-A | BB-6 | 825.9 [M + H]+ |

| Embodiments | Structure | Fragment 1 | Fragment 2 | MS m/z |
|---|---|---|---|---|
| 73 | AG_113 | BB-64-A | BB-37 | 798.2 [M + H]+ |
| 74 | AG_080_A | BB-64-A | BB-25 | 812.3 [M + H]+ |

| Embodiments | Structure | Fragment 1 | Fragment 2 | MS m/z |
|---|---|---|---|---|
| 75 | 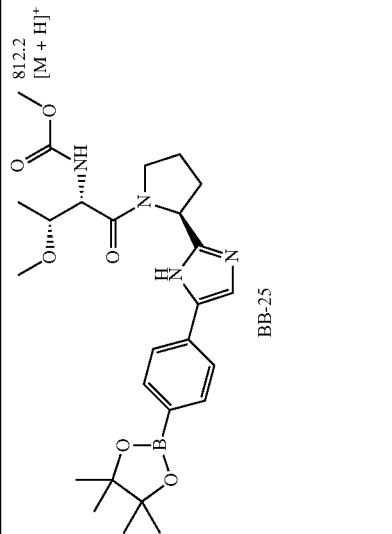 AG_080_B | 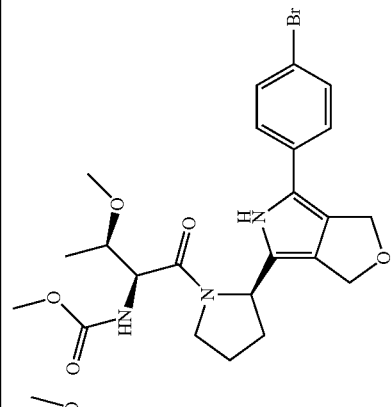 BB-64-B | 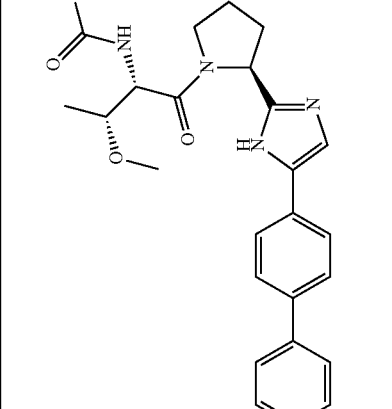 BB-25 | 812.2 [M + H]+ |
| 76 | 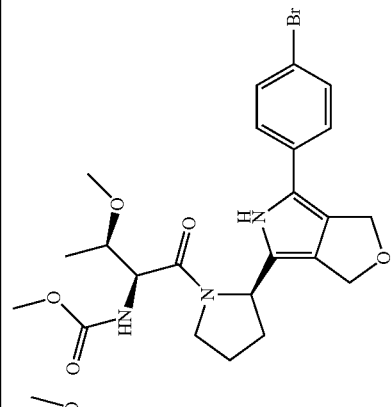 AG_088_A | 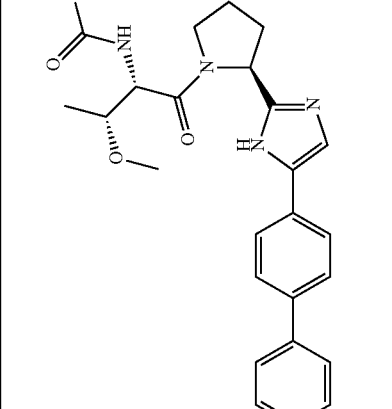 BB-64-A | 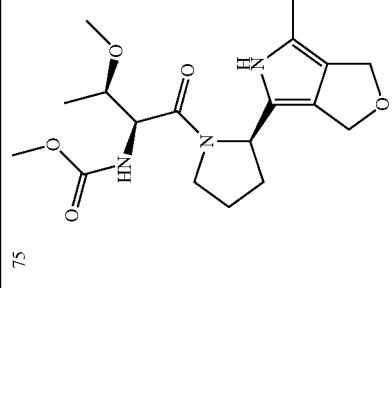 BB-64-A | 853.6 [M + H]+ |

| Embodiments | Structure | Fragment 1 | Fragment 2 | MS m/z |
|---|---|---|---|---|
| 77 | AG_105 | BB-64-A | BB-34 | 782.3 [M + H]+ |
| 78 | AG_116 | BB-64-A | BB-43 | 838.3 [M + H]+ |

| Embodiments | Structure | Fragment 1 | Fragment 2 | MS m/z |
|---|---|---|---|---|
| 79 | AG_117 | BB-64-A | BB-45 | 822.4 [M + H]+ |
| 80 | AG_111 | BB-64-A | BB-44 | 433.7 [1/2M + H]+ |

Embodiment 81: AG_122_A

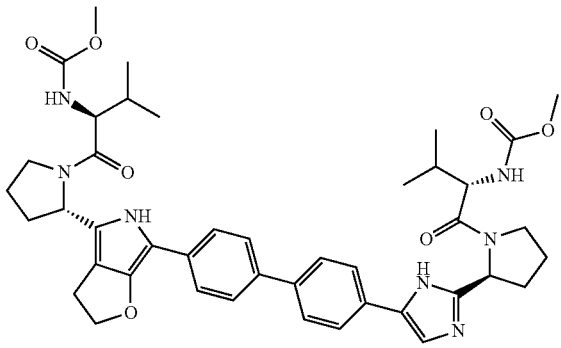

AG_122_A

Synthetic Route:

Step 1: Synthesis of Compound AG_122_A

Compound BB-65-A (30 mg, 0.061 mmol) and compound BB-21 (36 mg, 0.073 mmol) were dissolved in THF/DMF/H$_2$O=1:1:1 (6 mL), Pd(dppf)Cl$_2$ (5 mg, 0.007 mmol) and Na$_2$CO$_3$ (19 mg, 0.184 mmol) were added sequentially. The reaction mixture was stirred at 100° C. for 4 h under nitrogen gas atmosphere, and then diluted with ethyl acetate (20 mL). H$_2$O (10 mL) was added and the organic phase obtained from the extraction was dried over anhydrous sodium sulfate. After filtration, the solvent was removed under reduced pressure, the concentrated liquid was purified by preparative chromatography to deliver the target compound AG_122_A (10 mg, yield: 21%). $^1$H NMR (400 MHz, CDCl$_3$) δ: 9.14-9.12 (br, 1H), 7.82-7.80 (br, 1H), 7.57-7.51 (m, 5H), 7.40-7.33 (m, 2H), 7.21-7.18 (m, 2H), 5.49-5.40 (m, 2H), 5.32-5.25 (m, 2H), 4.93-4.89 (m, 2H), 4.33-4.31 (m, 2H), 3.82-3.62 (m, 8H), 3.50-3.45 (m, 1H), 3.05-2.98 (m, 3H), 2.38-2.22 (m, 2H), 2.18-2.05 (m, 4H), 2.02-1.88 (m, 2H), 1.08-0.98 (m, 1H), 0.92-0.86 (m, 11H).

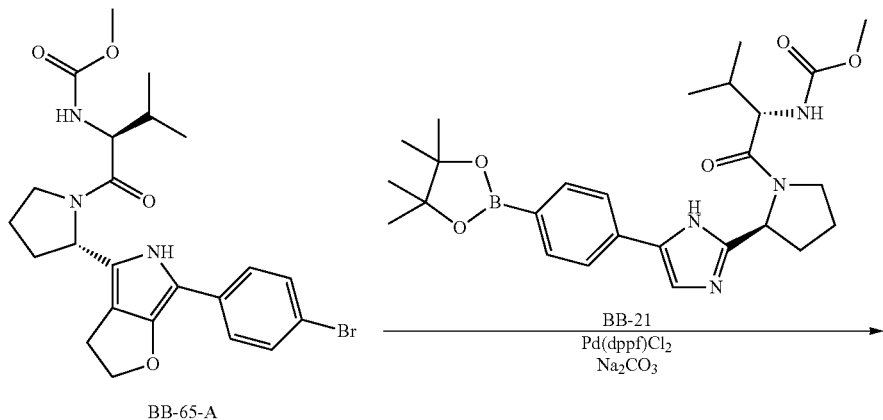

BB-65-A → BB-21, Pd(dppf)Cl$_2$, Na$_2$CO$_3$

AG_122_A

Embodiment 82: AG_122_B

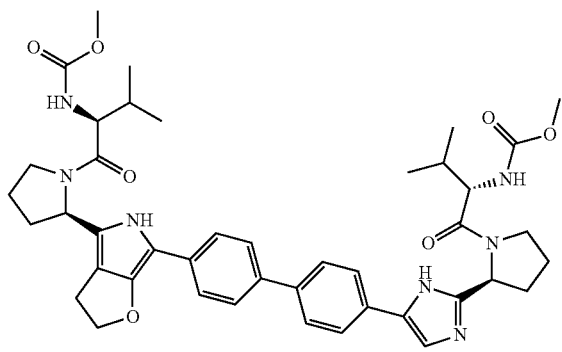

AG_122_B

Synthetic Route:

Step 1: Synthesis of Compound AG_122_B

Compound BB-65-B (30 mg, 0.061 mmol) and compound BB-21 (36 mg, 0.073 mmol) were dissolved in THF/DMF/H$_2$O=1:1:1 (6 mL), Pd(dppf)Cl$_2$ (5 mg, 0.007 mmol) and Na$_2$CO$_3$ (19 mg, 0.184 mmol) were added sequentially. The reaction mixture was stirred at 100° C. for 4 h under nitrogen gas atmosphere, and then diluted with ethyl acetate (20 mL). H$_2$O (10 mL) was added and the organic phase obtained from extraction was dried over anhydrous sodium sulfate. After filtration, the solvent was removed under reduced pressure, the concentrated liquid was purified by preparative chromatography to deliver the target compound AG_122_B (10 mg, 21%). $^1$H NMR (400 MHz, CDCl$_3$) δ: 10.80-10.70 (br, 1H), 10.40-10.30 (br, 1H), 9.14-9.12 (br, 1H), 7.78-7.68 (m, 1H), 7.58-7.49 (m, 7H), 7.21-7.19 (m, 2H), 5.41-5.38 (m, 2H), 5.28-5.26 (m, 2H), 4.92-4.89 (m, 2H), 4.32-4.25 (m, 2H), 3.92-3.82 (m, 2H), 3.72-3.68 (m, 3H), 3.59-3.55 (m, 4H), 3.04-2.98 (m, 3H), 2.41-2.28 (m, 2H), 2.12-1.95 (m, 6H), 1.04-0.84 (m, 12H).

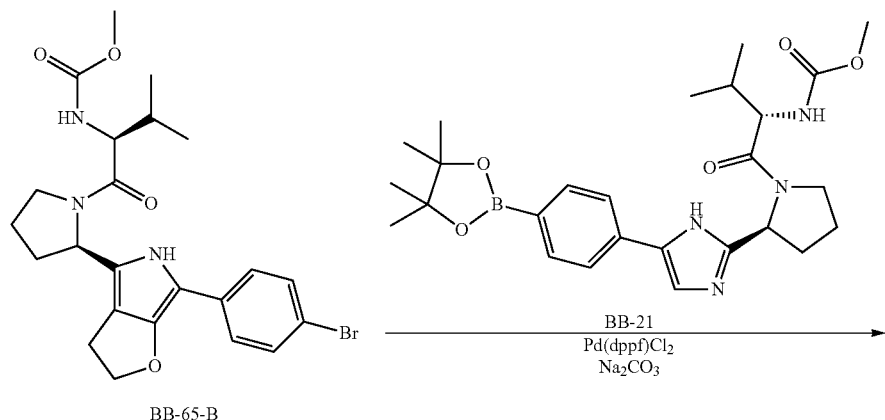

BB-65-B → BB-21, Pd(dppf)Cl$_2$, Na$_2$CO$_3$

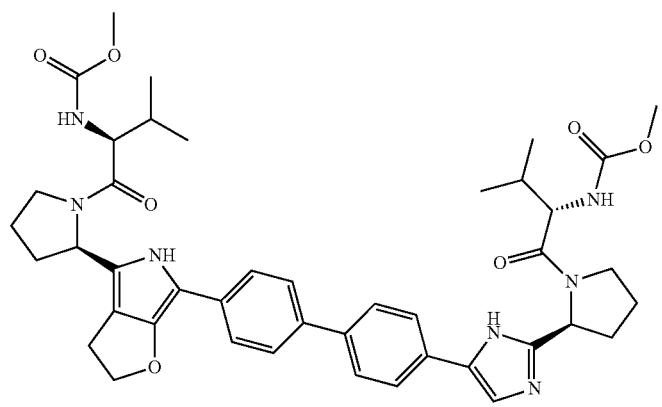

AG_122_B

Embodiment 83: AG_114_A

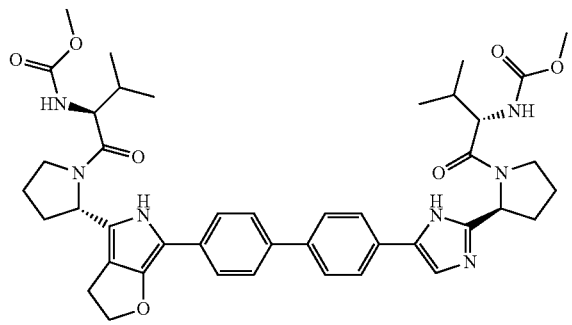

AG_114_A

Synthetic Route:

Step 1: Synthesis of Compound AG_114_A

Compound BB-66-A (15.0 mg, 0.03 mmol), compound BB-21 (14.7 mg, 0.03 mmol), Pd(dppf)Cl$_2$ (0.7 mg, 0.001 mmol) and Na$_2$CO$_3$ (9.5 mg, 0.09 mmol) were placed in a 50 mL round-bottom flask under nitrogen gas atmosphere. THF (1 mL), DMF (1 mL), H$_2$O (1 mL) were injected, and the reaction system was heated to 90° C. and stirred for 2 h. Stop heating and cool naturally. H$_2$O (5 mL) was added into the reaction solution and extracted with ethyl acetate (20 mL×3). The organic phases were combined and washed with saturated brines, dried over anhydrous sodium sulfate, the solvent was removed under reduced pressure and the residue was purified by preparative liquid chromatography to deliver the target compound AG_114_A (white solid, 0.9 mg, yield: 3.8%). $^1$H NMR (400 MHz, CDCl$_3$): δ: 7.81-7.48 (m, 8H), 7.21 (s, 1H), 5.39-5.14 (m, 4H), 4.35-4.07 (m, 5H), 3.61-3.55 (m, 8H), 2.72-2.54 (m, 3H), 2.23-1.96 (m, 9H). LCMS m/z: 794.3 [M+H]$^+$

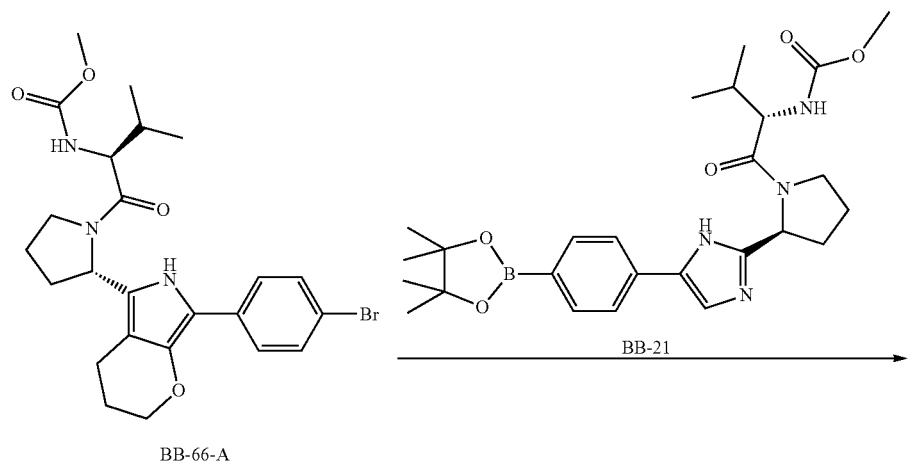

BB-66-A       BB-21

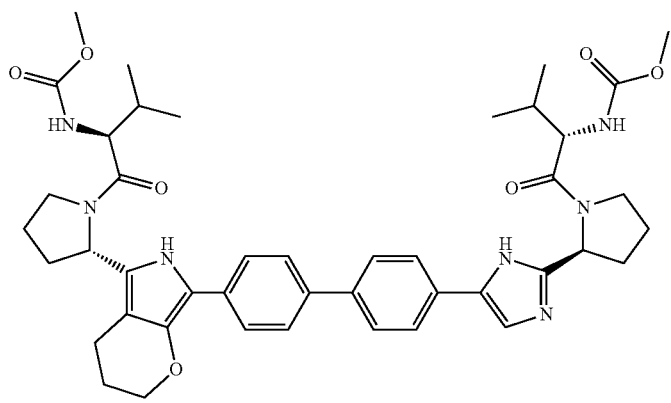

AG_114_A

Embodiment 84: AG_114_B

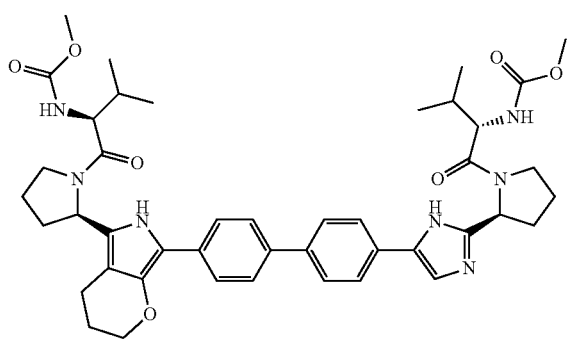

AG_114_B

Synthetic Route:

Step 1: Synthesis of Compound AG_114_B

Compound BB-66-B (15.0 mg, 0.03 mmol), compound BB-21 (14.7 mg, 0.03 mmol), Pd(dppf)Cl$_2$ (0.7 mg, 0.001 mmol) and Na$_2$CO$_3$ (9.5 mg, 0.09 mmol) were placed in a 50 mL round-bottom flask under nitrogen gas atmosphere. THF (1 mL), DMF (1 mL), H$_2$O (1 mL) were injected, the reaction system was heated to 90° C. and stirred for 2 h. Stop heating and cool naturally. H$_2$O (5 mL) was added into the reaction mixture and extracted with ethyl acetate (20 mL×3). The organic phases were combined and washed with saturated brines, dried over anhydrous sodium sulfate, the solvent was removed under reduced pressure and the residue was purified by preparative liquid chromatography to deliver the target compound AG_114_B (white solid, 1.2 mg, yield: 5.1%). $^1$H NMR (400 MHz, CDCl$_3$): δ: 7.68-7.52 (m, 8H), 7.21 (s, 1H), 5.39-5.14 (m, 4H), 4.35-4.07 (m, 5H), 3.61-3.55 (m, 8H), 2.44-1.96 (m, 12H), 0.95-0.871 (m, 12H). LCMS m/z: 794.3 [M+H]$^+$ The compound listed in the following table was synthesized according to the synthetic method and HPLC purification of step 1 in synthesizing AG_114_A:

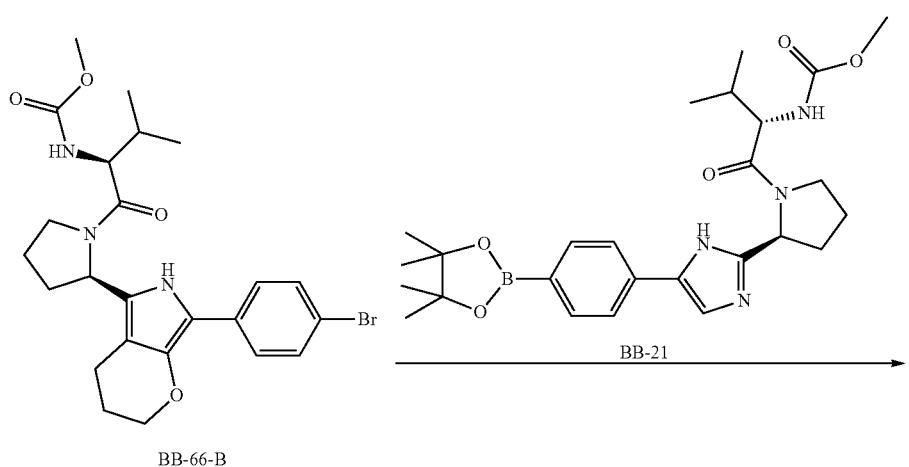

BB-66-B     BB-21

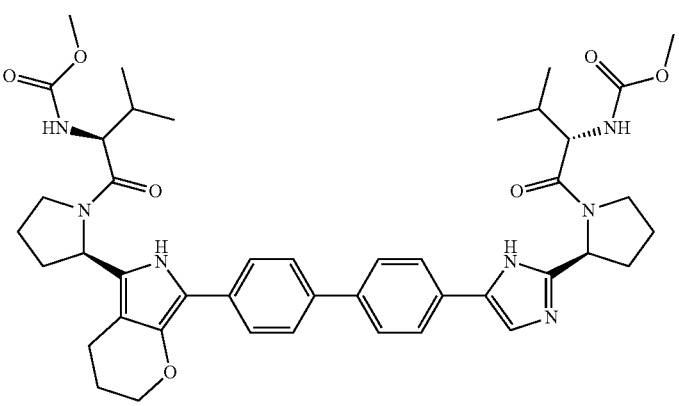

AG_114_B

| Embodiments | Structure |
|---|---|
| 85 | 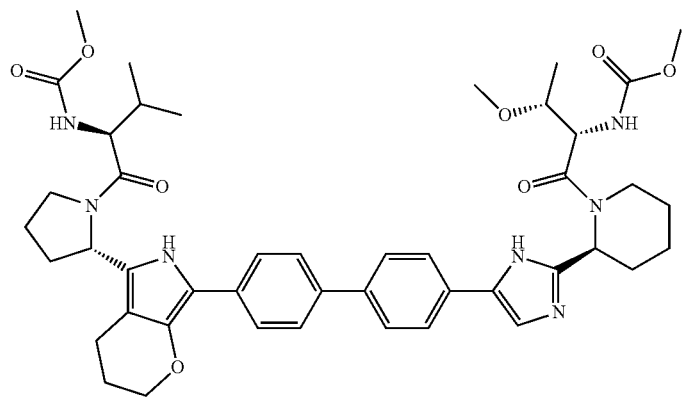<br>AG_121 |
| Embodiments | Fragment 1 | Fragment 2 | MS m/z |
|---|---|---|---|
| 85 | 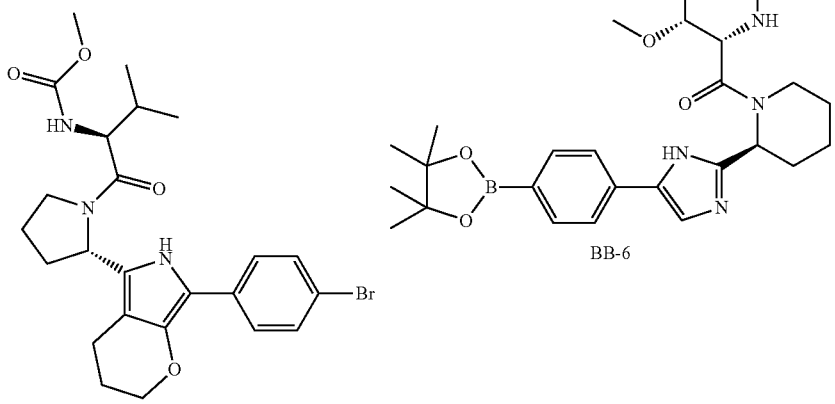<br>BB-66-A | BB-6 | 824.3 [M + H]+ |
Embodiment 86: AG_095
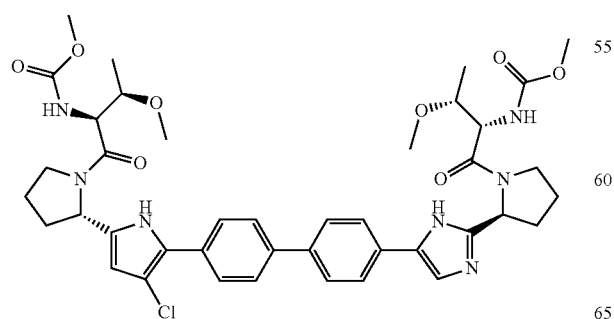
AG_095

Synthetic Route:

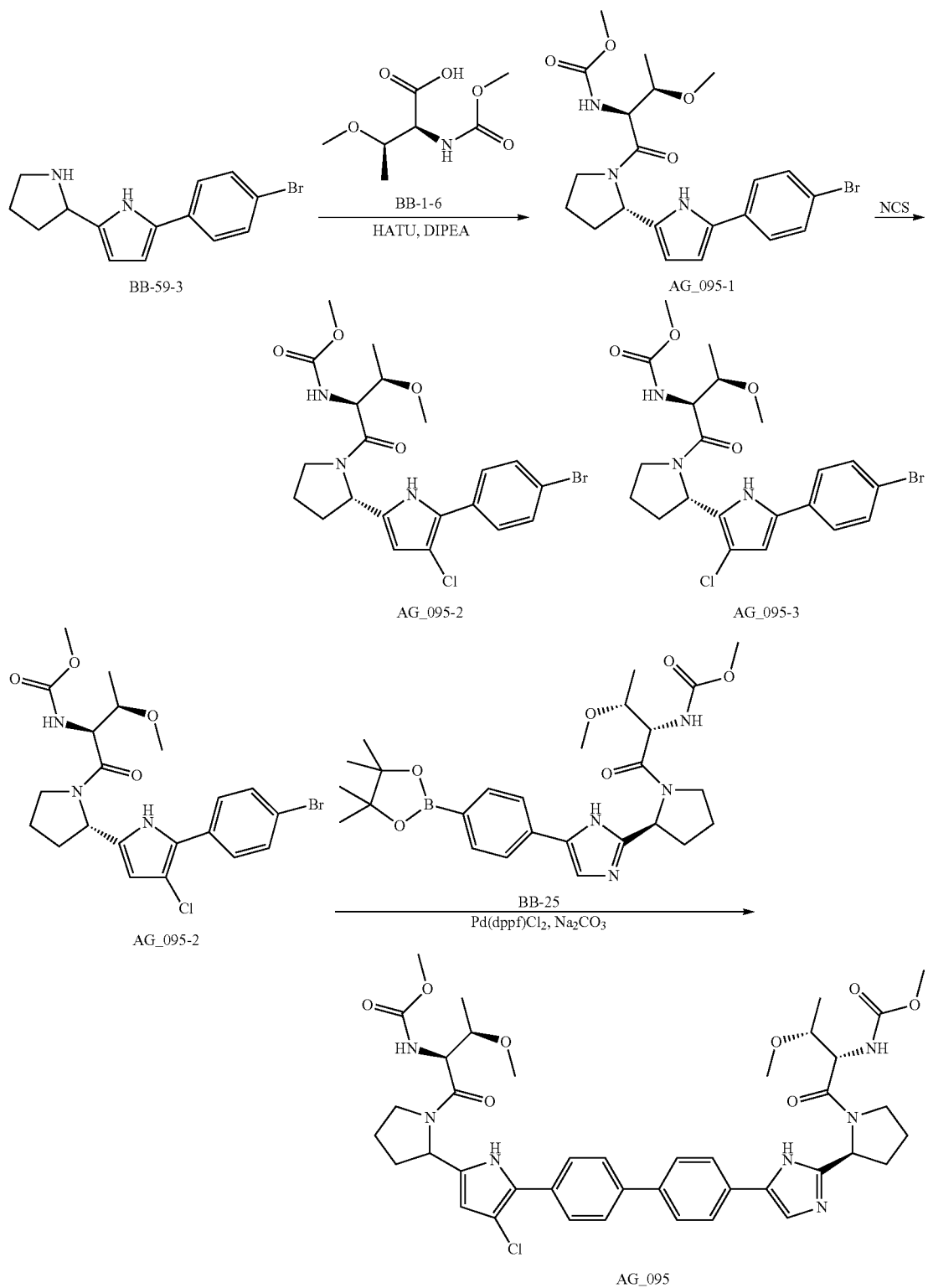

Step 1: Synthesis of Compound AG_095-1

Compound BB-59-3 (1.00 g, 3.43 mmol) and compound BB-1-6 (788 mg, 4.12 mmol) and HATU (3.02 g, 4.12 mmol) were dissolved in dichloromethane (30 mL), DIPEA (885 mg, 6.88 mmol) was added slowly under an ice bath, and the reaction mixture was stirred at room temperature overnight under nitrogen gas atmosphere. The reaction was quenched with saturated sodium bicarbonate solution and extracted with dichloromethane (30 mL×3). The organic phases were combined and dried over anhydrous sodium sulfate. After filtration, the filtrate was concentrated under reduced pressure. The resulting crude product was purified by silica gel column chromatography (eluting reagent: PE:EA=1:1) to deliver the target compound AG_095-1 (light purple solid, 220 mg, yield: 14%). LCMS m/z: 464 [M+H]+

Step 2: Synthesis of Compound AG_095-2 and AG_09-3

Compound AG_095-1 (200 mg, 0.43 mmol) was dissolved in DMF (5 mL), NCS (63 mg, 0.47 mmol) was added slowly, and the reaction mixture was stirred at room temperature overnight. The reaction was quenched with H₂O and extracted with dichloromethane (20 mL×3). The organic phases were combined and dried over anhydrous sodium sulfate. After filtration, the filtrate was concentrated under reduced pressure to deliver the crude product which was purified by preparative HPLC to deliver the target compound AG_095-2 (white solid, 20 mg, yield 9%) and AG_095-3 (white solid, 37 mg, yield 17%). AG_095-2: ¹H-NMR (400 MHz, CDCl3): & 9.75 (s, 1H), 7.48 (s, 4H), 6.00 (d, J=2.4 Hz, 1H), 5.66 (d, J=8.0 Hz, 1H), 5.32-5.29 (m, 1H), 4.52 (t, J=3.8 Hz, 1H), 3.79-3.52 (m, 6H), 3.16 (s, 3H), 2.24-2.06 (m, 4H), 1.09 (d, J=6.4 Hz, 3H). AG_095-3: ¹H-NMR (400 MHz, CDCl₃): δ: 9.24 (s, 1H), 7.41 (d, J=8.4 Hz, 2H), 7.21 (d, J=8.4 Hz, 2H), 6.32 (d, J=3.2 Hz, 1H), 5.63 (d, J=7.6 Hz, 1H), 5.40-5.37 (m, 1H), 4.79-4.76 (m, 1H), 3.91-3.88 (m, 1H), 3.82-3.79 (m, 1H), 3.70-3.67 (m, 4H), 3.41 (s, 3H), 2.39-2.00 (m, 4H), 1.14 (d, J=6.4 Hz, 3H).

Step 3: Synthesis of Compound AG_095

Compound AG_095_2 (37 mg, 0.074 mmol), BB-25 (38 mg, 0.074 mmol) were dissolved in a mixed solvent of DMF/THF/H₂O (2 mL/2 mL/2 mL), Pd(dppf)Cl₂ (5 mg, 0.007 mmol) and Na₂CO₃ (24 mg, 0.22 mmol) were added. The atmosphere was replaced by nitrogen gas for 3 times and the reaction mixture was heated to 90° C. and stirred for 2 h under nitrogen gas atmosphere. Stop heating and cool naturally. H₂O (10 mL) was added and the reaction mixture was extracted with ethyl acetate (10 mL×3). The ethyl acetate phases were combined and washed with saturated brines, dried over anhydrous sodium sulfate. The solvent was evaporated and the crude product was purified by preparative HPLC to deliver the target compound AG_095 (white solid, 16 mg, yield 27%). ¹H-NMR (400 MHz, CDCl₃): δ: 8.83 (s, 1H), 7.87-7.46 (m, 8H), 7.15 (s, 1H), 6.03 (s, 1H), 5.71-5.66 (m, 2H), 5.35 (s, 2H), 4.55 (s, 1H), 3.92-3.56 (m, 11H), 3.36-3.19 (m, 5H), 2.77 (s, 1H), 2.31-2.94 (m, 8H), 1.24-1.13 (m, 6H). LCMS m/z: 804 [M+H]+

Embodiment 87: AG_094

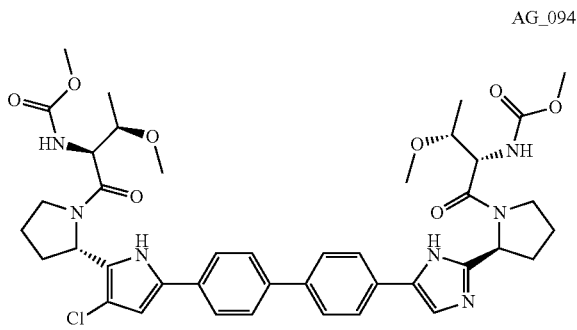

AG_094

Synthetic Route:

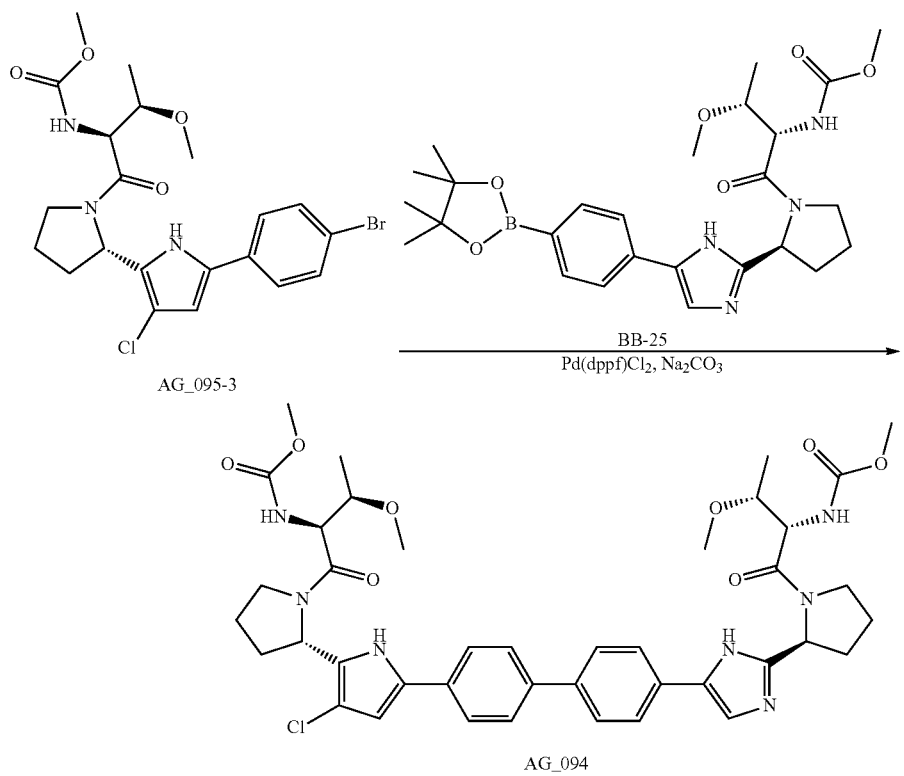

Step 1: Synthesis of Compound AG_094

Compound AG_095-3 (20 mg, 0.040 mmol), BB-25 (21 mg, 0.040 mmol) were dissolved in a mixed solvent of DMF/THF/H₂O (2 mL/2 mL/2 mL), Pd(dppf)Cl₂ (3 mg, 0.004 mmol) and Na₂CO₃ (14 mg, 0.12 mmol) were added. The atmosphere was replaced by nitrogen gas for 3 times and the reaction mixture was heated to 90° C. and stirred for 2 h under nitrogen gas atmosphere. Stop heating and cool naturally. H₂O (10 mL) was added and the reaction mixture was extracted with ethyl acetate (10 mL×3). The ethyl acetate phases were combined and washed with saturated brines, dried over anhydrous sodium sulfate. The solvent was evaporated and the crude product was purified by preparative HPLC to deliver the target compound AG_094 (white solid, 14 mg, yield 44%). ¹H-NMR (400 MHz, CDCl₃): δ: 9.74 (br, 1H), 7.54-7.40 (m, 8H), 6.98 (s, 1H), 6.38 (d, J=2.4 Hz, 1H), 5.69-5.66 (m, 1H), 5.33-5.29 (m, 2H), 4.71-4.69 (m, 1H), 4.53-4.50 (m, 1H), 3.92-3.67 (m, 10), 3.45-3.31 (m, 5H), 2.71-2.69 (m, 1H), 2.31-2.94 (m, 8H), 1.24-1.19 (m, 6H); LCMS m/z: 804 [M+H]⁺

Embodiment 88: AG_087

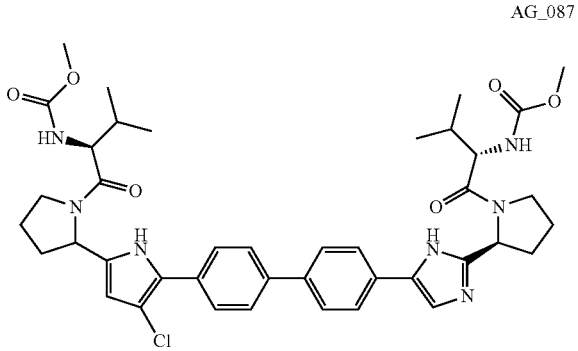

Synthetic Route:

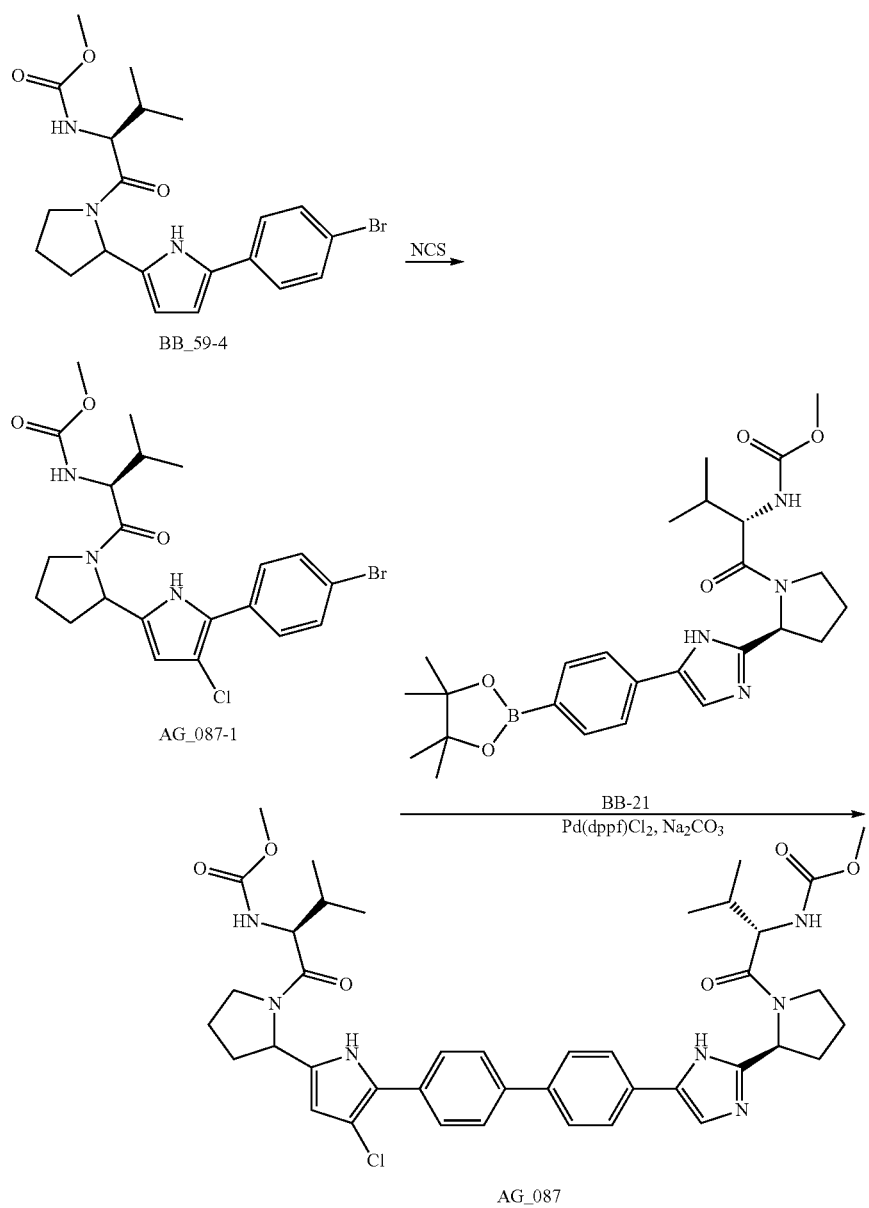

Step 1: Synthesis of Compound AG_087-1

Compound BB-59-4 (100 mg, 0.24 mmol) was dissolved in DMF (5 mL), NCS (33 mg, 0.24 mmol) was added slowly, and the reaction mixture was stirred at room temperature overnight. The reaction was quenched with $H_2O$ and extracted with dichloromethane (20 mL×3). The organic phases were combined and dried over anhydrous sodium sulfate. After filtration, the filtrate was concentrated under reduced pressure to deliver the crude product which was purified by preparative chromatography to deliver the target compound AG_087-1 (gray white solid, 26 mg, yield 24%) $^1$H-NMR (400 MHz, CDCl3): δ: 9.91 (br, 1H), 7.74-7.38 (m, 4H), 5.94 (d, J=2.4 Hz, 1H), 5.23-5.17 (m, 2H), 4.23-4.18 (m, 1H), 3.61-3.59 (m, 1H), 3.53-3.51 (m, 2H), 2.15-1.88 (m, 6H), 0.95-0.80 (m, 6H).

Step 2: Synthesis of Compound AG_087

Compound AG-087-1 (26 mg, 0.054 mmol), BB-21 (27 mg, 0.054 mmol) were dissolved in a mixed solvent of DMF/THF/$H_2O$ (2 mL/2 mL/2 mL), Pd(dppf)Cl$_2$ (4 mg, 0.0054 mmol) and Na$_2$CO$_3$ (17 mg, 0.16 mmol) were added. The atmosphere was replaced by nitrogen gas for 3 times and the reaction mixture was heated to 90° C. and stirred for 2 h under nitrogen gas atmosphere. Stop heating and cool naturally. $H_2O$ (10 mL) was added and the reaction mixture was extracted with ethyl acetate (10 mL×3). The ethyl acetate phases were combined and washed with saturated brines, dried over anhydrous sodium sulfate. The solvent was evaporated and the crude product was purified by preparative HPLC to deliver the target compound AG_087 (white solid, 3 mg, yield 7%). $^1$H-NMR (400 MHz, CDCl3): δ:10.68 (br, 0.4H), 10.27 (br, 1H), 9.92 (br, 1H), 7.74-7.40 (m, 8H), 7.16 (s, 1H), 5.98 (s, 1H), 5.35-5.20 (m, 4H), 4.25-4.23 (m, 2H), 3.77-3.51 (m, 9H), 3.08-2.93 (m, 1H), 2.27-1.90 (m, 8H), 0.95-0.80 (m, 12H); LCMS m/z: 772 [M+H]$^+$ Embodiment 89: AG_118_B

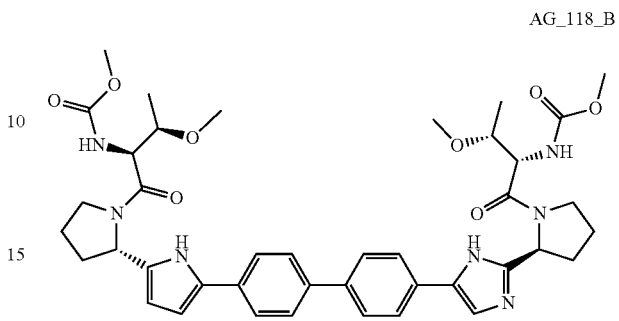

AG_118_B

Synthetic Route:

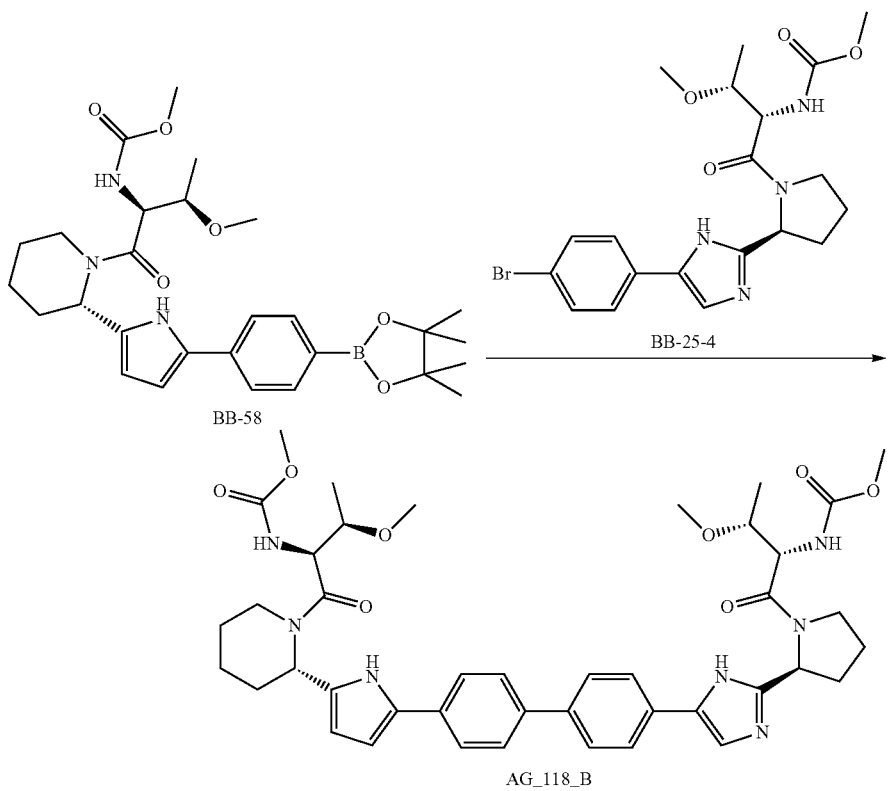

Step 1: Synthesis of Compound AG_118_B

AG_118_B was synthesized according to the synthetic method and HPLC purification of step 1 in synthesizing AG_114_A. $^1$H-NMR (400 MHz, CDCl$_3$): δ: 9.79 (br, 0.4H), 9.44 (br, 1H), 7.69-7.43 (m, 8H), 7.22 (s, 1H), 6.52 (s, 1H), 6.29-6.00 (m, 2H), 5.70-5.68 (m, 1H), 5.39-5.37 (m, 1H), 4.56-4.49 (m, 1H), 3.87-3.68 (m, 10H), 3.45-3.27 (m, 6H), 2.91-2.77 (m, 1H), 2.33-1.54 (m, 10H), 1.28-1.16 (m, 6H); LCMS m/z: 784 [M+H]$^+$ Embodiment 90: AG_096
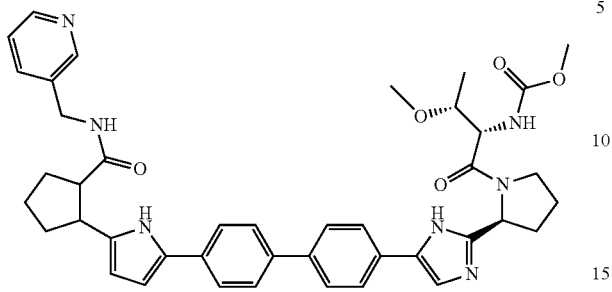
Synthetic Route:
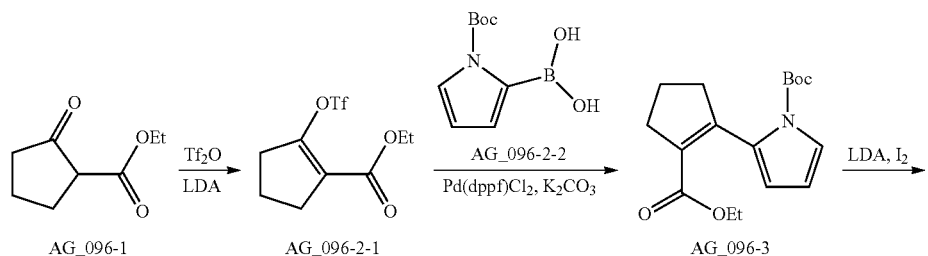
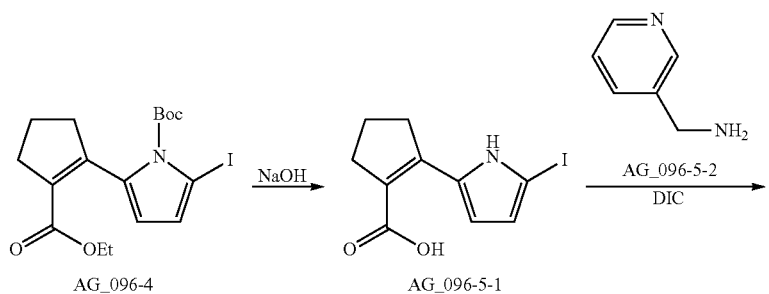
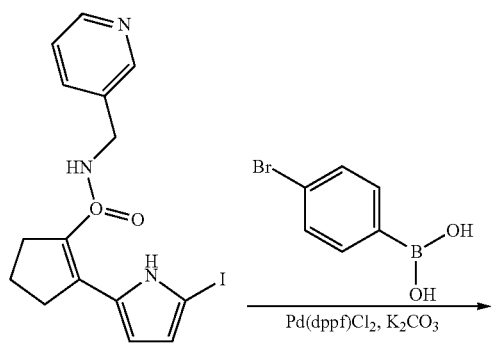

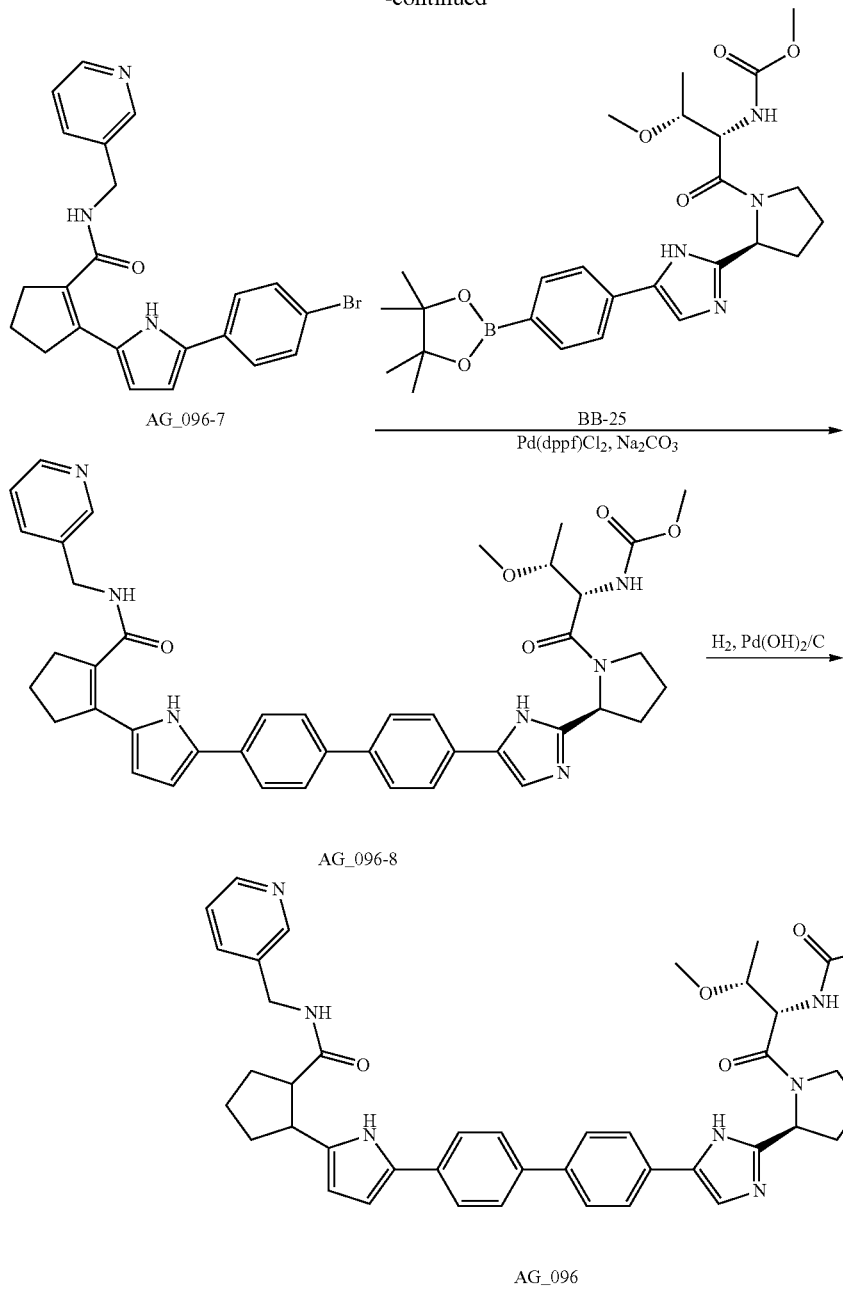

Step 1: Synthesis of Compound AG_096-2-1

Compound AG_096-1 (10 g, 64.03 mmol) was dissolved in THF (250 mL), 2.0M LDA solution (38.42 mL, 76.83 mmol) was added slowly at −78° C. After addition, the reaction mixture was stirred at −78° C. for 1 h. Tf$_2$O (21.68 g, 76.83 mmol) was added slowly, the reaction mixture was warmed to room temperature naturally and stirred overnight. The reaction was quenched with saturated ammonium chloride and extracted with ethyl acetate (150 mL×3). The ethyl acetate phases were combined and washed with saturated brines, dried over anhydrous sodium sulfate. The solvent was evaporated, the crude product was purified by silica gel column chromatography (eluting reagent: PE:EA=5:1) to deliver the target compound AG_096-2-1 (brown solid, 13.2 g, yield: 72%). LCMS m/z: 289 [M+H]$^+$ Step 2: Synthesis of Compound AG_096-3

In a 500 mL round-bottom flask, AG_096-2-1 (13.00 g, 45.10 mmol) and AG_096-2-2 (11.42 g, 70.77 mmol), catalyst Pd(dppf)Cl$_2$ (3.31 g, 4.51 mmol) and K$_2$CO$_3$ (18.70 g, 135.30 mmol) were dissolved in dioxane (200 mL) and H$_2$O (60 mL). The reaction mixture was heated to 80° C. and stirred for 2 h under nitrogen gas atmosphere. After the reaction was complete, H$_2$O (200 mL) was added and the reaction mixture was extracted with ethyl acetate (300 mL×3). The organic phase was washed with saturated brines, dried over anhydrous sodium. After filtration, the filtrate was concentrated under reduced pressure to deliver the crude product which was purified by silica gel column chromatography (eluting reagent: PE:EA=10:1) to deliver the target compound AG_096-3 (yellow solid, 11.5 g, yield 84%). LCMS m/z: 206 [M+H-100]+

Step 3: Synthesis of Compound AG_096-4

Compound AG_096-3 (8.6 g, 28.16 mmol) was dissolved in THF (150 mL), 2.0M LDA (28.16 mL, 56.33 mmol) was added slowly at −78° C. After addition, the reaction mixture was stirred at −78° C. for 1 h. Iodine (8.58 g, 33.80 mmol) was, the reaction mixture was warmed to room temperature naturally and stirred for 1 h. The reaction was quenched with saturated ammonium chloride and extracted with ethyl acetate (150 mL×3). The ethyl acetate phases were combined and washed with saturated brines, dried over anhydrous sodium sulfate. The solvent was evaporated and the crude was purified by silica gel column chromatography (eluting reagent: PE:EA=5:1) to deliver the target compound AG 096-4 (brown solid, 4.2 g, yield: 35%). LCMS m/z: 332 [M+H-100]+

Step 4: Synthesis of Compound AG_096-5

Compound AG_096-4 (4.2 g, 9.74 mmol) was dissolved in ethanol (100 mL), 2.0M NaOH aqueous solution (24 mL, 48.69 mmol) was added slowly. The reaction mixture was heated to 90° C. and stirred for 4 h. The reaction mixture was adjusted to pH=5-6 with dilute hydrochloric acid and extracted with ethyl acetate (150 mL×3). The ethyl acetate phases were combined and washed with saturated brines, dried over anhydrous sodium sulfate. The solvent was evaporated, the crude was purified by silica gel column chromatography (eluting reagent: PE:EA=2:1) to deliver the target compound AG 096-5 (brown solid, 1.5 g, yield: 51%). LCMS m/z: 304 [M+H]+

Step 5: Synthesis of Compound AG 096-6

Compound AG 096-5-1 (300 mg, 0.99 mol) and compound AG 096-5-2 (107 mg, 0.99 mol) were dissolved in acetonitrile (20 mL), DIC (125 mg, 0.99 mol) was added slowly. The reaction mixture was stirred at room temperature overnight. After filtration, the filtrate was concentrated to deliver the crude product which was purified by preparative TLC to deliver the target compound AG_096-6 (brown solid, 120 mg, yield: 31%). LCMS m/z: 394 [M+H]+

Step 6: Synthesis of Compound AG_096-7

In a 100 mL round-bottom flask, AG_096-6 (200 mg, 0.51 mmol) and 4-bromophenylboronic acid (102 mg, 0.51 mmol), catalyst Pd(dppf)Cl2 (37 mg, 0.051 mmol) and K2CO3 (211 mg, 1.53 mmol) were dissolved in dioxane (20 mL) and H2O (3 mL). The reaction mixture was heated to 80° C. and stirred for 2 h under nitrogen gas atmosphere. After the reaction was complete, H2O (20 mL) was added and the reaction mixture was extracted with ethyl acetate (30 mL×3). The organic phase was washed with saturated brines, dried over anhydrous sodium sulfate. After filtration, the filtrate was concentrated to deliver the crude product, which was purified by silica gel column chromatography (eluting reagent: PE:EA=10:1) to deliver the target compound AG_096-7 (yellow solid, 140 mg, yield 65%). LCMS m/z: 422 [M+H]+

Step 7: Synthesis of Compound AG_096-8

Compound AG_096-7 (160 mg, 0.38 mmol), BB-25 (194 mg, 0.38 mmol) were dissolved in a mixed solvent of DMF/THF/H2O (10 mL/10 mL/10 mL), Pd(dppf)Cl2 (28 mg, 0.038 mmol) and Na2CO3 (120 mg, 1.14 mmol) were added. The atmosphere was replaced by nitrogen gas for 3 times and the reaction mixture was heated to 90° C. and stirred for 2 h under nitrogen gas atmosphere. Stop heating and cool naturally. H2O (10 mL) was added and the reaction mixture was extracted with ethyl acetate (30 mL×3). The ethyl acetate phases were combined and washed with saturated brines, dried over anhydrous sodium sulfate. The solvent was evaporated and the crude product was purified by preparative TLC to deliver the target compound AG_096-8 (brown solid, 110 mg, yield 40%). LCMS m/z: 728 [M+H]+

Step 8: Synthesis of Compound AG_096

Compound AG_096-8 (110 mg, 0.15 mmol) was dissolved in methanol (5 mL) and ethyl acetate (5 mL), catalyst Pd(OH)2/C (20 mg) was added slowly under argon gas atmosphere. The atmosphere was replaced by hydrogen gas for 3 times and the reaction mixture was stirred at room temperature overnight. After filtration, the filtrate was concentrated under reduced pressure to obtain the crude product, which was purified by preparative HPLC to deliver the target compound AG_096 (white solid, 8 mg, yield 7%). 1H-NMR (400 MHz, CDCl3): δ: 9.06 (s, 1H), 8.30-8.27 (m, 1H), 7.78-7.62 (m, 9H), 7.18-7.13 (m, 2H), 6.93-6.91 (m, 1H), 6.42 (s, 1H), 6.01 (s, 1H), 5.81-5.71 (m, 2H), 5.33 (s, 1H), 4.59 (s, 1H), 4.25-4.23 (m, 1H), 3.73-3.63 (m, 7H), 3.46-3.24 (m, 5H), 2.89-2.87 (m, 2H), 2.22-1.99 (m, 10H), 1.22-1.13 (m, 3H); LCMS m/z: 730 [M+H]+

Embodiment 91: AG_103

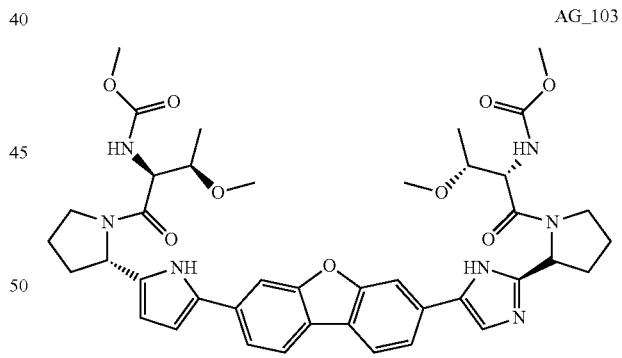

AG_103

Synthetic Route:

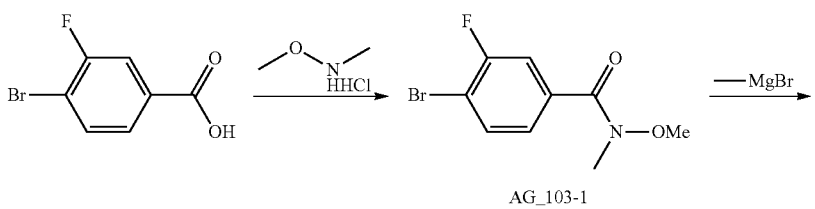

AG_103-1

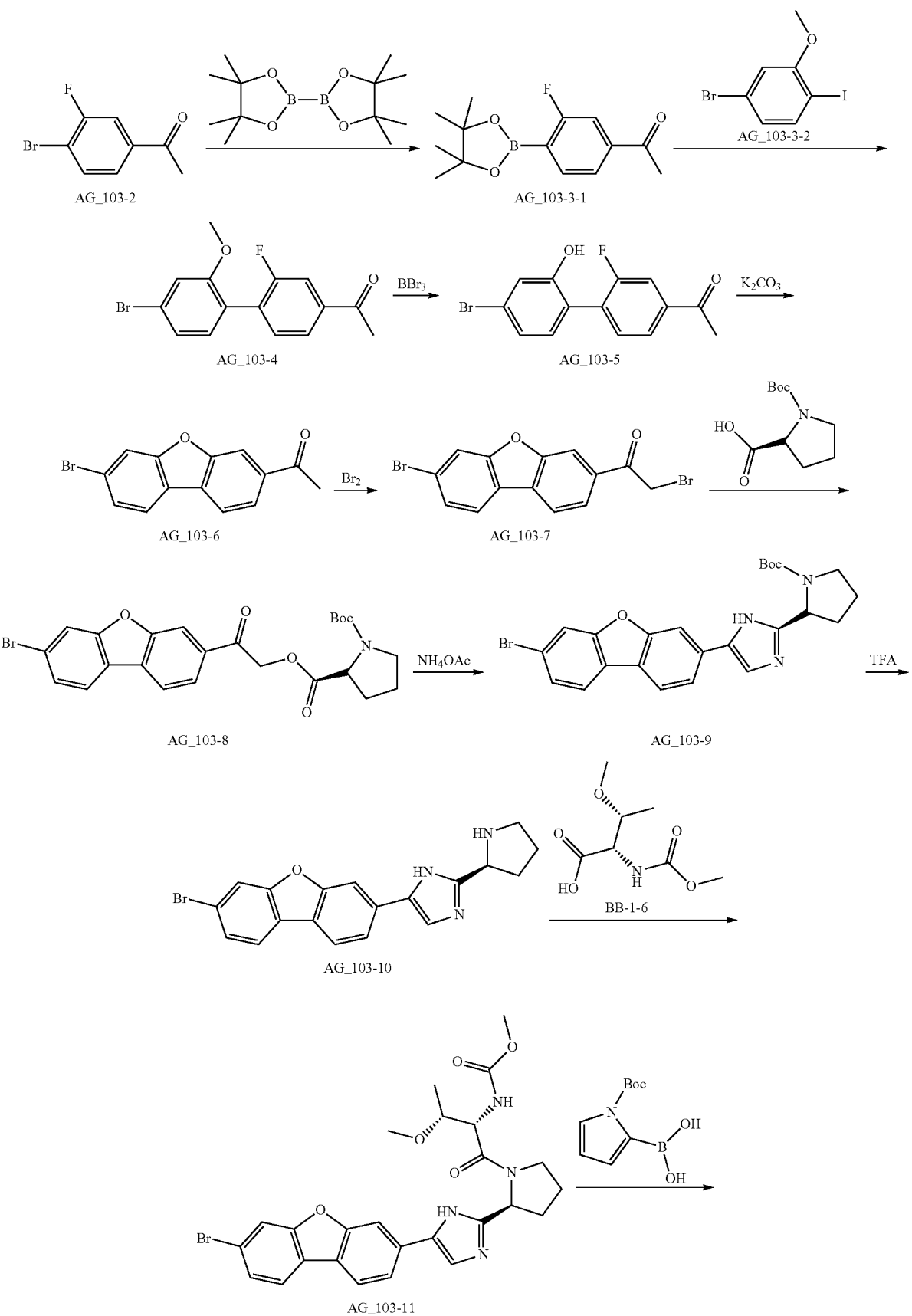

-continued
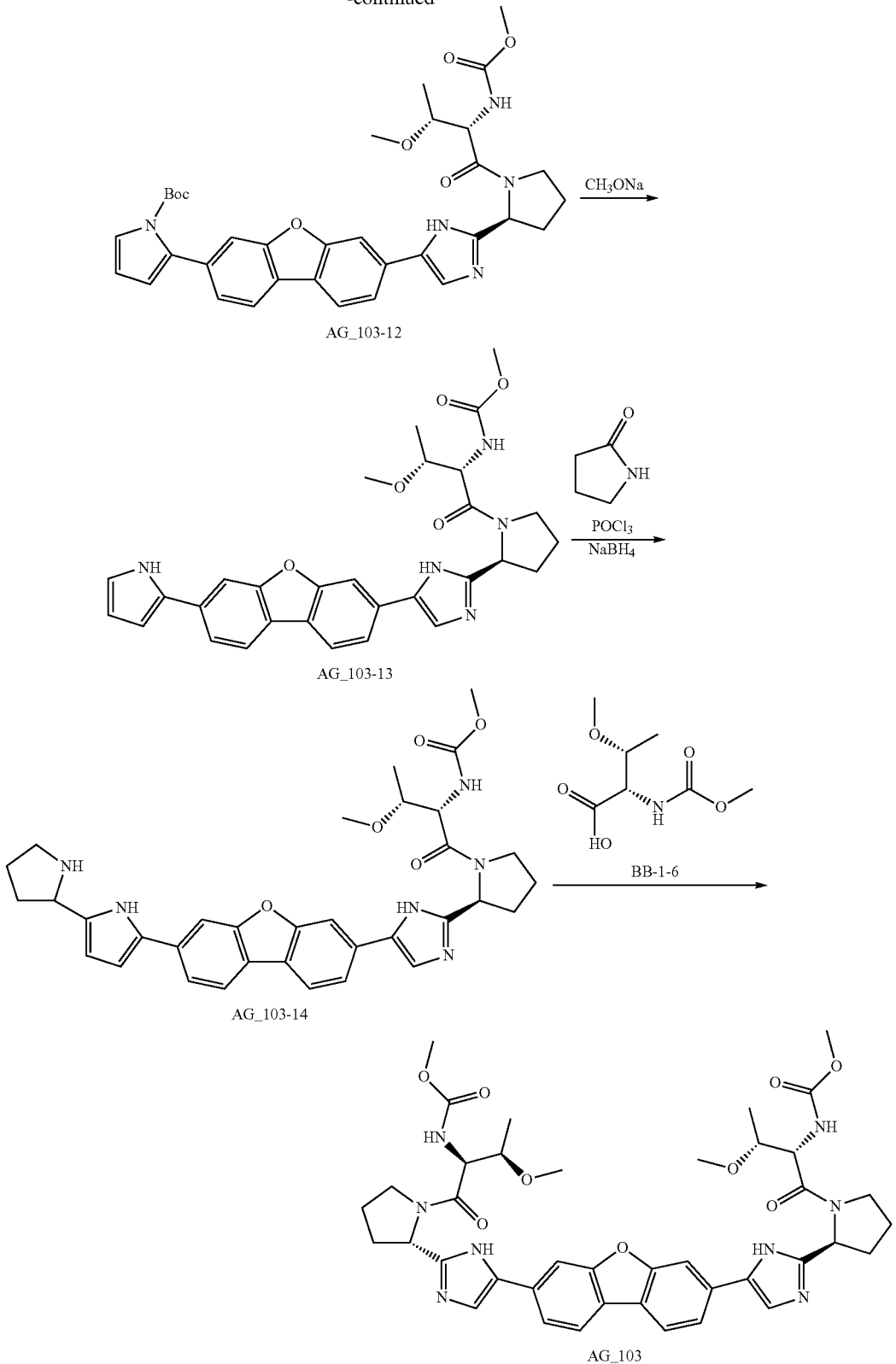
Step 1: Synthesis of Compound AG_103-1
Compound 4-bromo-3-fluoro benzoic acid (10 g, 45.66 mmol), O,N-dimethyl hydroxylamine hydrochloride (5.34 g, 54.79 mmol) and HATU (20.85 g, 54.79 mmol) were dissolved in dichloromethane (200 mL), DIPEA (17.67 g, 136.98 mmol) was added slowly under an ice bath, and the reaction mixture was stirred overnight under nitrogen gas atmosphere. The reaction was quenched with saturated sodium bicarbonate solution and extracted with dichloromethane (100 mL×3). The organic phases were combined and dried over anhydrous sodium sulfate. After filtration, the filtrate was concentrated under reduced pressure. The obtained crude product was purified by silica gel column chromatography (eluting reagent: PE:EA=3:1) to deliver the target compound AG 103-1 as gray solid (10.3 g, yield: 86%). LCMS m/z: 262 [M+H]$^+$ Step 2: Synthesis of Compound AG_103-2

Compound AG_103-1 (8.00 g, 30.53 mmol) was dissolved in THF (250 mL), methyl Grignard reagent (12.21 mL, 36.63 mmol) was added slowly at −78° C., and the reaction mixture was warmed to room temperature naturally and stirred for 18 h. After the reaction was complete, the reaction was quenched with $H_2O$ (150 mL) under an ice bath and extracted with ethyl acetate (150 mL×3). The organic phase was washed with saturated brines, dried over anhydrous sodium sulfate. After filtration, the filtrate was concentrated under reduced pressure to deliver the crude product which was purified by silica gel column chromatography (eluting reagent: PE:EA=3:1) to deliver the target compound AG 103-2 as gray solid (4.6 g, yield: 69%). LCMS m/z: 217 [M+H]$^+$ Step 3: Synthesis of Compound AG_103-3

Compound AG_103-2 (4.6 g, 21.19 mmol), bis(pinacolato)diboron (10.76 g, 42.397 mmol), KOAc (8.32 g, 84.78 mmol) and Pd(dppf)Cl$_2$ (777 mg, 1.06 mmol) were placed in a 250 mL three-neck flask under nitrogen gas atmosphere. 1,4-Dioxane (100 mL) was injected and the reaction system was heated to 90° C. and stirred overnight. Stop heating and cool naturally. After filtration, the filter cake was washed with ethyl acetate twice and the obtained filtrate was evaporated to remove the solvent, the crude product was purified by silica gel column chromatography (eluting reagent: PE:EA=5:1) to deliver the target compound AG_103-3 as white solid (4.2 g, yield 75%). $^1$H-NMR (400 MHz, CDCl$_3$): δ: 7.82-7.80 (m, 1H), 7.69-7.68 (m, 1H), 7.58-7.56 (m, 1H), 2.59 (s, 3H), 1.36 (s, 12H).

Step 4: Synthesis of Compound AG_103-4

In a 250 mL round-bottom flask, AG_103-3-1 (2.00 g, 7.57 mmol) and AG_103-3-2 (2.371 mg, 7.57 mmol), catalyst Pd(dppf)Cl$_2$ (560 mg, 0.76 mmol) and K$_2$CO$_3$ (3.14 g, 22.7 mmol) were dissolved in dioxane (50 mL) and H$_2$O (10 mL). The reaction mixture was heated to 80° C. and stirred for 2 h under nitrogen gas atmosphere. After the reaction was complete, H$_2$O (200 mL) was added and the reaction mixture was extracted with ethyl acetate (150 mL×3). The organic phase was washed with saturated brines, dried over anhydrous sodium sulfate. After filtration, the filtrate was concentrated under reduced pressure to obtain the crude product, which was purified by silica gel column chromatography (eluting reagent: PE:EA=1:1) to deliver the target compound AG_103-4 as gray solid (1.2 g, yield 49%). $^1$H-NMR (400 MHz, CDCl$_3$): δ: 7.78-7.68 (m, 2H), 7.43-7.41 (m, 1H), 7.18-7.11 (m, 3H), 3.80 (s, 3H), 2.61 (s, 3H).

Step 5: Synthesis of Compound AG_103-5

Compound AG_103-4 (1.00 g, 3.09 mmol) was dissolved in dichloromethane (50 mL), BBr$_3$ (1.94 g, 7.74 mmol) was added slowly at −78° C., and the reaction mixture was stirred for 2 h. After the reaction was complete, the reaction was quenched with H$_2$O (20 mL) under an ice bath and extracted with ethyl acetate (30 mL×3). The organic phase was washed with saturated brines, dried over anhydrous sodium sulfate. After filtration, the filtrate was concentrated under reduced pressure to obtain the crude product, which was purified by silica gel preparative plate (eluting reagent: PE:EA=3:1) to deliver the target compound AG_103-5 as gray solid (260 mg, yield 27%).

Step 6: Synthesis of Compound AG_103-6

Compound AG_103-5 (30 mg, 0.097 mmol) was dissolved in DMF (5 mL), K$_2$CO$_3$ (67 mg, 0.49 mmol) was added, and the reaction mixture was heated to 120° C. and stirred for 2 h. After the reaction was complete, H$_2$O (20 mL) was added and the reaction mixture was extracted with ethyl acetate (15 mL×3). The organic phase was washed with saturated brines, dried over anhydrous sodium sulfate. After filtration, the filtrate was concentrated under reduced pressure to deliver the crude target compound AG_103-6 as gray solid (25 mg, yield 89%). LCMS m/z: 289 [M+H]$^+$ Step 7: Synthesis of Compound AG_103-7

Compound AG_103-6 (25 mg, 0.086 mmol) was dissolved in dioxane (5 mL), Br$_2$ (14 mg, 0.086 mmol) was added slowly, and the reaction mixture was stirred at room temperature for 2 h. The reaction mixture was concentrated under reduced pressure to deliver the crude target compound AG_103-7 (brown solid, 28 mg, yield 88%).

Step 8: Synthesis of Compound AG_103-8

Compound AG_103-7 (28 mg, 0.076 mmol) and compound Boc-L-proline (16 mg, 0.076 mmol) were dissolved in dichloromethane (5 mL), DIPEA (10 mg, 0.076 mmol) was added slowly, and the reaction mixture was stirred overnight under nitrogen gas atmosphere. The reaction was quenched with saturated sodium bicarbonate solution and extracted with dichloromethane (10 mL×3). The organic phases were combined and dried over anhydrous sodium sulfate. After filtration, the filtrate was concentrated under reduced pressure to deliver the crude target compound AG_103-8 as brown solid (35 mg, yield: 92%). LCMS m/z: 402 [M+H-100]$^+$ Step 9: Synthesis of Compound AG_103-9

Compound AG_103-8 (35 mg, 0.070 mmol) was dissolved in toluene (10 mL), ammonium acetate (54 mg, 0.70 mmol) was added, and the reaction mixture was heated to reflux and stirred for 18 h. The reaction mixture was washed with H$_2$O and saturated brines. The organic phase was dried over anhydrous sodium sulfate, concentrated under reduced pressure to obtain the crude product, which was purified by silica gel preparative plate (eluting reagent: PE:EA=1:1) to deliver the target compound AG_103-9 as gray solid (27 mg, yield: 80%). LCMS m/z: 482 [M+H]$^+$ Step 10: Synthesis of Compound AG_103-10

Compound AG_103-9 (27 mg, 0.056 mmol) was dissolved in dichloromethane (4 mL), TFA (1 mL) was added slowly, and the reaction mixture was stirred at room temperature for 3 h. The reaction mixture was concentrated under reduced pressure, the residue was dissolved with NaHCO$_3$ solution and extracted with dichloromethane (10 mL×3). The organic phases were combined and dried over anhydrous sodium sulfate. After filtration, the filtrate was concentrated under reduced pressure to deliver the target compound AG_103-10 as gray solid (20 mg, yield: 93%). LCMS m/z: 382 [M+H]$^+$ Step 11: Synthesis of Compound AG_103_11

Compound AG_103-10 (20 mg, 0.052 mmol) and compound BB-1-6 (11 mg, 0.056 mmol) and HATU (21 mg, 0.056 mmol) were dissolved in dichloromethane (5 mL), DIPEA (13 mg, 0.10 mmol) was added slowly under an ice bath, and the reaction mixture was stirred overnight under nitrogen gas atmosphere. The reaction was quenched with saturated sodium bicarbonate solution and extracted with dichloromethane (10 mL×3). The organic phases were combined and dried over anhydrous sodium sulfate. After filtration, the filtrate was concentrated under reduced pressure to obtain the crude product which was purified by silica gel preparative plate (eluting reagent: PE:EA=1:1) to deliver the target compound AG_103_11 as gray solid (25 mg, yield: 86%). LCMS m/z: 555 [M+H]⁺

Step 12: Synthesis of Compound AG_103-12

In a 50 mL round-bottom flask, 1-tert-butoxycarbonyl-2-pyrrolyl boronic acid (10 mg, 0.050 mmol) and AG_103-11 (25 mg, 0.045 mmol), catalyst Pd(dppf)Cl₂ (2 mg, 0.002 mmol), K₂CO₃ (19 mg, 0.14 mmol) were dissolved in dioxane (2 mL) and H₂O (0.7 mL). The reaction mixture was heated to 80° C. and stirred for 2 h under nitrogen gas atmosphere. After the reaction was complete, H₂O (20 mL) was added and the reaction mixture was extracted with ethyl acetate (15 mL×3). The organic phase was washed with saturated brines, dried over anhydrous sodium sulfate. After filtration, the filtrate was concentrated under reduced pressure to obtain the crude product, which was purified by silica gel preparative plate (eluting reagent: PE:EA=1:1) to deliver the target compound AG_103-12 as gray solid (24 mg, yield 83%). LCMS m/z: 642 [M+H]⁺

Step 13: Synthesis of Compound AG_103-13

Compound AG_103-12 (24 mg, 0.037 mmol) was dissolved in a mixed solvent of methanol (2 mL) and THF (2 mL), MeONa (16 mg, 0.30 mmol) was added slowly, and the mixture was stirred at room temperature for 3 h. The reaction was quenched with H₂O and extracted with ethyl acetate (20 mL×3). The organic phases were combined and dried over anhydrous sodium sulfate. After filtration, the filtrate was concentrated under reduced pressure to deliver the target compound AG_103-13 as gray solid (18 mg, 89%). LCMS m/z: 542 [M+H]⁺

Step 14: Synthesis of Compound AG_103-14

Compound AG_103-13 (18 mg, 0.030 mmol) and 2-pyrrolidone (17 mg, 0.20 mmol) were dissolved in dichloromethane (5 mL), and under an ice bath, POCl₃ (25 mg, 0.17 mmol) was added slowly, the reaction mixture was stirred overnight under nitrogen gas atmosphere. The reaction was quenched by slowly pouring the reaction solution into a solution of saturated sodium acetate in ice-water. 10M NaOH solution was added to adjust pH to about 9-10 and the mixture was extracted with dichloromethane (10 mL×3). The organic phases were combined and dried over anhydrous sodium sulfate. After filtration, the filtrate was concentrated under reduced pressure. The residue was dissolved in methanol (10 mL), and under an ice bath, NaBH₄ (11 mg, 0.30 mmol) was added slowly, the mixture was stirred at room temperature for 2 h. The reaction was quenched with saturated brines and extracted with dichloromethane (10 mL×3). The organic phases were combined and dried over anhydrous sodium sulfate. After filtration, the filtrate was concentrated under reduced pressure to deliver the target product AG_103-14 as purple oil (15 mg, 74%). LCMS m/z: 611 [M+H]⁺

Step 15: Synthesis of Compound AG_103

Compound AG_103-14 (15 mg, 0.026 mmol) and compound BB-1-6 (6 mg, 0.029 mmol) and HATU (11 mg, 0.029 mmol) were dissolved in dichloromethane (2 mL), DIPEA (6 mg, 049 mmol) was added slowly under an ice bath, and the reaction mixture was stirred overnight under nitrogen gas atmosphere. The reaction was quenched with saturated sodium bicarbonate solution and extracted with dichloromethane (10 mL×3). The organic phases were combined and dried over anhydrous sodium sulfate. After filtration, the filtrate was concentrated under reduced pressure. The obtained crude product was purified by preparative HPLC to deliver the target compound AG_103 as gray solid (4 mg, yield: 21%). ¹H-NMR (400 MHz, CDCl₃): δ: 10.12 (br, 0.5H), 9.97 (br, 0.5H), 7.83-7.48 (m, 6H), 7.29 (s, 1H), 6.47 (d, J=3.6 Hz, 1H), 6.07 (s, 1H), 5.74-5.67 (m, 2H), 5.43-5.38 (m, 2H), 4.60-4.38 (m, 2H), 3.78-3.66 (m, 12H), 3.40-3.23 (m, 6H), 2.89-2.76 (m, 1H), 2.26-2.08 (m, 7H), 1.24-1.13 (m, 6H). LCMS m/z: 784 [M+H]⁺

Embodiment 92: AG_085

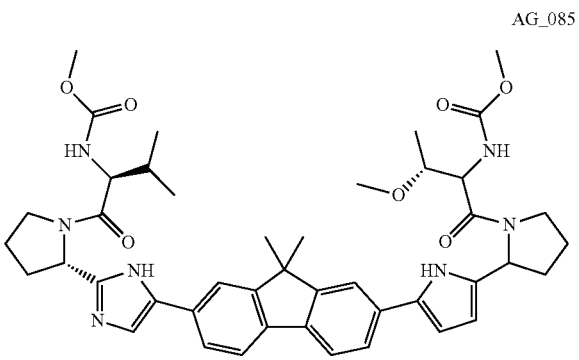

AG_085

Synthetic Route:

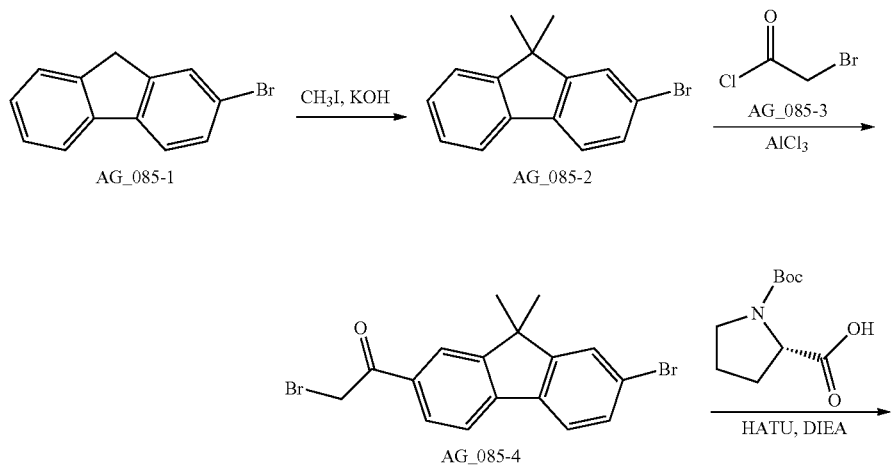

-continued
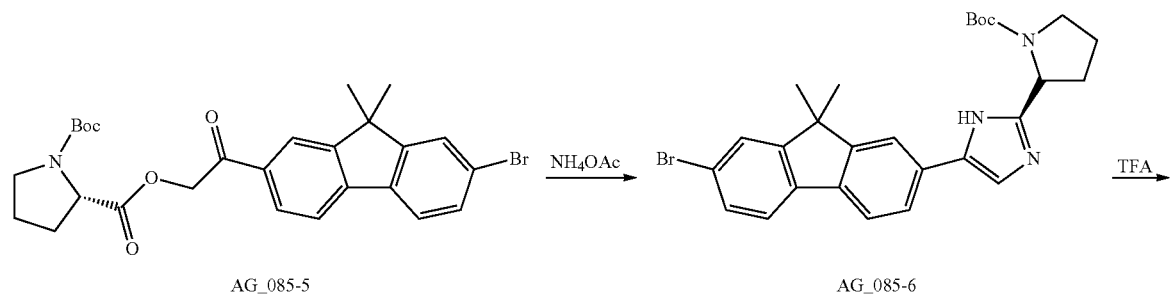
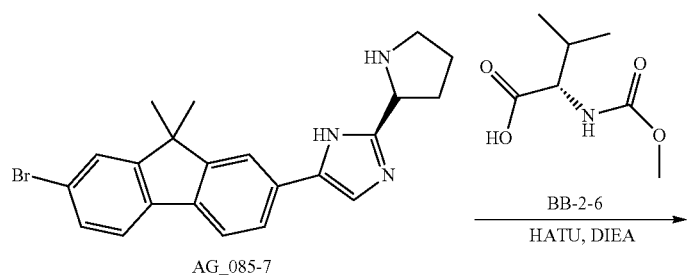
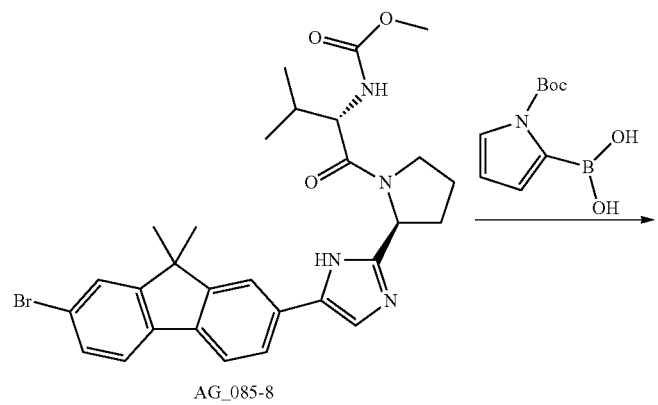
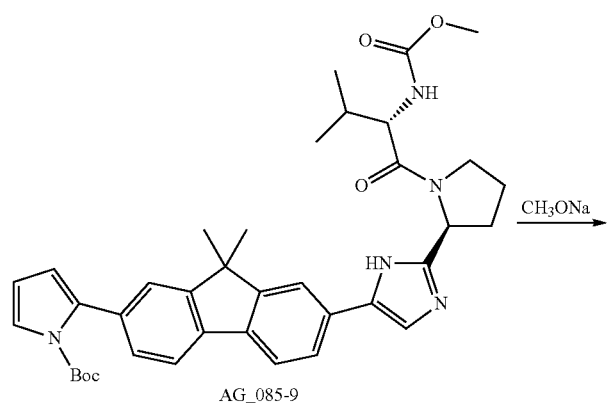

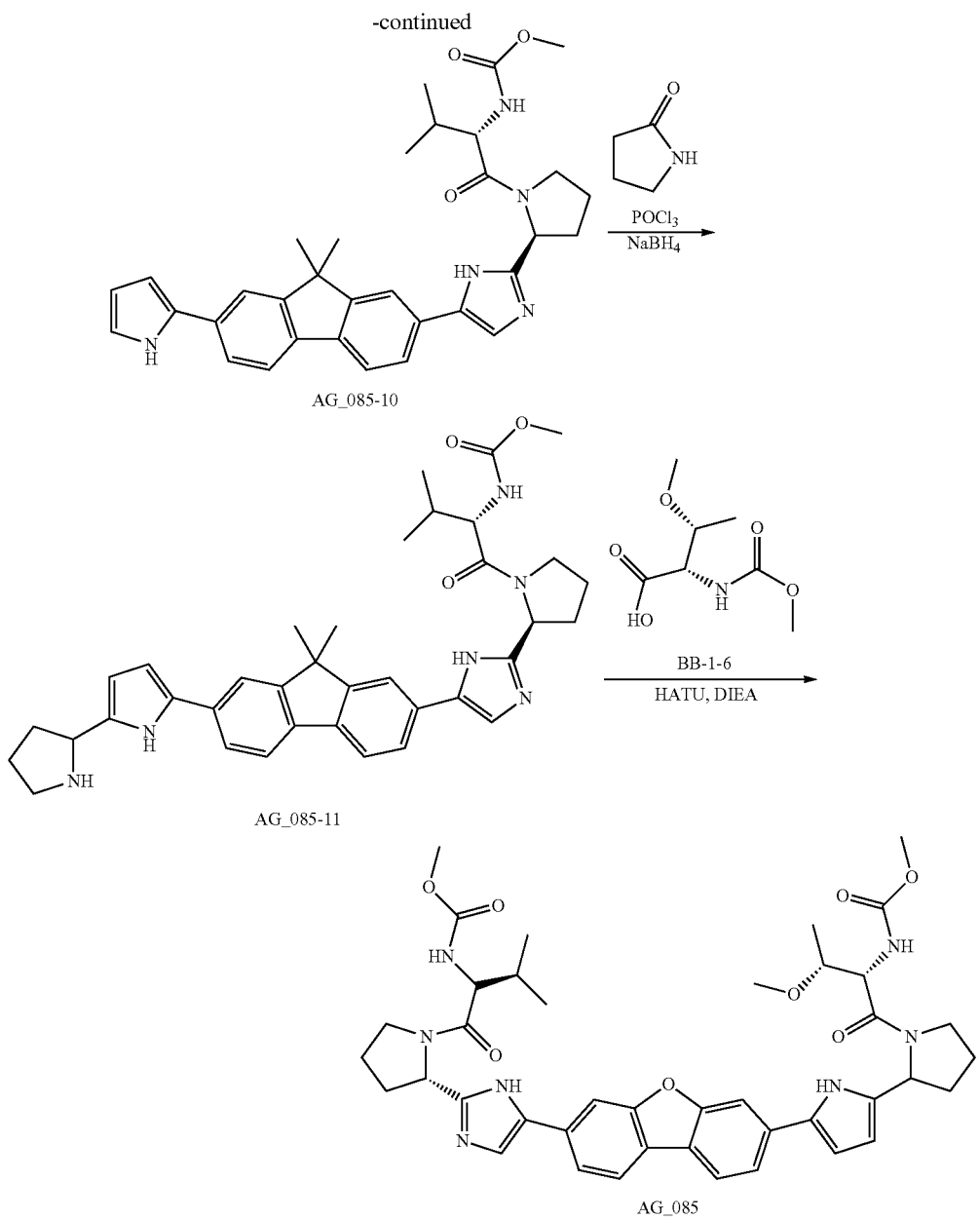

Step 1: Synthesis of Compound AG_085-2

Compound AG_085-1 (3.00 g, 12.24 mol) was dissolved in DMSO (30 mL), KOH (2.75 g, 48.96 mol) was added slowly at 0° C., and the reaction mixture was stirred for 1 h under nitrogen gas atmosphere. $CH_3I$ (2.80 g, 34.27 mol) was added and the reaction mixture was stirred overnight. The reaction was quenched with ice-water, and extracted with methyl tert-butyl ether (50 mL×3). The organic phases were combined and dried over anhydrous sodium sulfate. After filtration, the filtrate was concentrated under reduced pressure to deliver the crude target compound AG_085-2 (gray solid, 3.2 g, yield: 96%). $^1$H-NMR (400 MHz, $CDCl_3$): δ: 8.05-7.97 (m, 2H), 7.76 (d, J=8.0 Hz, 1H), 7.64 (d, J=8.0 Hz, 1H), 7.60-7.52 (m, 2H), 4.49 (s, 2H), 1.51 (s, 6H).

Step 2: Synthesis of Compound AG_085-4

Compound AG_085-2 (2.30 g, 14.58 mmol) and compound AG_085-3 (3.32 g, 12.15 mmol) were dissolved in dichloromethane (100 mL), $AlCl_3$ (1.94 g, 14.58 mmol) was added slowly, and the reaction mixture was stirred at room temperature overnight. The reaction was quenched with ice-water and extracted with dichloromethane (50 mL×3). The organic phases were combined and dried over anhydrous sodium sulfate. After filtration, the filtrate was concentrated under reduced pressure to deliver the crude product which was purified by silica gel column chromatography (eluting reagent: PE:EA=10:1) to deliver the target compound AG_085-4 (brown solid, 1.4 g, yield: 87%). $^1$H-NMR (400 MHz, $CDCl_3$): δ: 8.05-7.97 (m, 2H), 7.76 (d, J=8.0 Hz, 1H), 7.64 (d, J=8.0 Hz, 1H), 7.60-7.52 (m, 2H), 4.49 (s, 2H), 1.51 (s, 6H).

Step 3: Synthesis of Compound AG_085-5

Compound AG_085-4 (1.2 g, 3.04 mmol) and Boc-L-proline (655 mg, 3.04 mmol) were dissolved in dichloromethane (20 mL), DIPEA (433 mg, 3.35 mmol) was added slowly, and the reaction system was stirred overnight under nitrogen gas atmosphere. The reaction was quenched with saturated sodium bicarbonate solution, and extracted with dichloromethane (30 mL×3). The organic phases were combined and dried over anhydrous sodium sulfate. After filtration, the filtrate was concentrated under reduced pressure to deliver the crude target compound AG_085-5 (brown solid, 1.4 g, yield 87%). LCMS m/z: 428 [M+H-100]$^+$ Step 4: Synthesis of Compound AG_085-6

Compound AG_085-5 (1.4 g, 2.65 mmol) was dissolved in toluene (50 mL), ammonium acetate (3.06 g, 39.74 mmol) was added, and the reaction mixture was heated to reflux and stirred for 18 h. The reaction mixture was washed with $H_2O$ and saturated brines. The organic phase was dried over anhydrous sodium sulfate, concentrated under reduced pressure to obtain the crude product, which was purified by silica gel column chromatography (eluting reagent: PE:EA=1:1) to deliver the target compound AG_085-6 (gray solid, 800 mg, yield: 59%). LCMS m/z: 508 [M+H]$^+$ Step 5: Synthesis of Compound AG_085-7

Compound AG_085-6 (400 mg, 0.79 mmol) was dissolved in dichloromethane (10 mL), TFA (3 mL) was added slowly, and the reaction mixture was stirred at room temperature for 3 h. The reaction mixture was concentrated under reduced pressure, the residue was dissolved with $NaHCO_3$ solution and extracted with dichloromethane (30 mL×3). The organic phases were combined and dried over anhydrous sodium sulfate. After filtration, the filtrate was concentrated under reduced pressure to deliver the target compound AG_085-7 (gray solid, 280 mg, yield: 87%). LCMS m/z: 408 [M+H]$^+$ Step 6: Synthesis of Compound AG_085-8

Compound AG_085-7 (200 mg, 0.49 mmol) and compound BB-2-6 (103 mg, 0.59 mmol) and HATU (224 mg, 0.59 mmol) were dissolved in dichloromethane (10 mL), DIPEA (127 mg, 0.98 mmol) was slowly added under an ice bath, and the reaction mixture was stirred overnight under nitrogen gas atmosphere. The reaction was quenched with saturated sodium bicarbonate solution, and extracted with dichloromethane (20 mL×3). The organic phases were combined and dried over anhydrous sodium sulfate. After filtration, the filtrate was concentrated under reduced pressure to obtain the crude product which was purified by silica gel preparative plate (eluting reagent: PE:EA=1:1) to deliver the target compound AG_085-8 (gray solid, 220 mg, yield: 79%). LCMS m/z: 565 [M+H]$^+$ Step 7: Synthesis of Compound AG_085-9

In a 50 mL round-bottom flask, 1-tert-butoxycarbonyl-2-pyrrolyl boronic acid (54 mg, 0.25 mmol) and AG_085-8 (120 mg, 0.21 mmol), catalyst Pd(dppf)Cl$_2$ (15 mg, 0.021 mmol), $K_2CO_3$ (87 mg, 0.63 mmol) were dissolved in dioxane (10 mL) and $H_2O$ (3 mL), the reaction mixture was heated to 80° C. and stirred for 2 h under nitrogen gas atmosphere. After the reaction was complete, $H_2O$ (20 mL) was added and the reaction mixture was extracted with ethyl acetate (20 mL×3). The organic phase was washed with saturated brines, dried over anhydrous sodium sulfate. After filtration, the filtrate was concentrated under reduced pressure to deliver the crude target compound AG_085-9 (gray solid, 120 mg, yield 87%). LCMS m/z: 652 [M+H]$^+$ Step 8: Synthesis of Compound AG_085-10

Compound AG_085-9 (120 mg, 0.18 mmol) was dissolved in a mixed solvent of methanol (10 mL) and THF (10 mL), MeONa (80 mg, 1.47 mmol) was added slowly, and the mixture was stirred at room temperature for 3 h. The reaction was quenched with $H_2O$, and extracted with ethyl acetate (20 mL×3). The organic phases were combined and dried over anhydrous sodium sulfate. After filtration, the filtrate was concentrated under reduced pressure to deliver the target compound AG_085-10 (gray solid, 90 mg, 89%). LCMS m/z: 552 [M+H]$^+$ Step 9: Synthesis of Compound AG_085-11

Compound AG_085-10 (90 mg, 0.16 mmol) and 2-pyrrolidone (83 mg, 0.98 mmol) were dissolved in dichloromethane (10 mL), and under an ice bath, POCl$_3$ (125 mg, 0.82 mmol) was added slowly, the reaction mixture was stirred overnight under nitrogen gas atmosphere. The reaction was quenched by slowly pouring the reaction solution into a solution of saturated sodium acetate in ice-water. 10M NaOH solution was added to adjust pH to about 9-10, the mixture was extracted with dichloromethane (10 mL×3). The organic phases were combined and dried over anhydrous sodium sulfate. After filtration, the filtrate was concentrated under reduced pressure. The residue was dissolved in methanol (10 mL), under an ice bath, NaBH$_4$ (87 mg, 2.30 mmol) was added slowly, and the mixture was stirred at room temperature for 2 h. The reaction was quenched with saturated brines, and extracted with dichloromethane (10 mL×3). The organic phases were combined and dried over anhydrous sodium sulfate. After filtration, the filtrate was concentrated under reduced pressure to deliver the crude target product AG_085-11 (purple oil, 95 mg, 79%). LCMS m/z: 621 [M+H]$^+$ Step 10: Synthesis of Compound AG_085

Compound AG_085-11 (40 mg, 0.063 mmol) and compound BB-1-6 (15 mg, 0.077 mmol) and HATU (29 mg, 0.077 mmol) were dissolved in dichloromethane (5 mL), DIPEA (19 mg, 0.13 mmol) was added slowly under an ice bath, and the reaction mixture was stirred overnight under nitrogen gas atmosphere. The reaction was quenched with saturated sodium bicarbonate solution, and extracted with dichloromethane (10 mL×3). The organic phases were combined and dried over anhydrous sodium sulfate. After filtration, the filtrate was concentrated under reduced pressure. The obtained crude product was purified by preparative HPLC to deliver the target compound AG_085 as gray solid (5 mg, yield: 10%). $^1$H-NMR (400 MHz, CDCl$_3$) δ: 10.69 (br, 0.3H), 10.33 (br, 0.5H),10.11 (br, 0.5H), 9.87 (br, 0.5H), 7.83-7.63 (m, 3H), 7.49-7.39 (m, 3H), 7.24 (s, 1H), 6.41 (s, 1H), 6.07 (s, 1H), 5.74-5.67 (m, 1H), 5.42-5.27 (m, 3H), 4.53 (s, 1H), 4.31 (s, 1H), 3.83-3.60 (m, 10H), 3.39-3.20 (m, 5H), 2.89-2.76 (m, 1H), 2.37-2.08 (m, 8H), 1.59 (s, 6H), 1.24-0.87 (m, 9H); LCMS m/z: 794 [M+H]$^+$ Embodiment 93: AG_081_A and AG_081_B

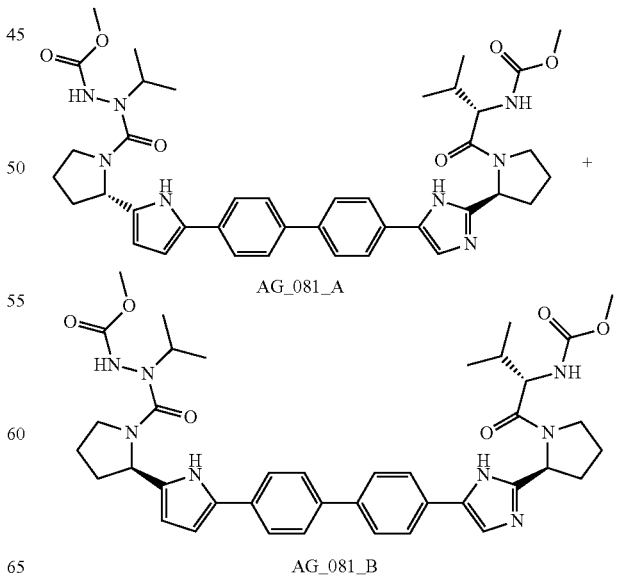

Synthetic Route:

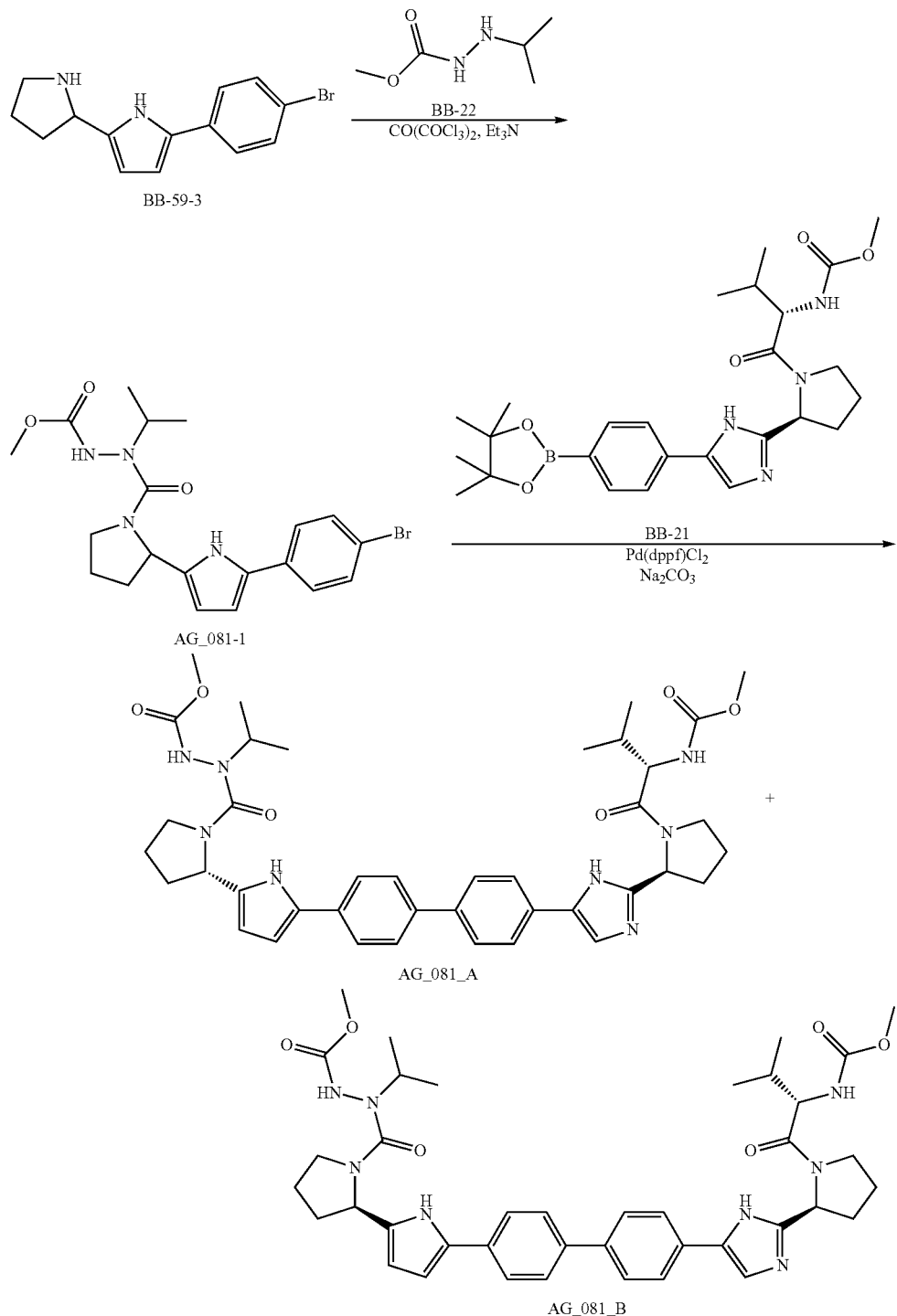

Step 1: Synthesis of Compound AG_081-1

Compound BB-22 (180 mg, 1.36 mmol) and oxalyl chloride (200 mg, 0.78 mmol) were dissolved in dichloromethane (10 mL), DIPEA (352 mg, 2.78 mmol) was added slowly under an ice bath, and the reaction system was stirred for 1 h under nitrogen gas atmosphere, then compound BB-59-3 (400 mg, 1.36 mmol) was added and the reaction mixture was stirred overnight. The reaction was quenched with saturated sodium bicarbonate solution, and extracted with dichloromethane (20 mL×3). The organic phases were combined and dried over anhydrous sodium sulfate. After filtration, the filtrate was concentrated under reduced pressure to obtain the crude product, which was purified by preparative HPLC to deliver the target compound AG_081-1 (grey solid, 130 mg, yield 21%). $^1$H-NMR (400 MHz, CDCl$_3$): δ: 9.91-9.79 (br, 1H), 7.42-7.36 (m, 4H), 6.52-6.43

(br, 1H), 6.36 (m, 1H), 6.03 (s, 1H), 5.18-5.16 (m, 1H), 3.67-3.58 (m, 4H), 3.42-3.40 (m, 1H), 2.28-1.86 (m, 4H), 1.15-1.05 (m, 6H).

Step 2: Synthesis of Compound AG_081_A and AG_081_B

Compound AG_081-1 (50 mg, 0.11 mmol), BB-21 (66 mg, 0.13 mmol) were dissolved in a mixed solvent of DMF/THF/H$_2$O (2 mL/2 mL/2 mL), Pd(dppf)Cl$_2$ (16 mg, 0.022 mmol) and Na$_2$CO$_3$ (35 mg, 0.33 mmol) were added. The atmosphere was replaced by nitrogen gas for 3 times and the reaction mixture was heated to 90° C. and stirred for 2 h under nitrogen gas atmosphere. Stop heating and cool naturally. H$_2$O (10 mL) was added and the reaction mixture was extracted with ethyl acetate (10 mL×3). The ethyl acetate phases were combined and washed with saturated brines, dried over anhydrous sodium sulfate. The solvent was evaporated and the crude product was purified by preparative HPLC to deliver the target compound AG_081_A (white solid, 6 mg, yield 7%) and AG_081_B (white solid, 5 mg, yield 6%). AG_081_A $^1$H-NMR (400 MHz, CDCl$_3$): δ: 9.98-9.84 (br, 1H), 7.82-7.47 (m, 8H), 7.19 (s, 1H), 6.51-6.45 (br, 1H), 6.42 (s, 1H), 6.07 (s, 1H), 5.42-5.21 (m, 3H), 4.33-4.31 (m, 1H), 3.82-3.48 (m, 11H), 3.09-2.98 (m, 1H), 2.37-1.88 (m, 8H), 1.16-0.87 (m, 12H); LCMS: m/z 739 [M+H]$^+$ AG_081_B $^1$H-NMR (400 MHz, CDCl$_3$):& 10.31 (br, 0.5H), 9.88 (br, 0.5H), 7.84-7.37 (m, 8H), 7.21 (s, 1H), 6.53-6.42 (br, 1H), 6.42 (s, 1H), 6.07 (s, 1H), 5.37-5.20 (m, 3H), 4.33-4.31 (m, 1H), 3.80-3.43 (m, 11H), 3.08-3.00 (m, 1H), 2.32-1.93 (m, 8H), 1.15-0.85 (m, 12H); LCMS m/z: 739 [M+H]$^+$ Embodiment 94: AA_007

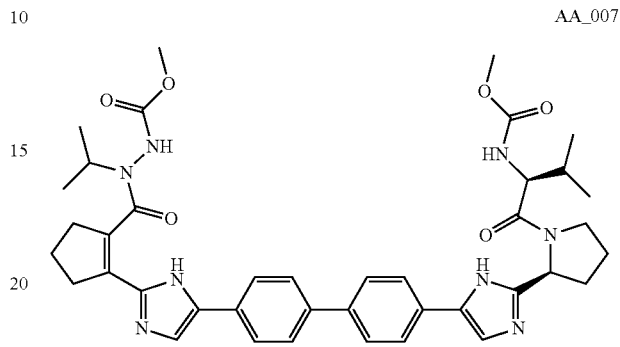

AA_007

Synthetic Route:

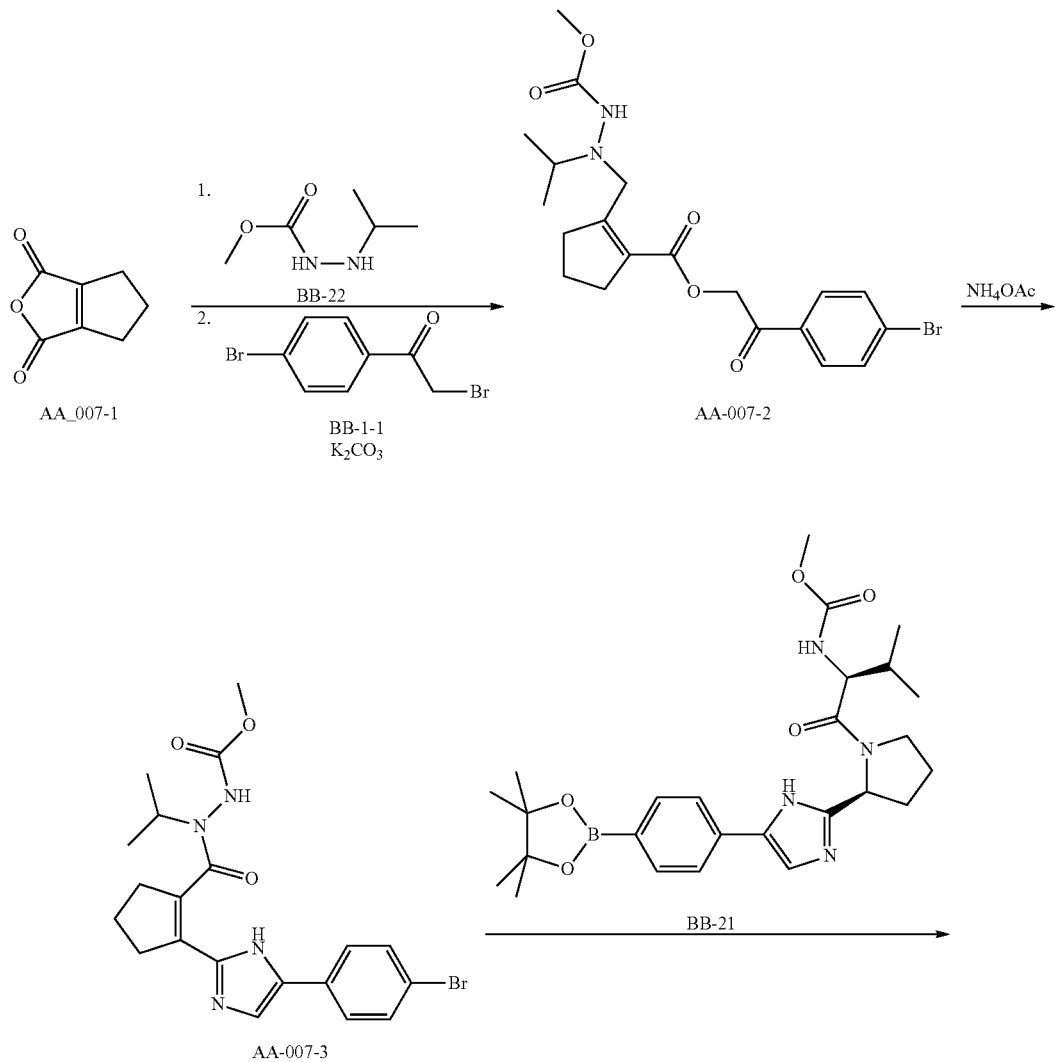

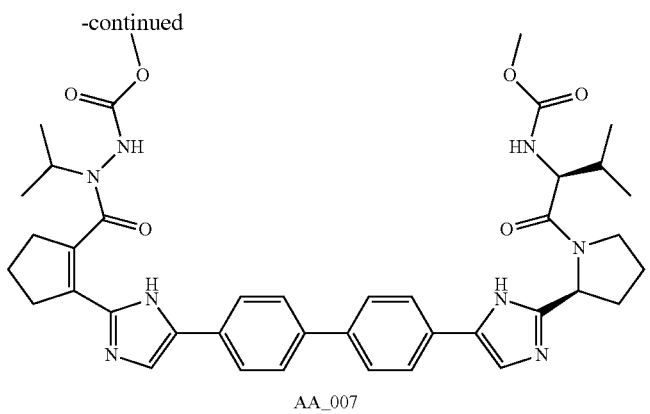

AA_007

Step 1: Synthesis of Compound AA_007-2

At room temperature, 1-cyclopentene-1,2-dicarboxylic anhydride (AA_007-1, 690 mg, 5 mmol) was dissolved in THF (20 mL), compound BB-22 (660 mg, 5 mmol) was added under nitrogen gas atmosphere. The reaction system was stirred at room temperature for 6 h. After the reaction was complete as detected by TLC, the solvent was removed by a rotary evaporator thereby giving colorless jelly. The colorless jelly and $K_2CO_3$ (1.6 g, 11.6 mmol) were suspended in DMF (20 mL), 2,4'-dibromoacetophenone (BB-1-1, 1.6 g, 5.8 mmol) was added at room temperature. The reaction mixture was stirred at room temperature for 1 h. After the reaction was complete as detected by TLC, the reaction was quenched with $H_2O$ (20 mL) and extracted with ethyl acetate (50 mL×3). The organic phases were combined and dried over anhydrous sodium sulfate. After filtration, the filtrate was concentrated under reduced pressure to remove the solvent. The residue was subject to silica gel column chromatography (PE:EA=4:1→1:4) to deliver the target compound AA_007-2 (light yellow powder, 2.0 g, yield for two steps 85.6%). LC/MS m/z: 490.8 [M+H]$^+$ Step 2: Synthesis of Compound AA_007-3

At room temperature, compound AA_007-2 (2 g, 4.28 mmol) was dissolved in toluene (20 mL), ammonium acetate (3.3 g, 42.8 mmol) was added. The reaction mixture was heated to reflux and stirred for 12 h under nitrogen gas atmosphere. After the reaction was complete as detected by TLC, the reaction mixture was cooled to room temperature and quenched with $H_2O$ (30 mL), extracted with ethyl acetate (50 mL×3). The organic phases were combined and dried over anhydrous sodium sulfate. After filtration, the filtrate was concentrated under reduced pressure to remove the solvent, the residue was purified by silica gel column chromatography (PE:EA=9:1→1:1) to deliver the target compound AA_007-3 (light yellow powder, 1.6 g, yield: 83.8%). LCMS m/z: 448.7 [M+H]$^+$ Step 3: Synthesis of Compound AA_007

At room temperature, compound AA_007-3 (40 mg, 0.089 mmol), BB-21 (44 mg, 0.088 mmol) were dissolved in a mixed solvent of 1,2-dimethoxy ethane/$H_2O$ (2 mL/0.2 mL), $Na_2CO_3$ (20 mg, 0.188 mmol) and Pd(dppf)$Cl_2$ (6 mg, 0.0081 mmol) were added under nitrogen gas atmosphere. The reaction mixture was heated to 100° C. and stirred for 8 h under nitrogen gas atmosphere. After the reaction was complete as detected by TLC, the reaction mixture was cooled to room temperature. After filtration, the filtrate was concentrated by a rotary evaporator to remove the solvent. The residue was purified by preparative HPLC to deliver the target compound AA_007 (white powder, 20 mg, yield 30.6%). LC/MS m/z: 737.2 [M+H]$^+$ Embodiment 95: AA_033

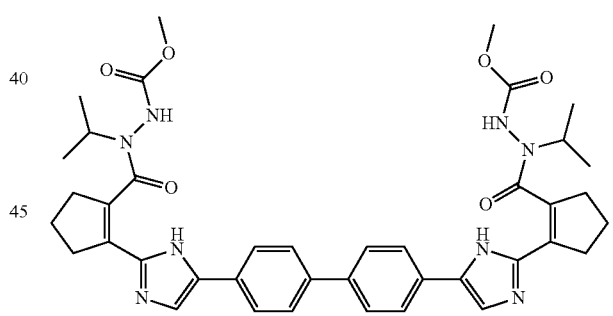

AA_033

Synthetic Route:

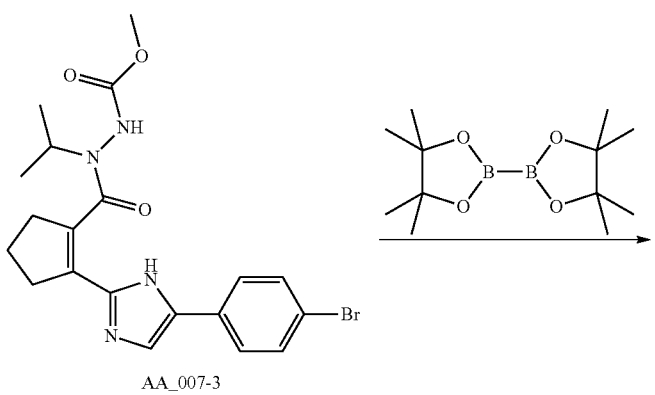

AA_007-3

-continued

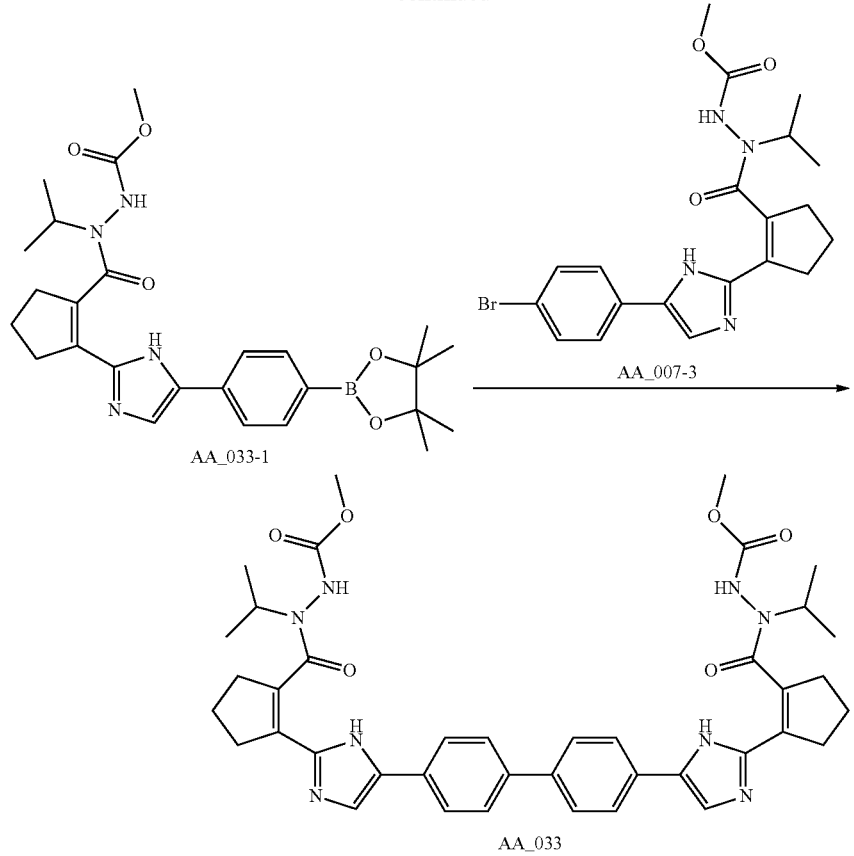

Step 1: Synthesis of Compound AA_033-1

At room temperature, compound AA_007-3 (300 mg, 0.671 mmol), bis(pinacolato)diboron (255 mg, 1.01 mmol) were dissolved in dioxane (10 mL), KOAc (131 mg, 1.342 mmol) and Pd(dppf)Cl$_2$ (50 mg, 0.067 mmol) were added under nitrogen gas atmosphere. The reaction mixture was stirred under 110° C. microwave for 2 h. After the reaction was complete as detected by TLC, the reaction mixture was cooled to room temperature. After filtration, the filtrate was concentrated by a rotary evaporator to remove the solvent, the residue was purified by silica gel column chromatography (PE/EtOAc=9:1→2:1) to deliver the target compound AA_033-1 (85 mg, yield 25.6%). LC/MS m/z: 495 [M+H]$^+$ Step 2: Synthesis of Compound AA_033

At room temperature, compound AA_007-3 (10 mg, 0.022 mmol), AA_033-1 (10 mg, 0.02 mmol) were dissolved in a mixed solvent of 1,2-dimethoxy ethane/H$_2$O (2 mL/0.2 mL), Na$_2$CO$_3$ (4.3 mg, 0.0404 mmol) and Pd(dppf)Cl$_2$ (2 mg, 0.002 mmol) were added under nitrogen gas atmosphere. The reaction mixture was stirred under 100° C. microwave for 8 h. After the reaction was complete as detected by TLC, the reaction mixture was cooled to room temperature. After filtration, the filtrate was concentrated by a rotary evaporator to remove the solvent. The residue was purified by preparative HPLC to deliver the target compound AA_033 (white solid, 4.5 mg, yield 30.3%). LC/MS m/z: 735.5 [M+H]$^+$ Embodiment 96: AA_008

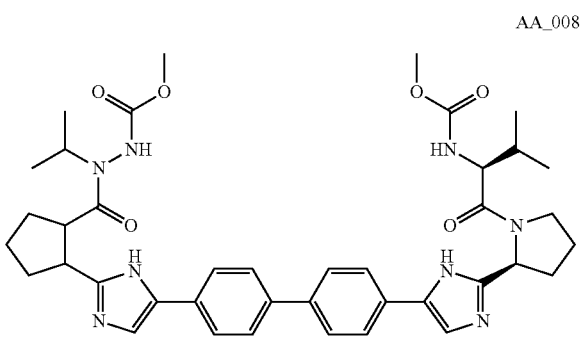

Synthetic Route:

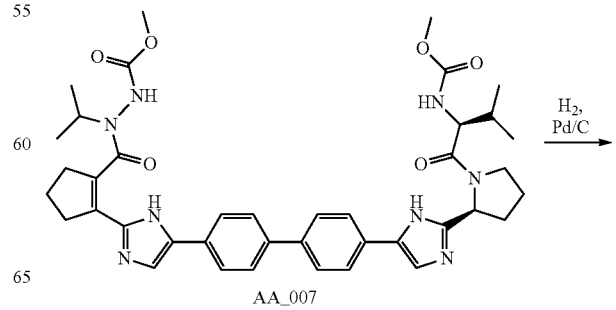

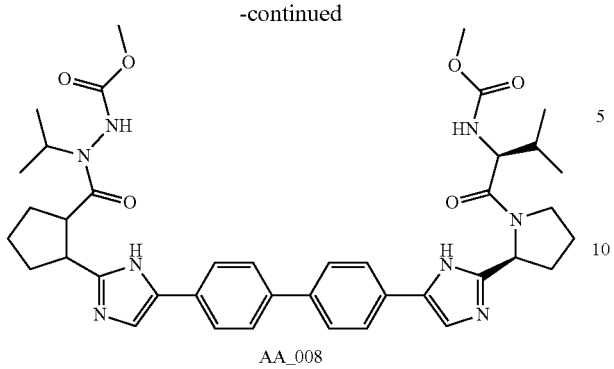

AA_008

Step 1: Synthesis of Compound AA_008

At room temperature, compound AA_007 (20 mg, 0.027 mmol) was dissolved in methanol (5 mL), Pd/C (2 mg) was added under nitrogen gas atmosphere. The reaction mixture was stirred at 50° C. and under a hydrogen gas pressure of 50 psi for 12 h. The reaction mixture was cooled to room temperature. After filtration, the filtrate was concentrated by a rotary evaporator to remove the solvent. The residue was purified by preparative HPLC to deliver the target compound AA_008 (white solid, 8 mg, yield 39.9%). LC/MS m/z: 739.3 [M+H]$^+$ Embodiment 97: AA_138

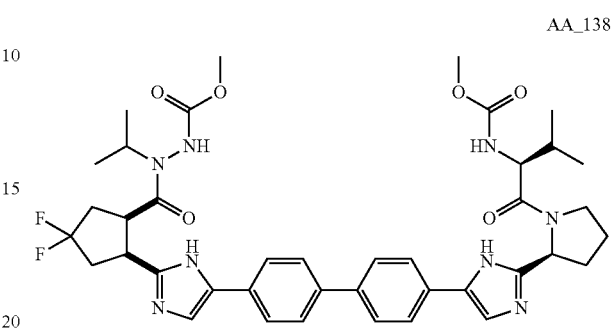

AA_138

Synthetic Route:

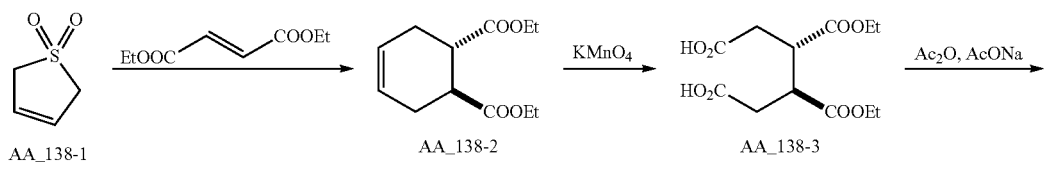

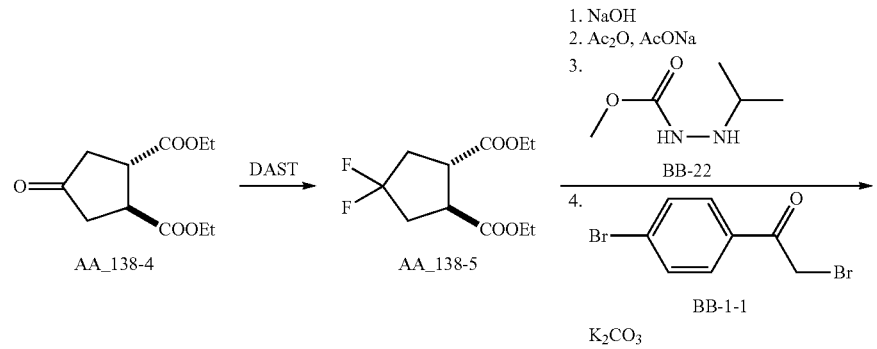

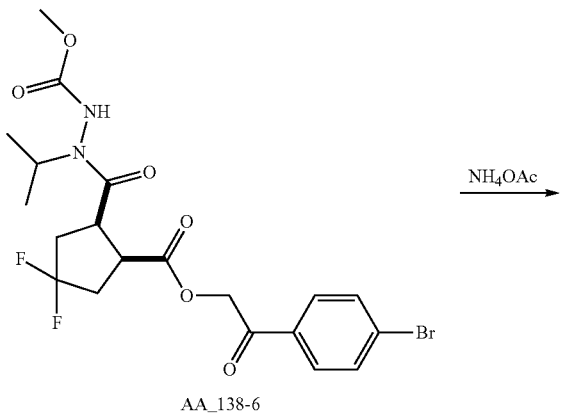

AA_138-6

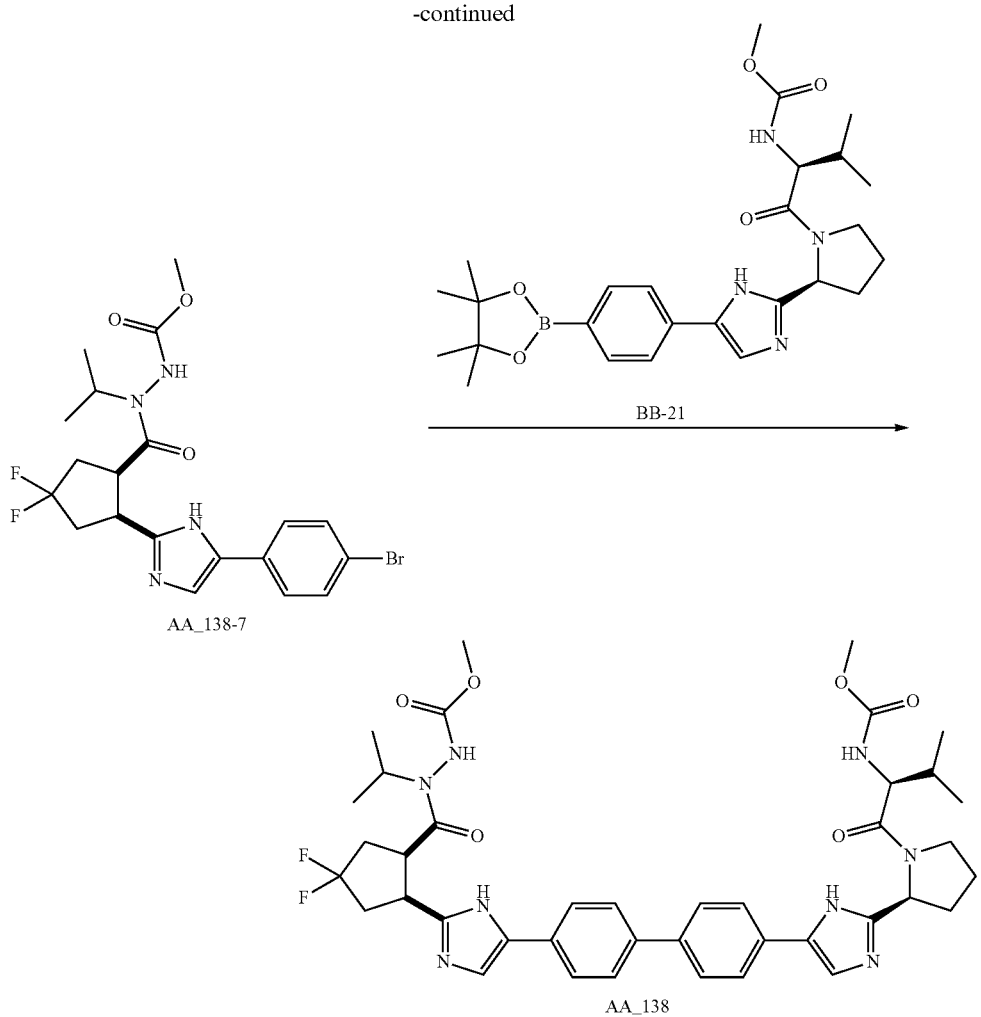

Step 1: Synthesis of Compound AA_138-2

3-Sulfolene (AA_138-1, 30 g, 254.74 mmol), diethyl fumarate (43 g, 249.74 mmol), hydroquinone (0.5 g, 4.5 mmol) were dissolved in anhydrous ethanol (45 mL), and placed in a sealed vessel. The reaction mixture was heated slowly to 125° C. and stirred for 24 h. After the reaction was complete as detected by TLC, the reaction mixture was cooled to room temperature. The reaction system was a yellow liquid, added into a solution of $Na_2CO_3/H_2O$ (30 g, 283 mmol/200 mL), stirred at room temperature for 10 min. The reaction mixture was extracted with petroleum ether (100 mL×3). The organic phases were combined and dried over anhydrous sodium sulfate. After filtration, the filtrate was concentrated by a rotary evaporator to remove the solvent thereby delivering the target compound AA_138-2 (clear liquid, 15 g, yield: 27%). The product was directly used for the next step without purification. $^1$H NMR ($CDCl_3$ 400 MHz): δ 5.68 (d, J=2.4 Hz, 2H), 4.16-4.10 (m, 4H), 2.84-2.82 (m, 2H), 2.44-2.39 (m, 2H), 2.20-2.17 (m, 2H), 1.27-1.22 (m, 6H).

Step 2: Synthesis of Compound AA_138-3

Potassium hypermanganate (11.2 g, 70.9 mmol) was dissolved in $H_2O$ (60 mL), stirred at room temperature for 1 h, cooled with an ice bath, and at no more than 10° C., a solution of compound AA_138-2 (5 g, 22.1 mmol) in acetone (6 mL) was dripped. After dripping, the reaction mixture was stirred overnight at room temperature. After the reaction was complete as detected by TLC, the reaction was quenched with sodium thiosulfate and stirred at room temperature for further 20 min, then cooled to no more than 5° C. under an ice bath, conc. HCl solution was dripped to adjust pH to about 2. The obtained clear reaction liquid was extracted with a mixed solvent of EA/THF (50 mL/50 mL) for 3 times. The organic phases were combined and dried over anhydrous sodium sulfate. After filtration, the filtrate was concentrated by a rotary evaporator to remove the solvent thereby delivering the target compound AA_138-3 (white solid, 3.75 g, yield 58.5%). The product was directly used for the next step without purification. $^1$H NMR (DMSO-d6, 400 MHz): δ 4.07-4.01 (m, 4H), 3.01 (d, J=11.6 Hz, 2H), 2.66-2.59 (m, 2H), 2.43-2.38 (m, 2H), 1.15 (t, J=7.2 Hz, 6H).

Step 3: Synthesis of Compound AA_138-4

Compound AA_138-3 (3.75 g, 12.9 mmol) was dissolved in acetic anhydride (19 mL). The reaction system was heated to 130° C. and stirred for 2 h, sodium acetate (0.94 g, 11.5 mmol) was added for one time, the reaction mixture was further stirred at 130° C. until no $CO_2$ was produced, and then cooled to room temperature. The reaction was quenched with methanol/$H_2O$ (10 mL/10 mL), the mixture was stirred at room temperature for 30 min and extracted with dichloromethane (50 mL×4). The organic phases were combined and dried over anhydrous sodium sulfate. After filtration, the filtrate was concentrated under reduced pressure to remove the solvent, the residue was purified by silica gel column chromatography (PE/EtOAc=20:1→5:1) to deliver the target compound AA_138-4 (yellow oil, 2.9 g, yield 98.6%). $^1$H NMR (CDCl$_3$ 400 MHz): δ 4.19-4.14 (m, 4H), 3.34-3.31 (m, 2H), 2.66-2.59 (m, 2H), 2.59-2.50 (m, 2H), 1.25 (t, J=7.6 Hz, 6H).

Step 4: Synthesis of Compound AA_138-5

Compound AA_138-4 (2.0 g, 8.76 mmol) was dissolved in anhydrous dichloromethane (20 mL). After cooling to 0° C., DAST (2.82 g, 17.53 mmol) was dripped. After the dripping, the reaction mixture was stirred at room temperature overnight. After the reaction was complete as detected by TLC, the reaction mixture was poured into ice-water (20 mL), saturated sodium bicarbonate solution was dripped to adjust pH to 7-8, then extracted with dichloromethane (30 mL×3). The organic phases were combined and dried over anhydrous sodium sulfate. After filtration, the filtrate was concentrated by a rotary evaporator to remove the solvent thereby delivering the target compound AA_138-5 (black oil, 1.5 g, yield 68.5%). The product was directly used for the next step without purification. $^1$H NMR (CDCl$_3$, 400 MHz): δ 4.18 (q, J=7.6 Hz, 4H), 3.34-3.29 (m, 2H), 2.51-2.34 (m, 4H), 1.26 (s, d=7.2 Hz, 6H).

Step 5: Synthesis of Compound AA_138-6

NaOH (959 mg, 23.98 mmol) was dissolved in a mixed solvent of methanol/H$_2$O (5 mL/5 mL), compound AA_138-5 (1.5 g, 5.99 mmol) was added. The reaction mixture was stirred at room temperature for 2 h. After the reaction was complete as detected by TLC, the solvent was removed by a rotary evaporator. The residue was dissolved in H$_2$O (20 mL), 2M HCl was dripped to adjust pH to 1-2, the mixture was extracted with dichloromethane (20 mL×3). The organic phases were combined and dried over anhydrous sodium sulfate. After filtration, the filtrate was concentrated by a rotary evaporator to remove the solvent thereby delivering milk-white solid (912 mg). The milk-white solid (912 mg, 5.18 mmol) was dissolved in acetic anhydride (15 mL), the reaction system was heated to reflux and stirred for 3 h. After the reaction was complete as detected by TLC, the solvent was removed by a rotary evaporator thereby delivering black oil (914 mg). The black oil (457 mg, 2.59 mmol) was dissolved in THF (10 mL), BB-22 (343 mg, 2.59 mmol) was added, and the reaction mixture was stirred at room temperature for 4 h. After the reaction was complete as detected by TLC, the solvent was removed by a rotary evaporator thereby delivering thick oil (780 mg). The thick oil (780 mg, 2.53 mmol) and DIPEA (1.09 g, 5.06 mmol) were dissolved in acetonitrile (5 mL), 2,4-dibromoacetophenone (BB-1-1, 721.3 mg, 2.6 mmol) was added. The reaction mixture was stirred at room temperature for 3 h. After the reaction was complete as detected by TLC, the solvent was removed under reduced pressure. The residue was purified by silica gel column chromatography (PE/EtOAc=10:1→5:1) to deliver the target compound AA_138-6 (yellow oil, 0.6 g, yield for four steps 19.8%). LC/MS m/z: 528.9 [M+Na]$^+$ Step 6: Synthesis of Compound AA_138-7

At room temperature, compound AA_138-6 (600 mg, 1.19 mmol) was dissolved in toluene (10 mL), ammonium acetate (784 mg, 10.18 mmol) was added. The reaction mixture was heated to reflux and stirred overnight under nitrogen gas atmosphere. After the reaction was complete as detected by TLC, the reaction mixture was cooled to room temperature and quenched with H$_2$O (10 mL), extracted with ethyl acetate (30 mL×3). The organic phases were combined and dried over anhydrous sodium sulfate. After filtration, the filtrate was concentrated under reduced pressure to remove the solvent, the residue was purified by silica gel column chromatography (PE/EA=9:1→1:1) to deliver the target compound AA_ 138-7 (yellow solid, 90 mg, yield: 16%). LC/MS m/z: 487.0 [M+H]$^+$ Step 7: Synthesis of Compound AA_138

Compound AA_138 was synthesized according to the synthetic step 3 in synthesizing AA_007, with compound AA_138-7 and BB-21 as the starting materials. LC/MS m/z: 775.5 [M+H]$^+$ Embodiment 98: AA_160

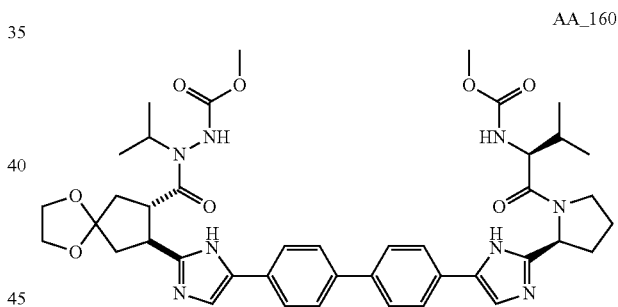

AA_160

Synthetic Route:

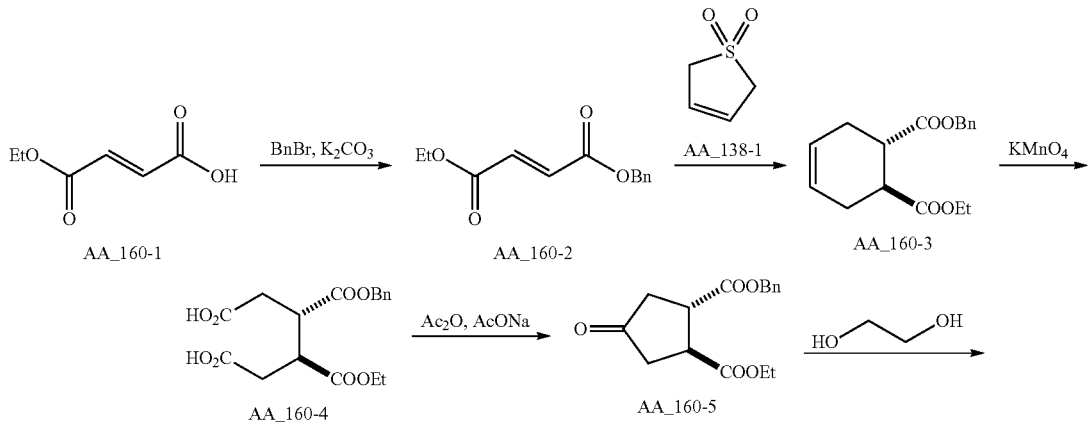

397 398
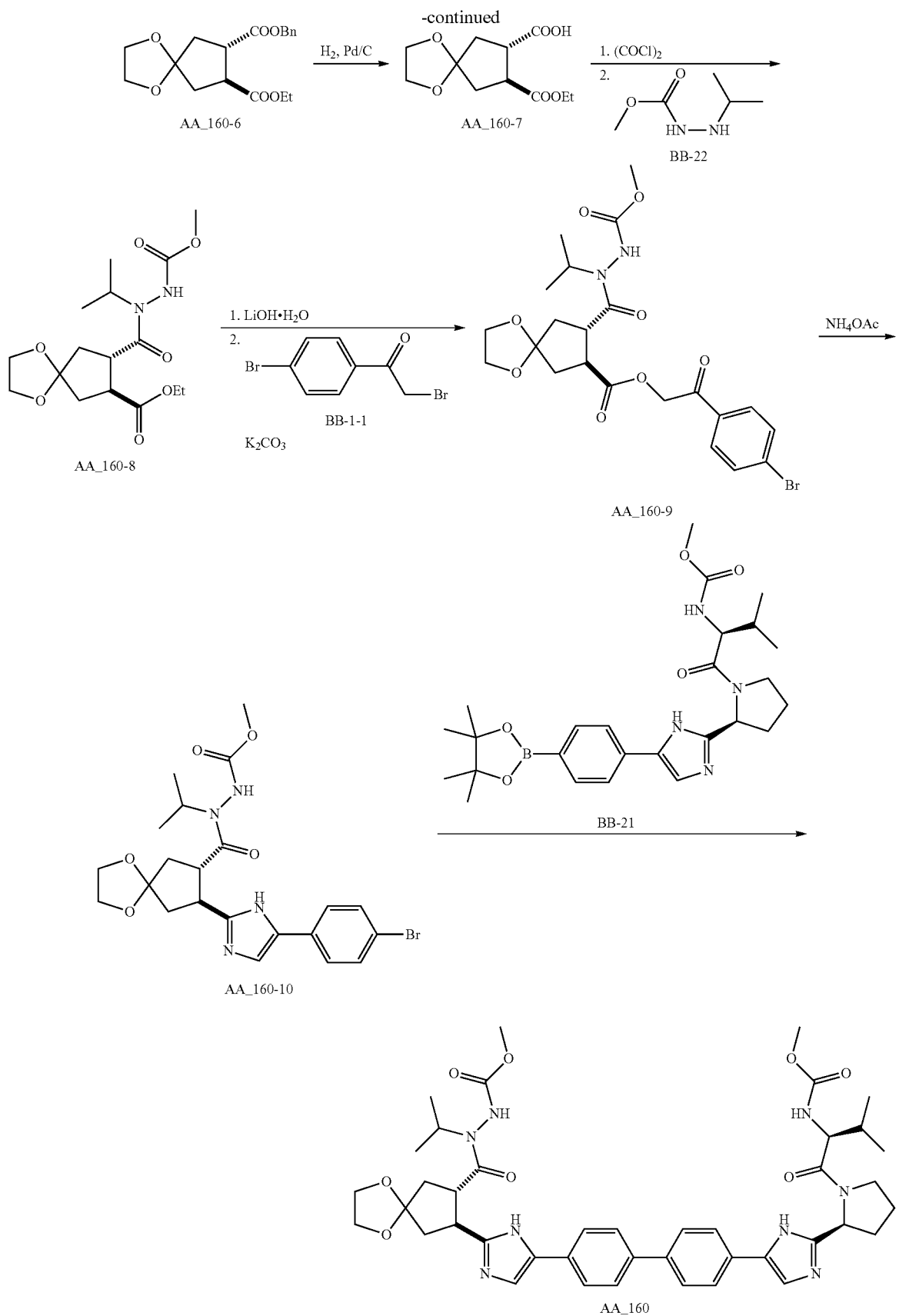

Step 1: Synthesis of Compound AA_160-2

Monoethyl fumarate (AA_160-1, 50 g, 347.2 mmol) and $K_2CO_3$ (95.89 g, 693.8 mmol) were suspended in DMF (1500 mL), benzyl bromide (59.34 g, 346.9 mmol) was dripped at room temperature. The reaction mixture was stirred at room temperature for 12 h. After the reaction was complete as detected by TLC, the reaction mixture was diluted with ethyl acetate (2 L) and washed with $H_2O$ (100 mL×4) and saturated brines (200 mL). The organic phases were combined and dried over anhydrous sodium sulfate. After filtration, the filtrate was concentrated by a rotary evaporator to remove the solvent thereby delivering the target compound AA_160-2 (light yellow oil, 79 g, yield: 97%). The product was directly used for the next step without purification. $^1$H NMR (CDCl$_3$, 400 MHz): δ 7.38-7.37 (m, 5H), 6.90 (s, 2H), 5.24 (s, 2H), 4.26 (q, J=6.8 Hz, 2H), 1.31 (t, J=6.8 Hz, 3H).

Step 2: Synthesis of Compound AA_160-3

Compound AA_160-3 (36 g, yield 97.5%) was synthesized according to the synthetic step 1 in synthesizing AA_138, with 3-sulfolene (AA_138-1, 15.43 g, 130.6 mmol), AA_160-2 (30 g, 128 mmol) and hydroquinone (0.24 g, 2.18 mmol) as the starting materials. $^1$H NMR (CDCl$_3$, 400 MHz): δ 7.36-7.31 (m, 5H), 5.71-5.66 (m, 2H), 5.19-5.08 (m, 2H), 4.13-4.07 (m, 2H), 2.94-2.86 (m, 2H), 2.43-2.42 (m, 2H), 2.22-2.19 (m, 2H), 1.20 (t, d=2.8 Hz, 3H).

Step 3: Synthesis of Compound AA_160-4

Compound AA_160-4 (44 g, yield 95%) was synthesized according to the synthetic step 2 in synthesizing AA_138, with compound AA_160-3 (38 g, 132 mmol) and potassium hypermanganate (64.5 g, 409 mmol) as the starting material, and $H_2O$ (330 mL) as the solvent. $^1$H NMR (DMSO d$_6$, 400 MHz) δ 7.36-7.31 (m, 5 H), 5.07 (s, 2 H), 4.02-3.98 (m, 2 H), 3.11-3.05 (m, 2 H), 2.66-2.62 (m, 2 H), 2.42-2.37 (m, 2 H), 1.12 (t, J=7.2 Hz, 3 H).

Step 4: Synthesis of Compound AA_160-5

Compound AA_160-5 (7.0 g, yield 63.1%) was synthesized according to the synthetic step 3 in synthesizing AA_138, with compound AA_160-4 (13.5 g, 38.3 mmol), acetic anhydride (67.5 mL), sodium acetate (2.7 g, 33.7 mmol) as the starting materials. $^1$H NMR (CDCl$_3$, 400 MHz) δ 7.36-7.32 (m, 5H), 5.17 (s, 2H), 4.14-4.10 (m, 2H), 3.44-3.36 (m, 2H), 2.68-2.61 (m, 2H), 2.56-2.49 (m, 2H), 1.19 (t, d=7.2 Hz, 3H).

Step 5: Synthesis of Compound AA_160-6

Compound AA_160-5 (5.0 g, 17.2 mmol), ethylene glycol (10.6 g, 172 mmol) were dissolved in toluene (150 mL), p-toluenesulfonic acid monohydrate (163 mg, 0.86 mmol) was added. The reaction system was heated to reflux under nitrogen gas atmosphere, stirred overnight. After the reaction was complete as detected by TLC, the reaction mixture was cooled to room temperature and washed with $H_2O$ (30 mL×3), saturated brines (30 mL). The organic phase was dried over anhydrous sodium sulfate. After filtration, the filtrate was concentrated by a rotary evaporator to remove the solvent thereby delivering the target compound AA_160-6 (yellow solid, 3.2 g, yield 55%). The product was directly used for the next step without purification. $^1$H NMR (CDCl$_3$, 400 MHz): δ 7.35-7.31 (m, 5H), 5.17-5.11 (m, 2H), 4.11 (q, J=2.0 Hz, 2H), 3.91-3.88 (m, 4H), 3.34-3.27 (m, 2H), 2.25-2.23 (m, 2H), 2.22-2.09 (m, 2H), 1.19 (t, d=6.8 Hz, 3H).

Step 6: Synthesis of Compound AA_160-7

At room temperature, compound AA_160-6 (3.9 g, 11.7 mmol) was dissolved in ethanol (40 mL), 10% Pd/C (0.5 g) was added under nitrogen gas atmosphere. The reaction mixture was stirred at 50° C. and under a hydrogen gas pressure of 1 atm for 3 h. The reaction mixture was cooled to room temperature, filtrated, the filtrate was concentrated by a rotary evaporator to remove the solvent thereby delivering the target compound AA_160-7 (yellow oil, 2.7 g, yield 94.7%). The product was directly used for the next step without purification. $^1$H NMR (CDCl$_3$, 400 MHz): δ 4.20-4.15 (m, 2H), 3.94-3.90 (m, 4H), 3.33-3.24 (m, 2H), 2.26-2.23 (m, 2H), 2.23-2.09 (m, 2H), 1.27-1.23 (m, 3H).

Step 7: Synthesis of Compound AA_160-8

At room temperature, compound AA_160-7 (356 mg, 1.46 mmol) was dissolved in dichloromethane (2 mL), oxalyl chloride (371 mg, 2.92 mmol) was dripped, 2 drops of DMF was added to catalyze the reaction. The reaction system was stirred at room temperature for 2 h. After the reaction was complete as detected by TLC, the solvent was removed by a rotary evaporator thereby obtaining an acyl chloride intermediate. The acyl chloride intermediate was dissolved in dichloromethane (5 mL), cooled to no more than 5° C. under an ice bath, BB-22 (192.6 mg, 1.46 mmol) was added, and then TEA (884 mg, 8.76 mmol) was dripped. The reaction mixture was stirred at room temperature overnight. After the reaction was complete as detected by TLC, the solvent was removed under reduced pressure, the residue was purified by silica gel column chromatography (PE/EtOAc=10:1→3:1) to deliver the target compound AA_160-8 (yellow powder, 670 mg, yield for two steps 76%). $^1$H NMR (CDCl$_3$, 400 MHz): δ: 4.77-4.75 (m, 1H), 4.15-4.04 (m, 2H), 3.86-3.84 (m, 3H), 3.72-3.65 (m, 4H), 3.48-3.53 (m, 2H), 2.75-2.25 (m, 2H), 2.25-2.20 (m, 2H), 1.20-1.17 (m, 3H), 1.04-0.97 (m, 6H).

Step 8: Synthesis of Compound AA_160-9

At room temperature, compound AA_160-8 (670 mg, 1.87 mmol) was dissolved in a mixed solvent of methanol/$H_2O$ (2.5 mL/2.5 mL), lithium hydroxide monohydrate (307 mg, 7.5 mmol) was added. The reaction system was stirred at 60° C. for 6 h. After the reaction was complete as detected by TLC, the reaction mixture was cooled to room temperature and 1M HCl aqueous solution was dripped to adjust pH to 2-3, extracted with dichloromethane (50 mL×3). The organic phases were combined and dried over anhydrous sodium sulfate. After filtration, the filtrate was concentrated by a rotary evaporator to remove the solvent thereby obtaining a carboxylic acid intermediate (210 mg). The carboxylic acid intermediate (210 mg) and $K_2CO_3$ (178 mg, 1.28 mmol) were suspended in DMF (5 mL), 2,4-dibromoacetophenone (BB-1-1, 177.92 mg, 0.64 mmol) was added at room temperature. The reaction mixture was stirred at room temperature for 2 h. After the reaction was complete as detected by TLC, the reaction mixture was poured into $H_2O$ (20 mL) and extracted with ethyl acetate (50 mL×3). The organic phases were combined and dried over anhydrous sodium sulfate. After filtration, the filtrate was concentrated under reduced pressure to remove the solvent, the residue was purified by silica gel column chromatography (PE/EtOAc=10:1→3:1) to deliver the target compound AA_160-9 (yellow oil, 700 mg, yield 71%). LC/MS m/z: 529.3 [M+H]$^+$, 549.0 [M+Na]$^+$ Step 9: Synthesis of Compound AA_160-10

At room temperature, compound AA_160-9 (70 mg, 0.133 mmol) was dissolved in toluene (20 mL), ammonium acetate (204 mg, 2.65 mmol) was added. The reaction mixture was heated to reflux and stirred overnight under nitrogen gas atmosphere. After the reaction was complete as detected by TLC, the reaction mixture was cooled to room temperature and quenched with H₂O (30 mL), extracted with ethyl acetate (50 mL×3). The organic phases were combined and dried over anhydrous sodium sulfate. After filtration, the filtrate was concentrated under reduced pressure to remove the solvent, the residue was purified by silica gel column chromatography (PE:EA=10:1→3:1) to deliver the target compound AA_160-10 (yellow solid, 40 mg, yield: 60%). LC/MS m/z: 507.1 [M+H]$^+$ Step 10: Synthesis of Compound AA_160

Compound AA_160 was synthesized according to the synthetic step 3 in synthesizing AA_007, with compound AA_160-10 and BB-21 as starting materials. LC/MS m/z: 797.5 [M+H]$^+$ Embodiment 99: AA_014

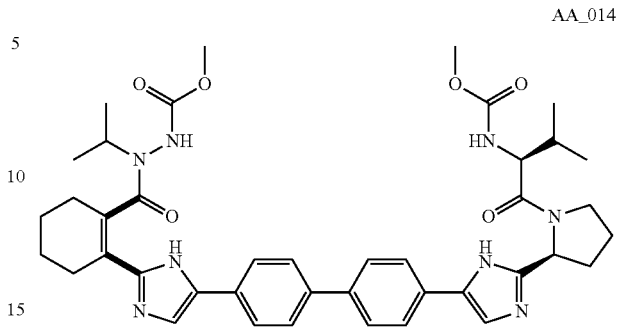

Synthetic Route:

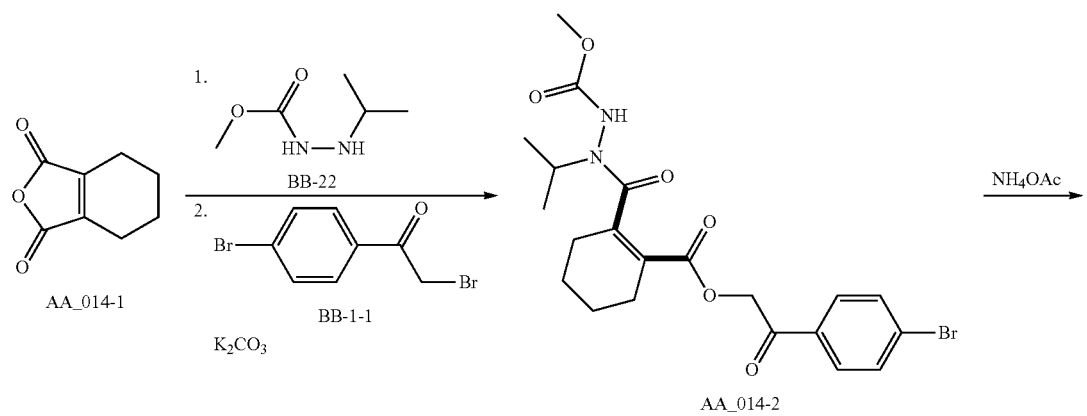

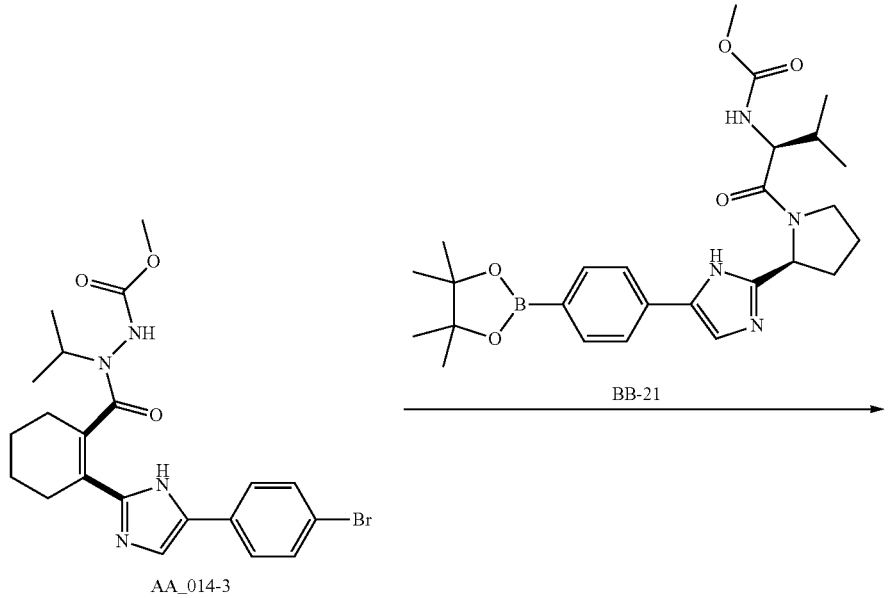

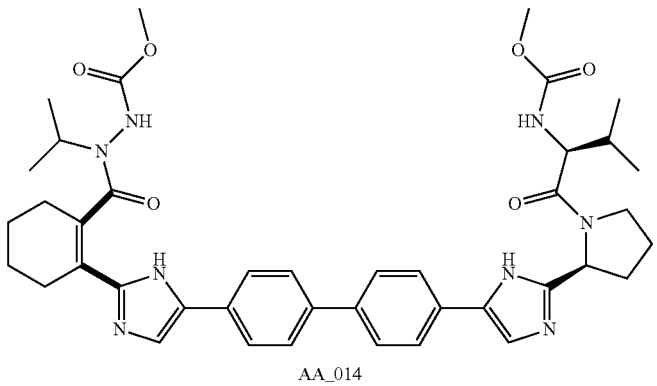

AA_014

Step 1: Synthesis of Compound AA_014-2

Compound BB-22 (0.5 g, 3.8 mmol) was dissolved in THF (10 mL), 1-cyclohexene-1,2-dicarboxylic anhydride (AA_014-1, 0.88 g, 5.78 mmol) was added at 10° C. The reaction system was stirred at 10° C. for 14 h. After the reaction was complete as detected by TLC, the solvent was removed by a rotary evaporator thereby giving colorless jelly (1.3 g). The colorless jelly and $K_2CO_3$ (1.3 g, 9.2 mmol) were suspended in DMF (15 mL), 2,4-dibromoacetophenone (BB-1-1, 1.3 g, 4.6 mmol) was added at room temperature. The reaction mixture was stirred at 10° C. for 12 h. After the reaction was complete as detected by TLC, the reaction was quenched with $H_2O$ (10 mL) and extracted with ethyl acetate (100 mL×2). The organic phases were combined and dried over anhydrous sodium sulfate. After filtration, the filtrate was concentrated under reduced pressure to obtain the crude product, which was purified by silica gel column chromatography (PE:EA=10:1→3:1) to deliver the target compound AA_014-2 (1 g, yield for two steps 35.9%). LC/MS (ESI) m/z 482.9 [M+H]$^+$ Step 2: Synthesis of Compound AA_014-3

At room temperature, compound AA_014-2 (1 g, 2.1 mmol) was dissolved in toluene (60 mL), ammonium acetate (10 g, 130 mmol) was added, and the reaction mixture was heated to 120° C. and stirred for 6 h under nitrogen gas atmosphere. After the reaction was complete as detected by TLC, the reaction mixture was cooled to room temperature and quenched with $H_2O$ (50 mL), extracted with ethyl acetate (100 mL×3). The organic phases were combined and dried over anhydrous sodium sulfate. After filtration, the filtrate was concentrated under reduced pressure to remove the solvent, the residue was purified by silica gel column chromatography (PE:EA=10:1→1:1) to deliver the target compound AA_014-3 (0.2 g, yield: 20%). LC/MS (ESI) m/z 460.9 [M+H]$^+$ Step 3: Synthesis of Compound AA_014

At room temperature, compound AA_014-3 (50 mg, 0.11 mmol), BB-21 (54 mg, 0.11 mmol) were dissolved in a mixed solvent of 1,2-dimethoxy ethane/$H_2O$ (2 mL/0.5 mL), $Na_2CO_3$ (35 mg, 0.33 mmol) and Pd(PPh$_3$)$_4$ (13 mg, 0.011 mmol) were added under nitrogen gas atmosphere. The reaction mixture was stirred under 120° C. microwave for 10 min. After the reaction was complete as detected by TLC, the reaction mixture was cooled to room temperature, filtrated, and the filtrate was concentrated under reduced pressure to remove the solvent thereby obtaining the residue, which was purified by preparative HPLC to deliver the target compound AA_014 (4.7 mg, yield 6%). LC/MS (ESI) m/z 751.2 [M+H]$^+$. $^1$H NMR (400 MHz, CD$_3$OD) δ 7.84-7.74 (m, 8H), 7.69-7.67 (m, 2H), 5.21-5.18 (m, 1H), 4.63 (brs, 1H), 4.26-4.24 (m, 1H), 4.02-3.99 (m, 1H), 3.92 (m, 1H), 3.80 (s, 3H), 3.68 (s, 3H), 2.40-2.19 (m, 2H), 2.08 (m, 3H), 1.82 (m, 3H), 1.31 (brs, 1H), 1.21-1.20 (m, 4H), 1.02-0.92 (m, 12H).

Embodiment 100: AA_013_A and AA_013_B

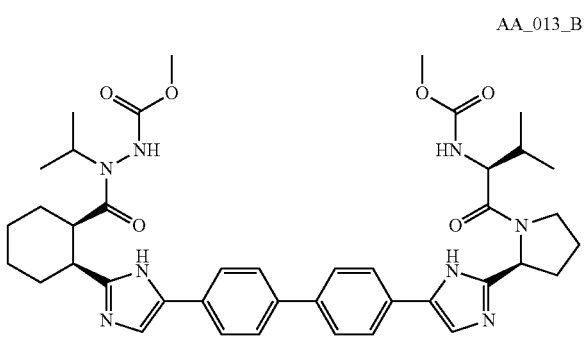

AA_013_B

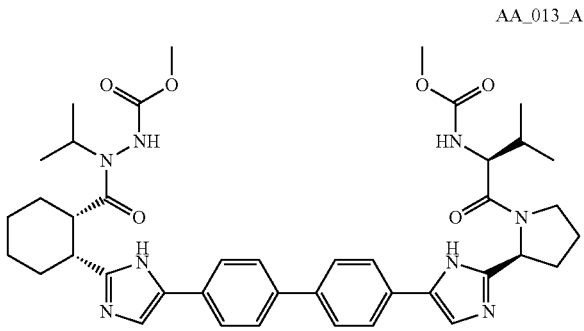

AA_013_A

Synthetic Route:
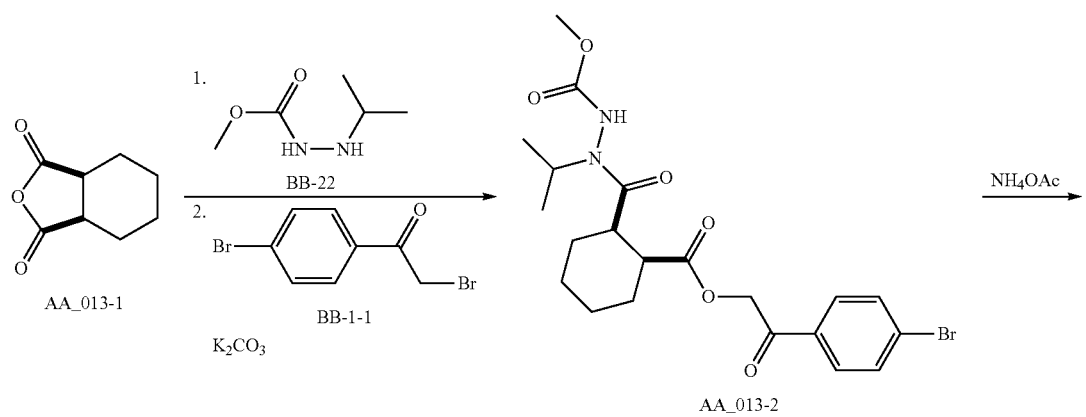
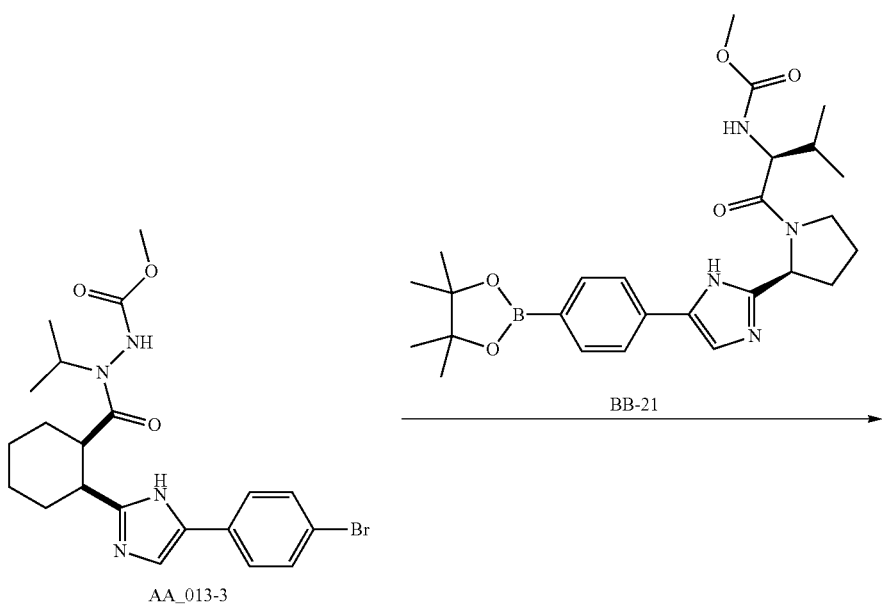
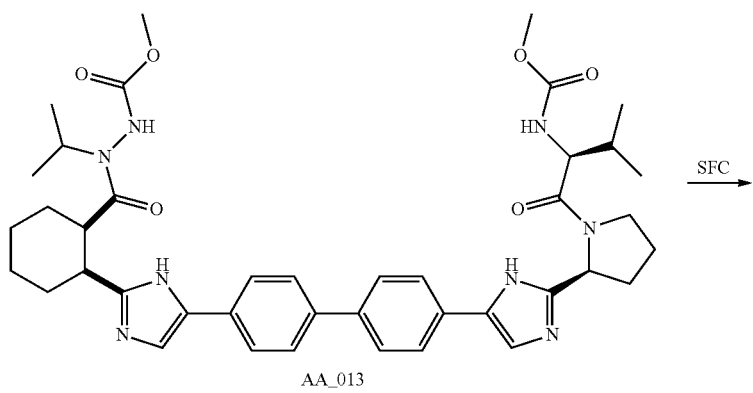

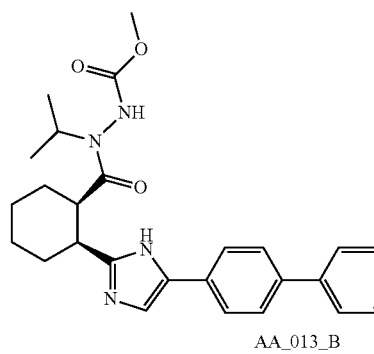

AA_013_B

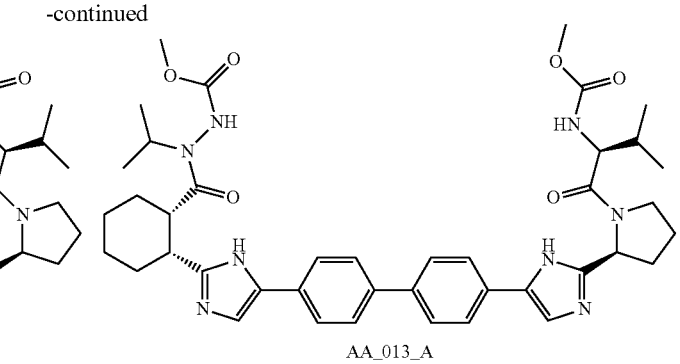

AA_013_A

Step 1: Synthesis of Compound AA_013-2

Compound BB-22 (1 g, 7.6 mmol) was dissolved in THF (10 mL), cis-1,2-cyclohexane-dicarboxylic anhydride (AA_013-1, 1 g, 6.5 mmol) was added at 10° C. The reaction system was stirred at 10° C. for 14 h. After the reaction was complete as detected by TLC, the solvent was evaporated by a rotary evaporator thereby giving colorless jelly (1.8 g), which was directly used for the next step without purification. The colorless jelly and $K_2CO_3$ (2 g, 14.0 mmol) were suspended in DMF (20 mL), 2,4-dibromoacetophenone (BB-1-1, 2 g, 7.0 mmol) was added at 10° C. The reaction mixture was stirred at 10° C. for 12 h. After the reaction was complete as detected by TLC, the reaction was quenched with $H_2O$ (10 mL) and extracted with ethyl acetate (100 mL×2). The organic phases were combined and dried over anhydrous sodium sulfate. After filtration, the filtrate was concentrated under reduced pressure to remove the solvent, the residue was purified by silica gel column chromatography (PE:EA=10:1→3:1) to deliver the target compound AA_013-2 (1 g, yield for two steps 31.9%). LC/MS m/z 482.8 $[M+H]^+$ Step 2: Synthesis of Compound AA_013-3

At room temperature, compound AA_013-2 (1 g, 2.1 mmol) was dissolved in toluene (40 mL), ammonium acetate (7 g, 91 mmol) was added, and the reaction mixture was heated to 120° C. and stirred for 6 h under nitrogen gas atmosphere. After the reaction was complete as detected by TLC, the reaction mixture was cooled to room temperature and quenched with $H_2O$ (30 mL), extracted with ethyl acetate (50 mL×3). The organic phases were combined and dried over anhydrous sodium sulfate. After filtration, the filtrate was concentrated under reduced pressure to remove the solvent, the residue was purified by silica gel column chromatography (PE:EA=10:1→1:1) to deliver the target compound AA_013-3 (0.4 g, yield: 41.7%). LC/MS (ESI) m/z 464.7 $[M+H]^+$ Step 3: Synthesis of Compound AA_013

At room temperature, compound AA_013-3 (300 mg, 0.65 mmol), BB-21 (330 mg, 0.64 mmol) were dissolved in a mixed solvent of 1,2-dimethoxy ethane/$H_2O$ (3 mL/0.5 mL), $Na_2CO_3$ (210 mg, 1.95 mmol) and $Pd(PPh_3)_4$ (150 mg, 0.13 mmol) were added under nitrogen gas atmosphere. The reaction mixture was stirred under 120° C. microwave for 10 min. After the reaction was complete as detected by TLC, the reaction mixture was cooled to room temperature. After filtration, the filtrate was concentrated under reduced pressure to remove the solvent, the residue was purified by preparative HPLC to deliver the target compound AA_013 (53 mg, yield 11%). $^1$H NMR (400 MHz, METHANOL-$d_4$) δ 0.79-1.35 (m, 14H), 1.43-2.13 (m, 10H), 2.17 (br. s., 5H), 3.03-3.26 (m, 2H), 3.67 (br. s., 5H), 3.82 (d, J=15.31 Hz, 5H), 4.25 (d, J=7.03 Hz, 1H), 4.49-4.73 (m, 1H), 5.19 (br. s., 1H), 7.33 (br. s., 2H), 7.68 (br. s., 8H).

Step 4: Synthesis of Compound AA_013_A and AA_013_B

Compound AA_013 (40 mg, 0.05 mmol) was separated by chiral preparative SFC to deliver the target compound AA_013_A (16.5 mg) and AA_013_B (14.5 mg). AA_013_A: $^1$H NMR (400 MHz, CD$_3$OD) □ δ 7.81-7.67 (m, 8H), 7.34 (brs, 2H), 5.21-5.18 (m, 1H), 4.26-4.24 (m, 1H), 4.03-3.89 (m, 2H), 3.85-3.81 (m, 2H), 3.67 (s, 3H), 3.52 (brs, 1H), 3.37 (s, 3H), 3.25-3.09 (m, 2H), 2.37-2.20 (m, 2H), 2.12-1.91 (m, 5H), 1.51-1.49 (m, 2H), 1.10-0.92 (m, 14H), 0.80 (m, 2H). AA_013_B: $^1$H NMR (400 MHz, CD$_3$OD) □ δ 7.78-7.68 (m, 8H), 7.36-7.33 (m, 2H), 5.19 (m, 1H), 4.26-4.24 (m, 1H), 4.05-3.91 (m, 2H), 3.84-3.80 (m, 2H), 3.67 (s, 3H), 3.52 (brs, 1H), 3.37-3.10 (m, 5H), 2.37-2.29 (m, 2H), 2.06-1.93 (m, 5H), 1.51 (m, 2H), 1.09-0.92 (m, 14H), 0.79 (m, 2H).

Embodiment 101: AA_090_A and AA_090_B

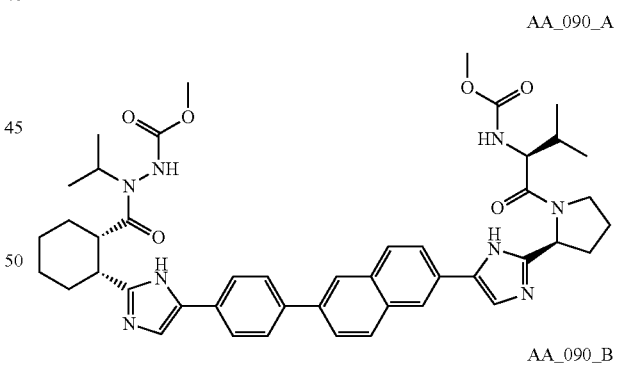

AA_090_A

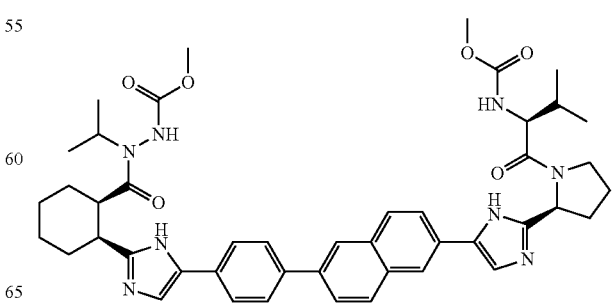

AA_090_B

Synthetic Route:
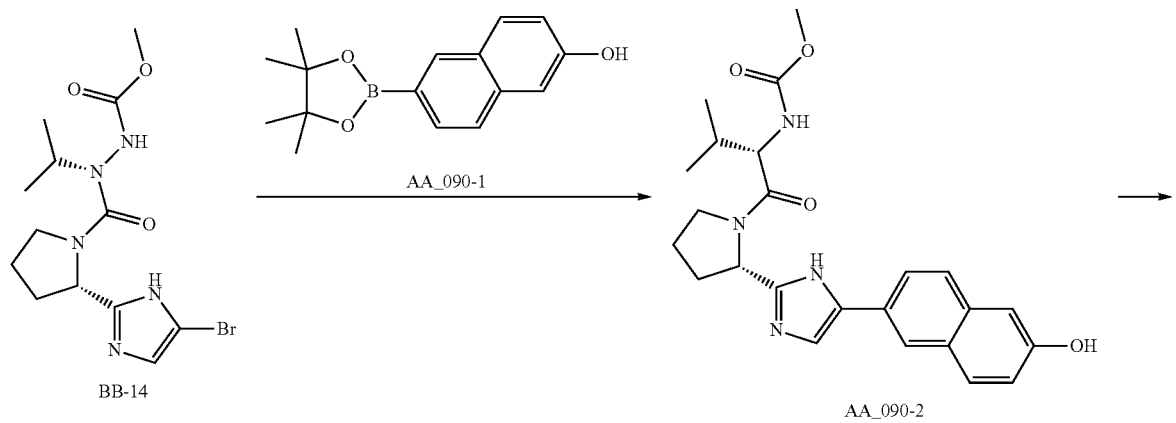
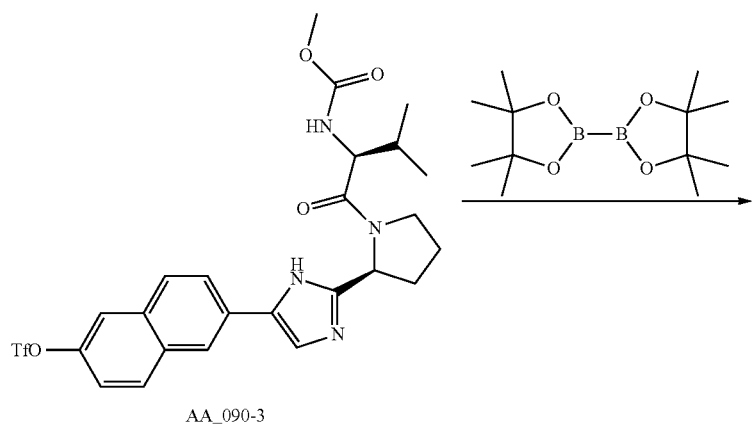
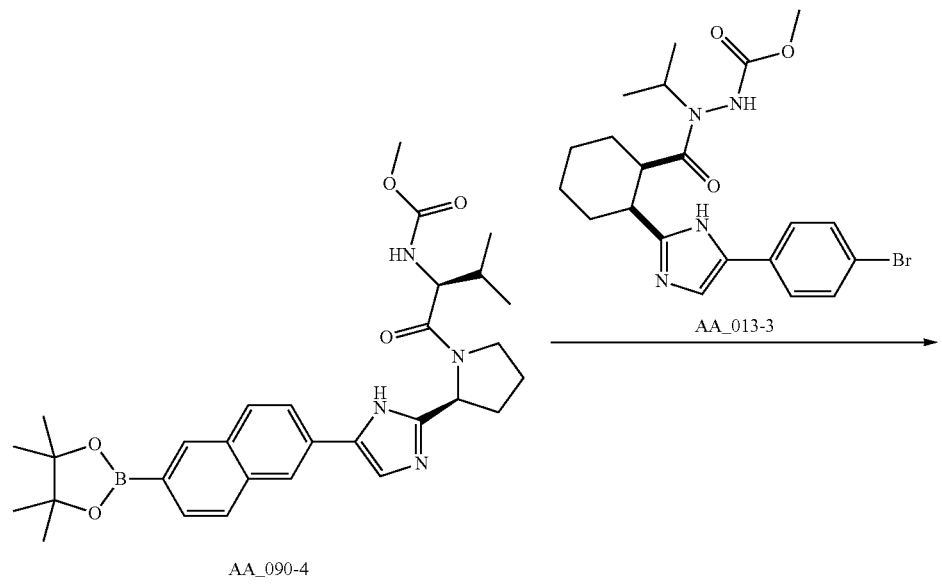

-continued

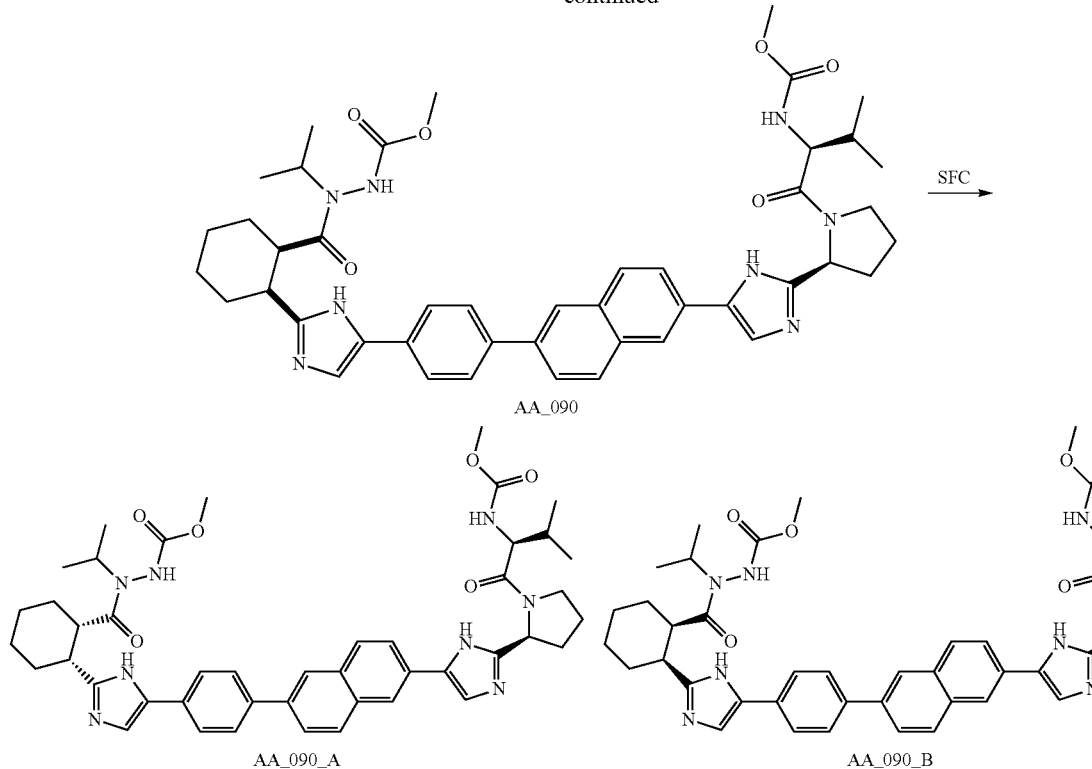

Step 1: Synthesis of Compound AA_090-2

At room temperature, compound BB-14 (303 mg, 0.814 mmol), AA_090-1 (200 mg, 0.74 mmol) were dissolved in a mixed solvent of DMF/THF/H$_2$O (2 mL/2 mL/2 mL), Na$_2$CO$_3$ (156 mg, 1.48 mmol) and Pd(dppf)Cl$_2$ (15.7 mg, 0.02 mmol) were added under nitrogen gas atmosphere. The reaction mixture was heated to 110° C. and stirred for 2 h under nitrogen gas atmosphere. After the reaction was complete as detected by TLC, the reaction mixture was cooled to room temperature, filtrated, the filtrate was concentrated by a rotary evaporator to remove the solvent, the residue was purified by silica gel column chromatography (PE:EA=1:2) to deliver the target compound AA_090-2 (220 mg, yield 68%). LC/MS m/z: 437.0 [M+H]$^+$.

Step 2: Synthesis of Compound AA_090-3

At room temperature, compound AA_090-2 (220 mg, 0.504 mmol), N-phenyl bis(trifluoromethanesulphon)imide (197 mg, 0.55 mmol) were dissolved in THF (10 mL), K$_2$CO$_3$ (104 mg, 0.75 mmol) was added. The reaction mixture was stirred at 30° C. for 5 h. After the reaction was complete as detected by TLC, the reaction was quenched with H$_2$O (10 mL) and extracted with ethyl acetate (50 mL×3). The organic phases were combined and dried over anhydrous sodium sulfate. After filtration, the filtrate was concentrated under reduced pressure to remove the solvent, the residue was purified by silica gel column chromatography (PE/EA=1:3) to deliver the target compound AA_090-3 (88 mg, yield: 30.9%). LC/MS m/z: 570.0 [M+H]$^+$.

Step 3: Synthesis of Compound AA_090-4

At room temperature, compound AA_090-3 (88 mg, 0.154 mmol), bis(pinacolato)diboron (58 mg, 0.232 mmol) were dissolved in dioxane (3 mL), potassium acetate (29.4 mg, 0.3 mmol) and Pd(dppf)Cl$_2$ (10.9 mg, 0.015 mmol) were added under nitrogen gas atmosphere. The reaction mixture was heated to 90° C. and stirred for 4 h under nitrogen gas atmosphere. After the reaction was complete as detected by TLC, the reaction mixture was cooled to room temperature, filtrated, the filtrate was concentrated under reduced pressure to remove the solvent, the residue was purified by silica gel column chromatography (PE/EA=9:1→1:4) to deliver the target compound AA_090-4 (60 mg, yield 70.8%). LC/MS m/z: 547.1 [M+H]$^+$.

Step 4: Synthesis of Compound AA_090

AA_090_A (10 mg) and AA_090_B (9 mg) were prepared according to the synthetic step 3 in synthesizing AA_013, with compound AA_090-4 (60 mg, 0.110 mmol) and AA_013-3 (61 mg, 0.132 mmol) as starting materials, and separated by chiral preparative SFC. AA_090_A: LC/MS m/z: 803.6 [M+H]$^+$. AA_090_B: LC/MS m/z: 804.3 [M+H]$^+$.

Embodiment 102: AA_029

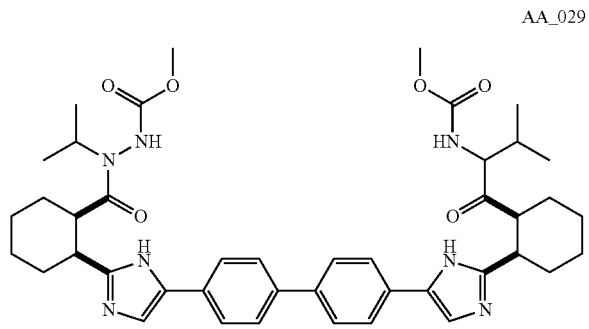

AA_029

Synthetic Route:

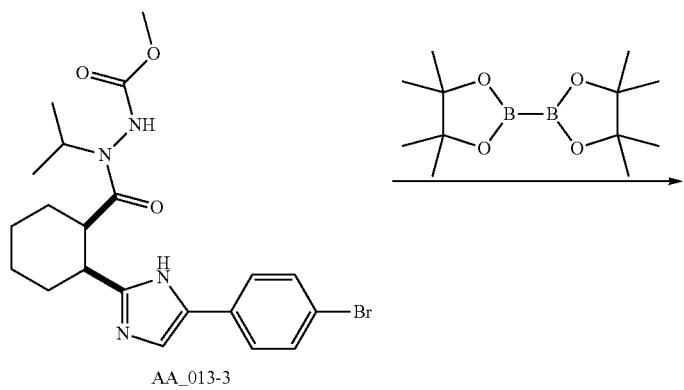

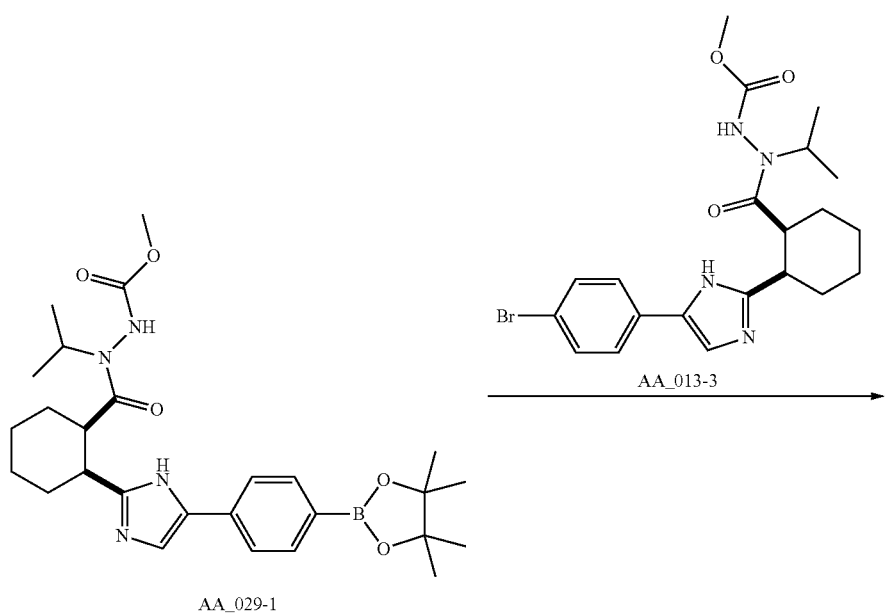

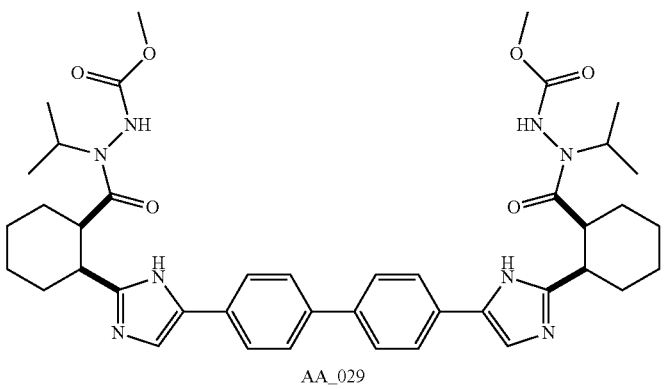

Step 1: Synthesis of Compound AA_029-1

At room temperature, compound AA_013-3 (50 mg, 0.11 mmol), bis(pinacolato)diboron (56 mg, 0.22 mmol) were dissolved in THF (1 mL), potassium acetate (33 mg, 0.33 mmol) and Pd(dppf)Cl₂ (10 mg, 0.011 mmol) were added under nitrogen gas atmosphere. The reaction mixture was stirred under 100° C. microwave for 60 min. After the reaction was complete as detected by TLC, the reaction mixture was cooled to room temperature, filtrated, the filtrate was concentrated by a rotary evaporator to remove the solvent, the residue was purified by silica gel column chromatography (PE/EA=10:1→1:1) to deliver the target compound AA_029-1 (50 mg, yield 89%). LC/MS m/z: 511.1 [M+H]⁺.

Step 2: Synthesis of Compound AA_029

At room temperature, compound AA_013-3 (50 mg, 0.11 mmol), AA_029-1 (50 mg, 0.097 mmol) were dissolved in a mixed solvent of DMF/THF/H₂O (0.5 mL/0.5 mL/0.5 mL), Na₂CO₃ (25 mg, 0.22 mmol)) and Pd(dppf)Cl₂ (10 mg, 0.011 mmol) were added under nitrogen gas atmosphere. The reaction mixture was stirred under 100° C. microwave for 30 min. After the reaction was complete as detected by TLC, the reaction mixture was cooled to room temperature, filtrated, the filtrate was concentrated by a rotary evaporator to remove the solvent, and the residue was purified by preparative HPLC to deliver the target compound AA_029 (7.5 mg, yield 9%). ¹H NMR (400 MHz, CD₃OD) δ 7.69-7.65 (m, 8H), 7.56-7.55 (m, 2H), 4.57-4.45 (m, 2H), 3.72-3.63 (m, 6H), 3.34 (m, 1H), 3.11 (m, 1H), 2.12 (m, 1H), 1.95-1.76 (m, 7H), 1.65-1.38 (m, 5H), 7.47-7.75 (m, 6H), 0.99-0.92 (m, 18H), 0.68 (m, 1H). LC/MS m/z 767.3 [M+H]⁺

Embodiment 103: AA_100

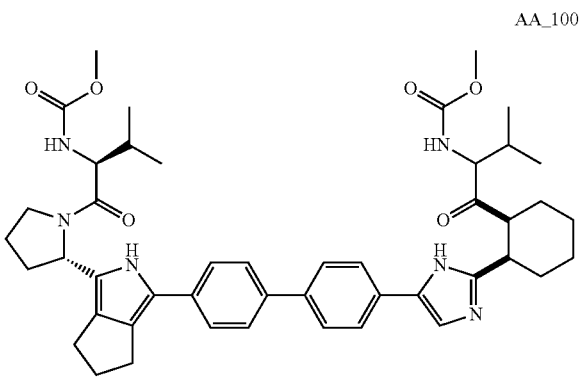

AA_100

Synthetic Route:

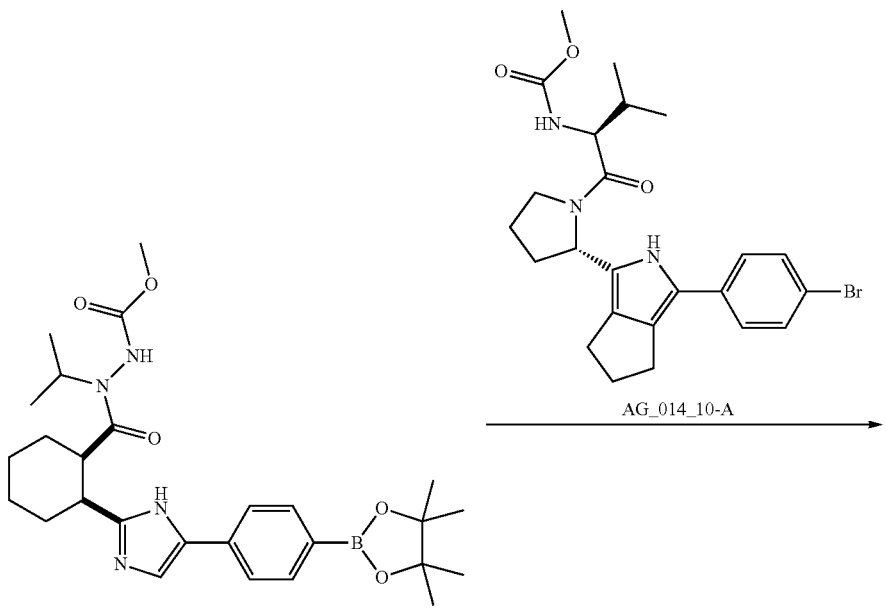

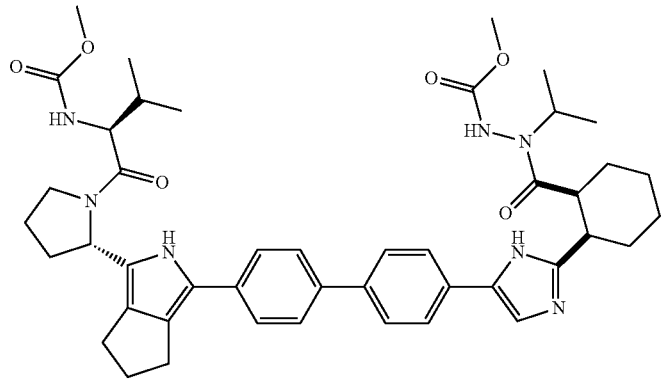

AA_100

Step 1: Synthesis of Compound AA_100
Compound AA_100 was synthesized according to the synthetic step 2 in synthesizing AA_029, with compound AA_029-1, AG_014_10-A as starting materials. LC/MS m/z 792.5 [M+H]⁺.
Embodiment 104: AA_108
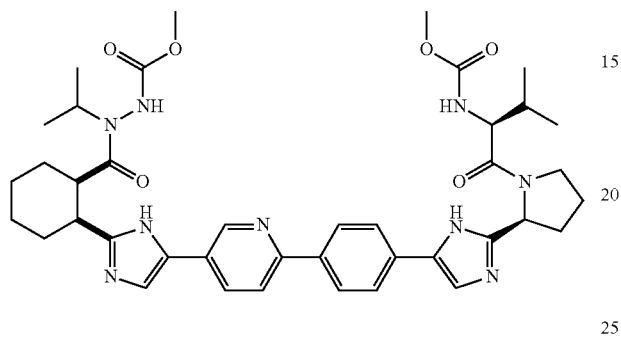
AA_108
Synthetic Route:
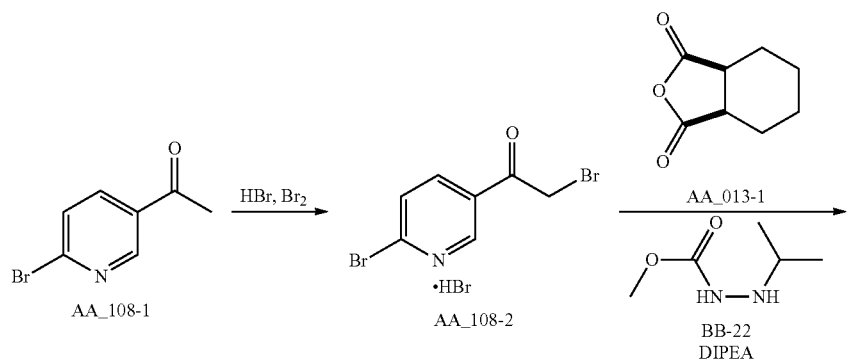
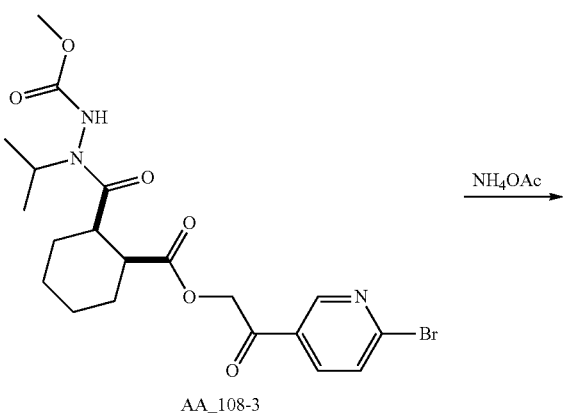

-continued

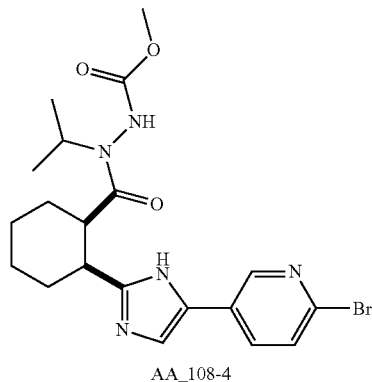
AA_108-4

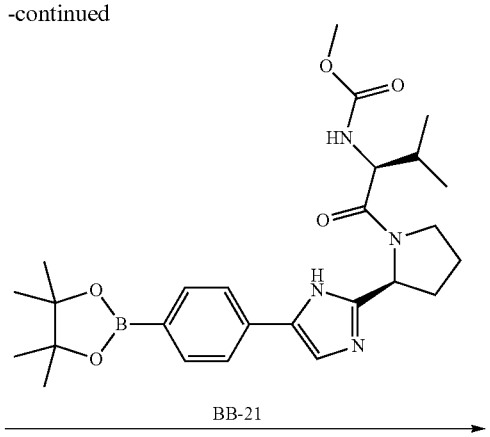
BB-21

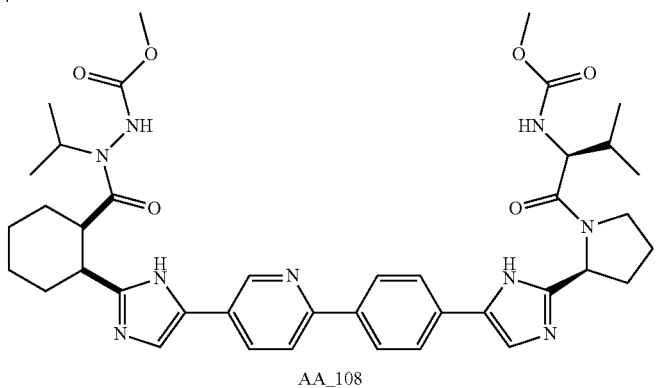
AA_108

Step 1: Synthesis of Compound AA_108-2

5-Acetyl-2-bromopyridine(AA_108-1, 2.00 g, 10.00 mmol) was dissolved in acetic acid (30 mL), liquid bromine (1.60 g, 10.01 mmol) was dripped, and then hydrobromic acid (0.68 mL, 6.00 mmol) was dripped. The reaction mixture was stirred at room temperature for 4 h. After the reaction was complete as detected by TLC, the solvent was removed by a rotary evaporator thereby delivering the target compound AA_108-2 (red brown solid, 3.60 g). The product was directly used for the next step without purification. $^1$H NMR (CDCl$_3$, 400 MHz): δ 8.88 (s, 1H), 8.13 (m, 1H), 7.71 (m, 1H), 7.63 (m, 1H), 4.56 (m, 2H).

Step 2: Synthesis of Compound AA_108-3

Compound BB-22 (6.5 g, 48.65 mmol) was dissolved in THF (100 mL), cis-1,2-cyclohexane-dicarboxylic anhydride (AA_013-1, 5 g, 32.43 mmol) was added. The reaction mixture was stirred at room temperature for 6 h. After the reaction was complete as detected by TLC, the solvent was removed by a rotary evaporator thereby giving colorless jelly (11.2 g). The colorless jelly (0.5 g, 1.75 mmol) and DIPEA (0.27 g, 2.10 mmol) were dissolved in DMF (7 mL), cooled to 0° C., compound AA_108-2 (0.63 g, 1.75 mmol) was added. The reaction mixture was stirred at 0° C. for 2 h. After the reaction was complete as detected by TLC, the reaction was quenched with H$_2$O (20 mL) and extracted with ethyl acetate (50 mL×3). The organic phases were combined and dried over anhydrous sodium sulfate. After filtration, the filtrate was concentrated under reduced pressure to remove the solvent, the residue was purified by silica gel column chromatography (PE/EA=2:1) to deliver the target compound AA_108-3 (white solid, 0.11 g, yield for two steps 13%). LC/MS m/z 485.9 [M+H]$^+$ Step 3: Synthesis of Compound AA_108-4

At room temperature, compound AA_108-3 (0.11 g, 0.19 mmol) was dissolved in toluene (50 mL), ammonium acetate (0.81 g, 10.51 mmol) was added, and the reaction mixture was heated to reflux and stirred overnight. After the reaction was complete as detected by TLC, the reaction mixture was cooled to room temperature and quenched with H$_2$O (50 mL), extracted with ethyl acetate (100 mL×3). The organic phases were combined and dried over anhydrous sodium sulfate. After filtration, the filtrate was concentrated under reduced pressure to remove the solvent, the residue was purified by silica gel column chromatography (PE/EA=3: 2→pure EA) to deliver the target compound AA_108-4 (yellow solid, 0.10 g, yield 70%). LC/MS m/z: 466.0 [M+H]$^+$ Step 4: Synthesis of Compound AA_108

Compound AA_108 was synthesized according to the synthetic step 3 in synthesizing AA_013_A, with compound AA-108-4, BB-21 as starting materials. LC/MS m/z 754.6 [M+H]$^+$.

Embodiment 105: AA_072
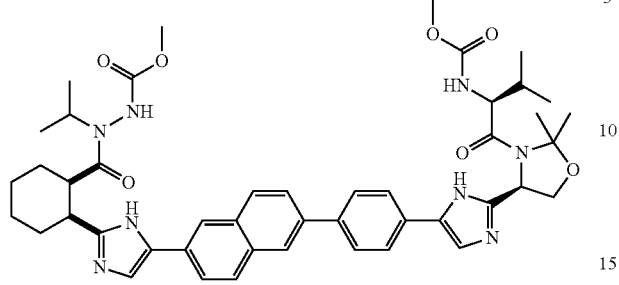
Synthetic Route:
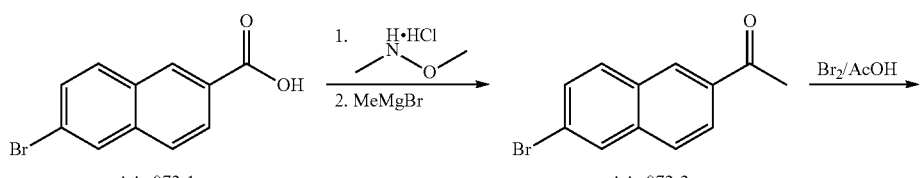
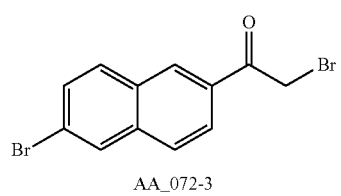
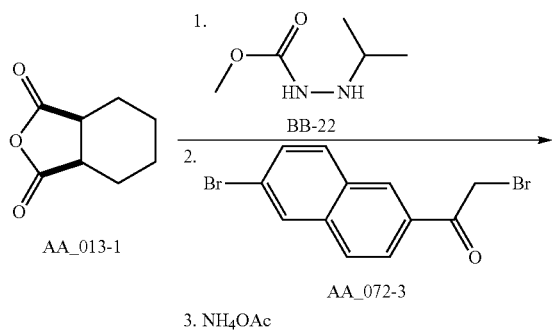
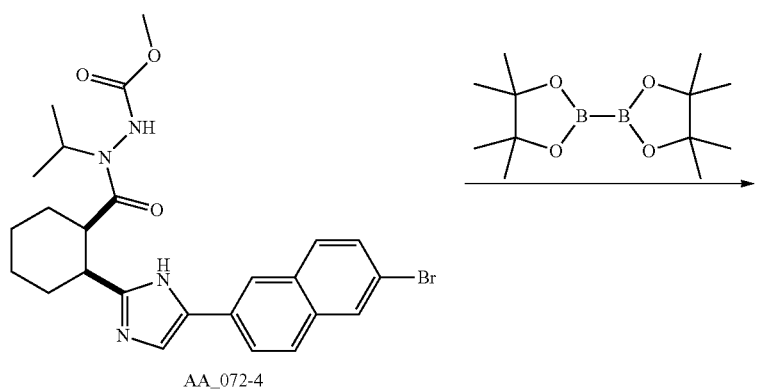

-continued

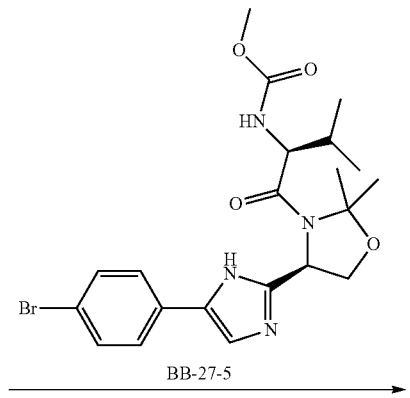
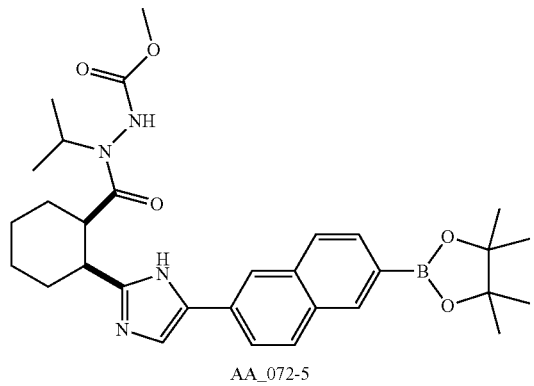

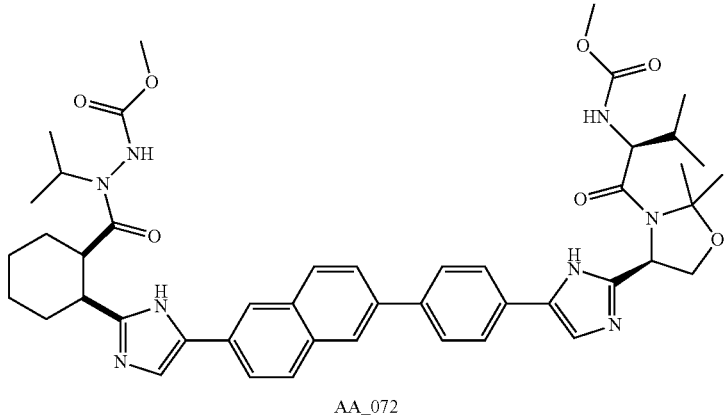

AA_072

Step 1: Synthesis of Compound AA_072-2

At room temperature, 6-bromo-2-naphthoic acid (AA_072-1, 10 g, 39.83 mmol), N,O-dimethyl hydroxylamine hydrochloride (5.05 g, 51.76 mmol) and DIPEA (15.44 g, 119.49 mmol) were dissolved in DMF (100 mL), HATU (23 g, 59.7 mmol) was added. The reaction mixture was stirred at room temperature for 4 h. After the reaction was complete as detected by TLC, methyl tert-butyl ether (300 mL) was added and the reaction mixture was washed with H₂O and saturated brines. The organic phase was dried over anhydrous sodium sulfate. After filtration, the filtrate was concentrated by a rotary evaporator to remove the solvent thereby giving Weinreb amide (5.8 g, yield 90%). The product was directly used for the next step without purification. The Weinreb amide (5.8 g, 35.9 mmol) was dissolved in THF (25 mL), cooled to 0° C., a solution of methyl magnesium bromide in ethyl ether (3 mol/L, 7.9 mL, 23.7 mmol) was dripped slowly. After dripping, the reaction mixture was stirred at room temperature for 2 h. After the reaction was complete as detected by TLC, the reaction was quenched with saturated ammonium chloride solution (50 mL) and extracted with ethyl acetate (50 mL×3). The organic phases were combined and dried over anhydrous sodium sulfate. After filtration, the filtrate was concentrated by a rotary evaporator to remove the solvent thereby delivering the target compound AA_072-2 (white solid, 4 g, yield: 40.4%). The product was directly used for the next step without purification. ¹H NMR (CDCl₃, 400 MHz): δ 8.43 (s, 1H), 8.06 7.85-7.80 (m, 2H), 7.85-7.80 (m, 2H), 7.65 (d, J=2.0 Hz, 1H).

Step 2: Synthesis of Compound AA_072-3

Compound AA_072-2 (3.5 g, 14.06 mmol) was dissolved in acetic acid (30 mL), liquid bromine (2.2 g, 14.06 mmol) was dripped slowly. After dripping, the reaction mixture was stirred at room temperature for 1 h. After the reaction was complete as detected by TLC, H₂O (80 mL) was added. The reaction mixture was filtrated and the solid was collected to deliver the target compound AA_072-3 (white solid, 1.74 g, yield 37.82%). The product was directly used for the next step without purification. ¹H NMR (CDCl₃, 400 MHz): δ 8.12-8.05 (m, 2H), 7.88-7.85 (m, 3H), 7.83-7.68 (m, 1H), 4.56 (s, 2H).

Step 3: Synthesis of Compound AA_072-4

Compound BB-22 (1 g, 7.6 mmol) was dissolved in THF (10 mL), cis-1,2-cyclohexane-dicarboxylic anhydride (AA_013-1, 1 g, 6.5 mmol) was added at 10° C. The reaction mixture was stirred at 10° C. for 14 h. After the reaction was complete as detected by TLC, the solvent was removed by a rotary evaporator thereby giving colorless jelly (1.8 g). The colorless jelly (1.8 g, 6.3 mmol) and K₂CO₃ (1.7 g, 12.6 mmol) were suspended in DMF (20 mL), compound AA_072-3 (1.74 g, 6.3 mmol) was added at room temperature. The reaction mixture was stirred at room temperature for 3 h. After the reaction was complete as detected by TLC, the reaction was quenched with $H_2O$ (10 mL) and extracted with ethyl acetate (100 mL×2). The organic phases were combined and dried over anhydrous sodium sulfate. After filtration, the filtrate was concentrated by a rotary evaporator to remove the solvent thereby obtaining yellow oil (3.8 g, yield 88.4%). The product was directly used for the next step without purification. At room temperature, the yellow oil (2 g, 4.28 mmol) was dissolved in toluene (100 mL), ammonium acetate (4.9 g, 63 mmol) was added. The reaction mixture was heated to reflux and stirred for 15 h under nitrogen gas atmosphere. After the reaction was complete as detected by TLC, the reaction mixture was cooled to room temperature, and then quenched with $H_2O$ (100 mL) and extracted with ethyl acetate (300 mL×3). The organic phases were combined and dried over anhydrous sodium sulfate. After filtration, the filtrate was concentrated under reduced pressure to remove the solvent, the residue was purified by silica gel column chromatography (PE/EA=10:1→3:1) to deliver the target compound AA_072-4 (yellow solid, 1.0 g, yield 30.3%). LCMS m/z: 514.8 $[M+H]^+$ Step 4: Synthesis of Compound AA_072-5

At room temperature, compound AA_072-4 (500 mg, 0.97 mmol), bis(pinacolato)diboron (371 mg, 1.46 mmol) were dissolved in 1,4-dioxane (10 mL), KOAc (191 mg, 1.95 mmol) and Pd(dppf)Cl$_2$ (71.2 mg, 0.097 mmol) were added under nitrogen gas atmosphere. The reaction system was heated to 100° C. and stirred for 2 h under nitrogen gas atmosphere. After the reaction was complete as detected by TLC, the reaction mixture was cooled to room temperature and filtrated. The filtrate was concentrated by a rotary evaporator to remove the solvent, the residue was purified by silica gel column chromatography (PE/EA=20:1→2:1) to deliver the target compound AA_072-5 (yellow solid, 395 mg, yield 72.5%). $^1$H NMR (CDCl$_3$, 400 MHz): δ: 8.43-8.31 (m, 1H), 8.19 (brs, 1H), 7.89-7.81 (m, 4H), 7.34 (m, 1H), 3.86 (s, 3H), 3.22 (m, 1H), 1.89 (m, 1H), 1.52-1.50 (m, 1H), 1.39 (s, 6H), 1.27-1.23 (m, 12H), 1.11-1.10 (m, 4H), 0.88 (m, 2H), 0.56 (brs, 2H).

Step 5: Synthesis of Compound AA_72

At room temperature, compound AA_072-5 (40 mg, 0.071 mmol), BB-27-5 (31 mg, 0.065 mmol) were dissolved in a mixed solvent of DMF/THF/H$_2$O (1.5 mL/1.5 mL/1.5 mL), Na$_2$CO$_3$ (14 mg, 0.13 mmol) and Pd(dppf)Cl$_2$ (5 mg, 0.0065 mmol) were added under nitrogen gas atmosphere. The reaction mixture was heated to 100° C. and stirred overnight under nitrogen gas atmosphere. After the reaction was complete as detected by TLC, the reaction mixture was cooled to room temperature and filtrated. The filtrate was concentrated by a rotary evaporator to remove the solvent, the residue was purified by preparative HPLC to deliver the target compound AA_072 (white solid, 4 mg, yield 7.4%). LC/MS (m/z) 833.7 $[M+H]^+$.

The compounds listed in the following table were synthesized according to the synthetic step 5 in synthesizing AA_072, with compound AA_072-5 as starting material:

| Embodiments | Structure | Fragment 1 | Fragment 2 | LCMS |
|---|---|---|---|---|
| 106 | AA_071 | AA_072-5 | BB-21-1 | 803.7 [M + H]+ |
| 107 | AA_073 | AA_072-5 | BB-28-7 | 861.4 [M + H]+ |

| Embodiments | Structure | | | LCMS |
|---|---|---|---|---|
| | | Fragment 1 | Fragment 2 | |
| 108 | AA_074 | AA_072-5 | AA_013-3 | 815.8 [M + H]⁺ |
| 109 | AA_075 | AA_072-5 | BB-16 | 841.9 [M + H]⁺ |

| Embodiments | Structure | Fragment 1 | Fragment 2 | LCMS |
|---|---|---|---|---|
| 110 | AA_076 | AA_072-5 | BB-23-6 | 831.6 [M+H]+ |
| 111 | AA_078 | AA_072-5 | BB-15 | 755.6 [M+H]+ |

| Em-bodi-ments | Structure | Fragment 1 | Fragment 2 | LCMS |
|---|---|---|---|---|
| 112 | AA_079 | AA_072-5 | BB-14 | 727.1 [M + H]+ |
| 113 | AA_092 | AA_072-5 | AA_106 | 831.5 [M + H]+ |

| Embodiments | Structure | Fragment 1 | Fragment 2 | LCMS |
|---|---|---|---|---|
| 114 | AA_094 | AA_072-5 | AG_014_10-A | 843.4 [M + H]⁺ |

Embodiment 115: AA_096
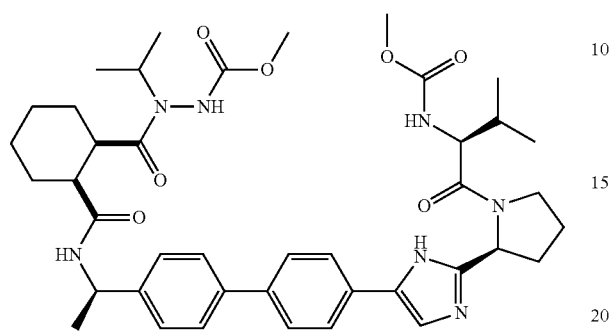
AA_096
Synthetic Route:
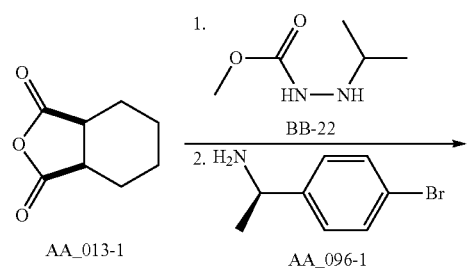
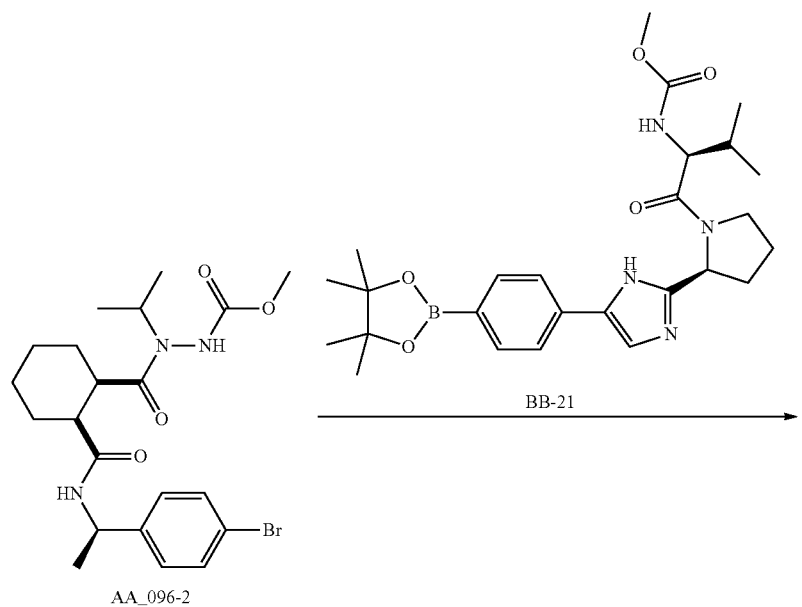

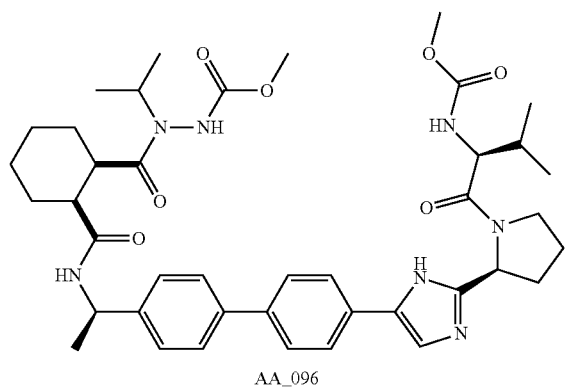

AA_096

Step 1: Synthesis of Compound AA_096-2

Compound BB-22 (6.5 g, 49.24 mmol) was dissolved in THF (100 mL), cis-1,2-cyclohexane-dicarboxylic anhydride (AA_013-1, 5 g, 32.43 mmol) was added. The reaction mixture was stirred at room temperature for 6 h. After the reaction was complete as detected by TLC, the solvent was removed by a rotary evaporator thereby giving colorless jelly (11.2 g). The colorless jelly (528 mg, 1.86 mmol), (R)-4-A-methyl benzyl bromide (AA_096-1, 385 mg, 1.92 mmol) and DIPEA (452 mg, 3.5 mmol) were dissolved in DMF (5 mL), HATU (730 mg, 1.92 mmol) was added. The reaction mixture was stirred at room temperature for 1 h. After the reaction was complete as detected by TLC, the reaction was quenched with H$_2$O (20 mL) and extracted with ethyl acetate (50 mL×3). The organic phases were combined and dried over anhydrous sodium sulfate. After filtration, the filtrate was concentrated under reduced pressure to remove the solvent, the residue was purified by silica gel column chromatography (PE:EA=2:1→1:4) to deliver the target compound AA_096-2 (light yellow solid, 0.65 g, yield for two steps 75.3%). LCMS m/z: 469.8 [M+H]$^+$ Step 2: Synthesis of Compound AA_096

At room temperature, compound AA_096-2 (40 mg, 0.0854 mmol), BB-21 (51 mg, 0.102 mmol) were dissolved in a mixed solvent of DMF/THF/H$_2$O (2 mL/2 mL/2 mL), Na$_2$CO$_3$ (18 mg, 0.171 mmol) and Pd(dppf)Cl$_2$ (3 mg, 0.0041 mmol) were added under nitrogen gas atmosphere. The reaction mixture was heated to 100° C. and stirred for 8 h under nitrogen gas atmosphere. After the reaction was complete as detected by TLC, the reaction mixture was cooled to room temperature and filtrated. The filtrate was concentrated by a rotary evaporator to remove the solvent, the residue was purified by preparative HPLC to deliver the target compound AA_096 (white solid, 14 mg, yield 21.6%). LC/MS (m/z) 380.0 [M/2+H]$^+$.

Embodiment 116: AA_097

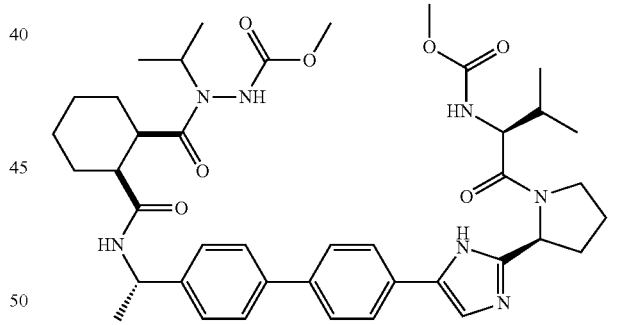

AA_097

Synthetic Route:

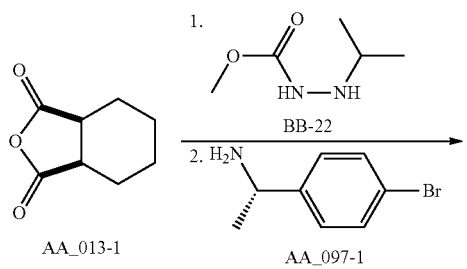

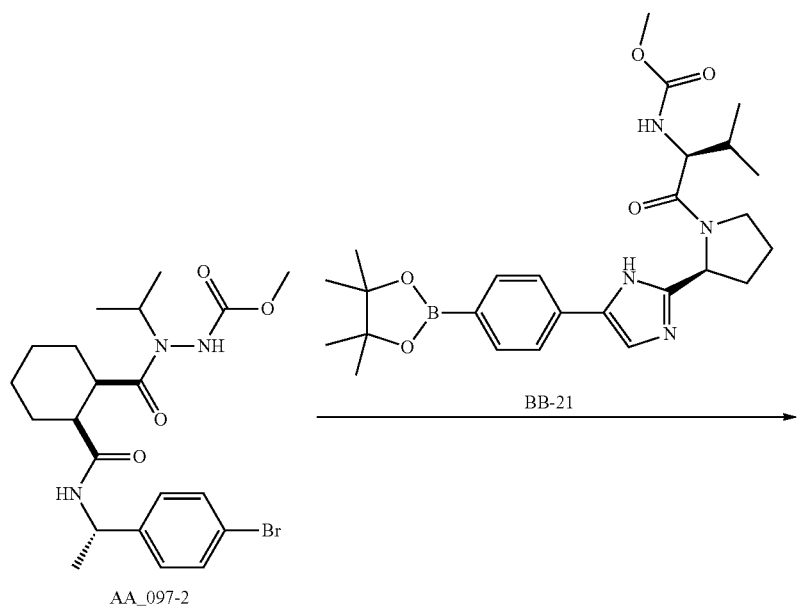
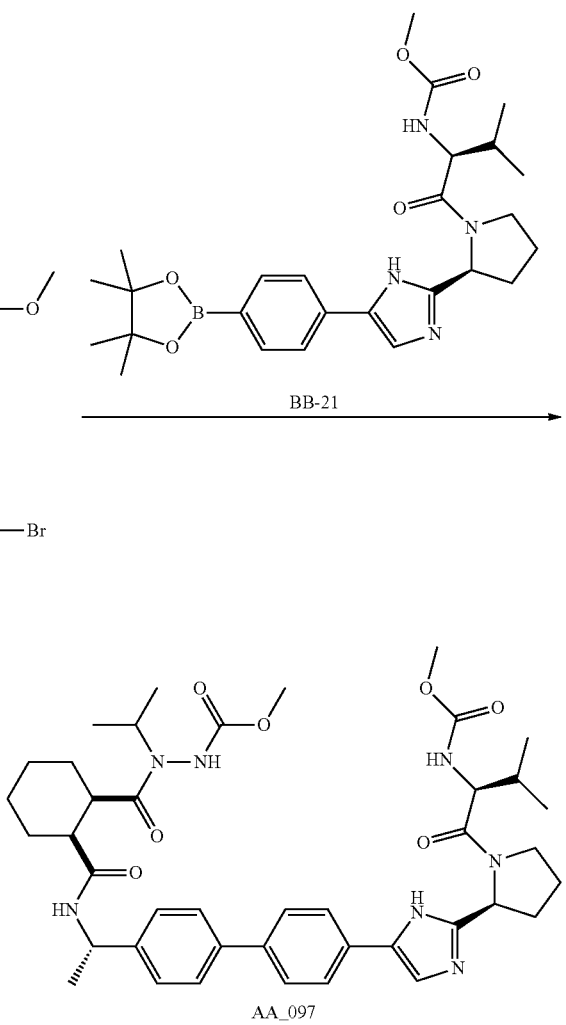
Step 1: Synthesis of Compound AA_097-2
Compound AA_097-2 could be synthesized according to the synthetic step 1 in synthesizing AA_096. LC/MS m/z: 469.8 [M+H]$^+$.
Step 2: Synthesis of Compound AA_097
Compound AA_097 could be synthesized according to the synthetic step 2 in synthesizing AA_096. LC/MS m/z: 379.9 [M/2+H]$^+$.
Embodiment 117: AA_106 and AA_107
-continued
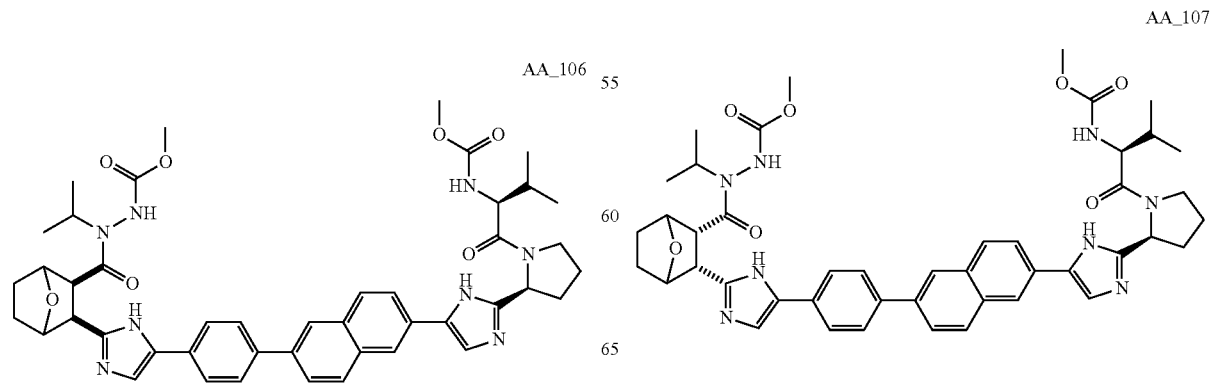

Synthetic Route:
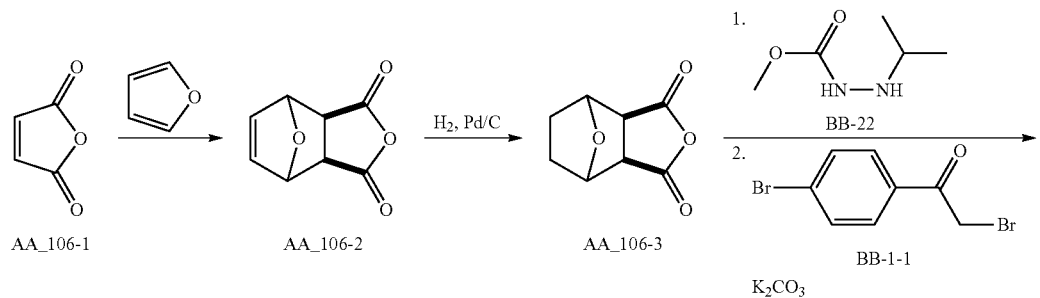
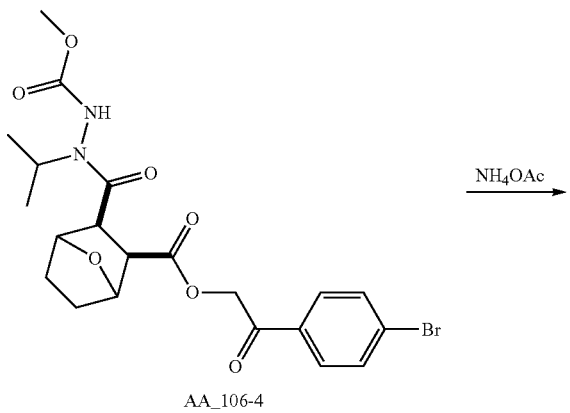
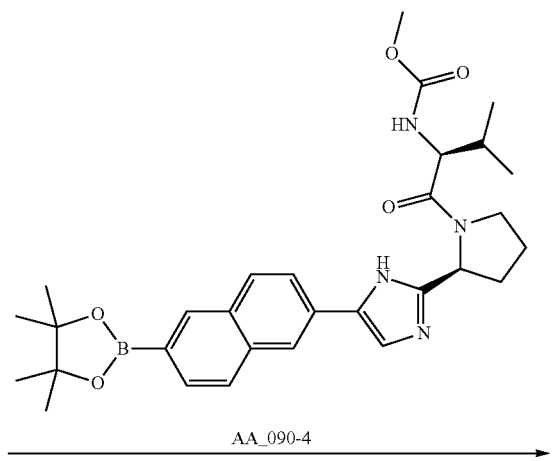
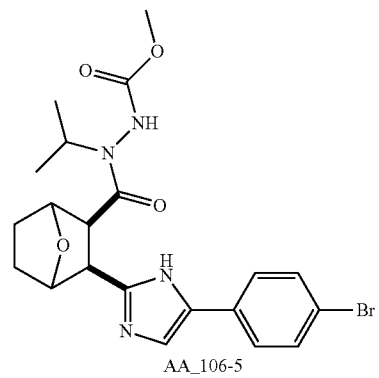

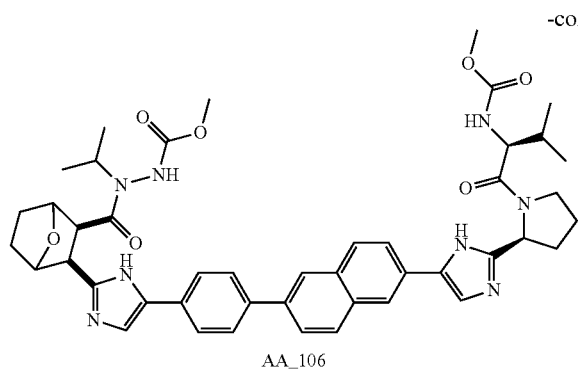

AA_106

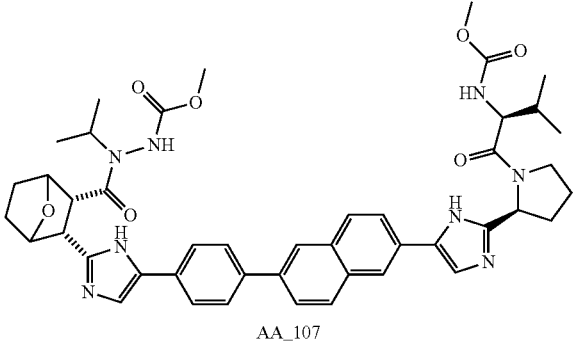

AA_107

Step 1: Synthesis of Compound AA_106-2

Maleic anhydride (AA_106-1, 4.00 g, 40.79 mmol) was mixed with furan (4.00 g, 58.76 mmol). The reaction mixture was stirred under 65° C. microwave for 10 min. After the reaction was complete as detected by TLC, the mixture was cooled to room temperature. The solid was comminuted and washed with a mixed solvent of petroleum ether/acetone (6 mL/24 mL). The solid was collected and dried to deliver AA_106-2 (white solid, 6.57 g, yield 96.9%). $^1$H NMR (CDCl$_3$ 400 MHz): δ 6.37 (s, 2H), 5.45 (s, 2H), 3.18 (s, 2H).

Step 2: Synthesis of Compound AA_106-3

Compound AA_106-2 (3 g, 18.06 mmol) was dissolved in THF (50 mL), 10% Pd/C (1.89 g) was added under nitrogen gas atmosphere. The reaction mixture was stirred at room temperature and under a hydrogen gas pressure of 1 atm for 5 h. After the reaction was complete as detected by TLC, the reaction mixture was filtrated and the filtrate was concentrated by a rotary evaporator to remove the solvent thereby delivering the target compound AA_106-3 (white solid, 2.99 g, yield 98%). The product was directly used for the next step without purification. $^1$H NMR (CDCl$_3$, 400 MHz): δ 5.02 (m, 2H), 3.16 (s, 2H), 1.87 (m, 2H), 1.61 (m, 2H).

Step 3: Synthesis of Compound AA_106-4

Compound BB-22 (0.79 g, 5.95 mmol) was dissolved in THF (15 mL), compound AA_106-3 (1.00 g, 5.95 mmol) was added. The reaction system was stirred at room temperature for 2 h. After the reaction was complete as detected by TLC, the solvent was removed by a rotary evaporator thereby giving colorless jelly (1.79 g). The product was directly used for the next step without purification. The colorless jelly and K$_2$CO$_3$ (1.65 g, 11.92 mmol) were suspended in DMF (10 mL), 2,4-dibromoacetophenone (BB-1-1, 1.66 g, 5.96 mmol) was added at room temperature. The reaction mixture was stirred at room temperature for 2 h. After the reaction was complete as detected by TLC, the reaction was quenched with H$_2$O (20 mL) and extracted with ethyl acetate (50 mL×3). The organic phases were combined and dried over anhydrous sodium sulfate. After filtration, the filtrate was concentrated under reduced pressure to remove the solvent, the residue was purified by silica gel column chromatography (PE/EA=4:1→1:2) to deliver the target compound AA_106-4 (white solid, 1.56 g, yield for two steps 53%). LC/MS m/z: 499.1 [M+H]$^+$ Step 4: Synthesis of Compound AA_106-5

At room temperature, compound AA_106-4 (1.56 g, 3.14 mmol) was dissolved in toluene (100 mL), ammonium acetate (10.54 g, 172.52 mmol) was added. The reaction mixture was heated to reflux under nitrogen gas atmosphere and stirred overnight. After the reaction was complete as detected by TLC, the reaction mixture was cooled to room temperature and quenched with H$_2$O (50 mL), extracted with ethyl acetate (100 mL×3). The organic phases were combined and dried over anhydrous sodium sulfate. After filtration, the filtrate was concentrated under reduced pressure to remove the solvent, the residue was purified by silica gel column chromatography (PE/EtOAc=1:2→pure EtOAc) to deliver the target compound AA_106-5 (yellow powder, 0.83 g, yield 55%). LC/MS m/z: 478.7 [M+H]$^+$ Step 5: Synthesis of Compound AA_106 and AA_107

Compound AA_106 and AA_107 were separated by preparative HPLC and synthesized according to the synthetic step 5 in synthesizing AA_072, with compound AA_106-5, AA_090-4 as starting materials. AA_106: LCMS m/z: 817.6 [M+H]$^+$. AA_107: LCMS m/z: 817.6 [M+H]$^+$.

Embodiment 118: AA_089

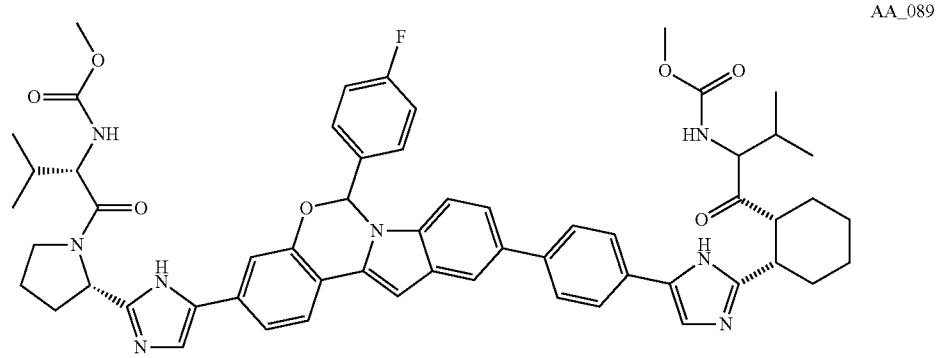

AA_089

Synthetic Route:
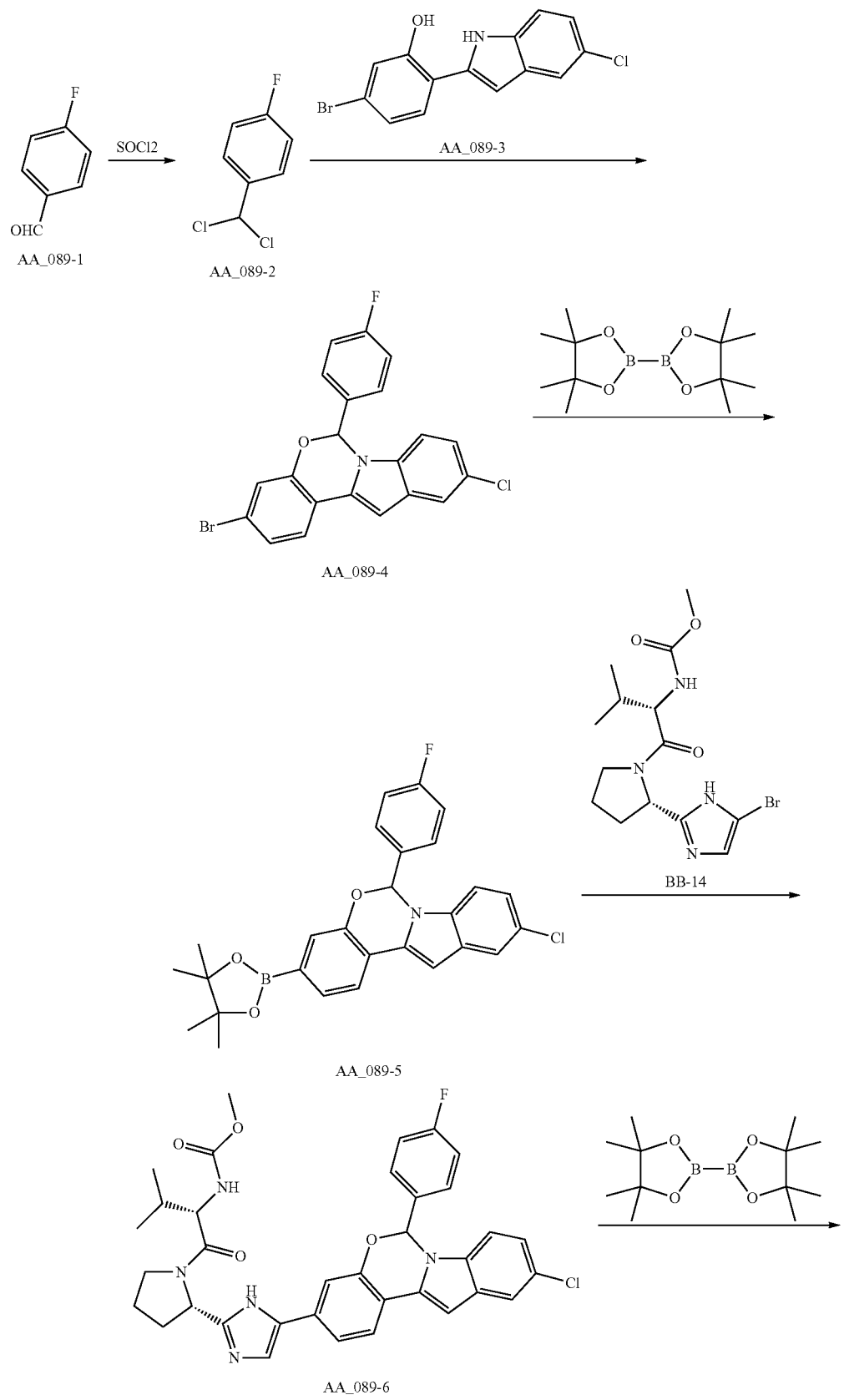

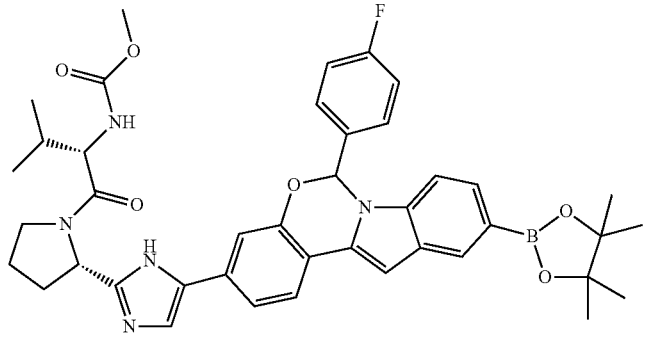

AA_089-7

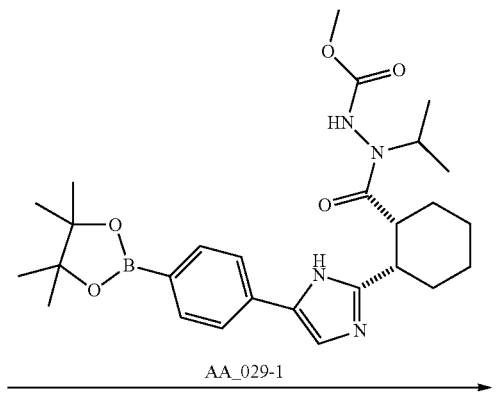

AA_029-1

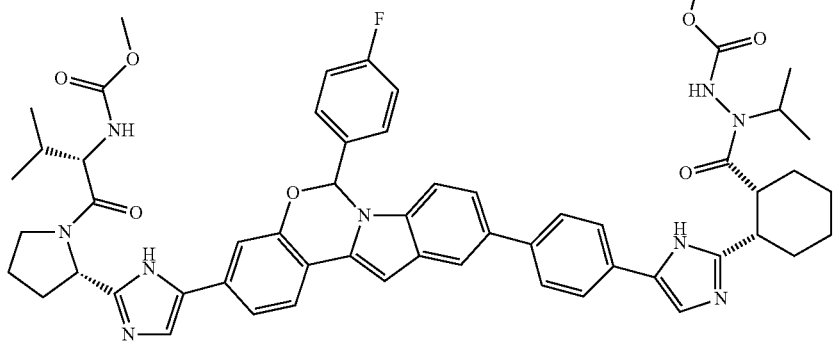

AA_089

Step 1: Synthesis of Compound AA_089-2

At room temperature, 4-fluorobenzaldehyde (AA_089-1, 2 g, 16.11 mmol) was dissolved in thionyl chloride (20 mL), and the reaction system was heated to reflux and stirred for 2 h. After the reaction was complete as detected by TLC, the solvent was removed by a rotary evaporator to deliver the target compound AA_089-2 (light yellow solid, 2.7 g, yield 93.75%). The product was directly used for the next step without purification. $^1$H NMR (CDCl$_3$, 400 MHz): δ 7.59 (m, 2H), 7.12 (m, 2H), 6.73 (s, 1H).

Step 2: Synthesis of Compound AA_089-4

At room temperature, compound AA_089-2 (2 g, 6.2 mmol) and Cs$_2$CO$_3$ (10 g, 31 mmol) were suspended in DMF (5 mL), compound AA_089-3 (2.8 g, 12.4 mmol) was added. The reaction mixture was heated to 100° C. and stirred for 3 h. After the reaction was complete as detected by TLC, the reaction mixture was cooled to room temperature and quenched with H$_2$O (50 mL), extracted with ethyl acetate (100 mL×3). The organic phases were combined and dried over anhydrous sodium sulfate. After filtration, the filtrate was concentrated under reduced pressure to remove the solvent, the residue was purified by silica gel column chromatography (PE/EA=9:1→1:1) to deliver the target compound AA_089-4 (solid, 1.4 g, yield 54%). $^1$H NMR (CDCl$_3$, 400 MHz): δ 7.66 (s, 1H), 7.65 (m, 1H), 7.22 (m, 2H), 7.05 (m, 6H), 7.00 (s, 1H), 6.86 (m, 1H).

Step 3: Synthesis of Compound AA_089-5

At room temperature, compound AA_089-4 (1.4 g, 3.27 mmol), bis(pinacolato)diboron (1.3 g, 4.89 mmol) were dissolved in dioxane (10 mL), potassium acetate (960 mg, 9.81 mmol) and Pd(dppf)Cl$_2$ (24 mg, 0.327 mmol) were added under nitrogen gas atmosphere. The reaction mixture was heated to 110° C. and stirred for 2 h under nitrogen gas atmosphere. After the reaction was complete as detected by TLC, the reaction mixture was cooled to room temperature and filtrated. The filtrate was concentrated by a rotary evaporator to remove the solvent, the residue was purified by silica gel column chromatography (PE/EA=9:1→2:1) to deliver the target compound AA_089-5 (solid, 1.3 g, yield 83.8%). LC/MS m/z: 475.8 [M+H]$^+$.

Step 4: Synthesis of Compound AA_089-6

At room temperature, compound AA_089-5 (800 mg, 1.68 mmol), BB-14 (753 mg, 2.02 mmol) were dissolved in a mixed solvent of DMF/THF/H$_2$O (2 mL/2 mL/2 mL), Na$_2$CO$_3$ (356 mg, 3.36 mmol) and Pd(dppf)Cl$_2$ (123 mg, 0.168 mmol) were added under nitrogen gas atmosphere. The reaction mixture was heated to 100° C. and stirred for 8 h under nitrogen gas atmosphere. After the reaction was complete as detected by TLC, the reaction mixture was cooled to room temperature and filtrated. The filtrate was concentrated by a rotary evaporator to remove the solvent, the residue was purified by silica gel column chromatography (PE/EA=4:1→2:3) to deliver the target compound AA_089-6 (white solid, 0.5 g, yield 51.3%). LC/MS m/z: 642.1 [M+H]⁺.

Step 5: Synthesis of Compound AA_089-7

At room temperature, compound AA_089-6 (0.5 g, 0.778 mmol), bis(pinacolato)diboron (0.24 g, 0.934 mmol) were dissolved in dioxane (10 mL), potassium acetate (153 mg, 1.6 mmol), Pd₂(dba)₃ (32 mg, 0.0343 mmol) and X-phos (32 mg, 0.0686 mmol) were added under nitrogen gas atmosphere. The reaction mixture was heated to 110° C. and stirred for 2 h under nitrogen gas atmosphere. After the reaction was complete as detected by TLC, the reaction mixture was cooled to room temperature and filtrated. The filtrate was concentrated by a rotary evaporator to remove the solvent, the residue was purified by silica gel column chromatography (PE/EA=9:1→1:4) to deliver the target compound AA_089-7 as yellow solid (0.48 g, yield 72.3%). LC/MS m/z: 734.2 [M+H]⁺.

Step 6: Synthesis of Compound AA_089

Compound AA_089 (11 mg, yield 23.8%) was synthesized according to the synthetic step 3 in synthesizing AA_013, with compound AA_089-7, AA_029-1 as starting materials. LCMS m/z: 496.1 [M/2+H]⁺.

Embodiment 119: AA_091_A and AA_091_B

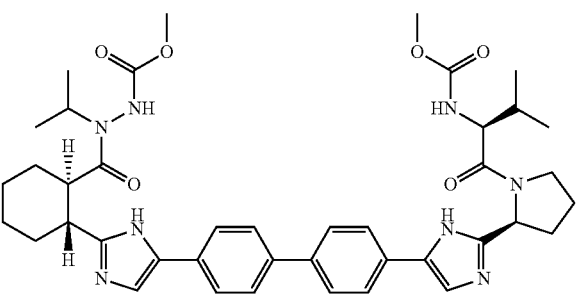

AA_091_A

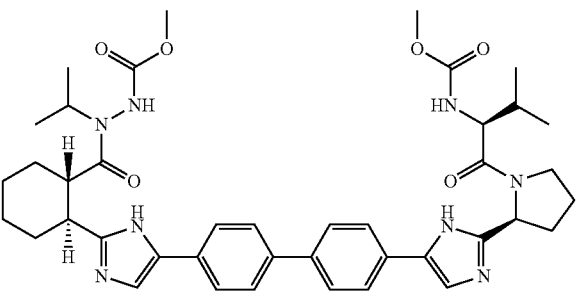

AA_091_B

Synthetic Route:

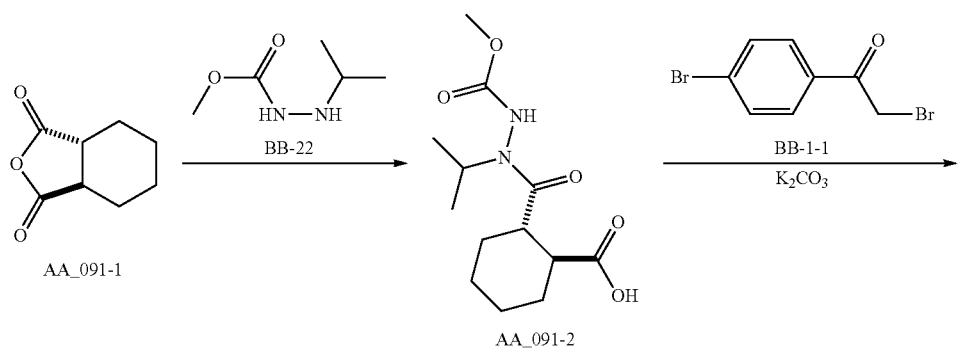

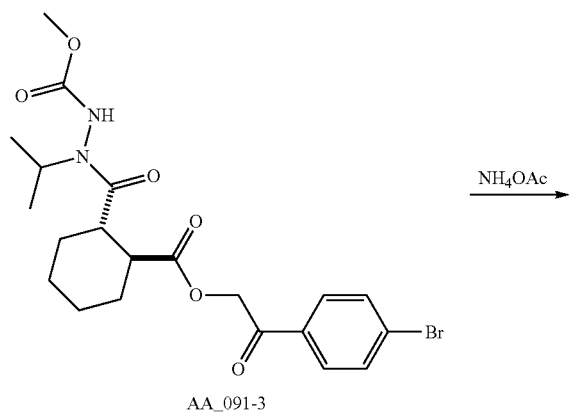

-continued
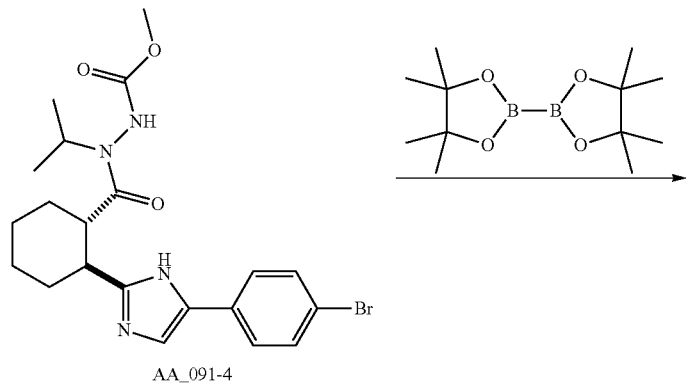
AA_091-4
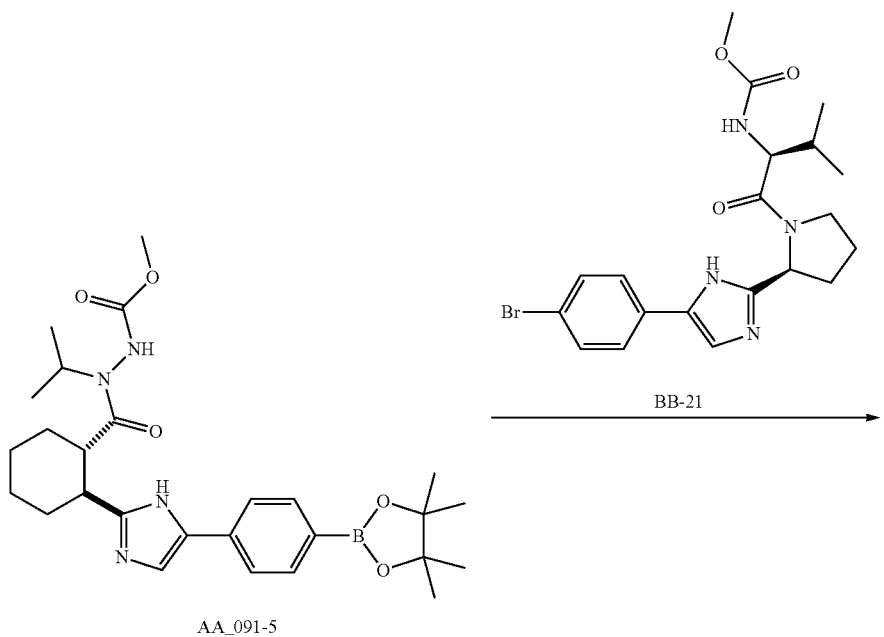
AA_091-5
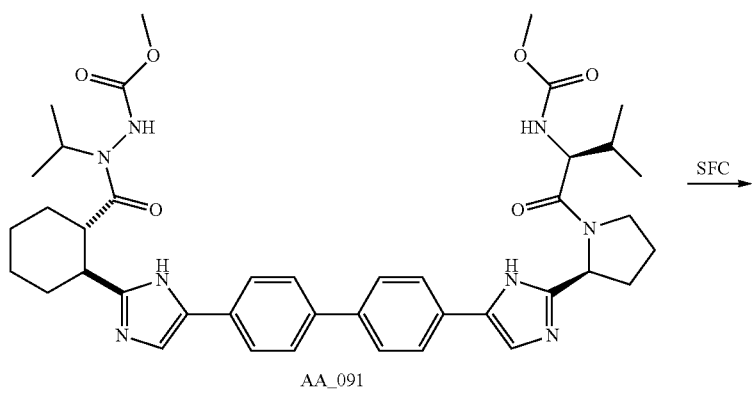
AA_091

-continued

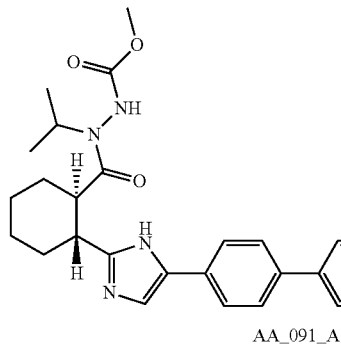
AA_091_A

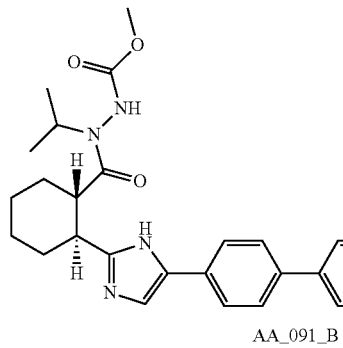
AA_091_B

Step 1: Synthesis of Compound AA_091-2

At room temperature, compound BB-22 (0.17 g, 1.3 mmol) was dissolved in THF (5 mL), trans-1,2-cyclohexane-dicarboxylic anhydride (AA_091-1, 0.1 g, 0.65 mmol) was added, and the reaction system was stirred at room temperature overnight. After the reaction was complete as detected by TLC, the solvent was removed by a rotary evaporator to deliver the target compound AA_091-2 (white solid, 0.18 g, yield 99.5%). The product was directly used for the next step without purification. LC/MS m/z 286.9 [M+H]$^+$ Step 2: Synthesis of Compound AA_091-3

At room temperature, compound AA_091-2 (0.25 g, 0.87 mmol) and K$_2$CO$_3$ (0.24 g, 1.75 mmol) were suspended in DMF (5 mL), 2,4-dibromoacetophenone (BB-1-1, 0.243 g, 0.87 mmol) was added at room temperature. The reaction mixture was stirred at room temperature for 3 h. After the reaction was complete as detected by TLC, the reaction was quenched with H$_2$O (3 mL) and extracted with ethyl acetate (5 mL×3). The organic phases were combined and dried over anhydrous sodium sulfate. After filtration, the filtrate was concentrated by a rotary evaporator to remove the solvent thereby delivering the target compound AA_091-3 (red solid, 0.3 g, yield 71.4%). The product was directly used for the next step without purification. LC/MS m/z 484.8 [M+H]$^+$ Step 3: Synthesis of Compound AA_091-4

At room temperature, compound AA_091-3 (0.3 g, 0.62 mmol) was dissolved in toluene (50 mL), ammonium acetate (7.2 g, 93.6 mmol) was added, and the reaction mixture was heated to 120° C. and stirred for 4 h under nitrogen gas atmosphere. After the reaction was complete as detected by TLC, the reaction mixture was cooled to room temperature and quenched with H$_2$O (50 mL), extracted with ethyl acetate (100 mL×3). The organic phases were combined and dried over anhydrous sodium sulfate. After filtration, the filtrate was concentrated under reduced pressure to remove the solvent, the residue was purified by silica gel column chromatography (PE/EtOAc=20:1→2:1) to deliver the target compound AA_091-4 (light red solid, 0.15 g, yield 52.3%). LC/MS m/z: 464.7 [M+H]$^+$.

Step 4: Synthesis of Compound AA_091-5

At room temperature, AA_091-4 (0.15 g, 0.32 mmol), bis(pinacolato)diboron (0.12 g, 0.48 mmol) were dissolved in dioxane (10 mL), potassium acetate (0.06 g, 0.65 mmol), Pd(dppf)Cl$_2$ (0.03 g, 0.032 mmol) were added under nitrogen gas atmosphere. The reaction mixture was heated to 100° C. and stirred for 2 h under nitrogen gas atmosphere. After the reaction was complete as detected by TLC, the reaction mixture was cooled to room temperature and filtrated. The filtrate was concentrated by a rotary evaporator to remove the solvent, the residue was purified by silica gel column chromatography (PE/EA=20:1→2:1) to deliver the target compound AA_091-5 (0.10 g, yield 60.6%). LC/MS m/z: 511.2 [M+H]$^+$.

Step 5: Synthesis of Compound AA_091

At room temperature, AA_091-5 (0.03 g, 0.065 mmol), BB-21 (0.035 g, 0.071 mmol) were dissolved in a mixed solvent of DMF/THF/H$_2$O (1.5 mL/1.5 mL/1.5 mL), Na$_2$CO$_3$ (0.014 g, 0.13 mmol) and Pd(dppf)Cl$_2$ (0.005 g, 0.0065 mmol) were added under nitrogen gas atmosphere. The reaction mixture was heated to 100° C. and stirred overnight under nitrogen gas atmosphere. After the reaction was complete as detected by TLC, the reaction mixture was cooled to room temperature and filtrated. The filtrate was concentrated by a rotary evaporator to remove the solvent, the residue was purified by preparative HPLC to deliver the target compound AA_091 (white solid, 0.018 g, yield 37.0%). LC/MS m/z: 753.5 [M+H]$^+$.

Step 6: Synthesis of Compound AA_091_A and AA_091_B

AA_091 (10 mg, 0.013 mmol) was separated by chiral preparative SFC to deliver target compound AA_091_A (0.5 mg) and AA_091_B (4 mg). AA_091_A: LC/MS m/z: 753.5 [M+H]$^+$. AA_091_B: LC/MS m/z: 753.5 [M+H]$^+$.

The compounds listed in the following table were synthesized according to the synthetic step 5 in synthesizing AA_091, with compound AA_091-5 as starting material:

| Embodiments | Structure |
|---|---|
| 120 | 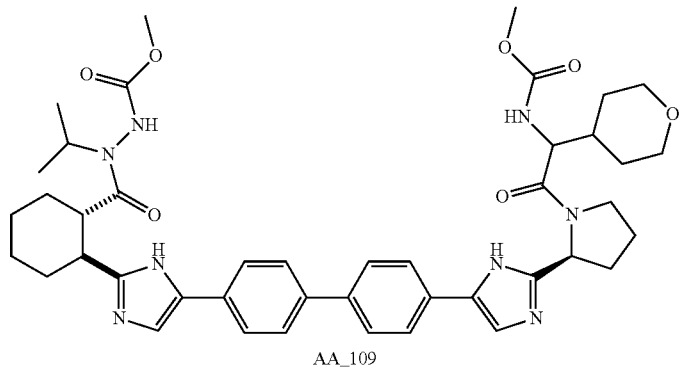
AA_109 |
| 121 | 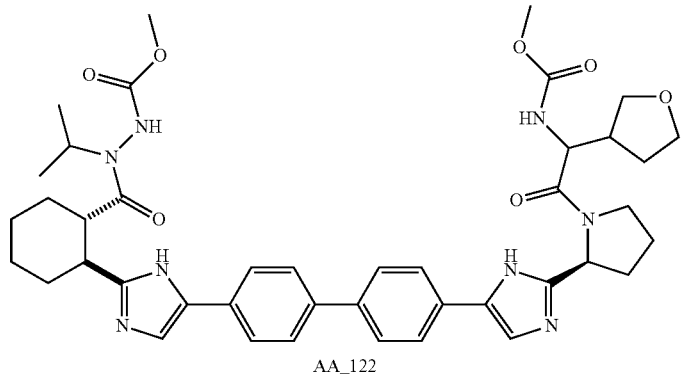
AA_122 |
| Embodiments | Fragment 1 | Fragment 2 | LCMS |
|---|---|---|---|
| 120 | 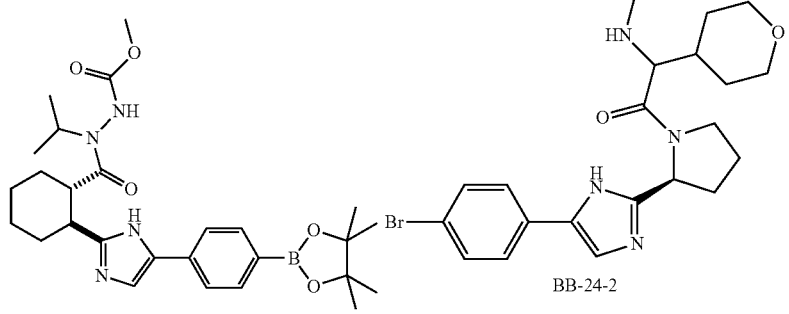 | | 795.6 [M + H]+ |

121
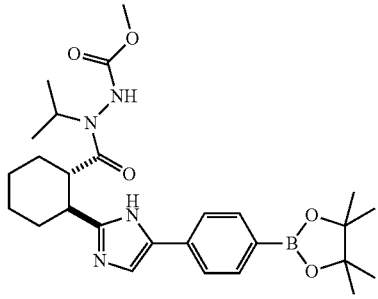
AA_091_5
BB-23-6
Embodiment 123: AA_117
AA_117
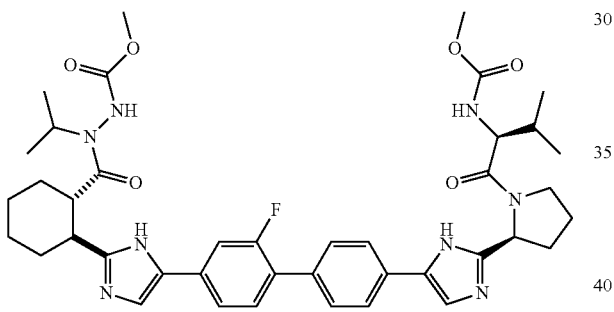
Synthetic Route:
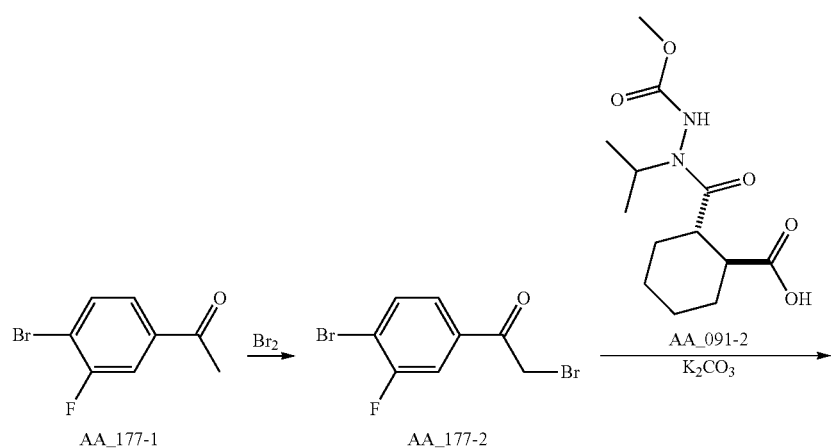

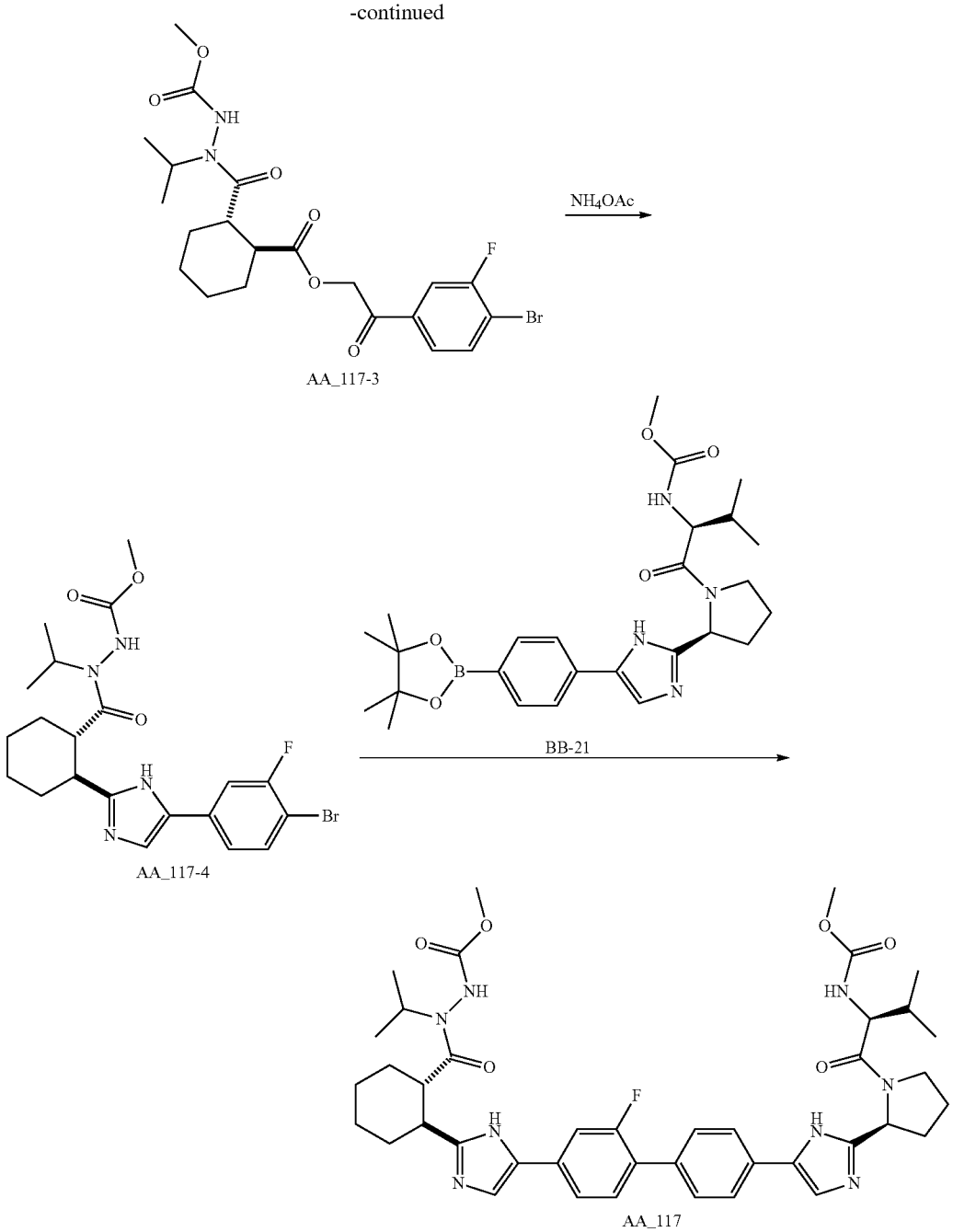

Step 1: Synthesis of Compound AA_117-2

3-Fluoro-4-bromo-acetophenone (AA_117-1, 2.00 g, 9.22 mmol) was dissolved in acetic acid (15 mL), liquid bromine (0.47 mL, 9.22 mmol) was dripped. The reaction mixture was stirred at room temperature for 3 h. After the reaction was complete as detected by TLC, the solvent was removed by a rotary evaporator to deliver the target compound AA_117-2 (red brown solid, 2.73 g). The product was directly used for the next step without purification. $^1$H NMR (CDCl$_3$, 400 MHz): δ 7.75-7.66 (m, 3H), 4.39 (s, 2H).

Step 2: Synthesis of Compound AA_117-3

Compound AA_091-2 (0.50 g, 1.75 mmol) and DIPEA (0.27 g, 2.10 mmol) was dissolved in DMF (7 mL), cooled to 0° C., compound AA_117-2 (0.57 g, 1.92 mmol) was added. The reaction mixture was stirred at 0° C. for 0.5 h. After the reaction was complete as detected by TLC, the reaction was quenched with H$_2$O (20 mL) and extracted with ethyl acetate (50 mL×3). The organic phases were combined and dried over anhydrous sodium sulfate. After filtration, the filtrate was concentrated under reduced pressure to remove the solvent, the residue was purified by silica gel column chromatography (PE/EtOAc=2:1) to deliver the target compound AA_117-3 (white solid, 0.35 g, yield for two steps 36.2%). LC/MS m/z: 524.8 [M+Na]$^+$.

Step 3: Synthesis of Compound AA_117-4

At room temperature, AA_117-3 (0.68 g, 1.36 mmol) was dissolved in toluene (70 mL), ammonium acetate (5.75 g, 74.60 mmol) was added, and the reaction mixture was heated to reflux and stirred overnight under nitrogen gas atmosphere. After the reaction was complete as detected by TLC, the reaction mixture was cooled to room temperature and quenched with H₂O (50 mL), extracted with ethyl acetate (100 mL×3). The organic phases were combined and dried over anhydrous sodium sulfate. After filtration, the filtrate was concentrated under reduced pressure to remove the solvent, the residue was purified by silica gel column chromatography (PE/EtOAc=2:3→pure EtOAc) to deliver the target compound AA_117-4 (yellow solid, 0.49 g, yield 76%). LC/MS m/z: 482.8 [M+H]⁺.

Step 4: Synthesis of Compound AA_117

Compound AA_117 was synthesized according to the synthetic step 5 in synthesizing AA_091, with compound AA_117-4 and BB-21 as starting materials. LC/MS m/z: 771.5 [M+H]⁺.

Embodiment 124: AA_118

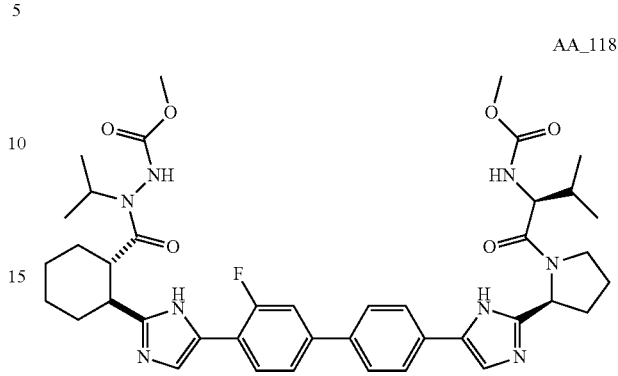

AA_118

Synthetic Route:

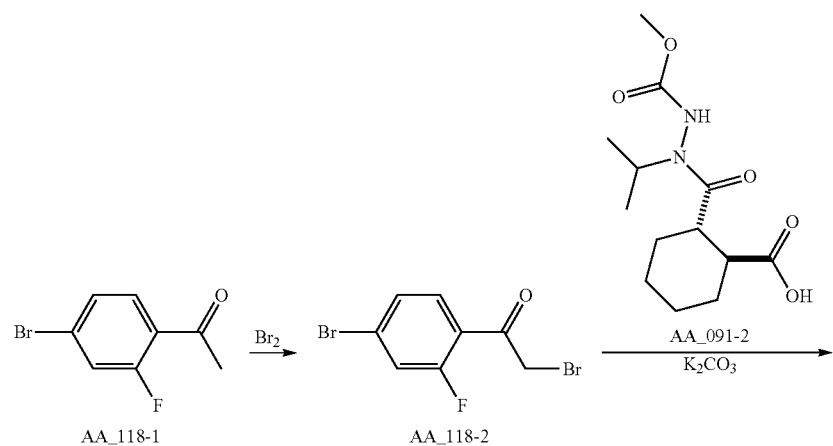

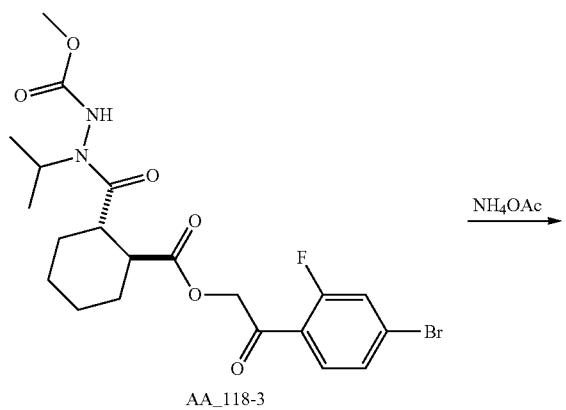

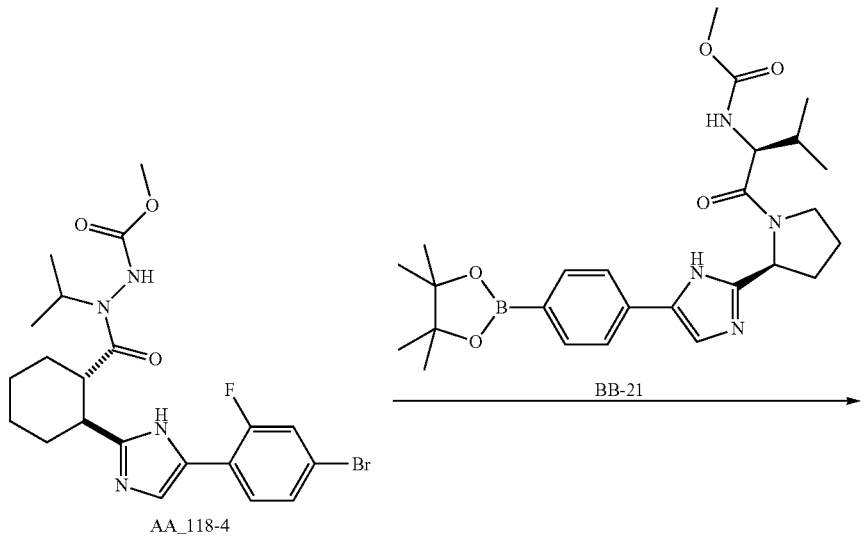

AA_118-4

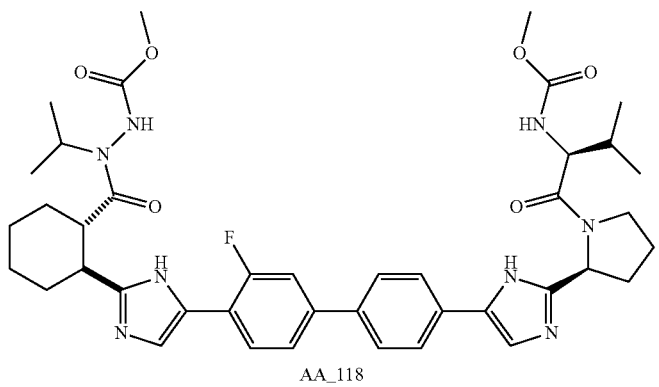

AA_118

Step 1: Synthesis of Compound AA_118-2

Compound AA_118-2 could be synthesized according to the synthetic step 1 in synthesizing AA_117. $^1$H NMR (CDCl$_3$, 400 MHz): δ 7.91-7.85 (m, 1 H), 7.48-7.40 (m, 2 H), 4.50 (d, J=2.0 Hz, 2 H).

Step 2: Synthesis of Compound AA_118-3

Compound AA_118-3 could be synthesized according to the synthetic step 2 in synthesizing AA_117. LC/MS m/z: 500.9 [M+H]$^+$ Step 3: Synthesis of Compound AA_118-4

Compound AA_118-4 could be synthesized according to the synthetic step 3 in synthesizing AA_117. LC/MS m/z: 480.9 [M+H]$^+$ Step 4: Synthesis of Compound AA_118

Compound AA_118 was synthesized according to the synthetic step 5 in synthesizing AA_091, with compound AA_118-4 and BB-21 as starting materials. LCMS m/z: 771.5 [M+H]$^+$.

Embodiment 125: AA_127

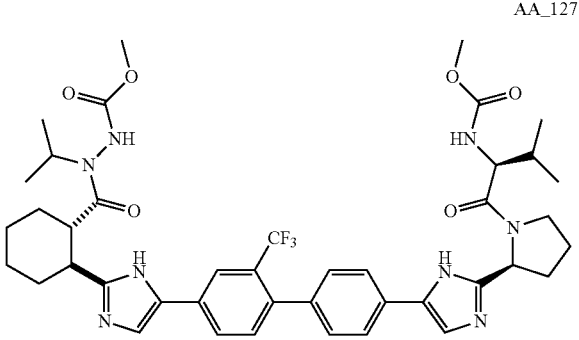

AA_127

Synthetic Route:

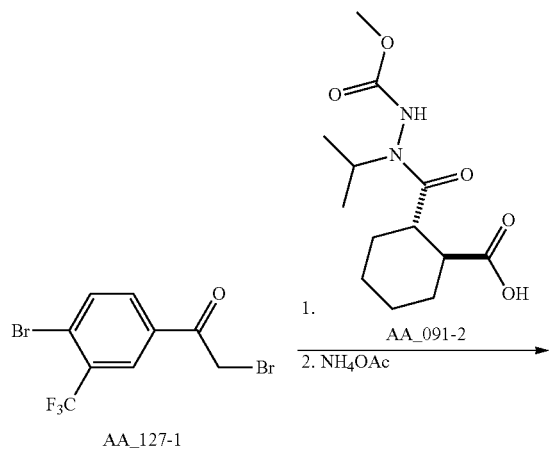

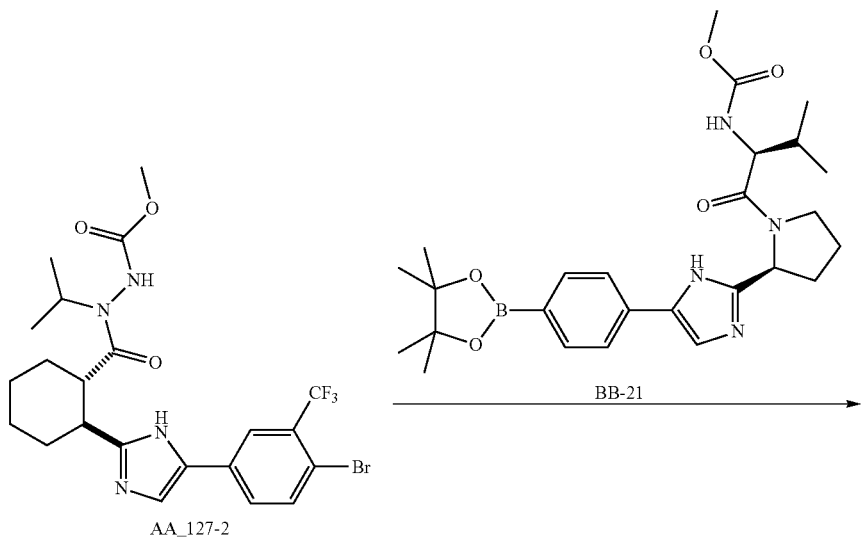

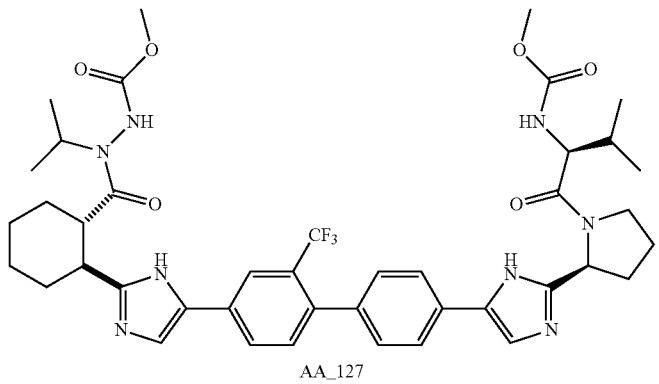

Step 1: Synthesis of Compound AA_127-2

Compound AA_091-2 (2.7 g, 9.43 mmol) and K₂CO₃ (1.8 g, 13.5 mmol) was suspended in DMF (20 mL), compound AA_127-1 (3.7 g, 10.8 mmol) was added at room temperature. The reaction mixture was stirred at room temperature for 2 h. After the reaction was complete as detected by TLC, the reaction was quenched with H₂O (20 mL) and extracted with ethyl acetate (50 mL×3). The organic phases were combined and dried over anhydrous sodium sulfate. After filtration, the filtrate was concentrated by a rotary evaporator to remove the solvent thereby delivering an intermediate as yellow oil. The yellow oil was dissolved in toluene (50 mL), ammonium acetate (6.9 g, 90 mmol) was added. The reaction mixture was heated to reflux and stirred for 12 h under nitrogen gas atmosphere. After the reaction was complete as detected by TLC, the reaction mixture was cooled to room temperature and then quenched with H₂O (30 mL), extracted with ethyl acetate (50 mL×3). The organic phases were combined and dried over anhydrous sodium sulfate. After filtration, the filtrate was concentrated under reduced pressure to remove the solvent, the residue was purified by silica gel column chromatography (PE/EtOAc=9:1→1:1) to deliver the target compound AA_127-2 (2.6 g, yield 54%). LC/MS m/z: 545.0 [M+H]⁺.

Step 2: Synthesis of Compound AA_ 127

Compound AA_127 was synthesized according to the synthetic step 5 in synthesizing AA_091, with compound AA_127-2 and compound BB-21 as starting materials. LC/MS m/z: 833.5 [M+H]⁺.

Embodiment 126: AL_003

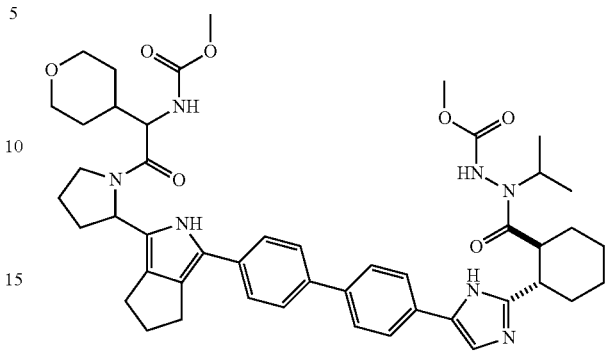

AL_003

Synthetic Route:

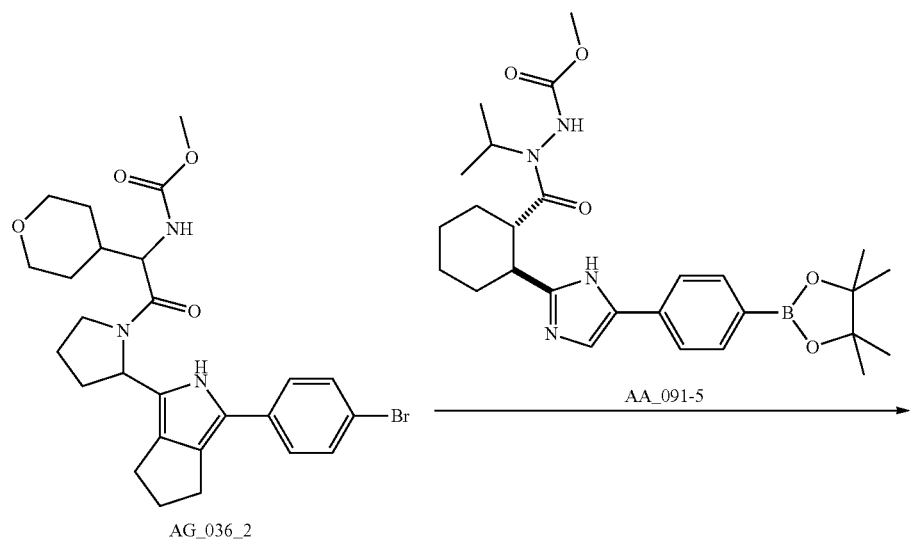

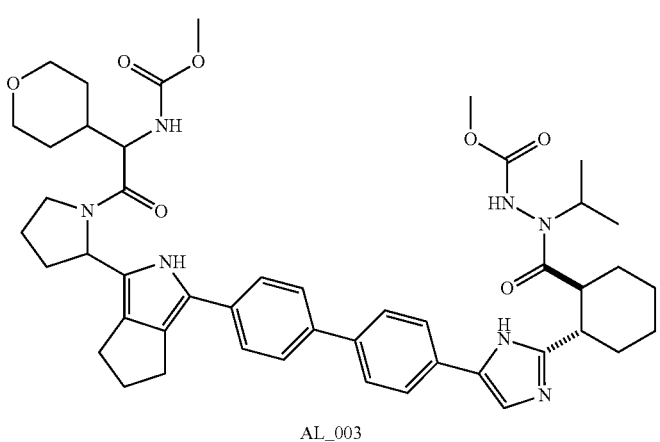

AL_003

Step 1: Synthesis of Compound AL_003

Compound AG_036-2 (20 mg, 0.038 mmol), AA_091-5 (21.2 mg, 0.042 mmol) were dissolved in a mixed solvent of DMF/THF/H$_2$O (2 mL/2 mL/2 mL), Pd(dppf)Cl$_2$ (2.8 mg, 0.004 mmol) and Na$_2$CO$_3$ (8 mg, 0.075 mmol) were added. The atmosphere was replaced by nitrogen gas for 3 times, and then the reaction mixture was heated to 100° C. and stirred overnight under nitrogen gas atmosphere. Stop heating and cool naturally. The reaction mixture was filtrated and the filtrate was concentrated by a rotary evaporator to remove the solvent, H$_2$O (10 mL) was added and the reaction mixture was extracted with ethyl acetate (10 mL×3). The ethyl acetate phases were combined and washed with saturated brines, dried over anhydrous sodium sulfate. The solvent was evaporated and the crude product was purified by preparative HPLC to deliver the target compound AL_003 (white solid, 7.8 mg, yield 25.2%). LC/MS m/z: 834.4[M+H]$^+$.

Embodiment 127: AA_032

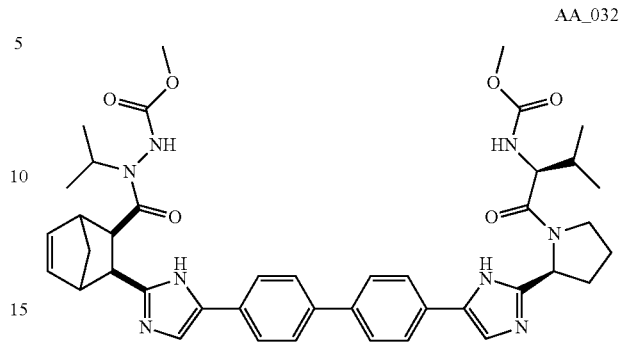

Synthetic Route:

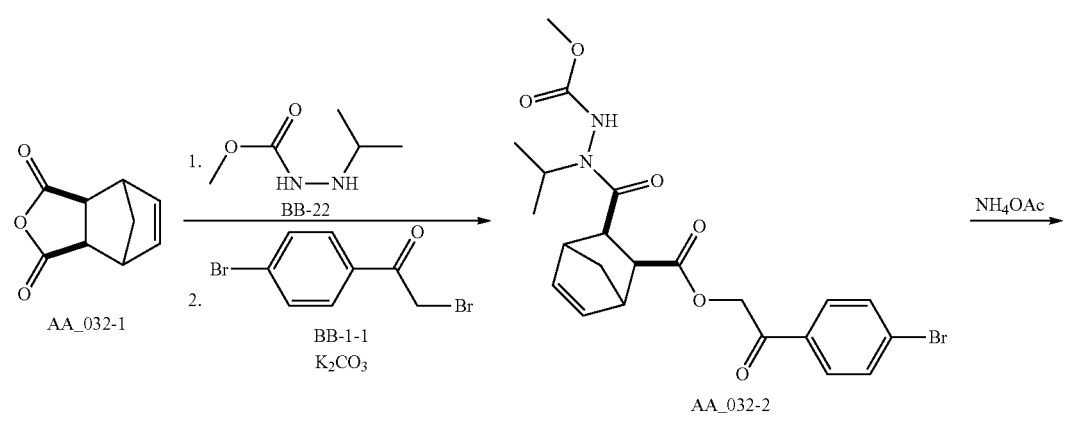

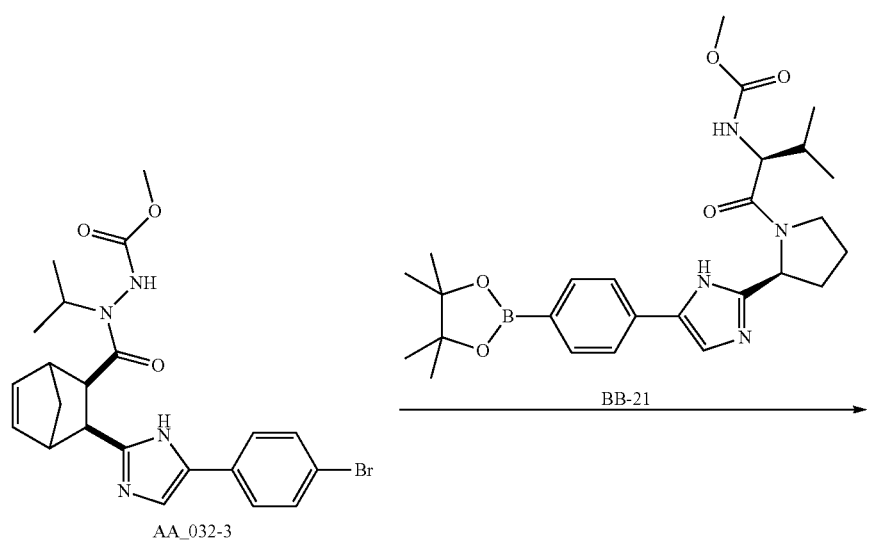

-continued

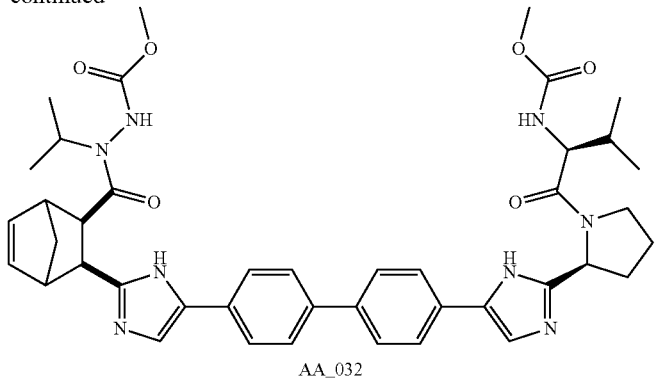

AA_032

Step 1: Synthesis of Compound AA_032-2

Compound BB-22 (0.5 g, 3.78 mmol) was dissolved in THF (10 mL), compound AA_032-1 (0.4 g, 2.44 mmol) was added at 10° C. The reaction system was stirred at 10° C. for 14 h. After the reaction was complete as detected by TLC, the solvent was removed by a rotary evaporator to deliver an intermediate as colorless jelly (0.9 g). The product was directly used for the next step without purification. The colorless jelly intermediate and $K_2CO_3$ (1 g, 7.25 mmol) were suspended in DMF (10 mL), 2,4-dibromoacetophenone (BB-1-1, 0.9 g, 3.24 mmol) was added at room temperature. The reaction mixture was stirred at 10° C. for 12 h. After the reaction was complete as detected by TLC, the reaction was quenched with $H_2O$ (10 mL) and extracted with ethyl acetate (10 mL×2). The organic phases were combined and dried over anhydrous sodium sulfate. After filtration, the filtrate was concentrated under reduced pressure to remove the solvent, the residue was purified by silica gel column chromatography (PE/EtOAc=10:1→3:1) to deliver the target compound AA_032-2 (0.9 g, yield for two steps 74.81%).

Step 2: Synthesis of Compound AA_032-3

At room temperature, compound AA_032-2 (0.5 g, 1.01 mmol) was dissolved in toluene (50 mL), ammonium acetate (0.8 g, 10.1 mmol) was added. The reaction mixture was heated to 120° C. and stirred for 6 h under nitrogen gas atmosphere. After the reaction was complete as detected by TLC, the reaction mixture was cooled to room temperature and quenched with $H_2O$ (50 mL), extracted with ethyl acetate (100 mL×3). The organic phases were combined and dried over anhydrous sodium sulfate. After filtration, the filtrate was concentrated under reduced pressure to remove the solvent, the residue was purified by silica gel column chromatography (PE/EtOAc=10:1→1:1) to deliver the target compound AA_032-3 (0.3 g, yield 64%). LC/MS m/z: 474.7 [M+H]$^+$.

Step 3: Synthesis of Compound AA_032

At room temperature, AA_032-3 (100 mg, 0.21 mmol), BB-21 (120 mg, 0.25 mmol) were dissolved in 1,2-dimethoxy ethane/$H_2O$ (2 mL/0.5 mL), $Na_2CO_3$ (45 mg, 0.42 mmol) and Pd(PPh$_3$)$_4$ (15 mg, 0.021 mmol) were added under nitrogen gas atmosphere. The reaction mixture was stirred under 120° C. microwave for 10 min. After the reaction was complete as detected by TLC, the reaction mixture was cooled to room temperature and filtrated. The filtrate was concentrated by a rotary evaporator to remove the solvent, the residue was purified by preparative HPLC to deliver the target compound AA_032 (5 mg, yield 3.1%). LC/MS m/z: 763.3 [M+H]$^+$.

Embodiment 128: AA_034

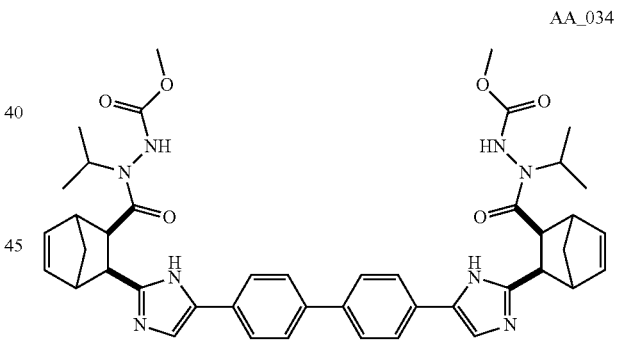

AA_034

Synthetic route:

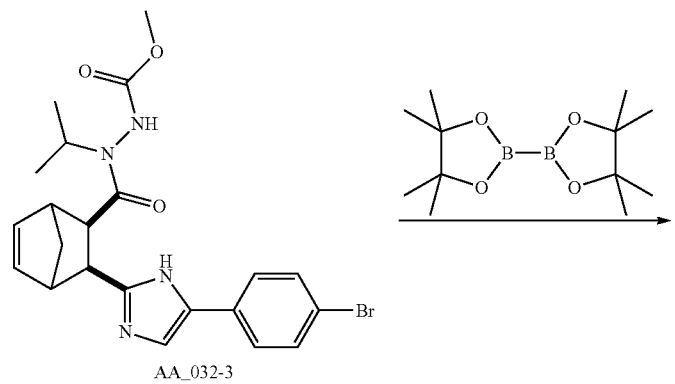

AA_032-3

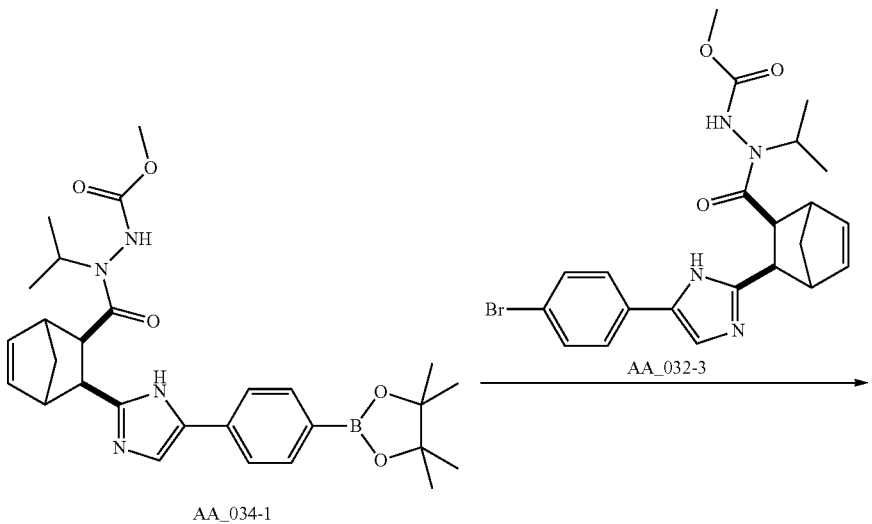

AA_034-1 → AA_032-3

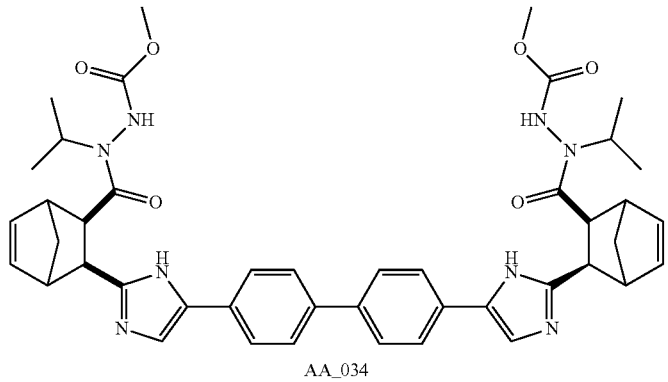

AA_034

Step 1: Synthesis of Compound AA_034-1

At room temperature, compound AA_032-3 (100 mg, 0.21 mmol), bis(pinacolato)diboron (80 mg, 0.32 mmol) were dissolved in THF (1 mL), KOAc (60 mg, 0.63 mmol) and Pd(dppf)Cl$_2$ (15 mg, 0.021 mmol) were added under nitrogen gas atmosphere. The reaction mixture was stirred under 110° C. microwave for 30 min. After the reaction was complete as detected by TLC, the reaction mixture was cooled to room temperature and filtrated. The filtrate was concentrated by a rotary evaporator to remove the solvent, the residue was purified by silica gel column chromatography (PE/EtOAc=10:1→1:1) to deliver the target compound AA_034-1 (80 mg, yield 73%). LC/MS m/z: 520.8 [M+H]$^+$.

Step 2: Synthesis of Compound AA_034

At room temperature, compound AA_032-3 (40 mg, 0.085 mmol), AA_034-1 (40 mg, 0.077 mmol) were dissolved in DMF/THF/H$_2$O (0.5 mL/0.5 mL/0.5 mL), Na$_2$CO$_3$ (20 mg, 0.17 mmol) and Pd(dppf)Cl$_2$ (10 mg, 0.0085 mmol) were added under nitrogen gas atmosphere. The reaction mixture was stirred under 100° C. microwave for 30 min. After the reaction was complete as detected by TLC, the reaction mixture was cooled to room temperature and filtrated. The filtrate was concentrated by a rotary evaporator to remove the solvent, the residue was purified by preparative HPLC to deliver the target compound AA 034 (1 mg, yield 1.5%). $^1$H NMR (400 MHz, CD$_3$OD) δ 7.69-7.67 (m, 8H), 7.28 (brs., 2H), 6.82 (m, 3H), 6.35 (m, 1H), 4.13-4.11 (m, 2H), 3.85 (s, 6H), 3.60-3.56 (m, 2H), 3.17-3.14 (m, 6H), 1.61 (s, 6H), 1.31 (m, 2H), 0.98-0.96 (m, 8H).

Embodiment 129: AA_016

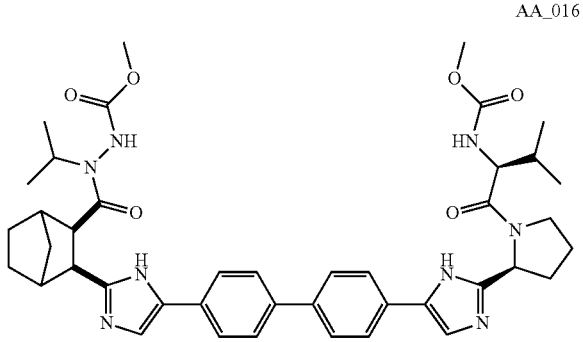

AA_016

Synthetic Route:

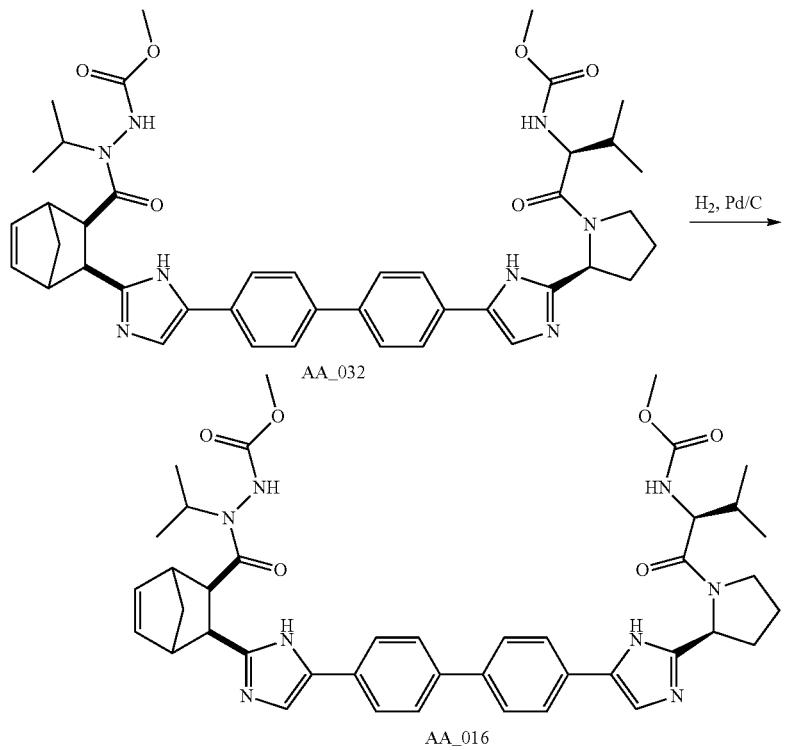

Step 1: Synthesis of Compound AA_016

At room temperature, compound AA_032 (30 mg, 0.04 mmol) was dissolved in ethanol (5 mL), Pd/C (10 mg) was added under nitrogen gas atmosphere. The reaction mixture was stirred at 20° C. and under a hydrogen gas pressure of 1 atm for 12 h. The reaction mixture was filtrated, the filtrate was concentrated by a rotary evaporator to remove the solvent, the residue was purified by preparative HPLC to deliver the target compound AA_016 (white solid, 21 mg, yield 70%). LC/MS m/z: 765.3 [M+H]$^+$.

Embodiment 130: AA_095

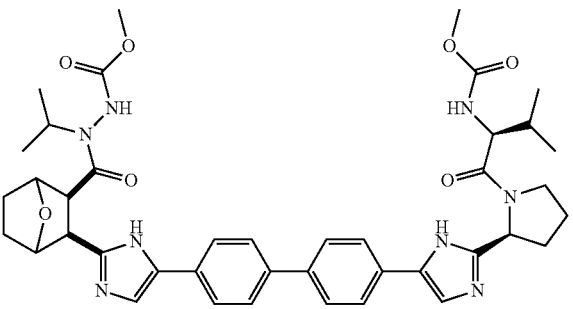

Synthetic Route:

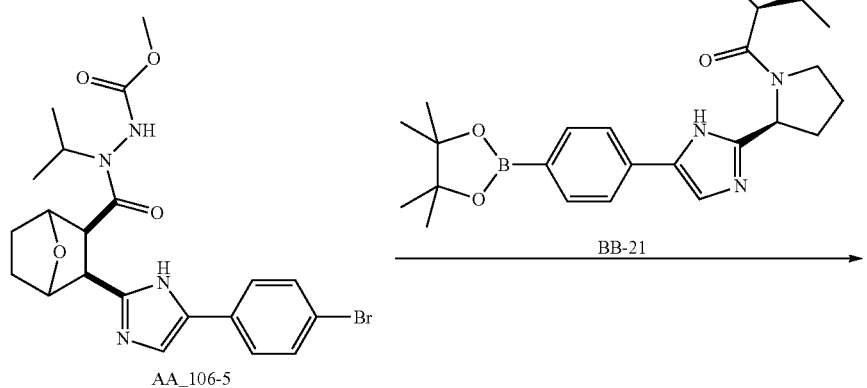

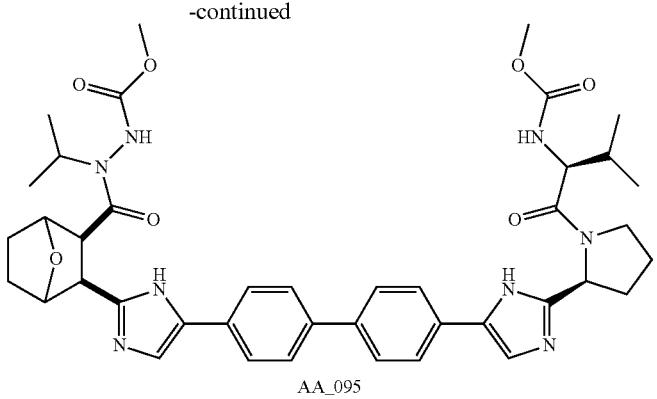
AA_095
Step 1: Synthesis of Compound AA_095
The target compound AA_095 was synthesized according to the synthetic step 5 in synthesizing AA_091, with compound AA_106-5, BB-21 as starting materials. LC/MS m/z: 767.4 [M+H]$^+$.
Embodiment 131: AA_190_A and AA_190_B
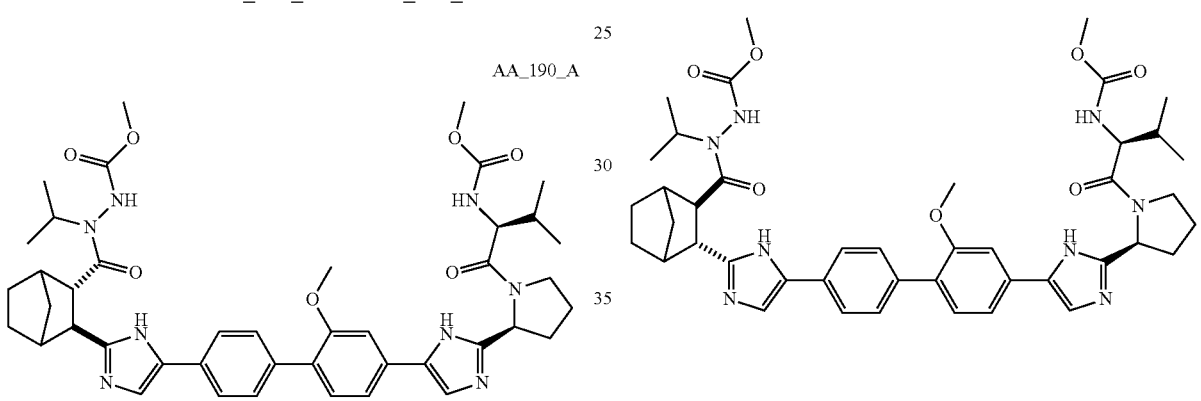
Synthetic Route:
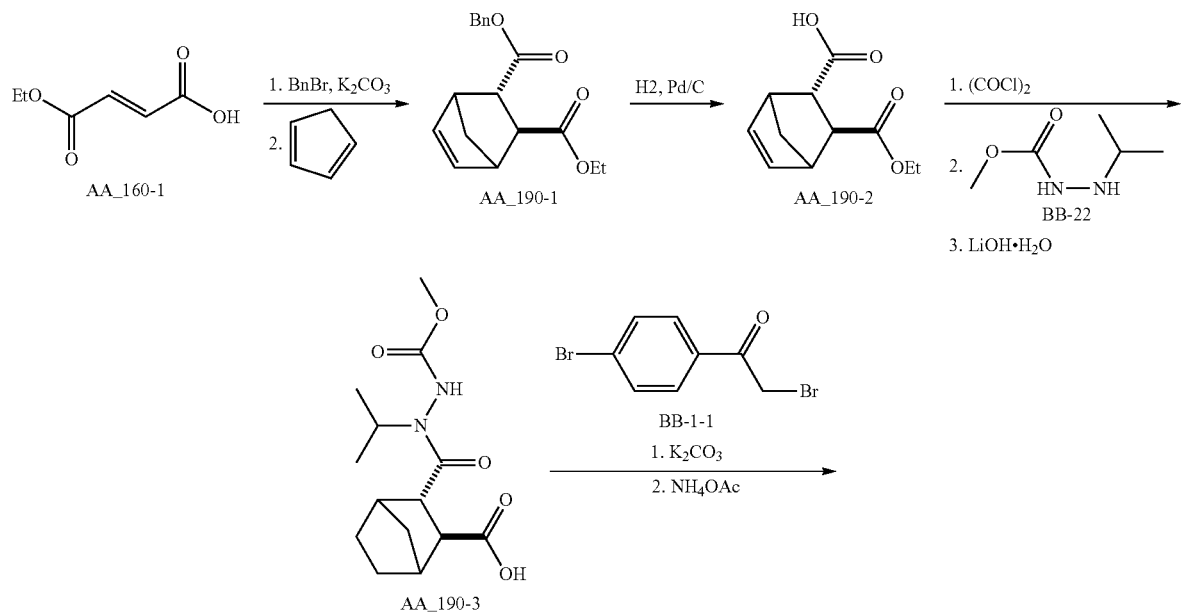

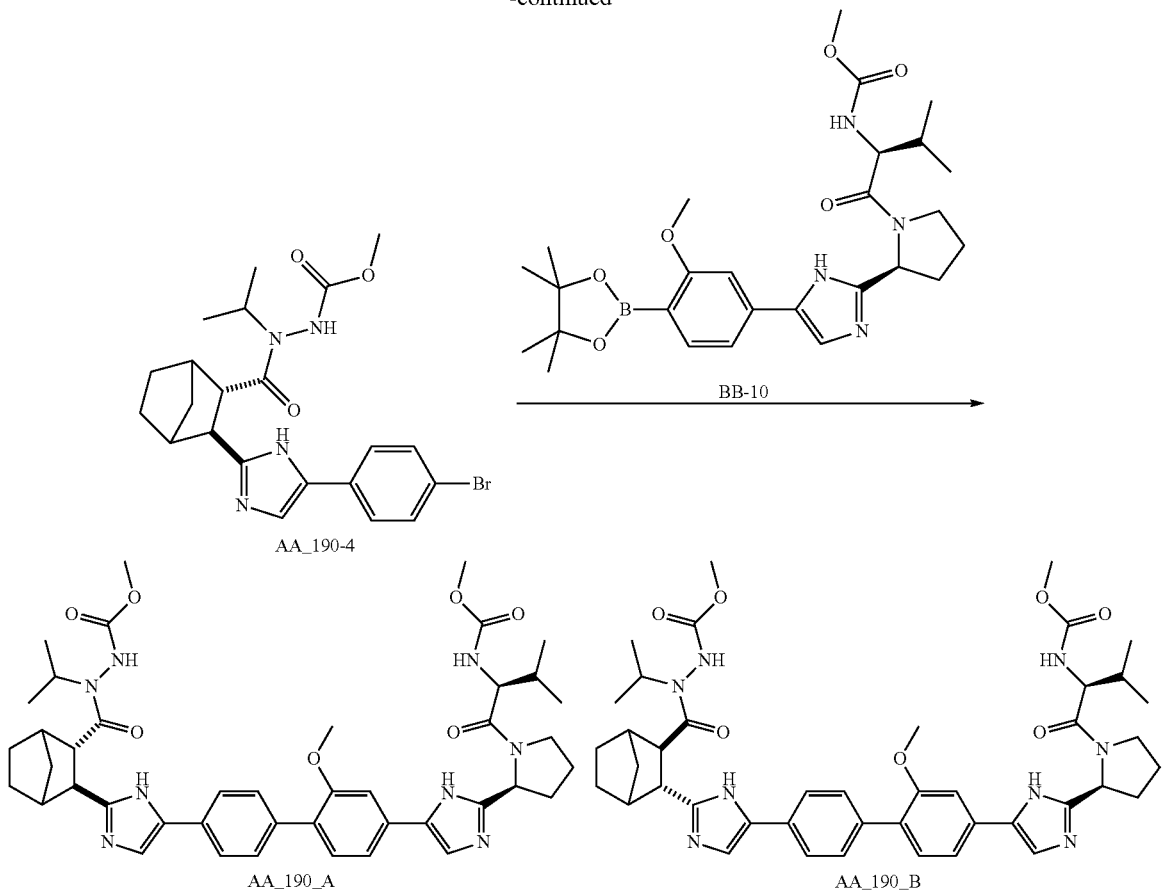

Step 1: Synthesis of Compound AA_190-1

Monoethyl maleate (AA_160-1, 50 g, 346.92 mmol) and K$_2$CO$_3$ (47.9 g, 347.1 mmol) were suspended in DMF (1 L), cooled to 0° C., benzyl bromide (57.3 g, 346.92 mmol) was dripped. The reaction mixture was stirred at room temperature for 10 h. After the reaction was complete as detected by TLC, the reaction mixture was diluted with ethyl acetate (1.5 L) and washed with saturated brines (500 mL×3). The organic phases were combined and dried over anhydrous sodium sulfate. After filtration, the filtrate was concentrated by a rotary evaporator to remove the solvent to deliver an intermediate as yellow oil. The yellow oil intermediate was dissolved in toluene (800 mL), cyclopentadiene (45.7 g, 693.8 mmol) was dripped, and the reaction mixture was heated to 90° C. and stirred for 10 h under nitrogen gas atmosphere. After the reaction was complete as detected by TLC, the solvent was removed under reduced pressure, the residue was purified by silica gel column chromatography (pure PE→PE/EtOAc=9:1) to deliver the target compound AA_190-1 (75 g, yield 72.1%). $^1$H NMR (CDCl$_3$, 400 MHz): δ 7.38-7.34 (m, 5H), 6.89 (s, 1H), 6.01-5.94 (m, 1H), 5.24 (s, 1H), 5.16-5.09 (m, 2H), 4.26 (q, J=3.2 Hz, 1H), 4.18-4.09 (m, 1H), 3.28-3.13 (m, 1H), 2.79-2.71 (m, 1H), 1.47-1.44 (m, 1H), 1.33-1.23 (m, 3H).

Step 2: Synthesis of Compound AA_190-2

At room temperature, compound AA_190-1 (75 g, 250 mmol) was dissolved in THF (5 mL), 10% Pd/C (7.5 g) was added under nitrogen gas atmosphere. The reaction mixture was stirred at room temperature and under a hydrogen gas pressure of 1 atm for 12 h. After the reaction was complete as detected by TLC, the reaction mixture was filtrated. The filtrate was concentrated by a rotary evaporator to remove the solvent thereby delivering the target compound AA_190-2 (white solid, 45.3 g, yield 85.5%). $^1$H NMR (CDCl$_3$, 400 MHz): δ 4.17-4.15 (m, 2H), 2.69-2.62 (m, 4H), 1.48-1.25 (m, 9H).

Step 3: Synthesis of Compound AA_190-3

At room temperature, compound AA_190-2 (10 g, 47.1 mmol) was dissolved in dichloromethane (100 mL), DMF (0.1 mL) was added to catalyze the reaction, the mixture was cooled to 0° C., oxalyl chloride (1.48 g, 116.6 mmol) was dripped. The reaction system was stirred at room temperature for 1 h. After the reaction was complete as detected by TLC, the solvent was removed by a rotary evaporator to obtain an intermediate as yellow oil. The yellow oil intermediate was dissolved in THF (100 mL), cooled to no more than 5° C. under an ice bath. Compound BB-22 (6.8 g, 51.8 mmol) was added, and DIPEA (18.2 g, 141.3 mmol) was dripped. The reaction mixture was stirred at room temperature for 10 h. After the reaction was complete as detected by TLC, ethyl acetate (100 mL) was added. The reaction mixture was washed with saturated brines (20 mL×3), dried over anhydrous sodium sulfate and then filtrated. The filtrate was concentrated under reduced pressure to remove the solvent, the residue was purified by silica gel column chromatography (PE/EtOAc=5:1) to deliver an intermediate as yellow oil (7.6 g, yield for two steps 55.7%). The yellow oil intermediate (7.6 g, 23.3 mmol) was dissolved in a mixed solvent of THF/MeOH/H$_2$O (30 mL/30 mL/30 mL), lithium hydroxide monohydrate (5.5 g, 233 mmol) was added. The reaction system was stirred at 60° C. for 10 h. After the reaction was complete as detected by TLC, the reaction mixture was cooled to room temperature, 1M HCl aqueous solution was dripped to adjust pH to 3-4, the mixture was extracted with ethyl acetate (100 mL×3). The organic phases were combined and dried over anhydrous sodium sulfate. After filtration, the filtrate was concentrated by a rotary evaporator to remove the solvent thereby delivering the target compound AA_190-3 (2.7 g, yield 19.3%). $^1$H NMR (CDCl$_3$, 400 MHz): δ 3.77 (s, 3H), 2.63-2.59 (m, 3H), 1.60-1.56 (m, 4H), 1.31-1.06 (m, 10H).

Step 4: Synthesis of Compound AA_190-4

At room temperature, compound AA_190-3 (2.7 g, 9.0 mmol) and K$_2$CO$_3$ (1.86 g, 13.5 mmol) were suspended in DMF (20 mL), 2,4-dibromoacetophenone (BB-1-1, 2.97 g, 10.8 mmol) was added at room temperature. The reaction mixture was stirred at room temperature for 2 h. After the reaction was complete as detected by TLC, the solvent was removed by a rotary evaporator, the residue was suspended in ethyl acetate (100 mL), washed with saturated brines (10 mL×3). The organic phases were combined and dried over anhydrous sodium sulfate. After filtration, the filtrate was concentrated under reduced pressure to remove the solvent thereby delivering an intermediate as yellow oil. The yellow oil intermediate was dissolved in toluene (50 mL), ammonium acetate (6.9 g, 90 mmol) was added. The reaction mixture was heated to reflux and stirred for 12 h under nitrogen gas atmosphere. After the reaction was complete as detected by TLC, the reaction mixture was cooled to room temperature and quenched with H$_2$O (30 mL), extracted with ethyl acetate (50 mL×3). The organic phases were combined and dried over anhydrous sodium sulfate. After filtration, the filtrate was concentrated under reduced pressure to remove the solvent, the residue was purified by silica gel column chromatography (PE/EA=9:1→1:1) to deliver the target compound AA_190-4 (2.3 g, yield for two steps: 53.9%). LC/MS m/z: 475.0 [M+H]$^+$ Step 5: Synthesis of Compound AA_190_A and AA_190_B Target compound AA_190_A (17.4 mg, yield 26.4%) and AA_190_B (17.2 mg, yield 26.3%) were separated and prepared according to the synthetic steps 5-6 in synthesizing AA_091, with compound AA_190-4 (40 mg, 0.084 mmol), compound BB-10 (55.0 mg, 0.105 mmol), Na$_2$CO$_3$ (18.5 mg, 0.174 mmol), Pd(dppf)Cl$_2$ (6.4 mg, 0.0087 mmol) as starting materials, and DMF/THF/H$_2$O (1.5 mL/1.5 mL/1.5 mL) as a mixed solvent. AA_190_A: LC/MS m/z: 795.6 [M+H]$^+$. AA_190_B: LC/MS m/z: 398.4 [M/2+H]$^+$.

The compounds listed in the following table were synthesized according to the synthetic steps 5-6 in synthesizing AA_091, with compound AA_090-4 as starting material:

| Embodiments | Structure | Fragment 1 | Fragment 2 | LCMS |
|---|---|---|---|---|
| 132 | AA_121_A | AA_190_4 | BB-21 | 765.5 [M + H]⁺ |
| 133 | AA_121_B | AA_190_4 | BB-21 | 765.4 [M + H]⁺ |

-continued

| Embodiments | Structure | Fragment 1 | Fragment 2 | LCMS |
|---|---|---|---|---|
| 134 | AA_166_A | AA_190_4 | BB-9 | 767.4 [M + H]+ |
| 135 | AA_166_B | AA_190_4 | BB-9 | 389.4 [M/2 + H]+ |

| Embodiments | Structure | Fragment 1 | Fragment 2 | LCMS |
|---|---|---|---|---|
| 136 | AA_169_A | AA_190_4 | BB-11 | 779.6 [M + H]+ |
| 137 | AA_169_B | AA_190_4 | BB-11 | 779.5 [M + H]+ |

| Embodiments | Structure | Fragment 1 | Fragment 2 | LCMS |
|---|---|---|---|---|
| 138 | AA_156 | AA_190_4 | BB-13 | 799.4 [M + H]⁺ |
| 139 | AA_167 | AA_190_4 | BB-12 | 779.5 [M + H]⁺ |

| Embodiments | Structure | | LCMS |
|---|---|---|---|
| | Fragment 1 | Fragment 2 | |
| 140 | AA_155 | AA_190_4 / AG_048_1_1 | 757.6 [M + H]+ |

Embodiment 141: AA_158
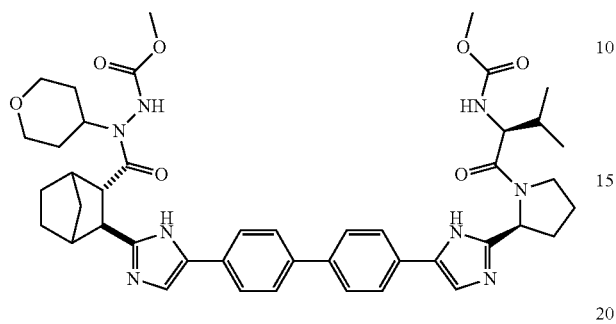
Synthetic Route:
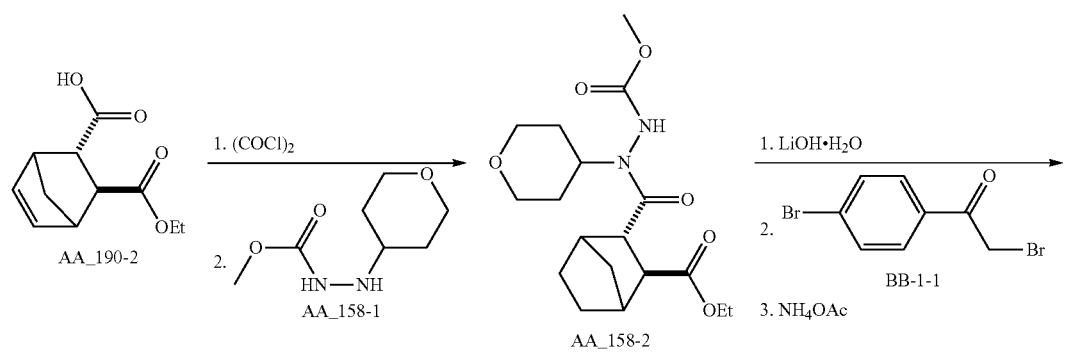
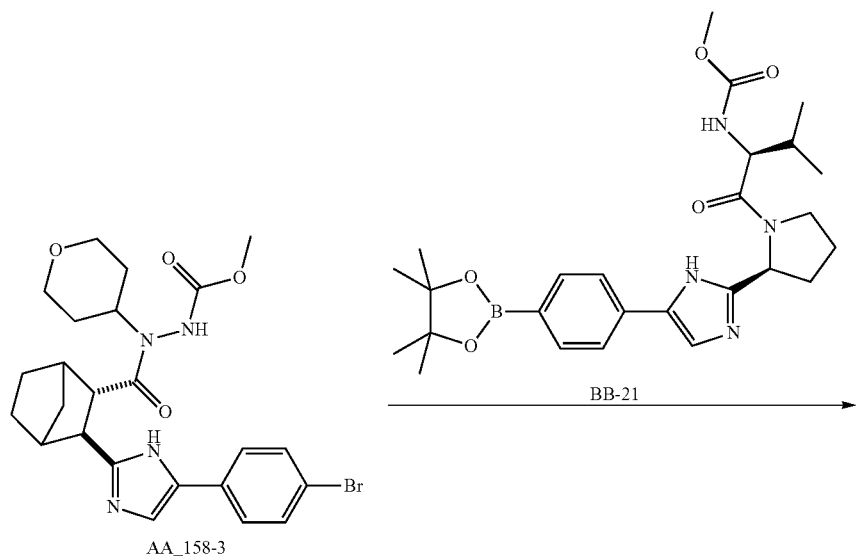

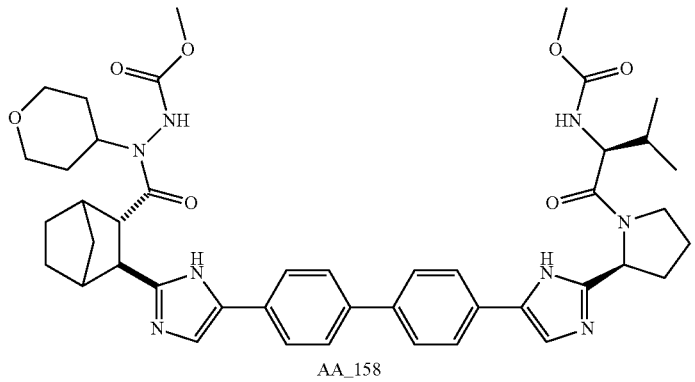

AA_158

Step 1: Synthesis of Compound AA_158-2

At room temperature, compound AA_190-2 (10 g, 47.1 mmol) was dissolved in dichloromethane (100 mL), DMF (0.1 mL) was added to catalyze the reaction, the mixture was cooled to 0° C., oxalyl chloride (1.48 g, 116.6 mmol) was dripped. The reaction system was stirred at room temperature for 1 h. After the reaction was complete as detected by TLC, the solvent was removed by a rotary evaporator to obtain an intermediate as yellow oil (10.8 g). The product was directly used for the next step without purification. The yellow oil intermediate (10.8 g, 47.1 mmol) was dissolved in THF (100 mL), cooled to no more than 5° C. under an ice bath, compound AA_158-1 (9.03 g, 51.8 mmol) was added, then DIPEA (18.2 g, 141.3 mmol) was dripped. The reaction mixture was stirred at room temperature for 10 h. After the reaction was complete as detected by TLC, ethyl acetate (100 mL) was added. The reaction mixture was washed with saturated brines (20 mL×3), dried over anhydrous sodium sulfate and then filtrated. The filtrate was concentrated under reduced pressure to remove the solvent, the residue was purified by silica gel column chromatography (PE/EtOAc=5:1) to deliver the target compound AA_158-2 (6.9 g, yield 40%).

Step 2: Synthesis of Compound AA_158-3

Target compound AA_158-3 (2.2 g, yield for two steps 22.9%) was obtained according to the synthetic step 4 in embodiment 131 (AA_190), with compound AA_158-2 (6.9 g, 18.73 mmol) as starting material. LC/MS m/z: 539.0 [M+Na]$^+$.

Step 3: Synthesis of Compound AA_158

Target compound AA_158 was obtained according to the synthetic step 5 in synthesizing AA_190, with compound AA_158-3, BB-21 as starting materials. LC/MS m/z: 807.3 [M+H]$^+$.

Embodiment 142: AA_027

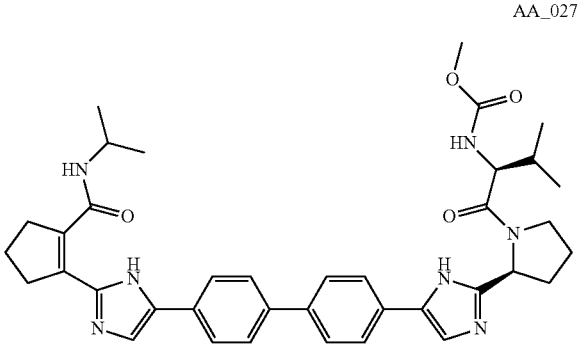

AA_027

Synthetic Route:

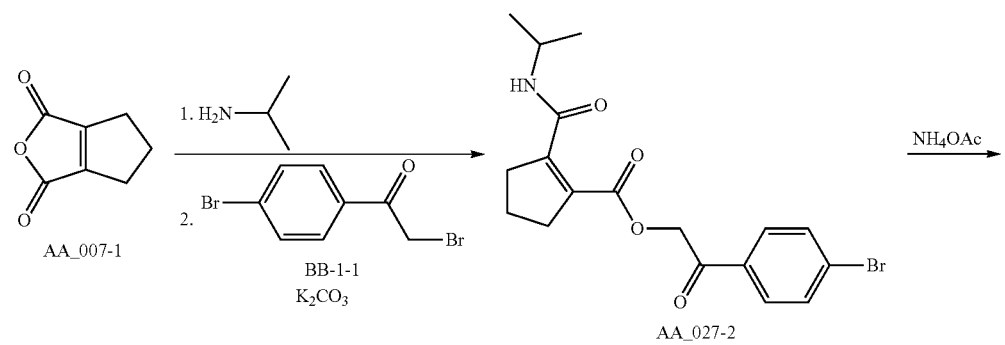

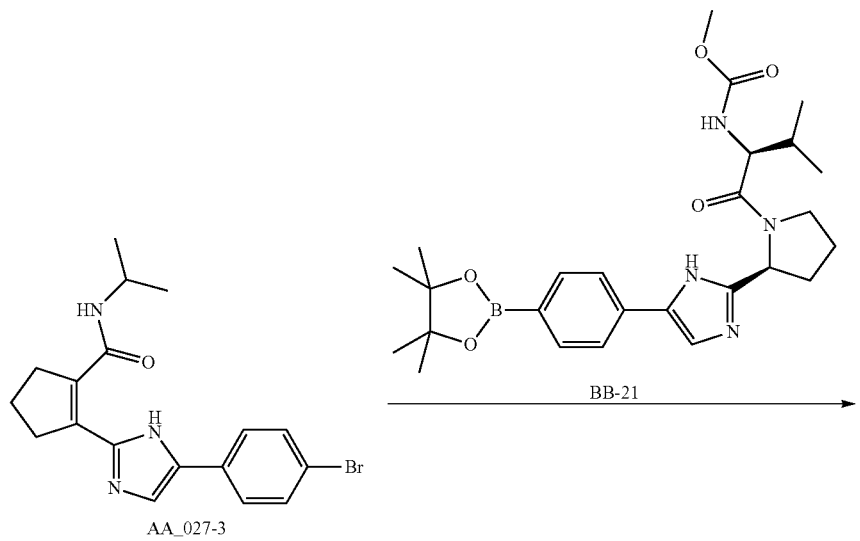

Step 1: Synthesis of Compound AA_027-2

Target compound AA_027-2 (1.1 g, yield for two steps 73.8%) was obtained according to the synthetic step 1 in synthesizing AA_007, with 1-cyclopentene-1,2-dicarboxylic anhydride (AA_007-1, 500 mg, 3.623 mmol), isopropyl amine (214 mg, 3.623 mmol) as starting materials. LC/MS m/z: 394 [M+H]+.

Step 2: Synthesis of Compound AA_027-3

Target compound AA_027-3 (yellow powder, 0.78 g, yield 82.8%) was obtained according to the synthetic step 2 in synthesizing AA_007, with compound AA_027-2 (1 g, 2.54 mmol), ammonium acetate (1.95 g, 25.4 mmol) as starting material. LC/MS m/z: 375.7 [M+H]+.

Step 3: Synthesis of Compound AA_027

Target compound AA_027 (white powder, 86 mg, yield 43.8%) was obtained according to the synthetic step 3 in synthesizing AA_007, with compound AA_027-3 (100 mg, 0.267 mmol), BB-21 (160 mg, 0.321 mmol), sodium carbonate (45 mg, 0.534 mmol) and Pd(dppf)Cl₂ (20 mg, 0.0267 mmol) as starting materials. LC/MS m/z: 664.1 [M+H]+.

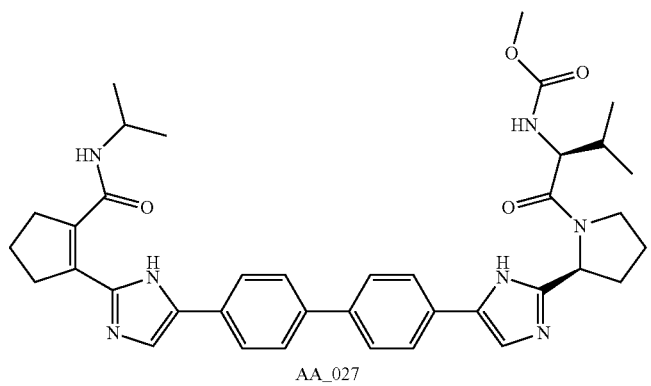

Embodiment 143: AA_047

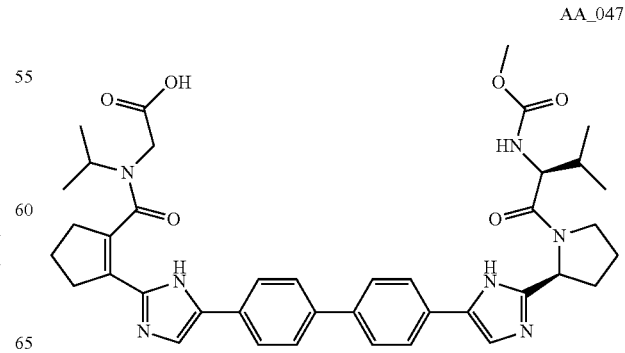

AA_047

Synthetic Route:

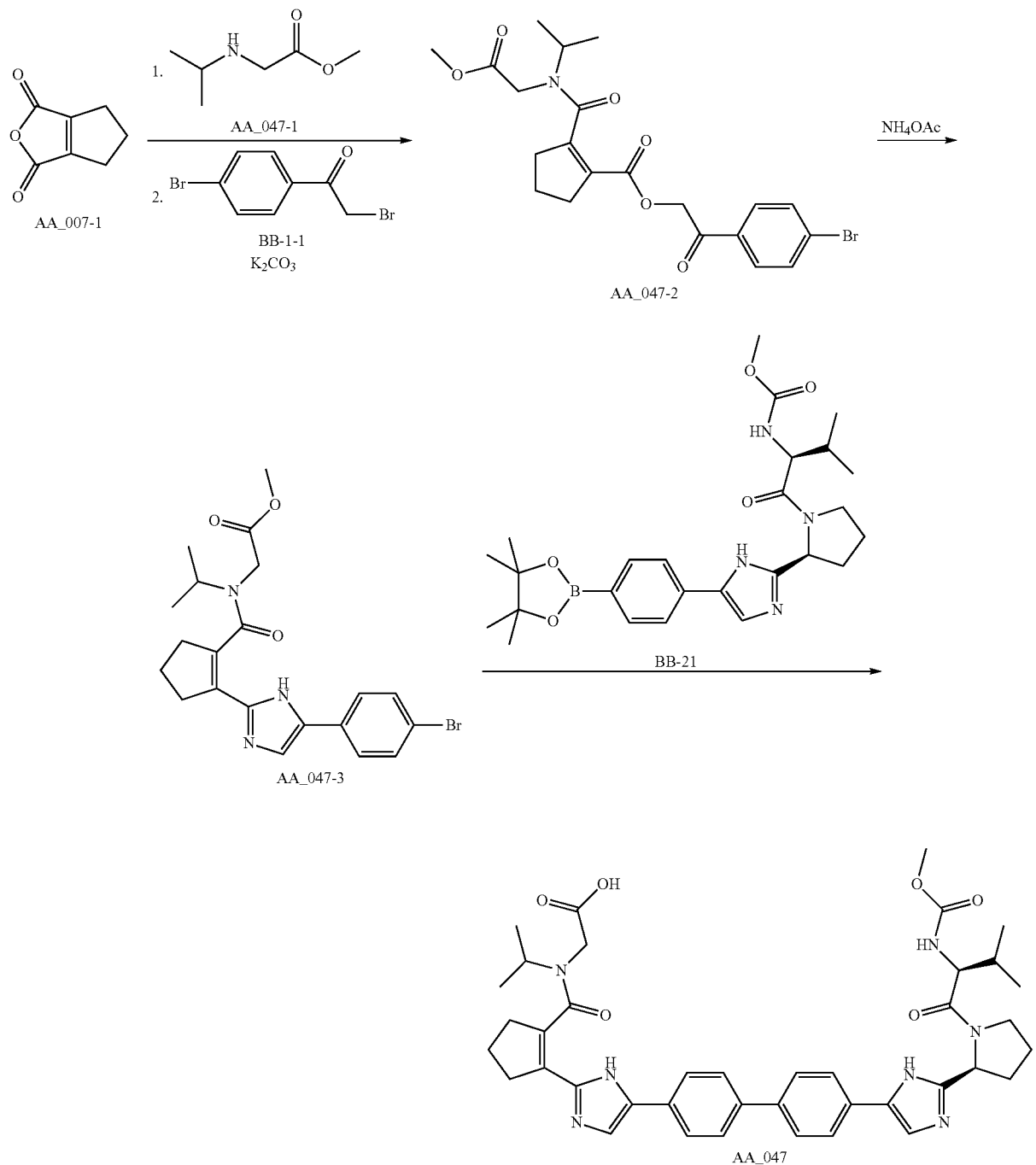

Step 1: Synthesis of Compound AA_047-2

Target compound AA_047-2 (138 mg, yield for two steps 83.8%) was obtained according to the synthetic step 1 in synthesizing AA_007, with 1-cyclopentene-1,2-dicarboxylic anhydride (AA_007-1, 50 mg, 0.362 mmol), AA_047-1 (48 mg, 0.362 mmol) as starting materials. LC/MS m/z: 465.8 [M+H]$^+$.

Step 2: Synthesis of Compound AA_047-3

Target compound AA_047-3 (milk-white powder, 100 mg, yield 73.8%) was obtained according to the synthetic step 2 in synthesizing AA_007, with compound AA_047-2 (138 mg, 0.296 mmol), ammonium acetate (228 mg, 2.96 mmol) as starting materials. LC/MS m/z: 447.7 [M+H]$^+$.

Step 3: Synthesis of Compound AA_047

Target compound AA_047 (white powder, 20 mg, yield 23.8%) was directly obtained according to the synthetic step 3 in synthesizing AA_007, with compound AA_047-3 (50 mg, 0.112 mmol), BB-21 (66 mg, 0.135 mmol), sodium carbonate (24 mg, 0.224 mmol) and Pd(dppf)Cl$_2$ (8 mg, 0.0112 mmol) as starting materials. LC/MS m/z: 722.2 [M+H]$^+$.

503

Embodiment 144: AA_064

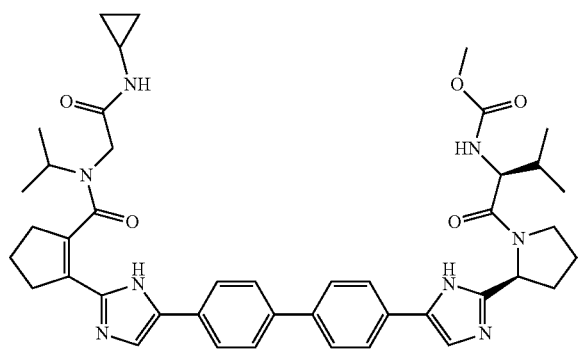

AA_064

504

Embodiment 145: AA_065

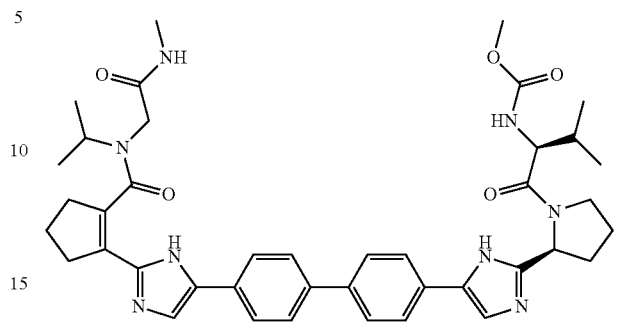

AA_065

Synthetic Route:

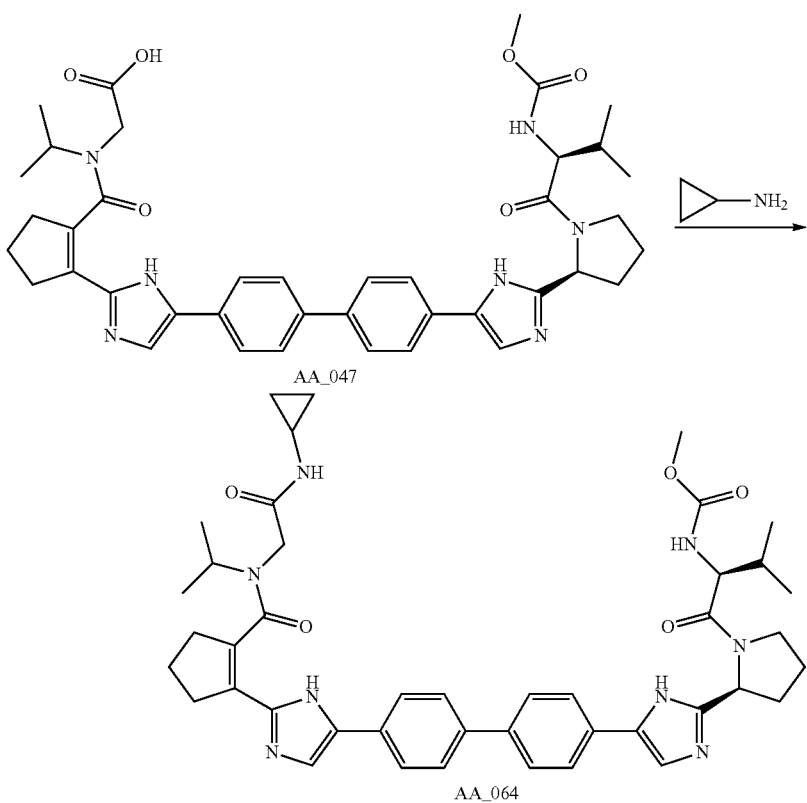

Step 1: Synthesis of Compound AA_064

At room temperature, compound AA_047 (20 mg, 0.0277 mmol), cyclopropyl amine (8 mg, 0.0305 mmol), DIPEA (10 mg, 0.0554 mmol) were dissolved in DMF (2 mL), HATU (12 mg, 0.0305 mmol) was added. The reaction mixture was stirred at room temperature for 1 h. After the reaction was complete as detected by TLC, the reaction was quenched with H$_2$O (10 mL) and extracted with ethyl acetate (30 mL×3). The organic phases were combined and dried over anhydrous sodium sulfate. After filtration, the filtrate was concentrated by a rotary evaporator to remove the solvent, the residue was purified by preparative HPLC to deliver the target compound AA_064 (milk-white powder, 10 mg, yield 25.8%). LC/MS MS m/z: 761.8 [M+1]$^+$.

Synthetic Route:

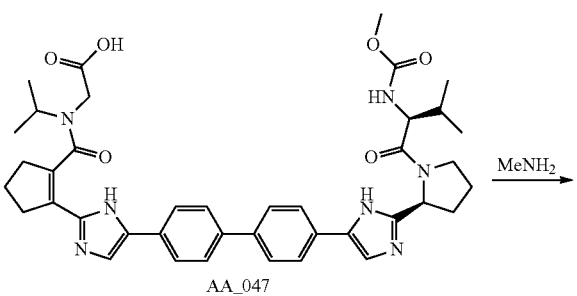

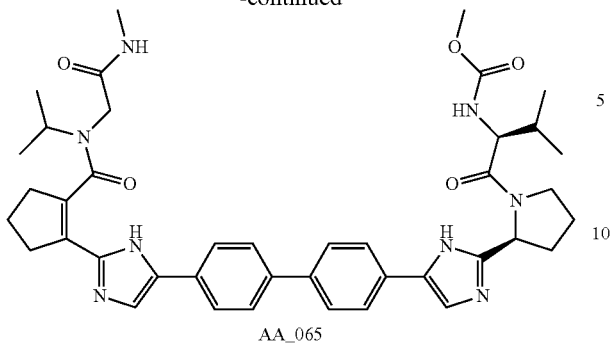

AA_065

Step 1: Synthesis of Compound AA_065

Target compound AA_065 (white powder, 11 mg, yield 25.8%) was obtained according to the synthetic step 1 in synthesizing AA_064, with compound AA_047, methylamine as starting materials. LCMS m/z: 368.4 [M/2+H]$^+$.

Embodiment 146: AA_028

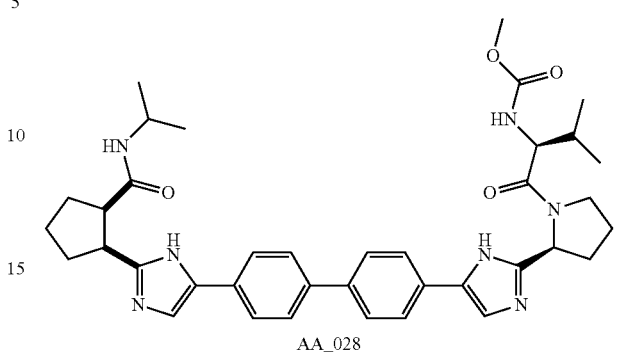

AA_028

Step 1: Synthesis of Compound AA_028

Target compound AA_028 (white powder, 8 mg, yield 33.8%) was obtained according to the synthetic step 1 in synthesizing AA_016, with compound AA_027 (20 mg, 0.0301 mmol) as starting material, and Pd/C (2 mg) as a catalyst. LC/MS m/z: 666.2 [M+H]$^+$.

Embodiment 147: AA_054

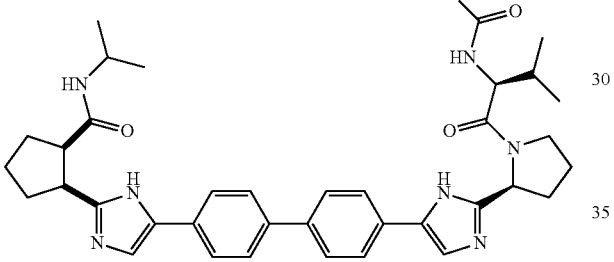

AA_028

Synthetic Route:

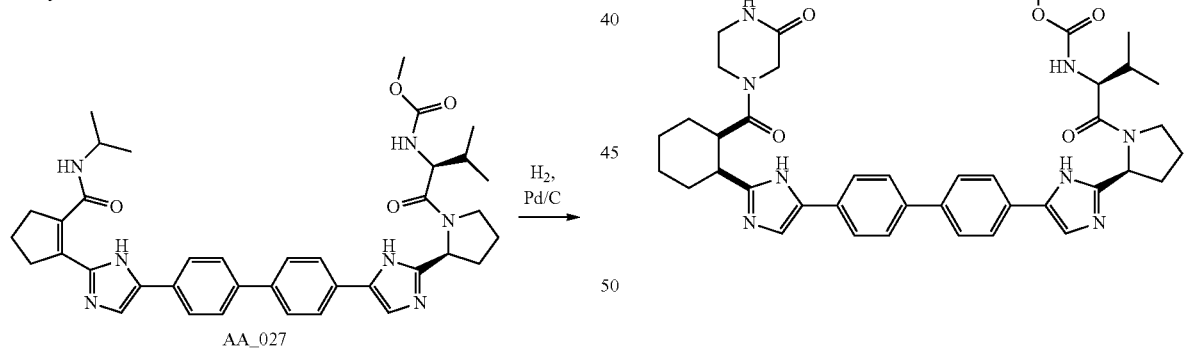

AA_054

Synthetic Route:

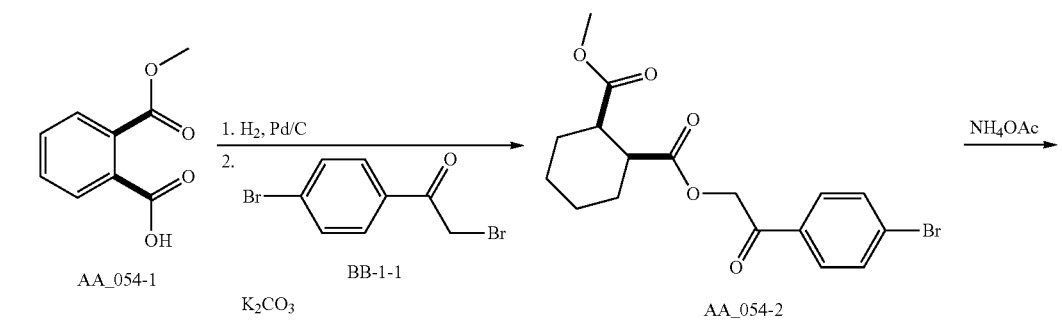

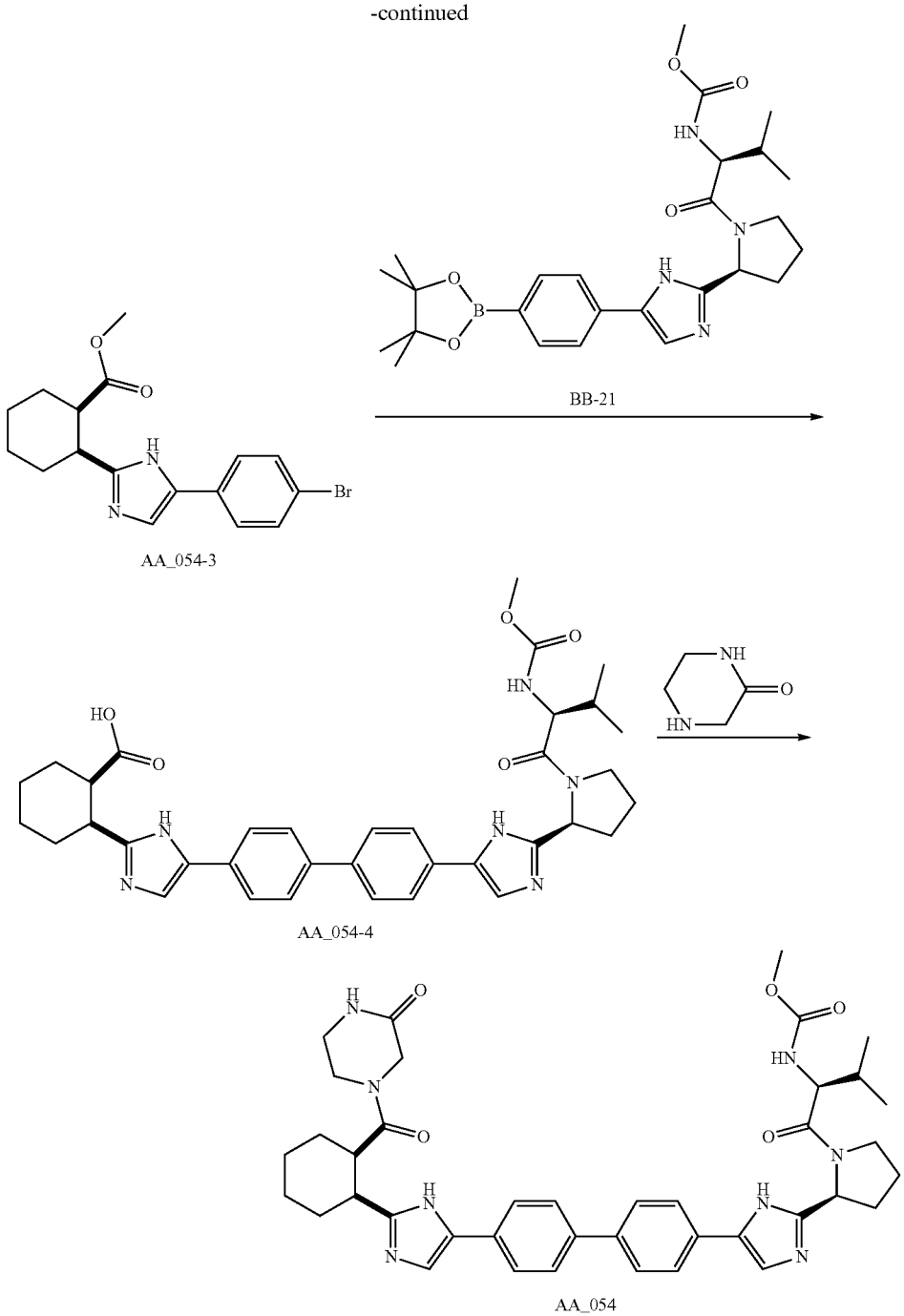

Step 1: Synthesis of Compound AA_054-2

At room temperature, compound AA_054-1 (500 mg, 2.7 mmol) was dissolved in ethanol (10 mL), Pd/C (200 mg) was added. The reaction mixture was stirred at 20° C. and under a hydrogen gas pressure of 1 atm for 5 h, then filtrated, the filtrate was concentrated by a rotary evaporator to remove the solvent thereby delivering an intermediate as yellow oil (500 mg, 2.7 mmol, yield 90%). The yellow oil intermediate and $K_2CO_3$ (0.8 g, 5.4 mmol) were suspended in DMF (15 mL), 2,4-dibromoacetophenone (BB-1-1, 0.9 g, 3.2 mmol) was added at 10° C. The reaction mixture was stirred at 10° C. for 12 h. After the reaction was complete as detected by TLC, the reaction was quenched with $H_2O$ (20 mL) and extracted with ethyl acetate (50 mL×3). The organic phases were combined and dried over anhydrous sodium sulfate. After filtration, the filtrate was concentrated by a rotary evaporator to remove the solvent, the residue was purified by silica gel column chromatography (PE/EA=10:1→3:1) to deliver the target compound AA_054-2 (1 g, yield for two steps: 95%). LC/MS m/z: 404.6 [M+Na]$^+$ Step 2: Synthesis of Compound AA_054-3

At room temperature, compound AA_054-2 (1 g, 2.6 mmol) was dissolved in toluene (60 mL), ammonium acetate (10 g, 130 mmol) was added. The reaction mixture was heated to 120° C. and stirred for 6 h under nitrogen gas atmosphere. After the reaction was complete as detected by TLC, the reaction mixture was cooled to room temperature and quenched with H$_2$O (30 mL), extracted with ethyl acetate (50 mL×3). The organic phases were combined and dried over anhydrous sodium sulfate. After filtration, the filtrate was concentrated under reduced pressure to remove the solvent, the residue was purified by silica gel column chromatography (PE/EtOAc=10:1→1:1) to deliver the target compound AA_054-3 (light yellow powder, 0.6 g, yield 70%). LC/MS m/z: 364.6 [M+H]$^+$.

Step 3: Synthesis of Compound AA_054-4

At room temperature, compound AA_054-3 (300 mg, 0.83 mmol), BB-21 (500 mg, 1 mmol) were dissolved in DMF/THF/H$_2$O (4 mL/4 mL/4 mL), K$_2$CO$_3$ (300 mg, 2.2 mmol) and Pd(dppf)Cl$_2$ (60 mg, 0.083 mmol) were added under nitrogen gas atmosphere. The reaction mixture was stirred under 100° C. microwave for 3 h. After the reaction was complete as detected by TLC, the reaction mixture was cooled to room temperature and filtrated. The filtrate was concentrated by a rotary evaporator to remove the solvent, the residue was purified by preparative HPLC to deliver the target compound AA_054-4 (white powder, 300 mg, yield 40%).

Step 4: Synthesis of Compound AA_054

At room temperature, compound AA_054-4 (50 mg, 0.078 mmol), piperazine-2-one (15 mg, 0.15 mmol), DIPEA (25 mg, 0.4 mmol) were dissolved in DMF (1 mL), HATU (50 mg, 0.15 mmol) was added. The reaction mixture was stirred at room temperature for 3 h. After the reaction was complete as detected by TLC, the reaction was quenched with H$_2$O (10 mL) and extracted with ethyl acetate (30 mL×3). The organic phases were combined and dried over anhydrous sodium sulfate. After filtration, the filtrate was concentrated by a rotary evaporator to remove the solvent, the residue was purified by preparative HPLC to deliver the target compound AA_054 (6 mg, yield 11%). $^1$H NMR (400 MHz, METHANOL-d$_4$) δ 0.92-1.00 (m, 6H), 1.31-2.37 (m, 20H), 3.19-4.75 (m, 12H), 5.18-5.22 (m, 1H), 7.33 (s, 2H), 7.60-7.80 (m, 8H).

The compounds listed in the following table were synthesized according to the synthetic steps 5-6 in synthesizing AA_091, with compound AA_054-4 as starting material:

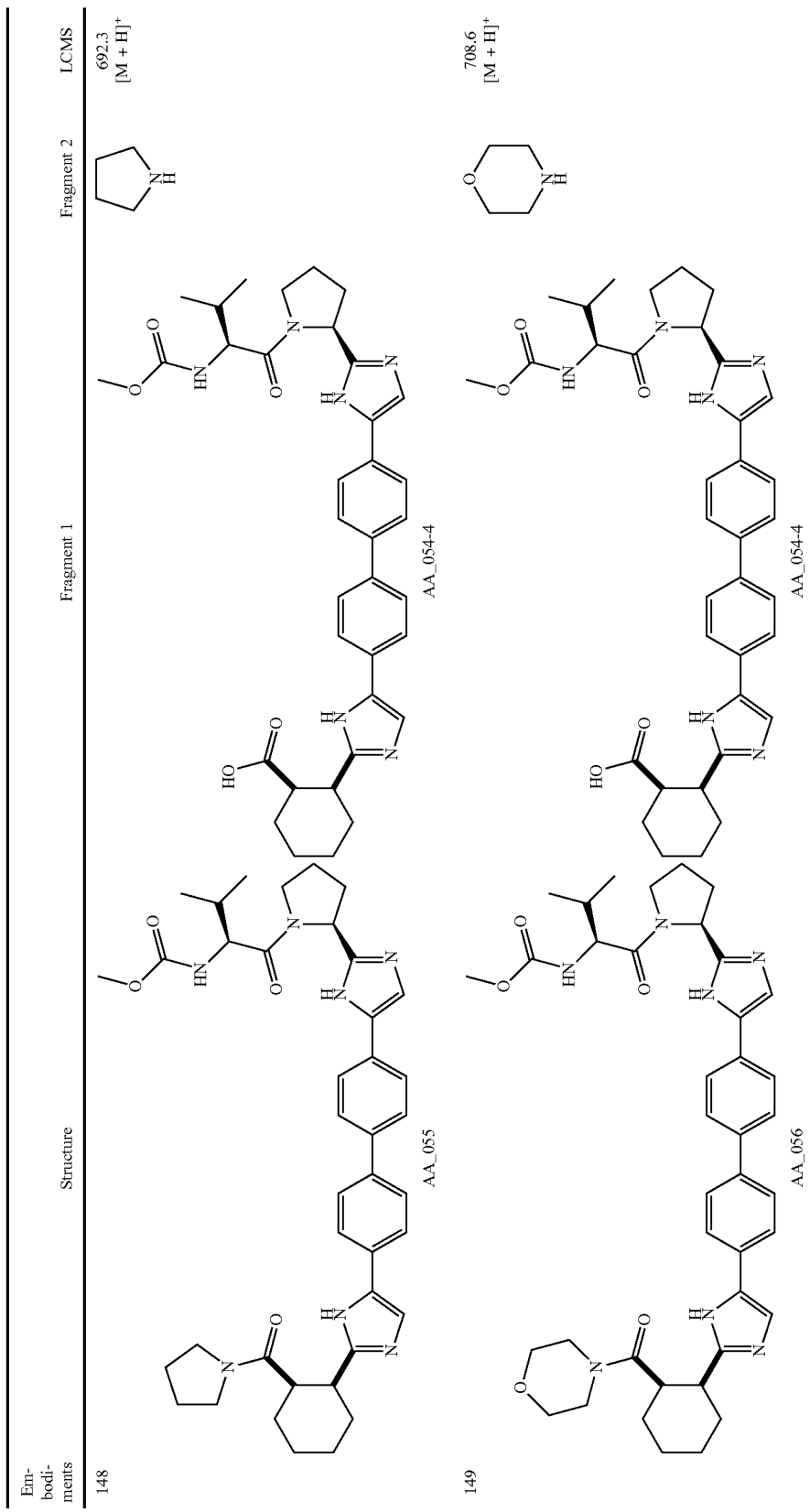

| Embodiments | Structure | Fragment 1 | Fragment 2 | LCMS |
|---|---|---|---|---|
| 150 | AA_057 | AA_054-4 | piperidine | 706.5 [M + H]+ |
| 151 | AA_113 | AA_054-4 | 3-(aminomethyl)pyridine | 729.5 [M + H]+ |

| Embodiments | Structure | Fragment 1 | Fragment 2 | LCMS |
|---|---|---|---|---|
| 152 | AA_114 | AA_054-4 | 3-methoxypropan-1-amine | 696.5 [M + H]⁺ |
| 153 | AA_115 | AA_054-4 | cyclopropylmethanamine | 692.6 [M + H]⁺ |

| Embodiments | Structure | Fragment 1 | Fragment 2 | LCMS |
|---|---|---|---|---|
| 154 | 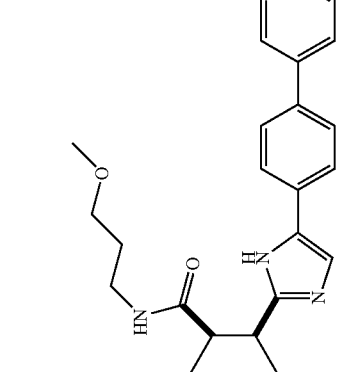 AA_116 | 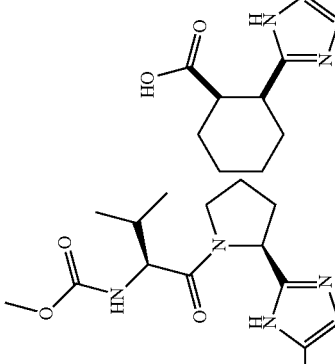 AA_054-4 | 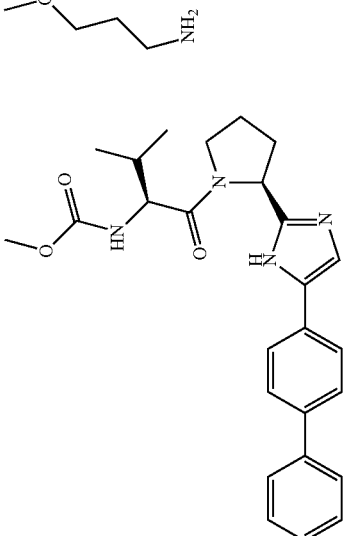 | 710.6 [M + H]+ |

Embodiment 155: AA_063
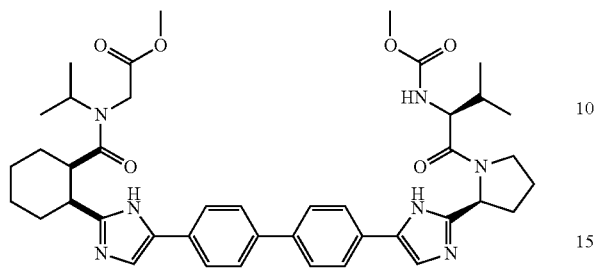
Synthetic Route:
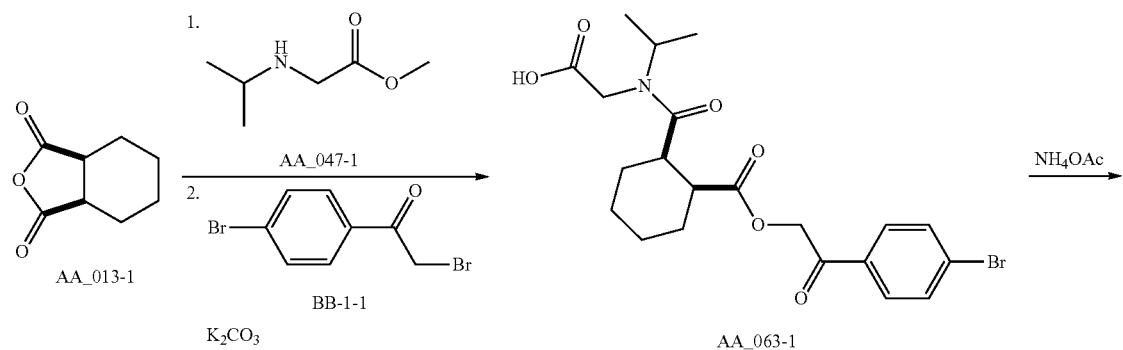
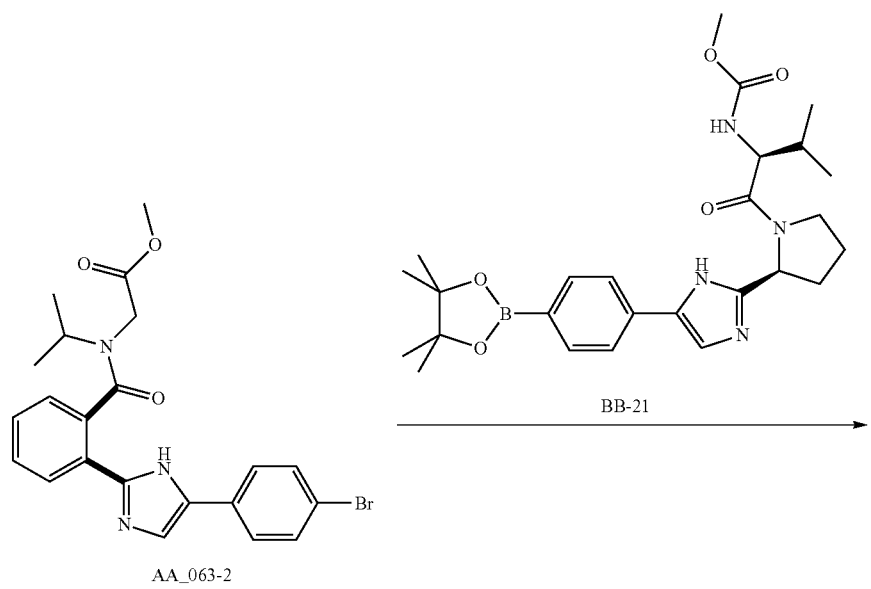

-continued

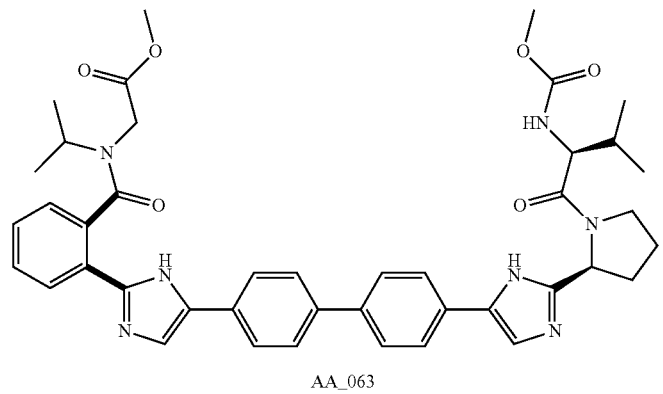

AA_063

Step 1: Synthesis of Compound AA_063-1

Compound AA_047-1 (0.5 g, 3.2 mmol) was dissolved in THF (10 mL), cis-1,2-cyclohexane-dicarboxylic anhydride (AA_013-1, 0.5 g, 3.9 mmol) was added at 10° C. The reaction mixture was stirred at 10° C. for 14 h. After the reaction was complete as detected by TLC, the reaction mixture was concentrated by a rotary evaporator to remove the solvent thereby giving colorless jelly (1 g). The colorless jelly (1 g, 3.2 mmol) and $K_2CO_3$ (1 g, 7.2 mmol) were suspended in DMF (10 mL), 2,4-dibromoacetophenone (BB-1-1, 1 g, 3.6 mmol) was added at 10° C. The reaction mixture was stirred at 10° C. for 2 h. After the reaction was complete as detected by TLC, the reaction was quenched with $H_2O$ (10 mL) and extracted with ethyl acetate (30 mL×2). The organic phases were combined and dried over anhydrous sodium sulfate. After filtration, the filtrate was concentrated under reduced pressure to remove the solvent, the residue was purified by silica gel column chromatography (PE/EA=10:1→3:1) to deliver the target compound AA_063-1 (0.6 g, yield for two steps: 40%). LC/MS m/z: 484.0 [M+H]$^+$ Step 2: Synthesis of Compound AA_063-2

At room temperature, compound AA_063-1 (0.3 g, 0.62 mmol) was dissolved in toluene (60 mL), ammonium acetate (3 g, 50 mmol) was added. The reaction mixture was heated to 120° C. and stirred for 6 h under nitrogen gas atmosphere. After the reaction was complete as detected by TLC, the reaction mixture was cooled to room temperature and quenched with $H_2O$ (30 mL), extracted with ethyl acetate (50 mL×3). The organic phases were combined and dried over anhydrous sodium sulfate. After filtration, the filtrate was concentrated under reduced pressure to remove the solvent, the residue was purified by silica gel column chromatography (PE/EtOAc=10:1→1:1) to deliver the target compound AA_063-2 (0.2 g, yield 70%). LC/MS m/z: 463.8 [M+H]$^+$.

Step 3: Synthesis of Compound AA_063

At room temperature, compound AA_063-2 (50 mg, 0.11 mmol), BB-21 (54 mg, 0.11 mmol) were dissolved in DMF/THF/$H_2O$ (0.5 mL/0.5 mL/0.5 mL), NaHCO$_3$ (20 mg, 0.22 mmol) and Pd(dppf)Cl$_2$ (10 mg, 0.011 mmol) were added under nitrogen gas atmosphere. The reaction mixture was stirred under 80° C. microwave for 5 min. After the reaction was complete as detected by TLC, the reaction mixture was cooled to room temperature and filtrated. The filtrate was concentrated by a rotary evaporator to remove the solvent, the residue was purified by preparative HPLC to deliver the target compound AA_063 (white powder, 10.5 mg, yield 13%). $^1$H NMR (400 MHz, METHANOL-d$_4$) δ 0.92-1.31 (m, 16H), 1.75-2.75 (m, 11H), 3.50-3.93 (m, 14H), 4.24-5.21 (m, 5H), 7.35-7.81 (m, 10H), 8.47 (br. s., 2H).

Embodiment 156: AA_237_A and AA_237_B

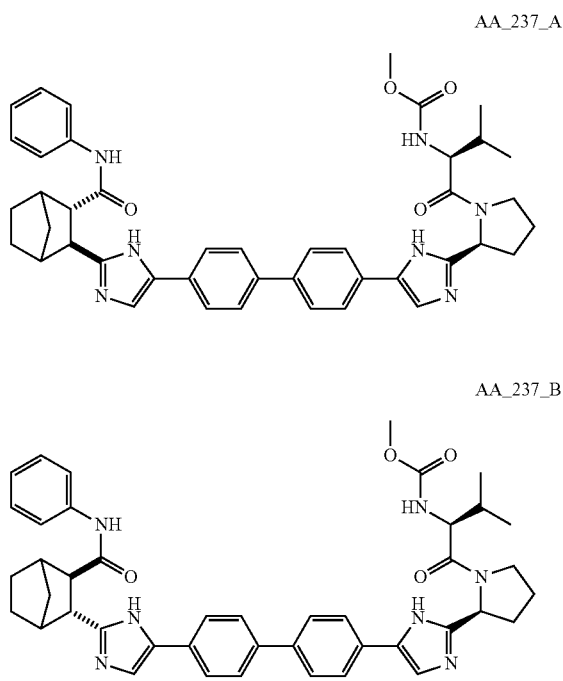

AA_237_A

AA_237_B

Synthetic Route:
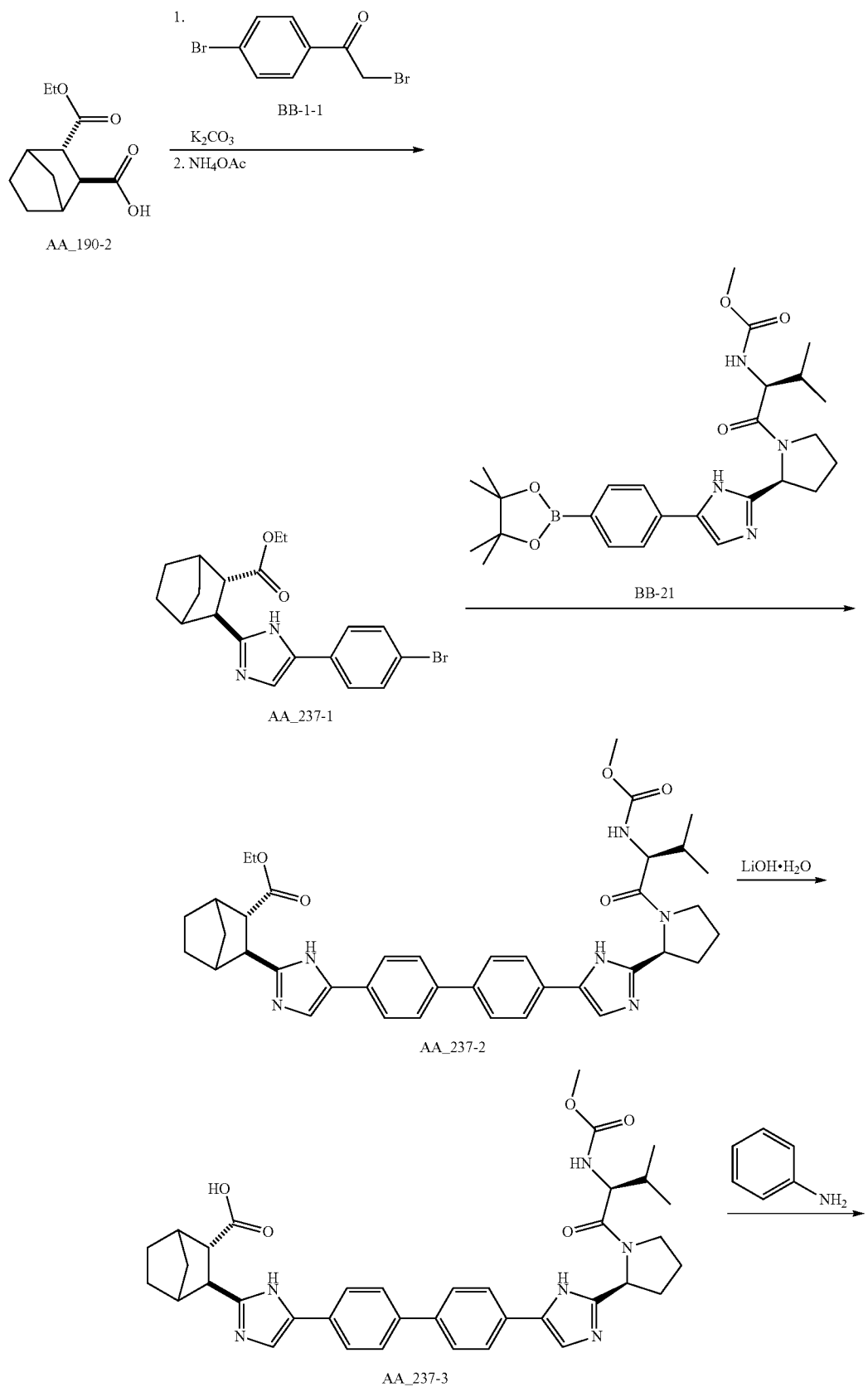

-continued

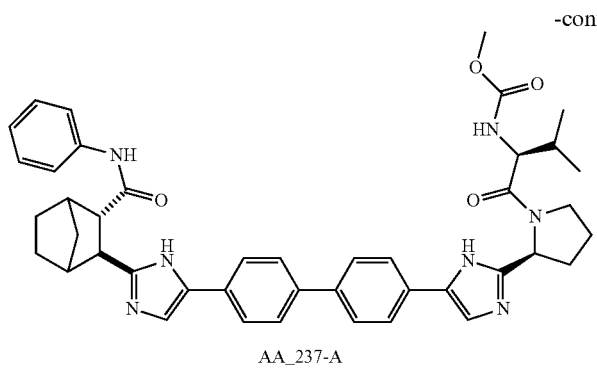

AA_237-A

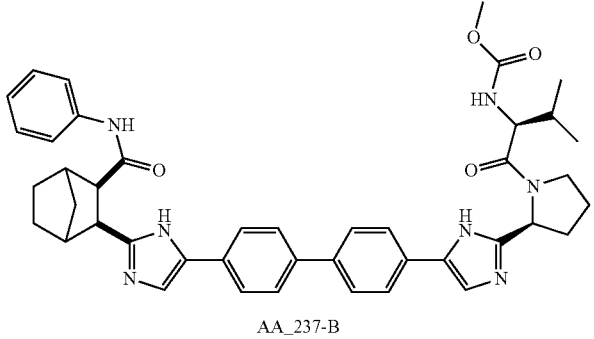

AA_237-B

Step 1: Synthesis of Compound AA_237-1

Compound AA_190-2 (19 g, 90 mmol) and $K_2CO_3$ (5.1 g, 135 mmol) were suspended in DMF (300 mL), 2,4'-dibromoacetophenone (BB-1-1, 37 g, 108 mmol) was added at room temperature. The reaction mixture was stirred at room temperature for 2 h. After the reaction was complete as detected by TLC, the reaction mixture was concentrated under reduced pressure to remove the solvent. Ethyl acetate (500 mL) was added into the residue, and then washed with saturated brines (100 mL×3). The organic phase was dried over anhydrous sodium sulfate. After filtration, the filtrate was concentrated by a rotary evaporator to remove the solvent thereby delivering an intermediate as yellow oil. At room temperature, the yellow oil intermediate was dissolved in toluene (500 mL), ammonium acetate (69.3 g, 900 mmol) was added. The reaction mixture was heated to reflux and stirred for 12 h under nitrogen gas atmosphere. After the reaction was complete as detected by TLC, the reaction mixture was cooled to room temperature, ethyl acetate (1 L) was added, and the mixture was washed with saturated brines (300 mL) The organic phase was dried over anhydrous sodium sulfate. After filtration, the filtrate was concentrated under reduced pressure to remove the solvent, the residue was purified by silica gel column chromatography (PE/EtOAc=9:1→1:1) to deliver the target compound AA_237-1 (light yellow powder, 22.6 g, yield 65%). LCMS m/z: 391.1 [M+H]$^+$ Step 2: Synthesis of Compound AA_237-2

Target compound AA_237-2 (3.7 g, yield 51.0%) was synthesized according to the synthetic step 5 in synthesizing AA_091, with compound AA_237-1 (3.9 g, 10.8 mmol), BB-21 (5.35 g, 10.8 mmol), $Na_2CO_3$ (2.28 g, 21.6 mmol) and Pd(dppf)Cl$_2$ (394 mg, 0.54 mmol) as starting materials, and DMF/THF/$H_2O$ (30 mL/30 mL/30 mL) as a mixed solvent. LCMS m/z: 680.4 [M+H]$^+$.

Step 3: Synthesis of Compound AA_237-3

Compound AA_237_2 (2 g, 2.8 mmol) was dissolved in a mixed solvent of THF/MeOH/$H_2O$ (5 mL/5 mL/5 mL), lithium hydroxide monohydrate (0.694 g, 28 mmol) was added, and the reaction mixture was stirred at 50° C. for 10 h. After the reaction was complete as detected by TLC, the reaction mixture was cooled to room temperature and extracted with ethyl acetate (5 mL×2), the aqueous phase was adjusted to pH 3-4 with 1N hydrochloric acid, and the solid precipitated was collected, dried to deliver the target compound AA_237-3 (1.33 g, yield 68.0%). LCMS m/z: 651.3 [M+H]$^+$.

Step 4: Synthesis of Compound AA_237_A and AA_237_B

At room temperature, compound AA_237-3 (30 mg, 0.046 mmol), aniline (6.4 mg, 0.069 mmol) were dissolved in THF (2 mL), DMTMM (19.1 mg, 0.069 mmol) was added. The reaction system was heated to 90° C. and stirred overnight. After the reaction was complete as detected by TLC, the solvent was evaporated by a rotary evaporator, the residue was purified by preparative HPLC to deliver the target compound AA_237_A (1.8 mg, yield 10%) and AA_237_B (2.2 mg, yield 12%). AA_237_A: LC/MS m/z: 726.0 [M+H]$^+$. AA_237_B: LC/MS m/z: 726.2 [M/2+H]$^+$.

The compounds listed in the following table were synthesized according to the synthetic step 4 in synthesizing AA_237, with compound AA_237-3 as starting material:

| Embodiments | Structure | Fragment 1 | Fragment 2 | LCMS |
|---|---|---|---|---|
| 157 | AA_162_A | AA_237-3 | | 741.5 [M + H]+ |
| 158 | AA_162_B | AA_237-3 | | 741.3 [M + H]+ |

| Embodiments | Structure | Fragment 1 | Fragment 2 | LCMS |
|---|---|---|---|---|
| 159 | AA_193 | AA_237-3 | HO-CH2CH2-NH2 | 694.4 [M + H]+ |
| 160 | AA_194 | AA_237-3 | 2-aminobenzylamine | 755.5 [M + H]+ |

| Embodiments | Structure | Fragment 1 | Fragment 2 | LCMS |
|---|---|---|---|---|
| 161 | AA_195_A | AA_237-3 | | 741.5 [M + H]+ |
| 162 | AA_195_B | AA_237-3 | | 741.4 [M + H]+ |

-continued

| Embodiments | Structure | Fragment 1 | Fragment 2 | LCMS |
|---|---|---|---|---|
| 163 | AA_196_A | AA_237-3 | (thiophen-2-ylmethanamine) | 746.5 [M + H]⁺ |
| 164 | AA_196_B | AA_237-3 | (thiophen-2-ylmethanamine) | 746.5 [M + H]⁺ |

| Embodiments | Structure | Fragment 1 | Fragment 2 | LCMS |
|---|---|---|---|---|
| 165 | AA_198_A | AA_237-3 | furfurylamine | 730.4 [M + H]⁺ |
| 166 | AA_198_B | AA_237-3 | furfurylamine | 730.5 [M + H]⁺ |

| Embodiments | Structure | Fragment 1 | Fragment 2 | LCMS |
|---|---|---|---|---|
| 167 | AA_199_A | AA_237-3 | | 755.6 [M + H]+ |
| 168 | AA_199_B | AA_237-3 | | 755.3 [M + H]+ |

-continued

| Embodiments | Structure | Fragment 1 | Fragment 2 | LCMS |
|---|---|---|---|---|
| 169 | AA_200_A | AA_237-3 | | 771.3 [M + H]+ |
| 170 | AA_200_B | AA_237-3 | | 771.3 [M + H]+ |

-continued

| Embodiments | Structure | Fragment 1 | Fragment 2 | LCMS |
|---|---|---|---|---|
| 171 | AA_201_A | AA_2237-3 | | 371.9 [M/2+H]+ |
| 172 | AA_201_B | AA_2237-3 | | 764.3 [M+Na]+ |

| Embodiments | Structure | Fragment 1 | Fragment 2 | LCMS |
|---|---|---|---|---|
| 173 | 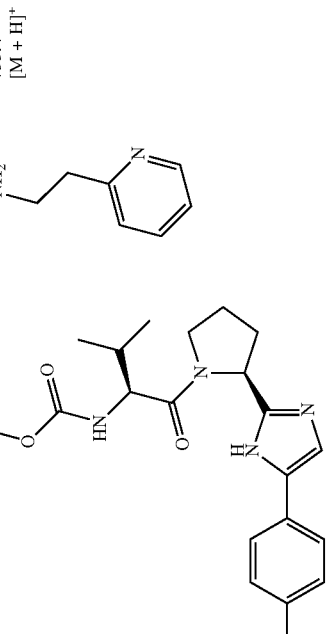 AA_202 | 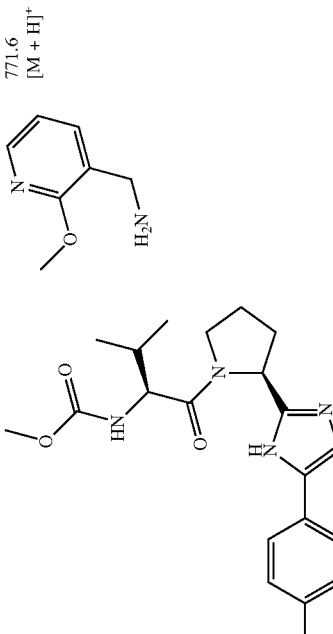 AA_2237-3 | 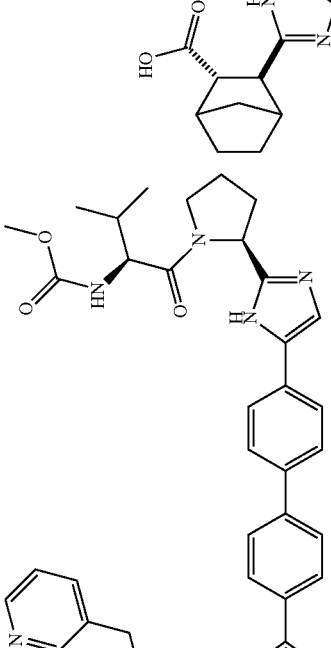 | 755.4 [M + H]+ |
| 174 | 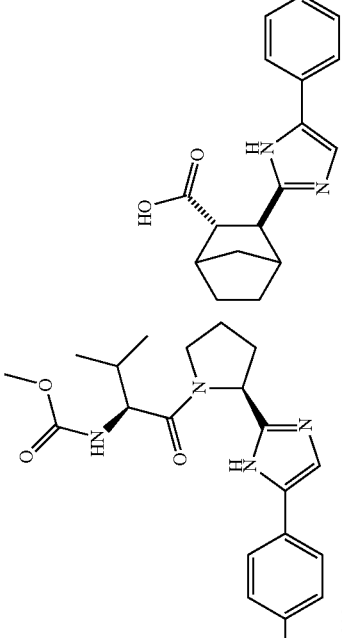 AA_203_A | 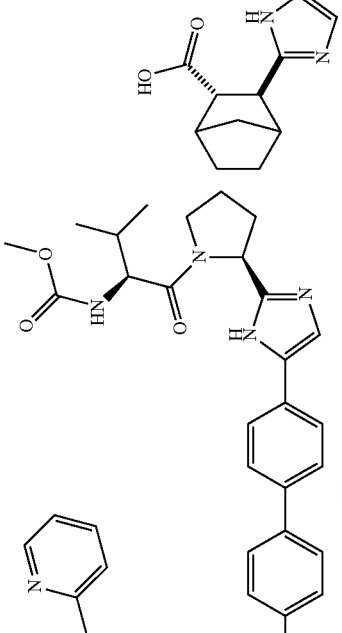 AA_2237-3 | 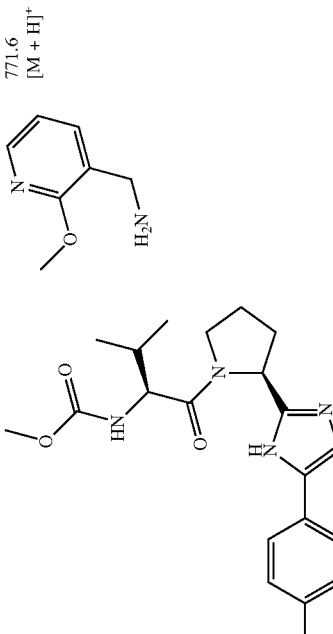 | 771.6 [M + H]+ |

| Embodiments | Structure | Fragment 1 | Fragment 2 | LCMS |
|---|---|---|---|---|
| 175 | AA_203_B | AA_237-3 | (2-methoxypyridin-3-yl)methanamine | 386.5 [M/2 + H]+ |
| 176 | AA_204_A | AA_237-3 | 1-(pyridin-3-yl)ethanamine | 755.3 [M + H]+ |

| Embodiments | Structure | Fragment 1 | Fragment 2 | LCMS |
|---|---|---|---|---|
| 177 | AA_204_B | AA_237-3 | | 755.3 [M + H]+ |
| 178 | AA_204_C | AA_237-3 | | 755.4 [M + H]+ |

| Embodiments | Structure | Fragment 1 | Fragment 2 | LCMS |
|---|---|---|---|---|
| 179 | AA_206_A | AA_237-3 | | 742.4 [M + H]⁺ |
| 180 | AA_206_B | AA_237-3 | | 742.4 [M + H]⁺ |

-continued

| Embodiments | Structure | Fragment 1 | Fragment 2 | LCMS |
|---|---|---|---|---|
| 181 | AA_207_A | AA_237-3 | benzylamine | 740.4 [M + H]+ |
| 182 | AA_207_B | AA_237-3 | benzylamine | 740.3 [M + H]+ |

-continued

| Embodiments | Structure | Fragment 1 | Fragment 2 | LCMS |
|---|---|---|---|---|
| 183 | AA_208_A | AA_237-3 | thiazol-2-ylmethanamine | 747.4 [M + H]+ |
| 184 | AA_208_B | AA_237-3 | thiazol-2-ylmethanamine | 747.4 [M + H]+ |

-continued

| Embodiments | Structure | Fragment 1 | Fragment 2 | LCMS |
|---|---|---|---|---|
| 185 | AA_209_A | AA_237-3 | 4-(2-aminoethyl)pyridine | 755.5 [M + H]⁺ |
| 186 | AA_209_B | AA_237-3 | 4-(2-aminoethyl)pyridine | 755.4 [M + H]⁺ |

-continued
| Em-bodi-ments | Structure | Fragment 1 | Fragment 2 | LCMS |
|---|---|---|---|---|
| 187 | 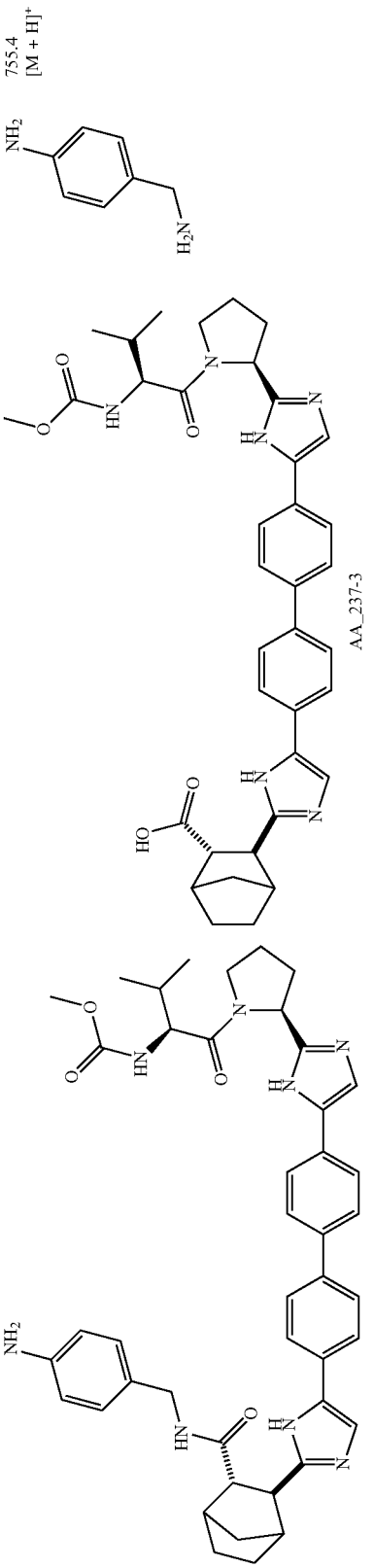 AA_210_A | 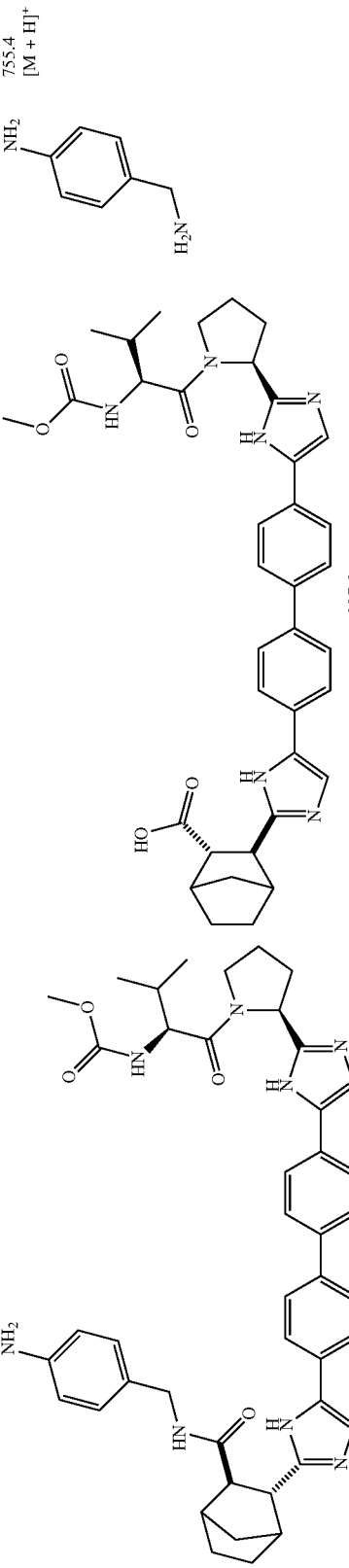 AA_2237-3 | 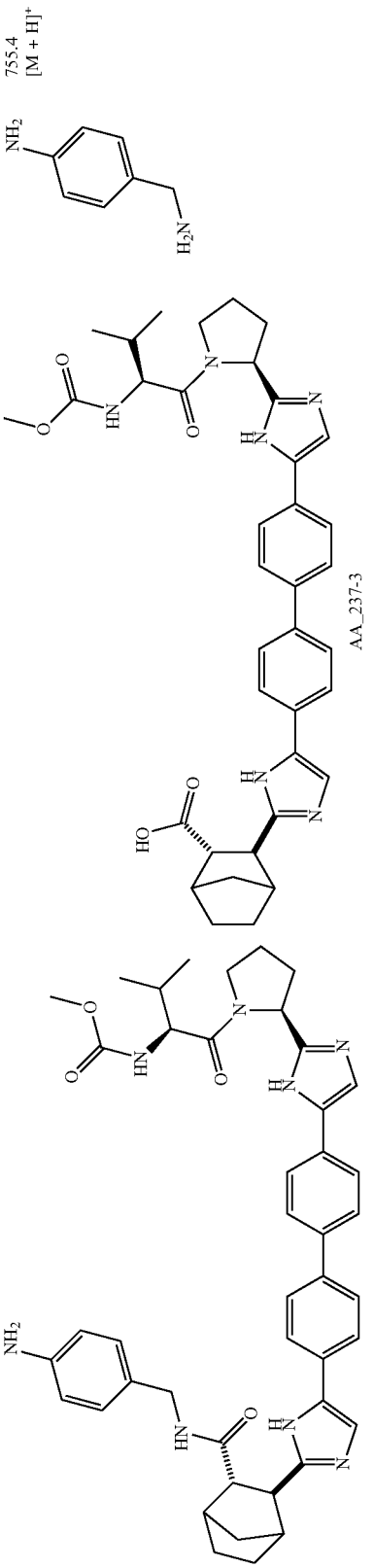 | 755.4 [M + H]+ |
| 188 | 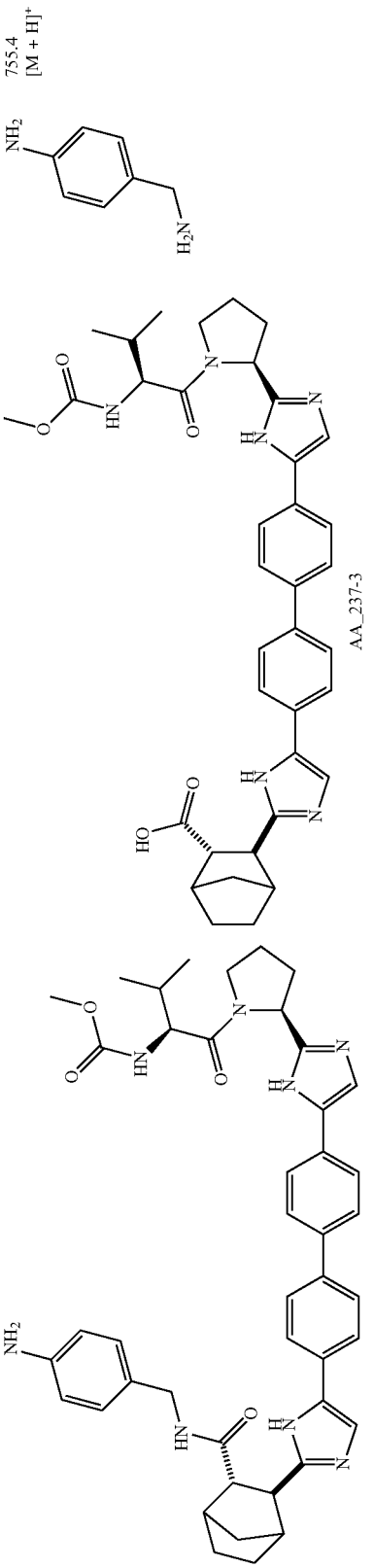 AA_210_B | 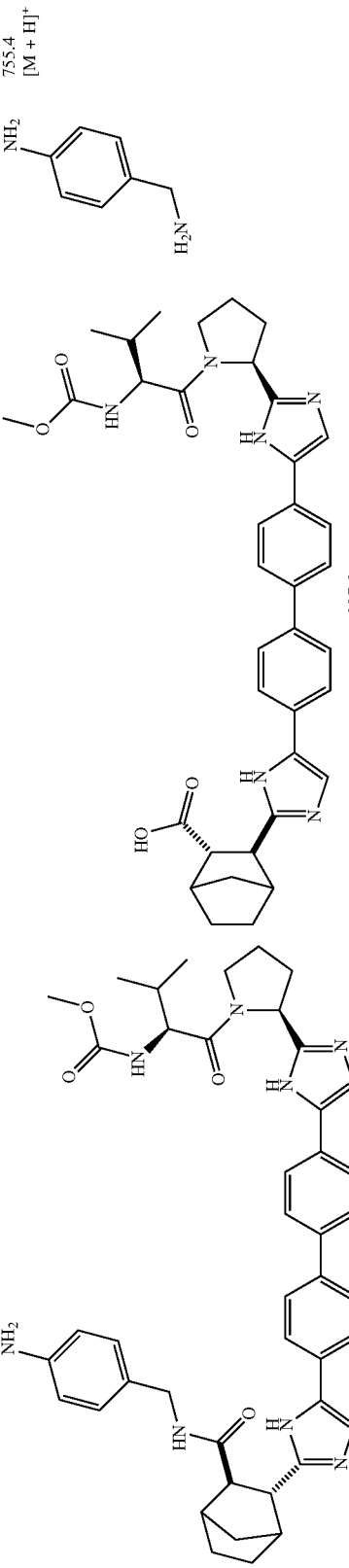 AA_2237-3 | 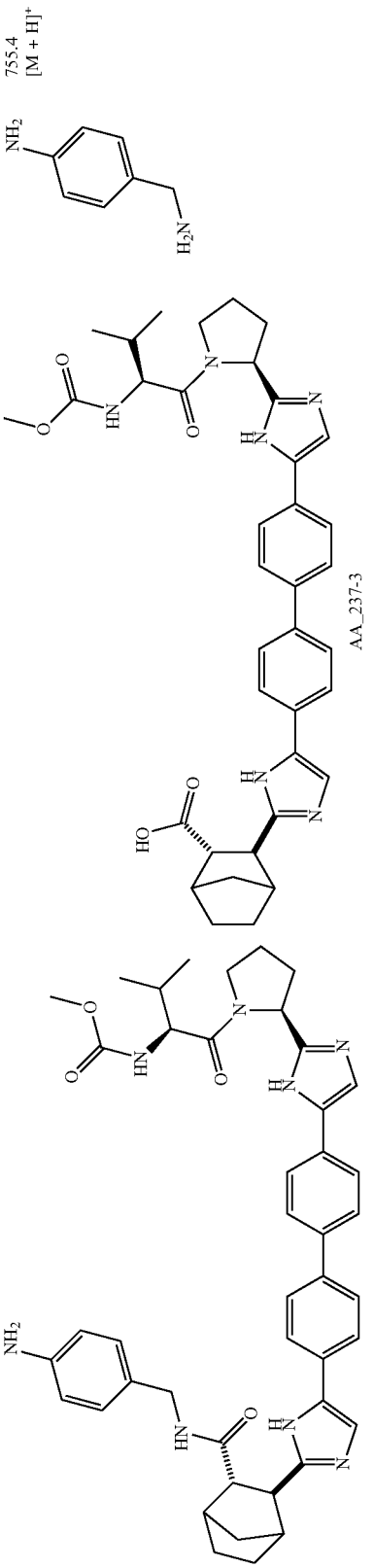 | 755.4 [M + H]+ |

-continued
| Embodiments | Structure | Fragment 1 | Fragment 2 | LCMS |
|---|---|---|---|---|
| 189 | 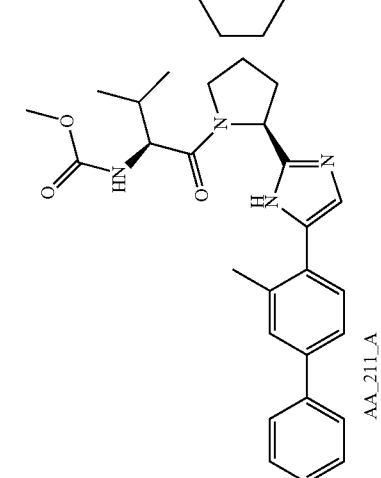 AA_211_A | 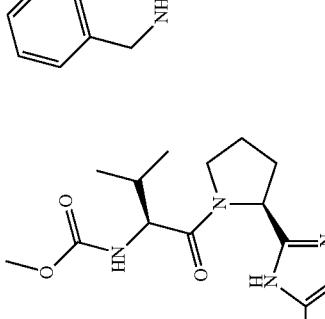 AA_237-3 |  | 755.4 [M + H]+ |
| 190 | 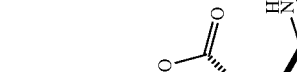 AA_211_B | 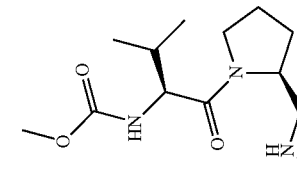 AA_237-3 | 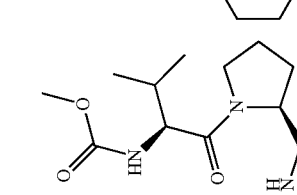 | 755.4 [M + H]+ |

| Embodiments | Structure | Fragment 1 | Fragment 2 | LCMS |
|---|---|---|---|---|
| 191 | AA_213 | AA_237-3 | | 813.6 [M + H]+ |
| 192 | AA_214_A | AA_237-3 | | 759.3 [M + H]+ |

-continued

| Embodiments | Structure | Fragment 1 | Fragment 2 | LCMS |
|---|---|---|---|---|
| 193 | AA_214_B | AA_237-3 | | 759.3 [M + H]+ |
| 194 | AA_215_A | AA_237-3 | | 783.4 [M + H]+ |

| Embodiments | Structure | Fragment 1 | Fragment 2 | LCMS |
|---|---|---|---|---|
| 195 | AA_215_B | AA_237-3 | | 783.4 [M + H]+ |
| 196 | AA_216_A | AA_237-3 | | 809.3 [M + H]+ |

| Embodiments | Structure | Fragment 1 | Fragment 2 | LCMS |
|---|---|---|---|---|
| 197 | AA_216_B | AA_237-3 | | 809.4 [M + H]+ |
| 198 | AA_217 | AA_237-3 | | 755.4 [M + H]+ |

| Embodiments | Structure | Fragment 1 | Fragment 2 | LCMS |
|---|---|---|---|---|
| 199 | AA_218 | AA_237-3 | (tetrahydroquinoline-CH₂NH₂) | 795.4 [M + H]⁺ |
| 200 | AA_224_A | AA_237-3 | (2-fluoropyridin-3-yl)CH₂NH₂ | 759.4 [M + H]⁺ |

| Embodiments | Structure | Fragment 1 | Fragment 2 | LCMS |
|---|---|---|---|---|
| 201 |  AA_224_B | 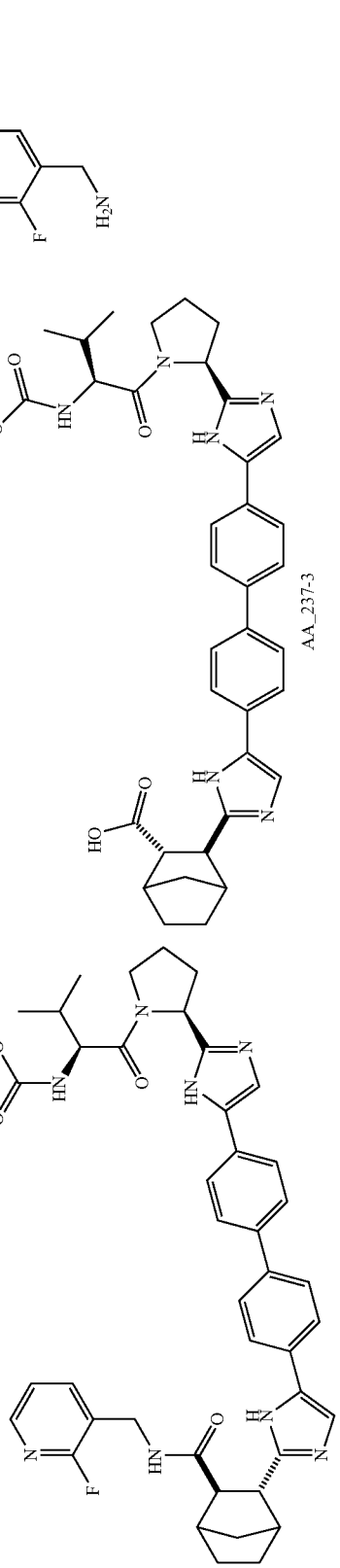 AA_237-3 |  | 759.4 [M + H]⁺ |
| 202 | 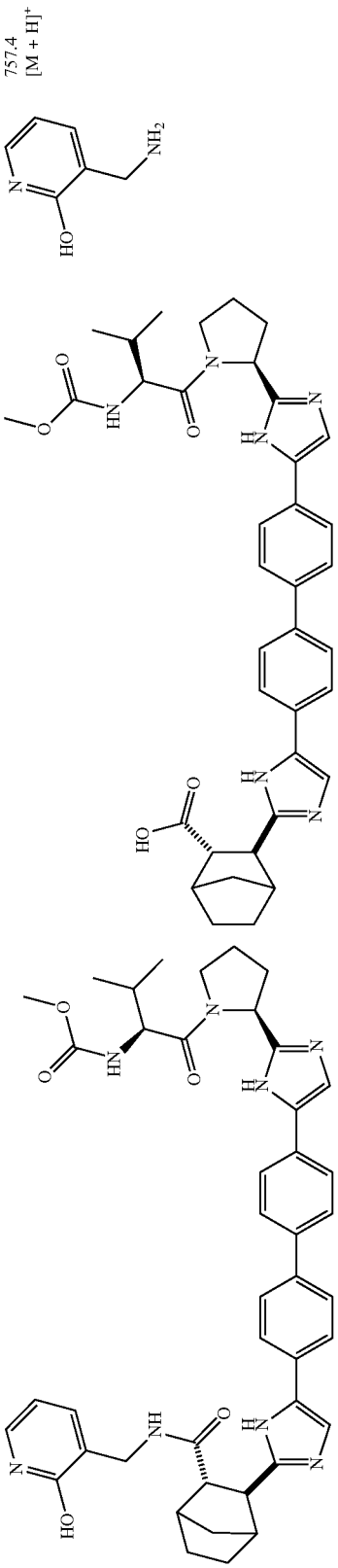 AA_228 | 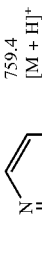 AA_237-3 |  | 757.4 [M + H]⁺ |

| Embodiments | Structure | Fragment 1 | Fragment 2 | LCMS |
|---|---|---|---|---|
| 203 | 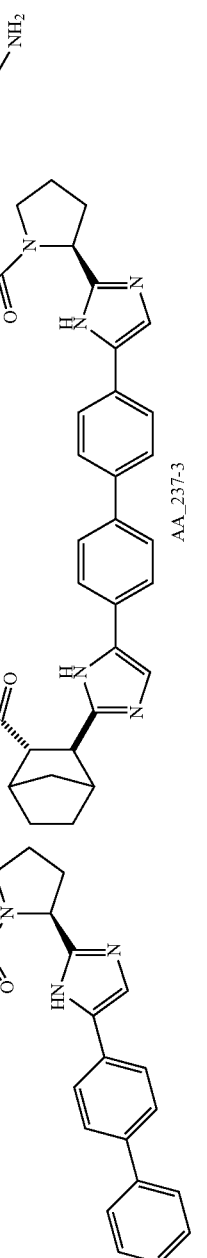 AA_232_A | 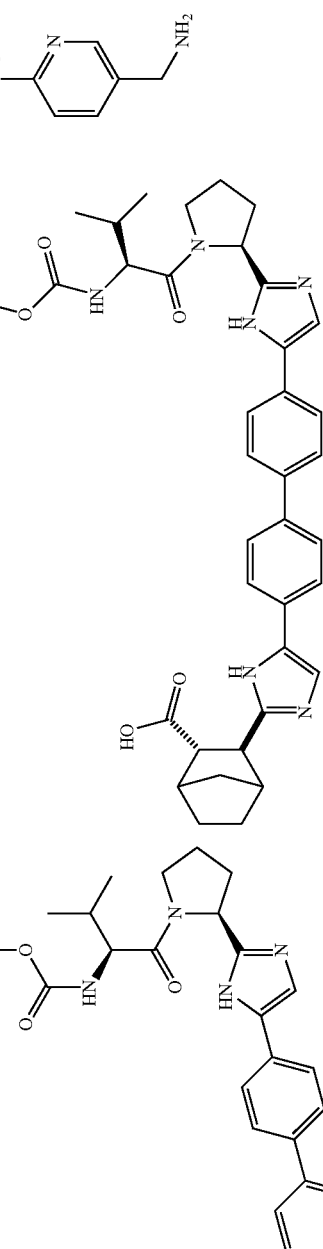 AA_237-3 | 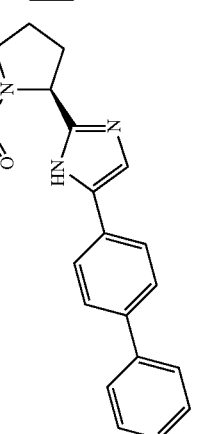 | 809.3 [M + H]+ |
| 204 | 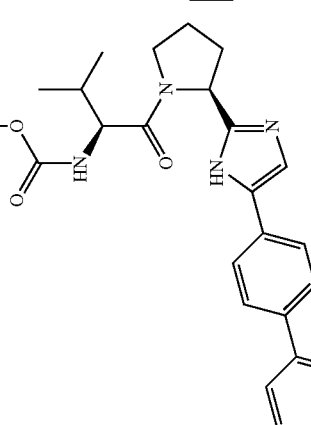 AA_232_B | 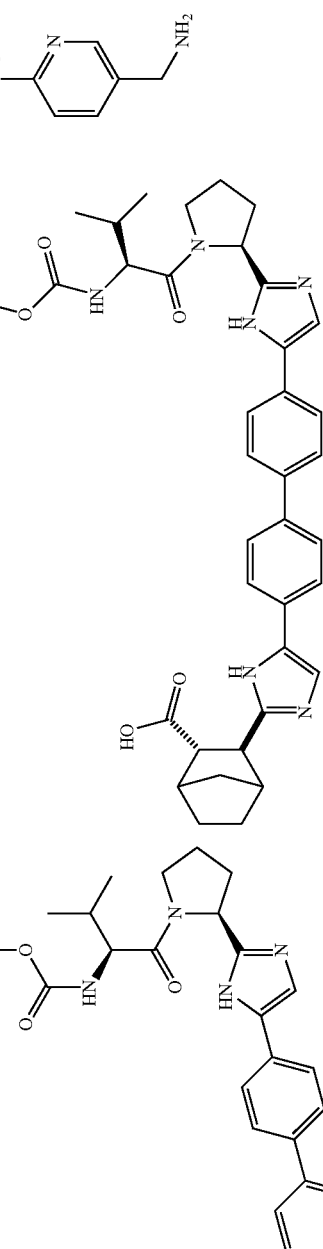 AA_237-3 | 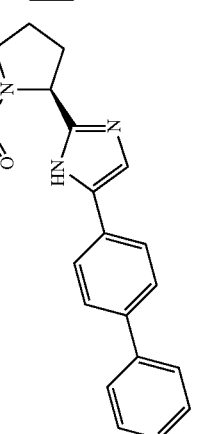 | 809.3 [M + H]+ |

| Embodiments | Structure | Fragment 1 | Fragment 2 | LCMS |
|---|---|---|---|---|
| 205 | AA_233_A | AA_237-3 | | 783.4 [M + H]+ |
| 206 | AA_233_B | AA_237-3 | | 392.4 [M/2 + H]+ |

| Embodiments | Structure | Fragment 1 | Fragment 2 | LCMS |
|---|---|---|---|---|
| 207 | AA_233_C | AA_237-3 | | 783.4 [M + H]+ |
| 208 | AA_234_A | AA_237-3 | | 391.2 [M/2 + H]+ |

| Embodiments | Structure | Fragment 1 | Fragment 2 | LCMS |
|---|---|---|---|---|
| 209 | AA_234_B | AA_237-3 | | 391.2 [M/2 + H]+ |
| 210 | AA_235_A | AA_237-3 | | 783.4 [M + H]+ |

-continued

| Embodiments | Structure | Fragment 1 | Fragment 2 | LCMS |
|---|---|---|---|---|
| 211 | AA_236_A | AA_237-3 | | 392.2 [M/2 + H]+ |
| 212 | AA_236_B | AA_237-3 | | 783.9 [M + H]+ |

| Embodiments | Structure | Fragment 1 | Fragment 2 | LCMS |
|---|---|---|---|---|
| 213 | AA_243_A | AA_237-3 | | 793.4 [M + Na]$^+$ |
| 214 | AA_243_B | AA_237-3 | | 793.4 [M + Na]$^+$ |

| Embodiments | Structure | Fragment 1 | Fragment 2 | LCMS |
|---|---|---|---|---|
| 215 | AA_244_A | AA_237-3 | | 389.3 [M/2 + H]+ |
| 216 | AA_275 | AA_237-3 | | 839.3 [M + H]+ |

| Embodiments | Structure | Fragment 1 | Fragment 2 | LCMS |
|---|---|---|---|---|
| 217 | AA_276 | AA_237-3 | | 813.3 [M + H]+ |
| 218 | AA_277 | AA_237-3 | | 771.4 [M + H]+ |

| Embodiments | Structure | Fragment 1 | Fragment 2 | LCMS |
|---|---|---|---|---|
| 219 | AA_278 | AA_237-3 | | 847.3 [M + H]⁺ |

Embodiment 220: AA_226
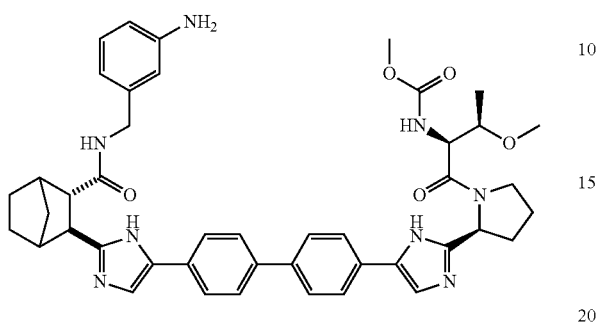
AA_226
Synthetic Route:
1.
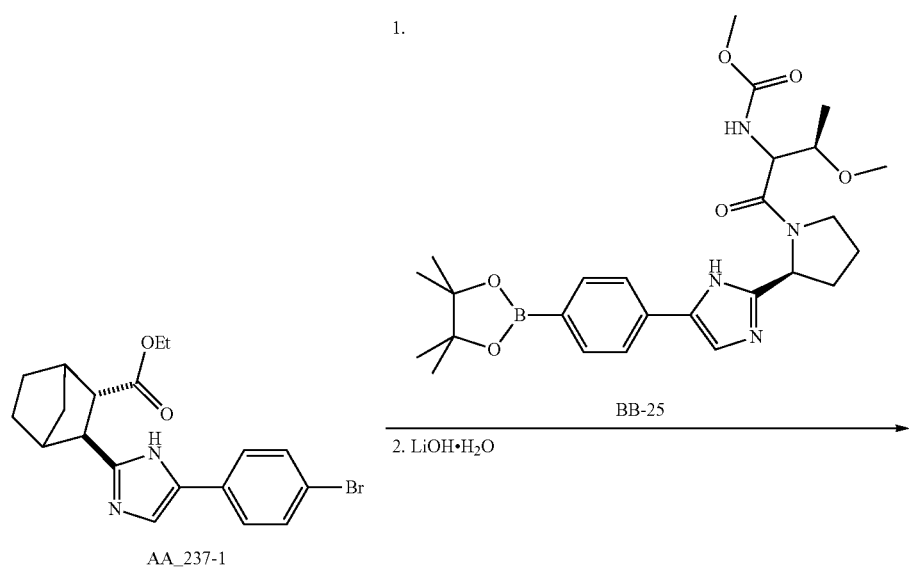
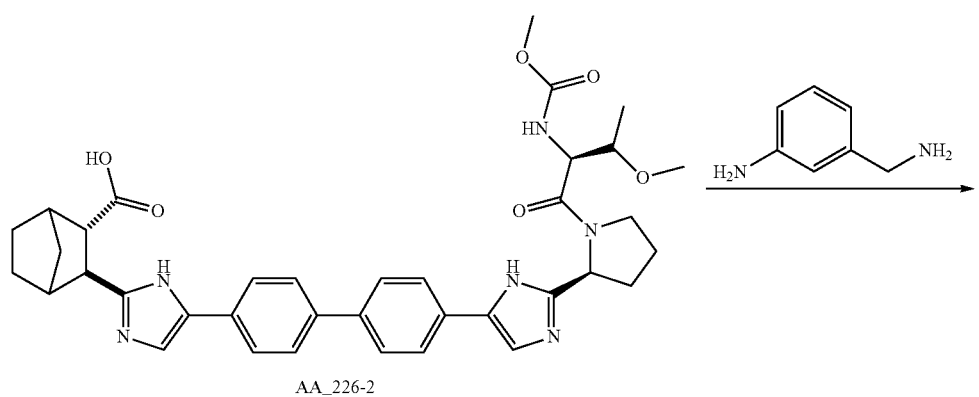

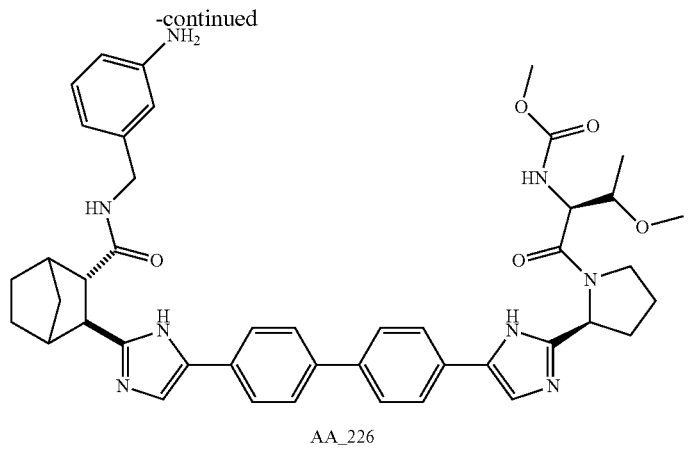

AA_226

Step 1: Synthesis of Compound AA_226-2

An intermediate as yellow oil (3.5 g, yield 46.6%) was obtained according to the synthetic step 5 in synthesizing AA_091, with compound AA_237-1 (3.9 g, 10.8 mmol), compound BB-25 (5.59 g, 10.8 mmol), $Na_2CO_3$ (2.28 g, 21.6 mmol) and $Pd(dppf)Cl_2$ (394 mg, 0.54 mmol) as starting materials, and $DMF/THF/H_2O$ (30 mL/30 mL/30 mL) as a mixed solvent. The yellow oil intermediate (2 g, 2.8 mmol) was dissolved in a mixed solvent of $THF/MeOH/H_2O$ (5 mL/5 mL/5 mL), lithium hydroxide monohydrate (0.694 g, 28 mmol) was added, and the reaction mixture was stirred at 50° C. for 10 h. After the reaction was complete as detected by TLC, the reaction mixture was cooled to room temperature and extracted with ethyl acetate (5 mL×2), the aqueous phase was adjusted to pH 3-4 with 1N hydrochloric acid. The solid precipitated was collected and dried to deliver the target compound AA_226-2 (1.33 g, yield 68.0%). LCMS m/z: 667.2 $[M+H]^+$.

Step 2: Synthesis of Compound AA_226

At room temperature, compound AA_226-2 (30 mg, 0.046 mmol), aniline (8.2 mg, 0.069 mmol) was dissolved in THF (2 mL), DMTMM (19.1 mg, 0.069 mmol) was added. The reaction system was heated to 60° C. and stirred overnight. After the reaction was complete as detected by TLC, the solvent was removed by a rotary evaporator, the residue was purified by preparative HPLC to deliver the target compound AA_226 (1.0 mg, yield 2.9%). LC/MS MS m/z: 386.3 $[M/2+H]^+$.

The compounds listed in the following table were synthesized according to the synthetic step 2 in synthesizing AA_226, with compound AA_226-2 as starting material:

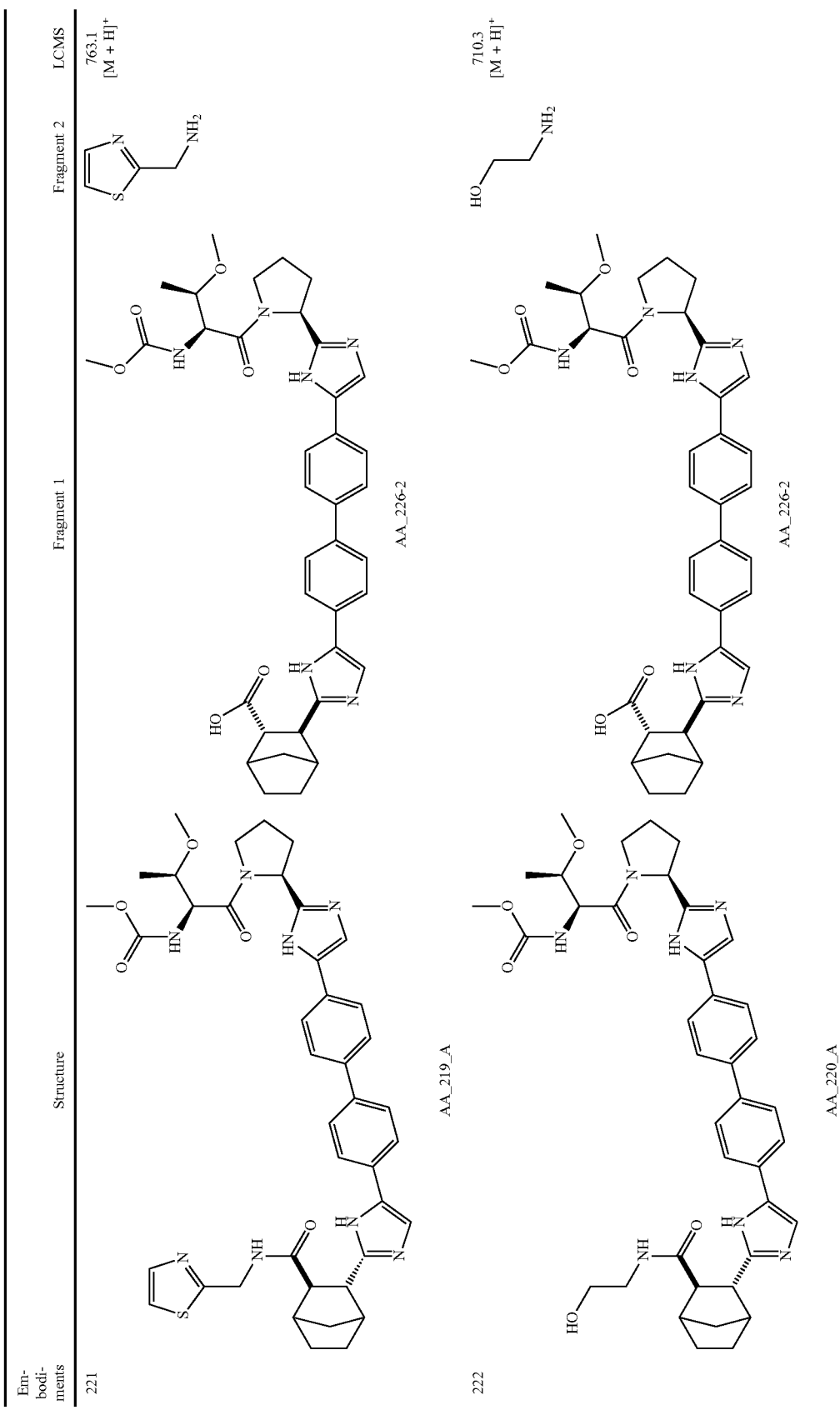

| Embodiments | Structure | Fragment 1 | Fragment 2 | LCMS |
|---|---|---|---|---|
| 223 | AA_220_B | AA_226-2 | HO-CH2CH2-NH2 | 710.3 [M + H]+ |
| 224 | AA_221_A | AA_226-2 | 2-pyridyl-CH2-NH2 | 379.4 [M/2 + H]+ |

| Embodiments | Structure | Fragment 1 | Fragment 2 | LCMS |
|---|---|---|---|---|
| 225 | AA_222_A | AA_226-2 | furan-2-ylmethanamine | 746.4 [M + H]⁺ |
| 226 | AA_223_A | AA_226-2 | (6-methoxypyridin-3-yl)methanamine | 394.3 [M/2 + H]⁺ |

-continued

| Embodi-ments | Structure | Fragment 1 | Fragment 2 | LCMS |
|---|---|---|---|---|
| 227 | AA_223_B | AA_226-2 | 2-methoxy-5-(aminomethyl)pyridine | 809.5 [M + Na]+ |
| 228 | AA_227 | AA_226-2 | 4-aminomethylaniline | 386.3 [M/2 + H]+ |

| Embodiments | Structure | Fragment 1 | Fragment 2 | LCMS |
|---|---|---|---|---|
| 229 | AA_245_A | AA_226-2 | | 799.4 [M + H]⁺ |
| 230 | AA_245_B | AA_226-2 | | 799.4 [M + H]⁺ |

| Embodiments | Structure | Fragment 1 | Fragment 2 | LCMS |
|---|---|---|---|---|
| 231 | AA_246_A | AA_226-2 | aniline | 742.4 [M + H]+ |
| 232 | AA_246_B | AA_226-2 | aniline | 742.4 [M + H]+ |

| Embodiments | Structure | Fragment 1 | Fragment 2 | LCMS |
|---|---|---|---|---|
| 233 | AA_247_A | AA_226-2 | | 757.4 [M + H]+ |
| 234 | AA_247_B | AA_226-2 | | 757.4 [M + H]+ |

-continued

| Embodiments | Structure | Fragment 1 | Fragment 2 | LCMS |
|---|---|---|---|---|
| 235 | AA_248_A | AA_226-2 | | 757.4 [M + H]⁺ |
| 236 | AA_248_B | AA_226-2 | | 757.3 [M + H]⁺ |

| Embodiments | Structure | Fragment 1 | Fragment 2 | LCMS |
|---|---|---|---|---|
| 237 | AA_249_A | AA_226-2 | (pyrimidin-5-ylmethanamine) | 758.4 [M + H]⁺ |
| 238 | AA_250_A | AA_226-2 | (3-chloropyrazin-2-yl)hydrazine | 793.3 [M + H]⁺ |

| Embodiments | Structure | Fragment 1 | Fragment 2 | LCMS |
|---|---|---|---|---|
| 239 | AA_250_B | AA_226-2 | chloro-pyrazinyl hydrazine | 793.9 [M + H]+ |
| 240 | AA_251_A | AA_226-2 | 1-(pyridin-3-yl)ethanamine | 771.3 [M + H]+ |

| Embodiments | Structure | Fragment 1 | Fragment 2 | LCMS |
|---|---|---|---|---|
| 241 | AA_251_B | AA_226-2 | | 771.3 [M + H]⁺ |
| 242 | AA_251_C | AA_226-2 | | 386.1 [M/2 + H]⁺ |

| Embodiments | Structure | Fragment 1 | Fragment 2 | LCMS |
|---|---|---|---|---|
| 243 | AA_252_A | AA_226-2 | | 775.4 [M + H]⁺ |
| 244 | AA_252_B | AA_226-2 | | 775.4 [M + H]⁺ |

| Embodiments | Structure | Fragment 1 | Fragment 2 | LCMS |
|---|---|---|---|---|
| 245 | AA_253_A | AA_226-2 | | 771.3 [M + H]⁺ |
| 246 | AA_253_B | AA_226-2 | | 771.3 [M + H]⁺ |

| Embodiments | Structure | Fragment 1 | Fragment 2 | LCMS |
|---|---|---|---|---|
| 247 | AA_253_C | AA_226-2 | | 386.1 [M/2 + H]+ |
| 248 | AA_254_A | AA_226-2 | | 799.4 [M + H]+ |

| Embodiments | Structure | Fragment 1 | Fragment 2 | LCMS |
|---|---|---|---|---|
| 249 | AA_255_A | AA_226-2 | | 825.3 [M + H]$^+$ |
| 250 | AA_255_B | AA_226-2 | | 825.2 [M + H]$^+$ |

| Embodiments | Structure | Fragment 1 | Fragment 2 | LCMS |
|---|---|---|---|---|
| 251 | AA_256_A | AA_226-2 | | 797.4 [M + H]⁺ |
| 252 | AA_257_A | AA_226-2 | | 787.4 [M + H]⁺ |

| Embodiments | Structure | Fragment 1 | Fragment 2 | LCMS |
|---|---|---|---|---|
| 253 | AA_258_B | AA_226-2 | | 758.6 [M + H]+ |
| 254 | AA_259_A | AA_226-2 | | 803.2 [M + H]+ |

| Embodiments | Structure | Fragment 1 | Fragment 2 | LCMS |
|---|---|---|---|---|
| 255 | AA_260_B | AA_226-2 | | 803.4 [M + H]+ |
| 256 | AA_261_A | AA_226-2 | | 763.3 [M + H]+ |

-continued

| Em-bodi-ments | Structure | Fragment 1 | Fragment 2 | LCMS |
|---|---|---|---|---|
| 257 | AA_262_B | AA_226-2 | (S)-1-phenylethan-1-amine | 771.2 [M + H]+ |
| 258 | AA_263_B | AA_226-2 | 3-(aminomethyl)pyridin-2-ol | 773.2 [M + H]+ |

-continued

| Embodi-ments | Structure | | Fragment 1 | Fragment 2 | LCMS |
|---|---|---|---|---|---|
| 259 | AA_263_C | | AA_226-2 | (2-hydroxypyridin-3-yl)methanamine | 773.2 [M + H]⁺ |
| 260 | AA_264_A | | AA_226-2 | (6-(trifluoromethyl)pyridin-3-yl)methanamine | 825.2 [M + H]⁺ |

-continued

| Embodiments | Structure | Fragment 1 | Fragment 2 | LCMS |
|---|---|---|---|---|
| 261 | AA_264_B | AA_226-2 | 6-(trifluoromethyl)pyridin-3-yl)methanamine | 825.2 [M + H]⁺ |
| 262 | AA_265_A | AA_226-2 | (6-isopropylpyridin-3-yl)methanamine | 799.3 [M + H]⁺ |

| Embodiments | Structure | Fragment 1 | Fragment 2 | LCMS |
|---|---|---|---|---|
| 263 | AA_265_B | AA_226-2 | (6-isopropylpyridin-3-yl)methanamine | 799.3 [M + H]⁺ |
| 264 | AA_266_A | AA_226-2 | 2-(pyridin-4-yl)ethanamine | 771.3 [M + H]⁺ |

| Embodiments | Structure | Fragment 1 | Fragment 2 | LCMS |
|---|---|---|---|---|
| 265 | AA_266_B | AA_226-2 | | 793.4 [M + Na]⁺ |
| 266 | AA_267_A | AA_226-2 | | 799.4 [M + H]⁺ |

| Embodiments | Structure | Fragment 1 | Fragment 2 | LCMS |
|---|---|---|---|---|
| 267 | AA_267_B | AA_226-2 | | 799.4 [M + H]⁺ |
| 268 | AA_268_A | AA_226-2 | | 758.3 [M + H]⁺ |

| Embodiments | Structure | Fragment 1 | Fragment 2 | LCMS |
|---|---|---|---|---|
| 269 | AA_268_B | AA_226-2 | | 758.4 [M + H]+ |
| 270 | AA_271_A | AA_226-2 | | 400.3 [M/2 + H]+ |

| Embodiments | Structure | Fragment 1 | Fragment 2 | LCMS |
|---|---|---|---|---|
| 271 | 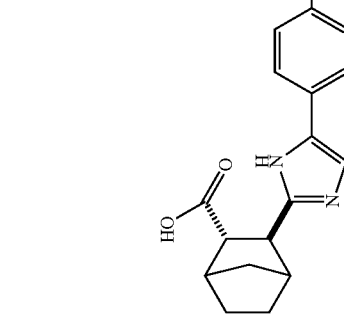 AA_271_B | 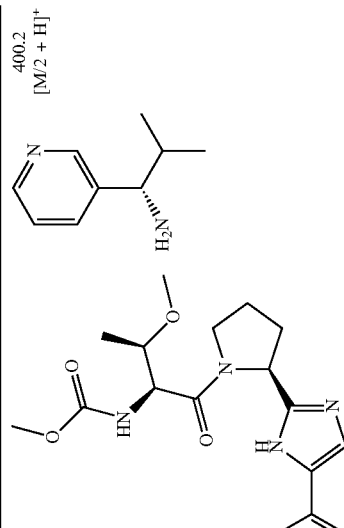 AA_226-2 | 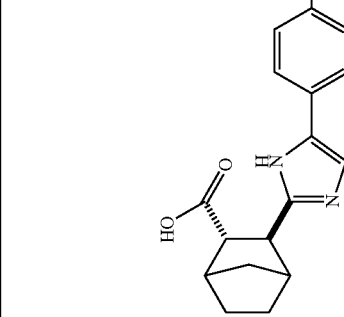 | 400.2 [M/2 + H]+ |
| 272 | 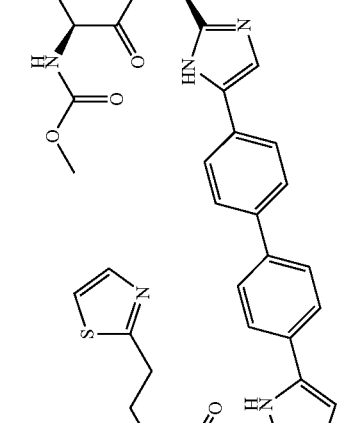 AA_272_B | 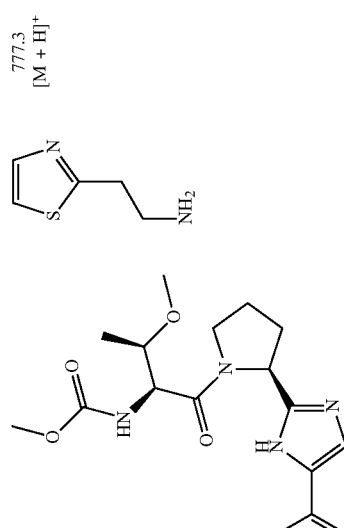 AA_226-2 | 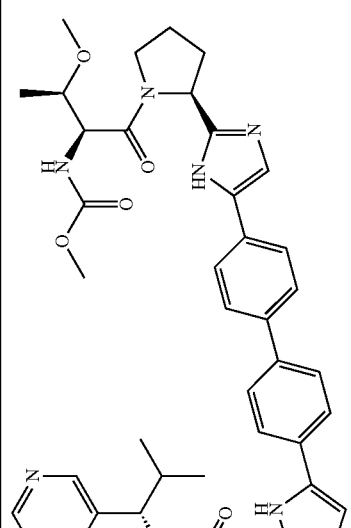 | 777.3 [M + H]+ |

-continued

| Embodiments | Structure | Fragment 1 | Fragment 2 | LCMS |
|---|---|---|---|---|
| 273 | AA_281_A | AA_226-2 | | 772.4 [M + H]⁺ |
| 274 | AA_281_B | AA_226-2 | | 772.3 [M + H]⁺ |

| Embodiments | Structure | Fragment 1 | Fragment 2 | LCMS |
|---|---|---|---|---|
| 275 | AA_281_C | AA_226-2 | | 772.3 [M + H]+ |

Embodiment 276: AA_192_A and AA_192_B
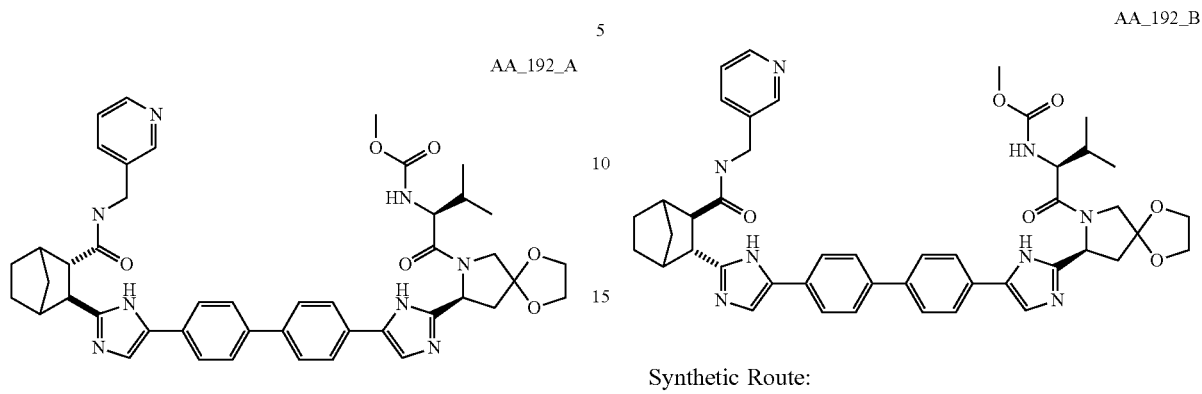
Synthetic Route:
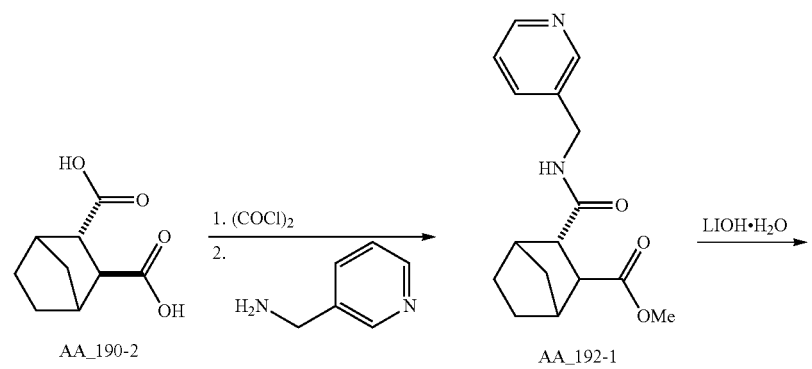
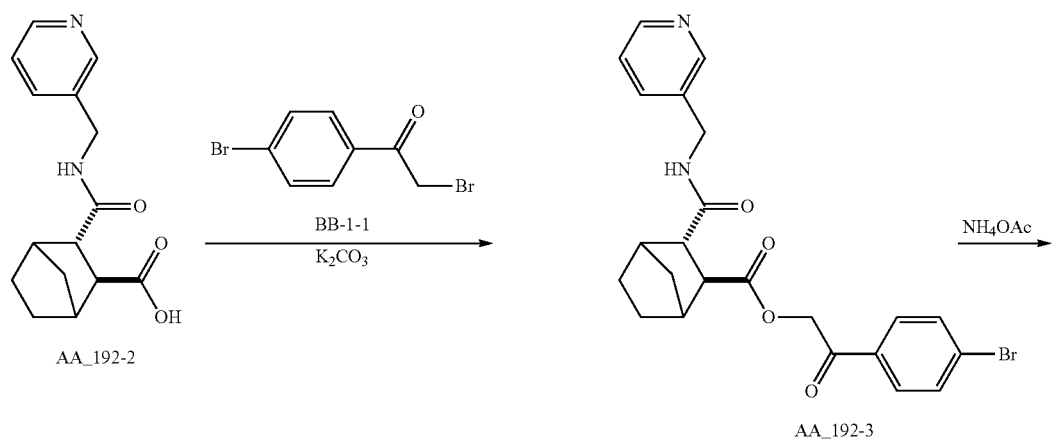

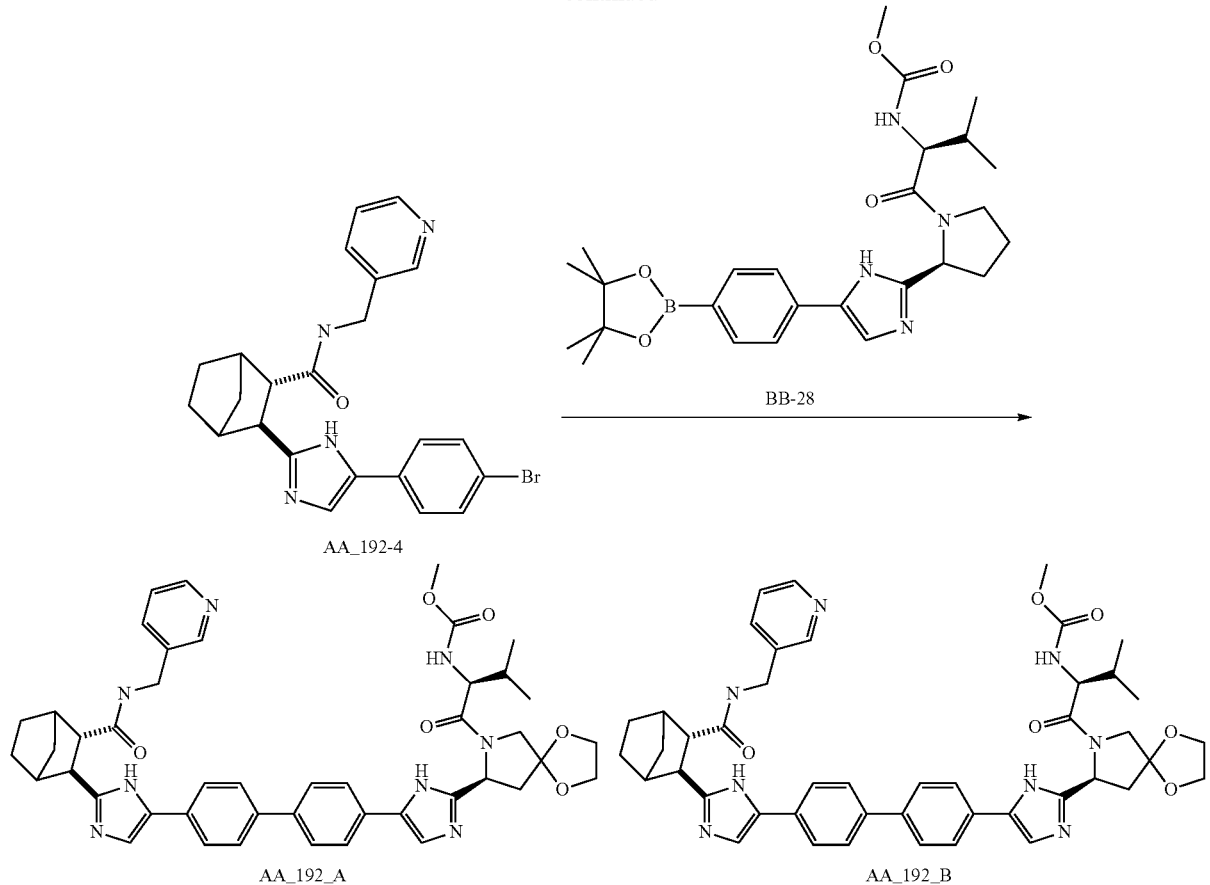

Step 1: Synthesis of Compound AA_192-1

At room temperature, compound AA_190-2 (10 g, 47.1 mmol) was dissolved in dichloromethane (100 mL), DMF (0.1 mL) was added to catalyze the reaction, the mixture was cooled to 0° C., oxalyl chloride (1.48 g, 116.6 mmol) was dripped. The reaction system was stirred at room temperature for 1 h. After the reaction was complete as detected by TLC, the solvent was removed by a rotary evaporator thereby giving an intermediate. The acyl chloride intermediate was dissolved in THF (100 mL), cooled to no more than 5° C. under an ice bath, 3-(aminomethyl)pyridine (5.59 g, 51.8 mmol) was added, and then DIPEA (18.2 g, 141.3 mmol) was dripped. The reaction mixture was stirred at room temperature for 10 h. After the reaction was complete as detected by TLC, the filtrate was concentrated by a rotary evaporator to remove the solvent. The residue was dissolved in ethyl acetate (100 mL), and then washed with saturated brines (20 mL×3), dried over anhydrous sodium sulfate. After filtration, the filtrate was concentrated under reduced pressure to remove the solvent, the residue was purified by silica gel column chromatography (PE/EtOAc=5:1) to deliver the target compound AA_192-1 (7.8 g, yield for two steps 55%). LCMS m/z: 302.9 [M+H]$^+$.

Step 2: Synthesis of Compound AA_192-2

Compound AA_192-1 (7.8 g, 25.8 mmol) was dissolved in a mixed solvent of THF/MeOH/H$_2$O (30 mL/30 mL/30 mL), lithium hydroxide monohydrate (6.19 g, 258 mmol) was added. The reaction mixture was stirred at 60° C. for 10 h. After the reaction was complete as detected by TLC, most solvent was removed under reduced pressure. The residue was extracted with ethyl acetate (5 mL×2), the aqueous phase was adjusted to pH 3-4 with 1N hydrochloric acid and extracted with ethyl acetate (20 mL×3). The organic phases were combined, dried over anhydrous sodium sulfate. After filtration, the filtrate was concentrated by a rotary evaporator to remove the solvent thereby delivering the target compound AA_192-2 (2.8 g, yield 40%). LCMS m/z: 274.9 [M+H]$^+$.

Step 3: Synthesis of Compound AA_192-3

Compound AA_192-2 (2.8 g, 10.2 mmol) and K$_2$CO$_3$ (0.51 g, 13.5 mmol) were suspended in DMF (30 mL), 2,4'-dibromoacetophenone (BB-1-1, 2.97 g, 10.8 mmol)) was added at room temperature. The reaction mixture was stirred at room temperature for 2 h. After the reaction was complete as detected by TLC, the solvent was removed under reduced pressure, the residue was dissolved in ethyl acetate (100 mL) and washed with saturated brines (10 mL×3). The organic phase was dried over anhydrous sodium sulfate. After filtration, the filtrate was concentrated by a rotary evaporator to remove the solvent thereby delivering the target compound AA_192-2 (4.7 g, yield 97.7%). The product was directly used for the next step without purification. LCMS m/z: 470.9 [M+H]$^+$.

Step 4: Synthesis of Compound AA_192-4

At room temperature, compound AA_192-3 (4.7 g, 99.7 mmol) was dissolved in toluene (50 mL), ammonium acetate (7.85 g, 102 mmol) was added. The reaction mixture was heated to reflux and stirred for 12 h under nitrogen gas atmosphere. After the reaction was complete as detected by TLC, the reaction mixture was cooled to room temperature, ethyl acetate (100 mL) was added, the mixture was washed with saturated brines (30 mL×3). The organic phase was dried over anhydrous sodium sulfate. After filtration, the filtrate was concentrated under reduced pressure to remove the solvent, the residue was purified by silica gel column chromatography (PE/EtOAc=1:1) to deliver the target compound AA_192-4 (3.0 g, yield 65.3%). LCMS m/z: 450.9 $[M+H]^+$.

Step 5: Synthesis of Compound AA_192_A and AA_192_B

Target compound AA_192_A (4.8 mg) and compound AA_192_B (5.6 mg) with a yield of 22.6% were prepared according to the synthetic steps 5-6 in synthesizing AA_091, with compound AA_192-4 (26.0 mg, 0.057 mmol), compound BB-28 (35 mg, 0.063 mmol), $Na_2CO_3$ (12.2 mg, 0.115 mmol) and $Pd(dppf)Cl_2$ (4.2 mg, 0.0057 mmol) as starting materials, and $DMF/THF/H_2O$ (1.5 mL/1.5 mL/1.5 mL) as a mixed solvent, separated by preparative HPLC. AA_192_A: LC/MS m/z: 799.6 $[M+H]^+$. AA_192_B: LC/MS m/z: 799.5 $[M+H]^+$ The compounds listed in the following table were synthesized according to the synthetic step 5 in synthesizing AA_192, with compound AA_192-4 as starting material:

| Embodiments | Structure | Fragment 1 | Fragment 2 | LCMS |
|---|---|---|---|---|
| 277 | AA_179_A | AA_192-4 | BB-25 | 757.6 [M + H]+ |
| 278 | AA_179_B | AA_192-4 | BB-25 | 757.5 [M + H]+ |

| Embodiments | Structure | Fragment 1 | Fragment 2 | LCMS |
|---|---|---|---|---|
| 279 | AA_191 | AA_192-4 | BB-24 | 783.6 [M + H]⁺ |
| 280 | AA_180 | AA_192-4 | AA_192-4 | 372.2 [M/2 + H]⁺ |

| Embodiments | Structure | Fragment 1 | Fragment 2 | LCMS |
|---|---|---|---|---|
| 281 | AA_197_A | AA_192-4 | AA_117_4 | 759.4 [M + H]⁺ |
| 282 | AA_197_B | AA_192-4 | AA_117_4 | 759.4 [M + H]⁺ |

| Embodiments | Structure | Fragment 1 | Fragment 2 | LCMS |
|---|---|---|---|---|
| 283 | AA_230_A | AA_192-4 | BB-29 | 771.4 [M + H]+ |
| 284 | AA_230_B | AA_192-4 | BB-29 | 771.5 [M + H]+ |

-continued

| Embodiments | Structure | Fragment 1 | Fragment 2 | LCMS |
|---|---|---|---|---|
| 285 | AA_231_A | AA_192-4 | BB-30 | 787.5 [M + H]⁺ |
| 286 | AA_231_B | AA_192-4 | BB-30 | 787.5 [M + H]⁺ |

| Embodiments | Structure | Fragment 1 | Fragment 2 | LCMS |
|---|---|---|---|---|
| 287 | AA_242_A | AA_192-4 | BB-31 | 379.7 [M/2 + H]⁺ |
| 288 | AA_242_B | AA_192-4 | BB-31 | 758.8 [M + H]⁺ |

| Embodiments | Structure | Fragment 1 | Fragment 2 | LCMS |
|---|---|---|---|---|
| 289 | AA_280_A | AA_192-4 | BB-32 | 388.1 [M/2 + H]+ |
| 290 | AA_280_B | AA_192-4 | BB-32 | 775.3 [M + H]+ |

Embodiment 291: AA_162_ENDOA2
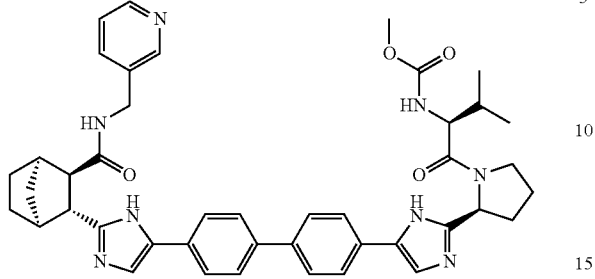
Synthetic Route:
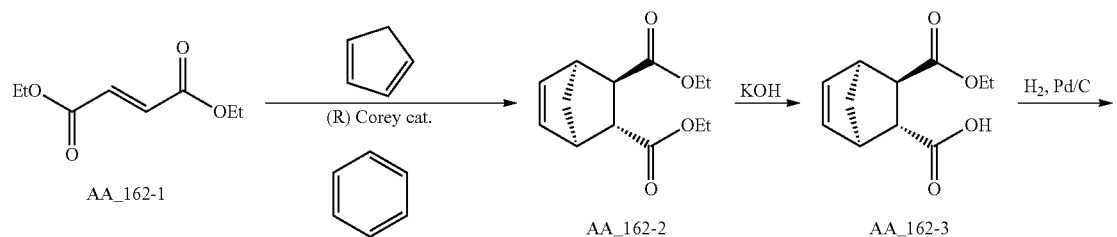
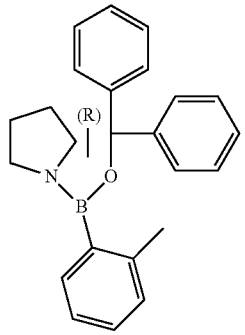
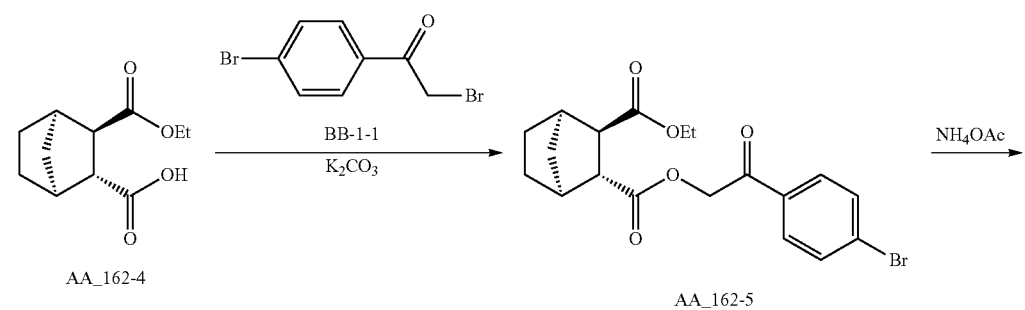
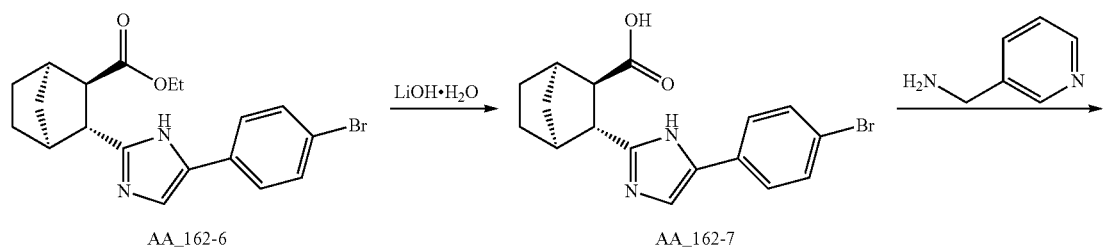

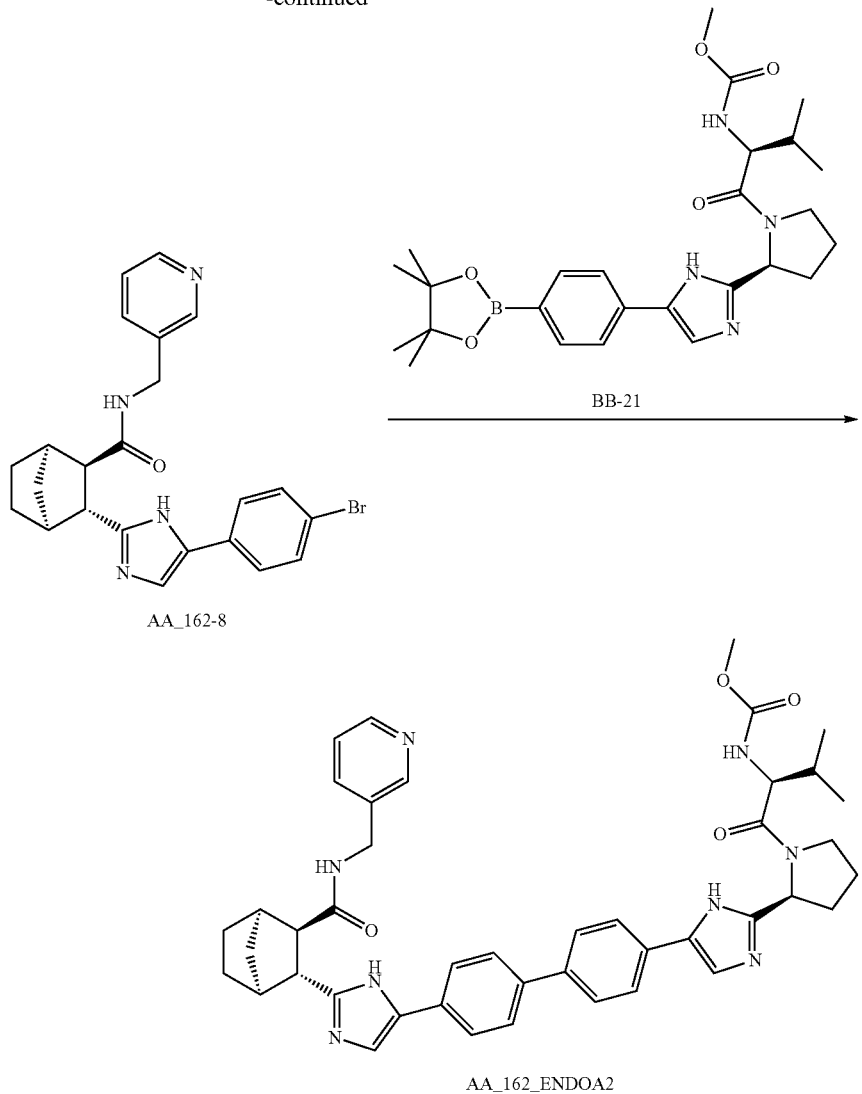

Step 1: Synthesis of Compound AA_162-2

(R)-2-(o-Methyl)phenyl-CBS-oxazaborolidine (4.11 g, 11.63 mmol) was dissolved in toluene (23 mL), cooled to −25° C., a solution of bis(trifluoromethanesulphon)imide (3.27 g, 11.63 mmol) in toluene (1M, 11.63 mL) was dripped under nitrogen gas atmosphere, and then the reaction mixture was stirred at −25° C. for 30 min. The reaction mixture was cooled to −60° C., diethyl fumarate (10.0 g, 54.18 mmol) was added, the mixture was stirred for 5 min. Then a solution of cyclopentadiene (19.2 g, 291 mmol) in toluene (10 mL) was dripped at −60° C. After dripping, the mixture was stirred for 16 h. After the reaction was complete as detected by TLC, the solvent was removed by a rotary evaporator, the residue was purified by silica gel column chromatography (PE/EA=2:1→1:4) to deliver the target compound AA_162-2 (yellow liquid, 10.0 g, yield: 72%). $^1$H NMR (CDCl$_3$, 400 MHz): δ 6.31-6.28 (m, 1H), 6.09-6.07 (m, 1H), 4.21-4.10 (m, 4H), 3.40-3.38 (m, 1H), 3.28 (s, 1H), 3.13 (s, 1H), 2.70-2.68 (m, 1H), 1.63 (d, J=8.8 Hz, 1H), 1.47 (d, J=8.8 Hz, 1H), 1.31-1.23 (m, 6H).

Step 2: Synthesis of Compound AA_162-3

Compound AA_162-2 (12 g, 50.36 mmol) was dissolved in a mixed solvent of DMSO/H$_2$O (100 mL/1000 mL), cooled to 0° C., 0.25M KOH aqueous solution (343 mL, 85.61 mmol) was dripped, the mixture was stirred for 3 h at 0° C. After the reaction was complete as detected by TLC, the reaction mixture was adjusted to pH to 3 by 1N hydrochloric acid at 0° C. The mixture was saturated with sodium chloride, then extracted with ethyl acetate (200 mL×3). The organic phases were combined, dried over anhydrous sodium sulfate. After filtration, the filtrate was concentrated by a rotary evaporator to remove the solvent thereby delivering the target compound AA_162-3 (10.4 g, yield 92.4%). $^1$H NMR (CDCl$_3$, 400 MHz): δ 6.31-6.29 (m, 1H), 6.10-6.08 (m, 1H), 4.11 (q, J=3.2 Hz, 2H), 3.38-3.36 (m, 1H), 3.29 (m, 1H), 3.23-3.20 (m, 1H), 2.74-2.72 (m, 1H), 1.63-1.61 (m, 1H), 2.74-2.72 (m, 1H), 1.49-1.47 (m, 1H), 1.24 (t, J=3.2 Hz, 3H).

Step 3: Synthesis of Compound AA_162-4

At room temperature, compound AA_162-3 (10.46 g, 43.91 mmol) was dissolved in ethanol (100 mL), 10% Pd/C (0.5 g) was added under nitrogen gas atmosphere. The reaction mixture was stirred at room temperature and under a hydrogen gas pressure of 25 psi for 12 h. After filtration, the filtrate was concentrated by a rotary evaporator to remove the solvent to deliver the target compound AA_162-4 (light yellow oil, 9.0 g, yield 87.5%). $^1$H NMR (CDCl$_3$, 400 MHz): δ 4.17-4.10 (m, 2 H), 2.65-2.62 (m, 4 H), 1.59-1.53 (m, 2 H), 1.36-1.22 (m, 7 H).

Step 4: Synthesis of Compound AA_162-5

Compound AA_162-4 (2 g, 9.42 mmol) and K$_2$CO$_3$ (2.6 g, 18.85 mmol) were suspended in DMF (10 mL), 2,4'-dibromoacetophenone (BB-1-1, 3.2 g, 11.31 mmol) was added at room temperature. The reaction mixture was stirred at room temperature for 1 h. After the reaction was complete as detected by TLC, H$_2$O (30 mL) was added to quench the reaction, the reaction mixture was extracted with ethyl acetate (50 mL×3). The organic phases were combined and dried over anhydrous sodium sulfate. After filtration, the filtrate was concentrated under reduced pressure to remove the solvent, the residue was purified by silica gel column chromatography (PE/EtOAc=4:1→1:4) to deliver the target compound AA_162-5 (light yellow powder, 3.4 g, yield for two steps 78.8%). LCMS m/z: 409 [M+H]$^+$.

Step 5: Synthesis of Compound AA_162-6

At room temperature, compound AA_162-5 (3.4 g, 8.31 mmol) was dissolved in toluene (100 mL), ammonium acetate (5.2 g, 66.55 mmol) was added. The reaction mixture was heated to reflux and stirred for 12 h under nitrogen gas atmosphere. After the reaction was complete as detected by TLC, the reaction mixture was cooled to room temperature. H$_2$O (30 mL) was added to quench the reaction, the mixture was extracted with ethyl acetate (50 mL×3). The organic phases were combined and dried over anhydrous sodium sulfate. After filtration, the filtrate was concentrated under reduced pressure to remove the solvent, the residue was purified by silica gel column chromatography (PE/EtOAc=9:1→1:1) to deliver the target compound AA_162-6 (light yellow powder, 2.88 g, yield 88.8%). LCMS m/z: 389.0 [M+H]$^+$.

Step 6: Synthesis of Compound AA_162-7

At room temperature, compound AA_162-6 (300 mg, 0.771 mmol) was dissolved in a mixed solvent of THF/MeOH/H$_2$O (2 mL/2 mL/2 mL), lithium hydroxide monohydrate (97 mg, 2.31 mmol) was added. The reaction mixture was stirred at room temperature for 8 h. After the reaction was complete as detected by TLC, most organic solvent was removed under reduced pressure. The mixture was cooled to 0° C. and adjusted to pH 6 with 1N hydrochloric acid. The solid was collected by filtration, dried to deliver the target compound AA_162-7 (milk-white powder, 250 mg, yield 89.8%). LCMS m/z: 360.9 [M+H]$^+$.

Step 7: Synthesis of Compound AA_162-8

At room temperature, compound AA_162-7 (150 mg, 0.415 mmol), 3-(aminomethyl)pyridine (54 mg, 0.498 mmol), DIPEA (107 mg, 0.830 mmol) were dissolved in DMF (2 mL), HATU (190 mg, 0.498 mmol) was added. The reaction mixture was stirred at room temperature for 1 h. After the reaction was complete as detected by TLC, the reaction was quenched with H$_2$O (10 mL) and extracted with ethyl acetate (30 mL×3). The organic phases were combined and dried over anhydrous sodium sulfate. After filtration, the filtrate was concentrated under reduced pressure to remove the solvent, the residue was purified by silica gel column chromatography (PE/EtOAc=2:1→1:4) to deliver the target compound AA_162-8 (light yellow powder, 135 mg, yield 72.8%). LC/MS m/z: 453.0 [M+H]$^+$.

Step 8: Synthesis of Compound AA_162_ENDOA2

Compound AA_162_ENDOA2 was synthesized according to the synthetic step 5 in synthesizing AA_192, with compound AA_162-8 and BB-21 as starting materials. LC/MS m/z: 741.3 [M+H]$^+$.

Embodiment 292: AA_273_ENDOA2

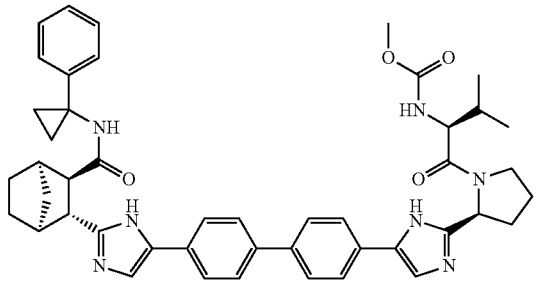

AA_273_ENDOA2

Synthetic Route:

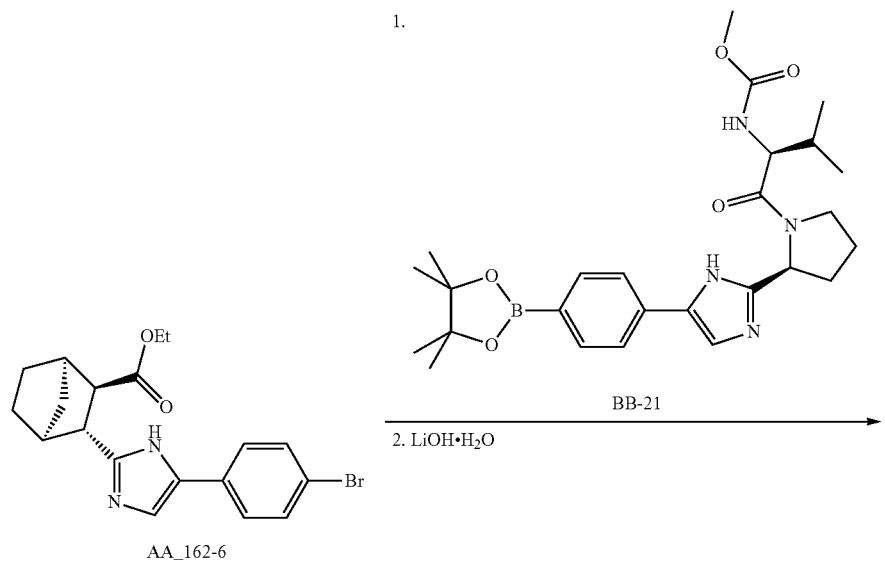

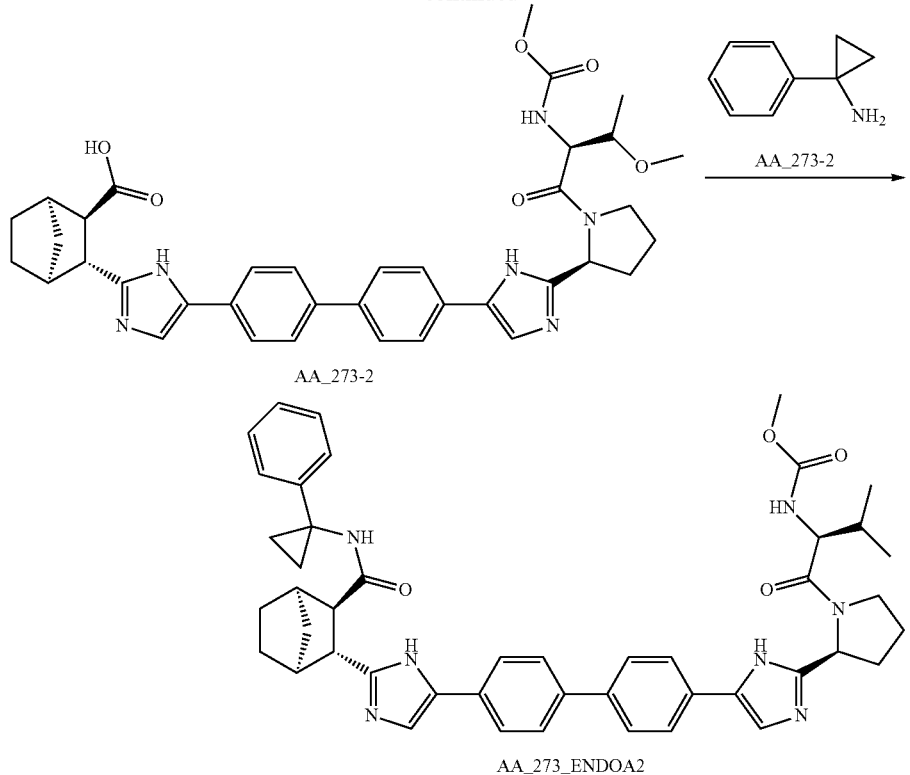

Step 1: Synthesis of Compound AA_273-1

Compound AA_273-1 was synthesized according to the synthetic steps 2-3 in synthesizing AA_237, with compound AA_162-6 and BB-21 as starting materials. LC/MS m/z: 651.3 [M+H]$^+$.

Step 2: Synthesis of Compound AA_273_ENDOA2

At room temperature, compound AA_273-1 (30 mg, 0.046 mmol), AA_273-2 (9.3 mg, 0.069 mmol) were dissolved in THF (2 mL), DMTMM (19.1 mg, 0.069 mmol) was added. The reaction system was heated to 90° C. and stirred overnight. After the reaction was complete as detected by TLC, the solvent was removed by a rotary evaporator, the residue was purified by preparative HPLC to deliver the target compound AA_273_ENDOA2 (2.8 mg, yield 7.9%). LC/MS m/z: 767.3 [M+H]$^+$.

The compounds listed in the following table were synthesized according to the synthetic step 2 in synthesizing AA_273_ENDOA2, with compound AA_273-1 as starting material:

| Embodiments | Structure | Fragment 1 | Fragment 2 | LCMS |
|---|---|---|---|---|
| 293 | AA_195_ENDOA2 | AA_273-1 | | 741.2 [M + H]+ |
| 294 | AA_201_ENDOA2 | AA_273-1 | | 742.2 [M + H]+ |

| Embodiments | Structure | Fragment 1 | Fragment 2 | LCMS |
|---|---|---|---|---|
| 295 | AA_204_ENDOA2_A | AA_273-1 | (3-pyridyl ethylamine) | 378.2 [M/2 + H]+ |
| 296 | AA_204_ENDOA2_B | AA_273-1 | (3-pyridyl ethylamine) | 755.2 [M + H]+ |

| Embodiments | Structure | Fragment 1 | Fragment 2 | LCMS |
|---|---|---|---|---|
| 297 | AA_206_ENDOA2 | AA_273-1 | (pyrazin-2-ylmethylamine) | 742.3 [M + H]⁺ |
| 298 | AA_208_ENDOA2 | AA_273-1 | (thiazol-2-ylmethylamine) | 747.3 [M + H]⁺ |

| Embodiments | Structure | Fragment 1 | Fragment 2 | LCMS |
|---|---|---|---|---|
| 299 | AA_214_ENDOA2 | AA_273-1 | 6-fluoropyridin-3-yl methanamine | 759.3 [M + H]⁺ |
| 300 | AA_224_ENDOA2 | AA_273-1 | 2-fluoropyridin-3-yl methanamine | 759.3 [M + H]⁺ |

-continued

| Embodiments | Structure | Fragment 1 | Fragment 2 | LCMS |
|---|---|---|---|---|
| 301 | AA_233_ENDOA2_A | AA_273-1 | | 783.1 [M + H]⁺ |
| 302 | AA_233_ENDOA2_B | AA_273-1 | | 392.1 [M/2 + H]⁺ |

| Embodiments | Structure | Fragment 1 | Fragment 2 | LCMS |
|---|---|---|---|---|
| 303 | AA_243_ENDOA2_A | AA_273-1 | | 386.1 [M/2 + H]+ |
| 304 | AA_243_ENDOA2_B | AA_273-1 | | 386.5 [M/2 + H]+ |

| Em-bodi-ments | Structure | Fragment 1 | Fragment 2 | LCMS |
|---|---|---|---|---|
| 305 | AA_270_ENDOA2_A | AA_273-1 | | 756.4 [M + H]+ |
| 306 | AA_270_ENDOA2_B | AA_273-1 | | 756.4 [M + H]+ |

| Em-bodi-ments | Structure | Fragment 1 | Fragment 2 | LCMS |
|---|---|---|---|---|
| 307 | AA_279_ENDOA2_A | AA_273-1 | | 761.2 [M + H]⁺ |
| 308 | AA_279_ENDOA2_B | AA_273-1 | | 761.2 [M + H]⁺ |

-continued

| Embodiments | Structure | Fragment 1 | Fragment 2 | LCMS |
|---|---|---|---|---|
| 309 | AA_282_ENDOA2 | AA_273-1 | | 764.1 [M + H]+ |
| 310 | AA_283_ENDOA2_A | AA_273-1 | | 773.1 [M + H]+ |

| Em-bodi-ments | Structure | Fragment 1 | Fragment 2 | LCMS |
|---|---|---|---|---|
| 311 | AA_283_ENDOA2_B | AA_273-1 | | 773.1 [M + H]+ |
| 312 | AA_284_ENDOA2 | AA_273-1 | | 650.1 [M + H]+ |

| Embodiments | Structure | Fragment 1 | Fragment 2 | LCMS |
|---|---|---|---|---|
| 313 | AA_285_ENDOA2 | AA_273-1 | | 783.2 [M + H]+ |
| 314 | AA_287_ENDOA2 | AA_273-1 | | 759.3 [M + H]+ |

| Embodiments | Structure | Fragment 1 | Fragment 2 | LCMS |
|---|---|---|---|---|
| 315 | AA_288_ENDOA2 | AA_273-1 | (1-methylimidazol-2-yl)methanamine | 744.2 [M + H]⁺ |
| 316 | AA_289_ENDOA2 | AA_273-1 | acetohydrazide | 707.3 [M + H]⁺ |

| Embodiments | Structure | Fragment 1 | Fragment 2 | LCMS |
|---|---|---|---|---|
| 317 | AA_290_ENDOA2 | AA_273-1 | | 821.3 [M + H]+ |
| 318 | AA_291_ENDOA2 | AA_273-1 | | 744.4 [M + H]+ |

| Embodiments | Structure | Fragment 1 | Fragment 2 | LCMS |
|---|---|---|---|---|
| 319 | AA_292_ENDOA2_M | AA_273-1 | | 756.3 [M + H]⁺ |
| 320 | AA_293_ENDOA2 | AA_273-1 | | 810.3 [M + H]⁺ |

| Embodiments | Structure | Fragment 1 | Fragment 2 | LCMS |
|---|---|---|---|---|
| 321 | AA_294_ENDOA2 | AA_273-1 | | 733.2 [M + H]⁺ |
| 322 | AA_295_ENDOA2_A | AA_273-1 | | 747.2 [M + H]⁺ |

| Embodiments | Structure | Fragment 1 | Fragment 2 | LCMS |
|---|---|---|---|---|
| 323 | AA_295_ENDOA2_B | AA_273-1 | | 747.2 [M + H]+ |
| 324 | AA_296_ENDOA2 | AA_273-1 | | 840.3 [M + H]+ |

| Em-bodi-ments | Structure | Fragment 1 | Fragment 2 | LCMS |
|---|---|---|---|---|
| 325 | AA_297_ENDOA2 | AA_273-1 | | 778.3 [M + H]⁺ |
| 326 | AA_298_ENDOA2 | AA_273-1 | | 763.3 [M + H]⁺ |

| Embodiments | Structure | Fragment 1 | Fragment 2 | LCMS |
|---|---|---|---|---|
| 327 | AA_299_ENDOA2 | AA_273-1 | | 765.2 [M + H]+ |
| 328 | AA_300_ENDOA2 | AA_273-1 | | 749.3 [M + H]+ |

-continued

| Embodiments | Structure | Fragment 1 | Fragment 2 | LCMS |
|---|---|---|---|---|
| 329 | AA_301_ENDOA2 | AA_273-1 | | 835.4 [M + H]⁺ |

Embodiment 330: AA_239
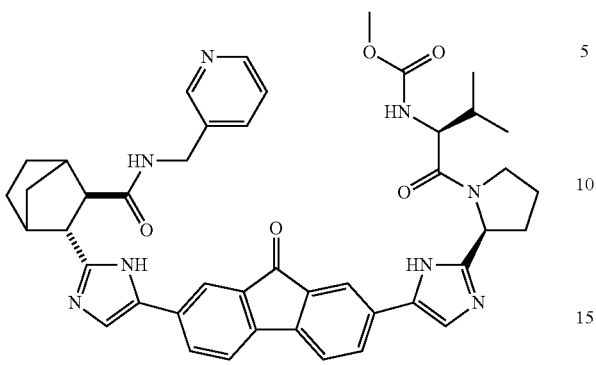
Synthetic Route:
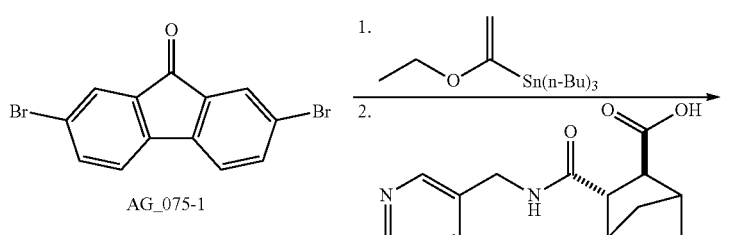
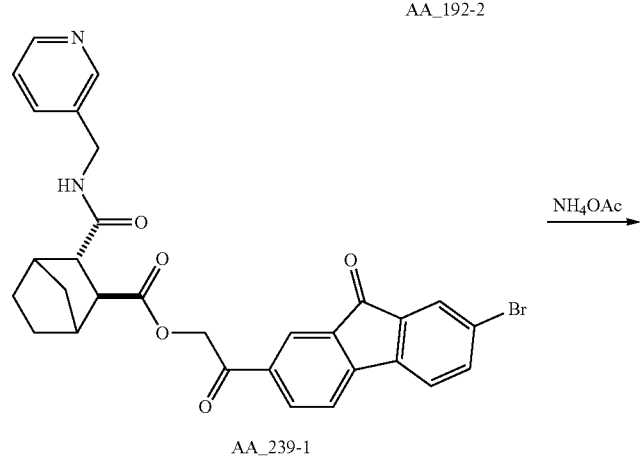
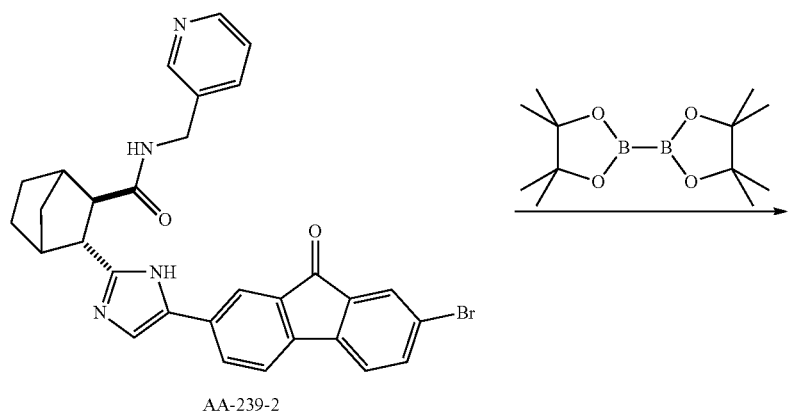

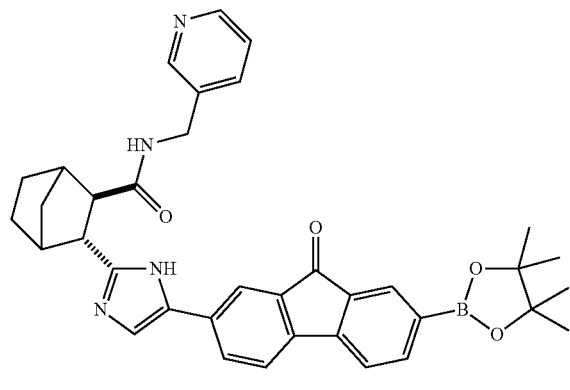

AA_239-3

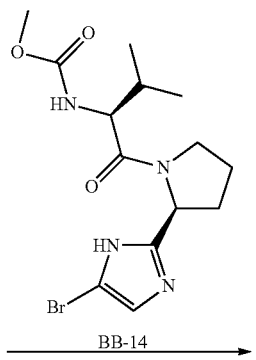

BB-14

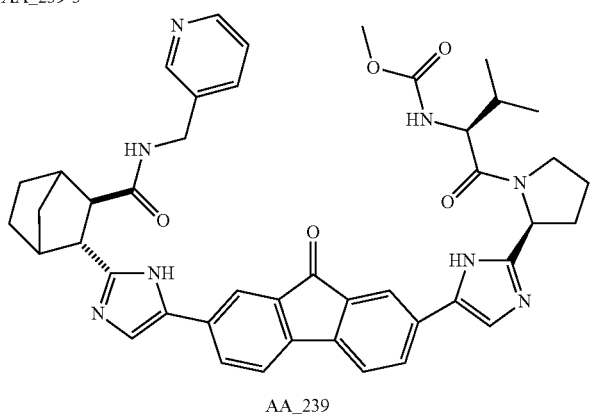

AA_239

Step 1: Synthesis of Compound AA_239-1

Compound AG_075-1 (2 g, 5.92 mmol), tributyl(1-ethoxyethenyl)stannane (2.34 g, 5.92 mmol) were dissolved in dioxane (20 mL), Pd(dppf)Cl$_2$ (870 mg, 1.28 mmol) and Pd(PPh$_3$)$_4$ (1370 mg, 1.28 mmol) were added under nitrogen gas atmosphere. The reaction mixture was heated to 80° C. and stirred for 4 h under nitrogen gas atmosphere. After the reaction was complete as detected by TLC, the mixture was cooled to room temperature. H$_2$O (8 mL) was added, then NBS (4.2 g, 23.67 mmol) was added, the mixture was stirred at room temperature for 12 h. After the reaction was complete as detected by TLC, H$_2$O (10 mL) was added. The mixture was extracted with ethyl acetate (50 mL×3) and the solvent was removed under reduced pressure to deliver an α-bromoketone intermediate; the intermediate was directly used for the next step without purification. The α-bromoketone intermediate and K$_2$CO$_3$ (1.64 g, 11.84 mmol) were suspended in DMF (20 mL), AA_192-2 (2.1 g, 7.7 mmol) was added at room temperature. The reaction mixture was stirred at room temperature for 2 h. After the reaction was complete as detected by TLC, H$_2$O (10 mL) was added. The reaction mixture was extracted with ethyl acetate (50 mL×3), dried over anhydrous sodium sulfate. After filtration, the filtrate was concentrated under reduced pressure to remove the solvent, the residue was purified by silica gel column chromatography (PE/EtOAc=9:1→3:2) to deliver the target compound AA_239-1 (1.1 g, yield for two steps 36.3%). LCMS m/z: 575.1 [M+H]$^+$.

Step 2: Synthesis of Compound AA_239-2

At room temperature, compound AA_239-1 (1 g, 1.74 mmol) was dissolved in toluene (100 mL), ammonium acetate (1.34 g, 17.4 mmol) was added. The reaction mixture was heated to reflux and stirred for 12 h under nitrogen gas atmosphere. After the reaction was complete as detected by TLC, the reaction mixture was cooled to room temperature. Ethyl acetate (100 mL) was added. The mixture was washed with saturated brines (30 mL×3). The organic phase was dried over anhydrous sodium sulfate. After filtration, the filtrate was concentrated under reduced pressure to remove the solvent, the residue was purified by silica gel column chromatography (PE/EtOAc=9:1→3:2) to deliver the target compound AA_239-2 (white solid, 0.45 g, yield 46.3%). LCMS m/z: 555.1 [M+H]$^+$.

Step 3: Synthesis of Compound AA_239-3

At room temperature, compound AA_239-2 (150 mg, 0.27 mmol), bis(pinacolato)diboron (345 mg, 1.37 mmol) were dissolved in dioxane (10 mL), KOAc (213 mg, 2.17 mmol) and Pd(dppf)Cl$_2$ (40 mg, 0.054 mmol) were added under nitrogen gas atmosphere. The reaction mixture was heated to 110° C. and stirred for 2 h under nitrogen gas atmosphere. After the reaction was complete as detected by TLC, the reaction mixture was cooled to room temperature. After filtration, the filtrate was concentrated by a rotary evaporator to remove the solvent, the residue was purified by silica gel column chromatography (PE/EtOAc=2:1→1:4) to deliver the target compound AA_239-3 (white solid, 115 mg, yield 70.5%). LCMS m/z: 601.1 [M+H]⁺.

Step 4: Synthesis of Compound AA_239

Compound AA_239-3 (30 mg, 0.049 mmol), BB-14 (23 mg, 0.059 mmol) were dissolved in a mixed solvent of THF/dimethoxy ethane/H₂O (2 mL/2 mL/2 mL), Na₂CO₃ (11 mg, 0.099 mmol) and Pd(dppf)Cl₂ (5 mg, 0.0098 mmol) were added under nitrogen gas atmosphere. The reaction mixture was heated to 100° C. and stirred for 8 h under nitrogen gas atmosphere. After the reaction was complete as detected by TLC, the reaction mixture was cooled to room temperature. After filtration, the filtrate was concentrated by a rotary evaporator to remove the solvent, the residue was purified by preparative HPLC to deliver the target compound AA_239 (white powder, 8 mg, yield 21.8%). LCMS m/z: 384.2 [M/2+H]⁺.

Embodiment 331: AA_238

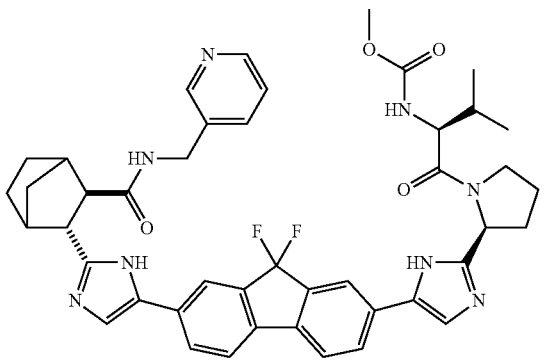

Synthetic Route:

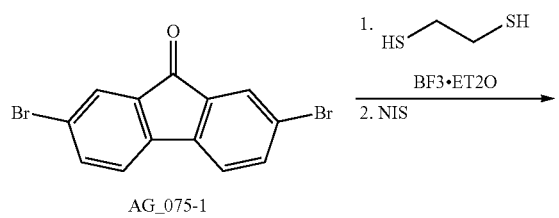

AG_075-1

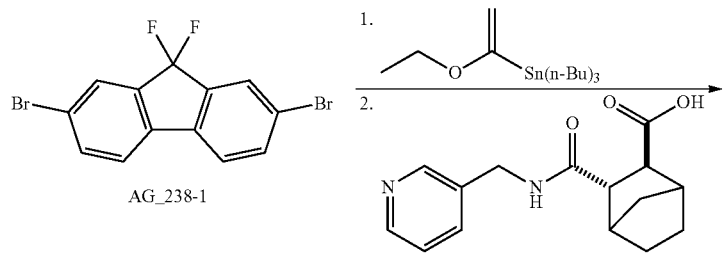

AG_238-1

AA_192-2

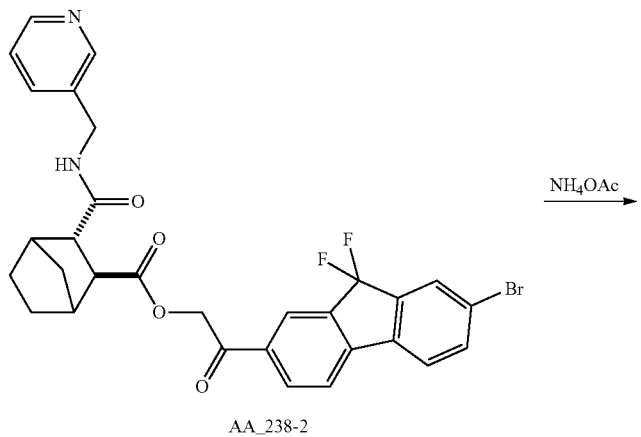

AA_238-2

-continued

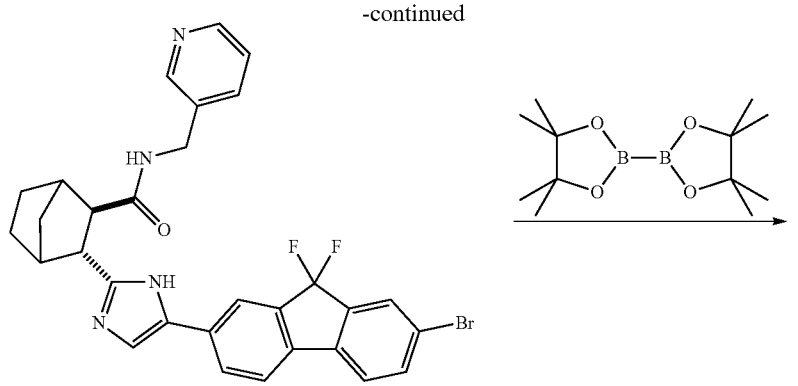

AA-238-3

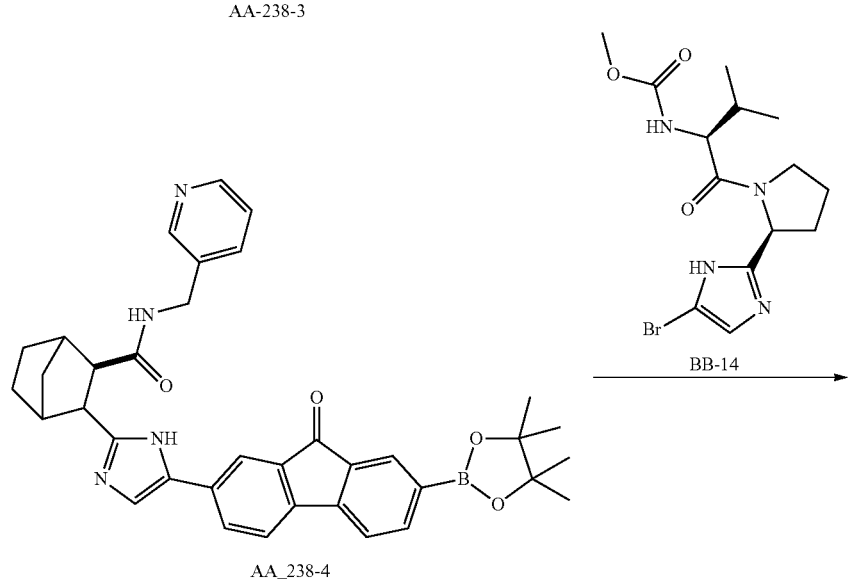

AA_238-4

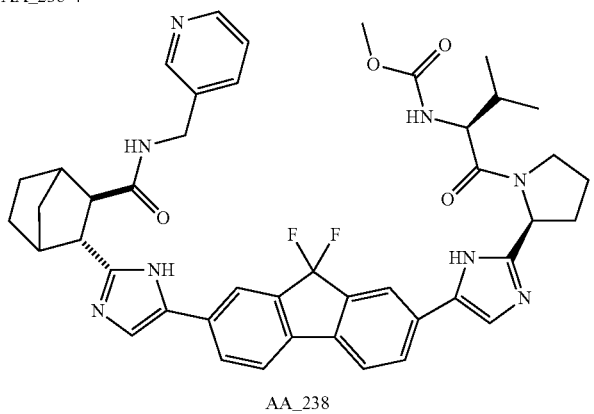

AA_238

Step 1: Synthesis of Compound AA_238-1

Compound AG_075-1 (15 g, 44.38 mmol), ethylene mercaptan (5 g, 53.26 mmol) were dissolved in chloroform (10 mL), BF$_3$Et$_2$O (5.5 mL, 44.38 mmol) was dripped. The reaction mixture was heated to reflux and stirred for 2 h under nitrogen gas atmosphere. After the reaction was complete as detected by TLC, the reaction mixture was cooled to room temperature and quenched with H$_2$O (10 mL), extracted with chloroform (30 mL×3). The organic phases were combined and dried over anhydrous sodium sulfate. After filtration, the filtrate was concentrated under reduced pressure to remove the solvent thereby delivering a thioketal intermediate (white solid, 17.5 g, yield 88.3%). N-Iodosuccinimide (NIS, 13.6 g, 60.36 mmol) was dissolved in dichloromethane (50 mL), cooled to −78° C., pyridine hydrofluoride (3.6 g, 36.22 mmol) was added under nitrogen gas atmosphere. The reaction mixture was stirred at this temperature for 1 h, a solution of the thioketal intermediate (5 g, 12.07 mmol) in dichloromethane (5 mL) was added. The mixture was stirred at −78° C. for further 1 h. After the reaction was complete as detected by TLC, the reaction mixture was quenched with H$_2$O (10 mL) and extracted with dichloromethane (50 mL×3). The organic phases were combined and dried over anhydrous sodium sulfate. After filtration, the filtrate was concentrated under reduced pressure to remove the solvent to deliver the target compound AA_238-1 (brown liquid, 3.2 g, yield 78.3%). $^1$H NMR (CDCl$_3$, 400 MHz): δ 7.75 (m, 2H), 7.61 (m, 2H), 7.40 (m, 2H).

Step 2: Synthesis of Compound AA_238-2

Compound AA_238-1 (7.48 g, 20.77 mmol), tributyl(1-ethoxyethenyl)stannane (7.5 g, 20.77 mmol) were dissolved in dioxane (100 mL), Pd(dppf)Cl$_2$ (3 g, 4.15 mmol) and Pd(PPh$_3$)$_4$ (4.8 g, 4.15 mmol) were added under nitrogen gas atmosphere. The reaction mixture was heated to 80° C. and stirred for 4 h under nitrogen gas atmosphere. After the reaction was complete as detected by TLC, the reaction mixture was cooled to room temperature. H$_2$O (20 mL) was added, then NBS (15 g, 83.07 mmol) was added, the mixture was stirred at room temperature for 12 h. After the reaction was complete as detected by TLC, H$_2$O (10 mL) was added and the mixture was extracted with ethyl acetate (50 mL×3). The solvent was removed under reduced pressure thereby delivering an α-bromoketone intermediate which was directly used for the next step without purification. The α-bromoketone intermediate and K$_2$CO$_3$ (1.5 g, 11.09 mmol) were suspended in DMF (20 mL), AA_192-2 (1.98 g, 7.21 mmol) was added at room temperature. The reaction mixture was stirred at room temperature for 2 h. After the reaction was complete as detected by TLC, H$_2$O (10 mL) was added. The reaction mixture was extracted with ethyl acetate (50 mL×3), dried over anhydrous sodium sulfate. After filtration, the filtrate was concentrated under reduced pressure to remove the solvent, the residue was purified by silica gel column chromatography (PE/EtOAc=9:1→3:2) to deliver the target compound AA_238-2 (1.3 g, yield for two steps 46.3%). LCMS m/z: 596.8 [M+H]$^+$.

Step 3: Synthesis of Compound AA_238-3

At room temperature, compound AA_238-2 (2.1 g, 4.45 mmol) was dissolved in toluene (100 mL), ammonium acetate (3.42 g, 44.5 mmol) was added. The reaction mixture was heated to reflux and stirred for 12 h under nitrogen gas atmosphere. After the reaction was complete as detected by TLC, the reaction mixture was cooled to room temperature, ethyl acetate (100 mL) was added, the mixture was washed with saturated brines (30 mL×3). The organic phase was dried over anhydrous sodium sulfate. After filtration, the filtrate was concentrated under reduced pressure to remove the solvent, the residue was purified by silica gel column chromatography (PE/EtOAc=9:1→3:2) to deliver the target compound AA_238-3 (white solid, 1.3 g, yield 62.3%). LCMS m/z: 577.1 [M+H]$^+$.

Step 4: Synthesis of Compound AA_238-4

At room temperature, compound AA_238-3 (150 mg, 0.26 mmol), bis(pinacolato)diboron (331 mg, 1.13 mmol) were dissolved in dioxane (10 mL), KOAc (205 mg, 2.09 mmol) and Pd(dppf)Cl$_2$ (40 mg, 0.052 mmol) were added under nitrogen gas atmosphere. The reaction mixture was heated to 110° C. and stirred for 2 h. After the reaction was complete as detected by TLC, the reaction mixture was cooled to room temperature and filtrated. The filtrate was concentrated by a rotary evaporator to remove the solvent, the residue was purified by silica gel column chromatography (PE/EtOAc=9:1→1:4) to deliver the target compound AA_238-4 (white solid, 105 mg, yield 66%). LCMS m/z: 623.3 [M+H]$^+$.

Step 5: Synthesis of Compound AA_238

Compound AA_238-4 (20 mg, 0.032 mmol), BB-14 (15 mg, 0.039 mmol) were dissolved in a mixed solvent of THF/dimethoxy ethane/H$_2$O(2 mL/2 mL/2 mL), Na$_2$CO$_3$ (9 mg, 0.064 mmol) and Pd(dppf)Cl$_2$ (5 mg, 0.0064 mmol) was added under nitrogen gas atmosphere. The reaction mixture was heated to 100° C. and stirred for 8 h under nitrogen gas atmosphere. After the reaction was complete as detected by TLC, the reaction mixture was cooled to room temperature and filtrated. The filtrate was concentrated by a rotary evaporator to remove the solvent, the residue was purified by preparative HPLC to deliver the target compound AA_238 (white solid, 8.2 mg, yield 27.8%). LCMS m/z: 395.2 [M/2+H]$^+$.

Embodiment 332: AA_241_A and AA_241_B

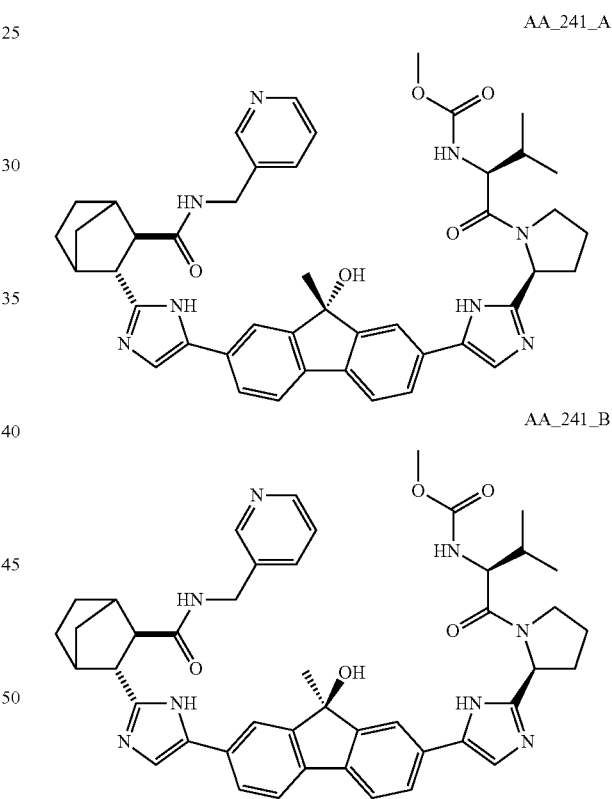

Synthetic Route:

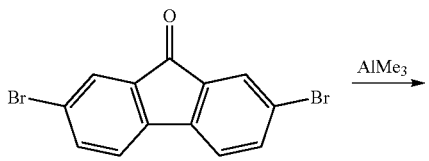

-continued
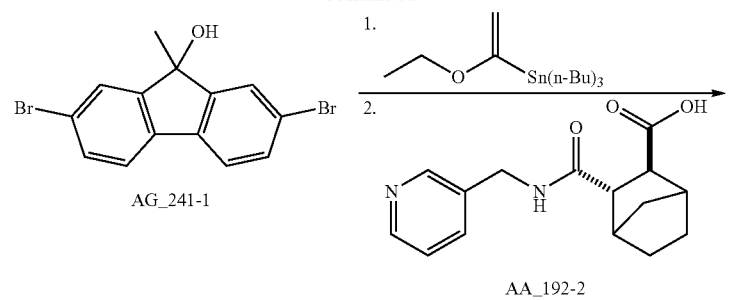
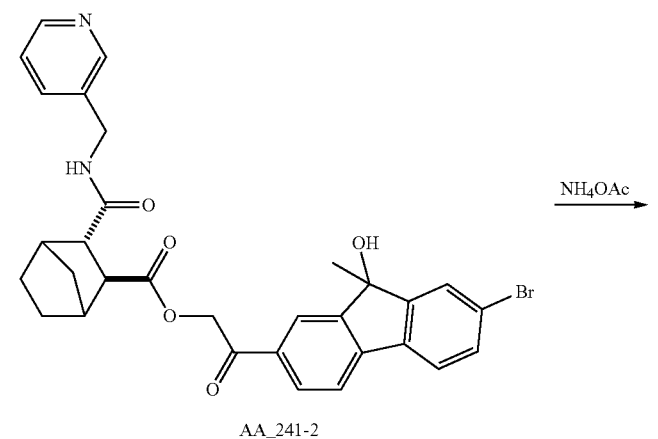
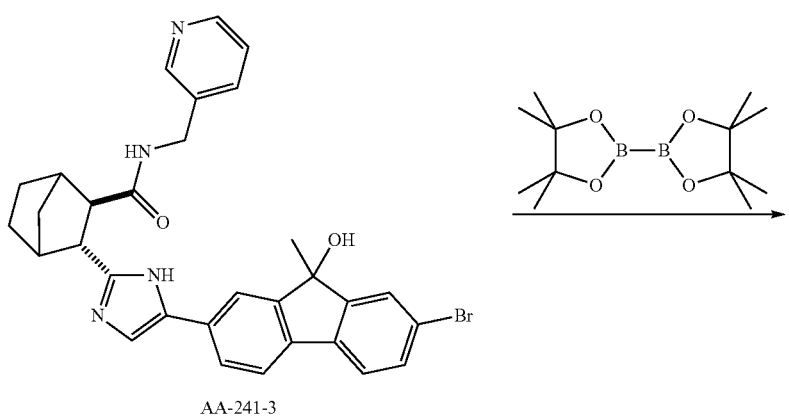
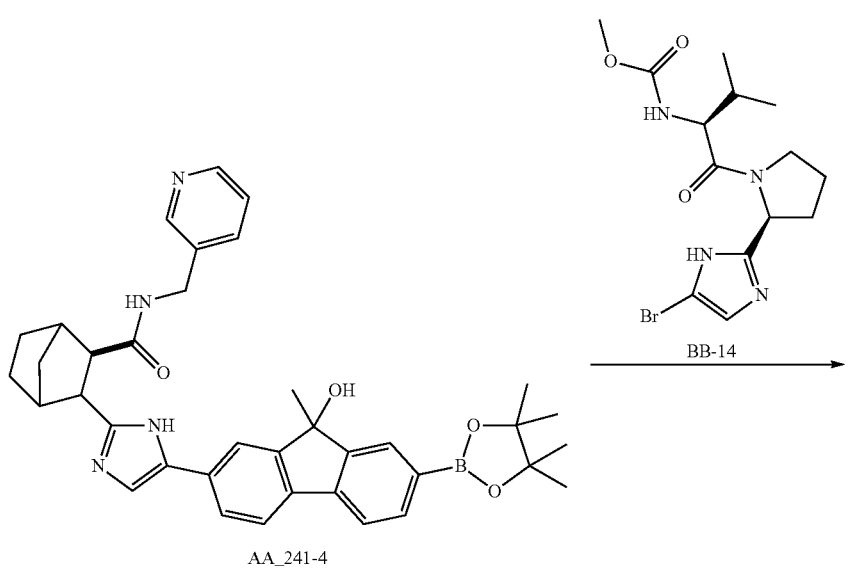

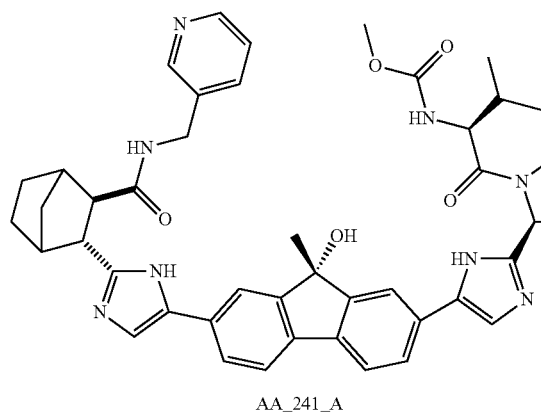

AA_241_A

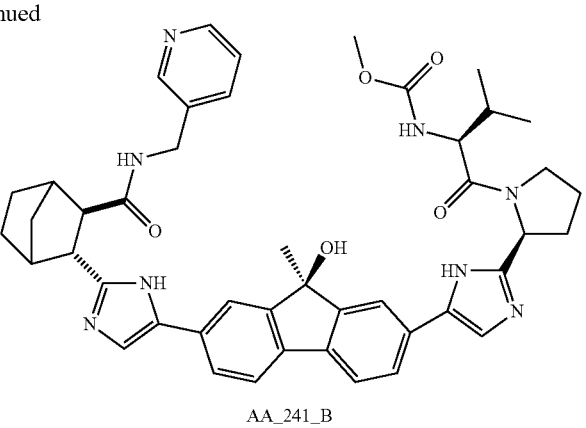

AA_241_B

Step 1: Synthesis of Compound AA_241-1

Compound AG_075-1 (1 g, 2.96 mmol) was dissolved in toluene (10 mL), cooled to 0° C., trimethylaluminium (5.92 mL, 11.83 mmol) was dripped under nitrogen gas atmosphere. The reaction mixture was stirred at room temperature for 1 h. After the reaction was complete as detected by TLC, the reaction mixture was cooled to 0° C. and quenched with $H_2O$ (10 mL), extracted with dichloromethane (50 mL×3). The organic phases were combined and dried over anhydrous sodium sulfate. After filtration, the filtrate was concentrated by a rotary evaporator to remove the solvent, the residue was purified by silica gel column chromatography (PE/EtOAc=9:1→3:2) to deliver the target compound AA_241-1 (yellow liquid, 0.82 g, yield 82.3%). $^1$H NMR (CDCl$_3$, 400 MHz): δ 7.68 (m, 2H), 7.49 (m, 4H), 1.719 (s, 3H).

Step 2: Synthesis of Compound AA_241-2

Compound AA_241-1 (1 g, 2.84 mmol), tributyl(1-ethoxyethenyl)stannane (1.03 g, 2.84 mmol) were dissolved in dioxane (20 mL), Pd(dppf)Cl$_2$ (417 mg, 0.57 mmol) and Pd(PPh$_3$)$_4$ (657 mg, 0.57 mmol) were added under nitrogen gas atmosphere. The reaction mixture was heated to 80° C. and stirred for 4 h under nitrogen gas atmosphere. After the reaction was complete as detected by TLC, the reaction mixture was cooled to room temperature. $H_2O$ (4 mL) was added, and then NBS (2 g, 11.36 mmol) was added, the mixture was stirred at room temperature for 12 h. After the reaction was complete as detected by TLC, $H_2O$ (10 mL) was added. The mixture was extracted with ethyl acetate (50 mL×3), the solvent was removed under reduced pressure to deliver an α-bromoketone intermediate which was directly used for the next step without purification. The α-bromoketone intermediate and K$_2$CO$_3$ (0.78 g, 5.68 mmol) were suspended in DMF (20 mL), AA_192-2 (1.01 g, 3.69 mmol) was added at room temperature. The reaction mixture was stirred at room temperature for 2 h. After the reaction was complete as detected by TLC, $H_2O$ (10 mL) was added. The reaction mixture was extracted with ethyl acetate (50 mL×3), dried over anhydrous sodium sulfate and then filtrated. The filtrate was concentrated under reduced pressure to remove the solvent, the residue was purified by silica gel column chromatography (PE/EtOAc=9:1→3:2) to deliver the target compound AA_241-2 (yellow solid, 0.65 g, yield for two steps 40.3%). LCMS m/z: 591.1 [M+H]$^+$.

Step 3: Synthesis of Compound AA_241-3

At room temperature, compound AA_241-2 (650 mg, 1.11 mmol) was dissolved in toluene (100 mL), ammonium acetate (853 mg, 11.1 mmol) was added. The reaction mixture was heated to reflux and stirred for 12 h under nitrogen gas atmosphere. After the reaction was complete as detected by TLC, the reaction mixture was cooled to room temperature. Ethyl acetate (100 mL) was added, the mixture was washed with saturated brines (30 mL×3). The organic phase was dried over anhydrous sodium sulfate. After filtration, the filtrate was concentrated under reduced pressure to remove the solvent, the residue was purified by silica gel column chromatography (PE/EtOAc=9:1→1:4) to deliver the target compound AA_241-3 (white solid, 320 mg, yield 52.3%). LCMS m/z: 571.1 [M+H]$^+$.

Step 4: Synthesis of Compound AA_241-4

At room temperature, compound AA_241-3 (120 mg, 0.21 mmol), bis(pinacolato)diboron (269 mg, 1.06 mmol) were dissolved in dioxane (10 mL), KOAc (166 mg, 1.69 mmol) and Pd(dppf)Cl$_2$ (36 mg, 0.044 mmol) were added under nitrogen gas atmosphere. The reaction mixture was heated to 110° C. and stirred for 2 h. After the reaction was complete as detected by TLC, the reaction mixture was cooled to room temperature and filtrated. The filtrate was concentrated by a rotary evaporator to remove the solvent, the residue was purified by silica gel column chromatography (PE/EtOAc=2:1→1:4) to deliver the target compound AA_241-4 (white solid, 85 mg, yield 66%). LCMS m/z: 617.2 [M+H]$^+$.

Step 5: Synthesis of Compound AA_241_A and AA_241_B

Compound AA_241-4 (70 mg, 0.114 mmol), BB-14 (213 mg, 0.568 mmol) were dissolved in a mixed solvent of THF/dimethoxy ethane/H$_2$O (2 mL/2 mL/2 mL), Na$_2$CO$_3$ (97 mg, 0.911 mmol) and Pd(dppf)Cl$_2$ (15 mg, 0.023 mmol) was added under nitrogen gas atmosphere. The reaction mixture was heated to 100° C. and stirred for 8 h. After the reaction was complete as detected by TLC, the reaction mixture was cooled to room temperature and filtrated. The filtrate was concentrated by a rotary evaporator to remove the solvent, the residue was purified by preparative HPLC (table 3, method 6) to deliver the target compound AA_241_A (white solid, 7 mg) and AA_241_B (white solid, 7 mg), yield 17.8%. AA_241_A: LCMS m/z: 384.1 [M/2+H]$^+$. AA_241_A: LCMS m/z: 384.1 [M/2+H]$^+$.

Embodiment 333: AA_242
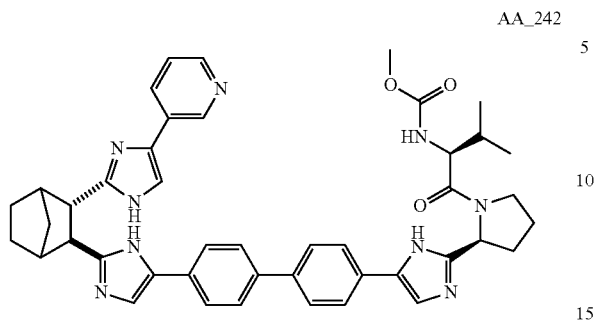
Synthetic Route:
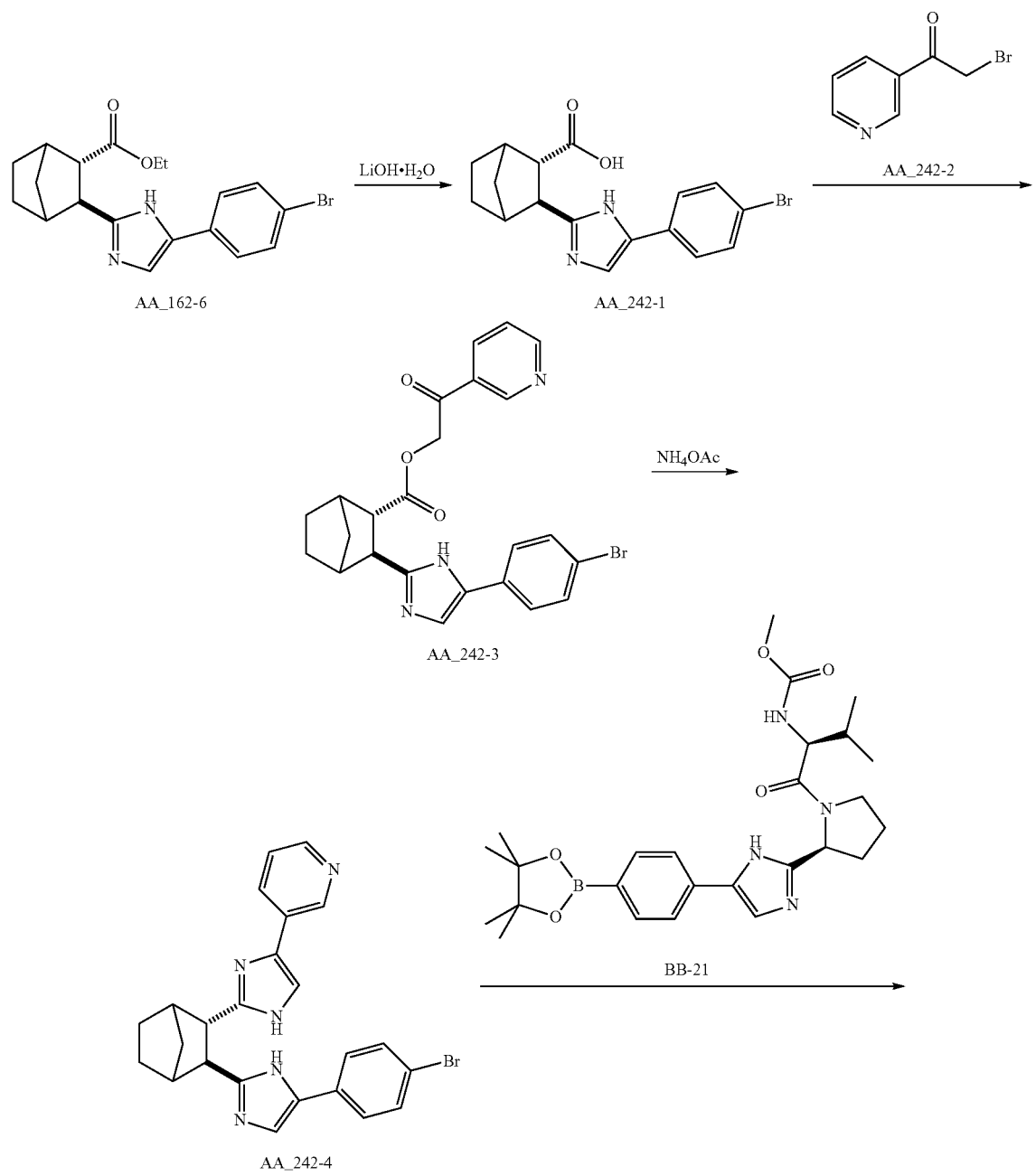

-continued

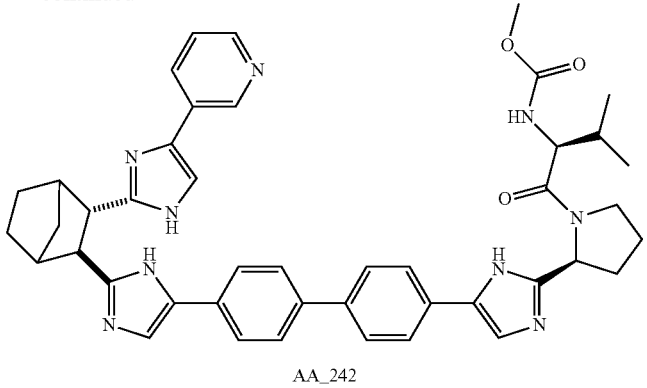

AA_242

Step 1: Synthesis of Compound AA_242-1

Compound AA_162_6 (1.0 g, 2.57 mmol) was dissolved in a mixed solvent of THF/MeOH/H$_2$O (5 mL/5 mL/5 mL), lithium hydroxide monohydrate (0.215 g, 5.14 mmol) was added. The reaction mixture was stirred at 50° C. for 10 h. After the reaction was complete as detected by TLC, the reaction mixture was cooled to room temperature and extracted with ethyl acetate (10 mL×2). The aqueous phase was adjusted to pH to 3-4 with 1N hydrochloric acid, the solid precipitated was collected and dried to deliver the target compound AA_242-1 (0.65 g, yield 70.0%). LCMS m/z: 362.9 [M+H]$^+$.

Step 2: Synthesis of Compound AA_242-3

Compound AA_242-1 (178 mg, 0.49 mmol) and DIPEA (191.1 g, 1.48 mmol) were dissolved in acetonitrile (5 mL), 3-(2-bromoacetyl) pyridine (AA_242-2, 128.1 mg, 0.64 mmol) was added at room temperature. The reaction mixture was stirred at room temperature for 2 h. After the reaction was complete as detected by TLC, the solvent was removed under reduced pressure, the residue was purified by silica gel column chromatography (PE/EtOAc=1:1→EtOAc) to deliver the target compound AA_242-3 (red oil, 50 mg, yield 21.1%). LCMS m/z: 480.0 [M+H]$^+$.

Step 3: Synthesis of Compound AA_242-4

At room temperature, compound AA_242-3 (20 mg, 0.021 mmol) and ammonium acetate (32 g, 0.42 mmol) were dissolved in toluene (10 mL), the reaction mixture was heated to reflux at 120° C. and stirred for 10 h. After the reaction was complete as detected by TLC, the solvent was removed under reduced pressure, the residue was purified by silica gel column chromatography (PE/EtOAc=1:1→EtOAc) to deliver the target compound AA_242-4 (yellow solid, 19 mg, yield 98.9%). LCMS m/z: 462.0 [M+H]$^+$.

Step 4: Synthesis of Compound AA_242

Compound AA_242 (2.5 g, yield 7.7%) was synthesized according to the synthetic step 4 in synthesizing AA_238, with AA_242-4 (20 mg, 0.0434 mmol), compound BB-21 (25.9 mg, 0.052 mmol), Na$_2$CO$_3$ (9.2 mg, 0.087 mmol) and Pd(dppf)Cl$_2$ (3.2 mg, 0.00434 mmol) as starting materials, and DMF/THF/H$_2$O (1.5 mL/1.5 mL/1.5 mL) as a mixed solvent. LCMS m/z: 750.2 [M+H]$^+$.

Embodiment 334: AA_150_A and AA_150_B

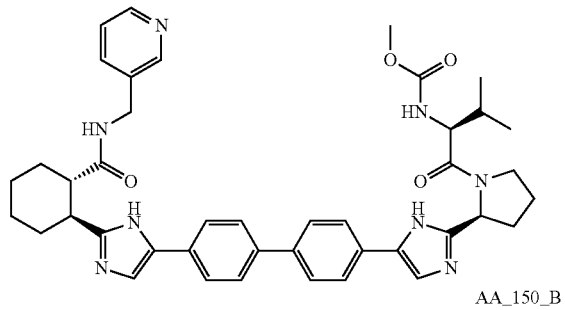

AA_150_A

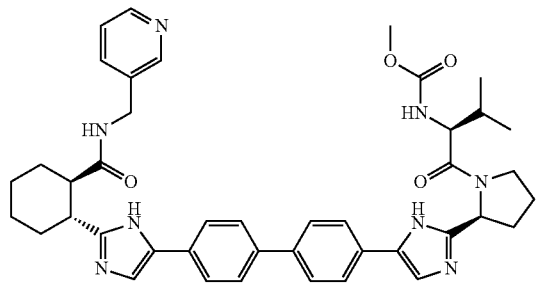

AA_150_B

Synthetic Route:

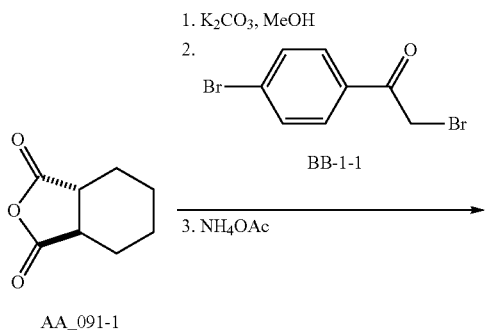

-continued
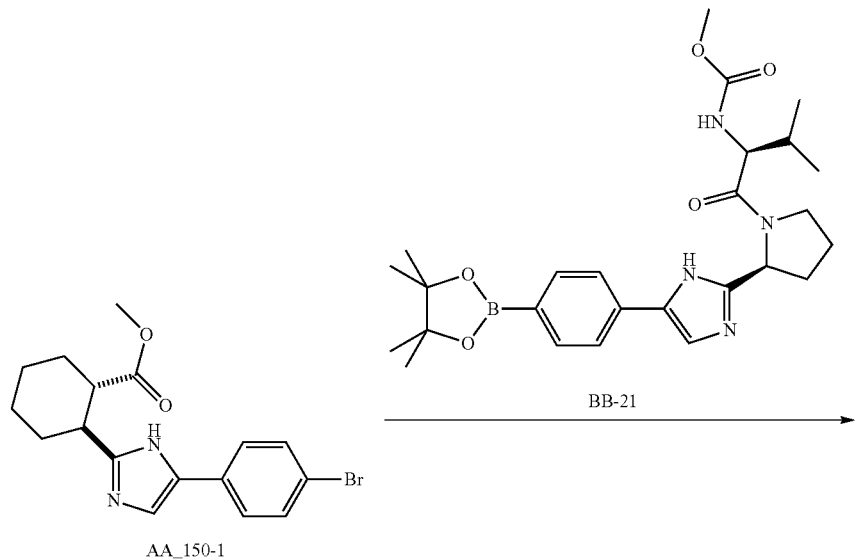
AA_150-1
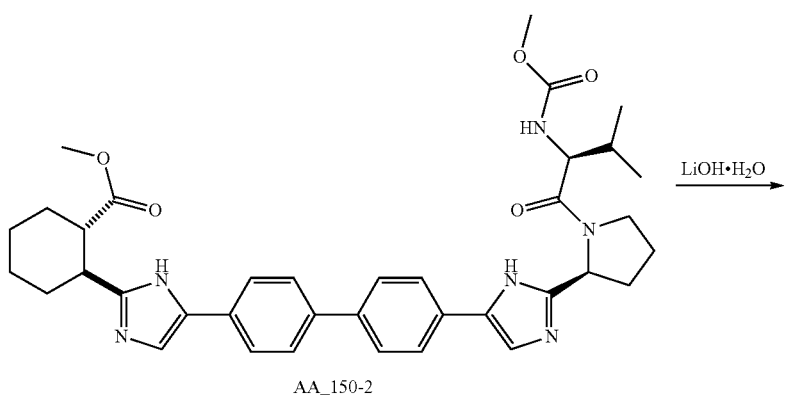
AA_150-2
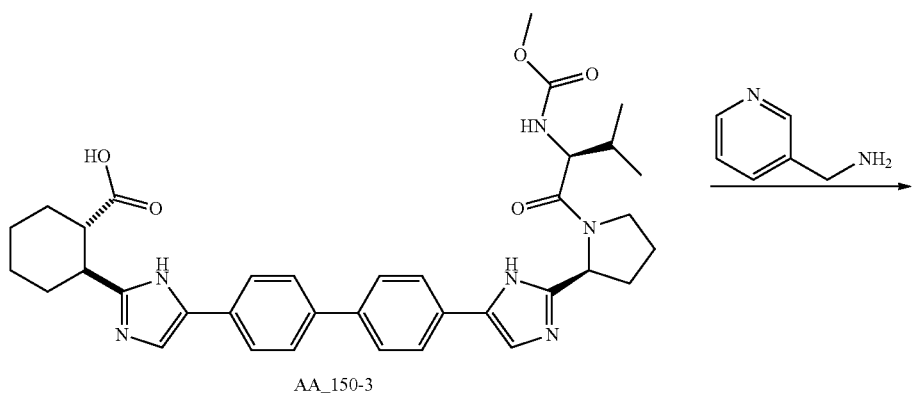
AA_150-3

-continued

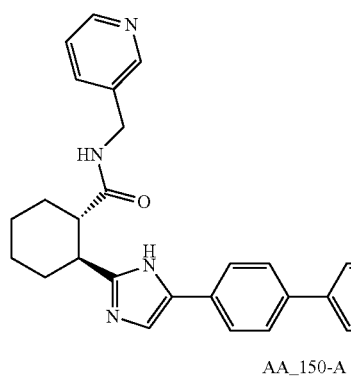

AA_150-A

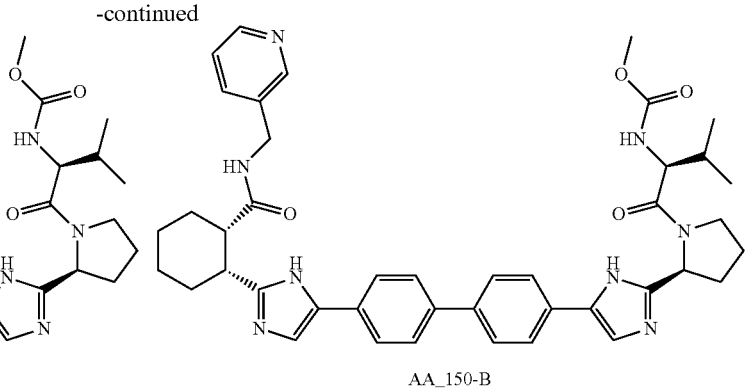

AA_150-B

Step 1: Synthesis of Compound AA_150-1

Compound AA_190-1 (2 g, 12.97 mmol) was suspended in methanol (30 mL), cooled to 0° C., $K_2CO_3$ (3.59 g, 25.95 mmol) was added slowly, the reaction mixture was stirred at room temperature for 2 h. After the reaction was complete as detected by TLC, the reaction mixture was cooled to 0° C. Conc. hydrochloric acid was dripped to adjust pH to 3-4, most organic solvent was removed under educed pressure. $H_2O$ (30 mL) was added into the residue, then extracted with ethyl acetate (100 mL×3). The organic phase was dried over anhydrous sodium sulfate. After filtration, the filtrate was concentrated by a rotary evaporator to remove the solvent thereby delivering an intermediate as white solid. The white solid intermediate and $K_2CO_3$ (3.59 g, 25.95 mmol) was suspended in acetonitrile (40 ml), 2,4'-dibromoacetophenone (BB-1-1, 3.61 g, 12.97 mmol) was added. The reaction mixture was stirred at room temperature for 12 h. After the reaction was complete as detected by TLC, the solvent was removed under reduced pressure. $H_2O$ (40 mL) was added, the mixture was extracted with ethyl acetate (100 mL×3). The organic phases were combined and dried over anhydrous sodium sulfate. After filtration, the filtrate was concentrated under reduced pressure to remove the solvent, the residue was purified by silica gel column chromatography (PE/EtOAc=3:1) to deliver an intermediate as brown solid. The yellow oil intermediate was dissolved in toluene (100 mL), ammonium acetate (10.0 g, 129.7 mmol) was added. The reaction mixture was heated to reflux and stirred for 12 h under nitrogen gas atmosphere. After the reaction was complete as detected by TLC, the reaction mixture was cooled to room temperature. Ethyl acetate (150 mL) was added and the mixture was washed with saturated brines (40 mL×2). The organic phase was dried over anhydrous sodium sulfate. After filtration, the filtrate was concentrated under reduced pressure to remove the solvent, the residue was purified by silica gel column chromatography (PE/EtOAc=1:1) to deliver the target compound AA_150-1 (light yellow powder, 1.07 g, yield for three steps 22.7%). LCMS m/z: 364.9 [M+H]$^+$. $^1$H NMR (CDCl$_3$, 400 MHz): δ 7.67-7.65 (m, 2H), 7.52-7.48 (m, 3H), 3.49 (s, 3H), 3.90-2.86 (m, 1H), 3.08 (m, 1H), 1.79-1.77 (m, 2H), 1.57 (m, 2H), 1.41-1.34 (m, 4H).

Step 2: Synthesis of Compound AA_150-2

Compound AA_150-2 (light yellow solid, 0.7 g, yield 36.5%) was synthesized according to the synthetic step 3 in synthesizing AA_007, with compound AA_150-1 (1.07 g, 3.0 mmol), compound BB-21 (1.64 g, 3.3 mmol), Na$_2$CO$_3$ (0.64 g, 6.0 mmol) and Pd(dppf)Cl$_2$ (220 mg, 0.3 mmol) as starting materials, and DMF/THF/H$_2$O (2 mL/2 mL/2 mL) as a mixed solvent. LCMS m/z: 653.3 [M+H]$^+$ Step 3: Synthesis of Compound AA_150-3

Compound AA_150-2 (700 mg, 1.07 mmol) was dissolved in a mixed solvent of THF/MeOH/H$_2$O (4 mL/4 mL/4 mL), NaOH (86 mg, 2.14 mmol) was added. The reaction mixture was stirred at room temperature overnight. After the reaction was complete as detected by TLC, the solvent was removed under reduced pressure. H$_2$O (5 mL) was added, the mixture was adjusted to pH to 3-4 with 1N hydrochloric acid. The solid precipitated was collected and dried to deliver the target compound AA_150-3 (385 mg, yield 60.7%). LCMS m/z: 639.2 [M+H]$^+$.

Step 4: Synthesis of Compound AA_150_A and AA_150_B

At room temperature, compound AA_150-3 (30 mg, 0.046 mmol), 3-(aminomethyl)pyridine (6.1 mg, 0.056 mmol) were dissolved in THF (2 mL), DMTMM (15.5 mg, 0.056 mmol) was added. The reaction system was heated to 90° C. and stirred overnight. After the reaction was complete as detected by TLC, the solvent was removed by a rotary evaporator, the residue was purified by preparative HPLC to deliver the target compound AA_150_A (2.0 mg) and AA_150_B (3.2 mg), yield 15.2%.

AA_150_A: LC/MS m/z: 729.3 [M+H]$^+$. AA_150_B: LC/MS m/z: 729.3 [M+H]$^+$.

The compounds listed in the following table were synthesized according to the synthetic step 4 in synthesizing AA_150, with compound AA_150-3 as starting material:

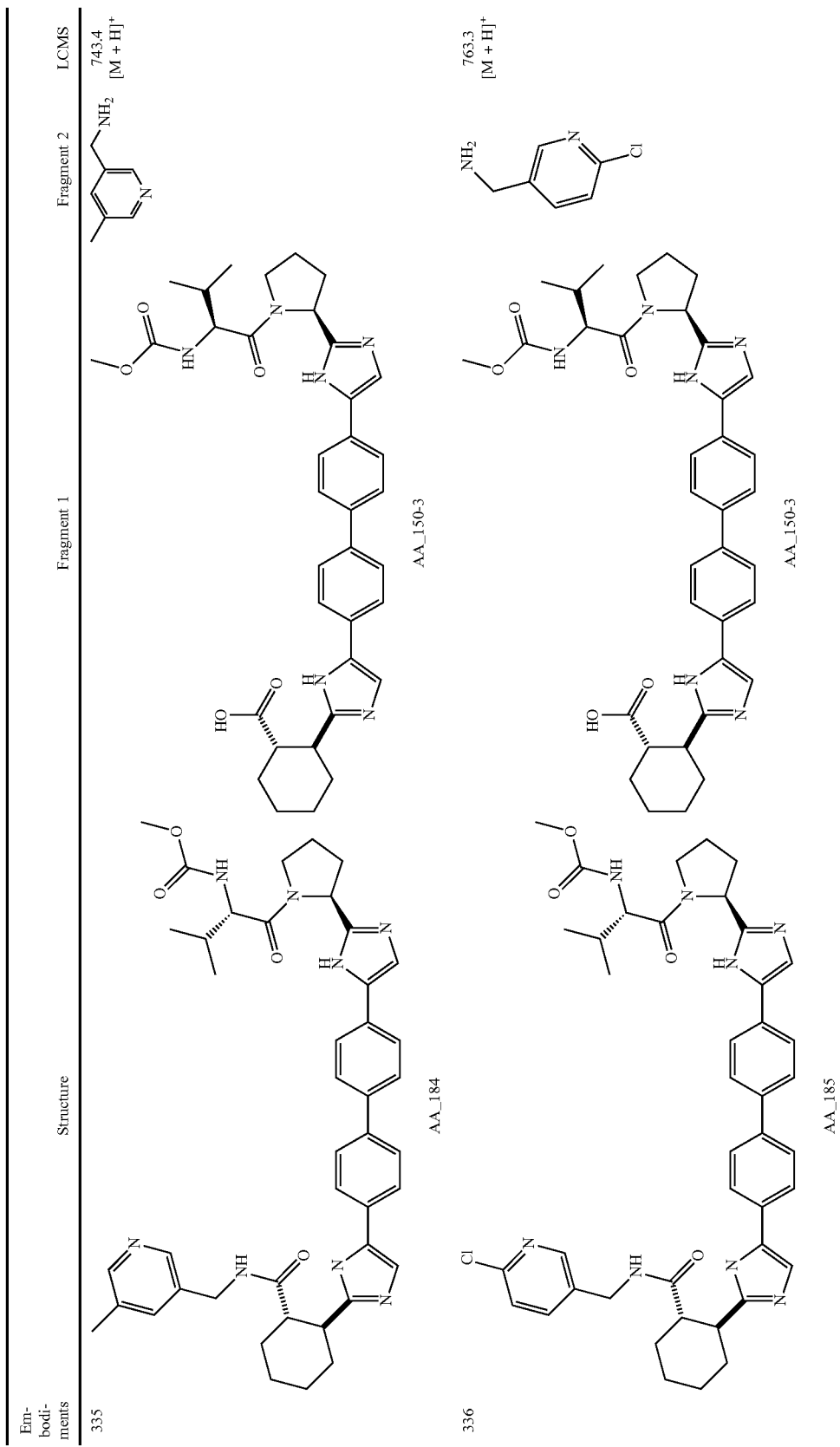

| Embodiments | Structure | Fragment 1 | Fragment 2 | LCMS |
|---|---|---|---|---|
| 337 | AA_186 | AA_150-3 | (1-(pyridin-3-yl)cyclopropyl)amine | 755.4 [M + H]⁺ |

Embodiment 338: AA_286
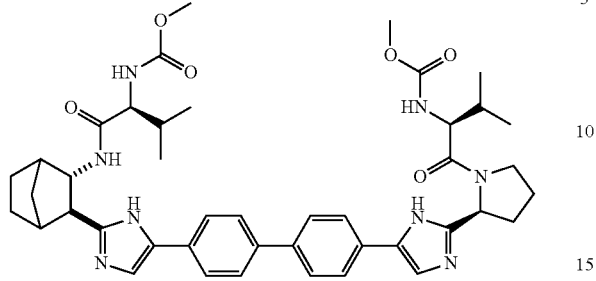
Synthetic Route:
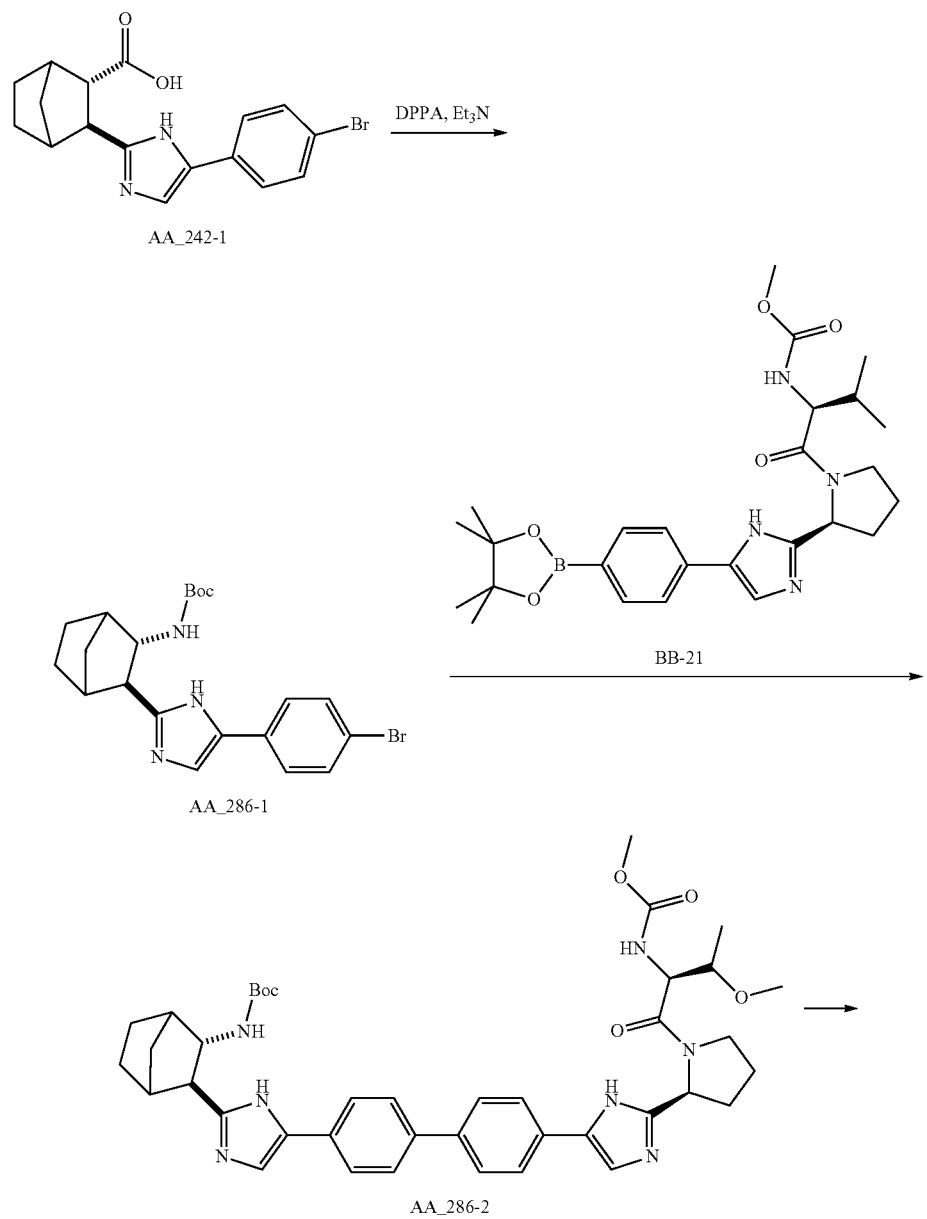

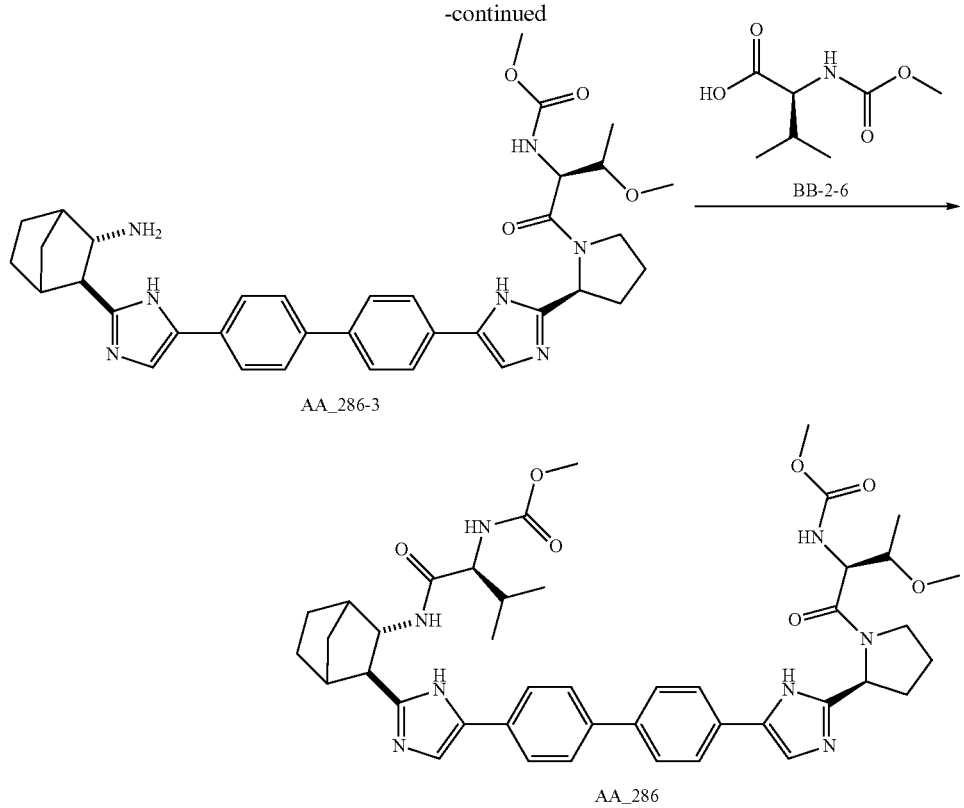

Step 1: Synthesis of Compound AA_286-1

Compound AA_242-1 (1.6 g, 4.43 mmol), TEA (0.896 g, 8.86 mmol) were dissolved in t-butanol (100 mL), DPPA (1.83 g, 6.64 mmol) was added slowly. The reaction mixture was heated to reflux and stirred overnight under nitrogen gas atmosphere. After the reaction was complete as detected by TLC, $H_2O$ (30 mL) was added to quench the reaction. The reaction mixture was extracted with ethyl acetate (50 mL×2). The organic phases were combined and dried over anhydrous sodium sulfate. After filtration, the filtrate was concentrated under reduced pressure to remove the solvent, the residue was purified by silica gel column chromatography (PE/EtOAc=3:1) to deliver the target compound AA_286-1 (0.49 g, yield 25.5%). LC/MS m/z: 434.2 [M+H]$^+$ Step 2: Synthesis of Compound AA_286-2

Compound AA_286-1 (150 mg, 0.46 mmol), BB-21 (276 mg, 0.56 mmol) were dissolved in DMF/THF/$H_2O$ (5 mL/5 mL/5 mL), $Na_2CO_3$ (74 mg, 0.93 mmol) and Pd(dppf)Cl$_2$ (40 mg, 0.046 mmol) were added under nitrogen gas atmosphere. The reaction mixture was heated to reflux and stirred overnight under nitrogen gas atmosphere. After the reaction was complete as detected by TLC, the reaction mixture was cooled to room temperature. After filtration, the filtrate was concentrated under reduced pressure to remove the solvent, the residue was purified by silica gel column chromatography (PE/EtOAc=5:1→1:1) to deliver the target compound AA_286-2 (196 mg, yield 56%). LC/MS m/z: 723.4 [M+H]$^+$ Step 3: Synthesis of Compound AA_286-3

Compound AA_286-2 (200 mg, 0.48 mmol) was dissolved in ethyl acetate (5 mL), cooled to 0° C., hydrogen chloride/ethyl acetate solution (HCl/EA, 4M, 15 mL) was added. The reaction mixture was stirred at room temperature for 1.5 h. After the reaction was complete as detected by TLC, the solvent was removed under reduced pressure at room temperature thereby delivering the target compound AA_286-3 (white solid, 171 mg, yield 99.4%). The product was directly used for the next step without purification. LCMS m/z: 622.4 [M+H]$^+$.

Step 4: Synthesis of Compound AA_286

At room temperature, the compound AA_286-3 (173 mg, 0.28 mmol), N-Moc-L-valine (BB-2-6, 58 mg, 0.33 mmol) and DIPEA (72 mg, 0.56 mmol) were dissolved in DMF (10 mL), HATU (130 mg, 0.34 mmol) was added. The reaction mixture was stirred at room temperature for 2 h. After the reaction was complete as detected by TLC, the reaction mixture was quenched with $H_2O$ (10 mL) and extracted with ethyl acetate (30 mL×3). The organic phases were combined and dried over anhydrous sodium sulfate. After filtration, the filtrate was concentrated under reduced pressure to remove the solvent, the residue was purified by silica gel column chromatography (PE/EtOAc=1:1→pure EtOAc) to deliver the target compound AA_286 (122 mg, yield 56.2%). LC/MS m/z: 779.4 [M+H]$^+$.

Experiment 1: Assay In Vitro

Experimental Objective:

The EC$_{50}$ and CC$_{50}$ values of anti-HCV compounds were determined by HCV genotype 1a (HCV-1a) and 1B (HCV-1b) stable transfer replication (replicon) cells. The source of genotype 1a replicon is H77 clones containing K1691R, K2040R and S2204I adaptive mutations. The source of genotype 1b replicon is Con1 clones containing E1202G, T1280I and K1846T adaptive mutations.

Background Introduction:

HCV 1a (HCV-1a) and 1b (HCV-1b) gene subtype replicon system contains the related HCV gene subtype non structural protein gene, G418 resistance gene NEO and luciferase gene, which results in that HCV related protein and luciferase can be stably expressed in cells. By detecting the level of expression of luciferase gene, the level of HCV replication can be determined. Therefore, the system is used as a model for screening the activity of anti-HCV compound in vitro.

Experimental Materials:

HCV Replicon Cell Lines: HCV-1a and HCV-1b Cells

Cell culture medium: DMEM (Invitrogen, Cat.#11960077) medium, add 10% fetal bovine serum (FBS, Sigma, Cat.#12003C) and 1% penicillin-streptomycin (penicillin 5000 IU/mL, streptomycin 10 mg/mL, Hyclone, Cat.# SV30010)

Trypsin (Invitrogen, Cat.#25200072)

PBS (Invitrogen, Cat.#10010023)

Trypan blue (Invitrogen, Cat. #15250061)

Cell Titer-fluor (Promega, Cat. # G6082)

Bright-Glo (Promega, Cat.# E2650)

$CO_2$ incubator, Thermo 240 I

Multidrop, Thermo

POD 810 Plate Assembler, Labcyte

Scepter Handheld Automated Cell Counter, Millipore

Microplate Spectrophotometer, Molecular Device.

Experimental Procedure and Method:

a) Preparation, Dilution and Addition of Compound Solution:

The compound powder was dissolved in 100% DMSO. Then the compound was diluted 5 times with 6 points, and added into the cell plate with Echo liquid handler. Ensure the final concentration of DMSO was 0.5%. Each compound was tested in double holes. Maximum initial concentration was 100, 10 or 1 nM, 5 times dilution, 6 points.

b) Cell Culture (HCV-1a or HCV-1b Replicon Cell):

1) absorbing the culture supernatant of the cell culture and washing the cells with 10 mL PBS.

2) adding preheated pancreatin to the washed cell culture flasks, rotating culture bottle to make the bottom of the culture bottle uniformly covered by pancreatin, then placed into 37° C., 5% $CO_2$ incubator to digest.

3) suspending cells in each T150 culture flask with 10-15 mL culture medium, absorbing 0.1 mL liquid and diluting 2 times by trypan blue solution as counted.

4) diluting cells to $8 \times 10^4$/mL with the culture medium, adding the diluted cells into the compound-containing 96-well plate (Greiner, Cat.#655090) (100 μL/well, 8000 cells/well) with automatic liquid separator (Thermo Scientific). Then place into a 37° C., 5% $CO_2$ incubator for 3 days. Cell control well: no compound, only containing 0.5% DMSO.

5) adding chemiluminescent substrate Cell Titer-fluor to the cell well, after incubation for 30 minutes, detecting the signal by chemiluminescence detection system Envison (Ex at 405 nm and read at 515 nm). The effect of the compounds on the activity of HCV replicon cells was analyzed according to the luminescence data, which was used to calculate the $CC_{50}$ values.

6) then adding luciferase luminescence substrate Bright-Glo, after incubation for 5 minutes, detecting the luciferase activity by chemical luminescence detection system Envison (wavelength>700 nm); analyzing the anti-HCV inhibitory activity of the compounds according to luciferase data, which was used to calculate $EC_{50}$ values.

c) Data Processing and Analysis:

The $EC_{50}$ or $CC_{50}$ values were obtained by nonlinear fitting analysis on inhibition percentage (inh %) data with GraphPad Prism software.

The results of the experiments were shown in Table 1:

TABLE 1

Experimental results of $EC_{50}$/$CC_{50}$ of HCV replicon cells

| Sample code | HCV 1b replicon cells | | HCV 1a replicon cells | |
| --- | --- | --- | --- | --- |
| | $EC_{50}$ | $CC_{50}$/nM | $EC_{50}$ | $CC_{50}$/nM |
| AG_015 | A | >10 | D | >100 |
| AG_046 | B | >100 | D | >100 |
| AG_047 | B | >100 | D | >100 |
| AG_040 | B | >10 | D | >100 |
| AG_027 | B | >10 | D | — |
| AG_045 | B | >100 | D | >100 |
| AG_015_A | A | >1 | D | — |
| AG_067 | A | >1 | D | — |
| AG_078_A | A | >5 | D | — |
| AG_078_B | B | >5 | D | — |
| AG_060 | A | >1 | B | — |
| AG_060_B | A | >10 | A | — |
| AG_077 | A | >5 | A | — |
| AG_104 | A | >1 | A | — |
| AG_079_A | A | >5 | A | — |
| AG_079_B | B | >5 | C | — |
| AG_123 | A | >1 | C | — |
| AG_124 | A | >1 | B | >100 |
| AG_113 | A | >1 | B | — |
| AG_080_A | A | >5 | A | — |
| AG_080_B | B | >5 | C | — |
| AG_088_A | A | >1 | B | — |
| AG_105 | A | >1 | B | — |
| AG_014 | B | >10 | D | — |
| AG_025_A | A | >10 | D | — |
| AG_025_B | A | >10 | D | — |
| AG_025_C | B | >10 | D | — |
| AG_014_A | A | >10 | C | — |
| AG_026_A | B | >10 | D | — |
| AG_048 | B | >100 | D | >100 |
| AG_049 | A | >100 | D | >100 |
| AG_050 | A | >100 | C | >100 |
| AG_063 | A | >1 | D | — |
| AG_066 | A | >1 | C | — |
| AG_068_A | A | >1 | C | — |
| AG_068_B | B | >1 | D | — |
| AG_069 | A | >1 | C | — |
| AG_076 | A | >5 | D | — |
| AG_089 | A | >1 | C | — |
| AG_092 | A | >1 | D | — |
| AG_093 | A | >1 | D | — |
| AG_106 | A | >1 | D | — |
| AG_115 | A | >1 | B | — |
| AG_116 | A | >1 | A | — |
| AG_117 | A | >1 | B | — |
| AG_122_A | A | >1 | C | — |
| AG_122_B | B | >1 | D | — |
| AG_114_A | B | >1 | D | — |
| AG_114_B | B | >1 | D | — |
| AG_110 | A | >1 | B | — |
| AG_101 | A | >1 | C | — |
| AG_107 | A | >1 | C | — |
| AG_111 | A | >1 | B | — |
| AG_121 | A | >1 | D | — |
| AG_084_A | B | >1 | C | — |
| AG_100 | A | >1 | B | — |
| AG_099 | B | — | C | — |
| AG_091 | A | >1 | C | — |
| AG_090 | A | >1 | C | — |
| AG_098 | A | — | C | — |
| AG_061_A | A | >1 | B | — |
| AG_095 | A | — | B | — |
| AG_094 | A | >1 | B | — |
| AG_102 | A | >1 | C | — |
| AG_072_A | A | >1 | A | — |
| AG_087 | A | >1 | B | — |
| AG_120 | A | >1 | C | — |
| AG_118_A | B | >1 | D | — |
| AG_118_B | A | >1 | C | — |
| AG_096 | A | — | D | — |

TABLE 1-continued

Experimental results of $EC_{50}/CC_{50}$ of HCV replicon cells

| Sample code | HCV 1b replicon cells $EC_{50}$ | $CC_{50}$/nM | HCV 1a replicon cells $EC_{50}$ | $CC_{50}$/nM |
|---|---|---|---|---|
| AG_086 | A | >1 | D | — |
| AG_054 | A | >10 | B | — |
| AG_001 | A | >1 | C | >10 |
| AG_011 | A | >1 | D | — |
| AG_022 | B | >10 | D | — |
| AG_052 | A | >100 | C | >100 |
| AG_053 | B | >100 | C | >100 |
| AG_037 | A | >10 | B | >100 |
| AG_112 | A | >1 | C | — |
| AG_061_B | A | >10 | B | — |
| AG_119 | A | >1 | B | — |
| AG_109 | A | >1 | B | — |
| AG_108 | A | >1 | B | — |
| AG_103 | A | >1 | C | — |
| AG_085 | A | >1 | D | — |
| AG_081_A | B | >5 | D | — |
| AG_081_B | A | >1 | D | — |
| AG_036 | A | >10 | C | >100 |
| AG_072_B | B | >1 | C | — |
| AG_042 | B | >100 | C | >100 |
| AG_038 | B | >10 | D | >100 |
| AG_097 | A | — | D | — |
| AG_035 | A | >10 | D | >100 |
| AG_051 | B | >100 | C | >100 |
| AG_062 | B | >10 | D | — |
| AA_007 | C | >100 | — | — |
| AA_033 | D | — | D | — |
| AA_008 | C | >100 | — | — |
| AA_138 | C | >100 | D | — |
| AA_160 | A | >50 | C | — |
| AA_014 | C | >100 | — | — |
| AA_013A | C | — | — | — |
| AA_013B | B | — | — | — |
| AA_090_A | C | — | — | — |
| AA_090_B | C | — | — | — |
| AA_029 | D | — | — | — |
| AA_100 | D | >10 | — | — |
| AA_108 | C | >10 | — | — |
| AA_072 | D | >10 | — | — |
| AA_071 | C | >10 | — | — |
| AA_073 | C | >10 | — | — |
| AA_074 | D | >10 | — | — |
| AA_075 | D | >10 | — | — |
| AA_076 | C | — | — | — |
| AA_078 | D | >10 | — | — |
| AA_079 | D | — | — | — |
| AA_092 | D | — | — | — |
| AA_094 | D | >10 | — | — |
| AA_096 | D | — | — | — |
| AA_097 | D | — | — | — |
| AA_106 | D | — | — | — |
| AA_107 | D | — | — | — |
| AA_089 | C | — | — | — |
| AA_091 | B | >10 | — | — |
| AA_091_A | C | >10 | — | — |
| AA_091_B | B | >10 | D | — |
| AA_109 | B | >100 | D | — |
| AA_122 | B | >100 | D | — |
| AA_117 | B | >10 | D | — |
| AA_118 | C | >10 | — | — |
| AA_127 | B | >10 | D | — |
| AL_003 | D | >10 | — | — |
| AA_032 | B | — | — | — |
| AA_034 | D | — | D | — |
| AA_016 | B | — | — | — |
| AA_095 | C | — | — | — |
| AA_190_A | B | >1 | D | — |
| AA_190_B | B | >1 | D | — |
| AA_121_A | C | >10 | D | — |
| AA_121_B | A | >10 | C | — |
| AA_166_A | A | >5 | D | — |
| AA_166_B | B | >5 | D | — |
| AA_169_A | A | >5 | C | — |
| AA_169_B | A | >5 | D | — |
| AA_156 | A | >1 | C | — |
| AA_167 | A | >1 | C | — |
| AA_155 | C | >100 | D | — |
| AA_158 | A | >1 | C | — |
| AA_027 | D | — | — | — |
| AA_047 | D | — | — | — |
| AA_064 | C | — | — | — |
| AA_065 | C | — | — | — |
| AA_028 | C | >100 | — | — |
| AA_054 | B | — | — | — |
| AA_055 | C | — | — | — |
| AA_056 | C | — | — | — |
| AA_057 | D | — | — | — |
| AA_113 | B | >10 | C | — |
| AA_114 | C | — | — | — |
| AA_115 | C | — | — | — |
| AA_116 | C | — | — | — |
| AA_063 | C | — | — | — |
| AA_237_A | B | >1 | D | — |
| AA_237_B | A | >1 | D | — |
| AA_162_A | A | >1 | C | — |
| AA_162_B | A | >1 | C | — |
| AA_193 | A | >1 | C | — |
| AA_194 | A | >1 | D | — |
| AA_195_A | A | >1 | B | — |
| AA_195_B | A | >1 | C | — |
| AA_196_A | A | >1 | C | — |
| AA_196_B | A | >1 | D | — |
| AA_198_A | A | >1 | C | — |
| AA_198_B | A | >1 | D | — |
| AA_199_A | A | >1 | C | — |
| AA_199_B | A | >1 | D | — |
| AA_200_A | A | >1 | C | — |
| AA_200_B | A | >1 | C | — |
| AA_201_A | A | >1 | B | — |
| AA_201_B | A | >1 | C | — |
| AA_202 | A | >1 | C | — |
| AA_203_A | A | >1 | C | — |
| AA_203_B | A | >1 | C | — |
| AA_204_A | A | >1 | B | — |
| AA_204_B | A | >1 | C | — |
| AA_204_C | A | >1 | C | — |
| AA_206_A | A | >1 | B | — |
| AA_206_B | A | >1 | C | — |
| AA_207_A | A | >1 | C | — |
| AA_207_B | A | >1 | D | — |
| AA_208_A | A | >1 | C | — |
| AA_208_B | A | >1 | C | — |
| AA_209_A | A | >1 | D | — |
| AA_209_B | B | >1 | D | — |
| AA_210_A | A | >1 | D | — |
| AA_210_B | A | >1 | D | — |
| AA_211_A | A | >1 | C | — |
| AA_211_B | A | >1 | C | — |
| AA_213 | A | >1 | C | — |
| AA_214_A | A | >1 | C | — |
| AA_214_B | A | >1 | D | — |
| AA_215_A | A | >1 | D | — |
| AA_215_B | A | >1 | D | — |
| AA_216_A | A | >1 | D | — |
| AA_216_B | A | >1 | D | — |
| AA_217 | C | >1 | D | — |
| AA_218 | B | >1 | D | — |
| AA_224_A | A | >1 | C | — |
| AA_224_B | A | >1 | C | — |
| AA_228 | A | >1 | C | — |
| AA_232_A | A | >1 | C | — |
| AA_232_B | A | >1 | C | — |
| AA_233_A | A | >1 | B | — |
| AA_233_B | A | >1 | C | — |
| AA_233_C | B | >1 | D | — |
| AA_234_A | A | >1 | C | — |

TABLE 1-continued

Experimental results of $EC_{50}/CC_{50}$ of HCV replicon cells

| Sample code | HCV 1b replicon cells $EC_{50}$ | $CC_{50}$/nM | HCV 1a replicon cells $EC_{50}$ | $CC_{50}$/nM |
|---|---|---|---|---|
| AA_234_B | A | >1 | D | — |
| AA_235_A | A | >1 | D | — |
| AA_236_A | A | >1 | D | — |
| AA_236_B | B | >1 | D | — |
| AA_243_A | A | >1 | D | — |
| AA_243_B | A | >1 | B | — |
| AA_244_A | B | >1 | D | — |
| AA_275 | A | — | D | — |
| AA_276 | C | — | D | — |
| AA_277 | A | — | B | — |
| AA_278 | B | — | D | — |
| AA_226 | A | >1 | D | — |
| AA_219_A | A | >1 | C | — |
| AA_220_A | B | >1 | D | — |
| AA_220_B | C | >1 | D | — |
| AA_221_A | A | >1 | C | — |
| AA_222_A | A | >1 | D | — |
| AA_223_A | B | >1 | D | — |
| AA_223_B | B | >1 | D | — |
| AA_227 | B | >1 | D | — |
| AA_245_A | A | >1 | D | — |
| AA_245_B | B | >1 | D | — |
| AA_246_A | A | >1 | D | — |
| AA_246_B | B | >1 | D | — |
| AA_247_A | A | >1 | B | — |
| AA_247_B | A | >1 | C | — |
| AA_248_A | B | >1 | D | — |
| AA_248_B | B | >1 | D | — |
| AA_249_A | A | >1 | B | — |
| AA_250_A | B | >1 | D | — |
| AA_250_B | C | >1 | D | — |
| AA_251_A | B | >1 | B | — |
| AA_251_B | B | >1 | C | — |
| AA_251_C | C | >1 | D | — |
| AA_252_A | B | >1 | C | — |
| AA_252_B | A | >1 | C | — |
| AA_253_A | B | >1 | D | — |
| AA_253_B | B | >1 | D | — |
| AA_253_C | C | >1 | D | — |
| AA_254_A | B | >1 | D | — |
| AA_255_A | A | >1 | D | — |
| AA_255_B | A | >1 | D | — |
| AA_256_A | A | >1 | D | — |
| AA_257_A | B | >1 | C | — |
| AA_258_B | C | >1 | D | — |
| AA_259_A | A | >1 | D | — |
| AA_260_B | A | >1 | D | — |
| AA_261_A | A | >1 | C | — |
| AA_262_B | A | >1 | B | — |
| AA_263_B | B | >1 | C | — |
| AA_263_C | B | >1 | D | — |
| AA_264_A | B | >1 | C | — |
| AA_264_B | B | >1 | D | — |
| AA_265_A | B | >1 | D | — |
| AA_265_B | B | >1 | D | — |
| AA_266_A | B | >1 | C | — |
| AA_266_B | B | >1 | D | — |
| AA_267_A | A | >1 | B | — |
| AA_267_B | B | >1 | C | — |
| AA_268_A | A | >1 | B | — |
| AA_268_B | A | >1 | C | — |
| AA_271_A | A | >1 | B | — |
| AA_271_B | B | >1 | D | — |
| AA_272_A | A | >1 | C | — |
| AA_281_A | A | >1 | B | — |
| AA_281_B | A | >1 | B | — |
| AA_281_C | B | >1 | C | — |
| AA_192_A | A | >1 | C | — |
| AA_192_B | A | >1 | C | — |
| AA_179_A | A | >1 | C | — |
| AA_179_B | A | >1 | C | — |
| AA_191 | B | >1 | C | — |
| AA_180 | C | >10 | D | — |
| AA_197_A | A | >1 | C | — |
| AA_197_B | A | >1 | C | — |
| AA_230_A | A | >1 | B | — |
| AA_230_B | A | >1 | C | — |
| AA_231_A | A | >1 | B | — |
| AA_231_B | A | >1 | C | — |
| AA_242_A | B | >1 | D | — |
| AA_242_B | B | >1 | D | — |
| AA_280_A | A | >1 | C | — |
| AA_280_B | A | >1 | B | — |
| AA_162_ENDOA2 | A | >1 | B | — |
| AA_273_ENDOA2 | A | >1 | C | — |
| AA_195_ENDOA2 | A | >1 | B | — |
| AA_201_ENDOA2 | A | >1 | B | — |
| AA_204_ENDOA2_A | A | >1 | A | — |
| AA_204_ENDOA2_B | A | >1 | C | — |
| AA_206_ENDOA2 | A | >1 | B | — |
| AA_208_ENDOA2 | A | >1 | B | — |
| AA_214_ENDOA2 | A | — | C | — |
| AA_224_ENDOA2 | A | >1 | B | — |
| AA_233_ENDOA2_A | A | >1 | B | — |
| AA_233_ENDOA2_B | A | >1 | D | — |
| AA_243_ENDOA2_A | A | >1 | C | — |
| AA_243_ENDOA2_B | A | >1 | B | — |
| AA_270_ENDOA2_A | A | >1 | A | — |
| AA_270_ENDOA2_B | A | >1 | C | — |
| AA_279_ENDOA2_A | A | — | B | — |
| AA_279_ENDOA2_B | A | — | C | — |
| AA_282_ENDOA2 | A | — | C | — |
| AA_283_ENDOA2_A | A | — | C | — |
| AA_283_ENDOA2_B | A | — | A | — |
| AA_284_ENDOA2 | A | — | D | — |
| AA_285_ENDOA2 | A | — | C | — |
| AA_287_ENDOA2 | A | — | B | — |
| AA_288_ENDOA2 | A | — | C | — |
| AA_289_ENDOA2 | B | — | D | — |
| AA_290_ENDOA2 | B | — | D | — |
| AA_291_ENDOA2 | A | — | C | — |
| AA_292_ENDOA2_M | B | — | C | — |
| AA_293_ENDOA2 | A | — | C | — |
| AA_294_ENDOA2 | A | — | D | — |
| AA_295_ENDOA2_A | B | — | D | — |
| AA_295_ENDOA2_B | B | — | D | — |
| AA_296_ENDOA2 | B | — | C | — |
| AA_297_ENDOA2 | B | — | D | — |
| AA_298_ENDOA2 | A | >1 | C | — |
| AA_299_ENDOA2 | A | >1 | D | — |
| AA_300_ENDOA2 | B | >1 | D | — |
| AA_301_ENDOA2 | B | >1 | D | — |
| AA_239 | A | >1 | C | — |
| AA_238 | A | >1 | C | — |
| AA_241_A | B | >1 | D | — |
| AA_241_B | B | >1 | D | — |
| AA_242 | B | >1 | D | — |
| AA_150_A | B | >10 | D | — |
| AA_150_B | A | >10 | B | — |
| AA_184 | B | >5 | D | — |
| AA_185 | B | >5 | D | — |
| AA_186 | B | >5 | C | — |
| AA_286 | A | — | D | — |

Note:

$EC_{50}$ indicated the anti-HCV activity of molecule in vitro, $EC_{50}$ which was less than 1 uM represented that the compound has activity in vitro. Four ranges were divided according to the degree of the activity: A (0.001 nM-0.1 nM); B (0.101 nM-1.0 nM); C (1.001 nM-10 nM); D (10.001 nM-100 nM). The value of $CC_{50}$ indicated the toxicity of the molecule in vitro, and the greater the value was, the smaller the toxicity was.

CONCLUSION the compounds of the present invention have excellent anti-HCV activity in vitro.

What is claimed is:

1. A compound represented by formula (V) or a pharmaceutically acceptable salt thereof,

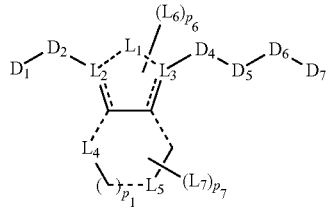

(V)

wherein, $D_1D_7$ are each independently selected from

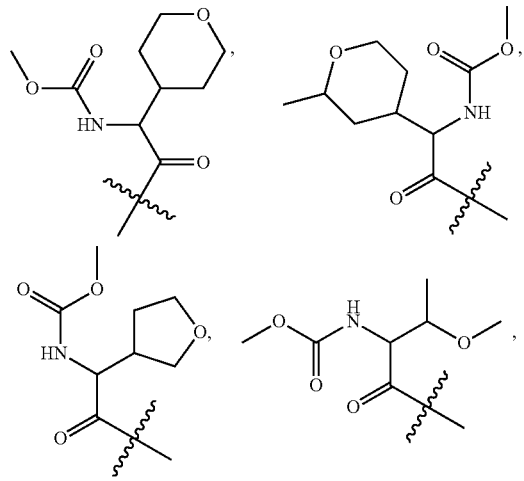

$D_2$ $D_6$ are each independently selected from

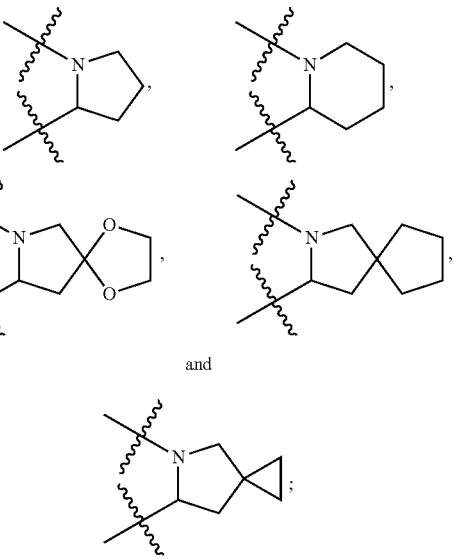

and $D_5$ is selected from a single bond,

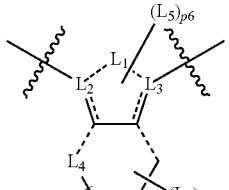

and

;

the structure unit

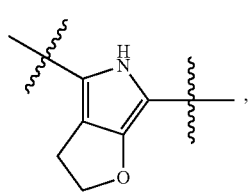

is selected from

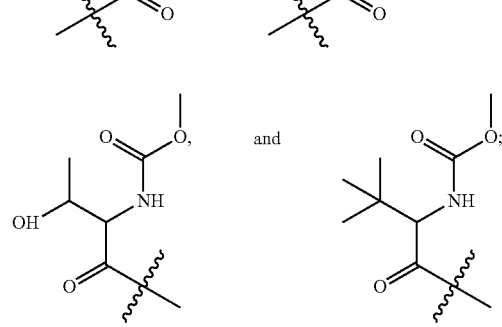

755
-continued
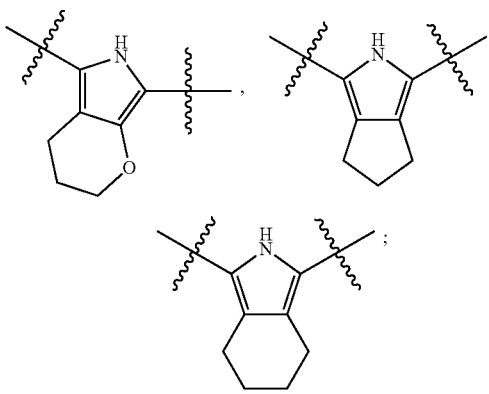
D₄ is selected from
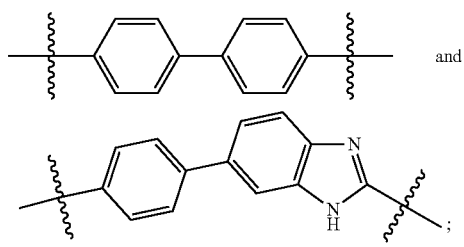
optionally, the compound or the pharmaceutically acceptable salt thereof contains one or multiple chiral centers.
2. The compound according to claim 1, which includes:
AG_015
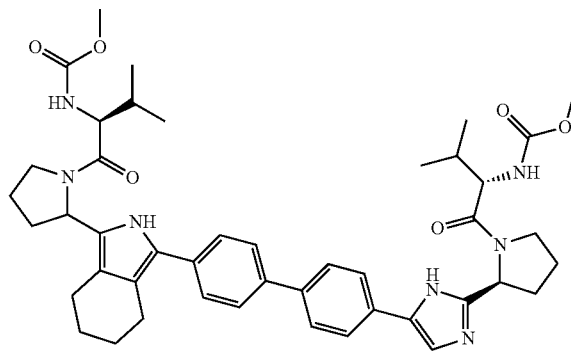
756
-continued
AG_067
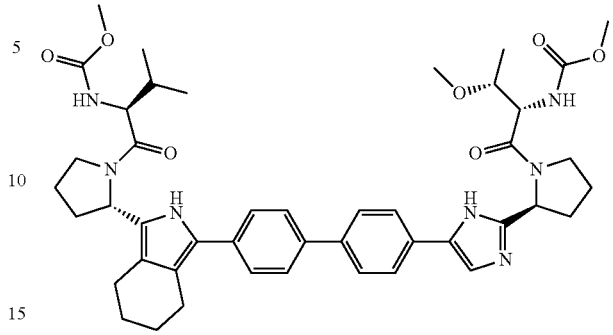
AG_078_A
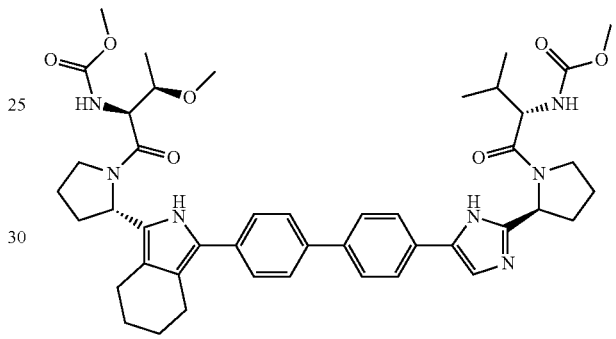
AG_025_A
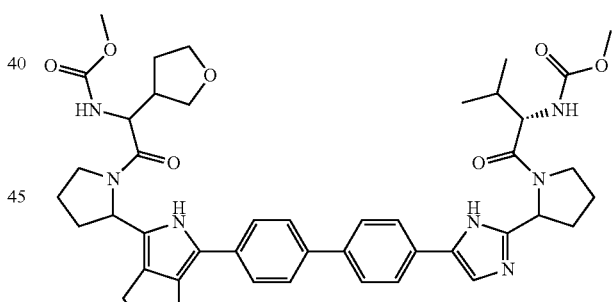
AG_025_B
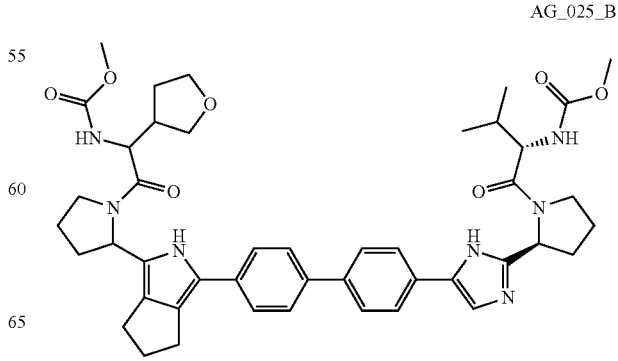

-continued
AG_014_A
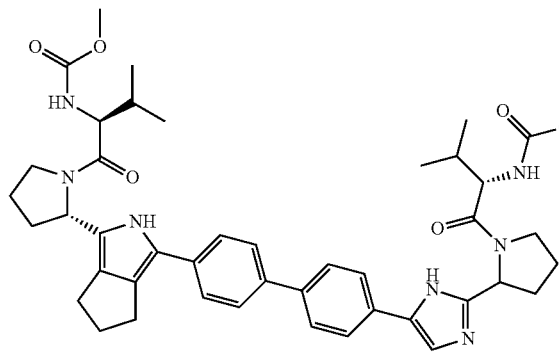
AG_049
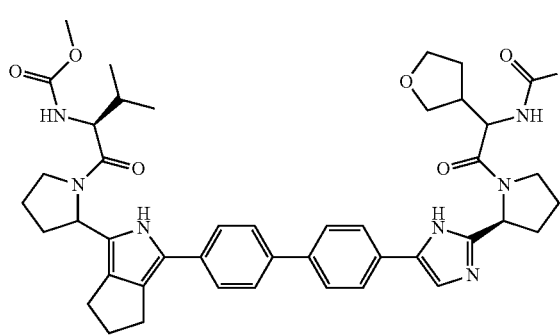
AG_050
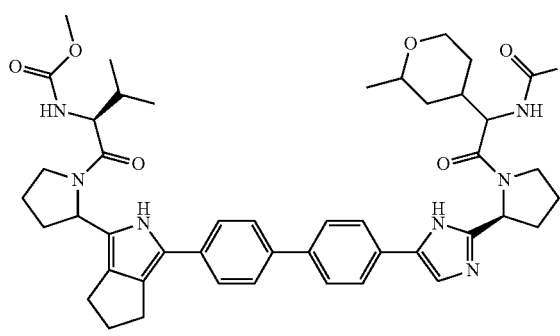
AG_063
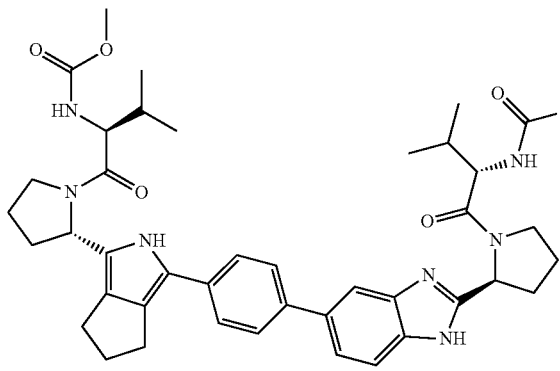
-continued
AG_066
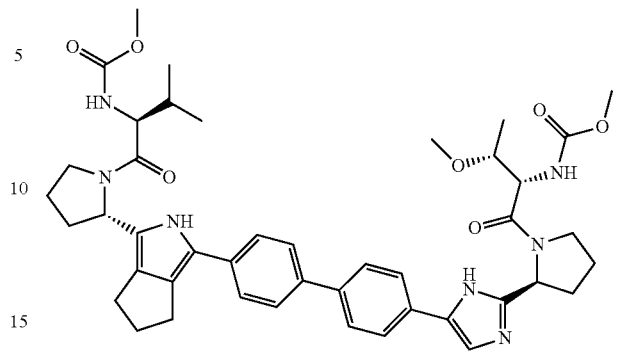
AG_068_A
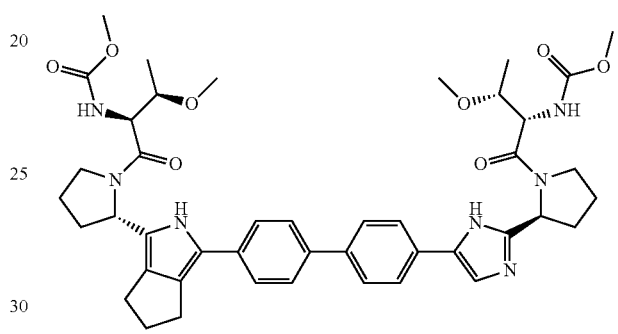
AG_069
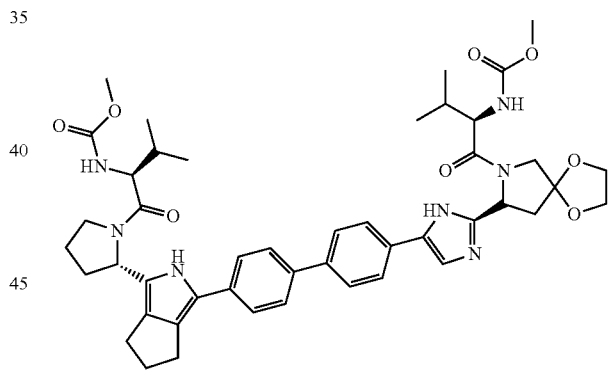
AG_089
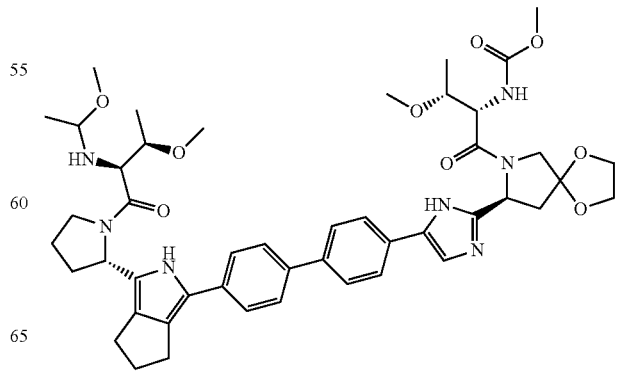

759
-continued
AG_092
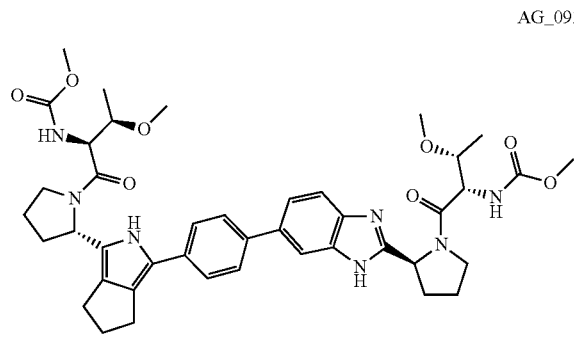
AG_093
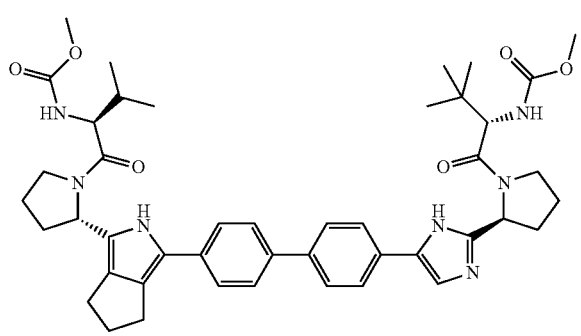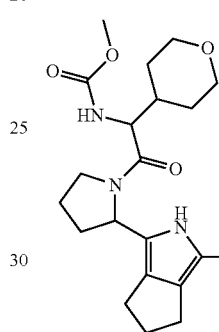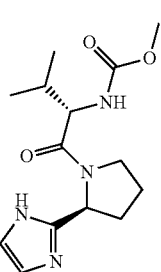
AG_091
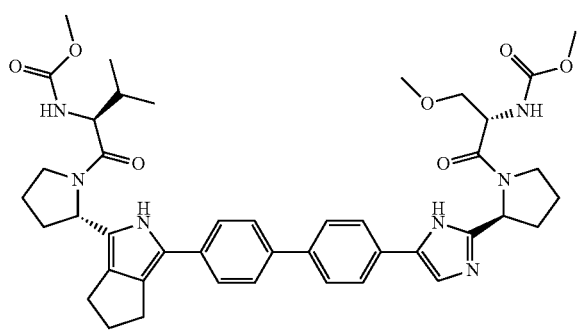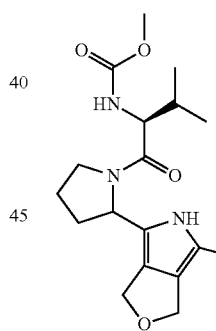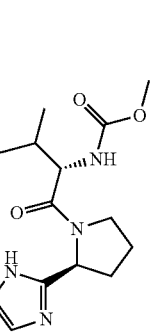
AG_090
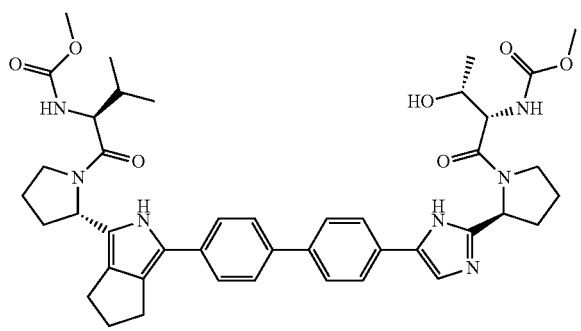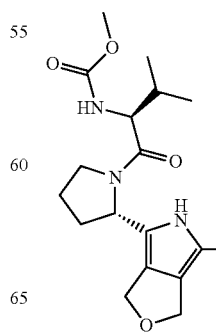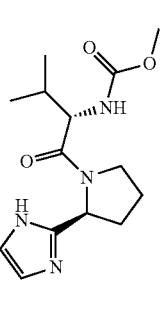
760
-continued
AG_086
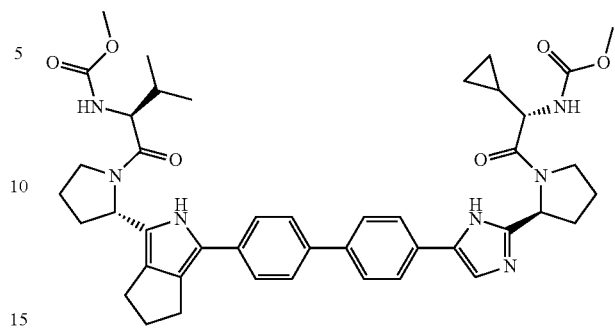
AG_036
AG_060
AG_060_B -continued
AG_077
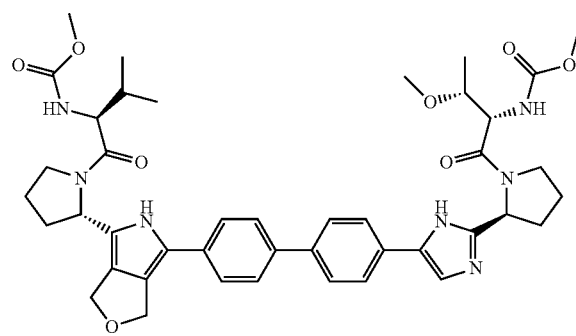
AG_124
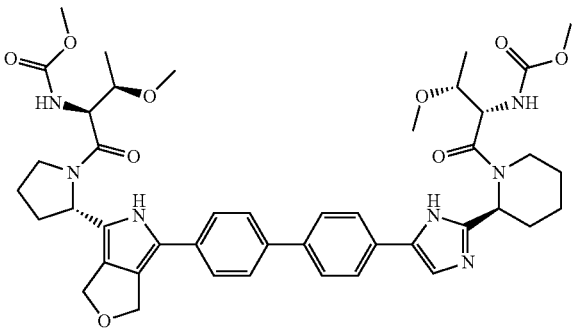
AG_104
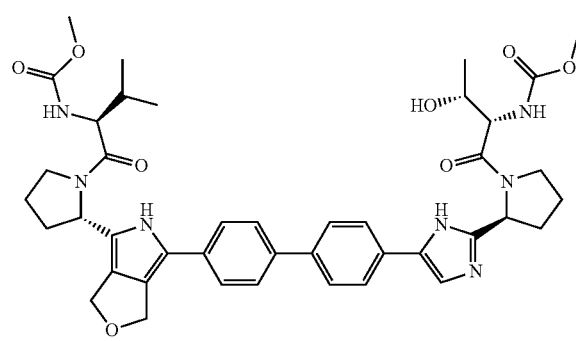
AG_113
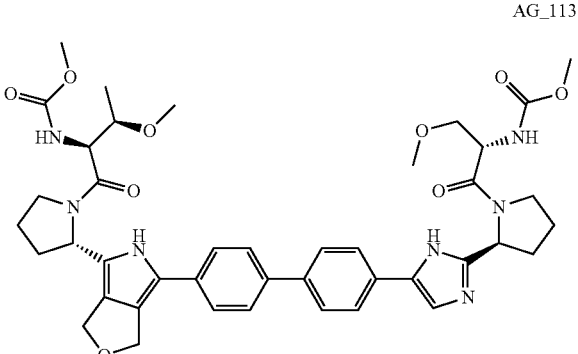
AG_079_A
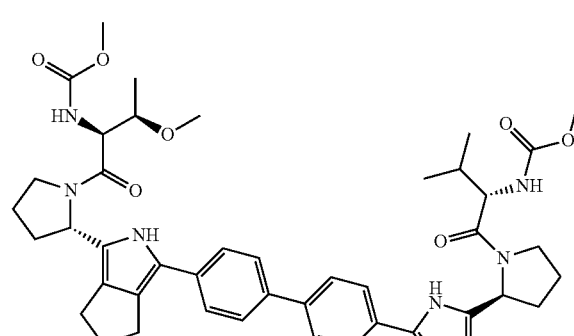
AG_080_A
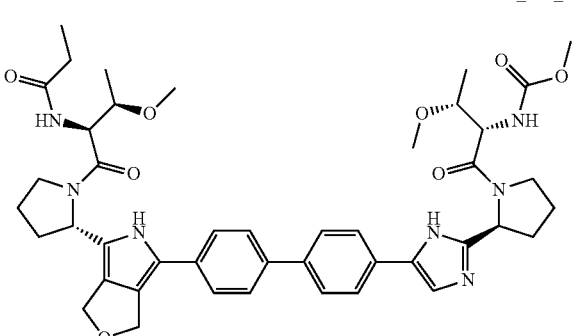
AG_123
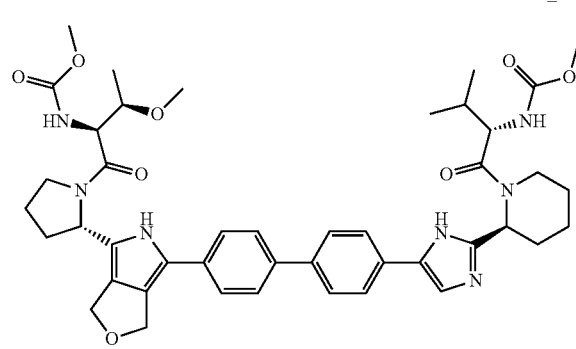
AG_088_A
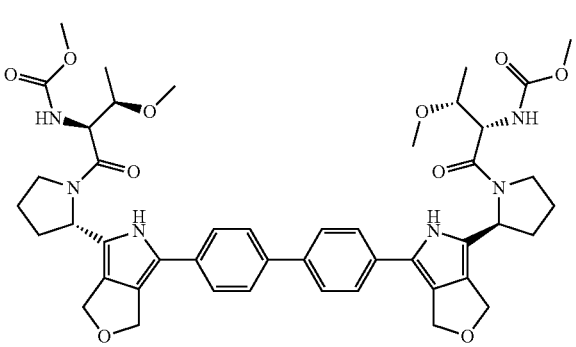

AG_105
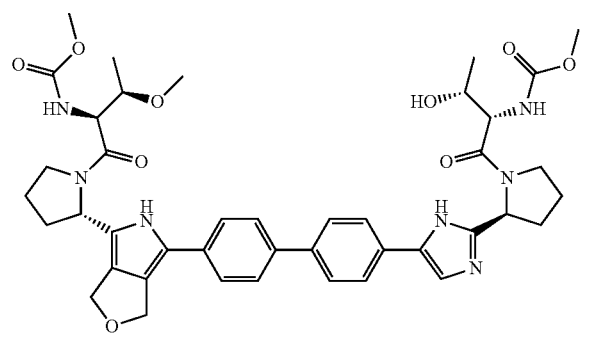
AG_122_A
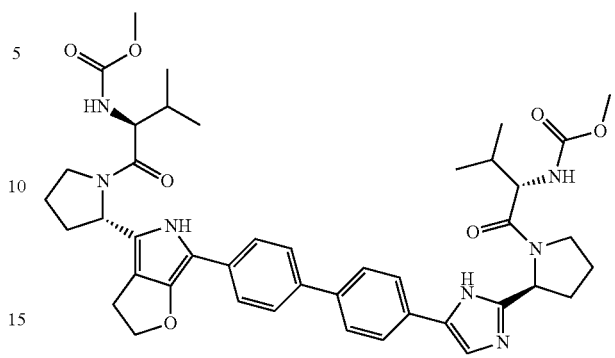
AG_116
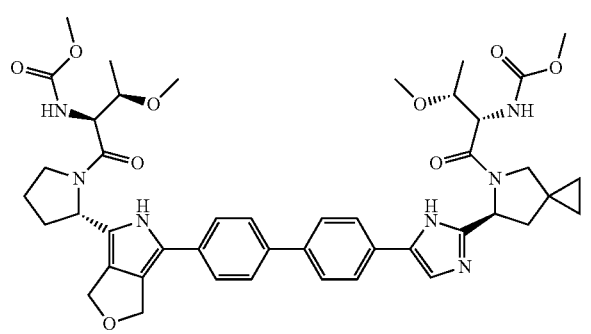
AG_121
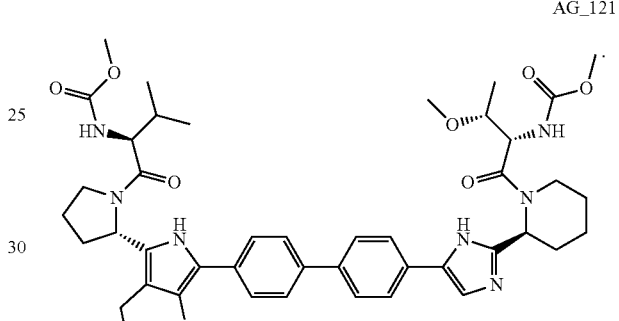
AG_117
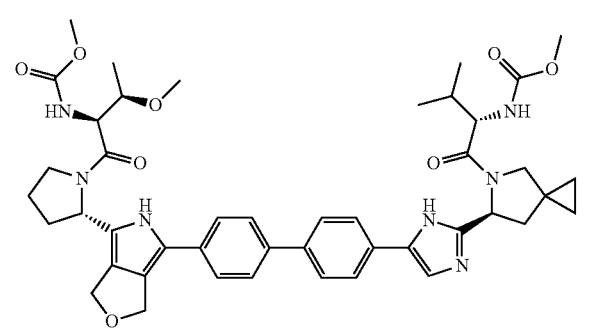
3. The compound or the pharmaceutically acceptable salt thereof according to claim 1, wherein, $D_2$, $D_6$ are each independently selected from
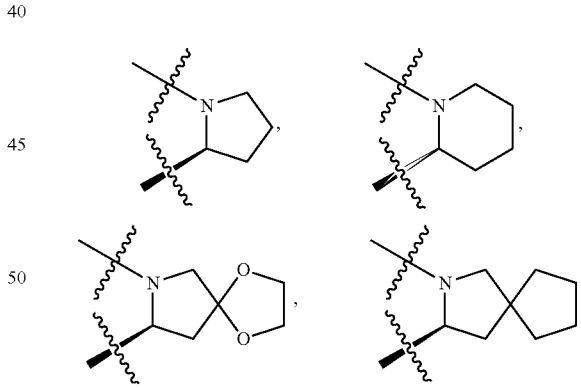
and
AG_111
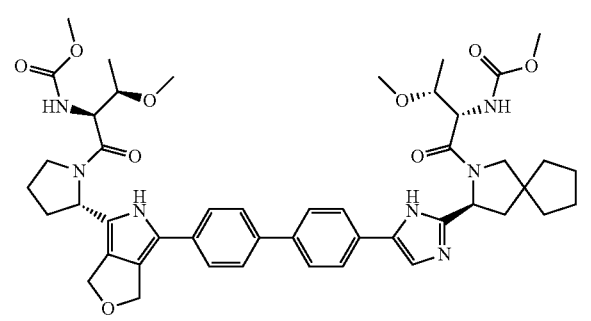
4. The compound or the pharmaceutically acceptable salt thereof according to claim 1, wherein, $D_2$, $D_6$ are each independently selected from

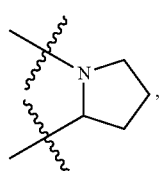 [SMILES: *C1CCCN1*]

5. The compound or the pharmaceutically acceptable salt thereof according to claim 1, wherein, $D_1$, $D_7$ are each independently selected from

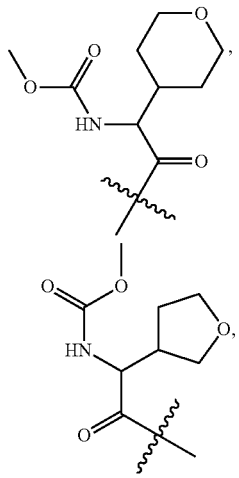
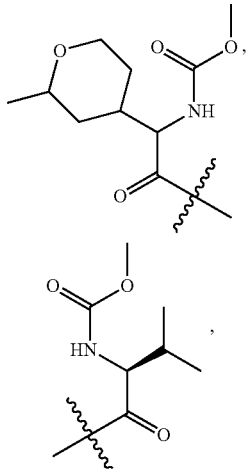

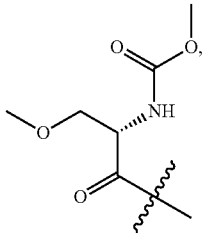
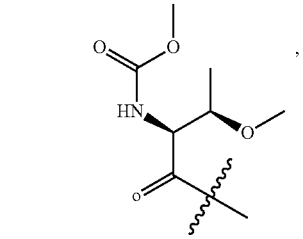

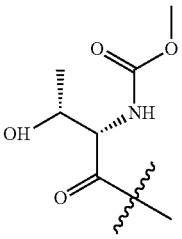 and 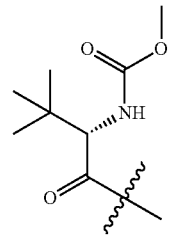

6. A pharmaceutical composition, which comprises a therapeutically effective amount of the compound or the pharmaceutically acceptable salt thereof according to claim 1, and a pharmaceutically acceptable carrier.

7. A process for treating HCV in a subject in need thereof, comprising administering an effective amount of the compound or the pharmaceutically acceptable salt thereof according to claim 1 or the pharmaceutical composition according to claim 6 to the subject.

* * * * *